(12) United States Patent  
Freeman et al.

(10) Patent No.: US 9,988,452 B2  
(45) Date of Patent: Jun. 5, 2018

(54) ANTIBODY MOLECULES TO PD-L1 AND USES THEREOF

(71) Applicants: Novartis AG, Basel (CH); DANA-FARBER CANCER INSTITUTE, INC., Boston, MA (US); PRESIDENT AND FELLOWS OF HARVARD COLLEGE, Cambridge, MA (US)

(72) Inventors: Gordon James Freeman, Brookline, MA (US); Arlene Helen Sharpe, Brookline, MA (US); Gerhard Johann Frey, San Diego, CA (US); Hwai Wen Chang, San Marcos, CA (US); Jennifer Marie Mataraza, Cambridge, MA (US); Glenn Dranoff, Cambridge, MA (US)

(73) Assignees: Novartis AG, Basel (CH); DANA-FARBER CANCER INSTITUTE, INC., Boston, MA (US); PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 0 days. days.

(21) Appl. No.: 14/881,888

(22) Filed: Oct. 13, 2015

(65) Prior Publication Data  
US 2016/0108123 A1  Apr. 21, 2016

Related U.S. Application Data

(60) Provisional application No. 62/213,076, filed on Sep. 1, 2015, provisional application No. 62/198,545, filed (Continued)

(51) Int. Cl.  
C07K 16/28 (2006.01)  
C07K 16/30 (2006.01)  
(Continued)

(52) U.S. Cl.  
CPC .......... C07K 16/2827 (2013.01); A61K 45/06 (2013.01); A61N 5/10 (2013.01); (Continued)

(58) Field of Classification Search  
None  
See application file for complete search history.

(56) References Cited

U.S. PATENT DOCUMENTS 5,968,511 A    10/1999  Akita et al.  
7,449,300 B2   11/2008  Chen et al.  
(Continued)

FOREIGN PATENT DOCUMENTS

EP    2417984 A1    2/2012  
WO    0114556 A1    3/2001  
(Continued)

OTHER PUBLICATIONS

Ohno et al., (May 1985) Antigen-binding specificities of antibodies are primarily determined by seven residues of VH, Proc. Natl. Acad. Sci. USA, 82:2945-2949. (Year: 1985).*

(Continued)

*Primary Examiner* — Claire Kaufman  
(74) *Attorney, Agent, or Firm* — Lando & Anastasi, LLP

(57) ABSTRACT

Antibody molecules that specifically bind to PD-L1 are disclosed. Combination therapies comprising the anti-PD-L1 antibody molecules are also disclosed. The anti-PD-L1 antibody molecules can be used to treat, prevent and/or diagnose cancerous or infectious conditions and disorders.

27 Claims, 21 Drawing Sheets

Related U.S. Application Data on Jul. 29, 2015, provisional application No. 62/094,847, filed on Dec. 19, 2014, provisional application No. 62/063,852, filed on Oct. 14, 2014.

(51) Int. Cl.

| | | |
|---|---|---|
| *C12N 15/11* | (2006.01) | |
| *C12N 5/10* | (2006.01) | |
| *A61K 45/06* | (2006.01) | |
| *A61N 5/10* | (2006.01) | |
| *G01N 33/574* | (2006.01) | |
| *A61K 39/00* | (2006.01) | |

(52) U.S. Cl.
CPC ....... *C07K 16/30* (2013.01); *G01N 33/57492* (2013.01); *A61K 2039/505* (2013.01); *C07K 2317/14* (2013.01); *C07K 2317/24* (2013.01); *C07K 2317/33* (2013.01); *C07K 2317/56* (2013.01); *C07K 2317/76* (2013.01); *C07K 2317/92* (2013.01); *G01N 2333/70532* (2013.01)

(56) References Cited

U.S. PATENT DOCUMENTS

| | | | |
|---|---|---|---|
| 7,595,048 | B2 | 9/2009 | Honjo et al. |
| 7,943,743 | B2 | 5/2011 | Korman et al. |
| 8,008,449 | B2 | 8/2011 | Korman et al. |
| 8,168,179 | B2 | 5/2012 | Honjo et al. |
| 8,217,149 | B2 | 7/2012 | Irving et al. |
| 8,354,509 | B2 | 1/2013 | Carven et al. |
| 8,460,927 | B2 | 6/2013 | Chen |
| 8,552,154 | B2 | 10/2013 | Freeman et al. |
| 8,617,546 | B2 | 12/2013 | Kang et al. |
| 8,779,108 | B2 | 7/2014 | Queva et al. |
| 9,045,545 | B1 | 6/2015 | Clube |
| 9,109,034 | B1 | 8/2015 | Clube |
| 9,175,082 | B2 | 11/2015 | Zhou et al. |
| 9,409,970 | B2 | 8/2016 | Mikesell et al. |
| 9,605,070 | B2 | 3/2017 | Sabatos-Peyton et al. |
| 9,683,048 | B2 | 6/2017 | Freeman et al. |
| 9,815,898 | B2 | 11/2017 | Freeman et al. |
| 2009/0055944 | A1 | 2/2009 | Korman et al. |
| 2011/0150892 | A1 | 6/2011 | Thudium et al. |
| 2011/0195068 | A1 | 8/2011 | Langermann et al. |
| 2011/0209230 | A1 | 8/2011 | Korman et al. |
| 2011/0280877 | A1 | 11/2011 | Tamada |
| 2012/0114649 | A1 | 5/2012 | Langermann et al. |
| 2012/0201824 | A1 | 8/2012 | Wasik |
| 2013/0133091 | A1 | 5/2013 | Korman et al. |
| 2013/0230514 | A1 | 9/2013 | Langermann et al. |
| 2015/0210769 | A1 | 7/2015 | Freeman et al. |
| 2015/0218274 | A1 | 8/2015 | Sabatos-Peyton et al. |
| 2015/0259420 | A1 | 9/2015 | Triebel et al. |
| 2016/0108123 | A1 | 4/2016 | Freeman et al. |
| 2016/0222121 | A1 | 8/2016 | Johnson et al. |
| 2017/0190777 | A1 | 7/2017 | Sabatos-Peyton et al. |
| 2017/0198041 | A1 | 7/2017 | Sabatos-Peyton et al. |
| 2017/0209574 | A1 | 7/2017 | Cao et al. |
| 2017/0210804 | A1 | 7/2017 | Triebel et al. |
| 2017/0247456 | A1 | 8/2017 | Freeman et al. |
| 2017/0281624 | A1 | 10/2017 | Peters et al. |
| 2017/0296659 | A1 | 10/2017 | Lebwohl et al. |
| 2017/0304443 | A1 | 10/2017 | Lebwohl et al. |
| 2017/0340733 | A1 | 11/2017 | Cao |

FOREIGN PATENT DOCUMENTS

| | | | |
|---|---|---|---|
| WO | 0139722 | A2 | 6/2001 |
| WO | 01083750 | A2 | 11/2001 |
| WO | 200194413 | A2 | 12/2001 |
| WO | 0200692 | | 1/2002 |
| WO | 0224891 | A2 | 3/2002 |
| WO | 02078731 | A1 | 10/2002 |
| WO | 02086083 | A2 | 10/2002 |
| WO | 03042402 | A2 | 5/2003 |
| WO | 03063792 | A2 | 8/2003 |
| WO | 2004004771 | A1 | 1/2004 |
| WO | 2004007679 | A2 | 1/2004 |
| WO | 2004056875 | A1 | 7/2004 |
| WO | 2004078928 | A2 | 9/2004 |
| WO | 2006004988 | A2 | 1/2006 |
| WO | 2006042237 | A2 | 4/2006 |
| WO | 2006121168 | A1 | 11/2006 |
| WO | 2006133396 | A2 | 12/2006 |
| WO | 2007005874 | A2 | 1/2007 |
| WO | 2007113648 | A2 | 10/2007 |
| WO | 2008071447 | A2 | 6/2008 |
| WO | 2008083174 | A2 | 7/2008 |
| WO | 2009029342 | A2 | 3/2009 |
| WO | 2009101611 | A1 | 8/2009 |
| WO | 2009114335 | A2 | 9/2009 |
| WO | 2010019570 | A2 | 2/2010 |
| WO | 2010027827 | A2 | 3/2010 |
| WO | 2010036959 | A2 | 4/2010 |
| WO | 2010051502 | A2 | 5/2010 |
| WO | 2010077634 | A1 | 7/2010 |
| WO | 2010089411 | A2 | 8/2010 |
| WO | 2010102278 | A1 | 9/2010 |
| WO | 2011011027 | A1 | 1/2011 |
| WO | 2011066342 | A2 | 6/2011 |
| WO | 2011066389 | A1 | 6/2011 |
| WO | 2011159877 | A2 | 12/2011 |
| WO | 2012022814 | A1 | 2/2012 |
| WO | 2012145493 | A1 | 10/2012 |
| WO | 2012177624 | A2 | 12/2012 |
| WO | 2013006490 | A2 | 1/2013 |
| WO | 2013019906 | A1 | 2/2013 |
| WO | 2013043647 | A1 | 3/2013 |
| WO | 2013079174 | A1 | 6/2013 |
| WO | 2013079945 | A1 | 6/2013 |
| WO | 2013173223 | A1 | 11/2013 |
| WO | 2013181452 | A1 | 12/2013 |
| WO | 2013181634 | A1 | 12/2013 |
| WO | 2014022138 | A2 | 2/2014 |
| WO | 2014022332 | A1 | 2/2014 |
| WO | 2014022758 | A1 | 2/2014 |
| WO | 2014047350 | A1 | 3/2014 |
| WO | 2014055897 | A2 | 4/2014 |
| WO | 2014100079 | A1 | 6/2014 |
| WO | 2014165082 | A2 | 10/2014 |
| WO | 2014165422 | A1 | 10/2014 |
| WO | 2014189805 | A1 | 11/2014 |
| WO | 2015026634 | A1 | 2/2015 |
| WO | 2015026684 | A1 | 2/2015 |
| WO | 2015036499 | A1 | 3/2015 |
| WO | 2015036511 | A1 | 3/2015 |
| WO | 2015048520 | A1 | 4/2015 |
| WO | 2015061668 | A1 | 4/2015 |
| WO | 2015081158 | A1 | 6/2015 |
| WO | 2015095423 | A2 | 6/2015 |
| WO | 2015095811 | A2 | 6/2015 |
| WO | 2015103602 | A1 | 7/2015 |
| WO | 2015109124 | A2 | 7/2015 |
| WO | 2015112805 | A1 | 7/2015 |
| WO | 2015112900 | A1 | 7/2015 |
| WO | 2015117002 | A1 | 8/2015 |
| WO | 2015118175 | A2 | 8/2015 |
| WO | 2015119944 | A1 | 8/2015 |
| WO | 2015120198 | A1 | 8/2015 |
| WO | 2015138920 | A1 | 9/2015 |
| WO | 2015181342 | A1 | 12/2015 |
| WO | 2015195163 | A1 | 12/2015 |
| WO | 2016000619 | A1 | 1/2016 |
| WO | 2016028672 | A1 | 2/2016 |
| WO | 2016/040892 | A1 | 3/2016 |
| WO | 2016040880 | A1 | 3/2016 |
| WO | 2016040882 | A1 | 3/2016 |
| WO | 2016/054555 | A2 | 4/2016 |
| WO | 2016/100882 | A1 | 6/2016 |
| WO | 2017019894 | A1 | 2/2017 |

(56) References Cited

FOREIGN PATENT DOCUMENTS

| WO | 2017019896 A1 | 2/2017 |
|----|---------------|--------|
| WO | 2017019897 A1 | 2/2017 |
| WO | 2017106656 A1 | 6/2017 |

OTHER PUBLICATIONS

Entzminger et al., (Published online Aug. 31, 2017) De novo design of antibody complementarity determining regions binding a FLAG tetrapeptide, Scientific Reports, 7: 10295, [retrieved on Jan. 12, 2018] Retrieved from Internet <URL: https://www.nature.com/articles/s41598-017-10737-9.pdf?origin=ppub>. (Year: 2017).*

Anderson et al. "Tim-3, a negative regulator of anti-tumor immunity" Current Opinion in Immunology (2012) vol. 24, No. 2, pp. 213-216.

Benson et al. "The PD-1/PD-L1 axis modulates the natural killer cell versus multiple myeloma effect: a therapeutic target for CT-011, a novel monoclonal anti-PD-1 antibody" Blood (2010) vol. 116, No. 13, pp. 2286-2294.

Berrien-Elliott et al., "Durable Adoptive Immunotherapy for Leukemia Produced by Manipulation of Multiple Regulatory Pathways of CD8+ T-Cell Tolerance," Cancer Research (2012) vol. 73, pp. 605-616.

Hallett et al., "Immunosuppressive Effects of Multiple Myeloma Are Overcome by PD-L1 Blockade" Biol Blood Marrow Transplant (2011) vol. 17, No. 8, pp. 1133-1145.

Kearl et al., "Programmed Death Receptor-1/Programmed Death Receptor Ligand-1 Blockage after transient Lymphodepletion to Treat Myeloma," J Immunol (2013) vol. 190, pp. 5620-5628.

Li et al., "Contribution of PD-L1 to oncogenesis of lymphoma and its RNAi-based targeting therapy" Leukemia & Lymphoma (2012) vol. 53, No. 10, pp. 2015-2023.

Miska et al., "Autoimmunity-mediated antitumor immunity: Tumor as an immunoprivileged self," Eur J Immunol (2012) vol. 42, pp. 2584-2596.

Supplementary European Search Report for European Application No. EP 1484888, dated May 31, 2017.

Zhou et al., "Coexpression of Tim-3 and PD-1 identifies a CD8 T-cell exhaustion phenotype in mice with disseminated acute myelogenous leukemia" Blood (2011) vol. 117 No. 17 pp. 4501-4510.

Acquaviva et al: "FGFR3 Translocations in Bladder Cancer: Differential Sensitivity to HSP90 Inhibition Based on Drug Metabolism". Molecular Cancer Research. vol. 12. No. 7. Jul. 1, 2014 (Jul. 1, 2014). pp. 1042-1054.

Allard et al. "Targeting CD73 Enhances the Antitumor Activity of Anti-FD-1 and Anti-CTLA-4 mAbs" Clinical Cancer Research (2013) vol. 19, No. 20, pp. 5626-5635.

Amin et al: "Nivolumab (anti-PD-1; BMS-936558, ONO-4538) in combination with sunitinib or pazopanib in patients (pts) with metastatic renal cell carcinoma (mRCC)" Journal of Clinical Oncology (2014) vol. 32, No. 15 suppl, Abstract 5010.

Ascierto et al. "Future perspectives in melanoma research" meeting report from the "Melanoma Bridge", Napoli, Dec. 5-8, 2013 Journal of Translational Medicine (2014) vol. 12, No. 277, pp. 1-29.

Ashworth et al. "Management of a Patient With Advanced BRAF-Mutant Melanoma" Journal of the National Comprehensive Cancer Network (2014) vol. 12, No. 3, pp. 315-319.

Batus et al. "Optimal Management of Metastatic Melanoma: Current Strategies and Future Directions" Am. J. Clin. Dermatol. (2013) vol. 14, No. 3, pp. 179-194.

Bellucci et al: "JAKI and JAK2 Modulate Tumor Cell Susceptibility to Natural Killer (NK) Cells Through Regulation of PDLI Expression", Blood (Nov. 15, 2013), Retrieved from the Internet: URL:http://www.bloodjournal.orgjcontent/122/21/3472.full.pdf [retrieved on Apr. 14, 2016].

Blank et al "Combination of targeted therapy and immunotherapy in melanoma" Cancer Immunol Immunother (2011) vol. 60, pp. 1359-1371.

Brahmer et al. "Safety and Activity of Anti-PD-LI Antibody in Patients with Advanced Cancer" New England Journal of Medicine (2012) vol. 366, No. 26, pp. 2455-2465.

Brown et al, "Blockade of Programmed Death-1 Ligands on Dendritic Cells Enhances T Cell Activation and Cytokine Production", J. Immunol. (2003) vol. 170, pp. 1257-1266.

Butte et al, "Interaction of human PD-L1 and B7-1", Mol Immunol (2008) vol. 45, pp. 3567-3572.

Chervontseva A M et al: "Effect of cytarabine on expression of cell adhesion molecules and on endothelium-leukocyte interaction in vitro.", Terapevticheskii Arkhiv 2006, vol. 78, No. 7, 2006, pp. 67-72.

Christiansen et al: "Eradication of solid tumors using histone deacetylase inhibitors combined with irrmune-stimulating antibodies", Proceedings of the National Academy of Sciences, vol. 108 No. 10, Feb. 22, 2011 (Feb. 22, 2011), pp. 4141-4146.

Christiansson Lisa et al: "The tyrosine kinase inhibitors imatinib and dasatinib reduce myeloid suppressor cells and release effector lymphocyte responses.", Molecular Cancer Therapeutics, vol. 14, No. 5, May 2015 (May 2015), pp. 1181-1191.

ClincalTrials.gov Identifier: NCT01988896 "A Phase 1 b Study of MPDL3280A (an Engineered Anti-PDL1 Antibody) in Combination With Cobimetinib in Patients With Locally Advanced or Metastatic Solid Tumors" Clinicaltrials.gov, last updated Dec. 1, 2014.

ClinicalTrials.gov Identifier: NCT02040064 "Tolerability and Efficacy of Tremelimumab in Combination With Gefitinib in NSCLC Patients", ClinicalTrials.gov; last updated Jan. 17, 2014.

ClinicalTrials.gov Identifier: NCT02263508 "A Phase 1 b/3, Multicenter, Open-label Trial of Tafimogene Laherparepvec in Combination With Pembrolizumab (MK-3475) for Treatment of Unresected,Stage IIIB to IVM1c Melanoma (Masterkey-265)", ClinicalTrials.gov; last updated Jun. 22, 2015.

ClinicalTrials.gov Identifier: NCT02339571 "Randomized Phase II/III Study of Nivolumab Plus Ipilimumab Plus Sargramostim Versus Nivolumab Plus Ipilimumab in Patients With Unresectable Stage III or Stage IV Melanoma", ClinicalTrials.gov; last updated Apr. 9, 2015.

Dey et al: "Nutl in-3 inhibits the NF[kappa]B Pathway in a p53 Dependent Manner: Implications in Lung Cancer Therapy". Cell Cycle, vol. 6, No. 17, Sep. 1, 2007 (Sep. 1, 2007), pp. 2178-2185.

Dong et al., "Tumor-associated B7-H1 promotes T-cell apoptosis: A potential mechanism of immune evasion", Nat Med (2002) vol. 8 pp. 793-800.

Freeman et al., "Engagement of the PD-1 immunoinhibitory receptor by a novel B7 family member leads to negative regulation of lymphocyte activation", J Exp Med. (2000) vol. 192, No. 7, pp. 1027-1034.

Garcia et al: "The Pan-PIM Kinase Inhibitor LGH447 Shows Activity in PIM2-Dependent Multiple Myeloma and in AML Models", Blood (2013) Retrieved from the Internet: URL:http://www.bloodjournal.orgjcontent/12 2/21/1666 [retrieved on Apr. 14, 2016].

Garrison K et al: "The small molecule TGF-[beta] signaling inhibitor SM16 synergizes with agonistic OX40 antibody to suppress established mammary tumors and reduce spontaneous metastasis" Cancer Immunology, Immunotherapy (2012) vol. 61 No. 4 pp. 511-521.

Gettinger et al. "Safety and Response 1-98 With Nivolumab (Anti-PD-1; BMS-936558, ONO-4538) Plus Erlotinib in Patients (Pts) With Epidermal Growth Factor Receptor Mutant (EGFR MT) Advanced Non-Small Cell Lung Cancer (NSCLC} Metastatic Non-Small Cell Lung Cancer" International Journal of Radiation: Oncology Biology Physics (2014) vol. 90, No. 5, pp. S34-S35.

Grygielewicz Paulina et al: "Epithelial-mesenchymal transition confers resistance to selective FGFR inhibitors in SNU-16 gastric cancer cells". Gastric Cancer. Springer Japan. Tokyo. vol. 19. No. 1., Nov. 19, 2014 (Nov. 19, 2014). pp. 53-62.

Hamid et al., "Safety and Tumor Responses with Lambrolizumab (Anti-PD-1) in Melanoma" New England Journal of Medicine (2013) vol. 369 No. 2 pp. 134-144.

Hu Yi et al: "Essential role of AKT in tumor cells addicted to FGFR.", Anti-Cancer Drugs, vol. 25, No. 2, Feb. 2014 (Feb. 2014), pp. 183-188.

(56) References Cited

OTHER PUBLICATIONS

International Search Report and Written Opinion for International Appliaction No. PCT/US2016/044545 dated Oct. 28, 2016.
International Search Report and Written Opinion for International Application No. PCT/US2015/049826 dated Dec. 16, 2015.
International Search Report and Written Opinion for International Application No. PCT/US2015/055390, dated Dec. 17, 2015.
International Search Report and Written Opinion for International Application No. PCT/US2015/066812 dated Mar. 23, 2016.
International Search Report and Written Opinion for International Application No. PCT/US2016/044547 dated Oct. 18, 2016.
International Search Report and Written Opinion for International Application No. PCT/US2016/044549.
International Search Report and Written Opinion for PCT/US2014/057491 dated Jan. 7, 2015.
International Search Report and Written Opinion for PCT/US2015/012754 dated May 20, 2015.
International Search Report and Written Opinion for PCT/US2015/053799 dated May 17, 2016.
Iwai et al, "Involvement of PD-L1 on tumor cells in the escape from host immune system and tumor immunotherapy by PD-L1 blockade" PNAS (2002) vol. 99, pp. 12293-12297.
Iwai et al, "PD-1 blockade inhibits hematogenous spread of poorly immunogenic tumor cells by enhanced recruitment of effector T cells", J. Immunol. (2005) vol. 17, pp. 133-144.
Jiang et al, "mTOR Kinase Inhibitor AZD8855 Enhances the Inmunotherapeutic Activity of an Agonist CD40 Antibody in Cancer Treatment" Cancer Research (2011) vol. 71 No. 12.
Jiang X et al: "The activation of MAPK in melanoma cells resistant to BRAF inhibition promotes PD-L1 expression that is reversible by MEK and PI3K inhibition", Clinical Cancer Research, The American Association for Cancer Research, US, vol. 19, No. 3, Feb. 1, 2013 (Feb. 1, 2013). pp. 598-609.
Khalil et al. "The New Era of Cancer Immunotherapy: Manipulating T-Cell Activity to Overcome Malignancy" Immunotherapy of Cancer In: Advances in Cancer Research (2015) vol. 128, pp. 1-68.
Kim et al: "Eradication of metastatic mouse cancers resistant to irrmune checkpoint blockade by suppression of myeloid-derived cells. (Includes Supporting Information)", Proceedings of the National Academy of Sciences of the United States of America, vol. 111, No. 32, Aug. 12, 2014 (Aug. 12, 2014), pp. 11774-11777.
Kirkwood et al, "Immunotherapy of cancer in 2012" CA: A Cancer Journal for Clinicians (2012) vol. 62 No. 5 pp. 309-335.
Klein Jan M et al: "The histone deacetylase inhibitor LBH589 (panobinostat) modulates the crosstalk of lymphocytes with Hodgkin lymphoma cell lines.", PLOS One, vol. 8, No. 11, E79582, 2813, pp. 1-6.
Knight et al. "Host immunity contributes to the antimelanoma activity of BRAE inhibitors" The Journal of Clinical Investigation (2013) vol. 123, No. 3, pp. 1371-1381.
Knights et al., "Inhibitor of apoptosis protein (IAP) antagonists demonstrate divergent immunomodulatory properties in human immune subsets with implications for combination therapy" Cancer Immunology and Immunotherapy (2013) vol. 62 No. 2 pp. 321-335.
Lehmann et al, "Identification of human triple-negative breast cancer subtypes and preclinical models for selection of targeted therapies", J Clin Invest., 121(7): 2750-2767.
Manning et al, "A model of multiple myeloma: culture of 5T33 murine myeloma cells and evaluation of tumorigenicity in the C57BL/KaLwRij mouse.", Br J Cancer., 66(6): 1088-1093 (1992).
Masters et al., "Abstract 5016: Antitumor activity of anti-PD-1 in combination with tyrosine kinase inhibitors in a preclinical renal cell carcinoma model" AACR Annual Meeting (2014) vol. 74, No. 5016.
Menzies et al. "Recent advances in melanoma systemic therapy. BRAF inhibitors, CTLA4 antibodies and beyond" European Journal of Cancer (2013) vol. 49, pp. 3229-3241.
Menzies et al. "Systemic treatment for BRAF-mutant melanoma: where do we go next?" The Lancet (2014) vol. 15, pp. e371-e381.

Mittendorf Elizabeth A et al: "PD-L1 expression in triple-negative breast cancer." Cancer Immunology Research. vol. 2. No. 4. Apr. 2014 (Apr. 2014). pp. 361-370.
Mokyr et al, "Realization of the Therapeutic Potential of CTLA-4 Blockade in Low-Dose Chemotherapy-treated Tumor-bearing Mice", Cancer Research, 58:5301-5304 (1998).
Moreira Da Silva, "Nivolumab Anti-PD-1 monoclonal antibody cancer immunotherapy" Drugs of the Future (2014) vol. 39 No. 1 pp. 15-24.
Nakae et al., "Mast cells enhance T cell activation: importance of mast cell costimulatory molecules and secreted TNF" The Journal of Immunology (2006) vol. 176 No. 4 pp. 2238-2248.
Ohigashi et al, "Clinical Significance of Programmed Death-1 Ligand-1 and Programmed Death-1 Ligand-2 Expression in Human Esophageal Cancer" Clin Cancer Research (2005) vol. 11, pp. 2947-2953.
Okazaki et al, "PD-1 and PD-1 ligands: from discovery to clinical application" Intern. Immun. (2007) vol. 19, pp. 813-824.
Oki Y et al: "Immune regulatory effects of panobinostat in patients with Hodgkin lymphoma through modulation of serum cytokine levels and T-cell PD1 expression .", Blood Cancer Journal, vol. 4, E236, 2014, pp. 1-4.
Pardoll et al. "The blockade of immune checkpoints in cancer immunotherapy" Nature Reviews Cancer (2012) vol. 12, pp. 252-264.
Patel et al. "Taming dendritic cells with TIM-3: another immunosuppressive strategy used by tumors" Immunotherapy (2012) vol. 4, No. 12, pp. 1795-1798.
Perez-Gracia et al, "Orchestrating immune check-point blockade for cancer inmunotherapy in combinations", Current Opinion in Immunology. vol. 27 pp. 89-97.
Pinzon-Ortiz et al: "S710: The combination of JAK inhibitor, ruxolitinib, pan-PIM inhibitor, LGH447, and CDK4/6 inhibitor, LEE011, in a preclinical mouse model of myeloproliferative neoplasia", Haematologica, The Hematology Journal: Official Organ of the European Hematology Association, vol. 99. No. Supp 1 (2014) p. 252.
Quintarelli et al: "Selective strong synergism of Ruxolitinib and second generation tyrosine kinase inhibitors to overcome bone marrow stroma related drug resistance in chronic myelogenous leukemia", Leukemia Research, New York,NY, US, vol. 38, No. 2, Nov. 15, 2013 (Nov. 15, 2013), pp. 236-242.
Rothe et al. "Enhancing dendritic cell-induced T-cell responses by immunomodulating molecules" 13th CIMT Annual Meeting (2015) p. 74.
Sakuishi et al, "Targeting Tim-3 and PD-1 pathways to reverse T cell exhaustion and restore anti-tumor immunity", J Exp Med., 207(10): 2187-2194 (2010).
Song et al: "3681 Phenotypic and Functional Effects of Novel HDAC Inhibitor LBH589 on Human Lymphocyte Populations", 51st ASH Annual Meeting and Exposition (2009) Retrieved from the Internet: URL:https:jjash.confex.comjash/2889/webprogramjPaper22684.html [retrieved on 2816-84-14].
Song W et al: "HDAC inhibition by LBH589 affects the phenotype and function of human myeloid dendritic cells.", Leukemia JAN 2811, vol. 25, No. 1, Jan. 2011 (Jan. 2011), pp. 161-168.
Thompson et al, "Tumor B7-H1 Is Associated with Poor Prognosis in Renal Cell Carcinoma Patients with Long-term Follow-up" Cancer Res. (2006) vol. 66, pp. 3381-3385.
Topalian et al. "Safety, Activity, and Immune Correlates of Anti-PD-1 Antibody in Cancer" New England Journal of Medicine (2012) vol. 366, No. 26, pp. 2443-2454.
Vanneman et al: "Combining immunotherapy and targeted therapies in cancer treatment" Nature Reviews Cancer (2012) vol. 12 No. 4 pp. 237-251.
Verbrugge et al: "The curative outcome of radioinmunotherapy in a mouse breast cancer model relies on mTOR signaling", Radiation Research. Radiation Research Society, GB, vol. 182 No. 2 pp. 219-229.
Wang et al., "The Mdm2 inhibitor, NVP-CGM097, in combination with the BRAF inhibitor NVP-LGX818 elicits synergistic antitumor effects in melanoma" Cancer Research (2014) Retrieved from the

(56) References Cited

OTHER PUBLICATIONS

Internet: URL:http://cancerres.aacrjournals.orgjcontent/74/19 Supplement/5466 [retrieved on Apr. 14, 2016].
Wang et al: "Abstract 2929: The Mdm2 inhibitor NVP-CGM097 enhances the anti-tumor activityof NVP-LDK378 in ALK mutant neuroblastomamodels", Cancer Research (2014) Retrieved from the Internet: URL:http:jjcancerres.aacrjournals.orgjcontent/74/19 Supplement/2929 [retrieved on Apr. 14, 2016].
Woods David M et al: "HDAC Inhibition Upregulates PD-1 Ligands in Melanoma and Augments Immunotherapy with PD-1 Blockade.",Cancer Immunology Research, vol. 3, No. 12, Dec. 2815 (Dec. 2015), pp. 1375-1385.
Woods David M et al: "The antimelanoma activity of the histone deacetylase inhibitor panobinostat (LBH589) is mediated by direct tumor cytotoxicity and increased tumor immunogenicity.", Melanoma Research, vol. 23, No. 5, October 2813 (Oct. 2013), pp. 341-348.
Woods et al: "Abstract 4090: Inhibition of class I histone deacetylases promotes robust and durable enhancement of PDL1 expression in melanoma: Rationale for combination therapy", Cancer Research (2014)Retrieved from the Internet: URL:http://cancerres.aacrjournals.orgjcont ent/74/19 Supplement/4090.short [retrieved on Apr. 14, 2016].
Yuan Z et al, "Blockade of inhibitors of apoptosis (IAPs) in combination with tumor-targeted delivery of tumor necrosis factor-[alpha] leads to synergistic antitumor activity" Cancer Gene Therapy (2013) vol. 20 No. 1 pp. 46-56.
Zamarin et al. "Immune checkpoint modulation: Rational design of combindation strategies" Pharmacology & Therapeutics (2015) vol. 150, pp. 23-32.
Zhuang J et al: "Selective IAP inhibition results in sensitization of unstimulated but not CD40-stimulated chronic lymphocytic leukaemia cells to TRAIL-induced apoptosis" Pharmacology Research & Perspectives. John Wiley & Sons Ltd, GB, vol. 2 No. 6 pp. 1-14.
Opposition filed by Laboratorios LeGrand S.A. in corresponding Colombian Application No. NC2017/0003490 dated Dec. 7, 2017, admitted Dec. 19, 2017, published Dec. 20, 2017.
Opposition filed by ASILFA AG in corresponding Chilean Application No. 2017-00888 on Oct. 24, 2017, assigned litigation file number by the National Institute of Industrial Property of Chile (INAPI) on Feb. 27, 2018, notified by INAPI to agent on Mar. 2, 2018.
Herbst et al., "A study of MPDL3280A, an engineered PD-L1 antibody in patients with locally advanced or metastatic tumors," J Clin Oncol (2013) vol. 31, No. 15 (Supp), Abstract 3000.
Searh Report and Written Opinion issued in Singapore Application No. 11201702401R, dated Mar. 29, 2018.
Stewart et al., "MEDI4736: Delivering effective blockade of immunosuppression to enhance tumor rejection: Monoclonal antibody discovery and practical development," Cancer Res (2011) vol. 71, No. 8 (Supp), Abstract LB-158.

* cited by examiner

Heavy Chain (murine IgG1)

```
       FWH1                 CDRH1         FWH2           CDRH2
QVHLQQPGAE LVKPGASVKL SCKASGYTFT SYWMYWVKQG PGRGLEWIGR IDPNSGSTKY
           FWH3                         CDRH3        FWH4
NEKFKNKATL TVDKSSSTAY MQLSSLTSED SAVYYCARDY RKGLYAMDYW GQGTSVTVSS
```

Light Chain (murine κ)

```
       FWL1                 CDRL1         FWL2           CDRL2
DIVMTQSHKF MSTSVGDRVS ITCKASQDVG TAVAWYQQKP GQSPKLLIYW ASTRHTGVPD
           FWL3                 CDRL3    FWL4
RFTGSGSGTD FTLTISNVQS EDLADYFCQQ YNSYPLTFGA GSKLELK
```

FIGURE 1

Heavy Chain

```
GL       QVQLQQPGAE LVKPGASVKL SCKASGYTFT SYWMHWVKQR PGRGLEWIGR IDPNSGGTKY
Mu mAb   --H------- ---------- ---------- ----Y----G ---------- ------S---

GL       NEKFKSKATL TVDKPSSTAY MQLSSLTSED SAVYYCAR
Mu mAb   ------N---- ----S----- ---------- --------DY RKGLYAMDYW GQGTSVTVSS
```

Light Chain

```
GL       DIVMTQSHKF MSTSVGDRVS ITCKASQDVG TAVAWYQQKP GQSPKLLIYW ASTRHTGVPD
Mu mAb   ---------- ---------- ---------- ---------- ---------- ----------

GL       RFTGSGSGTD PTLTISNVQS EDLADYFCQQ YSSYPLTFGA GSKLELK
Mu mAb   ---------- ---------- ---------- -N-------- -------
```

FIGURE 2

| Clone No. | Concentration µg/mL | Sequence | | | | | |
|---|---|---|---|---|---|---|---|
| | | HC | | | LC | | |
| | | FW1 | FW2 | FW3 | FW1 | FW2 | FW3 |
| | | 9 unique HC | | | 9 unique LC | | |
| 1 | 22.0 | a | a | a | c | c | c |
| 2 | 21.2 | a | a | a | d | c | d |
| 3 | 16.8 | c | a | b | a | c | e |
| 4 | 30.5 | b | a' | c | a | c | b |
| 5 | 30.3 | c | c | d | a | c | b |
| 6 | 31.3 | b | b | b | a | c | b |
| 7 | 25.2 | a | c | a | e | c | f |
| 8 | 1.4 | b | d | d | b | a | a |
| 9 | 30.6 | b | b | b | c | c | c |
| 10 | 0.5 | d | e | b | b | a | a |
| 11 | 18.6 | c | a | b | b | a | a |
| 12 | 21.5 | b | a' | c | d | a | b |
| 13 | 47.6 | c | d | e | f | c | g |
| 14 | 33.5 | a | a | a | a | a | a |
| 15 | 20.1 | b | b | b | a | a | a |
| 16 | 31.7 | a | c | a | a | a | a |
| 17 | 44.7 | b | d | d | a | a | a |

FIGURE 4

| Clone No. | Conc. μg/mL | Sequence | | | | | | Rank | Comp. binding |
|---|---|---|---|---|---|---|---|---|---|
| | | HC | | | LC | | | | |
| | | FW1 | FW2 | FW3 | FW1 | FW2 | FW3 | | |
| | | 9 unique HC | | | 9 unique LC | | | | |
| 1 | 22.0 | a | a | a | c | c | c | 17 | 2.56 |
| 2 | 21.2 | a | a | a | d | c | d | 17 | 2.14 |
| 3 | 16.8 | c | a | b | a | c | e | 1 | 1.87 |
| 4 | 30.5 | b | a' | c | a | c | b | 3 | 1.13 |
| 5 | 30.3 | c | c | d | a | c | b | 2 | 1.71 |
| 6 | 31.3 | b | b | b | a | c | b | 2 | 1.39 |
| 7 | 25.2 | a | c | a | e | c | f | 2 | 1.8 |
| 8 | 1.4 | b | d | d | b | a | a | 17 | 3.38 |
| 9 | 30.6 | b | b | b | c | c | c | 3 | 1.96 |
| 10 | 0.5 | d | e | b | b | a | a | 4 | n.b. |
| 11 | 18.6 | c | a | b | b | a | a | 4 | 1.3 |
| 12 | 21.5 | b | a' | c | d | a | b | 4 | 2.27 |
| 13 | 47.6 | c | d | e | f | c | g | 2 | 2.91 |
| 14 | 33.5 | a | a | a | a | a | a | 4 | 4.59 |
| 15 | 20.1 | b | b | b | a | a | a | 17 | 4.64 |
| 16 | 31.7 | a | c | a | a | a | a | 4 | 2.47 |
| 17 | 44.7 | b | d | d | a | a | a | 4 | 2.16 |

FIGURE 6

```
                      10        20        30        40        50        60
BAP-chi HC        ....|....|....|....|....|....|....|....|....|....|....|....|
                  EVQLQQSGAELVKPGASVKLSCKASGYTFTSYWMYWVKQGPGRGLEWIGRIDPNSGSTKY
BAP058-hum01-HC   QVQLVQSGAEVKKPGASVKVSCKASGYTFTSYWMYWVRQATGQGLEWMGRIDPNSGSTKY
BAP058-hum02-HC   QVQLVQSGAEVKKPGASVKVSCKASGYTFTSYWMYWVRQATGQGLEWMGRIDPNSGSTKY
BAP058-hum14-HC   QVQLVQSGAEVKKPGASVKVSCKASGYTFTSYWMYWVRQATGQGLEWMGRIDPNSGSTKY
BAP058-hum06-HC   EVQLVQSGAEVKKPGESLRISCKGSGYTFTSYWMYWIRQPPGKGLEWIGRIDPNSGSTKY
BAP058-hum09-HC   EVQLVQSGAEVKKPGESLRISCKGSGYTFTSYWMYWIRQPPGKGLEWIGRIDPNSGSTKY
BAP058-hum15-HC   EVQLVQSGAEVKKPGESLRISCKGSGYTFTSYWMYWIRQPPGKGLEWIGRIDPNSGSTKY
BAP058-hum03-HC   EVQLVQSGAEVKKPGATVKISCKVSGYTFTSYWMYWVRQATGQGLEWMGRIDPNSGSTKY
BAP058-hum11-HC   EVQLVQSGAEVKKPGATVKISCKVSGYTFTSYWMYWVRQATGQGLEWMGRIDPNSGSTKY
BAP058-hum04-HC   EVQLVQSGAEVKKPGESLRISCKGSGYTFTSYWMYWVRQAPGQGLEWMGRIDPNSGSTKY
BAP058-hum12-HC   EVQLVQSGAEVKKPGESLRISCKGSGYTFTSYWMYWVRQAPGQGLEWMGRIDPNSGSTKY
BAP058-hum07-HC   QVQLVQSGAEVKKPGASVKVSCKASGYTFTSYWMYWIRQSPSRGLEWLGRIDPNSGSTKY
BAP058-hum16-HC   QVQLVQSGAEVKKPGASVKVSCKASGYTFTSYWMYWIRQSPSRGLEWLGRIDPNSGSTKY
BAP058-hum08-HC   EVQLVQSGAEVKKPGESLRISCKGSGYTFTSYWMYWVRQARGQRLEWLGRIDPNSGSTKY
BAP058-hum17-HC   EVQLVQSGAEVKKPGESLRISCKGSGYTFTSYWMYWVRQARGQRLEWLGRIDPNSGSTKY
BAP058-hum05-HC   EVQLVQSGAEVKKPGATVKISCKVSGYTFTSYWMYWIRQSPSRGLEWIGRIDPNSGSTKY
BAP058-hum10-HC   QITLKESGPTLVKPTQTLTLTCTFSGYTFTSYWMYWVRQAPGKGLEWVSRIDPNSGSTKY
BAP058-hum13-HC   EVQLVQSGAEVKKPGATVKISCKVSGYTFTSYWMYWIRQARGQRLEWIGRIDPNSGSTKY 70        80        90       100       110
BAP-chi HC        ....|....|....|....|....|....|....|....|....|....|...
                  NEKFKNKATLTVDKSSSTAYMQLSSLTSEDSAVYYCARDYRKGLYAMDYWGQG
BAP058-hum01-HC   NEKFKNRFTISRDDSKNTAYLQMNSLKTEDTAVYYCARDYRKGLYAMDYWGQG
BAP058-hum02-HC   NEKFKNRFTISRDDSKNTAYLQMNSLKTEDTAVYYCARDYRKGLYAMDYWGQG
BAP058-hum14-HC   NEKFKNRFTISRDDSKNTAYLQMNSLKTEDTAVYYCARDYRKGLYAMDYWGQG
BAP058-hum06-HC   NEKFKNRVTITADKSTSTAYMELSSLRSEDTAVYYCARDYRKGLYAMDYWGQG
BAP058-hum09-HC   NEKFKNRVTITADKSTSTAYMELSSLRSEDTAVYYCARDYRKGLYAMDYWGQG
BAP058-hum15-HC   NEKFKNRVTITADKSTSTAYMELSSLRSEDTAVYYCARDYRKGLYAMDYWGQG
BAP058-hum03-HC   NEKFKNRVTITADKSTSTAYMELSSLRSEDTAVYYCARDYRKGLYAMDYWGQG
BAP058-hum11-HC   NEKFKNRVTITADKSTSTAYMELSSLRSEDTAVYYCARDYRKGLYAMDYWGQG
BAP058-hum04-HC   NEKFKNRVTISVDTSKNQFSLKLSSVTAADTAVYYCARDYRKGLYAMDYWGQG
BAP058-hum12-HC   NEKFKNRVTISVDTSKNQFSLKLSSVTAADTAVYYCARDYRKGLYAMDYWGQG
BAP058-hum07-HC   NEKFKNRFTISRDDSKNTAYLQMNSLKTEDTAVYYCARDYRKGLYAMDYWGQG
BAP058-hum16-HC   NEKFKNRFTISRDDSKNTAYLQMNSLKTEDTAVYYCARDYRKGLYAMDYWGQG
BAP058-hum08-HC   NEKFKNRLTISKDTSKNQVVLTMTNMDPVDTATYYCARDYRKGLYAMDYWGQG
BAP058-hum17-HC   NEKFKNRLTISKDTSKNQVVLTMTNMDPVDTATYYCARDYRKGLYAMDYWGQG
BAP058-hum05-HC   NEKFKNRLTISKDTSKNQVVLTMTNMDPVDTATYYCARDYRKGLYAMDYWGQG
BAP058-hum10-HC   NEKFKNRVTITADKSTSTAYMELSSLRSEDTAVYYCARDYRKGLYAMDYWGQG
BAP058-hum13-HC   NEKFKNRFTISRDNSKNTLYLQMNSLRAEDTAVYYCARDYRKGLYAMDYWGQG
```

FIGURE 8A

```
                       10        20        30        40        50        60
BAP-chi HC        ....|....|....|....|....|....|....|....|....|....|....|....|
                  EVQLQQSGAELVKPGASVKLSCKASGYTFTSYWMYWVKQGPGRGLEWIGRIDPNSGSTKY
BAP058-hum01-HC   Q...V.....VK.......V.................R.AT.Q....M............
BAP058-hum02-HC   Q...V.....VK.......V.................R.AT.Q....M............
BAP058-hum14-HC   Q...V.....VK.......V.................R.AT.Q....M............
BAP058-hum06-HC   ....V.....VK...E.LRI...G.............IR.P..K................
BAP058-hum09-HC   ....V.....VK...E.LRI...G.............IR.P..K................
BAP058-hum15-HC   ....V.....VK...E.LRI...G.............IR.P..K................
BAP058-hum03-HC   ....V.....VK....T..I...V.............R.AT.Q....M............
BAP058-hum11-HC   ....V.....VK....T..I...V.............R.AT.Q....M............
BAP058-hum04-HC   ....V.....VK...E.LRI...G.............R.A..Q....M............
BAP058-hum12-HC   ....V.....VK...E.LRI...G.............R.A..Q....M............
BAP058-hum07-HC   Q...V.....VK.......V.................IR.S.S.....L............
BAP058-hum16-HC   Q...V.....VK.......V.................IR.S.S.....L............
BAP058-hum08-HC   ....V.....VK...E.LRI...G.............R.AR.QR................
BAP058-hum17-HC   ....V.....VK...E.LRI...G.............R.AR.QR................
BAP058-hum05-HC   ....V.....VK....T..I...V.............IR.S.S.....L............
BAP058-hum10-HC   QIT.KE..PT....TQTLT.T.TF..............R.A..K....VS............
BAP058-hum13-HC   ....V.....VK....T..I...V.............R.AR.QR................

70        80        90       100       110
BAP-chi HC        ....|....|....|....|....|....|....|....|....|....|....|...
                  NEKFKNKATLTVDKSSSTAYMQLSSLTSEDSAVYYCARDYRKGLYAMDYWGQG
BAP058-hum01-HC   ......RF.ISR.D.KN...L.MN..KT..T.....................
BAP058-hum02-HC   ......RF.ISR.D.KN...L.MN..KT..T.....................
BAP058-hum14-HC   ......RF.ISR.D.KN...L.MN..KT..T.....................
BAP058-hum06-HC   ......RV.I.A...T.....E....R...T.....................
BAP058-hum09-HC   ......RV.I.A...T.....E....R...T.....................
BAP058-hum15-HC   ......RV.I.A...T.....E....R...T.....................
BAP058-hum03-HC   ......RV.I.A...T.....E....R...T.....................
BAP058-hum11-HC   ......RV.I.A...T.....E....R...T.....................
BAP058-hum04-HC   ......RV.IS..T.KNQFSLK...V.AA.T.....................
BAP058-hum12-HC   ......RV.IS..T.KNQFSLK...V.AA.T.....................
BAP058-hum07-HC   ......RF.ISR.D.KN...L.MN..KT..T.....................
BAP058-hum16-HC   ......RF.ISR.D.KN...L.MN..KT..T.....................
BAP058-hum08-HC   ......RL.ISK.T.KNQVVLTMTNMDPV.T.T....................
BAP058-hum17-HC   ......RL.ISK.T.KNQVVLTMTNMDPV.T.T....................
BAP058-hum05-HC   ......RL.ISK.T.KNQVVLTMTNMDPV.T.T....................
BAP058-hum10-HC   ......RV.I.A...T.....E....R...T.....................
BAP058-hum13-HC   ......RF.ISR.N.KN.LYL.MN..RA..T.....................
```

FIGURE 8B

```
                        10         20         30         40         50         60
                ....|....|....|....|....|....|....|....|....|....|....|....|
BAP-chi LC      DIMMTQSHKFMSTSVGDRVSITCKASQDVGTAVAWYQQKPGQSPKLLIYWASTRHTGVPD
BAP058-hum14-LC EIVLTQSPDFQSVTPKEKVTITCKASQDVGTAVAWYQQKPGQAPRLLIYWASTRHTGVPS
BAP058-hum15-LC EIVLTQSPDFQSVTPKEKVTITCKASQDVGTAVAWYQQKPGQAPRLLIYWASTRHTGVPS
BAP058-hum16-LC EIVLTQSPDFQSVTPKEKVTITCKASQDVGTAVAWYQQKPGQAPRLLIYWASTRHTGVPS
BAP058-hum17-LC EIVLTQSPDFQSVTPKEKVTITCKASQDVGTAVAWYQQKPGQAPRLLIYWASTRHTGVPS
BAP058-hum04-LC EIVLTQSPDFQSVTPKEKVTITCKASQDVGTAVAWYLQKPGQSPQLLIYWASTRHTGVPS
BAP058-hum05-LC EIVLTQSPDFQSVTPKEKVTITCKASQDVGTAVAWYLQKPGQSPQLLIYWASTRHTGVPS
BAP058-hum06-LC EIVLTQSPDFQSVTPKEKVTITCKASQDVGTAVAWYLQKPGQSPQLLIYWASTRHTGVPS
BAP058-hum08-LC DVVMTQSPLSLPVTLGQPASISCKASQDVGTAVAWYQQKPGQAPRLLIYWASTRHTGVPS
BAP058-hum10-LC DVVMTQSPLSLPVTLGQPASISCKASQDVGTAVAWYQQKPGQAPRLLIYWASTRHTGVPS
BAP058-hum11-LC DVVMTQSPLSLPVTLGQPASISCKASQDVGTAVAWYQQKPGQAPRLLIYWASTRHTGVPS
BAP058-hum01-LC DIVMTQTPLSLPVTPGEPASISCKASQDVGTAVAWYLQKPGQSPQLLIYWASTRHTGIPA
BAP058-hum09-LC DIVMTQTPLSLPVTPGEPASISCKASQDVGTAVAWYLQKPGQSPQLLIYWASTRHTGIPA
BAP058-hum02-LC DIQMTQSPSSLSASVGDRVTITCKASQDVGTAVAWYLQKPGQSPQLLIYWASTRHTGVPS
BAP058-hum03-LC EIVLTQSPDFQSVTPKEKVTITCKASQDVGTAVAWYLQKPGQSPQLLIYWASTRHTGVPD
BAP058-hum07-LC EIVLTQSPATLSLSPGERATLSCKASQDVGTAVAWYLQKPGQSPQLLIYWASTRHTGIPP
BAP058-hum13-LC AIQLTQSPSSLSASVGDRVTITCKASQDVGTAVAWYLQKPGQSPQLLIYWASTRHTGVPS
BAP058-hum12-LC DIQMTQSPSSLSASVGDRVTITCKASQDVGTAVAWYQQKPGQAPRLLIYWASTRHTGVPS 70         80         90         100
                ....|....|....|....|....|....|....|....|....|..
BAP-chi LC      RFTGSGSGTDFTLTISNVQSEDLADYFCQQYNSYPLTFGQGTKVEIK
BAP058-hum14-LC RFSGSGSGTEFTLTISSLQPDDFATYYCQQYNSYPLTFGQGTKVEIK
BAP058-hum15-LC RFSGSGSGTEFTLTISSLQPDDFATYYCQQYNSYPLTFGQGTKVEIK
BAP058-hum16-LC RFSGSGSGTEFTLTISSLQPDDFATYYCQQYNSYPLTFGQGTKVEIK
BAP058-hum17-LC RFSGSGSGTEFTLTISSLQPDDFATYYCQQYNSYPLTFGQGTKVEIK
BAP058-hum04-LC RFSGSGSGTDFTFTISSLQPEDIATYYCQQYNSYPLTFGQGTKVEIK
BAP058-hum05-LC RFSGSGSGTDFTFTISSLQPEDIATYYCQQYNSYPLTFGQGTKVEIK
BAP058-hum06-LC RFSGSGSGTDFTFTISSLQPEDIATYYCQQYNSYPLTFGQGTKVEIK
BAP058-hum08-LC RFSGSGSGTEFTLTISSLQPDDFATYYCQQYNSYPLTFGQGTKVEIK
BAP058-hum10-LC RFSGSGSGTEFTLTISSLQPDDFATYYCQQYNSYPLTFGQGTKVEIK
BAP058-hum11-LC RFSGSGSGTEFTLTISSLQPDDFATYYCQQYNSYPLTFGQGTKVEIK
BAP058-hum01-LC RFSGSGSGTEFTLTISSLQSEDFAVYYCQQYNSYPLTFGQGTKVEIK
BAP058-hum09-LC RFSGSGSGTEFTLTISSLQSEDFAVYYCQQYNSYPLTFGQGTKVEIK
BAP058-hum02-LC RFSGSGSGTDFTLTISSLQPEDFATYYCQQYNSYPLTFGQGTKVEIK
BAP058-hum03-LC RFSGSGSGTDFTLKISRVEAEDVGVYYCQQYNSYPLTFGQGTKVEIK
BAP058-hum07-LC RFSGSGYGTDFTLTINNIESEDAAYYFCQQYNSYPLTFGQGTKVEIK
BAP058-hum13-LC RFSGSGSGTDFTFTISSLEAEDAATYYCQQYNSYPLTFGQGTKVEIK
BAP058-hum12-LC RFSGSGSGTDFTFTISSLQPEDIATYYCQQYNSYPLTFGQGTKVEIK
```

FIGURE 9A

```
                        10        20        30        40        50        60
             ....|....|....|....|....|....|....|....|....|....|....|....|
BAP-chi LC   DIMMTQSHKFMSTSVGDRVSITCKASQDVGTAVAWYQQKPGQSPKLLIYWASTRHTGVPD
BAP058-hum14-LC  E.VL...PD.Q.VTPKEK.T.................A.R..............S
BAP058-hum15-LC  E.VL...PD.Q.VTPKEK.T.................A.R..............S
BAP058-hum16-LC  E.VL...PD.Q.VTPKEK.T.................A.R..............S
BAP058-hum17-LC  E.VL...PD.Q.VTPKEK.T.................A.R..............S
BAP058-hum04-LC  E.VL...PD.Q.VTPKEK.T.............L.......Q.............S
BAP058-hum05-LC  E.VL...PD.Q.VTPKEK.T.............L.......Q.............S
BAP058-hum06-LC  E.VL...PD.Q.VTPKEK.T.............L.......Q.............S
BAP058-hum08-LC  .VV....PLSLPVTL.QPA...S..............A.R..............S
BAP058-hum10-LC  .VV....PLSLPVTL.QPA...S..............A.R..............S
BAP058-hum11-LC  .VV....PLSLPVTL.QPA...S..............A.R..............S
BAP058-hum01-LC  ..V....TPLSLPVTP.EPA..S..........L.......Q.............I.A
BAP058-hum09-LC  ..V....TPLSLPVTP.EPA..S..........L.......Q.............I.A
BAP058-hum02-LC  ..Q....PSSL.A......T.............L.......Q.............S
BAP058-hum03-LC  E.VL...PD.Q.VTPKEK.T.............L.......Q.............
BAP058-hum07-LC  E.VL...PATL.L.P.E.ATLS...........L.......Q.............I.P
BAP058-hum13-LC  A.QL...PSSL.A......T.............L.......Q.............S
BAP058-hum12-LC  ..Q....PSSL.A......T.................A.R..............S 70        80        90        100
             ....|....|....|....|....|....|....|....|....|..
BAP-chi LC   RFTGSGSGTDFTLTISNVQSEDLADYFCQQYNSYPLTFGQGTKVEIK
BAP058-hum14-LC  ..S......E......SL.PD.F.T.Y.....................
BAP058-hum15-LC  ..S......E......SL.PD.F.T.Y.....................
BAP058-hum16-LC  ..S......E......SL.PD.F.T.Y.....................
BAP058-hum17-LC  ..S......E......SL.PD.F.T.Y.....................
BAP058-hum04-LC  ..S.........F...SL.P..I.T.Y.....................
BAP058-hum05-LC  ..S.........F...SL.P..I.T.Y.....................
BAP058-hum06-LC  ..S.........F...SL.P..I.T.Y.....................
BAP058-hum08-LC  ..S......E......SL.PD.F.T.Y.....................
BAP058-hum10-LC  ..S......E......SL.PD.F.T.Y.....................
BAP058-hum11-LC  ..S......E......SL.PD.F.T.Y.....................
BAP058-hum01-LC  ..S......E......SL....F.V.Y.....................
BAP058-hum09-LC  ..S......E......SL....F.V.Y.....................
BAP058-hum02-LC  ..S.............SL.P..F.T.Y.....................
BAP058-hum03-LC  ..S.........K..R.EA..VGV.Y.....................
BAP058-hum07-LC  ..S...Y.........N.IE...A.Y.....................
BAP058-hum13-LC  ..S.........F...SLEA..A.T.Y.....................
BAP058-hum12-LC  ..S.........F...SL.P..I.T.Y.....................
```

FIGURE 9B

ANTIBODY MOLECULES TO PD-L1 AND USES THEREOF

CROSS REFERENCE TO RELATED APPLICATIONS

This application claims the benefit of U.S. Provisional Application No. 62/063,852, filed Oct. 14, 2014, U.S. Provisional Application No. 62/094,847, filed Dec. 19, 2014, U.S. Provisional Application No. 62/198,545, filed Jul. 29, 2015, and U.S. Provisional Application No. 62/213,076, filed Sep. 1, 2015, the contents of the aforementioned applications are hereby incorporated by reference in their entirety.

SEQUENCE LISTING

The instant application contains a Sequence Listing which has been submitted electronically in ASCII format and is hereby incorporated by reference in its entirety. Said ASCII copy, created on Oct. 13, 2015, is named C2160-700310_SL.txt and is 294,860 bytes in size.

BACKGROUND

The ability of T cells to mediate an immune response against an antigen requires two distinct signaling interactions (Viglietta, V. et al. (2007) *Neurotherapeutics* 4:666-675; Korman, A. J. et al. (2007) *Adv. Immunol.* 90:297-339). First, an antigen that has been arrayed on the surface of antigen-presenting cells (APC) is presented to an antigen-specific naïve CD4+ T cell. Such presentation delivers a signal via the T cell receptor (TCR) that directs the T cell to initiate an immune response specific to the presented antigen. Second, various co-stimulatory and inhibitory signals mediated through interactions between the APC and distinct T cell surface molecules trigger the activation and proliferation of the T cells and ultimately their inhibition.

The immune system is tightly controlled by a network of costimulatory and co-inhibitory ligands and receptors. These molecules provide the second signal for T cell activation and provide a balanced network of positive and negative signals to maximize immune responses against infection, while limiting immunity to self (Wang, L. et al. (Epub Mar. 7, 2011) *J. Exp. Med.* 208(3):577-92; Lepenies, B. et al. (2008) *Endocrine, Metabolic & Immune Disorders—Drug Targets* 8:279-288). Examples of costimulatory signals include the binding between the B7.1 (CD80) and B7.2 (CD86) ligands of the APC and the CD28 and CTLA-4 receptors of the CD4+ T-lymphocyte (Sharpe, A. H. et al. (2002) *Nature Rev. Immunol.* 2:116-126; Lindley, P. S. et al. (2009) *Immunol. Rev.* 229:307-321). Binding of B7.1 or B7.2 to CD28 stimulates T cell activation, whereas binding of B7.1 or B7.2 to CTLA-4 inhibits such activation (Dong, C. et al. (2003) *Immunolog. Res.* 28(1):39-48; Greenwald, R. J. et al. (2005) *Ann. Rev. Immunol.* 23:515-548). CD28 is constitutively expressed on the surface of T cells (Gross, J., et al. (1992) *J. Immunol.* 149:380-388), whereas CTLA-4 expression is rapidly up-regulated following T-cell activation (Linsley, P. et al. (1996) *Immunity* 4:535-543).

Other ligands of the CD28 receptor include a group of related B7 molecules, also known as the "B7 Superfamily" (Coyle, A. J. et al. (2001) *Nature Immunol.* 2(3):203-209; Sharpe, A. H. et al. (2002) *Nature Rev. Immunol.* 2:116-126; Collins, M. et al. (2005) *Genome Biol.* 6:223.1-223.7; Korman, A. J. et al. (2007) *Adv. Immunol.* 90:297-339). Several members of the B7 Superfamily are known, including B7.1 (CD80), B7.2 (CD86), the inducible co-stimulator ligand (ICOS-L), the programmed death-1 ligand (PD-L1; B7-H1), the programmed death-2 ligand (PD-L2; B7-DC), B7-H3, B7-H4 and B7-H6 (Collins, M. et al. (2005) *Genome Biol.* 6:223.1-223.7).

The Programmed Death 1 (PD-1) protein is an inhibitory member of the extended CD28/CTLA-4 family of T cell regulators (Okazaki et al. (2002) *Curr Opin Immunol* 14: 391779-82; Bennett et al. (2003) *J. Immunol.* 170:711-8). Other members of the CD28 family include CD28, CTLA-4, ICOS and BTLA. Two cell surface glycoprotein ligands for PD-1 have been identified, Program Death Ligand 1 (PD-L1) and Program Death Ligand 2 (PD-L2). PD-L1 and PD-L2 have been shown to downregulate T cell activation and cytokine secretion upon binding to PD-1 (Freeman et al. (2000) *J Exp Med* 192:1027-34; Latchman et al. (2001) *Nat Immunol* 2:261-8; Carter et al. (2002) *Eur J Immunol* 32:634-43; Ohigashi et al. (2005) *Clin Cancer Res* 11:2947-53).

PD-L1 (also known as cluster of differentiation 274 (CD274) or B7 homolog 1 (B7-H1)) is a 40 kDa type 1 transmembrane protein. PD-L1 binds to its receptor, PD-1, found on activated T cells, B cells, and myeloid cells, to modulate activation or inhibition. Both PD-L1 and PD-L2 are B7 homologs that bind to PD-1, but do not bind to CD28 or CTLA-4 (Blank et al. (2005) *Cancer Immunol Immunother.* 54:307-14). Binding of PD-L1 with its receptor PD-1 on T cells delivers a signal that inhibits TCR-mediated activation of IL-2 production and T cell proliferation. The mechanism involves inhibition of ZAP70 phosphorylation and its association with CD3ζ (Sheppard et al. (2004) *FEBS Lett.* 574:37-41). PD-1 signaling attenuates PKC-θ activation loop phosphorylation resulting from TCR signaling, necessary for the activation of transcription factors NF-κB and AP-1, and for production of IL-2. PD-L1 also binds to the costimulatory molecule CD80 (B7-1), but not CD86 (B7-2) (Butte et al. (2008) *Mol Immunol.* 45:3567-72).

Expression of PD-L1 on the cell surface has been shown to be upregulated through IFN-γ stimulation. PD-L1 expression has been found in many cancers, including human lung, ovarian and colon carcinoma and various myelomas, and is often associated with poor prognosis (Iwai et al. (2002) *PNAS* 99:12293-7; Ohigashi et al. (2005) *Clin Cancer Res* 11:2947-53; Okazaki et al. (2007) *Intern. Immun.* 19:813-24; Thompson et al. (2006) *Cancer Res.* 66:3381-5). PD-L1 has been suggested to play a role in tumor immunity by increasing apoptosis of antigen-specific T-cell clones (Dong et al. (2002) *Nat Med* 8:793-800). It has also been suggested that PD-L1 might be involved in intestinal mucosal inflammation and inhibition of PD-L1 suppresses wasting disease associated with colitis (Kanai et al. (2003) *J Immunol* 171:4156-63).

Given the importance of immune checkpoint pathways in regulating an immune response, the need exists for developing novel agents that modulate the activity of immunoinhibitory proteins, such as PD-L1, thus leading to activation of the immune system. Such agents can be used, e.g., for cancer immunotherapy and treatment of other conditions, such as chronic infection.

SUMMARY

Disclosed herein are antibody molecules (e.g., humanized antibody molecules) that bind to Programmed Death-Ligand 1 (PD-L1) with high affinity and specificity. In one embodiment, the anti-PD-L1 antibody molecules comprise a novel combination of framework regions (e.g., FW1, FW2, FW3 and/or FW4), e.g., novel combinations of a heavy chain framework regions and/or light chain framework regions. Nucleic acid molecules encoding the antibody molecules, expression vectors, host cells and methods for making the antibody molecules are also provided. Immunoconjugates, multi- or bispecific antibody molecules and pharmaceutical compositions comprising the antibody molecules are also provided. The anti-PD-L1 antibody molecules disclosed herein can be used (alone or in combination with other agents or therapeutic modalities) to treat, prevent and/or diagnose disorders, such as cancerous disorders (e.g., solid and soft-tissue tumors), as well as infectious diseases (e.g., chronic infectious disorders or sepsis). Additionally disclosed herein are methods and compositions comprising a combination of two, three or more therapeutic agents chosen from one, two, or all of the following categories (i)-(iii): (i) an agent that enhances antigen presentation (e.g., tumor antigen presentation); (ii) an agent that enhances an effector cell response (e.g., B cell and/or T cell activation and/or mobilization); or (iii) an agent that decreases tumor immunosuppression. In some embodiments, the combination includes an inhibitor of PD-L1 (e.g., an anti-PD-L1 antibody molecule as described herein). Thus, compositions and methods for detecting PD-L1, as well as methods for treating various disorders including cancer and/or infectious diseases, using the anti-PD-L1 antibody molecules and combinations thereof are disclosed herein.

Accordingly, in one aspect, the invention features an antibody molecule (e.g., an isolated or recombinant antibody molecule) having one or more of the following properties:

(i) binds to PD-L1, e.g., human PD-L1, with high affinity, e.g., with an affinity constant of at least about $10^7$ $M^{-1}$, typically about $10^8$ $M^{-1}$, and more typically, about $10^9$ $M^{-1}$ to $10^{10}$ $M^{-1}$ or stronger;

(ii) does not substantially bind to CD28, CTLA-4, ICOS or BTLA;

(iii) inhibits or reduces binding of PD-L1 to a receptor, e.g., PD-1 or CD80 (B7-1), or both;

(iv) binds specifically to an epitope on PD-L1, e.g., the same or similar epitope as the epitope recognized by murine monoclonal antibody BAP058 or a chimeric antibody BAP058, e.g., BAP058-chi;

(v) shows the same or similar binding affinity or specificity, or both, as any of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-O;

(vi) shows the same or similar binding affinity or specificity, or both, as an antibody molecule (e.g., an heavy chain variable region and light chain variable region) described in Table 1;

(vii) shows the same or similar binding affinity or specificity, or both, as an antibody molecule (e.g., an heavy chain variable region and light chain variable region) having an amino acid sequence shown in Table 1;

(viii) shows the same or similar binding affinity or specificity, or both, as an antibody molecule (e.g., an heavy chain variable region and light chain variable region) encoded by the nucleotide sequence shown in Table 1;

(ix) inhibits, e.g., competitively inhibits, the binding of a second antibody molecule to PD-L1, wherein the second antibody molecule is an antibody molecule described herein, e.g., an antibody molecule chosen from, e.g., any of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-O;

(x) binds the same or an overlapping epitope with a second antibody molecule to PD-L1, wherein the second antibody molecule is an antibody molecule described herein, e.g., an antibody molecule chosen from, e.g., any of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-O;

(xi) competes for binding, and/or binds the same epitope, with a second antibody molecule to PD-L1, wherein the second antibody molecule is an antibody molecule described herein, e.g., an antibody molecule chosen from, e.g., any of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-O;

(xii) has one or more biological properties of an antibody molecule described herein, e.g., an antibody molecule chosen from, e.g., any of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-O;

(xiii) has one or more pharmacokinetic properties of an antibody molecule described herein, e.g., an antibody molecule chosen from, e.g., any of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-0;

(xiv) inhibits one or more activities of PD-L1, e.g., results in one or more of: an increase in tumor infiltrating lymphocytes, an increase in T-cell receptor mediated proliferation, or a decrease in immune evasion by cancerous cells; or (xv) binds human PD-L1 and is cross-reactive with cynomolgus PD-L1.

In some embodiments, the antibody molecule binds to PD-L1 with high affinity, e.g., with a $K_D$ that is about the same, or at least about 10%, 20%, 30%, 40%, 50%, 60%, 70%, 80% or 90% higher or lower than the $K_D$ of a murine or chimeric anti-PD-L1 antibody molecule, e.g., a murine or chimeric anti-PD-L1 antibody molecule described herein. In some embodiments, the $K_D$ of the murine or chimeric anti-PD-L1 antibody molecule is less than about 0.4, 0.3, 0.2, 0.1, or 0.05 nM, e.g., measured by a Biacore method. In some embodiments, the $K_D$ of the murine or chimeric anti-PD-L1 antibody molecule is less than about 0.2 nM, e.g., about 0.171 nM. In other embodiments, the $K_D$ of the murine or chimeric anti PD-L1 antibody molecule is less than about 10, 5, 3, 2, or 1 nM, e.g., measured by binding on cells expressing PD-L1 (e.g., 300.19 cells). In some embodiments, the $K_D$ of the murine or chimeric anti PD-L1 antibody molecule is less than about 1 nM, e.g., about 0.285 nM.

In some embodiments, the anti-PD-L1 antibody molecule binds to PD-L1 with a $K_d$ slower than $1 \times 10^{-4}$, $5 \times 10^{-5}$, or $1 \times 10^{-5}$ s$^{-1}$, e.g., about $6.33 \times 10^{-5}$ s$^{-1}$. In some embodiments, the the anti-PD-L1 antibody molecule binds to PD-L1 with a $K_a$ faster than $1 \times 10^4$, $5 \times 10^4$, $1 \times 10^5$, or $5 \times 10^5$ M$^{-1}$ s$^{-1}$, e.g., about $3.07 \times 10^5$ M$^{-1}$ s$^{-1}$.

In some embodiments, the expression level of the antibody molecule is higher, e.g., at least about 0.5, 1, 2, 3, 4, 5, 6, 7, 8, 9 or 10-fold higher, than the expression level of a murine or chimeric antibody molecule, e.g., a murine or chimeric anti-PD-L1 antibody molecule described herein. In some embodiments, the antibody molecule is expressed in CHO cells.

In some embodiments, the anti-PD-L1 antibody molecule reduces one or more PD-L1-associated activities with an $IC_{50}$ (concentration at 50% inhibition) that is about the same or lower, e.g., at least about 10%, 20%, 30%, 40%, 50%, 60%, 70%, 80% or 90% lower, than the $IC_{50}$ of a murine or chimeric anti-PD-L1 antibody molecule, e.g., a murine or chimeric anti-PD-L1 antibody molecule described herein. In some embodiments, the $IC_{50}$ of the murine or chimeric anti-PD-L1 antibody molecule is less than about 6, 5, 4, 3, 2, or 1 nM, e.g., measured by binding on cells expressing PD-L1 (e.g., 300.19 cells). In some embodiments, the $IC_{50}$ of the murine or chimeric anti-PD-L1 antibody molecule is less than about 4 nM, e.g., about 3.40 nM (or about 0.51 µg/mL). In some embodiments, the PD-L1-associated activity reduced is the binding of PD-L1 and/or PD-L2 to PD-1. In some embodiments, the anti-PD-L1 antibody molecule binds to peripheral blood mononucleated cells (PBMCs) activated by Staphylococcal enterotoxin B (SEB). In other embodiments, the anti-PD-L1 antibody molecule increases the expression of IL-2 on whole blood activated by SEB. For example, the anti-PD-L1 antibody increases the expression of IL-2 by at least about 2, 3, 4, or 5-fold, compared to the expression of IL-2 when an isotype control (e.g., IgG4) is used.

In some embodiments, the anti-PD-L1 antibody molecule has improved stability, e.g., at least about 0.5, 1, 2, 3, 4, 5, 6, 7, 8, 9 or 10-fold more stable in vivo or in vitro, than a murine or chimeric anti-PD-L1 antibody molecule, e.g., a murine or chimeric anti-PD-L1 antibody molecule described herein.

In one embodiment, the anti PD-L1 antibody molecule is a humanized antibody molecule and has a risk score based on T cell epitope analysis of 300 to 700, 400 to 650, 450 to 600, or a risk score as described herein.

In another embodiment, the anti-PD-L1 antibody molecule comprises at least one antigen-binding region, e.g., a variable region or an antigen-binding fragment thereof, from an antibody described herein, e.g., an antibody chosen from any of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-O; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequences.

In yet another embodiment, the anti-PD-L1 antibody molecule comprises at least one, two, three or four variable regions from an antibody described herein, e.g., an antibody chosen from any of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-O; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequences.

In yet another embodiment, the anti-PD-L1 antibody molecule comprises at least one or two heavy chain variable regions from an antibody described herein, e.g., an antibody chosen from any of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-O; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequences.

In yet another embodiment, the anti-PD-L1 antibody molecule comprises at least one or two light chain variable regions from an antibody described herein, e.g., an antibody chosen from any of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-O; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequences.

In yet another embodiment, the anti-PD-L1 antibody molecule includes a heavy chain constant region for an IgG4, e.g., a human IgG4. In one embodiment, the human IgG4 includes a substitution at position 228 (e.g., a Ser to Pro substitution). In still another embodiment, the anti-PD-L1 antibody molecule includes a heavy chain constant region for an IgG1, e.g., a human IgG1. In one embodiment, the human IgG1 includes a substitution at position 297 (e.g., an Asn to Ala substitution). In one embodiment, the human IgG1 includes a substitution at position 265, a substitution at position 329, or both (e.g., an Asp to Ala substitution at position 265 and/or a Pro to Ala substitution at position 329). In one embodiment, the human IgG1 includes a substitution at position 234, a substitution at position 235, or both (e.g., a Leu to Ala substitution at position 234 and/or a Leu to Ala substitution at position 235). In one embodiment, the heavy chain constant region comprises an amino sequence set forth in Table 3, or a sequence substantially identical (e.g., at least 80%, 85%, 90%, 92%, 95%, 97%, 98%, 99% or higher identical) thereto.

In yet another embodiment, the anti-PD-L1 antibody molecule includes a kappa light chain constant region, e.g., a human kappa light chain constant region. In one embodiment, the light chain constant region comprises an amino sequence set forth in Table 3, or a sequence substantially identical (e.g., at least 80%, 85%, 90%, 92%, 95%, 97%, 98%, 99% or higher identical) thereto.

In another embodiment, the anti-PD-L1 antibody molecule includes a heavy chain constant region for an IgG4, e.g., a human IgG4, and a kappa light chain constant region, e.g., a human kappa light chain constant region, e.g., a heavy and light chain constant region comprising an amino sequence set forth in Table 3, or a sequence substantially identical (e.g., at least 80%, 85%, 90%, 92%, 95%, 97%, 98%, 99% or higher identical) thereto. In yet another embodiment, the anti-PD-L1 antibody molecule includes a heavy chain constant region for an IgG1, e.g., a human IgG1, and a kappa light chain constant region, e.g., a human kappa light chain constant region, e.g., a heavy and light chain constant region comprising an amino sequence set forth in Table 3, or a sequence substantially identical (e.g., at least 80%, 85%, 90%, 92%, 95%, 97%, 98%, 99% or higher identical) thereto. In one embodiment, the human IgG1 includes a substitution at position 297 (e.g., an Asn to Ala substitution). In one embodiment, the human IgG1 includes a substitution at position 265, a substitution at position 329, or both (e.g., an Asp to Ala substitution at position 265 and/or a Pro to Ala substitution at position 329). In one embodiment, the human IgG1 includes a substitution at position 234, a substitution at position 235, or both (e.g., a Leu to Ala substitution at position 234 and/or a Leu to Ala substitution at position 235).

In another embodiment, the anti-PD-L1 antibody molecule includes a heavy chain variable domain and a constant region, a light chain variable domain and a constant region, or both, comprising the amino acid sequence of BAP058-Clone-K, BAP058-Clone-L, BAP058-Clone-M, BAP058-Clone-N, or BAP058-Clone-O; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequences. The anti-PD-1 antibody molecule, optionally, comprises a leader sequence from a heavy chain, a light chain, or both.

In yet another embodiment, the anti-PD-L1 antibody molecule includes at least one, two, or three complementarity determining regions (CDRs) from a heavy chain variable region of an antibody described herein, e.g., an antibody chosen from any of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-O; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequences.

In yet another embodiment, the anti-PD-L1 antibody molecule includes at least one, two, or three CDRs (or collectively all of the CDRs) from a heavy chain variable region comprising an amino acid sequence shown in Table 1, or encoded by a nucleotide sequence shown in Table 1. In one embodiment, one or more of the CDRs (or collectively all of the CDRs) have one, two, three, four, five, six or more changes, e.g., amino acid substitutions or deletions, relative to the amino acid sequence shown in Table 1, or encoded by a nucleotide sequence shown in Table 1.

In yet another embodiment, the anti-PD-L1 antibody molecule includes at least one, two, or three CDRs from a light chain variable region of an antibody described herein, e.g., an antibody chosen from any of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-O; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequence.

In yet another embodiment, the anti-PD-L1 antibody molecule includes at least one, two, or three CDRs (or collectively all of the CDRs) from a light chain variable region comprising an amino acid sequence shown in Table 1, or encoded by a nucleotide sequence shown in Table 1. In one embodiment, one or more of the CDRs (or collectively all of the CDRs) have one, two, three, four, five, six or more changes, e.g., amino acid substitutions or deletions, relative to the amino acid sequence shown in Table 1, or encoded by a nucleotide sequence shown in Table 1. In certain embodiments, the anti-PD-L1 antibody molecule includes a substitution in a light chain CDR, e.g., one or more substitutions in a CDR1, CDR2 and/or CDR3 of the light chain.

In another embodiment, the anti-PD-L1 antibody molecule includes at least one, two, three, four, five or six CDRs (or collectively all of the CDRs) from a heavy and light chain variable region comprising an amino acid sequence shown in Table 1, or encoded by a nucleotide sequence shown in Table 1. In one embodiment, one or more of the CDRs (or collectively all of the CDRs) have one, two, three, four, five, six or more changes, e.g., amino acid substitutions or deletions, relative to the amino acid sequence shown in Table 1, or encoded by a nucleotide sequence shown in Table 1.

In one embodiment, the anti-PD-L1 antibody molecule includes all six CDRs from an antibody described herein, e.g., an antibody chosen from any of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-0; or as described in Table 1, or encoded by the nucleotide sequence in Table 1, or closely related CDRs, e.g., CDRs which are identical or which have at least one amino acid alteration, but not more than two, three or four alterations (e.g., substitutions, deletions, or insertions, e.g., conservative substitutions). In one embodiment, the anti-PD-L1 antibody molecule may include any CDR described herein. In certain embodiments, the anti-PD-L1 antibody molecule includes a substitution in a light chain CDR, e.g., one or more substitutions in a CDR1, CDR2 and/or CDR3 of the light chain. In another embodiment, the anti-PD-L1 antibody molecule includes at least one, two, or three CDRs according to Kabat et al. (e.g., at least one, two, or three CDRs according to the Kabat definition as set out in Table 1) from a heavy chain variable region of an antibody described herein, e.g., an antibody chosen from any of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-0; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, or three CDRs according to Kabat et al. shown in Table 1.

In another embodiment, the anti-PD-L1 antibody molecule includes at least one, two, or three CDRs according to Kabat et al. (e.g., at least one, two, or three CDRs according to the Kabat definition as set out in Table 1) from a light chain variable region of an antibody described herein, e.g., an antibody chosen from any of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-O; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, or three CDRs according to Kabat et al. shown in Table 1. In yet another embodiment, the anti-PD-L1 antibody molecule includes at least one, two, three, four, five, or six CDRs according to Kabat et al. (e.g., at least one, two, three, four, five, or six CDRs according to the Kabat definition as set out in Table 1) from the heavy and light chain variable regions of an antibody described herein, e.g., an antibody chosen from any of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-O; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, three, four, five, or six CDRs according to Kabat et al. shown in Table 1.

In yet another embodiment, the anti-PD-L1 antibody molecule includes all six CDRs according to Kabat et al. (e.g., all six CDRs according to the Kabat definition as set out in Table 1) from the heavy and light chain variable regions of an antibody described herein, e.g., an antibody chosen from any of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-O; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to all six CDRs according to Kabat et al. shown in Table 1. In one embodiment, the anti-PD-L1 antibody molecule may include any CDR described herein.

In another embodiment, the anti-PD-L1 antibody molecule includes at least one, two, or three Chothia hypervariable loops (e.g., at least one, two, or three hypervariable loops according to the Chothia definition as set out in Table 1) from a heavy chain variable region of an antibody described herein, e.g., an antibody chosen from any of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-O; or as described in Table 1, or encoded by the nucleotide sequence in Table 1; or at least the amino acids from those hypervariable loops that contact PD-L1; or which have at least one amino acid alteration, but not more than two, three or four alterations (e.g., substitutions, deletions, or insertions, e.g., conservative substitutions) relative to one, two, or three hypervariable loops according to Chothia et al. shown in Table 1.

In another embodiment, the anti-PD-L1 antibody molecule includes at least one, two, or three Chothia hypervariable loops (e.g., at least one, two, or three hypervariable loops according to the Chothia definition as set out in Table 1) of a light chain variable region of an antibody described herein, e.g., an antibody chosen from any of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-O; or as described in Table 1, or encoded by the nucleotide sequence in Table 1; or at least the amino acids from those hypervariable loops that contact PD-L1; or which have at least one amino acid alteration, but not more than two, three or four alterations (e.g., substitutions, deletions, or insertions, e.g., conservative substitutions) relative to one, two, or three hypervariable loops according to Chothia et al. shown in Table 1.

In yet another embodiment, the anti-PD-L1 antibody molecule includes at least one, two, three, four, five, or six hypervariable loops (e.g., at least one, two, three, four, five, or six hypervariable loops according to the Chothia definition as set out in Table 1) from the heavy and light chain variable regions of an antibody described herein, e.g., an antibody chosen from any of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-O; or as described in Table 1, or encoded by the nucleotide sequence in Table 1; or at least the amino acids from those hypervariable loops that contact PD-L1; or which have at least one amino acid alteration, but not more than two, three or four alterations (e.g., substitutions, deletions, or insertions, e.g., conservative substitutions) relative to one, two, three, four, five or six hypervariable loops according to Chothia et al. shown in Table 1.

In one embodiment, the anti-PD-L1 antibody molecule includes all six hypervariable loops (e.g., all six hypervariable loops according to the Chothia definition as set out in Table 1) of an antibody described herein, e.g., an antibody chosen from any of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-O, or closely related hypervariable loops, e.g., hypervariable loops which are identical or which have at least one amino acid alteration, but not more than two, three or four alterations (e.g., substitutions, deletions, or insertions, e.g., conservative substitutions); or which have at least one amino acid alteration, but not more than two, three or four alterations (e.g., substitutions, deletions, or insertions, e.g., conservative substitutions) relative to all six hypervariable loops according to Chothia et al. shown in Table 1. In one embodiment, the anti-PD-L1 antibody molecule may include any hypervariable loop described herein.

In still another embodiment, the anti-PD-L1 antibody molecule includes at least one, two, or three hypervariable loops that have the same canonical structures as the corresponding hypervariable loop of an antibody described herein, e.g., an antibody chosen from any of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-O, e.g., the same canonical structures as at least loop 1 and/or loop 2 of the heavy and/or light chain variable domains of an antibody described herein. See, e.g., Chothia et al., (1992) *J. Mol. Biol.* 227:799-817; Tomlinson et al., (1992) *J. Mol. Biol.* 227:776-798 for descriptions of hypervariable loop canonical structures. These structures can be determined by inspection of the tables described in these references.

In certain embodiments, the anti-PD-L1 antibody molecule includes a combination of CDRs or hypervariable loops defined according to the Kabat et al. and Chothia et al.

In one embodiment, the anti-PD-L1 antibody molecule includes at least one, two or three CDRs or hypervariable loops from a heavy chain variable region of an antibody described herein, e.g., an antibody chosen from any of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-O, according to the Kabat and Chothia definition (e.g., at least one, two, or three CDRs or hypervariable loops according to the Kabat and Chothia definition as set out in Table 1); or encoded by the nucleotide sequence in Table 1; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, or three CDRs or hypervariable loops according to Kabat and/or Chothia shown in Table 1.

For example, the anti-PD-L1 antibody molecule can include VH CDR1 according to Kabat et al. or VH hypervariable loop 1 according to Chothia et al., or a combination thereof, e.g., as shown in Table 1. In one embodiment, the combination of Kabat and Chothia CDR of VH CDR1 comprises the amino acid sequence GYTFTSYWMY (SEQ ID NO: 195), or an amino acid sequence substantially identical thereto (e.g., having at least one amino acid alteration, but not more than two, three or four alterations (e.g., substitutions, deletions, or insertions, e.g., conservative substitutions)). The anti-PD-L1 antibody molecule can further include, e.g., VH CDRs 2-3 according to Kabat et al. and VL CDRs 1-3 according to Kabat et al., e.g., as shown in Table 1. Accordingly, in some embodiments, framework regions are defined based on a combination of CDRs defined according to Kabat et al. and hypervariable loops defined according to Chothia et al. For example, the anti-PD-L1 antibody molecule can include VH FR1 defined based on VH hypervariable loop 1 according to Chothia et al. and VH FR2 defined based on VH CDRs 1-2 according to Kabat et al., e.g., as shown in Table 1. The anti-PD-L1 antibody molecule can further include, e.g., VH FRs 3-4 defined based on VH CDRs 2-3 according to Kabat et al. and VL FRs 1-4 defined based on VL CDRs 1-3 according to Kabat et al.

The anti-PD-L1 antibody molecule can contain any combination of CDRs or hypervariable loops according to the Kabat and Chothia definitions. In one embodiment, the anti-PD-L1 antibody molecule includes at least one, two or three CDRs from a light chain variable region of an antibody described herein, e.g., an antibody chosen from any of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-O, according to the Kabat and Chothia definition (e.g., at least one, two, or three CDRs according to the Kabat and Chothia definition as set out in Table 1).

In an embodiment, e.g., an embodiment comprising a variable region, a CDR (e.g., Chothia CDR or Kabat CDR), or other sequence referred to herein, e.g., in Table 1, the antibody molecule is a monospecific antibody molecule, a bispecific antibody molecule, or is an antibody molecule that comprises an antigen binding fragment of an antibody, e.g., a half antibody or antigen binding fragment of a half antibody. In embodiments the antibody molecule is a bispecific antibody molecule having a first binding specificity for PD-L1 and a second binding specificity for TIM-3, LAG-3, CEACAM (e.g., CEACAM-1 and/or CEACAM-5), PD-1 or PD-L2. In embodiments, the second binding specificity for TIM-3, LAG-3 and/or PD-1 includes an amino acid sequence, or is encoded by a nucleotide sequence as described herein (e.g., as disclosed in the section entitled "Inhibitors of Immune Checkpoint Molecules" starting on page 218 hereinbelow (including all publications mentioned therein).

In one embodiment, the anti-PD-L1 antibody molecule includes:

(i) a heavy chain variable region (VH) including a VHCDR1 amino acid sequence chosen from SEQ ID NO: 1, SEQ ID NO: 4 or SEQ ID NO: 195; a VHCDR2 amino acid sequence of SEQ ID NO: 2; and a VHCDR3 amino acid sequence of SEQ ID NO: 3; and (ii) a light chain variable region (VL) including a VLCDR1 amino acid sequence of SEQ ID NO: 9, a VLCDR2 amino acid sequence of SEQ ID NO: 10, and a VLCDR3 amino acid sequence of SEQ ID NO: 11.

In another embodiment, the anti-PD-L1 antibody molecule includes:

(i) a heavy chain variable region (VH) including a VHCDR1 amino acid sequence chosen from SEQ ID NO: 1, SEQ ID NO: 4 or SEQ ID NO: 195; a VHCDR2 amino acid sequence of SEQ ID NO: 5, and a VHCDR3 amino acid sequence of SEQ ID NO: 3; and (ii) a light chain variable region (VL) including a VLCDR1 amino acid sequence of SEQ ID NO: 12, a VLCDR2 amino acid sequence of SEQ ID NO: 13, and a VLCDR3 amino acid sequence of SEQ ID NO: 14.

In one embodiment, the anti-PD-L1 antibody molecule comprises the VHCDR1 amino acid sequence of SEQ ID NO: 1. In another embodiment, the anti-PD-L1 antibody molecule comprises the VHCDR1 amino acid sequence of SEQ ID NO: 4. In yet another embodiment, the anti-PD-L1 antibody molecule comprises the VHCDR1 amino acid sequence of SEQ ID NO: 195.

In one embodiment, the light or the heavy chain variable framework (e.g., the region encompassing at least FR1, FR2, FR3, and optionally FR4) of the anti-PD-L1 antibody molecule can be chosen from: (a) a light or heavy chain variable framework including at least 80%, 85%, 87% 90%, 92%, 93%, 95%, 97%, 98%, or preferably 100% of the amino acid residues from a human light or heavy chain variable framework, e.g., a light or heavy chain variable framework residue from a human mature antibody, a human germline sequence, or a human consensus sequence; (b) a light or heavy chain variable framework including from 20% to 80%, 40% to 60%, 60% to 90%, or 70% to 95% of the amino acid residues from a human light or heavy chain variable framework, e.g., a light or heavy chain variable framework residue from a human mature antibody, a human germline sequence, or a human consensus sequence; (c) a non-human framework (e.g., a rodent framework); or (d) a non-human framework that has been modified, e.g., to remove antigenic or cytotoxic determinants, e.g., deimmunized, or partially humanized. In one embodiment, the light or heavy chain variable framework region (particularly FR1, FR2 and/or FR3) includes a light or heavy chain variable framework sequence at least 70, 75, 80, 85, 87, 88, 90, 92, 94, 95, 96, 97, 98, 99% identical or identical to the frameworks of a VL or VH segment of a human germline gene.

In certain embodiments, the anti-PD-L1 antibody molecule comprises a heavy chain variable domain having at least one, two, three, four, five, six, seven, ten, fifteen, twenty or more changes, e.g., amino acid substitutions or deletions, from an amino acid sequence of BAP058-chi-HC, e.g., the amino acid sequence of the FR region in the entire variable region, e.g., shown in FIGS. 8A-8B, or SEQ ID NO: 16. In one embodiment, the anti-PD-L1 antibody molecule comprises a heavy chain variable domain having one or more of: Q at position 1, I at position 2, T at position 3, V or K at position 5, P at position 9, T at position 10, V at position 11, K at position 12, T at position 15, E or Q at position 16, T at position 17, L at position 18, R or T at position 19, I or V at position 20, T at position 21, T at position 23, G, V, or F at position 24, I at position 37, R at position 38, A or P or S at position 40, T or R at position 41, S at position 42, Q or K at position 43, M or L or V at position 48, R at position 67, F or V or L at position 68, I at position 70, S at position 71, A, K, or R at position 72, D or T or N at position 74, T or K at position 76, N at position 77, Q at position 78, F or V or L at position 79, S or V at position 80, L at position 81, E or K or T at position 82, M at position 83, T or N at position 84, N at position 85, V or M at position 86, K or R or D at position 87, T or A or P at position 88, A or V at position 89, T at position 91, or T at position 93, of amino acid sequence of BAP058-chi-HC, e.g., the amino acid sequence of the FR in the entire variable region, e.g., shown in FIGS. 8A-8B, or SEQ ID NO: 16.

Alternatively, or in combination with the heavy chain substitutions of BAP058-chi-HC described herein, the anti-PD-L1 antibody molecule comprises a light chain variable domain having at least one, two, three, four, five, six, seven, ten, fifteen, twenty or more amino acid changes, e.g., amino acid substitutions or deletions, from an amino acid sequence of BAP058-chi-LC, e.g., the amino acid sequence shown in FIGS. 9A-9B, or SEQ ID NO: 17. In one embodiment, the anti-PD-L1 antibody molecule comprises a heavy chain variable domain having one or more of: E or A at position 1, V at position 2, V or Q at position 3, L at position 4, T at position 7, P at position 8, D or L or S or A at position 9, S or T at position 10, Q or L at position 11, P at position 12, V or L or A at position 13, T at position 14, P or L at position 15, K at position 16, Q or E at position 17, K or P at position 18, A at position 19, T at position 20, L at position 21, S at position 22, L at position 37, A at position 43, R or Q at position 45, I at position 58, A or S or P at position 60, S at position 63, Y at position 67, E at position 70, F at position 73, K at position 74, N at position 76, S or R at position 77, I or L at position 78, E at position 79, P or A at position 80, D at position 81, F or I or V or A at position 83, G at position 84, T or V or Y at position 85, or Y at position 87 of the amino acid sequence of BAP058-chi-LC, e.g., the amino acid sequence shown in FIGS. 10A-10B, or SEQ ID NO: 24 or 26.

In other embodiments, the anti-PD-L1 antibody molecule includes one, two, three, or four heavy chain framework regions (e.g., a VHFW amino acid sequence shown in Table 2, or encoded by the nucleotide sequence shown in Table 2), or a sequence substantially identical thereto.

In yet other embodiments, the anti-PD-L1 antibody molecule includes one, two, three, or four light chain framework regions (e.g., a VLFW amino acid sequence shown in Table 2, or encoded by the nucleotide sequence shown in Table 2), or a sequence substantially identical thereto.

In other embodiments, the anti-PD-L1 antibody molecule includes one, two, three, or four heavy chain framework regions (e.g., a VHFW amino acid sequence shown in Table 2, or encoded by the nucleotide sequence shown in Table 2), or a sequence substantially identical thereto; and one, two, three, or four light chain framework regions (e.g., a VLFW amino acid sequence shown in Table 2, or encoded by the nucleotide sequence shown in Table 2), or a sequence substantially identical thereto.

In some embodiments, the anti-PD-L1 antibody molecule comprises the heavy chain framework region 1 (VHFW1) of BAP058-hum01, BAP058-hum02, BAP058-hum07, BAP058-hum14, or BAP058-hum16 (e.g., SEQ ID NO: 124). In some embodiments, the antibody molecule comprises the heavy chain framework region 1 (VHFW1) of BAP058-hum04, BAP058-hum06, BAP058-hum08, BAP058-hum09, BAP058-hum12, BAP058-hum15, BAP058-hum17, BAP058-Clone-L, or BAP058-Clone-M (e.g., SEQ ID NO: 126). In some embodiments, the antibody molecule comprises the heavy chain framework region 1 (VHFW1) of BAP058-hum03, BAP058-hum05, BAP058-hum11, BAP058-hum13, BAP058-Clone-K, BAP058-Clone-N, or BAP058-Clone-O (e.g., SEQ ID NO: 128). In some embodiments, the antibody molecule comprises the heavy chain framework region 1 (VHFW1) of BAP058-hum10 (e.g., SEQ ID NO: 130).

In some embodiments, the anti-PD-L1 antibody molecule comprises the heavy chain framework region 2 (VHFW2) of BAP058-hum01, BAP058-hum02, BAP058-hum03, BAP058-hum11, BAP058-hum14, BAP058-Clone-K, or BAP058-Clone-N (e.g., SEQ ID NO: 132). In some embodiments, the antibody molecule comprises the heavy chain framework region 2 (VHFW2) of BAP058-hum04, BAP058-hum12, or BAP058-Clone-L (e.g., SEQ ID NO: 134). In some embodiments, the antibody molecule comprises the heavy chain framework region 2 (VHFW2) of BAP058-hum06, BAP058-hum09, BAP058-hum15, or BAP058-Clone-M (e.g., SEQ ID NO: 136). In some embodiments, the antibody molecule comprises the heavy chain framework region 2 (VHFW2) of BAP058-hum05, BAP058-hum07, or BAP058-hum16 (e.g., SEQ ID NO: 138). In some embodiments, the antibody molecule comprises the heavy chain framework region 2 (VHFW2) of BAP058-hum08, BAP058-hum13, BAP058-hum17, or BAP058-Clone-O (e.g., SEQ ID NO: 140). In some embodiments, the antibody molecule comprises the heavy chain framework region 2 of BAP058-hum10 (e.g., SEQ ID NO: 142).

In some embodiments, the anti-PD-L1 antibody molecule comprises the heavy chain framework region 3 (VHFW3) of BAP058-hum01, BAP058-hum02, BAP058-hum07, BAP058-hum14, or BAP058-hum16, (e.g., SEQ ID NO: 144). In some embodiments, the antibody molecule comprises the heavy chain framework region 3 (VHFW3) of BAP058-hum03, BAP058-hum06, BAP058-hum09, BAP058-hum10, BAP058-hum11, BAP058-hum15, BAP058-Clone-K, BAP058-Clone-M, or BAP058-Clone-N (e.g., SEQ ID NO: 146). In some embodiments, the antibody molecule comprises the heavy chain framework region 3 (VHFW3) of BAP058-hum04, BAP058-hum12, or BAP058-Clone-L (e.g., SEQ ID NO: 148). In some embodiments, the antibody molecule comprises the heavy chain framework region 3 (VHFW3) of BAP058-hum05, BAP058-hum08, or BAP058-hum17 (e.g., SEQ ID NO: 150). In some embodiments, the antibody molecule comprises the heavy chain framework region 3 (VHFW3) of BAP058-hum13 or BAP058-Clone-O (e.g., SEQ ID NO: 152). In some embodiments, the anti-PD-L1 antibody molecule comprises the heavy chain framework region 4 (VHFW4) of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-O (e.g., SEQ ID NO: 154).

In some embodiments, the anti-PD-L1 antibody molecule comprises the light chain framework region 1 (VLFW1) of BAP058-hum03, BAP058-hum04, BAP058-hum05, BAP058-hum06, BAP058-hum14, BAP058-hum15, BAP058-hum16, BAP058-hum17, BAP058-Clone-K, BAP058-Clone-L, or BAP058-Clone-M (e.g., SEQ ID NO: 156). In some embodiments, the antibody molecule comprises the light chain framework region 1 (VLFW1) of BAP058-BAPhum08, BAP058-hum10, BAP058-hum11, or BAP058-Clone-N (e.g., SEQ ID NO: 158). In some embodiments, the antibody molecule comprises the light chain framework region 1 (VLFW1) of BAP058-hum01 or BAP058-hum09 (e.g., SEQ ID NO: 160). In some embodiments, the antibody molecule comprises the light chain framework region 1 (VLFW1) of BAP058-hum02 or BAP058-hum12 (e.g., SEQ ID NO: 162). In some embodiments, the antibody molecule comprises the light chain framework region 1 (VLFW1) of BAP058-hum07 (e.g., SEQ ID NO: 164). In some embodiments, the antibody molecule comprises the light chain framework region 1 (VLFW1) of BAP058-hum13 or BAP058-Clone-O (e.g., SEQ ID NO: 166).

In some embodiments, the anti-PD-L1 antibody molecule comprises the light chain framework region 2 (VLFW2) of BAP058-hum08, BAP058-hum10, BAP058-hum11, BAP058-hum12, BAP058-hum14, BAP058-hum15, BAP058-hum16, BAP058-hum17, or BAP058-Clone-N (e.g., SEQ ID NO: 168). In some embodiments, the antibody molecule comprises the light chain framework region 2 (VLFW2) of BAP058-hum01, BAP058-hum02, BAP058-hum03, BAP058-hum04, BAP058-hum05, BAP058-hum06, BAP058-hum07, BAP058-hum09, BAP058-hum13, BAP058-Clone-K, BAP058-Clone-L, BAP058-Clone-M, or BAP058-Clone-O (e.g., SEQ ID NO: 170).

In some embodiments, the anti-PD-L1 antibody molecule comprises the light chain framework region 3 (VLFW3) of BAP058-hum08, BAP058-hum10, BAP058-hum11, BAP058-hum14, BAP058-hum15, BAP058-hum16, BAP058-hum17, or BAP058-Clone-N (e.g., SEQ ID NO: 172). In some embodiments, the antibody molecule comprises the light chain framework region 3 (VLFW3) of BAP058-hum04, BAP058-hum05, BAP058-hum06, BAP058-hum12, BAP058-Clone-L, or BAP058-Clone-M (e.g., SEQ ID NO: 174). In some embodiments, the antibody molecule comprises the light chain framework region 3 (VLFW3) of BAP058-hum01 or BAP058-hum09 (e.g., SEQ ID NO: 176). In some embodiments, the antibody molecule comprises the light chain framework region 3 (VLFW3) of BAP058-hum02 (e.g., SEQ ID NO: 178). In some embodiments, the antibody molecule comprises the light chain framework region 3 (VLFW3) of BAP058-hum03 or BAP058-Clone-K (e.g., SEQ ID NO: 180). In some embodiments, the antibody molecule comprises the light chain framework region 3 (VLFW3) of BAP058-hum07 (e.g., SEQ ID NO: 182). In some embodiments, the antibody molecule comprises the light chain framework region 3 (VLFW3) of BAP058-hum13 or BAP058-Clone-O (e.g., SEQ ID NO: 184).

In some embodiments, the anti-PD-L1 antibody molecule comprises the light chain framework region 4 (VLFW4) of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-O (e.g., SEQ ID NO: 186).

In some embodiments, the anti-PD-L1 antibody molecule comprises the heavy chain framework regions 1-3 of BAP058-hum01, BAP058-hum02, or BAP058-hum14 (e.g., SEQ ID NO: 124 (VHFW1), SEQ ID NO: 132 (VHFW2), and SEQ ID NO: 144 (VHFW3)). In some embodiments, the antibody molecule comprises the heavy chain framework regions 1-3 of BAP058-hum07, or BAP058-hum16 (e.g., SEQ ID NO: 124 (VHFW1), SEQ ID NO: 138 (VHFW2), and SEQ ID NO: 144 (VHFW3)). In some embodiments, the antibody molecule comprises the heavy chain framework regions 1-3 of BAP058-hum04, BAP058-hum12, or BAP058-Clone-L (e.g., SEQ ID NO: 126 (VHFW1), SEQ ID NO: 134 (VHFW2), and SEQ ID NO: 148 (VHFW3)). In some embodiments, the antibody molecule comprises the heavy chain framework regions 1-3 of BAP058-hum06, BAP058-hum09, BAP058-hum15, or BAP058-Clone-M (e.g., SEQ ID NO: 126 (VHFW1), SEQ ID NO: 136 (VHFW2), and SEQ ID NO: 146 (VHFW3)). In some embodiments, the antibody molecule comprises the heavy chain framework regions 1-3 of BAP058-hum08 or BAP058-hum17 (e.g., SEQ ID NO: 126 (VHFW1), SEQ ID NO: 140 (VHFW2), and SEQ ID NO: 150 (VHFW3)). In some embodiments, the antibody molecule comprises the heavy chain framework regions 1-3 of BAP058-hum03, BAP058-hum11, BAP058-Clone-K, or BAP058-Clone-N (e.g., SEQ ID NO: 128 (VHFW1), SEQ ID NO: 132 (VHFW2), and SEQ ID NO: 146 (VHFW3)). In some embodiments, the antibody molecule comprises the heavy chain framework regions 1-3 of BAP058-hum13 or BAP058-Clone-O (e.g., SEQ ID NO: 128 (VHFW1), SEQ ID NO: 140 (VHFW2), and SEQ ID NO: 152 (VHFW3)). In some embodiments, the antibody molecule comprises the heavy chain framework regions 1-3 of BAP058-hum05 (e.g., SEQ ID NO: 128 (VHFW1), SEQ ID NO: 138 (VHFW2), and SEQ ID NO: 150 (VHFW3)). In some embodiments, the antibody molecule comprises the heavy chain framework regions 1-3 of BAP058-hum10 (e.g., SEQ ID NO: 130 (VHFW1), SEQ ID NO: 142 (VHFW2), and SEQ ID NO: 146 (VHFW3)). In some embodiments, the antibody molecule further comprises the heavy chain framework region 4 (VHFW4) of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-O (e.g., SEQ ID NO: 154).

In some embodiments, the anti-PD-L1 antibody molecule comprises the light chain framework regions 1-3 of BAP058-hum01 or BAP058-hum09 (e.g., SEQ ID NO: 160 (VLFW1), SEQ ID NO: 170 (VLFW2), and SEQ ID NO: 176 (VLFW3)). In some embodiments, the antibody molecule comprises the light chain framework regions 1-3 of BAP058-hum14, BAP058-hum15, BAP058-hum16, or BAP058-hum17 (e.g., SEQ ID NO: 156 (VLFW1), SEQ ID NO: 168 (VLFW2), and SEQ ID NO: 172 (VLFW3)). In some embodiments, the antibody molecule comprises the light chain framework regions 1-3 of BAP058-hum04, BAP058-hum05, BAP058-hum06, BAP058-Clone-L, or BAP058-Clone-M (e.g., SEQ ID NO: 156 (VLFW1), SEQ ID NO: 170 (VLFW2), and SEQ ID NO: 174 (VLFW3)). In some embodiments, the antibody molecule comprises the light chain framework regions 1-3 of BAP058-hum08, BAP058-hum10, or BAP058-hum11 (e.g., SEQ ID NO: 158 (VLFW1), SEQ ID NO: 168 (VLFW2), and SEQ ID NO: 172 (VLFW3)). In some embodiments, the antibody molecule comprises the light chain framework regions 1-3 of BAP058-hum13 or BAP058-Clone-O (e.g., SEQ ID NO: 166 (VLFW1), SEQ ID NO: 170 (VLFW2), and SEQ ID NO: 184 (VLFW3)). In some embodiments, the antibody molecule comprises the light chain framework regions 1-3 of BAP058-hum02 (e.g., SEQ ID NO: 162 (VLFW1), SEQ ID NO: 170 (VLFW2), and SEQ ID NO: 178 (VLFW3)). In some embodiments, the antibody molecule comprises the light chain framework regions 1-3 of BAP058-hum03 (e.g., SEQ ID NO: 156 (VLFW1), SEQ ID NO: 170 (VLFW2), and SEQ ID NO: 180 (VLFW3)). In some embodiments, the antibody molecule comprises the light chain framework regions 1-3 of BAP058-hum07 (e.g., SEQ ID NO: 164 (VLFW1), SEQ ID NO: 170 (VLFW2), and SEQ ID NO: 182 (VLFW3)). In some embodiments, the antibody molecule comprises the light chain framework regions 1-3 of BAP058-hum12 (e.g., SEQ ID NO: 162 (VLFW1), SEQ ID NO: 168 (VLFW2), and SEQ ID NO: 174 (VLFW3)). In some embodiments, the antibody molecule comprises the light chain framework regions 1-3 of BAP058-Clone-K (e.g., SEQ ID NO: 156 (VLFW1), SEQ ID NO: 168 (VLFW2), and SEQ ID NO: 180 (VLFW3)). In some embodiments, the antibody molecule comprises the light chain framework regions 1-3 of BAP058-Clone-N (e.g., SEQ ID NO: 158 (VLFW1), SEQ ID NO: 170 (VLFW2), and SEQ ID NO: 172 (VLFW3)). In some embodiments, the antibody molecule further comprises the light chain framework region 4 (VLFW4) of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-O (e.g., SEQ ID NO: 186).

In some embodiments, the anti-PD-L1 antibody molecule comprises the heavy chain framework regions 1-3 of BAP058-hum01 (e.g., SEQ ID NO: 124 (VHFW1), SEQ ID NO: 132 (VHFW2), and SEQ ID NO: 144 (VHFW3)) and the light chain framework regions 1-3 of BAP058-hum01 (e.g., SEQ ID NO: 160 (VLFW1), SEQ ID NO: 170 (VLFW2), and SEQ ID NO: 176 (VLFW3)).

In some embodiments, the anti-PD-L1 antibody molecule comprises the heavy chain framework regions 1-3 of BAP058-hum02 (e.g., SEQ ID NO: 124 (VHFW1), SEQ ID NO: 132 (VHFW2), and SEQ ID NO: 144 (VHFW3)) and the light chain framework regions 1-3 of BAP058-hum02 (e.g., SEQ ID NO: 162 (VLFW1), SEQ ID NO: 170 (VLFW2), and SEQ ID NO: 178 (VLFW3)).

In some embodiments, the anti-PD-L1 antibody molecule comprises the heavy chain framework regions 1-3 of BAP058-hum03 (e.g., SEQ ID NO: 128 (VHFW1), SEQ ID NO: 132 (VHFW2), and SEQ ID NO: 146 (VHFW3)) and the light chain framework regions 1-3 of BAP058-hum03 (e.g., SEQ ID NO: 156 (VLFW1), SEQ ID NO: 170 (VLFW2), and SEQ ID NO: 180 (VLFW3)).

In some embodiments, the anti-PD-L1 antibody molecule comprises the heavy chain framework regions 1-3 of BAP058-hum04 or BAP058-Clone-L (e.g., SEQ ID NO: 126 (VHFW1), SEQ ID NO: 134 (VHFW2), and SEQ ID NO: 148 (VHFW3)) and the light chain framework regions 1-3 of BAP058-hum04 or BAP058-Clone-L (e.g., SEQ ID NO: 156 (VLFW1), SEQ ID NO: 170 (VLFW2), and SEQ ID NO: 174 (VLFW3)).

In some embodiments, the anti-PD-L1 antibody molecule comprises the heavy chain framework regions 1-3 of BAP058-hum05 (e.g., SEQ ID NO: 128 (VHFW1), SEQ ID NO: 138 (VHFW2), and SEQ ID NO: 150 (VHFW3)) and the light chain framework regions 1-3 of BAP058-hum05 (e.g., SEQ ID NO: 156 (VLFW1), SEQ ID NO: 170 (VLFW2), and SEQ ID NO: 174 (VLFW3)).

In some embodiments, the anti-PD-L1 antibody molecule comprises the heavy chain framework regions 1-3 of BAP058-hum06 or BAP058-Clone-M (e.g., SEQ ID NO: 126 (VHFW1), SEQ ID NO: 136 (VHFW2), and SEQ ID NO: 146 (VHFW3)) and the light chain framework regions 1-3 of BAP058-hum06 or BAP058-Clone-M (e.g., SEQ ID NO: 156 (VLFW1), SEQ ID NO: 170 (VLFW2), and SEQ ID NO: 174 (VLFW3)).

In some embodiments, the anti-PD-L1 antibody molecule comprises the heavy chain framework regions 1-3 of BAP058-hum07 (e.g., SEQ ID NO: 124 (VHFW1), SEQ ID NO: 138 (VHFW2), and SEQ ID NO: 144 (VHFW3)) and the light chain framework regions 1-3 of BAP058-hum07 (e.g., SEQ ID NO: 164 (VLFW1), SEQ ID NO: 170 (VLFW2), and SEQ ID NO: 182 (VLFW3)).

In some embodiments, the anti-PD-L1 antibody molecule comprises the heavy chain framework regions 1-3 of BAP058-hum08 (e.g., SEQ ID NO: 126 (VHFW1), SEQ ID NO: 140 (VHFW2), and SEQ ID NO: 150 (VHFW3)) and the light chain framework regions 1-3 of BAP058-hum08 (e.g., SEQ ID NO: 158 (VLFW1), SEQ ID NO: 168 (VLFW2), and SEQ ID NO: 172 (VLFW3)).

In some embodiments, the anti-PD-L1 antibody molecule comprises the heavy chain framework regions 1-3 of BAP058-hum09 (e.g., SEQ ID NO: 126 (VHFW1), SEQ ID NO: 136 (VHFW2), and SEQ ID NO: 146 (VHFW3)) and the light chain framework regions 1-3 of BAP058-hum09 (e.g., SEQ ID NO: 160 (VLFW1), SEQ ID NO: 170 (VLFW2), and SEQ ID NO: 176 (VLFW3)).

In some embodiments, the anti-PD-L1 antibody molecule comprises the heavy chain framework regions 1-3 of BAP058-hum10 (e.g., SEQ ID NO: 130 (VHFW1), SEQ ID NO: 142 (VHFW2), and SEQ ID NO: 146 (VHFW3)) and the light chain framework regions 1-3 of BAP058-hum10 (e.g., SEQ ID NO: 158 (VLFW1), SEQ ID NO: 168 (VLFW2), and SEQ ID NO: 172 (VLFW3)).

In some embodiments, the anti-PD-L1 antibody molecule comprises the heavy chain framework regions 1-3 of BAP058-hum11 (e.g., SEQ ID NO: 128 (VHFW1), SEQ ID NO: 132 (VHFW2), and SEQ ID NO: 146 (VHFW3)) and the light chain framework regions 1-3 of BAP058-hum11 (e.g., SEQ ID NO: 158 (VLFW1), SEQ ID NO: 168 (VLFW2), and SEQ ID NO: 172 (VLFW3)).

In some embodiments, the anti-PD-L1 antibody molecule comprises the heavy chain framework regions 1-3 of BAP058-hum12 (e.g., SEQ ID NO: 126 (VHFW1), SEQ ID NO: 134 (VHFW2), and SEQ ID NO: 148 (VHFW3)) and the light chain framework regions 1-3 of BAP058-hum12 (e.g., SEQ ID NO: 162 (VLFW1), SEQ ID NO: 168 (VLFW2), and SEQ ID NO: 174 (VLFW3)).

In some embodiments, the anti-PD-L1 antibody molecule comprises the heavy chain framework regions 1-3 of BAP058-hum13 or BAP058-Clone-O (e.g., SEQ ID NO: 128 (VHFW1), SEQ ID NO: 140 (VHFW2), and SEQ ID NO: 152 (VHFW3)) and the light chain framework regions 1-3 of BAP058-hum13 or BAP058-Clone-O (e.g., SEQ ID NO: 166 (VLFW1), SEQ ID NO: 170 (VLFW2), and SEQ ID NO: 184 (VLFW3)).

In some embodiments, the anti-PD-L1 antibody molecule comprises the heavy chain framework regions 1-3 of BAP058-hum14 (e.g., SEQ ID NO: 124 (VHFW1), SEQ ID NO: 132 (VHFW2), and SEQ ID NO: 144 (VHFW3)) and the light chain framework regions 1-3 of BAP058-hum14 (e.g., SEQ ID NO: 156 (VLFW1), SEQ ID NO: 168 (VLFW2), and SEQ ID NO: 172 (VLFW3)).

In some embodiments, the anti-PD-L1 antibody molecule comprises the heavy chain framework regions 1-3 of BAP058-hum15 (e.g., SEQ ID NO: 126 (VHFW1), SEQ ID NO: 136 (VHFW2), and SEQ ID NO: 146 (VHFW3)) and the light chain framework regions 1-3 of BAP058-hum15 (e.g., SEQ ID NO: 156 (VLFW1), SEQ ID NO: 168 (VLFW2), and SEQ ID NO: 172 (VLFW3)).

In some embodiments, the anti-PD-L1 antibody molecule comprises the heavy chain framework regions 1-3 of BAP058-hum16 (e.g., SEQ ID NO: 124 (VHFW1), SEQ ID NO: 138 (VHFW2), and SEQ ID NO: 144 (VHFW3)) and the light chain framework regions 1-3 of BAP058-hum16 (e.g., SEQ ID NO: 156 (VLFW1), SEQ ID NO: 168 (VLFW2), and SEQ ID NO: 172 (VLFW3)).

In some embodiments, the anti-PD-L1 antibody molecule comprises the heavy chain framework regions 1-3 of BAP058-hum17 (e.g., SEQ ID NO: 126 (VHFW1), SEQ ID NO: 140 (VHFW2), and SEQ ID NO: 150 (VHFW3)) and the light chain framework regions 1-3 of BAP058-hum17 (e.g., SEQ ID NO: 156 (VLFW1), SEQ ID NO: 168 (VLFW2), and SEQ ID NO: 172 (VLFW3)).

In some embodiments, the anti-PD-L1 antibody molecule comprises the heavy chain framework regions 1-3 of BAP058-Clone-N (e.g., SEQ ID NO: 128 (VHFW1), SEQ ID NO: 132 (VHFW2), and SEQ ID NO: 146 (VHFW3)) and the light chain framework regions 1-3 of BAP058-Clone-N (e.g., SEQ ID NO: 158 (VLFW1), SEQ ID NO: 170 (VLFW2), and SEQ ID NO: 172 (VLFW3)).

In some embodiments, the anti-PD-L1 antibody molecule further comprises the heavy chain framework region 4 (VHFW4) of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-O (e.g., SEQ ID NO: 154) and the light chain framework region 4 (VLFW4) of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-O (e.g., SEQ ID NO: 186).

In some embodiments, the anti-PD-L1 antibody molecule comprises a heavy chain framework region having a combination of framework regions FW1, FW2 and FW3 as showing in FIG. 4 or 6. In other embodiment, the antibody molecule comprises a light chain framework region having a combination of framework regions FW1, FW2 and FW3 as showing in FIG. 4 or 6. In yet other embodiments, the antibody molecule comprises a heavy chain framework region having a combination of framework regions FW1, FW2 and FW3 as showing in FIG. 4 or 6, and a light chain framework region having a combination of framework regions FW1, FW2 and FW3 as showing in FIG. 4 or 6.

In one embodiment, the heavy or light chain variable domain, or both, of the anti-PD-L1 antibody molecule includes an amino acid sequence, which is substantially identical to an amino acid disclosed herein, e.g., at least 80%, 85%, 90%, 92%, 95%, 97%, 98%, 99% or higher identical to a variable region of an antibody described herein, e.g., an antibody chosen from any of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-O; or as described in Table 1, or encoded by the nucleotide sequence in Table 1; or which differs at least 1 or 5 residues, but less than 40, 30, 20, or 10 residues, from a variable region of an antibody described herein.

In one embodiment, the heavy or light chain variable region, or both, of the anti-PD-L1 antibody molecule includes an amino acid sequence encoded by a nucleic acid sequence described herein or a nucleic acid that hybridizes to a nucleic acid sequence described herein (e.g., a nucleic acid sequence as shown in Tables 1 and 2) or its complement, e.g., under low stringency, medium stringency, or high stringency, or other hybridization condition described herein.

In another embodiment, the anti-PD-L1 antibody molecule comprises at least one, two, three, or four antigen-binding regions, e.g., variable regions, having an amino acid sequence as set forth in Table 1, or a sequence substantially identical thereto (e.g., a sequence at least about 85%, 90%, 95%, 99% or more identical thereto, or which differs by no more than 1, 2, 5, 10, or 15 amino acid residues from the sequences shown in Table 1. In another embodiment, the anti-PD-L1 antibody molecule includes a VH and/or VL domain encoded by a nucleic acid having a nucleotide sequence as set forth in Table 1, or a sequence substantially identical thereto (e.g., a sequence at least about 85%, 90%, 95%, 99% or more identical thereto, or which differs by no more than 3, 6, 15, 30, or 45 nucleotides from the sequences shown in Table 1.

In yet another embodiment, the anti-PD-L1 antibody molecule comprises at least one, two, or three CDRs from a heavy chain variable region having an amino acid sequence as set forth in Table 1, or a sequence substantially homologous thereto (e.g., a sequence at least about 85%, 90%, 95%, 99% or more identical thereto, and/or having one, two, three or more substitutions, insertions or deletions, e.g., conserved substitutions). In yet another embodiment, the anti-PD-L1 antibody molecule comprises at least one, two, or three CDRs from a light chain variable region having an amino acid sequence as set forth in Table 1, or a sequence substantially homologous thereto (e.g., a sequence at least about 85%, 90%, 95%, 99% or more identical thereto, and/or having one, two, three or more substitutions, insertions or deletions, e.g., conserved substitutions). In yet another embodiment, the anti-PD-L1 antibody molecule comprises at least one, two, three, four, five or six CDRs from heavy and light chain variable regions having an amino acid sequence as set forth in Table 1), or a sequence substantially homologous thereto (e.g., a sequence at least about 85%, 90%, 95%, 99% or more identical thereto, and/or having one, two, three or more substitutions, insertions or deletions, e.g., conserved substitutions).

In one embodiment, the anti-PD-L1 antibody molecule comprises at least one, two, or three CDRs and/or hypervariable loops from a heavy chain variable region having an amino acid sequence of an antibody described herein, e.g., an antibody chosen from any of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-O, as summarized in Table 1, or a sequence substantially identical thereto (e.g., a sequence at least about 85%, 90%, 95%, 99% or more identical thereto, and/or having one, two, three or more substitutions, insertions or deletions, e.g., conserved substitutions). In another embodiment, the anti-PD-L1 antibody molecule comprises at least one, two, or three CDRs and/or hypervariable loops from a light chain variable region having an amino acid sequence of of an antibody described herein, e.g., an antibody chosen from any of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-O, as summarized in Table 1, or a sequence substantially identical thereto (e.g., a sequence at least about 85%, 90%, 95%, 99% or more identical thereto, and/or having one, two, three or more substitutions, insertions or deletions, e.g., conserved substitutions). In one embodiment, the anti-PD-L1 antibody molecule comprises all six CDRs and/or hypervariable loops described herein, e.g., described in Table 1.

In one embodiment, the anti-PD-L1 antibody molecule has a variable region that is identical in sequence, or which differs by 1, 2, 3, or 4 amino acids from a variable region described herein (e.g., an FR region disclosed herein).

In one embodiment, the anti-PD-L1 antibody molecule is a full antibody or fragment thereof (e.g., a Fab, F(ab')$_2$, Fv, or a single chain Fv fragment (scFv)). In certain embodiments, the anti-PD-L1 antibody molecule is a monoclonal antibody or an antibody with single specificity. The anti-PD-L1 antibody molecule can also be a humanized, chimeric, camelid, shark, or an in vitro-generated antibody molecule. In one embodiment, the anti-PD-L1 antibody molecule thereof is a humanized antibody molecule. The heavy and light chains of the anti-PD-L1 antibody molecule can be full-length (e.g., an antibody can include at least one, and preferably two, complete heavy chains, and at least one, and preferably two, complete light chains) or can include an antigen-binding fragment (e.g., a Fab, F(ab')$_2$, Fv, a single chain Fv fragment, a single domain antibody, a diabody (dAb), a bivalent antibody, or bispecific antibody or fragment thereof, a single domain variant thereof, or a camelid antibody).

In certain embodiments, the anti-PD-L1 antibody molecule is in the form of a bispecific or a multispecific antibody molecule. In one embodiment, the bispecific antibody molecule has a first binding specificity for PD-L1 and a second binding specificity for TIM-3, LAG-3, CEACAM (e.g., CEACAM-1, CEACAM-3 and/or CEACAM-5), PD-1 or PD-L2. In one embodiment, the bispecific antibody molecule binds to PD-L1 and TIM-3. In another embodiment, the bispecific antibody molecule binds to PD-L1 and LAG- 3. In another embodiment, the bispecific antibody molecule binds to PD-L1 and CEACAM (e.g., CEACAM-1, CEACAM-3 and/or CEACAM-5). In another embodiment, the bispecific antibody molecule binds to PD-L1 and CEACAM-1. In yet another embodiment, the bispecific antibody molecule binds to PD-L1 and CEACAM-5. In another embodiment, the bispecific antibody molecule binds to PD-L1 and PD-1. In yet another embodiment, the bispecific antibody molecule binds to PD-L1 and PD-L2. Any combination of the aforesaid molecules can be made in a multispecific antibody molecule, e.g., a trispecific antibody that includes a first binding specificity to PD-L1, and a second and third binding specificity to one or more of: TIM-3, LAG-3, CEACAM (e.g., CEACAM-1, CEACAM-3 and/or CEACAM-5), PD-1 or PD-L2. In embodiments, the second and/or third binding specificity for TIM-3, LAG-3 and/or PD-1 includes an amino acid sequence, or is encoded by a nucleotide sequence as disclosed herein (e.g., as disclosed in the section entitled "Inhibitors of Immune Checkpoint Molecules" starting on page 218 herein below (including all publications mentioned therein).

In other embodiments, the anti-PD-L1 antibody molecule is used in combination with a bispecific molecule comprising one or more of: TIM-3, LAG-3, CEACAM (e.g., CEACAM-1, CEACAM-3 and/or CEACAM-5), PD-1 or PD-L2. In one embodiment, the bispecific antibody molecule used in combination binds to CEACAM (e.g., CEACAM-1, CEACAM-3 and/or CEACAM-5) and LAG-3. In another embodiment, the bispecific antibody molecule used in combination binds to CEACAM (e.g., CEACAM-1, CEACAM-3 and/or CEACAM-5) and TIM-3. In another embodiment, the bispecific antibody molecule used in combination binds to LAG-3 and TIM-3.

In yet other embodiments, the anti-PD-L1 antibody molecule has a heavy chain constant region (Fc) chosen from, e.g., the heavy chain constant regions of IgG1, IgG2, IgG3, IgG4, IgM, IgA1, IgA2, IgD, and IgE; particularly, chosen from, e.g., the heavy chain constant regions of IgG1, IgG2, IgG3, and IgG4, more particularly, the heavy chain constant region of IgG1 or IgG2 (e.g., human IgG1, IgG2 or IgG4). In one embodiment, the heavy chain constant region is human IgG1. In another embodiment, the anti-PD-L1 antibody molecule has a light chain constant region chosen from, e.g., the light chain constant regions of kappa or lambda, preferably kappa (e.g., human kappa). In one embodiment, the constant region is altered, e.g., mutated, to modify the properties of the anti-PD-L1 antibody molecule (e.g., to increase or decrease one or more of: Fc receptor binding, antibody glycosylation, the number of cysteine residues, effector cell function, or complement function). For example, the constant region is mutated at positions 296 (M to Y), 298 (S to T), 300 (T to E), 477 (H to K) and 478 (N to F) to alter Fc receptor binding (e.g., the mutated positions correspond to positions 132 (M to Y), 134 (S to T), 136 (T to E), 313 (H to K) and 314 (N to F) of SEQ ID NOs: 212 or 214; or positions 135 (M to Y), 137 (S to T), 139 (T to E), 316 (H to K) and 317 (N to F) of SEQ ID NOs: 215, 216, 217 or 218). In another embodiment, the heavy chain constant region of an IgG4, e.g., a human IgG4, is mutated at position 228 (e.g., S to P), e.g., as shown in Table 3. In certain embodiments, the anti-PD-L1 antibody molecules comprises a human IgG4 mutated at position 228 (e.g., S to P), e.g., as shown in Table 3; and a kappa light chain constant region, e.g., as shown in Table 3. In still another embodiment, the heavy chain constant region of an IgG1, e.g., a human IgG1, is mutated at one or more of position 297 (e.g., N to A), position 265 (e.g., D to A), position 329 (e.g., P to A), position 234 (e.g., L to A), or position 235 (e.g., L to A), e.g., as shown in Table 3. In certain embodiments, the anti-PD-L1 antibody molecules comprises a human IgG1 mutated at one or more of the aforesaid positions, e.g., as shown in Table 3; and a kappa light chain constant region, e.g., as shown in Table 3.

In one embodiment, the anti-PD-L1 antibody molecule is isolated or recombinant.

In one embodiment, the anti-PD-L1 antibody molecule is a humanized antibody molecule.

The invention also features a nucleic acid molecule that comprise one or both nucleotide sequences that encode heavy and light chain variable regions, CDRs, hypervariable loops, framework regions of the anti-PD-L1 antibody molecules, as described herein. In certain embodiments, the nucleotide sequence that encodes the anti-PD-L1 antibody molecule is codon optimized. For example, the invention features a first and second nucleic acid encoding heavy and light chain variable regions, respectively, of an anti-PD-L1 antibody molecule chosen from one or more of, e.g., any of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-O, as summarized in Table 1, or a sequence substantially identical thereto. For example, the nucleic acid can comprise a nucleotide sequence as set forth in Tables 1 and 2, or a sequence substantially identical thereto (e.g., a sequence at least about 85%, 90%, 95%, 99% or more identical thereto, or which differs by no more than 3, 6, 15, 30, or 45 nucleotides from the sequences shown in Tables 1 and 2).

In other embodiments, the nucleic acid molecule comprises a nucleotide sequence that encodes a heavy chain variable domain and/or a heavy chain constant region comprising the amino acid sequence of BAP058-Clone-K, BAP058-Clone-L, BAP058-Clone-M, BAP058-Clone-N, or BAP058-Clone-O; or as described in Table 1; or the nucleotide sequence in Table 1; or a sequence substantially identical (e.g., a sequence at least about 85%, 90%, 95%, 99% or more identical) to any of the aforesaid sequences.

In other embodiments, the nucleic acid molecule comprises a nucleotide sequence that encodes a light chain variable domain and/or a light chain constant region comprising the amino acid sequence of BAP058-Clone-K, BAP058-Clone-L, BAP058-Clone-M, BAP058-Clone-N, or BAP058-Clone-O; or as described in Table 1; or the nucleotide sequence in Table 1; or a sequence substantially identical (e.g., a sequence at least about 85%, 90%, 95%, 99% or more identical) to any of the aforesaid sequences.

The aforesaid nucleotide sequences encoding the anti-PD-L1 heavy and light chain variable domain and constant regions can be present in a separate nucleic acid molecule, or in the same nucleic acid molecule. In certain embodiments, the nucleic acid molecules comprise a nucleotide sequence encoding a leader sequence.

In certain embodiments, the nucleic acid molecule comprises a nucleotide sequence encoding at least one, two, or three CDRs, or hypervariable loops, from a heavy chain variable region having an amino acid sequence as set forth in Table 1, or a sequence substantially homologous thereto (e.g., a sequence at least about 85%, 90%, 95%, 99% or more identical thereto, and/or having one, two, three or more substitutions, insertions or deletions, e.g., conserved substitutions).

In another embodiment, the nucleic acid molecule comprises a nucleotide sequence encoding at least one, two, or three CDRs, or hypervariable loops, from a light chain variable region having an amino acid sequence as set forth in Table 1, or a sequence substantially homologous thereto (e.g., a sequence at least about 85%, 90%, 95%, 99% or more identical thereto, and/or having one, two, three or more substitutions, insertions or deletions, e.g., conserved substitutions).

In yet another embodiment, the nucleic acid molecule comprises a nucleotide sequence encoding at least one, two, three, four, five, or six CDRs, or hypervariable loops, from heavy and light chain variable regions having an amino acid sequence as set forth in Table 1, or a sequence substantially homologous thereto (e.g., a sequence at least about 85%, 90%, 95%, 99% or more identical thereto, and/or having one, two, three or more substitutions, insertions or deletions, e.g., conserved substitutions).

In another embodiment, the nucleic acid molecule includes one or more heavy chain framework region (e.g., any of VHFW1 (type a), VHFW1 (type b), VHFW1 (type c), VHFW1 (type d), VHFW2 (type a), VHFW2 (type a'), VHFW2 (type b), VHFW2 (type c), VHFW2 (type d), VHFW2 (type e), VHFW3 (type a), VHFW3 (type b), VHFW3 (type c), VHFW3 (type d), VHFW3 (type e), or VHFW4, or any combination thereof, e.g., a framework combination as described herein) for any of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-O, as summarized in Table 1 and 2, or a sequence substantially identical thereto. For example, the nucleic acid molecule can comprise a nucleotide sequence as set forth in Tables 1 and 2, or a sequence substantially identical thereto (e.g., a sequence at least about 85%, 90%, 95%, 99% or more identical thereto, or which differs by no more than 3, 6, 15, 30, or 45 nucleotides from the sequences shown in Tables 1 and 2).

In another embodiment, the nucleic acid molecule includes one or more light chain framework region (e.g., any of VLFW1 (type a), VLFW1 (type b), VLFW1 (type c), VLFW1 (type d), VLFW1 (type e), VLFW1 (type f), VLFW2 (type a), VLFW2 (type c), VLFW3 (type a), VLFW3 (type b), VLFW3 (type c), VLFW3 (type d), VLFW3 (type e), VLFW3 (type f), VLFW3 (type g), or VLFW4, or any combination thereof, e.g., a framework combination as described herein) for any of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-O, as summarized in Table 1 and 2, or a sequence substantially identical thereto. For example, the nucleic acid molecule can comprise a nucleotide sequence as set forth in Tables 1 and 2, or a sequence substantially identical thereto (e.g., a sequence at least about 85%, 90%, 95%, 99% or more identical thereto, or which differs by no more than 3, 6, 15, 30, or 45 nucleotides from the sequences shown in Tables 1 and 2).

In another embodiment, the nucleic acid molecule includes one or more heavy chain framework region and one or more light chain framework region as described herein. The heavy and light chain framework regions may be present in the same vector or separate vectors.

In another aspect, the application features host cells and vectors containing the nucleic acids described herein. The nucleic acids may be present in a single vector or separate vectors present in the same host cell or separate host cell. The host cell can be a eukaryotic cell, e.g., a mammalian cell, an insect cell, a yeast cell, or a prokaryotic cell, e.g., *E. coli*. For example, the mammalian cell can be a cultured cell or a cell line. Exemplary mammalian cells include lymphocytic cell lines (e.g., NSO), Chinese hamster ovary cells (CHO), COS cells, oocyte cells, and cells from a transgenic animal, e.g., mammary epithelial cell.

In one aspect, the invention features a method of providing an antibody molecule described herein. The method includes: providing a PD-L1 antigen (e.g., an antigen comprising at least a portion of a PD-L1 epitope); obtaining an antibody molecule that specifically binds to the PD-L1 polypeptide; and evaluating if the antibody molecule specifically binds to the PD-L1 polypeptide, or evaluating efficacy of the antibody molecule in modulating, e.g., inhibiting, the activity of the PD-L1. The method can further include administering the antibody molecule to a subject, e.g., a human or non-human animal.

In another aspect, the invention provides, compositions, e.g., pharmaceutical compositions, which include a pharmaceutically acceptable carrier, excipient or stabilizer, and at least one of the anti-PD-L1 antibody molecules described herein. In one embodiment, the composition, e.g., the pharmaceutical composition, includes a combination of the antibody molecule and one or more agents, e.g., a therapeutic agent or other antibody molecule, as described herein. In one embodiment, the antibody molecule is conjugated to a label or a therapeutic agent.

The anti-PD-L1 antibody molecules disclosed herein can inhibit, reduce or neutralize one or more activities of PD-L1, resulting in blockade or reduction of an immune checkpoint. In one embodiment, the antibody molecule results in one or more of: an increase in tumor infiltrating lymphocytes, an increase in T-cell receptor mediated proliferation, a decrease in immune evasion by cancerous cells, restoration of effector cell function (e.g., one or more of T cell proliferation, IFN-γ secretion or cytolytic function), inhibition of regulatory T cell function, or an effect on the activity of multiple cell types, such as regulatory T cell, effector T cells and NK cells). Thus, such antibody molecules can be used to treat or prevent disorders where enhancing an immune response in a subject is desired.

Uses of the Anti-PD-L1 Antibody Molecules

Accordingly, in another aspect, a method of modulating an immune response in a subject is provided. The method comprises administering to the subject an anti-PD-L1 antibody molecule disclosed herein (e.g., a therapeutically effective amount of an anti-PD-L1 antibody molecule), alone or in combination with one or more agents or procedures, such that the immune response in the subject is modulated. In one embodiment, the antibody molecule enhances, stimulates or increases the immune response in the subject. The subject can be a mammal, e.g., a primate, preferably a higher primate, e.g., a human (e.g., a patient having, or at risk of having, a disorder described herein). In one embodiment, the subject is in need of enhancing an immune response. In one embodiment, the subject has, or is at risk of, having a disorder described herein, e.g., a cancer or an infectious disorder as described herein. In certain embodiments, the subject is, or is at risk of being, immunocompromised. For example, the subject is undergoing or has undergone a chemotherapeutic treatment and/or radiation therapy. Alternatively, or in combination, the subject is, or is at risk of being, immunocompromised as a result of an infection.

In one aspect, a method of treating (e.g., one or more of reducing, inhibiting, or delaying progression) a cancer or a tumor in a subject is provided. The method comprises administering to the subject an anti-PD-L1 antibody molecule described herein, e.g., a therapeutically effective amount of an anti-PD-L1 antibody molecule, alone or in combination with one or more agents or procedures. In certain embodiments, the anti-PD-L1 antibody molecule is administered in combination with a modulator of a costimulatory molecule (e.g., an agonist of a costimulatory molecule) or a modulator of an inhibitory molecule (e.g., an inhibitor of an immune checkpoint inhibitor), e.g., as described herein.

In certain embodiments, the cancer treated with the anti-PD-L1 antibody molecule, includes but is not limited to, a solid tumor, a hematological cancer (e.g., leukemia, lymphoma, myeloma, e.g., multiple myeloma), and a metastatic lesion. In one embodiment, the cancer is a solid tumor. Examples of solid tumors include malignancies, e.g., sarcomas and carcinomas, e.g., adenocarcinomas, and carcinomas, of the various organ systems, such as those affecting the lung, breast, ovarian, lymphoid, gastrointestinal (e.g., colon), anal, genitals and genitourinary tract (e.g., renal, urothelial, bladder cells, prostate), pharynx, CNS (e.g., brain, neural or glial cells), head and neck, skin (e.g., melanoma), a nasopharyngeal cancer, e.g., differentiated or undifferentiated metastatic or locally recurrent nasopharyngeal carcinoma), and pancreas, as well as adenocarcinomas which include malignancies such as colon cancers, rectal cancer, renal-cell carcinoma, liver cancer, non-small cell lung cancer, cancer of the small intestine and cancer of the esophagus. The cancer may be at an early, intermediate, late stage or metastatic cancer.

In one embodiment, the cancer is chosen from a lung cancer (e.g., a non-small cell lung cancer (NSCLC) (e.g., a NSCLC with squamous and/or non-squamous histology, or a NSCLC adenocarcinoma)), a melanoma (e.g., an advanced melanoma), a renal cancer (e.g., a renal cell carcinoma), a liver cancer, a myeloma (e.g., a multiple myeloma), a prostate cancer, a breast cancer (e.g., a breast cancer that does not express one, two or all of estrogen receptor, progesterone receptor, or Her2/neu, e.g., a triple negative breast cancer), a colorectal cancer, a pancreatic cancer, a head and neck cancer (e.g., head and neck squamous cell carcinoma (HNSCC), anal cancer, gastro-esophageal cancer, thyroid cancer, cervical cancer, a lymphoproliferative disease (e.g., a post-transplant lymphoproliferative disease) or a hematological cancer, T-cell lymphoma, B-cell lymphoma, a non-Hogdkin lymphoma, or a leukemia (e.g., a myeloid leukemia or a lymphoid leukemia).

In another embodiment, the cancer is chosen form a carcinoma (e.g., advanced or metastatic carcinoma), melanoma or a lung carcinoma, e.g., a non-small cell lung carcinoma.

In one embodiment, the cancer is a lymphoma, e.g., diffuse large B-cell lymphoma, Hodgkin lymphoma, non-Hodgkin's lymphoma.

In one embodiment, the cancer is a breast cancer, e.g., metastic breast cancer.

In one embodiment, the cancer is leukemia, e.g., chronic myelogenous leukemia.

In one embodiment, the cancer is a head and neck cancer, e.g., head and neck squamous cell carcinoma (HNSCC).

In one embodiment, the cancer is myelodysplastic syndrome.

In one embodiment, the cancer is a bladder cancer (e.g., transitional cell carcinoma).

In one embodiment, the cancer is a colon cancer.

In one embodiment, the cancer is a lung cancer, e.g., a non-small cell lung cancer (NSCLC), e.g., stage IV or recurrent NSCLC, a NSCLC adenocarcinoma, or a NSCLC squamous cell carcinoma or small cell lung cancer.

In one embodiment, the cancer is skin cancer, e.g., melanoma (e.g., stage III or IV melanoma) or Merkel cell carcinoma. In one embodiment, the cancer is a melanoma, e.g., an advanced melanoma. In one embodiment, the cancer is an advanced or unresectable melanoma that does not respond to other therapies. In other embodiments, the cancer is a melanoma with a BRAF mutation (e.g., a BRAF V600 mutation). In yet other embodiments, the anti-PD-L1 antibody molecule is administered after treatment with an anti-CTLA-4 antibody (e.g., ipilimumab) with or without a BRAF inhibitor (e.g., vemurafenib or dabrafenib).

In another embodiment, the cancer is a hepatocarcinoma, e.g., an advanced hepatocarcinoma, with or without a viral infection, e.g., a chronic viral hepatitis.

In another embodiment, the cancer is a prostate cancer, e.g., an advanced prostate cancer.

In yet another embodiment, the cancer is a myeloma, e.g., multiple myeloma.

In yet another embodiment, the cancer is a renal cancer, e.g., a renal cell carcinoma (RCC) (e.g., a metastatic RCC or clear cell renal cell carcinoma (CCRCC), e.g., advanced or metastatic clear-cell renal cell carcinoma).

In one embodiment, the cancer microenvironment has an elevated level of PD-L1 expression. Alternatively, or in combination, the cancer microenvironment can have increased IFNγ and/or CD8 expression. In one embodiment, alternatively or in combination, the subject has elevated level of Bim expression (e.g., in PD-1+CD8+ T cells compared to PD-1-CD8+ T cells).

In some embodiments, the subject has, or is identified as having, a tumor that has one or more of high PD-L1 level or expression, or as being Tumor Infiltrating Lymphocyte (TIL)+(e.g., as having an increased number of TILs), or both. In certain embodiments, the subject has, or is identified as having, a tumor that has high PD-L1 level or expression and that is TIL+. In some embodiments, the methods described herein further include identifying a subject based on having a tumor that has one or more of high PD-L1 level or expression, or as being TIL+, or both. In certain embodiments, the methods described herein further include identifying a subject based on having a tumor that has high PD-L1 level or expression and as being TIL+. In some embodiments, tumors that are TIL+ are positive for CD8 and IFNγ. In some embodiments, the subject has, or is identified as having, a high percentage of cells that are positive for one, two or more of PD-L1, CD8, and/or IFNγ. In certain embodiments, the subject has or is identified as having a high percentage of cells that are positive for all of PD-L1, CD8, and IFNγ. The subject can be identified prior to, during, or after receiving a therapy, e.g., an anti-PD-L1 antibody molecule therapy and/or another therapy as described herein. In one embodiment, the subject is identified prior to receiving a therapy, e.g., a therapy as described herein (e.g., prior to the onset of a therapy or between treatment intervals).

In some embodiments, the methods described herein further include identifying a subject based on having a high percentage of cells that are positive for one, two or more of PD-L1, CD8, and/or IFNγ. In certain embodiments, the methods described herein further include identifying a subject based on having a high percentage of cells that are positive for all of PD-L1, CD8, and IFNγ. In some embodiments, the subject has, or is identified as having, one, two or more of PD-L1, CD8, and/or IFNγ, and one or more of a lung cancer, e.g., squamous cell lung cancer or lung adenocarcinoma; a head and neck cancer; a squamous cell cervical cancer; a stomach cancer; an esophageal cancer; a thyroid cancer; a melanoma, and/or a nasopharyngeal cancer (NPC). In certain embodiments, the methods described herein further describe identifying a subject based on having one, two or more of PD-L1, CD8, and/or IFNγ, and one or more of a lung cancer, e.g., squamous cell lung cancer or lung adenocarcinoma; a head and neck cancer; a squamous cell cervical cancer; a stomach cancer; a thyroid cancer; a melanoma, and or a nasopharyngeal cancer. The subject can be identified prior to, during, or after receiving a therapy, e.g., an anti-PD-L1 antibody molecule therapy and/or another therapy as described herein. In one embodiment, the subject is identified prior to receiving a therapy, e.g., a therapy as described herein (e.g., prior to the onset of a therapy or between treatment intervals).

Methods and compositions disclosed herein are useful for treating metastatic lesions associated with the aforementioned cancers.

In a further aspect, the invention provides a method of treating an infectious disease in a subject, comprising administering to a subject a therapeutically effective amount of an anti-PD-L1 antibody molecule described herein, alone or in combination with one or more agents or procedures. In one embodiment, the infection disease is chosen from hepatitis (e.g., hepatitis C infection), or sepsis.

Still further, the invention provides a method of enhancing an immune response to an antigen in a subject, comprising administering to the subject: (i) the antigen; and (ii) an anti-PD-L1 antibody molecule, such that an immune response to the antigen in the subject is enhanced. The antigen can be, for example, a tumor antigen, a viral antigen, a bacterial antigen or an antigen from a pathogen.

The anti-PD-L1 antibody molecule can be administered to the subject systemically (e.g., orally, parenterally, subcutaneously, intravenously, rectally, intramuscularly, intraperitoneally, intranasally, transdermally, or by inhalation or intracavitary installation), topically, or by application to mucous membranes, such as the nose, throat and bronchial tubes.

Dosages and therapeutic regimens of the anti-PD-L1 antibody molecule can be determined by a skilled artisan. In certain embodiments, the anti-PD-L1 antibody molecule is administered by injection (e.g., subcutaneously or intravenously) at a dose of about 1 to 30 mg/kg, e.g., about 5 to 25 mg/kg, about 10 to 20 mg/kg, about 1 to 5 mg/kg, or about 3 mg/kg. The dosing schedule can vary from e.g., once a week to once every 2, 3, or 4 weeks. In one embodiment, the anti-PD-L1 antibody molecule is administered at a dose from about 10 to 20 mg/kg every other week. In one embodiment, the anti-PD-L1 antibody molecule is administered, alone or in combination (e.g., in combination with an anti-LAG-3 antibody molecule), at a dose of less than, or about, 5 mg/kg; less than, or about, 4 mg/kg; less than, or about, 3 mg/kg; less than, or about, 2 mg/kg; less than, or about, 1 mg/kg, every other week. In one embodiment, the anti-PD-L1 antibody molecule is administered at a dose of 1 to 5 mg/kg every other week; 1 to 4 mg/kg every other week, 1 to 3 mg/kg every other week, or 1 to 2 mg/kg every other week. In one embodiment, the anti-LAG-3 antibody molecule is administered, alone or in combination (e.g., in combination with an anti-PD-L1 antibody molecule) at a dose of 1 to 5 mg/kg every other week; 1 to 4 mg/kg every other week, 1 to 3 mg/kg every other week, or 1 to 2 mg/kg every other week.

The antibody molecules described herein can be used in the methods described herein, although other anti-PD-L1 antibodies can be used instead, or in combination with an anti-PD-L1 antibody molecule of the invention.

Combination Therapies

The methods and compositions described herein can be used in combination with other agents or therapeutic modalities. In one embodiment, the methods described herein include administering to the subject an anti-PD-L1 antibody molecule as described herein, in combination with an agent or therapeutic procedure or modality, in an amount effective to treat or prevent a disorder. The anti-PD-L1 antibody molecule and the agent or therapeutic procedure or modality can be administered simultaneously or sequentially in any order. Any combination and sequence of the anti-PD-L1 antibody molecules and other therapeutic agents, procedures or modalities (e.g., as described herein) can be used. The antibody molecule and/or other therapeutic agents, procedures or modalities can be administered during periods of active disorder, or during a period of remission or less active disease. The antibody molecule can be administered before the other treatment, concurrently with the treatment, post-treatment, or during remission of the disorder.

In certain embodiments, the methods and compositions described herein are administered in combination with one or more of other antibody molecules, chemotherapy, other anti-cancer therapy (e.g., targeted anti-cancer therapies, gene therapy, viral therapy, RNA therapy bone marrow transplantation, nanotherapy, or oncolytic drugs), cytotoxic agents, immune-based therapies (e.g., cytokines or cell-based immune therapies), surgical procedures (e.g., lumpectomy or mastectomy) or radiation procedures, or a combination of any of the foregoing. The additional therapy may be in the form of adjuvant or neoadjuvant therapy. In some embodiments, the additional therapy is an enzymatic inhibitor (e.g., a small molecule enzymatic inhibitor) or a metastatic inhibitor. Exemplary cytotoxic agents that can be administered in combination with include antimicrotubule agents, topoisomerase inhibitors, anti-metabolites, mitotic inhibitors, alkylating agents, anthracyclines, *vinca* alkaloids, intercalating agents, agents capable of interfering with a signal transduction pathway, agents that promote apoptosis, proteosome inhibitors, and radiation (e.g., local or whole body irradiation (e.g., gamma irradiation). In other embodiments, the additional therapy is surgery or radiation, or a combination thereof. In other embodiments, the additional therapy is a therapy targeting one or more of PI3K/AKT/mTOR pathway, an HSP90 inhibitor, or a tubulin inhibitor.

Alternatively, or in combination with the aforesaid combinations, the methods and compositions described herein can be administered in combination with one or more of: an immunomodulator (e.g., an activator of a costimulatory molecule or an inhibitor of an inhibitory molecule, e.g., an immune checkpoint molecule); a vaccine, e.g., a therapeutic cancer vaccine; or other forms of cellular immunotherapy.

Exemplary non-limiting combinations and uses of the anti-PD-L1 antibody molecules include the following.

In certain embodiments, the anti-PD-L1 antibody molecule is administered in combination with a modulator of a costimulatory molecule or an inhibitory molecule, e.g., a co-inhibitory ligand or receptor.

In one embodiment, the anti-PD-L1 antibody molecule is administered in combination with a modulator, e.g., agonist, of a costimulatory molecule. In one embodiment, the agonist of the costimulatory molecule is chosen from an agonist (e.g., an agonistic antibody or antigen-binding fragment thereof, or a soluble fusion) of OX40, CD2, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3 or CD83 ligand.

In one embodiment, the anti-PD-L1 antibody molecule is administered in combination with an inhibitor of an inhibitory (or immune checkpoint) molecule chosen from PD-1, PD-L2, CTLA-4, TIM-3, LAG-3, CEACAM (e.g., CEACAM-1, CEACAM-3 and/or CEACAM-5), VISTA, BTLA, TIGIT, LAIR1, CD160, 2B4 and/or TGFR beta. Inhibition of an inhibitory molecule can be performed by inhibition at the DNA, RNA or protein level. In embodiments, an inhibitory nucleic acid (e.g., a dsRNA, siRNA or shRNA), can be used to inhibit expression of an inhibitory molecule. In other embodiments, the inhibitor of an inhibitory signal is, a polypeptide e.g., a soluble ligand, or an antibody or antigen-binding fragment thereof, that binds to the inhibitory molecule. In one embodiment, the inhibitor is a soluble ligand (e.g., a CTLA-4-Ig), or an antibody or antibody fragment that binds to PD-1, PD-L2 or CTLA-4. For example, the anti-PD-L1 antibody molecule can be administered in combination with an anti-CTLA-4 antibody, e.g., ipilimumab, for example, to treat a cancer (e.g., a cancer chosen from: a melanoma, e.g., a metastatic melanoma; a lung cancer, e.g., a non-small cell lung carcinoma; or a prostate cancer). In one embodiment, the anti-PD-1 antibody molecule is administered after treatment with an anti-CTLA-4 antibody (e.g., ipilimumab) with or without a BRAF inhibitor (e.g., vemurafenib or dabrafenib).

In another embodiment, the anti-PD-L1 antibody molecule is administered in combination with an anti-LAG-3 antibody or antigen-binding fragment thereof.

In another embodiment, the anti-PD-L1 antibody molecule is administered in combination with an anti-TIM-3 antibody or antigen-binding fragment thereof.

In yet other embodiments, the anti-PD-L1 antibody molecule is administered in combination with an anti-LAG-3 antibody and an anti-TIM-3 antibody (or antigen-binding fragments thereof).

In another embodiment, the anti-PD-L1 antibody is administered in combination with a CEACAM inhibitor (e.g., CEACAM-1, CEACAM-3 and/or CEACAM-5), e.g., an anti-CEACAM antibody molecule. In another embodiment, the anti-PD-L1 antibody molecule is administered in combination with a CEACAM-1 inhibitor, e.g., an anti-CEACAM-1 antibody molecule. In another embodiment, the anti-PD-L1 antibody molecule is administered in combination with a CEACAM-5 inhibitor, e.g., an anti-CEACAM-5 antibody molecule.

The combination of antibodies recited herein can be administered separately, e.g., as separate antibodies or antigen-binding fragments thereof, or linked, e.g., as a bispecific or trispecific antibody molecule. In one embodiment, a bispecific antibody that includes an anti-PD-L1 antibody molecule and an anti-TIM-3, anti-CEACAM (e.g., CEACAM-1, CEACAM-3 and/or CEACAM-5), or anti-LAG-3 antibody, or an antigen-binding fragment thereof, is administered. In certain embodiments, the combination of antibodies recited herein is used to treat a cancer, e.g., a cancer as described herein (e.g., a solid tumor or a hematologic malignancy).

In some embodiments, the antibody molecule (e.g., mono-, bi- or trispecific antibody) for TIM-3, LAG-3 and/or PD-1 used in any of the methods and compositions disclosed herein includes an amino acid sequence, or is encoded by a nucleotide sequence as described herein (e.g., as disclosed in the section entitled "Inhibitors of Immune Checkpoint Molecules" starting on page 218 hereinbelow (including all publications mentioned therein).

In other embodiments, the anti-PD-L1 antibody molecule is administered in combination with a cytokine. The cytokine can be administered as a fusion to the anti-PD-L1 antibody molecule, or as separate compositions. In one embodiment, the anti-PD-L1 antibody is administered in combination with one, two, three or more cytokines, e.g., as a fusion molecule or as separate compositions. In one embodiment, the cytokine is an interleukin (IL) chosen from one, two, three or more of IL-1, IL-2, IL-15 or IL-21. In certain embodiments, the combination of anti-PD-L1 antibody molecule and the cytokine described herein is used to treat a cancer, e.g., a cancer as described herein (e.g., a solid tumor).

In certain embodiments, the anti-PD-L1 antibody molecule is administered in combination with an antibody specific against an HLA C, e.g., an antibody specific to Killer-cell Immunoglobulin-like Receptors (also referred to herein as an "anti-KIR antibody"). In certain embodiments, the combination of anti-PD-L1 antibody molecule and anti-KIR antibody is used to treat a cancer, e.g., a cancer as described herein (e.g., a solid tumor, e.g., an advanced solid tumor).

In one embodiment, the anti-PD-L1 antibody molecule is administered in combination with a cellular immunotherapy (e.g., Provenge® (e.g., Sipuleucel-T)), and optionally in combination with cyclophosphamide. In certain embodiments, the combination of anti-PD-L1 antibody molecule, Provenge® and/or cyclophosphamide is used to treat a cancer, e.g., a cancer as described herein (e.g., a prostate cancer, e.g., an advanced prostate cancer).

In another embodiment, the anti-PD-L1 antibody molecule is administered in combination with a vaccine, e.g., a cancer vaccine, (e.g., a dendritic cell renal carcinoma (DC-RCC) vaccine). In one embodiment, the vaccine is peptide-based, DNA-based, RNA-based, or antigen-based, or a combination thereof. In embodiments, the vaccine comprises one or more peptides, nucleic acids (e.g., DNA or RNA), antigens, or a combination thereof. In certain embodiments, the combination of anti-PD-L1 antibody molecule and the DC-RCC vaccine is used to treat a cancer, e.g., a cancer as described herein (e.g., a renal carcinoma, e.g., metastatic renal cell carcinoma (RCC) or clear cell renal cell carcinoma (CCRCC)).

In another embodiment, the anti-PD-1 antibody molecule is administered in combination with an adjuvant.

In yet another embodiment, the anti-PD-L1 antibody molecule is administered in combination with chemotherapy, and/or immunotherapy. For example, the anti-PD-L1 antibody molecule can be used to treat a myeloma, alone or in combination with one or more of: chemotherapy or other anti-cancer agents (e.g., thalidomide analogs, e.g., lenalidomide), an anti-TIM-3 antibody, tumor antigen-pulsed dendritic cells, fusions (e.g., electrofusions) of tumor cells and dendritic cells, or vaccination with immunoglobulin idiotype produced by malignant plasma cells. In one embodiment, the anti-PD-L1 antibody molecule is used in combination with an anti-TIM-3 antibody to treat a myeloma, e.g., a multiple myeloma.

In one embodiment, the anti-PD-L1 antibody molecule is used in combination with chemotherapy to treat a lung cancer, e.g., non-small cell lung cancer. In one embodiment, the anti-PD-L1 antibody molecule is used with standard lung, e.g., NSCLC, chemotherapy, e.g., platinum doublet therapy, to treat lung cancer. In yet other embodiments, the anti-PD-L1 antibody molecule is used in combination with an indoleamine-pyrrole 2,3-dioxygenase (IDO) inhibitor (e.g., (4E)-4-[(3-chloro-4-fluoroanilino)-nitrosomethylidene]-1,2,5-oxadiazol-3-amine (also known as INCB24360), indoximod (1-methyl-D-tryptophan), α-cyclohexyl-5H-Imidazo[5,1-a]isoindole-5-ethanol (also known as NLG919), etc.)) in a subject with advanced or metastatic cancer (e.g., a patient with metastic and recurrent NSCL cancer).

In yet other embodiments, the anti-PD-L1 antibody molecule is used in combination with one or more of: an immune-based strategy (e.g., interleukin-2 or interferon-α), a targeting agent (e.g., a VEGF inhibitor such as a monoclonal antibody to VEGF); a VEGF tyrosine kinase inhibitor such as sunitinib, sorafenib, axitinib and pazopanib; an RNAi inhibitor; or an inhibitor of a downstream mediator of VEGF signaling, e.g., an inhibitor of the mammalian target of rapamycin (mTOR), e.g., everolimus and temsirolimus. Any of such combinations can be used to treat a renal cancer, e.g., renal cell carcinoma (RCC) (e.g., clear cell renal cell carcinoma (CCRCC)) or metastatic RCC.

In some embodiments, the anti-PD-L1 antibody molecule, e.g., the anti-PD-L1 antibody molecule described herein, is used in combination with a MEK inhibitor (e.g., a MEK inhibitor as described herein). In some embodiments, the combination of the anti-PD-L1 antibody and the MEK inhibitor is used to treat a cancer (e.g., a cancer described herein). In some embodiments, the cancer treated with the combination is chosen from a melanoma, a colorectal cancer, a non-small cell lung cancer, an ovarian cancer, a breast cancer, a prostate cancer, a pancreatic cancer, a hematological malignancy or a renal cell carcinoma. In certain embodiments, the cancer includes a BRAF mutation (e.g., a BRAF V600E mutation), a BRAF wildtype, a KRAS wildtype or an activating KRAS mutation. The cancer may be at an early, intermediate or late stage.

In another embodiment, the anti-PD-L1 antibody molecule is used in combination with one, two or all of oxaliplatin, leucovorin or 5-FU (e.g., a FOLFOX co-treatment). Alternatively or in combination, combination further includes a VEGF inhibitor (e.g., a VEGF inhibitor as disclosed herein). In some embodiments, the combination of the anti-PD-L1 antibody, the FOLFOX co-treatment, and the VEGF inhibitor is used to treat a cancer (e.g., a cancer described herein). In some embodiments, the cancer treated with the combination is chosen from a melanoma, a colorectal cancer, a non-small cell lung cancer, an ovarian cancer, a breast cancer, a prostate cancer, a pancreatic cancer, a hematological malignancy or a renal cell carcinoma. The cancer may be at an early, intermediate or late stage.

In other embodiments, the anti-PD-L1 antibody molecule is administered with a tyrosine kinase inhibitor (e.g., axitinib) to treat renal cell carcinoma and other solid tumors.

In other embodiments, the anti-PD-L1 antibody molecule is administered with a 4-1BB receptor targeting agent (e.g., an antibody that stimulates signaling through 4-1BB (CD-137), e.g., PF-2566). In one embodiment, the anti-PD-L1 antibody molecule is administered in combination with a tyrosine kinase inhibitor (e.g., axitinib) and a 4-1BB receptor targeting agent.

The anti-PD-L1 antibody molecule can be bound to a substance, e.g., a cytotoxic agent or moiety (e.g., a therapeutic drug; a compound emitting radiation; molecules of plant, fungal, or bacterial origin; or a biological protein (e.g., a protein toxin) or particle (e.g., a recombinant viral particle, e.g., via a viral coat protein). For example, the antibody can be coupled to a radioactive isotope such as an α-, β-, or γ-emitter, or a β- and γ-emitter.

Any combination and sequence of the anti-PD-L1 antibody molecules and other therapeutic agents, procedures or modalities (e.g., as described herein) can be used. The antibody molecule and/or other therapeutic agents, procedures or modalities can be administered during periods of active disorder, or during a period of remission or less active disease. The antibody molecule can be administered before the other treatment, concurrently with the treatment, post-treatment, or during remission of the disorder.

Additional Combination Therapies

The methods and compositions described herein (e.g., PD-L1 antibodies and methods of using them) can be used in combination with other agents or therapeutic modalities, e.g., a second therapeutic agent chosen from one or more of the agents listed in Table 6. In one embodiment, the methods described herein include administering to the subject an anti-PD-L1 antibody molecule as described herein (optionally in combination with one or more inhibitors of PD-1, LAG-3, TIM-3, CEACAM (e.g., CEACAM-1, CEACAM-3, and/or CEACAM-5), or CTLA-4)), further include administration of a second therapeutic agent chosen from one or more of the agents listed in Table 6, in an amount effective to treat or prevent a disorder, e.g., a disorder as described herein, e.g., a cancer. When administered in combination, the anti-PD-L1 antibody molecule, the additional agent (e.g., second or third agent), or all, can be administered in an amount or dose that is higher, lower or the same than the amount or dosage of each agent used individually, e.g., as a monotherapy. In certain embodiments, the administered amount or dosage of the anti-PD-L1 antibody, the additional agent (e.g., second or third agent), or all, is lower (e.g., at least 20%, at least 30%, at least 40%, or at least 50%) than the amount or dosage of each agent used individually, e.g., as a monotherapy. In other embodiments, the amount or dosage of the anti-PD-L1 antibody, the additional agent (e.g., second or third agent), or all, that results in a desired effect (e.g., treatment of cancer) is lower (e.g., at least 20%, at least 30%, at least 40%, or at least 50% lower).

In other embodiments, the second therapeutic agent is chosen from one or more of the agents listed in Table 6 In one embodiment, the cancer is chosen from a lung cancer (e.g., a non-small cell lung cancer (NSCLC) (e.g., a NSCLC with squamous and/or non-squamous histology, or a NSCLC adenocarcinoma), or disclosed in a publication listed in Table 6. In some embodiments, the second therapeutic agent is chosen from one or more of: 1) a protein kinase C (PKC) inhibitor; 2) a heat shock protein 90 (HSP90) inhibitor; 3) an inhibitor of a phosphoinositide 3-kinase (PI3K) and/or target of rapamycin (mTOR); 4) an inhibitor of cytochrome P450 (e.g., a CYP17 inhibitor or a 17alpha-Hydroxylase/C17-20 Lyase inhibitor); 5) an iron chelating agent; 6) an aromatase inhibitor; 7) an inhibitor of p53, e.g., an inhibitor of a p53/Mdm2 interaction; 8) an apoptosis inducer; 9) an angiogenesis inhibitor; 10) an aldosterone synthase inhibitor; 11) a smoothened (SMO) receptor inhibitor; 12) a prolactin receptor (PRLR) inhibitor; 13) a Wnt signaling inhibitor; 14) a CDK4/6 inhibitor; 15) a fibroblast growth factor receptor 2 (FGFR2)/fibroblast growth factor receptor 4 (FGFR4) inhibitor; 16) an inhibitor of macrophage colony-stimulating factor (M-CSF); 17) an inhibitor of one or more of c-KIT, histamine release, Flt3 (e.g., FLK2/STK1) or PKC; 18) an inhibitor of one or more of VEGFR-2 (e.g., FLK-1/KDR), PDGFRbeta, c-KIT or Raf kinase C; 19) a somatostatin agonist and/or a growth hormone release inhibitor; 20) an anaplastic lymphoma kinase (ALK) inhibitor; 21) an insulin-like growth factor 1 receptor (IGF-1R) inhibitor; 22) a P-Glycoprotein 1 inhibitor; 23) a vascular endothelial growth factor receptor (VEGFR) inhibitor; 24) a BCR-ABL kinase inhibitor; 25) an FGFR inhibitor; 26) an inhibitor of CYP11B2; 27) a HDM2 inhibitor, e.g., an inhibitor of the HDM2-p53 interaction; 28) an inhibitor of a tyrosine kinase; 29) an inhibitor of c-MET; 30) an inhibitor of JAK; 31) an inhibitor of DAC; 32) an inhibitor of 11β-hydroxylase; 33) an inhibitor of IAP; 34) an inhibitor of PIM kinase; 35) an inhibitor of Porcupine; 36) an inhibitor of BRAF, e.g., BRAF V600E or wild-type BRAF; 37) an inhibitor of HER3; 38) an inhibitor of MEK; or 39) an inhibitor of a lipid kinase, e.g., as described herein and in Table 6.

In one embodiment, the second therapeutic agent is chosen from one or more of: Compound A8, Compound A17, Compound A23, Compound A24, Compound A27, Compound A29, Compound A33, and Compound A13.

In other embodiments, the second therapeutic agent is chosen from one or more of: Compound A5, Compound A8, Compound A17, Compound A23, Compound A24, Compound A29, and Compound A40.

In other embodiments, the second therapeutic agent is chosen from one or more of: Compound A9, Compound A16, Compound A17, Compound A21, Compound A22, Compound A25, Compound A28, Compound A48, and Compound 49.

In some embodiments, the second therapeutic agent is administered at a therapeutic or lower-than therapeutic dose. In certain embodiments, the concentration of the second therapeutic agent that is required to achieve inhibition, e.g., growth inhibition, is lower when the second therapeutic agent is administered in combination with the anti-PD-L1 antibody molecule than when the second therapeutic agent is administered individually. In certain embodiments, the concentration of the anti-PD-L1 antibody molecule that is required to achieve inhibition, e.g., growth inhibition, is lower when the anti-PD-L1 antibody molecule is administered in combination with the second therapeutic agent than when the anti-PD-L1 antibody molecule is administered individually. In certain embodiments, in a combination therapy, the concentration of the second therapeutic agent that is required to achieve inhibition, e.g., growth inhibition, is lower than the therapeutic dose of the second therapeutic agent as a monotherapy, e.g., 10-20%, 20-30%, 30-40%, 40-50%, 50-60%, 60-70%, 70-80%, or 80-90% lower. In certain embodiments, in a combination therapy, the concentration of the anti-PD-L1 antibody molecule that is required to achieve inhibition, e.g., growth inhibition, is lower than the therapeutic dose of the anti-PD-L1 antibody molecule as a monotherapy, e.g., 10-20%, 20-30%, 30-40%, 40-50%, 50-60%, 60-70%, 70-80%, or 80-90% lower.

Additional Features and Embodiments

Alternatively, or in combination with, the methods disclosed herein, the invention features a method of treating (e.g., inhibiting, reducing, ameliorating, or preventing) a disorder, e.g., a hyperproliferative condition or disorder (e.g., a cancer) in a subject. The method includes administering to the subject a combination of two, three or more therapeutic agents chosen from one, two or all of the following categories (i)-(iii): (i) an agent that enhances antigen (e.g., tumor antigen) presentation; (ii) an agent that enhances an effector cell response (e.g., B cell and/or T cell activation and/or mobilization); or (iii) an agent that decreases tumor immunosuppression, thereby treating the disorder, e.g., the hyperproliferative condition or disorder (e.g., the cancer). In some embodiments, the combination includes a PD-L1 inhibitor (e.g., an anti-PD-L1 antibody molecule as described herein). The cancer treated can be, e.g., a cancer described herein, such as lung cancer (squamous), lung cancer (adenocarcinoma), head and neck cancer, cervical cancer (squamous), stomach cancer, thyroid cancer, melanoma, nasopharyngeal cancer, or breast cancer.

In another aspect, the invention features a method of reducing an activity (e.g., growth, survival, or viability, or all), of a hyperproliferative (e.g., a cancer) cell. The method includes contacting the cell with a combination of two, three or more therapeutic agents chosen from one, two or all of the following categories (i)-(iii): (i) an agent that enhances antigen (e.g., tumor antigen) presentation; (ii) an agent that enhances an effector cell response (e.g., B cell and/or T cell activation and/or mobilization); or (iii) an agent that decreases tumor immunosuppression, thereby reducing an activity in the hyperproliferative cell. In some embodiments, the combination includes a PD-L1 inhibitor (e.g., an anti-PD-L1 antibody molecule as described herein). The method can be performed in a subject, e.g., as part of a therapeutic protocol. The cancer cell can be, e.g., a cell from a cancer described herein, such as lung cancer (squamous), lung cancer (adenocarcinoma), head and neck cancer, cervical cancer (squamous), stomach cancer, thyroid cancer, melanoma, nasopharyngeal cancer, or breast cancer.

In certain embodiments of the methods disclosed herein, the method further includes determining the level and/or distribution of an immune cell (e.g., a T cell) infiltrate (e.g., the level and/or distribution of tumor infiltrating lymphocytes (TIL)) in the subject. In one embodiment, the level and/or distribution of the immune cell infiltrate is determined in vivo, e.g., non-invasively (e.g., by detecting an antibody to a T cell marker detectably labeled using a suitable imaging technique, e.g., positron emission tomography (PET) scan). In other embodiments, the level of the immune cell infiltrate is determined in a sample (e.g., a tumor biopsy) acquired from the subject (e.g., using immunohistochemical techniques). In some embodiments, an elevated level and/or more widespread distribution of the TIL in a cancer, e.g., a tumor, (e.g., relative to a reference or a control) is indicative of a better prognosis for the subject, e.g., more positive therapeutic outcome. In some embodiments, a decreased level and/or less widespread distribution of the TIL in a cancer, e.g., a tumor, (e.g., relative to a reference or a control) is indicative of a worse prognosis for the subject, e.g., more negative therapeutic outcome. In some embodiments, the reference is a subject at a different time interval, e.g., prior to, or an earlier stage in therapy). In embodiments, responsive to a low level of, or no detectable, tumor infiltrate in the subject, one or more agents of categories (i) or (ii), or both (i) and (ii), is/are administered. In other embodiments, responsive to a detectable level, or an elevated level, of tumor infiltrate in the subject, one or more agents of category (iii) is/are administered. The detection steps can also be used, e.g., to monitor the effectiveness of a therapeutic agent described herein. For example, the detection step can be used to monitor the effectiveness of therapeutic agents of categories (i), (ii) and/or (iii).

In another aspect, the invention features a composition (e.g., one or more compositions or dosage forms), that includes a combination of two, three or more therapeutic agents chosen from one, two or all of the following categories (i)-(iii): (i) an agent that enhances antigen (e.g., tumor antigen) presentation; (ii) an agent that enhances an effector cell response (e.g., activation and/or mobilization of B cell and/or T cell); or (iii) an agent that decreases tumor immunosuppression. In some embodiments, the combination includes a PD-L1 inhibitor (e.g., an anti-PD-L1 antibody molecule as described herein).

In yet another aspect, the invention features a composition (e.g., one or more compositions or dosage forms as described hereom), for use in treating a disorder, e.g., a cancer. In embodiments, the composition for use includes a combination of two, three or more therapeutic agents chosen from one, two or all of the following categories (i)-(iii): (i) an agent that enhances antigen (e.g., tumor antigen) presentation; (ii) an agent that enhances an effector cell response (e.g., activation and/or mobilization of B cell and/or T cell); or (iii) an agent that decreases tumor immunosuppression. In some embodiments, the combination used includes a PD-L1 inhibitor (e.g., an anti-PD-L1 antibody molecule as described herein). The cancer can be, e.g., a cancer described herein, such as lung cancer (squamous), lung cancer (adenocarcinoma), head and neck cancer, cervical cancer (squamous), stomach cancer, thyroid cancer, melanoma, nasopharyngeal cancer, or breast cancer.

Formulations, e.g., dosage formulations, and kits, e.g., therapeutic kits, that include a combination of two, three or more therapeutic agents chosen from one, two or all of the following categories (i)-(iii): (i) an agent that enhances antigen (e.g., tumor antigen) presentation; (ii) an agent that enhances an effector cell response (e.g., activation and/or mobilization of B cell and/or T cell); or (iii) an agent that decreases tumor immunosuppression, thereby reducing an activity in the cell, and (optionally) instructions for use, are also disclosed. In some embodiments, the combination includes a PD-L1 inhibitor (e.g., an anti-PD-L1 antibody molecule as described herein).

The combinations of therapeutic agents disclosed herein include two or more therapeutic agents described herein. The therapeutic agents in the combination can belong to the same category, e.g., two or more therapeutic agents of category (i), or can include at least one agent of two or more categories (e.g., a therapeutic agent of category (i) combined with a therapeutic agent of category (ii)), as described below. Certain therapeutic agents can belong to two or more categories of categories (i)-(iii). For example, a therapeutic agent (e.g., a GITR agonist, an IDO antagonist, a TGF-b inhibitor, among others) can act as a therapeutic agent in multiple categories.

In certain embodiments, the combination disclosed herein includes one, two, three, four or more therapeutic agents that enhance antigen (e.g., tumor antigen) presentation (referred to herein as an "antigen-presentation combination"). In certain embodiments, the antigen presentation combination includes one or more of: an agent that enhances antigen presentation (e.g., a vaccine, e.g., a cell- or antigen-based vaccine); an agent that enhances lysis of tumor cells (e.g., an oncolytic virus; an agent that stimulates (e.g., disinhibits) a phagocyte, e.g., a Type I interferon (IFN) activator (e.g., a TLR agonist, a RIG-I-like receptor agonist (RLRs)), and/or an agent that activates and/or recruits a dendritic cell or a macrophage (e.g., a macrophage I), e.g., a bi- or tri-specific cell engager.

In some embodiments, the antigen-presentation combination includes one, two, three, four, five or more therapeutic agents chosen from: (i) an agonist of Stimulator of Interferon Genes (a STING agonist), (ii) an agonist of a Toll-like receptor (TLR) (e.g., an agonist of TLR-3, -4, -5, -7, -8, or -9), (iii) a TIM-3 modulator (e.g., an anti-TIM-3 antibody molecule), (iv) a vascular endothelial growth factor receptor (VEGFR) inhibitor, (v) a c-Met inhibitor, (vi) a TGFb inhibitor (e.g., an anti-TGFb antibody), (vii) an IDO/TDO inhibitor, (viii) an A2AR antagonist, (ix) an oncolytic virus, (x) a vaccine (e.g., a scaffold vaccine), or (xi) a bi- or tri-specific cell engager. Any combination of the aforesaid agents (i)-(xi) can be used in the antigen-presentation combination. In one exemplary embodiment, the antigen-presentation combination includes a STING agonist. In another exemplary embodiment, the antigen-presentation combination includes a TLR agonist (e.g., a TLR7 agonist). In another exemplary embodiment, the antigen-presentation combination includes a STING agonist and a TLR agonist (e.g., a TLR7 agonist). In some embodiments, the antigen presentation combination is chosen from a STING agonist, a TLR agonist, an A2AR antagonist, or an oncolytic virus or a combination thereof, and optionally, one or more of (iii)-(vii) or (x)-(xi). In some embodiments, the antigen presentation combination is chosen from a STING agonist or a TLR agonist, or a combination of both, and optionally, one or more of (iii)-(xi). In another embodiment, the antigen-presentation combination includes a STING agonist, a TLR agonist (e.g., a TLR7 agonist) and a TIM-3 modulator (e.g., an anti-TIM-3 inhibitor). In another embodiment, the antigen-presentation combination includes a STING agonist, a TLR agonist (e.g., a TLR7 agonist) and a VEGFR inhibitor. In another embodiment, the antigen-presentation combination includes a STING agonist, a TLR agonist (e.g., a TLR7 agonist) and a c-MET inhibitor. In yet other embodiments, the antigen-presenting combination includes an oncolytic virus. In other embodiments, the antigen-presenting combination includes an oncolytic virus and a cytokine, e.g., an oncolytic virus expressing one or more of GM-CSF, or a CSF (e.g., CSF1, or CSF2). In some embodiments, the antigen-presenting combination includes a bi- or tri-specific cell engager, e.g., a bi- or tri-specific antibody molecule to CD47 and CD19, with or without an Fc domain. In some embodiments, the antigen-presenting combination includes a TGFb inhibitor (e.g., an anti-TGFb antibody). In other embodiments, the antigen-presenting combination includes an IDO/TDO inhibitor. In yet other embodiments, the antigen-presenting combination includes an A2AR antagonist. In yet other embodiments, the antigen-presenting combination includes a vaccine (e.g., IL-2 in combination with MUC1, or a dendritic cell based vaccine (e.g., Provenge®)). In yet other embodiments, the antigen-presenting combination includes a vaccine and a TLR agonist (e.g., a TLR agonist as described herein). In certain embodiment, the antigen-presentation combination includes a vaccine and a STING agonist. In certain embodiment, the antigen-presentation combination includes a vaccine, a STING agonist and a TLR agonist.

In certain embodiments, the combination includes one, two, three, four, five or more therapeutic agents that enhance an effector cell response (referred to herein as an "effector cell combination"). In some embodiments, the effector cell combination includes a lymphocyte activator, e.g., an NK cell activator and/or a T cell activator. In some embodiments, the effector cell combination activates (e.g., disinhibits) a tumor infiltrating lymphocyte (TIL), e.g., an NK cell or a T cell. In some embodiments, the effector cell combination includes an NK cell modulator chosen from a modulator (e.g., an antibody molecule) of an NK receptor (e.g., a modulator of one or more of NKG2A, KIR3DL, NKp46, MICA or CEACAM1); an interleukin or an interleukin variant (e.g., IL-2, IL-15, IL-21, IL-13R or IL-12 cytokine or variant thereof, or a combination thereof); a bi- or tri-specific cell engager (e.g., a bispecific antibody molecule of NKG2A and CD138, or a bispecific antibody molecule of CD3 and TCR); an NK cell therapy; or a vaccine that includes NK cells and an antigen/immune stimulant. In some embodiments, the effector cell combination includes an immunomodulator (e.g., one or more of: an activator of a costimulatory molecule or an inhibitor of an immune checkpoint molecule as described herein). In some embodiments, the effector cell combination includes a T cell modulator chosen from an inhibitor of a checkpoint inhibitor (e.g., an inhibitor of one or more of: PD-1, PD-L1, TIM-3, LAG-3, VISTA, DKG-α, B7-H3, B7-H4, TIGIT, CTLA-4, BTLA, CD160, TIM1, IDO, LAIR1, IL-12, or a combination thereof, e.g., an inhibitor of PD-1 and TIM-3, or an inhibitor of PD-1 and LAG-3). In some embodiment, the inhibitor of the checkpoint inhibitor is an antibody molecule (e.g., a mono- or bispecific antibody or fragment thereof as described herein). For example, the inhibitor of the checkpoint inhibitor is an antibody molecule against PD-1, PD-L1, TIM-3, LAG-3, VISTA, B7-H4, CTLA-4 or TIGIT, or any combination thereof (e.g. a combination as described herein). In some embodiments, the effector cell combination includes a T cell modulator chosen from an agonist or an activator of a costimulatory molecule. In one embodiment, the agonist of the costimulatory molecule is chosen from an agonist (e.g., an agonistic antibody or antigen-binding fragment thereof, or a soluble fusion) of GITR, OX40, ICOS, SLAM (e.g., SLAMF7), HVEM, LIGHT, CD2, CD27, CD28, CDS, ICAM-1, LFA-1 (CD11a/CD18), ICOS (CD278), 4-1BB (CD137), CD30, CD40, BAFFR, CD7, NKG2C, NKp80, CD160, B7-H3, or CD83 ligand. In other embodiments, the effector cell combination includes a bispecific T cell engager (e.g., a bispecific antibody molecule that binds to CD3 and a tumor antigen (e.g., EGFR, PSCA, PSMA, EpCAM, HER2 among others).

In some embodiments, the effector cell combination includes one, two, three, four, five or more therapeutic agents chosen from: (i) a GITR modulator (e.g., a GITR agonist), (ii) a PD-L1 inhibitor (e.g., an anti-PD-L1 antibody molecule as described herein), (iii) a PD-1 inhibitor, (iv) an inhibitor of IAP (Inhibitor of Apoptosis Protein), (v) an inhibitor of EGFR (Epidermal Growth Factor Receptor), (vi) an inhibitor of target of rapamycin (mTOR), (vii) IL-15 or a variant thereof, (viii) a CTLA-4 inhibitor, (ix) a bispecific T cell engager (e.g., a bispecific antibody molecule that binds to CD3 and a tumor antigen (e.g., EGFR, PSCA, PSMA, EpCAM, HER2 among others), (x) a CD40 agonist (e.g., an anti-CD40 antibody molecule), (xi) an OX40 agonist (e.g., an anti-OX40 antibody molecule), or (xii) a CD27 agonist (e.g., an anti-CD27 antibody molecule). Any combination of the aforesaid agents can be used in the effector cell combination. In one exemplary embodiment, the effector cell combination includes a GITR agonist. In another embodiment, the effector cell combination includes a PD-L1 inhibitor (e.g., an anti-PD-L1 antibody molecule as described herein). In another embodiment, the effector cell combination includes a PD-1 inhibitor. In other embodiments, the effector cell combination includes a GITR agonist and a PD-L1 inhibitor (e.g., an anti-PD-L1 antibody molecule as described herein). In other embodiments, the effector cell combination includes a GITR agonist and a PD-1 inhibitor. In other embodiments, the effector cell combination includes a GITR agonist, a PD-L1 inhibitor (e.g., an anti-PD-L1 antibody molecule as described herein), and a PD-1 inhibitor. In other embodiments, the effector cell combination includes a PD-L1 inhibitor (e.g., an anti-PD-L1 antibody molecule as described herein), and a PD-1 inhibitor. In one embodiment, the effector cell combination includes a GITR agonist and an inhibitor of IAP. In another embodiment, the effector cell combination includes a GITR agonist and an inhibitor of an EGFR inhibitor. In yet another embodiment, the effector cell combination includes a GITR agonist and an inhibitor of an mTOR inhibitor. In one embodiment, the effector cell combination includes IL-15 or a variant thereof. In one embodiment, the effector cell combination includes a CTLA-4 inhibitor. In one embodiment, the effector cell combination includes a bispecific T cell engager (e.g., a bispecific antibody molecule that binds to CD3 and a tumor antigen (e.g., EGFR, PSCA, PSMA, EpCAM, HER2 among others). In one embodiment, the effector cell combination includes a CD40 agonist (e.g., an anti-CD40 antibody molecule). In one embodiment, the effector cell combination includes an OX40 agonist (e.g., an anti-OX40 antibody molecule). In one embodiment, the effector cell combination includes a CD27 agonist (e.g., an anti-CD27 antibody molecule).

In certain embodiments, the combination includes one, two, three, four, five or more therapeutic agents that decrease tumor immunosuppression (referred to herein as an "anti-tumor immunosuppression combination"). In some embodiments, the combination modulates the activity or level of one or more of $T_{reg}$, macrophage 2 or MDSCs. In some embodiments, the combination increases one or more of M2 polarization, $T_{reg}$ depletion, or T cell recruitment. In some embodiments, the anti-tumor immunosuppression combination includes one, two, three, four, five or more therapeutic agents chosen from: (i) an immunomodulator (e.g., one or more of: an activator of a costimulatory molecule (e.g., a GITR agonist), or an inhibitor of an immune checkpoint molecule (e.g., one or more of PD-L1, PD-1, LAG-3, TIM-3 or CTLA-4), as described herein), (ii) a CSF-1/1R inhibitor (e.g., an inhibitor of macrophage colony-stimulating factor (M-CSF)), (iii) an IL-17 inhibitor, (iv) an IL-1beta inhibitor, (v) a CXCR2 inhibitor, (vi) an inhibitor of a phosphoinositide 3-kinase (PI3K, e.g., PI3Kdelta or PI3Kgamma), (vii) a BAFF-R inhibitor, (viii) a MALT-1/BTK inhibitor, (ix) a JAK inhibitor, (x) a CRTH2 inhibitor, (xi) a VEGFR inhibitor, (xiii) an IL-15 or a variant thereof, (xiv) a CTLA-4 inhibitor, (xv) an IDO/TDO inhibitor, (xvi) an A2AR antagonist, (xvii) a TGFb inhibitor, or (xviii) a PFKFB3 inhibitor. In certain embodiments, the immunomodulator is an inhibitor of an immune checkpoint molecule (e.g., an inhibitor of PD-L1, PD-1, LAG-3, TIM-3, CEACAM (e.g., CEACAM-1, -3 and/or -5), or CTLA-4, or any combination thereof). Any combination of the aforesaid agents can be used in the tumor immunosuppression combination. In one exemplary embodiment, the anti-tumor immunosuppression combination includes one, two, three, four, five or more therapeutic agents chosen from a PD-L1 inhibitor (e.g., an anti-PD-L1 antibody molecule as described herein), a PD-1 inhibitor, a LAG-3 inhibitor, a TIM-3 modulator (e.g., an anti-TIM-3 inhibitor), a GITR agonist, a CSF-1/1R inhibitor (e.g., an M-CSF inhibitor), an IL-17 inhibitor, an IL-1beta inhibitor, or a CXCR2 inhibitor. In one embodiment, the anti-tumor immunosuppression combination includes one, two, or all of a CSF-1/1R inhibitor (e.g., an M-CSF inhibitor), an IL-17 inhibitor, an IL-1beta inhibitor. In one embodiment, the anti-tumor immunosuppression combination includes an IL-17 inhibitor, a CXCR2 inhibitor, a CRTH2 inhibitor, an A2AR antagonist, or a PFKFB3 inhibitor, or a combination thereof.

In some embodiments, the combination includes one or more therapeutic agents of the antigen-presentation combination. In other embodiments, the combination includes one or more therapeutic agents of the effector cell combination. In yet other embodiments, the combination includes one or more therapeutic agents of the anti-tumor immunosuppression combination. In other embodiments, the combination includes one or more therapeutic agents of the antigen-presentation combination and one or more therapeutic agents of the effector cell combination. In other embodiments, the one or more therapeutic agents of the antigen-presentation combination and one or more therapeutic agents of the anti-tumor immunosuppression combination. In other embodiments, the combination includes one or more therapeutic agents of the antigen-presentation combination, one or more therapeutic agents of the effector cell combination and one or more therapeutic agents of the anti-tumor immunosuppression combination. In other embodiments, the combination includes one or more therapeutic agents of the antigen-presentation combination, one or more therapeutic agents of the effector cell combination and one or more therapeutic agents of the anti-tumor immunosuppression combination.

In certain embodiments, the combination includes:

(i) one or more therapeutic agents of the antigen-presentation combination chosen from one, two or all of a STING agonist, a TLR agonist (e.g., a TLR7 agonist), or a TIM-3 modulator (e.g., a TIM-3 inhibitor);

(ii) one or more therapeutic agents of the effector cell combination chosen from one, two or all of a GITR modulator (e.g., a GITR agonist), a PD-L1 inhibitor (e.g., an anti-PD-L1 antibody molecule as described herein), or a PD-1 inhibitor;

(iii) one or more therapeutic agents of the anti-tumor immunosuppression combination chosen from one, two or all of a CSF-1/1R inhibitor (e.g., an M-CSF inhibitor), an IL-17 inhibitor, or an IL-1beta inhibitor:

(iv) a combination of (i) and (ii);

(v) a combination of (i) and (iii);

(vi) a combination of (ii) and (iii); or (vii) a combination of (i), (ii) and (iii).

The combination can be used to treat a cancer as described herein, such as lung cancer (squamous), lung cancer (adenocarcinoma), head and neck cancer, cervical cancer (squamous), stomach cancer, thyroid cancer, melanoma (e.g., advanced melanoma), nasopharyngeal cancer, or breast cancer.

In other embodiments, the combination includes a therapeutic agent from the antigen-presentation combination (e.g., one or more of a STING agonist, a TLR agonist, a vaccine or an oncolytic virus) in combination with a therapeutic agent from the effector cell and/or anti-tumor immunosuppression combination (e.g., an inhibitor of a checkpoint inhibitor, e.g., an inhibitor of PD-L1, PD-1, LAG-3, TIM-3, CEACAM (e.g., CEACAM-1, -3 and/or -5), or CTLA-4, or any combination thereof. In one embodiment, one or more of a STING agonist, a TLR agonist, a vaccine or an oncolytic virus is administered in combination with an anti-PD-L1 antibody molecule as described herein. In one embodiment, a STING agonist and/or a vaccine is administered in combination with an anti-PD-L1 antibody molecule as described herein. In one embodiment, an oncolytic virus is administered in combination with an anti-PD-L1 antibody molecule as described herein. The combination can be used to treat a cancer as described herein, such as lung cancer (squamous), lung cancer (adenocarcinoma), head and neck cancer, cervical cancer (squamous), stomach cancer, thyroid cancer, melanoma (e.g., advanced melanoma), nasopharyngeal cancer, or breast cancer.

In certain embodiments, the combination includes a combination of therapeutic agents as provided in the section entitled "Exemplary Combinations of Antigen-Presentation Combinations, Effector Cell Combinations and Anti-tumor Immunosuppression Combinations" provided in the Detailed Description.

The combinations disclosed herein can be administered together in a single composition or administered separately in two or more different compositions, e.g., compositions or dosage forms as described herein. The administration of the therapeutic agents can be in any order. The first agent and the additional agents (e.g., second, third agents) can be administered via the same administration route or via different administration routes. For example, a first therapeutic agent can be administered concurrently with, prior to, or subsequent to, the additional agent. In certain embodiments, a first agent is administered locally, e.g., a therapeutic agent of any of categories (i)-(iii) can be coupled to a tumor targeting agent, e.g., a tumor-targeting antibody (e.g., to form an antibody-drug conjugate), or any other delivery agent (e.g., a formulation such as a targeted formulation) such that administration of the first agent is localized to a desired site, e.g., a tumor site (e.g., a dendritic cell-enriched site). In one embodiment, the therapeutic agent is an antigen (e.g., a vaccine, e.g., an in situ cancer vaccine), which is targeted to the tumor environment, thus resulting in activation of dendritic cells. The therapeutic agent also can be locally administered, e.g., injected, at a tumor site (e.g., intratumoral or peritumoral administration). Localized delivery or administration of the therapeutic agent can reduce one or more side effects or toxicities that would otherwise be associated with systemic administration of the therapeutic agent. In one exemplary embodiment, a therapeutic agent (e.g., STING or a TLR) can be conjugated to a tumor-binding antibody (e.g., an antibody that binds to HER2), thereby delivering the therapeutic agent to a HER-2-expressing cell.

Detection/Theranostics

In another aspect, the invention features methods for detecting the presence of PD-L1 in a sample, e.g., in vitro or in vivo (e.g., a biological sample, e.g., serum, semen or urine, or a tissue biopsy, e.g., from a hyperproliferative or cancerous lesion). The subject method can be used to evaluate (e.g., monitor treatment or progression of, diagnose and/or stage a disorder described herein, e.g., a hyperproliferative or cancerous disorder, in a subject). The method includes: (i) contacting the sample with (and optionally, a reference, e.g., a control sample), or administering to the subject, an antibody molecule as described herein, under conditions that allow interaction to occur, and (ii) detecting formation of a complex between the antibody molecule, and the sample (and optionally, the reference, e.g., control, sample). Formation of the complex is indicative of the presence of PD-L1, and can indicate the suitability or need for a treatment described herein. In some embodiments, PD-L1 is detected prior to treatment, e.g., prior to an initial treatment, or prior to a treatment after a treatment interval. Detection can involve an immunohistochemistry, immunocytochemistry, FACS, antibody molecule complexed magnetic beads, ELISA assays, PCR-techniques (e.g., RT-PCR), or an in vivo imaging technique. Typically, the antibody molecule used in the in vivo and in vitro detection methods is directly or indirectly labeled with a detectable substance to facilitate detection of the bound or unbound binding agent. Suitable detectable substances include various biologically active enzymes, prosthetic groups, fluorescent materials, luminescent materials, paramagnetic (e.g., nuclear magnetic resonance active) materials, and radioactive materials. In other embodiments, the antibody molecule is detected in vivo, e.g., using an in vivo imaging technique as described herein (e.g., PET imaging).

Additional embodiments provide a method of treating a cancer, comprising: identifying in a subject, e.g., a sample (e.g., a subject's sample comprising cancer cells and optionally immune cells such as TILs) the presence of one, two or all of PD-L1, CD8, or IFN-γ, thereby providing a value for one, two or all of PD-L1, CD8, and IFN-γ. The method can further include comparing the PD-L1, CD8, and/or IFN-γ values to a reference value, e.g., a control value. If the PD-L1, CD8, and/or IFN-γ values are greater than the reference value, e.g., the control values, administering a therapeutically effective amount of an anti-PD-L1 antibody (e.g., an anti-PD-L1 antibody described herein) to the subject, optionally in combination with one or more other agents, thereby treating the cancer. In some embodiments, the subject is identified prior to treatment, e.g., prior to an initial treatment, or prior to a treatment after a treatment interval. The cancer may be, e.g., a cancer described herein, such as lung cancer (squamous), lung cancer (adenocarcinoma), head and neck cancer, cervical cancer (squamous), stomach cancer, thyroid cancer, melanoma, nasopharyngeal cancer, or breast cancer, e.g., TN breast cancer, e.g., IM-TN breast cancer. In some embodiments, the cancer is ER+ breast cancer or pancreatic cancer.

Also provided is a method of treating a cancer, comprising: testing a subject, e.g., a sample (e.g., a subject's sample comprising cancer cells) for the presence of PD-L1, thereby identifying a PD-L1 value, comparing the PD-L1 value to a control value, and if the PD-L1 value is greater than the control value, administering a therapeutically effective amount of an anti-PD-L1 antibody (e.g., an anti-PD-L1 antibody described herein) to the subject, optionally in combination with one or more other agents, thereby treating the cancer. The cancer may be, e.g., a cancer as described herein, such as cancer is non-small cell lung (NSCLC) adenocarcinoma (ACA), NSCLC squamous cell carcinoma (SCC), or hepatocellular carcinoma (HCC).

Without being bound by theory, it is believed that a subject that shows a pre-existing immune response to a cancer, for example, an immune reaction prior to an immunomodulator therapy (e.g., a checkpoint molecule inhibitor therapy) can have a prolonged and/or more robust response to the therapy, compared to a subject that does not have the same immune response. Thus, in some embodiments, evaluation of a subject's status of immune cell (e.g., T cell) activation prior to an immunomodulator therapy can serve as a means for evaluating and/or monitoring a subject's responsiveness to the immunomodulator therapy. In embodiments, such evaluation can be used to identify, select and/or stratify a subject (e.g., a patient or a patient population) as being more or less likely to respond to the immunomodulator therapy.

Accordingly, alternatively, or in combination with the methods described herein, a method for evaluating a subject's status of immune cell (e.g., T cell) activation (e.g., evaluating a subject's likely responsiveness to an immunomodulator therapy) is disclosed. The method includes determining the level and/or distribution of T cell activation in the subject. In one embodiment, the level and/or distribution of T activation includes a measure of the level and/or distribution of one or more of: CD8, PD-L1, or other checkpoint inhibitor (e.g., one or more of PD-1, LAG-3, TIM-3, CEACAM (e.g., CEACAM-1, -3 and/or -5), or CTLA-4), or any combination thereof. For example, the level and/or distribution of CD8-expressing cells can be evaluated as a marker for activated T cells. In other embodiments, the level and/or distribution of cells expressing PD-L1, or other checkpoint inhibitor can be evaluated. The subject can be evaluated prior to, during, or after, administration of the immunomodulator therapy. In one embodiment, the subject is evaluated prior to the immunomodulator therapy (e.g., the checkpoint molecule inhibitor therapy), e.g., prior to an initial treatment, or prior to a treatment after a treatment interval. In one embodiment, an elevated level of one or more of CD8, PD-L1, or other checkpoint inhibitor in the subject (e.g., relative to a reference, e.g., control) is indicative of increased responsiveness of the subject to the therapy (also referred to herein as "a positive immune activation status"). In another embodiment, a decreased level of one or more of CD8, PD-L1, or other checkpoint inhibitor in the subject (e.g., relative to a reference, e.g., control) is indicative of decreased responsiveness of the subject to the therapy (also referred to herein as "a negative immune activation status"). The method can, optionally, include administration of the immunomodulator therapy as described herein (e.g., a checkpoint molecule inhibitor therapy as described herein), if the subject is determined to have a positive immune activation status.

In one embodiment, the immunomodulator therapy includes an activator of a costimulatory molecule, e.g., one or more activators as described herein (e.g., an agonist of a GITR molecule as described herein). In other embodiments, the immunomodulator therapy includes an inhibitor of an immune checkpoint molecule, e.g., one or more inhibitors of checkpoint inhibitor as described herein (e.g., an inhibitor of one or more of PD-L1, PD-1, TIM-3, or CTLA-4, as described herein). In one embodiment, the immunomodulator therapy includes an anti-PD-L1 antibody molecule as described herein. In other embodiments, the immunomodulator therapy includes a combination of an activator of a costimulatory molecule and an inhibitor of a checkpoint inhibitor.

In some embodiments, the level and/or distribution of the CD8, PD-L1, or other checkpoint inhibitor is determined in vivo, e.g., non-invasively (e.g., by detecting an antibody to a T cell marker detectably labeled using a suitable imaging technique, e.g., positron emission tomography (PET) scan. For example, target antibody-PET or immune-PET (e.g., an anti-CD8 PET or an anti-PD-L1 PET) can be used to detect the level and/or distribution (e.g., tumor localization) of the target CD8- or PD-L1-expressing cells in vivo. Techniques for antibody imaging (e.g., antibody-PET imaging) are known in the art, e.g., as described by Lamberts, L. E. et al. (2015) *J. Clin. Oncol.* 33 (DOI: 10.1200/JCO.2014.57.8278); Tavare, R. et al. (2014) PNAS 111(3): 1108-1113; and Boerman and Oyen (2011) *The Journal of Nuclear Medicine* 52 (8):1171-72, incorporated herein by reference. In other embodiments, the level of the CD8, PD-L1, or other checkpoint inhibitor is determined in a sample (e.g., a tumor biopsy) acquired from the subject (e.g., using immunohistochemical techniques).

As an illustrative embodiment, an increased number of, or a change in location of, CD8-expressing cells from a tumor margin to the interior of the tumor may be indicative of an improved outcome, e.g., increased responsiveness, of the subject to the immunomodulator therapy. In certain embodiments, the positive immune activation status (e.g., an increase in activated T cells) occurs in response to a previous treatment of the cancer, for example, in response to one or more of radiotherapy, a chemotherapy, an oncolytic virus, a bispecific T cell engager, a biologic or a targeted therapy (e.g., an anti-cancer therapy as described herein). In some embodiments, a subject that shows a positive immune activation status in response to the previous treatment becomes a better candidate for the immunomodulator therapy. In one embodiment, the subject that has a B-Raf mutation (e.g., a B-Raf mutation as described herein) is treated with a B-Raf inhibitor (e.g., a B-Raf inhibitor as described herein). The subject may have an increase in CD8-expressing T cells after treatment with the B-Raf inhibitor, and thus may become a better candidate for the immunomodulator therapy.

In another illustrative embodiment, an expression of PD-L1 or other checkpoint inhibitors (e.g., relative to a reference) can be used to determine or analyze a subject's responsiveness to a cancer therapy. In one embodiment, a PET imaging agent can show that a subject has pre-existing expression of PD-L1 or other checkpoint molecules. Expression of these molecules on a tumor could help stratify patients for a companion diagnostic purpose. If a subject had no detectable immune response pre-existing to the immunomodulator therapy and no detectable checkpoint molecule expression, such subject is likely to be a poor candidate for the therapy. PET imaging can also show heterogeneity of expression, and show those tumors (positive for PET) that are the actual tumors best/lesions suited for response. This would be beneficial because sampling of a small number of target lesions could be misleading; for example, for determining if the subject was responding or not by sampling error of the biopsy technique and low number of samples. Using PET imaging, it is possible to detect most of the tumors and thereby obtain a more accurate determination of tumor burden efficacy and better understand how the therapies are working.

In another aspect, the invention features diagnostic or therapeutic kits that include the antibody molecules described herein and instructions for use.

All publications, patent applications, patents, and other references mentioned herein are incorporated by reference in their entirety.

Other features, objects, and advantages of the invention will be apparent from the description and drawings, and from the claims.

BRIEF DESCRIPTION OF THE DRAWINGS

FIG. 1 depicts the amino acid sequences of the light (SEQ ID NO: 8) and heavy chain (SEQ ID NO: 6) variable regions of murine anti-PD-L1 mAb BAP058. The light and heavy chain CDR sequences based on Kabat numbering are underlined. The light heavy chain CDR sequences based on Chothia numbering are shown in bold italics.

FIG. 2 depicts the amino acid sequences of the light (SEQ ID NOS 8 and 249, respectively, in order of appearance) and heavy chain (SEQ ID NOS 6 and 248, respectively, in order of appearance) variable regions of murine anti-PD-L1 mAb BAP058 aligned with the germline sequences. The upper and lower sequences are the germline (GL) and BAP058 (Mu mAb) sequences, respectively. The light and heavy chain CDR sequences based on Kabat numbering are underlined. The light heavy chain CDR sequences based on Chothia numbering are shown in bold italics. "-" means identical amino acid residue.

FIG. 4 depicts the structural analysis of the humanized BAP0058 clones (a, b, c, d, e, f, and g represent various types of framework region sequences). The concentrations of the mAbs in the samples are also shown.

FIG. 6 depicts the ranking of humanized BAP058 clones based on FACS data, competition binding and structural analysis. The concentrations of the mAbs in the samples are also shown.

FIGS. 8A-8B depict the alignment of heavy chain variable domain sequences for the seventeen humanized BAP058 clones and BAP058-chi In FIG. 8A, all of the sequences are shown. FIG. 8A discloses SEQ ID NOS 250, 251, 251, 251, 252, 252, 252, 253, 253, 254, 254, 255, 255, 256, 256, 257, 258, 259, respectively, in order of appearance. In FIG. 8B, only amino acid sequences that are different from mouse sequence are shown. FIG. 8B discloses SEQ ID NOS 250, 251, 251, 251, 252, 252, 252, 253, 253, 254, 254, 255, 255, 256, 256, 257, 258, 259, respectively, in order of appearance.

FIGS. 9A-9B depict the alignment of light chain variable domain sequences for the seventeen humanized BAP058 clones and BAP058-chi In FIG. 9A, all of the sequences are shown. FIG. 9A discloses SEQ ID NOS 17, 86, 86, 86, 86, 42, 42, 42, 66, 66, 66, 22, 22, 26, 34, 58, 82, 74, respectively, in order of appearance. In FIG. 9B, only amino acid sequences that are different from mouse sequence are shown. FIG. 9B discloses SEQ ID NOS 17, 86, 86, 86, 86, 42, 42, 42, 66, 66, 66, 22, 22, 26, 34, 58, 82, 74, respectively, in order of appearance.

BRIEF DESCRIPTION OF THE TABLES

Figure 3:
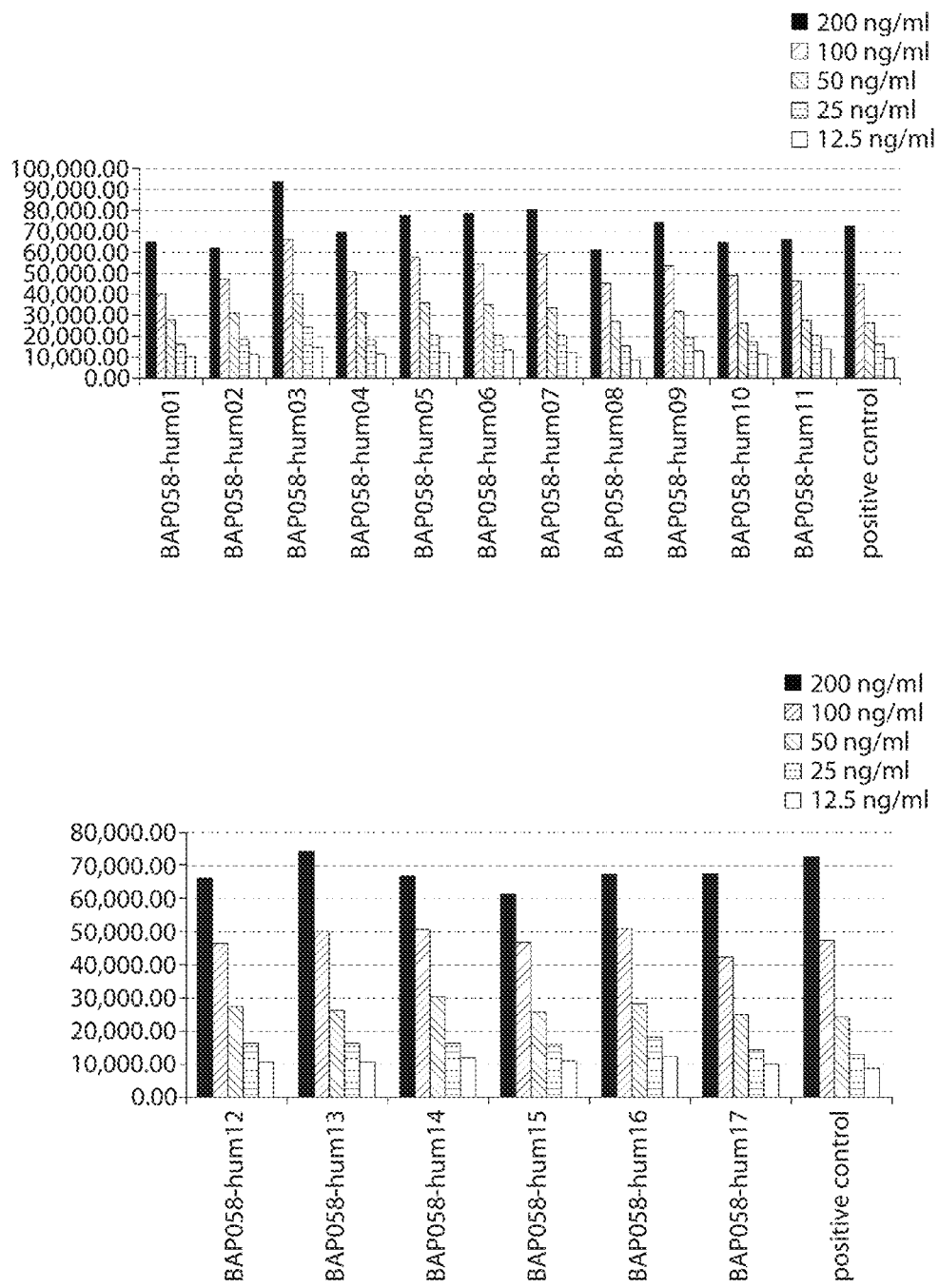
FIG. 3 is a bar graph showing the results of FACS binding analysis for the seventeen humanized BAP058 clones (BAP058-hum01 to BAP058-hum17). The antibody concentrations are 200, 100, 50, 25 and 12.5 ng/ml from the leftmost bar to the rightmost bar for each tested mAb.

Table 1 is a summary of the amino acid and nucleotide sequences for the murine, chimeric and humanized anti-PD-L1 antibody molecules. The antibody molecules include murine mAb BAP058, chimeric mAb BAP058-chi, and humanized mAbs BAP058-hum01 to BAP058-hum17 and BAP058-Clone-K to BAP058-Clone-O. The amino acid and nucleotide sequences of the heavy and light chain CDRs, the amino acid and nucleotide sequences of the heavy and light chain variable regions, and the amino acid and nucleotide sequences of the heavy and light chains are shown in this Table.

Table 2 depicts the amino acid and nucleotide sequences of the heavy and light chain framework regions for humanized mAbs BAP058-hum01 to BAP058-hum17 and BAP058-Clone-K to BAP058-Clone-O.

Table 3 depicts constant region amino acid sequences of human IgG heavy chains and human kappa light chain.

Table 4 is a summary of yield, titre, monomer content and endotoxin levels for selected humanized BAP058 mAbs expressed in CHO cells.

Table 5 shows the charge isoforms as detected by Novex IEF analysis for selected humanized BAP058 mAbs expressed in CHO cells.

Table 6 is a summary of selected therapeutic agents that can be administered in combination with the anti-PD-1 antibody molecules and other immunomodulators (e.g., one or more of: an activator of a costimulatory molecule and/or an inhibitor of an immune checkpoint molecule) described herein. Table 6 provides from left to right the following: the Compound Designation of the second therapeutic agent, the Compound structure, and Patent publication(s) disclosing the Compound.

Table 7 provides an exemplary listing of the therapeutic agents from Antigen-Presentation Combinations (Category A), Effector Cell Combinations (Category B) and Antitumor Immunosuppression Combinations (Category C).

Table 8 shows cross species binding of exemplary anti-PD-L1 antibodies as assessed by Biacore.

DETAILED DESCRIPTION

The immune system has the capability of recognizing and eliminating tumor cells; however, tumors can use multiple strategies to evade immunity. Blockade of immune checkpoints is one of the approaches to activating or reactivating therapeutic antitumor immunity. Programmed Death Ligand 1 (PD-L1) has been described as a ligand for the immunoinhibiotry receptor Programmed Death 1 (PD-1). Binding of PD-L1 to PD-1 leads to the inhibition of T cell receptor-mediated lymphocyte proliferation and cytokine secretion (Freeman et al. (2000) *J Exp Med* 192:1027-34). Thus, blocking of PD-L1 can lead to enhancement of antitumor immunity.

Several cell types express PD-L1. For example, PD-L1 is expressed on activated T cells, dendritic cells (DCs), natural killer (NK) cells, macrophages, B cells, monocytes, and vascular endothelium cells. PD-L1 is expressed in many cancers, including human lung, ovarian and colon carcinoma and various myelomas, (Iwai et al. (2002) *PNAS* 99:12293-7; Ohigashi et al. (2005) *Clin Cancer Res* 11:2947-53; Okazaki et al. (2007) *Intern. Immun.* 19:813-24; Thompson et al. (2006) *Cancer Res.* 66:3381-5). PD-L1 expression strongly correlates with unfavorable prognosis in various types of cancer including kidney, ovarian, bladder, breast, gastric and pancreatic cancer.

Many tumor infiltrating T lymphocytes predominantly express PD-1 compared to T lymphocytes in normal tissues and peripheral blood T lymphocytes. This indicates that up-regulation of PD-1 on tumor-reactive T cells can contribute to impaired antitumor immune responses (Ahmadzadeh et al. (2009) *Blood* 114:1537-44). Thus, PD-L1 signaling mediated by PD-L1 expressing tumor cells interacting with PD-1 expressing T cells may lead to attenuation of T cell activation and evasion of immune surveillance (Sharpe et al. (2002) *Nat Rev Immunol.* 2:116-26; Keir et al. (2008) *Annu Rev Immunol.* 26:677-704). PD-1 blockade can inhibit hematogenous spread of poorly immunogenic tumor cells by enhanced recruitment of effector T cells (Iwai et al. (2005) *Int. Immunol.* 17:133-144).

Anti-PD-L1 can enhance T-cell immunity, e.g., through blocking both its inhibitory interactions with PD-1 and B7-1. Anti-PD-1 can also allow for immune regulation via PD-L2/PD-1. Both PD-1 and B7-1 are expressed on T cells, B cells, DCs, and macrophages, which provides potential for bidirectional interactions between B7-1 and PD-L1 on these cell types. PD-L1 on non-hematopoietic cells may interact with B7-1 as well as PD-1 on T cells.

Figure 5:
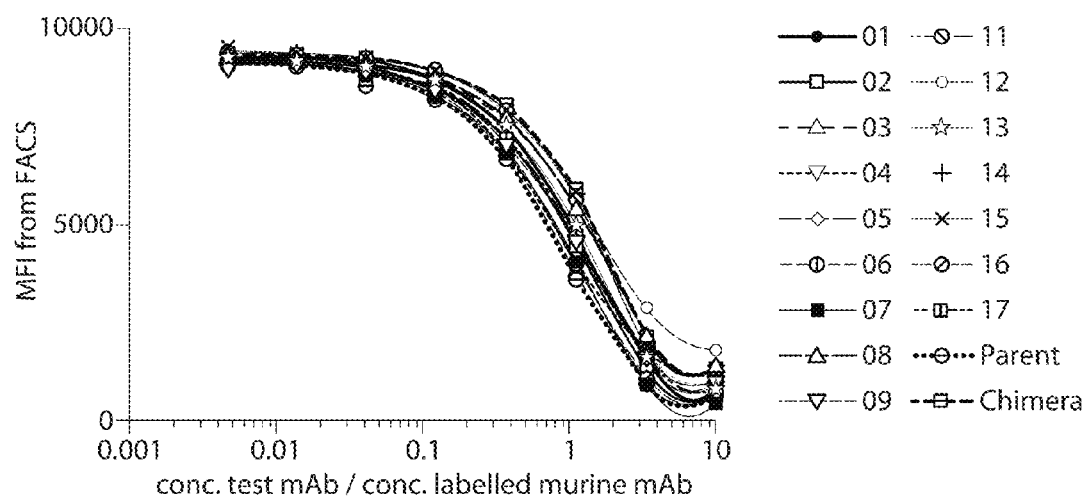
FIG. 5 depicts the binding affinity and specificity of humanized BAP058 mAb measured in a competition binding assay using a constant concentration of Alexa 488-labeled murine mAb BAP058, serial dilutions of the test antibodies, and PD-L1-expressing 300.19 cells.
Figure 7:
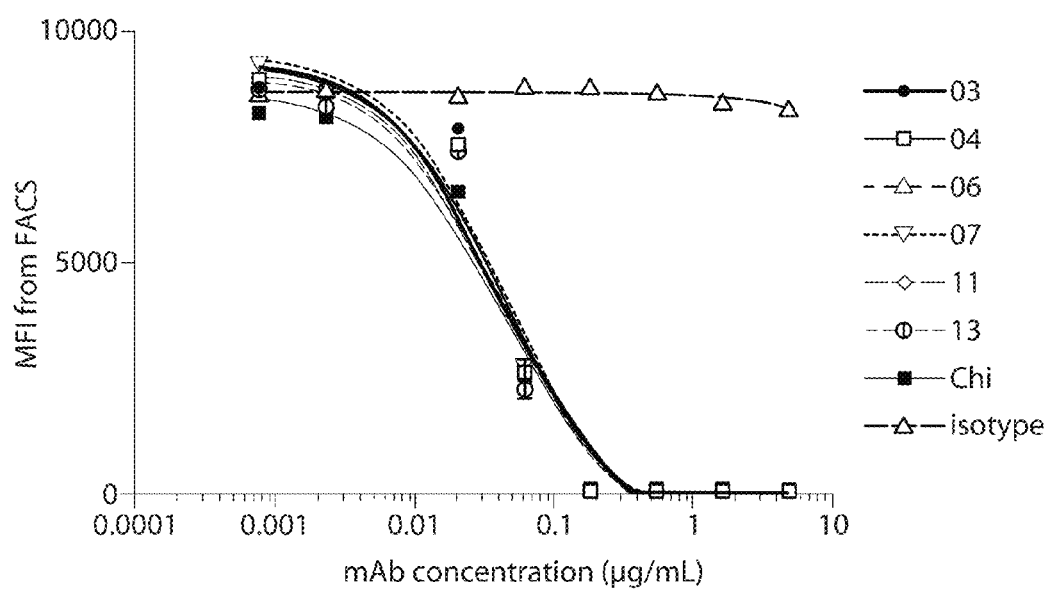
FIG. 7 depicts blocking of ligand binding to PD-1 by selected humanized BAP058 clones. Blocking of PD-1-Ig to PD-L1 expressing cells is shown BAP058-hum01, BAP058-hum03, BAP058-hum04, BAP058-hum06, BAP058-hum07, BAP058-hum11, and BAP058-hum13 were evaluated. Murine mAb BAP058 and chimeric mAb were also included in the analyses.

Accordingly, the present invention provides, at least in part, antibody molecules (e.g., humanized antibody molecules) that bind to Programmed Death Ligand 1 (PD-L1) with high affinity and specificity. In one embodiment, humanized antibodies against PD-L1 are disclosed, which show a surprisingly low immunogenicity. For example, humanized anti-PD-L1 antibodies can have a risk score of less than 650, 600, 550, or less than 500, according to a T cell epitope assay. In other embodiments, selected combination of framework regions, e.g., as shown in FIGS. 5 and 7, were shown to have distinct production efficiencies and binding properties.

Additional aspects of the invention include nucleic acid molecules encoding the antibody molecules, expression vectors, host cells and methods for making the antibody molecules. Immunoconjugates, multi- or bispecific molecules and pharmaceutical compositions comprising the antibody molecules are also provided. The anti-PD-L1 antibody molecules disclosed herein can be used to treat, prevent and/or diagnose cancerous or malignant disorders (e.g., solid and soft-tissue tumors; melanoma, e.g., advanced melanoma; hepatocellular carcinoma; pancreatic cancer; renal cell carcinoma (RCC), e.g., metastatic RCC or clear cell RCC; gliomas or glioblastomas; multiple myeloma; colorectal cancer; and lung cancer, e.g., non-small cell carcinoma), as well as infectious diseases (e.g., infectious disorders such as hepatitis, e.g., hepatitis C (e.g., chronic viral hepatitis); sepsis). Thus, methods for detecting PD-L1, as well as methods for treating various disorders, including cancer and infectious diseases using the anti-PD-L1 antibody molecules are disclosed herein.

Figure 20:
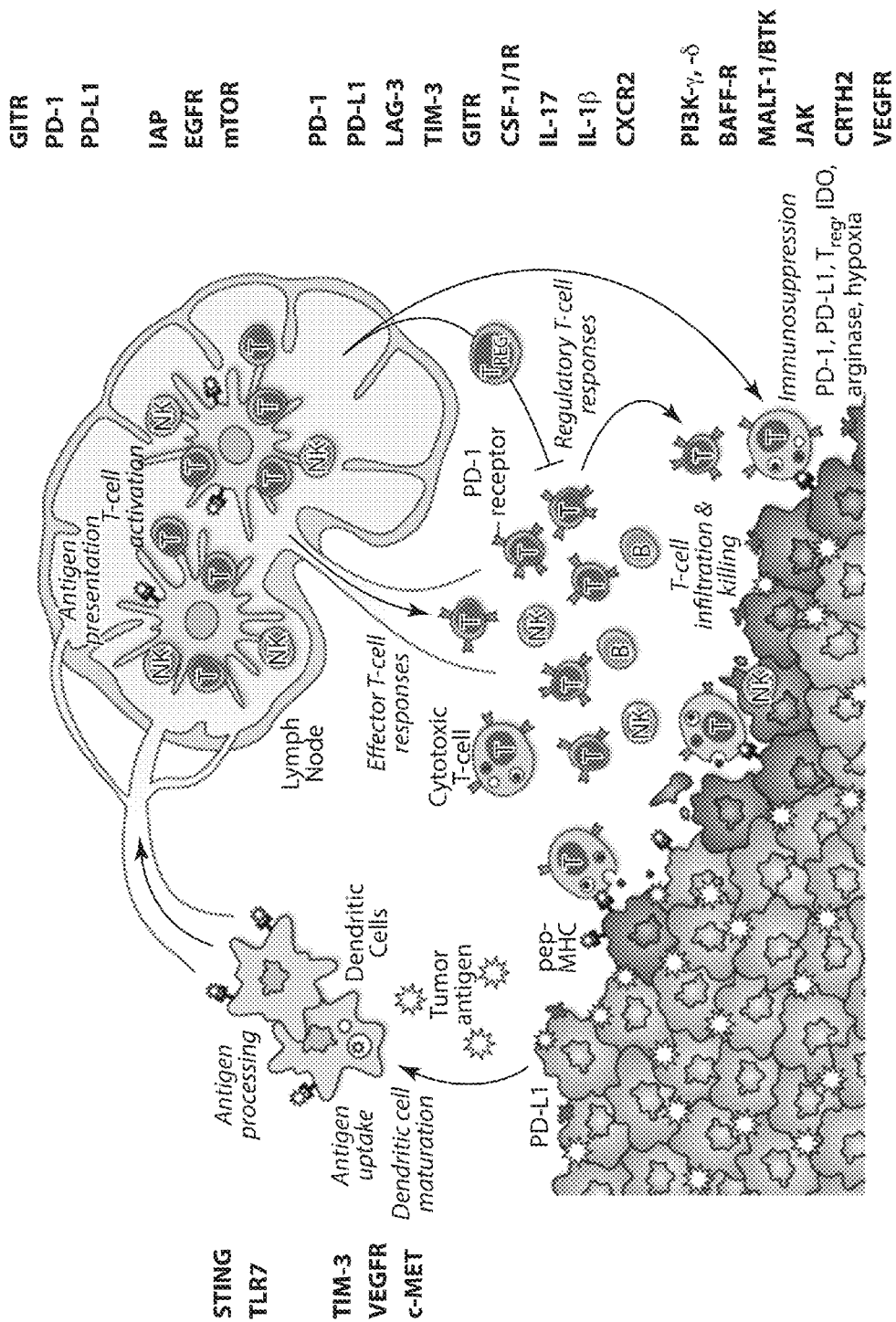
FIG. 20 is a schematic diagram that outlines the antigen processing and presentation, effector cell responses and immunosuppression pathways targeted by the combination therapies disclosed herein.

Additionally disclosed herein are methods and compositions comprising a combination of two, three or more therapeutic agents chosen from one, two, or all of the following categories (i)-(iii): (i) an agent that enhances antigen presentation (e.g., tumor antigen presentation) (e.g., by enhancing one or more of dendritic cell activity or maturation, antigen uptake, or antigen processing); (ii) an agent that enhances an effector cell response (e.g., an immune effector cell response, e.g., B cell and/or T cell activation and/or mobilization, e.g., in the lymph node); or (iii) an agent that decreases tumor immunosuppression (e.g., increasing T cell infiltration and tumor cell killing). In some embodiments, the combination includes a PD-L1 inhibitor (e.g., an anti-PD-L1 antibody molecule as described herein). Without wishing to be bound by theory, it is believed that therapeutic approaches that enhance anti-tumor immunity work more effectively when the immune response is optimized via multiple targets at different stages of the immune response. Each of these stages in depicted in schematic form in FIG. 20. For example, approaches that result in activation of dendritic cells combined with approaches that enhance cellular and humoral immune can result in a more effective and/or prolonged therapeutic response.

The term "Programmed Death Ligand 1" or "PD-L1" include isoforms, mammalian, e.g., human PD-L1, species homologs of human PD-1, and analogs comprising at least one common epitope with PD-L1. The amino acid sequence of PD-L1, e.g., human PD-1, is known in the art, e.g., Dong et al. (1999) *Nat Med.* 5(12):1365-9; Freeman et al. (2000) *J Exp Med.* 192(7):1027-34).

Additional terms are defined below and throughout the application.

As used herein, the articles "a" and "an" refer to one or to more than one (e.g., to at least one) of the grammatical object of the article.

The term "or" is used herein to mean, and is used interchangeably with, the term "and/or", unless context clearly indicates otherwise.

"About" and "approximately" shall generally mean an acceptable degree of error for the quantity measured given the nature or precision of the measurements. Exemplary degrees of error are within 20 percent (%), typically, within 10%, and more typically, within 5% of a given value or range of values.

By "a combination" or "in combination with," it is not intended to imply that the therapy or the therapeutic agents must be administered at the same time and/or formulated for delivery together, although these methods of delivery are within the scope described herein. The therapeutic agents in the combination can be administered concurrently with, prior to, or subsequent to, one or more other additional therapies or therapeutic agents. The therapeutic agents or therapeutic protocol can be administered in any order. In general, each agent will be administered at a dose and/or on a time schedule determined for that agent. In will further be appreciated that the additional therapeutic agent utilized in this combination may be administered together in a single composition or administered separately in different compositions. In general, it is expected that additional therapeutic agents utilized in combination be utilized at levels that do not exceed the levels at which they are utilized individually. In some embodiments, the levels utilized in combination will be lower than those utilized individually.

In embodiments, the additional therapeutic agent is administered at a therapeutic or lower-than therapeutic dose. In certain embodiments, the concentration of the second therapeutic agent that is required to achieve inhibition, e.g., growth inhibition, is lower when the second therapeutic agent is administered in combination with the first therapeutic agent, e.g., the anti-PD-L1 antibody molecule, than when the second therapeutic agent is administered individually. In certain embodiments, the concentration of the first therapeutic agent that is required to achieve inhibition, e.g., growth inhibition, is lower when the first therapeutic agent is administered in combination with the second therapeutic agent than when the first therapeutic agent is administered individually. In certain embodiments, in a combination therapy, the concentration of the second therapeutic agent that is required to achieve inhibition, e.g., growth inhibition, is lower than the therapeutic dose of the second therapeutic agent as a monotherapy, e.g., 10-20%, 20-30%, 30-40%, 40-50%, 50-60%, 60-70%, 70-80%, or 80-90% lower. In certain embodiments, in a combination therapy, the concentration of the first therapeutic agent that is required to achieve inhibition, e.g., growth inhibition, is lower than the therapeutic dose of the first therapeutic agent as a monotherapy, e.g., 10-20%, 20-30%, 30-40%, 40-50%, 50-60%, 60-70%, 70-80%, or 80-90% lower.

The term "inhibition," "inhibitor," or "antagonist" includes a reduction in a certain parameter, e.g., an activity, of a given molecule, e.g., an immune checkpoint inhibitor. For example, inhibition of an activity, e.g., a PD-1 or PD-L1 activity, of at least 5%, 10%, 20%, 30%, 40% or more is included by this term. Thus, inhibition need not be 100%.

The term "activation," "activator," or "agonist" includes an increase in a certain parameter, e.g., an activity, of a given molecule, e.g., a costimulatory molecule. For example, increase of an activity, e.g., a costimulatory activity, of at least 5%, 10%, 25%, 50%, 75% or more is included by this term.

The term "anti-cancer effect" refers to a biological effect which can be manifested by various means, including but not limited to, e.g., a decrease in tumor volume, a decrease in the number of cancer cells, a decrease in the number of metastases, an increase in life expectancy, decrease in cancer cell proliferation, decrease in cancer cell survival, or amelioration of various physiological symptoms associated with the cancerous condition. An "anti-cancer effect" can also be manifested by the ability of the peptides, polynucleotides, cells and antibodies in prevention of the occurrence of cancer in the first place.

The term "anti-tumor effect" refers to a biological effect which can be manifested by various means, including but not limited to, e.g., a decrease in tumor volume, a decrease in the number of tumor cells, a decrease in tumor cell proliferation, or a decrease in tumor cell survival.

The term "cancer" refers to a disease characterized by the rapid and uncontrolled growth of aberrant cells. Cancer cells can spread locally or through the bloodstream and lymphatic system to other parts of the body. Examples of various cancers are described herein and include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like. The terms "tumor" and "cancer" are used interchangeably herein, e.g., both terms encompass solid and liquid, e.g., diffuse or circulating, tumors. As used herein, the term "cancer" or "tumor" includes premalignant, as well as malignant cancers and tumors.

The term "antigen presenting cell" or "APC" refers to an immune system cell such as an accessory cell (e.g., a B-cell, a dendritic cell, and the like) that displays a foreign antigen complexed with major histocompatibility complexes (MHC's) on its surface. T-cells may recognize these complexes using their T-cell receptors (TCRs). APCs process antigens and present them to T-cells.

The term "costimulatory molecule" refers to the cognate binding partner on a T cell that specifically binds with a costimulatory ligand, thereby mediating a costimulatory response by the T cell, such as, but not limited to, proliferation. Costimulatory molecules are cell surface molecules other than antigen receptors or their ligands that are required for an efficient immune response. Costimulatory molecules include, but are not limited to, an MHC class I molecule, TNF receptor proteins, Immunoglobulin-like proteins, cytokine receptors, integrins, signaling lymphocytic activation molecules (SLAM proteins), activating NK cell receptors, BTLA, a Toll ligand receptor, OX40, CD2, CD7, CD27, CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83.

"Immune effector cell," or "effector cell" as that term is used herein, refers to a cell that is involved in an immune response, e.g., in the promotion of an immune effector response. Examples of immune effector cells include T cells, e.g., alpha/beta T cells and gamma/delta T cells, B cells, natural killer (NK) cells, natural killer T (NKT) cells, mast cells, and myeloid-derived phagocytes.

"Immune effector" or "effector" "function" or "response," as that term is used herein, refers to function or response, e.g., of an immune effector cell, that enhances or promotes an immune attack of a target cell. E.g., an immune effector function or response refers a property of a T or NK cell that promotes killing or the inhibition of growth or proliferation, of a target cell. In the case of a T cell, primary stimulation and co-stimulation are examples of immune effector function or response.

The term "effector function" refers to a specialized function of a cell. Effector function of a T cell, for example, may be cytolytic activity or helper activity including the secretion of cytokines.

The term "immune activation status" refers to the likelihood that a subject has for responding to a therapy, e.g., an immunomodulator therapy. In embodiments, the immune activation status can be a positive status or a negative status. In embodiments, a positive immune activation status means that there is more than a 50% probability (e.g., more than 50%, 60%, 70%, 80%, 90%, or greater probability) that the subject will respond to the therapy, e.g., the immunomodulator therapy. In embodiments, a negative immune activation status means that there is more than a 50% probability (e.g., more than 50%, 60%, 70%, 80%, 90%, or greater probability) that the subject will not respond to the therapy e.g., the immunomodulator therapy.

As used herein, the terms "treat", "treatment" and "treating" refer to the reduction or amelioration of the progression, severity and/or duration of a disorder, e.g., a proliferative disorder, or the amelioration of one or more symptoms (preferably, one or more discernible symptoms) of the disorder resulting from the administration of one or more therapies. In specific embodiments, the terms "treat," "treatment" and "treating" refer to the amelioration of at least one measurable physical parameter of a proliferative disorder, such as growth of a tumor, not necessarily discernible by the patient. In other embodiments the terms "treat", "treatment" and "treating"-refer to the inhibition of the progression of a proliferative disorder, either physically by, e.g., stabilization of a discernible symptom, physiologically by, e.g., stabilization of a physical parameter, or both. In other embodiments the terms "treat", "treatment" and "treating" refer to the reduction or stabilization of tumor size or cancerous cell count.

The compositions and methods of the present invention encompass polypeptides and nucleic acids having the sequences specified, or sequences substantially identical or similar thereto, e.g., sequences at least 85%, 90%, 95% identical or higher to the sequence specified. In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain having at least about 85%, 90%. 91%, 92%, 93%, 94%, 95%, 96%, 97%, 98% or 99% identity to a reference sequence, e.g., a sequence provided herein.

In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 85%, 90%, 91%, 92%, 93%, 94%, 95%, 96%, 97%, 98% or 99% identity to a reference sequence, e.g., a sequence provided herein.

The term "functional variant" refers to polypeptides that have a substantially identical amino acid sequence to the naturally-occurring sequence, or are encoded by a substantially identical nucleotide sequence, and are capable of having one or more activities of the naturally-occurring sequence.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology").

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch ((1970) *J. Mol. Biol.* 48:444-453) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller ((1989) *CABIOS,* 4:11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215: 403-10. BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997) *Nucleic Acids Res.* 25:3389-3402. When utilizing BLAST and Gapped BLAST programs, the default parameters of the respective programs (e.g., XBLAST and NBLAST) can be used. See http://www.ncbi.nlm.nih.gov.

As used herein, the term "hybridizes under low stringency, medium stringency, high stringency, or very high stringency conditions" describes conditions for hybridization and washing. Guidance for performing hybridization reactions can be found in *Current Protocols in Molecular Biology*, John Wiley & Sons, N.Y. (1989), 6.3.1-6.3.6, which is incorporated by reference. Aqueous and nonaqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5 M sodium phosphate, 7% SDS at 65° C., followed by one or more washes at 0.2×SSC, 1% SDS at 65° C. Very high stringency conditions (4) are the preferred conditions and the ones that should be used unless otherwise specified.

It is understood that the molecules of the present invention may have additional conservative or non-essential amino acid substitutions, which do not have a substantial effect on their functions.

The term "amino acid" is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of any of the foregoing. As used herein the term "amino acid" includes both the D- or L-optical isomers and peptidomimetics.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The terms "polypeptide", "peptide" and "protein" (if single chain) are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. The polypeptide can be isolated from natural sources, can be a produced by recombinant techniques from a eukaryotic or prokaryotic host, or can be a product of synthetic procedures.

The terms "nucleic acid," "nucleic acid sequence," "nucleotide sequence," or "polynucleotide sequence," and "polynucleotide" are used interchangeably. They refer to a polymeric form of nucleotides of any length, either deoxyribonucleotides or ribonucleotides, or analogs thereof. The polynucleotide may be either single-stranded or double-stranded, and if single-stranded may be the coding strand or non-coding (antisense) strand. A polynucleotide may comprise modified nucleotides, such as methylated nucleotides and nucleotide analogs. The sequence of nucleotides may be interrupted by non-nucleotide components. A polynucleotide may be further modified after polymerization, such as by conjugation with a labeling component. The nucleic acid may be a recombinant polynucleotide, or a polynucleotide of genomic, cDNA, semisynthetic, or synthetic origin which either does not occur in nature or is linked to another polynucleotide in a nonnatural arrangement.

The term "isolated," as used herein, refers to material that is removed from its original or native environment (e.g., the natural environment if it is naturally occurring). For example, a naturally-occurring polynucleotide or polypeptide present in a living animal is not isolated, but the same polynucleotide or polypeptide, separated by human intervention from some or all of the co-existing materials in the natural system, is isolated. Such polynucleotides could be part of a vector and/or such polynucleotides or polypeptides could be part of a composition, and still be isolated in that such vector or composition is not part of the environment in which it is found in nature.

Various aspects of the invention are described in further detail below. Additional definitions are set out throughout the specification.

Antibody Molecules

In one embodiment, the antibody molecule binds to a mammalian, e.g., human, PD-L1. For example, the antibody molecule binds specifically to an epitope, e.g., linear or conformational epitope, (e.g., an epitope as described herein) on PD-L1.

As used herein, the term "antibody molecule" refers to a protein, e.g., an immunoglobin chain or fragment thereof, comprising at least one immunoglobulin variable domain sequence. The term "antibody molecule" includes, for example, a monoclonal antibody (including a full length antibody which has an immunoglobulin Fc region). In an embodiment, an antibody molecule comprises a full length antibody, or a full length immunoglobin chain. In an embodiment, an antibody molecule comprises an antigen binding or functional fragment of a full length antibody, or a full length immunoglobin chain.

In an embodiment, an antibody molecule is a monospecific antibody molecule and binds a single epitope. E.g., a monospecific antibody molecule having a plurality of immunoglobulin variable domain sequences, each of which binds the same epitope.

In an embodiment an antibody molecule is a multispecific antibody molecule, e.g., it comprises a plurality of immunoglobulin variable domains sequences, wherein a first immunoglobulin variable domain sequence of the plurality has binding specificity for a first epitope and a second immunoglobulin variable domain sequence of the plurality has binding specificity for a second epitope. In an embodiment the first and second epitopes are on the same antigen, e.g., the same protein (or subunit of a multimeric protein). In an embodiment the first and second epitopes overlap. In an embodiment the first and second epitopes do not overlap. In an embodiment the first and second epitopes are on different antigens, e.g., the different proteins (or different subunits of a multimeric protein). In an embodiment a multispecific antibody molecule comprises a third, fourth or fifth immunoglobulin variable domain. In an embodiment, a multispecific antibody molecule is a bispecific antibody molecule, a trispecific antibody molecule, or tetraspecific antibody molecule, In an embodiment a multispecific antibody molecule is a bispecific antibody molecule. A bispecific antibody has specificity for no more than two antigens. A bispecific antibody molecule is characterized by a first immunoglobulin variable domain sequence which has binding specificity for a first epitope and a second immunoglobulin variable domain sequence that has binding specificity for a second epitope. In an embodiment the first and second epitopes are on the same antigen, e.g., the same protein (or subunit of a multimeric protein). In an embodiment the first and second epitopes overlap. In an embodiment the first and second epitopes do not overlap. In an embodiment the first and second epitopes are on different antigens, e.g., the different proteins (or different subunits of a multimeric protein). In an embodiment a bispecific antibody molecule comprises a heavy chain variable domain sequence and a light chain variable domain sequence which have binding specificity for a first epitope and a heavy chain variable domain sequence and a light chain variable domain sequence which have binding specificity for a second epitope. In an embodiment a bispecific antibody molecule comprises a half antibody having binding specificity for a first epitope and a half antibody having binding specificity for a second epitope. In an embodiment a bispecific antibody molecule comprises a half antibody, or fragment thereof, having binding specificity for a first epitope and a half antibody, or fragment thereof, having binding specificity for a second epitope. In an embodiment a bispecific antibody molecule comprises a scFv, or fragment thereof, have binding specificity for a first epitope and a scFv, or fragment thereof, have binding specificity for a second epitope. In an embodiment the first epitope is located on PD-L1 and the second epitope is located on a TIM-3, LAG-3, CEACAM (e.g., CEACAM-1, CEACAM-3, and/or CEACAM-5), PD-1, or PD-L2.

In an embodiment, an antibody molecule comprises a diabody, and a single-chain molecule, as well as an antigen-binding fragment of an antibody (e.g., Fab, F(ab')$_2$, and Fv). For example, an antibody molecule can include a heavy (H) chain variable domain sequence (abbreviated herein as VH), and a light (L) chain variable domain sequence (abbreviated herein as VL). In an embodiment an antibody molecule comprises or consists of a heavy chain and a light chain (referred to herein as a half antibody). In another example, an antibody molecule includes two heavy (H) chain variable domain sequences and two light (L) chain variable domain sequence, thereby forming two antigen binding sites, such as Fab, Fab', F(ab')$_2$, Fc, Fd, Fd', Fv, single chain antibodies (scFv for example), single variable domain antibodies, diabodies (Dab) (bivalent and bispecific), and chimeric (e.g., humanized) antibodies, which may be produced by the modification of whole antibodies or those synthesized de novo using recombinant DNA technologies. These functional antibody fragments retain the ability to selectively bind with their respective antigen or receptor. Antibodies and antibody fragments can be from any class of antibodies including, but not limited to, IgG, IgA, IgM, IgD, and IgE, and from any subclass (e.g., IgG1, IgG2, IgG3, and IgG4) of antibodies. The preparation of antibody molecules can be monoclonal or polyclonal. An antibody molecule can also be a human, humanized, CDR-grafted, or in vitro generated antibody. The antibody can have a heavy chain constant region chosen from, e.g., IgG1, IgG2, IgG3, or IgG4. The antibody can also have a light chain chosen from, e.g., kappa or lambda. The term "immunoglobulin" (Ig) is used interchangeably with the term "antibody" herein.

Examples of antigen-binding fragments of an antibody molecule include: (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a diabody (dAb) fragment, which consists of a VH domain; (vi) a camelid or camelized variable domain; (vii) a single chain Fv (scFv), see e.g., Bird et al. (1988) *Science* 242:423-426; and Huston et al. (1988) *Proc. Natl. Acad. Sci. USA* 85:5879-5883); (viii) a single domain antibody. These antibody fragments are obtained using conventional techniques known to those with skill in the art, and the fragments are screened for utility in the same manner as are intact antibodies.

The term "antibody" includes intact molecules as well as functional fragments thereof. Constant regions of the antibodies can be altered, e.g., mutated, to modify the properties of the antibody (e.g., to increase or decrease one or more of: Fc receptor binding, antibody glycosylation, the number of cysteine residues, effector cell function, or complement function).

Antibody molecules can also be single domain antibodies. Single domain antibodies can include antibodies whose complementary determining regions are part of a single domain polypeptide. Examples include, but are not limited to, heavy chain antibodies, antibodies naturally devoid of light chains, single domain antibodies derived from conventional 4-chain antibodies, engineered antibodies and single domain scaffolds other than those derived from antibodies. Single domain antibodies may be any of the art, or any future single domain antibodies. Single domain antibodies may be derived from any species including, but not limited to mouse, human, camel, llama, fish, shark, goat, rabbit, and bovine. According to another aspect of the invention, a single domain antibody is a naturally occurring single domain antibody known as heavy chain antibody devoid of light chains. Such single domain antibodies are disclosed in WO 9404678, for example. For clarity reasons, this variable domain derived from a heavy chain antibody naturally devoid of light chain is known herein as a VHH or nanobody to distinguish it from the conventional VH of four chain immunoglobulins. Such a VHH molecule can be derived from antibodies raised in Camelidae species, for example in camel, llama, dromedary, alpaca and guanaco. Other species besides Camelidae may produce heavy chain antibodies naturally devoid of light chain; such VHHs are within the scope of the invention.

The VH and VL regions can be subdivided into regions of hypervariability, termed "complementarity determining regions" (CDR), interspersed with regions that are more conserved, termed "framework regions" (FR or FW).

The extent of the framework region and CDRs has been precisely defined by a number of methods (see, Kabat, E. A., et al. (1991) Sequences of Proteins of Immunological Interest, Fifth Edition, U.S. Department of Health and Human Services, NIH Publication No. 91-3242; Chothia, C. et al. (1987) *J. Mol. Biol.* 196:901-917; and the AbM definition used by Oxford Molecular's AbM antibody modeling software. See, generally, e.g., *Protein Sequence and Structure Analysis of Antibody Variable Domains*. In: Antibody Engineering Lab Manual (Ed.: Duebel, S. and Kontermann, R., Springer-Verlag, Heidelberg).

The terms "complementarity determining region," and "CDR," as used herein refer to the sequences of amino acids within antibody variable regions which confer antigen specificity and binding affinity. In general, there are three CDRs in each heavy chain variable region (HCDR1, HCDR2, HCDR3) and three CDRs in each light chain variable region (LCDR1, LCDR2, LCDR3).

The precise amino acid sequence boundaries of a given CDR can be determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme), Al-Lazikani et al., (1997) *JMB* 273,927-948 ("Chothia" numbering scheme). As used herein, the CDRs defined according the "Chothia" number scheme are also sometimes referred to as "hypervariable loops."

For example, under Kabat, the CDR amino acid residues in the heavy chain variable domain (VH) are numbered 31-35 (HCDR1), 50-66 (HCDR2), and 99-109 (HCDR3); and the CDR amino acid residues in the light chain variable domain (VL) are numbered 24-34 (LCDR1), 50-56 (LCDR2), and 89-97 (LCDR3). Under Chothia the CDR amino acids in the VH are numbered 26-32 (HCDR1), 52-57 (HCDR2), and 99-109 (HCDR3); and the amino acid residues in VL are numbered 26-32 (LCDR1), 50-52 (LCDR2), and 91-96 (LCDR3). By combining the CDR definitions of both Kabat and Chothia, the CDRs consist of amino acid residues 26-35 (HCDR1), 50-66 (HCDR2), and 99-109 (HCDR3) in human VH and amino acid residues 24-34 (LCDR1), 50-56 (LCDR2), and 89-97 (LCDR3) in human VL.

Generally, unless specifically indicated, the anti-PD-L1 antibody molecules can include any combination of one or more Kabat CDRs and/or Chothia hypervariable loops, e.g., described in Table 1. In one embodiment, the following definitions are used for the anti-PD-L1 antibody molecules described in Table 1: HCDR1 according to the combined CDR definitions of both Kabat and Chothia, and HCCDRs 2-3 and LCCDRs 1-3 according the CDR definition of Kabat. Under all definitions, each VH and VL typically includes three CDRs and four FRs, arranged from amino-terminus to carboxy-terminus in the following order: FR1, CDR1, FR2, CDR2, FR3, CDR3, FR4.

As used herein, an "immunoglobulin variable domain sequence" refers to an amino acid sequence which can form the structure of an immunoglobulin variable domain. For example, the sequence may include all or part of the amino acid sequence of a naturally-occurring variable domain. For example, the sequence may or may not include one, two, or more N- or C-terminal amino acids, or may include other alterations that are compatible with formation of the protein structure.

The term "antigen-binding site" refers to the part of an antibody molecule that comprises determinants that form an interface that binds to the PD-L1 polypeptide, or an epitope thereof. With respect to proteins (or protein mimetics), the antigen-binding site typically includes one or more loops (of at least four amino acids or amino acid mimics) that form an interface that binds to the PD-L1 polypeptide. Typically, the antigen-binding site of an antibody molecule includes at least one or two CDRs and/or hypervariable loops, or more typically at least three, four, five or six CDRs and/or hypervariable loops.

The terms "monoclonal antibody" or "monoclonal antibody composition" as used herein refer to a preparation of antibody molecules of single molecular composition. A monoclonal antibody composition displays a single binding specificity and affinity for a particular epitope. A monoclonal antibody can be made by hybridoma technology or by methods that do not use hybridoma technology (e.g., recombinant methods).

An "effectively human" protein is a protein that does not evoke a neutralizing antibody response, e.g., the human anti-murine antibody (HAMA) response. HAMA can be problematic in a number of circumstances, e.g., if the antibody molecule is administered repeatedly, e.g., in treatment of a chronic or recurrent disease condition. A HAMA response can make repeated antibody administration potentially ineffective because of an increased antibody clearance from the serum (see, e.g., Saleh et al., Cancer Immunol. Immunother., 32:180-190 (1990)) and also because of potential allergic reactions (see, e.g., LoBuglio et al., Hybridoma, 5:5117-5123 (1986)).

The antibody molecule can be a polyclonal or a monoclonal antibody. In other embodiments, the antibody can be recombinantly produced, e.g., produced by phage display or by combinatorial methods.

Phage display and combinatorial methods for generating antibodies are known in the art (as described in, e.g., Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) Bio/Technology 9:1370-1372; Hay et al. (1992) Hum Antibod Hybridomas 3:81-85; Huse et al. (1989) Science 246:1275-1281; Griffths et al. (1993) EMBO J 12:725-734; Hawkins et al. (1992) J Mol Biol 226:889-896; Clackson et al. (1991) Nature 352:624-628; Gram et al. (1992) PNAS 89:3576-3580; Garrad et al. (1991) Bio/Technology 9:1373-1377; Hoogenboom et al. (1991) Nuc Acid Res 19:4133-4137; and Barbas et al. (1991) PNAS 88:7978-7982, the contents of all of which are incorporated by reference herein).

In one embodiment, the antibody is a fully human antibody (e.g., an antibody made in a mouse which has been genetically engineered to produce an antibody from a human immunoglobulin sequence), or a non-human antibody, e.g., a rodent (mouse or rat), goat, primate (e.g., monkey), camel antibody. Preferably, the non-human antibody is a rodent (mouse or rat antibody). Methods of producing rodent antibodies are known in the art.

Human monoclonal antibodies can be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906, Kucherlapati et al. PCT publication WO 91/10741; Lonberg et al. International Application WO 92/03918; Kay et al. International Application 92/03917; Lonberg, N. et al. 1994 Nature 368:856-859; Green, L. L. et al. 1994 Nature Genet. 7:13-21; Morrison, S. L. et al. 1994 Proc. Natl. Acad. Sci. USA 81:6851-6855; Bruggeman et al. 1993 Year Immunol 7:33-40; Tuaillon et al. 1993 PNAS 90:3720-3724; Bruggeman et al. 1991 Eur J Immunol 21:1323-1326).

An antibody can be one in which the variable region, or a portion thereof, e.g., the CDRs, are generated in a non-human organism, e.g., a rat or mouse. Chimeric, CDR-grafted, and humanized antibodies are within the invention. Antibodies generated in a non-human organism, e.g., a rat or mouse, and then modified, e.g., in the variable framework or constant region, to decrease antigenicity in a human are within the invention.

Chimeric antibodies can be produced by recombinant DNA techniques known in the art (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125,023; Better et al. (1988 Science 240:1041-1043); Liu et al. (1987) PNAS 84:3439-3443; Liu et al., 1987, J. Immunol. 139:3521-3526; Sun et al. (1987) PNAS 84:214-218; Nishimura et al., 1987, Canc. Res. 47:999-1005; Wood et al. (1985) Nature 314:446-449; and Shaw et al., 1988, J. Natl Cancer Inst. 80:1553-1559).

A humanized or CDR-grafted antibody will have at least one or two but generally all three recipient CDRs (of heavy and or light immuoglobulin chains) replaced with a donor CDR. The antibody may be replaced with at least a portion of a non-human CDR or only some of the CDRs may be replaced with non-human CDRs. It is only necessary to replace the number of CDRs required for binding of the humanized antibody to PD-L1. Preferably, the donor will be a rodent antibody, e.g., a rat or mouse antibody, and the recipient will be a human framework or a human consensus framework. Typically, the immunoglobulin providing the CDRs is called the "donor" and the immunoglobulin providing the framework is called the "acceptor." In one embodiment, the donor immunoglobulin is a non-human (e.g., rodent). The acceptor framework is a naturally-occurring (e.g., a human) framework or a consensus framework, or a sequence about 85% or higher, preferably 90%, 95%, 99% or higher identical thereto.

As used herein, the term "consensus sequence" refers to the sequence formed from the most frequently occurring amino acids (or nucleotides) in a family of related sequences (See e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensus sequence. A "consensus framework" refers to the framework region in the consensus immunoglobulin sequence.

An antibody can be humanized by methods known in the art (see e.g., Morrison, S. L., 1985, Science 229:1202-1207, by Oi et al., 1986, BioTechniques 4:214, and by Queen et al. U.S. Pat. No. 5,585,089, U.S. Pat. No. 5,693,761 and U.S. Pat. No. 5,693,762, the contents of all of which are hereby incorporated by reference).

Humanized or CDR-grafted antibodies can be produced by CDR-grafting or CDR substitution, wherein one, two, or all CDRs of an immunoglobulin chain can be replaced. See e.g., U.S. Pat. No. 5,225,539; Jones et al. 1986 Nature 321:552-525; Verhoeyan et al. 1988 Science 239:1534; Beidler et al. 1988 J. Immunol. 141:4053-4060; Winter U.S. Pat. No. 5,225,539, the contents of all of which are hereby expressly incorporated by reference. Winter describes a CDR-grafting method which may be used to prepare the humanized antibodies of the present invention (UK Patent Application GB 2188638A, filed on Mar. 26, 1987; Winter U.S. Pat. No. 5,225,539), the contents of which is expressly incorporated by reference.

Also within the scope of the invention are humanized antibodies in which specific amino acids have been substituted, deleted or added. Criteria for selecting amino acids from the donor are described in U.S. Pat. No. 5,585,089, e.g., columns 12-16 of U.S. Pat. No. 5,585,089, e.g., columns 12-16 of U.S. Pat. No. 5,585,089, the contents of which are hereby incorporated by reference. Other techniques for humanizing antibodies are described in Padlan et al. EP 519596 A1, published on Dec. 23, 1992.

The antibody molecule can be a single chain antibody. A single-chain antibody (scFV) may be engineered (see, for example, Colcher, D. et al. (1999) *Ann N Y Acad Sci* 880:263-80; and Reiter, Y. (1996) *Clin Cancer Res* 2:245-52). The single chain antibody can be dimerized or multimerized to generate multivalent antibodies having specificities for different epitopes of the same target protein.

In yet other embodiments, the antibody molecule has a heavy chain constant region chosen from, e.g., the heavy chain constant regions of IgG1, IgG2, IgG3, IgG4, IgM, IgA1, IgA2, IgD, and IgE; particularly, chosen from, e.g., the (e.g., human) heavy chain constant regions of IgG1, IgG2, IgG3, and IgG4. In another embodiment, the antibody molecule has a light chain constant region chosen from, e.g., the (e.g., human) light chain constant regions of kappa or lambda. The constant region can be altered, e.g., mutated, to modify the properties of the antibody (e.g., to increase or decrease one or more of: Fc receptor binding, antibody glycosylation, the number of cysteine residues, effector cell function, and/or complement function). In one embodiment the antibody has: effector function; and can fix complement. In other embodiments the antibody does not; recruit effector cells; or fix complement. In another embodiment, the antibody has reduced or no ability to bind an Fc receptor. For example, it is a isotype or subtype, fragment or other mutant, which does not support binding to an Fc receptor, e.g., it has a mutagenized or deleted Fc receptor binding region.

Methods for altering an antibody constant region are known in the art. Antibodies with altered function, e.g. altered affinity for an effector ligand, such as FcR on a cell, or the C1 component of complement can be produced by replacing at least one amino acid residue in the constant portion of the antibody with a different residue (see e.g., EP 388,151 A1, U.S. Pat. No. 5,624,821 and U.S. Pat. No. 5,648,260, the contents of all of which are hereby incorporated by reference). Similar type of alterations could be described which if applied to the murine, or other species immunoglobulin would reduce or eliminate these functions.

An antibody molecule can be derivatized or linked to another functional molecule (e.g., another peptide or protein). As used herein, a "derivatized" antibody molecule is one that has been modified. Methods of derivatization include but are not limited to the addition of a fluorescent moiety, a radionucleotide, a toxin, an enzyme or an affinity ligand such as biotin. Accordingly, the antibody molecules of the invention are intended to include derivatized and otherwise modified forms of the antibodies described herein, including immunoadhesion molecules. For example, an antibody molecule can be functionally linked (by chemical coupling, genetic fusion, noncovalent association or otherwise) to one or more other molecular entities, such as another antibody (e.g., a bispecific antibody or a diabody), a detectable agent, a cytotoxic agent, a pharmaceutical agent, and/or a protein or peptide that can mediate association of the antibody or antibody portion with another molecule (such as a streptavidin core region or a polyhistidine tag).

One type of derivatized antibody molecule is produced by crosslinking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Useful detectable agents with which an antibody molecule of the invention may be derivatized (or labeled) to include fluorescent compounds, various enzymes, prosthetic groups, luminescent materials, bioluminescent materials, fluorescent emitting metal atoms, e.g., europium (Eu), and other anthanides, and radioactive materials (described below). Exemplary fluorescent detectable agents include fluorescein, fluorescein isothiocyanate, rhodamine, 5dimethylamine-1-napthalenesulfonyl chloride, phycoerythrin and the like. An antibody may also be derivatized with detectable enzymes, such as alkaline phosphatase, horseradish peroxidase, β-galactosidase, acetylcholinesterase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody molecule may also be derivatized with a prosthetic group (e.g., streptavidin/biotin and avidin/biotin). For example, an antibody may be derivatized with biotin, and detected through indirect measurement of avidin or streptavidin binding. Examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of bioluminescent materials include luciferase, luciferin, and aequorin.

Labeled antibody molecule can be used, for example, diagnostically and/or experimentally in a number of contexts, including (i) to isolate a predetermined antigen by standard techniques, such as affinity chromatography or immunoprecipitation; (ii) to detect a predetermined antigen (e.g., in a cellular lysate or cell supernatant) in order to evaluate the abundance and pattern of expression of the protein; (iii) to monitor protein levels in tissue as part of a clinical testing procedure, e.g., to determine the efficacy of a given treatment regimen.

An antibody molecules may be conjugated to another molecular entity, typically a label or a therapeutic (e.g., a cytotoxic or cytostatic) agent or moiety. Radioactive isotopes can be used in diagnostic or therapeutic applications. Radioactive isotopes that can be coupled to the anti-PSMA antibodies include, but are not limited to α-, β-, or γ-emitters, or β- and γ-emitters. Such radioactive isotopes include, but are not limited to iodine ($^{131}$I or $^{125}$I), yttrium ($^{90}$Y), lutetium ($^{177}$Lu), actinium ($^{225}$Ac), praseodymium, astatine ($^{211}$At) rhenium ($^{186}$Re), bismuth ($^{212}$Bi or $^{213}$Bi) indium ($^{111}$In), technetium ($^{99}$mTc), phosphorus ($^{32}$P), rhodium ($^{188}$Rh), sulfur ($^{35}$S), carbon ($^{14}$C), tritium ($^{3}$H), chromium ($^{51}$Cr), chlorine ($^{36}$Cl), cobalt ($^{57}$Co or $^{58}$Co), iron ($^{59}$Fe), selenium ($^{75}$Se), or gallium ($^{67}$Ga). Radioisotopes useful as therapeutic agents include yttrium ($^{90}$Y), lutetium ($^{177}$Lu), actinium ($^{225}$Ac), praseodymium, astatine ($^{211}$At), rhenium ($^{186}$Re), bismuth ($^{212}$Bi or $^{213}$Bi), and rhodium ($^{188}$Rh). Radioisotopes useful as labels, e.g., for use in diagnostics, include iodine ($^{131}$I or $^{125}$I), indium ($^{111}$In) technetium ($^{99}$mTc), phosphorus ($^{32}$P), carbon ($^{14}$C), and tritium ($^{3}$H), or one or more of the therapeutic isotopes listed above.

The invention provides radiolabeled antibody molecules and methods of labeling the same. In one embodiment, a method of labeling an antibody molecule is disclosed. The method includes contacting an antibody molecule, with a chelating agent, to thereby produce a conjugated antibody. The conjugated antibody is radiolabeled with a radioisotope, e.g., $^{111}$Indium, $^{90}$Yttrium and $^{177}$Lutetium, to thereby produce a labeled antibody molecule.

As is discussed above, the antibody molecule can be conjugated to a therapeutic agent. Therapeutically active radioisotopes have already been mentioned. Examples of other therapeutic agents include taxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, maytansinoids, e.g., maytansinol (see U.S. Pat. No. 5,208,020), CC-1065 (see U.S. Pat. Nos. 5,475,092, 5,585,499, 5,846, 545) and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, CC-1065, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclinies (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, taxol and maytansinoids).

In one aspect, the invention features a method of providing a target binding molecule that specifically binds to a PD-L1 receptor. For example, the target binding molecule is an antibody molecule. The method includes: providing a target protein that comprises at least a portion of non-human protein, the portion being homologous to (at least 70, 75, 80, 85, 87, 90, 92, 94, 95, 96, 97, 98% identical to) a corresponding portion of a human target protein, but differing by at least one amino acid (e.g., at least one, two, three, four, five, six, seven, eight, or nine amino acids); obtaining an antibody molecule that specifically binds to the antigen; and evaluating efficacy of the binding agent in modulating activity of the target protein. The method can further include administering the binding agent (e.g., antibody molecule) or a derivative (e.g., a humanized antibody molecule) to a human subject.

In certain embodiments, the antibody molecule is a multispecific (e.g., a bispecific or a trispecific) antibody molecule. Protocols for generating bispecific or heterodimeric antibody molecules are known in the art; including but not limited to, for example, the "knob in a hole" approach described in, e.g., U.S. Pat. No. 5,731,168; the electrostatic steering Fc pairing as described in, e.g., WO 09/089004, WO 06/106905 and WO 2010/129304; Strand Exchange Engineered Domains (SEED) heterodimer formation as described in, e.g., WO 07/110205; Fab arm exchange as described in, e.g., WO 08/119353, WO 2011/131746, and WO 2013/060867; double antibody conjugate, e.g., by antibody cross-linking to generate a bi-specific structure using a heterobifunctional reagent having an amine-reactive group and a sulfhydryl reactive group as described in, e.g., U.S. Pat. No. 4,433,059; bispecific antibody determinants generated by recombining half antibodies (heavy-light chain pairs or Fabs) from different antibodies through cycle of reduction and oxidation of disulfide bonds between the two heavy chains, as described in, e.g., U.S. Pat. No. 4,444,878; trifunctional antibodies, e.g., three Fab' fragments cross-linked through sulfhdryl reactive groups, as described in, e.g., U.S. Pat. No. 5,273,743; biosynthetic binding proteins, e.g., pair of scFvs cross-linked through C-terminal tails preferably through disulfide or amine-reactive chemical cross-linking, as described in, e.g., U.S. Pat. No. 5,534,254; bifunctional antibodies, e.g., Fab fragments with different binding specificities dimerized through leucine zippers (e.g., c-fos and c-jun) that have replaced the constant domain, as described in, e.g., U.S. Pat. No. 5,582,996; bispecific and oligospecific mono- and oligovalent receptors, e.g., VH-CH1 regions of two antibodies (two Fab fragments) linked through a polypeptide spacer between the CH1 region of one antibody and the VH region of the other antibody typically with associated light chains, as described in, e.g., U.S. Pat. No. 5,591,828; bispecific DNA-antibody conjugates, e.g., crosslinking of antibodies or Fab fragments through a double stranded piece of DNA, as described in, e.g., U.S. Pat. No. 5,635,602; bispecific fusion proteins, e.g., an expression construct containing two scFvs with a hydrophilic helical peptide linker between them and a full constant region, as described in, e.g., U.S. Pat. No. 5,637,481; multivalent and multispecific binding proteins, e.g., dimer of polypeptides having first domain with binding region of Ig heavy chain variable region, and second domain with binding region of Ig light chain variable region, generally termed diabodies (higher order structures are also encompassed creating for bispecifc, trispecific, or tetraspecific molecules, as described in, e.g., U.S. Pat. No. 5,837,242; minibody constructs with linked VL and VH chains further connected with peptide spacers to an antibody hinge region and CH3 region, which can be dimerized to form bispecific/multivalent molecules, as described in, e.g., U.S. Pat. No. 5,837, 821; VH and VL domains linked with a short peptide linker (e.g., 5 or 10 amino acids) or no linker at all in either orientation, which can form dimers to form bispecific diabodies; trimers and tetramers, as described in, e.g., U.S. Pat. No. 5,844,094; String of VH domains (or VL domains in family members) connected by peptide linkages with cross-linkable groups at the C-terminus further associated with VL domains to form a series of FVs (or scFvs), as described in, e.g., U.S. Pat. No. 5,864,019; and single chain binding polypeptides with both a VH and a VL domain linked through a peptide linker are combined into multivalent structures through non-covalent or chemical crosslinking to form, e.g., homobivalent, heterobivalent, trivalent, and tetravalent structures using both scFV or diabody type format, as described in, e.g., U.S. Pat. No. 5,869,620. Additional exemplary multispecific and bispecific molecules and methods of making the same are found, for example, in U.S. Pat. No. 5,910,573, U.S. Pat. No. 5,932,448, U.S. Pat. No. 5,959,083, U.S. Pat. No. 5,989,830, U.S. Pat. No. 6,005,079, U.S. Pat. No. 6,239,259, U.S. Pat. No. 6,294,353, U.S. Pat. No. 6,333,396, U.S. Pat. No. 6,476,198, U.S. Pat. No. 6,511,663, U.S. Pat. No. 6,670,453, U.S. Pat. No. 6,743,896, U.S. Pat. No. 6,809,185, U.S. Pat. No. 6,833,441, U.S. Pat. No. 7,129,330, U.S. Pat. No. 7,183,076, U.S. Pat. No. 7,521,056, U.S. Pat. No. 7,527,787, U.S. Pat. No. 7,534,866, U.S. Pat. No. 7,612,181, US2002004587A1, US2002076406A1, US2002103345A1, US2003207346A1, US2003211078A1, US2004219643A1, US2004220388A1, US2004242847A1, US2005003403A1, US2005004352A1, US2005069552A1, US2005079170A1, US2005100543A1, US2005136049A1, US2005136051A1, US2005163782A1, US2005266425A1, US2006083747A1, US2006120960A1, US2006204493A1, US2006263367A1, US2007004909A1, US2007087381A1, US2007128150A1, US2007141049A1, US2007154901A1, US2007274985A1, US2008050370A1, US2008069820A1, US2008152645A1, US2008171855A1, US2008241884A1, US2008254512A1, US2008260738A1, US2009130106A1, US2009148905A1, US2009155275A1, US2009162359A1, US2009162360A1, US2009175851A1, US2009175867A1, US2009232811A1, US2009234105A1, US2009263392A1, US2009274649A1, EP346087A2, WO0006605A2, WO02072635A2, WO04081051A1, WO06020258A2, WO2007044887A2, WO2007095338A2, WO2007137760A2, WO2008119353A1, WO2009021754A2, WO2009068630A1, WO9103493A1, WO9323537A1, WO9409131A1, WO9412625A2, WO9509917A1, WO9637621A2, WO9964460A1. The contents of the above-referenced applications are incorporated herein by reference in their entireties.

In other embodiments, the anti-PD-L1 antibody molecule (e.g., a monospecific, bispecific, or multispecific antibody molecule) is covalently linked, e.g., fused, to another partner e.g., a protein e.g., one, two or more cytokines, e.g., as a fusion molecule for example a fusion protein. In other embodiments, the fusion molecule comprises one or more proteins, e.g., one, two or more cytokines. In one embodiment, the cytokine is an interleukin (IL) chosen from one, two, three or more of IL-1, IL-2, IL-12, IL-15 or IL-21. In one embodiment, a bispecific antibody molecule has a first binding specificity to a first target (e.g., to PD-L1), a second binding specificity to a second target (e.g., LAG-3 or TIM-3), and is optionally linked to an interleukin (e.g., IL-12) domain e.g., full length IL-12 or a portion thereof.

A "fusion protein" and a "fusion polypeptide" refer to a polypeptide having at least two portions covalently linked together, where each of the portions is a polypeptide having a different property. The property may be a biological property, such as activity in vitro or in vivo. The property can also be simple chemical or physical property, such as binding to a target molecule, catalysis of a reaction, etc. The two portions can be linked directly by a single peptide bond or through a peptide linker, but are in reading frame with each other.

This invention provides an isolated nucleic acid molecule encoding the above antibody molecule, vectors and host cells thereof. The nucleic acid molecule includes but is not limited to RNA, genomic DNA and cDNA.

Exemplary Anti-PD-L1 Antibody Molecules

In certain embodiments, the anti-PD-L1 antibody molecule comprises:

(i) a heavy chain variable region (VH) comprising a VHCDR1 amino acid sequence chosen from SEQ ID NO: 1, SEQ ID NO: 4 or SEQ ID NO: 195; a VHCDR2 amino acid sequence of SEQ ID NO: 2; and a VHCDR3 amino acid sequence of SEQ ID NO: 3; and (ii) a light chain variable region (VL) comprising a VLCDR1 amino acid sequence of SEQ ID NO: 9, a VLCDR2 amino acid sequence of SEQ ID NO: 10, and a VLCDR3 amino acid sequence of SEQ ID NO: 11.

In other embodiments, the anti-PD-L1 antibody molecule comprises:

(i) a heavy chain variable region (VH) comprising a VHCDR1 amino acid sequence chosen from SEQ ID NO: 1, SEQ ID NO: 4 or SEQ ID NO: 195; a VHCDR2 amino acid sequence of SEQ ID NO: 5, and a VHCDR3 amino acid sequence of SEQ ID NO: 3; and (ii) a light chain variable region (VL) comprising a VLCDR1 amino acid sequence of SEQ ID NO: 12, a VLCDR2 amino acid sequence of SEQ ID NO: 13, and a VLCDR3 amino acid sequence of SEQ ID NO: 14.

In embodiments of the aforesaid antibody molecules, the VHCDR1 comprises the amino acid sequence of SEQ ID NO: 1. In other embodiments, the VHCDR1 comprises the amino acid sequence of SEQ ID NO: 4. In yet other embodiments, the VHCDR1 amino acid sequence of SEQ ID NO: 195.

In embodiments, the aforesaid antibody molecules have a heavy chain variable region comprising at least one framework (FW) region comprising the amino acid sequence of any of SEQ ID NOs: 124, 126, 128, 130, 132, 134, 136, 138, 140, 142, 144, 146, 148, 150, 152, or 154, or an amino acid sequence at least 90% identical thereto, or having no more than two amino acid substitutions, insertions or deletions compared to the amino acid sequence of any of SEQ ID NOs: 124, 126, 128, 130, 132, 134, 136, 138, 140, 142, 144, 146, 148, 150, 152, or 154.

In other embodiments, the aforesaid antibody molecules have a heavy chain variable region comprising at least one framework region comprising the amino acid sequence of any of SEQ ID NOs: 124, 126, 128, 130, 132, 134, 136, 138, 140, 142, 144, 146, 148, 150, 152, or 154.

In yet other embodiments, the aforesaid antibody molecules have a heavy chain variable region comprising at least two, three, or four framework regions comprising the amino acid sequences of any of SEQ ID NOs: 124, 126, 128, 130, 132, 134, 136, 138, 140, 142, 144, 146, 148, 150, 152, or 154.

In other embodiments, the aforesaid antibody molecules comprise a VHFW1 amino acid sequence of SEQ ID NO: 124, 126, 128, or 130, a VHFW2 amino acid sequence of SEQ ID NO: 132, 134, 136, 138, 140, or 142, and a VHFW3 amino acid sequence of SEQ ID NO: 144, 146, 148, 150, or 152, and, optionally, further comprising a VHFW4 amino acid sequence of SEQ ID NO: 154.

In other embodiments, the aforesaid antibody molecules have a light chain variable region comprising at least one framework region comprising the amino acid sequence of any of SEQ ID NOs: 156, 158, 160, 162, 164, 166, 168, 170, 172, 174, 176, 178, 180, 182, 184, or 186, or an amino acid sequence at least 90% identical thereto, or having no more than two amino acid substitutions, insertions or deletions compared to the amino acid sequence of any of 156, 158, 160, 162, 164, 166, 168, 170, 172, 174, 176, 178, 180, 182, 184, or 186.

In other embodiments, the aforesaid antibody molecules have a light chain variable region comprising at least one framework region comprising the amino acid sequence of any of SEQ ID NOs: 156, 158, 160, 162, 164, 166, 168, 170, 172, 174, 176, 178, 180, 182, 184, or 186.

In other embodiments, the aforesaid antibody molecules have a light chain variable region comprising at least two, three, or four framework regions comprising the amino acid sequences of any of SEQ ID NOs: 156, 158, 160, 162, 164, 166, 168, 170, 172, 174, 176, 178, 180, 182, 184, or 186.

In other embodiments, the aforesaid antibody molecules comprise a VLFW1 amino acid sequence of SEQ ID NO: 156, 158, 160, 162, 164, or 166, a VLFW2 amino acid sequence of SEQ ID NO: 168 or 170, and a VLFW3 amino acid sequence of SEQ ID NO: 172, 174, 176, 178, 180, 182, or 184, and, optionally, further comprising a VLFW4 amino acid sequence of SEQ ID NO: 186.

In other embodiments, the aforesaid antibodies comprise a heavy chain variable domain comprising an amino acid sequence at least 85% identical to any of SEQ ID NOs: 18. 30. 38, 46, 50, 54, 62, 70, or 78.

In other embodiments, the aforesaid antibody molecules comprise a heavy chain variable domain comprising the amino acid sequence of SEQ ID NO: 18, 30, 38, 46, 50, 54, 62, 70, or 78.

In other embodiments, the aforesaid antibody molecules comprise a light chain variable domain comprising an amino acid sequence at least 85% identical to any of SEQ ID NOs: 22, 26, 34, 42, 58, 66, 74, 82, or 86.

In other embodiments, the aforesaid antibody molecules comprise a light chain variable domain comprising the amino acid sequence of SEQ ID NO: 22, 26, 34, 42, 58, 66, 74, 82, or 86.

In other embodiments, the aforesaid antibody molecules comprise a heavy chain variable domain comprising the amino acid sequence of SEQ ID NO: 18.

In other embodiments, the aforesaid antibody molecules comprise a heavy chain comprising the amino acid sequence of SEQ ID NO: 20.

In other embodiments, the aforesaid antibody molecules comprise a heavy chain variable domain comprising the amino acid sequence of SEQ ID NO: 30.

In other embodiments, the aforesaid antibody molecules comprise a heavy chain comprising the amino acid sequence of SEQ ID NO: 32.

In other embodiments, the aforesaid antibody molecules comprise a heavy chain comprising the amino acid sequence of SEQ ID NO: 96.

In other embodiments, the aforesaid antibody molecules comprise a heavy chain comprising the amino acid sequence of SEQ ID NO: 197.

In other embodiments, the aforesaid antibody molecules comprise a heavy chain variable domain comprising the amino acid sequence of SEQ ID NO: 38.

In other embodiments, the aforesaid antibody molecules comprise a heavy chain comprising the amino acid sequence of SEQ ID NO: 40.

In other embodiments, the aforesaid antibody molecules comprise a heavy chain comprising the amino acid sequence of SEQ ID NO: 91.

In other embodiments, the aforesaid antibody molecules comprise a heavy chain variable domain comprising the amino acid sequence of SEQ ID NO: 46.

In other embodiments, the aforesaid antibody molecules comprise a heavy chain comprising the amino acid sequence of SEQ ID NO: 48.

In other embodiments, the aforesaid antibody molecules comprise a heavy chain variable domain comprising the amino acid sequence of SEQ ID NO: 50.

In other embodiments, the aforesaid antibody molecules comprise a heavy chain comprising the amino acid sequence of SEQ ID NO: 52.

In other embodiments, the aforesaid antibody molecules comprise a heavy chain variable domain comprising the amino acid sequence of SEQ ID NO: 54.

In other embodiments, the aforesaid antibody molecules comprise a heavy chain comprising the amino acid sequence of SEQ ID NO: 56.

In other embodiments, the aforesaid antibody molecules comprise a heavy chain variable domain comprising the amino acid sequence of SEQ ID NO: 62.

In other embodiments, the aforesaid antibody molecules comprise a heavy chain comprising the amino acid sequence of SEQ ID NO: 64.

In other embodiments, the aforesaid antibody molecules comprise a heavy chain variable domain comprising the amino acid sequence of SEQ ID NO: 70.

In other embodiments, the aforesaid antibody molecules comprise a heavy chain comprising the amino acid sequence of SEQ ID NO: 72.

In other embodiments, the aforesaid antibody molecules comprise a heavy chain variable domain comprising the amino acid sequence of SEQ ID NO: 78.

In other embodiments, the aforesaid antibody molecules comprise a heavy chain comprising the amino acid sequence of SEQ ID NO: 80.

In other embodiments, the aforesaid antibody molecules comprise a heavy chain comprising the amino acid sequence of SEQ ID NO: 247.

In other embodiments, the aforesaid antibody molecules comprise a heavy chain comprising the amino acid sequence of SEQ ID NO: 260.

In other embodiments, the aforesaid antibody molecules comprise a light chain variable domain comprising the amino acid sequence of SEQ ID NO: 22. In other embodiments, the aforesaid antibody molecules comprise a light chain comprising the amino acid sequence of SEQ ID NO: 24.

In other embodiments, the aforesaid antibody molecules comprise a light chain variable domain comprising the amino acid sequence of SEQ ID NO: 26.

In other embodiments, the aforesaid antibody molecules comprise a light chain comprising the amino acid sequence of SEQ ID NO: 28.

In other embodiments, the aforesaid antibody molecules comprise a light chain variable domain comprising the amino acid sequence of SEQ ID NO: 34.

In other embodiments, the aforesaid antibody molecules comprise a light chain comprising the amino acid sequence of SEQ ID NO: 36.

In other embodiments, the aforesaid antibody molecules comprise a light chain variable domain comprising the amino acid sequence of SEQ ID NO: 42.

In other embodiments, the aforesaid antibody molecules comprise a light chain comprising the amino acid sequence of SEQ ID NO: 44.

In other embodiments, the aforesaid antibody molecules comprise a light chain variable domain comprising the amino acid sequence of SEQ ID NO: 58.

In other embodiments, the aforesaid antibodies comprise a light chain comprising the amino acid sequence of SEQ ID NO: 60.

In other embodiments, the aforesaid antibody molecules comprise a light chain variable domain comprising the amino acid sequence of SEQ ID NO: 66.

In other embodiments, the aforesaid antibody molecules comprise a light chain comprising the amino acid sequence of SEQ ID NO: 68.

In other embodiments, the aforesaid antibody molecules comprise a light chain variable domain comprising the amino acid sequence of SEQ ID NO: 74.

In other embodiments, the aforesaid antibody molecules comprise a light chain comprising the amino acid sequence of SEQ ID NO: 76

In other embodiments, the aforesaid antibody molecules comprise a light chain variable domain comprising the amino acid sequence of SEQ ID NO: 82.

In other embodiments, the aforesaid antibody molecules comprise a light chain comprising the amino acid sequence of SEQ ID NO: 84.

In other embodiments, the aforesaid antibody molecules comprise a light chain variable domain comprising the amino acid sequence of SEQ ID NO: 86.

In other embodiments, the aforesaid antibody molecules comprise a light chain comprising the amino acid sequence of SEQ ID NO: 88.

In other embodiments, the aforesaid antibody molecules comprise a heavy chain variable domain comprising the amino acid sequence of SEQ ID NO: 18 and a light chain variable domain comprising the amino acid sequence of SEQ ID NO: 22.

In other embodiments, the aforesaid antibody molecules comprise a heavy chain variable domain comprising the amino acid sequence of SEQ ID NO: 18 and a light chain variable domain comprising the amino acid sequence of SEQ ID NO: 26.

In other embodiments, the aforesaid antibody molecules comprise a heavy chain variable domain comprising the amino acid sequence of SEQ ID NO: 18 and a light chain variable domain comprising the amino acid sequence of SEQ ID NO: 86.

In other embodiments, the aforesaid antibody molecules comprise a heavy chain variable domain comprising the amino acid sequence of SEQ ID NO: 30 and a light chain variable domain comprising the amino acid sequence of SEQ ID NO: 34.

In other embodiments, the aforesaid antibody molecules comprise a heavy chain variable domain comprising the amino acid sequence of SEQ ID NO: 30 and a light chain variable domain comprising the amino acid sequence of SEQ ID NO: 66.

In other embodiments, the aforesaid antibody molecules comprise a heavy chain variable domain comprising the amino acid sequence of SEQ ID NO: 38 and a light chain variable domain comprising the amino acid sequence of SEQ ID NO: 42.

In other embodiments, the aforesaid antibody molecules comprise a heavy chain variable domain comprising the amino acid sequence of SEQ ID NO: 38 and a light chain variable domain comprising the amino acid sequence of SEQ ID NO: 74.

In other embodiments, the aforesaid antibody molecules comprise a heavy chain variable domain comprising the amino acid sequence of SEQ ID NO: 46 and a light chain variable domain comprising the amino acid sequence of SEQ ID NO: 42.

In other embodiments, the aforesaid antibody molecules comprise a heavy chain variable domain comprising the amino acid sequence of SEQ ID NO: 50 and a light chain variable domain comprising the amino acid sequence of SEQ ID NO: 42.

In other embodiments, the aforesaid antibody molecules comprise a heavy chain variable domain comprising the amino acid sequence of SEQ ID NO: 50 and a light chain variable domain comprising the amino acid sequence of SEQ ID NO: 22.

In other embodiments, the aforesaid antibody molecules comprise a heavy chain variable domain comprising the amino acid sequence of SEQ ID NO: 50 and a light chain variable domain comprising the amino acid sequence of SEQ ID NO: 86.

In other embodiments, the aforesaid antibody molecules comprise a heavy chain variable domain comprising the amino acid sequence of SEQ ID NO: 54 and a light chain variable domain comprising the amino acid sequence of SEQ ID NO: 58.

In other embodiments, the aforesaid antibody molecules comprise a heavy chain variable domain comprising the amino acid sequence of SEQ ID NO: 54 and a light chain variable domain comprising the amino acid sequence of SEQ ID NO: 86.

In other embodiments, the aforesaid antibody molecules comprise a heavy chain variable domain comprising the amino acid sequence of SEQ ID NO: 62 and a light chain variable domain comprising the amino acid sequence of SEQ ID NO: 66.

In other embodiments, the aforesaid antibody molecules comprise a heavy chain variable domain comprising the amino acid sequence of SEQ ID NO: 62 and a light chain variable domain comprising the amino acid sequence of SEQ ID NO: 86.

In other embodiments, the aforesaid antibody molecules comprise a heavy chain variable domain comprising the amino acid sequence of SEQ ID NO: 70 and a light chain variable domain comprising the amino acid sequence of SEQ ID NO: 66.

In other embodiments, the aforesaid antibody molecules comprise a heavy chain variable domain comprising the amino acid sequence of SEQ ID NO: 78 and a light chain variable domain comprising the amino acid sequence of SEQ ID NO: 82.

In other embodiments, the aforesaid antibody molecules comprise a heavy chain comprising the amino acid sequence of SEQ ID NO: 20 and a light chain comprising the amino acid sequence of SEQ ID NO: 24.

In other embodiments, the aforesaid antibody molecules comprise a heavy chain comprising the amino acid sequence of SEQ ID NO: 20 and a light chain comprising the amino acid sequence of SEQ ID NO: 28.

In other embodiments, the aforesaid antibody molecules comprise a heavy chain comprising the amino acid sequence of SEQ ID NO: 20 and a light chain comprising the amino acid sequence of SEQ ID NO: 88.

In other embodiments, the aforesaid antibody molecules comprise a heavy chain comprising the amino acid sequence of SEQ ID NO: 32 and a light chain comprising the amino acid sequence of SEQ ID NO: 36.

In other embodiments, the aforesaid antibody molecules comprise a heavy chain comprising the amino acid sequence of SEQ ID NO: 32 and a light chain comprising the amino acid sequence of SEQ ID NO: 68.

In other embodiments, the aforesaid antibody molecules comprise a heavy chain comprising the amino acid sequence of SEQ ID NO: 40 and a light chain comprising the amino acid sequence of SEQ ID NO: 44.

In other embodiments, the aforesaid antibody molecules comprise a heavy chain comprising the amino acid sequence of SEQ ID NO: 40 and a light chain comprising the amino acid sequence of SEQ ID NO: 76.

In other embodiments, the aforesaid antibody molecules comprise a heavy chain comprising the amino acid sequence of SEQ ID NO: 48 and a light chain comprising the amino acid sequence of SEQ ID NO: 44.

In other embodiments, the aforesaid antibody molecules comprise a heavy chain comprising the amino acid sequence of SEQ ID NO: 52 and a light chain comprising the amino acid sequence of SEQ ID NO: 44.

In other embodiments, the aforesaid antibody molecules comprise a heavy chain comprising the amino acid sequence of SEQ ID NO: 52 and a light chain comprising the amino acid sequence of SEQ ID NO: 24.

In other embodiments, the aforesaid antibodies comprise a heavy chain comprising the amino acid sequence of SEQ ID NO: 52 and a light chain comprising the amino acid sequence of SEQ ID NO: 88.

In other embodiments, the aforesaid antibody molecules comprise a heavy chain comprising the amino acid sequence of SEQ ID NO: 260 and a light chain comprising the amino acid sequence of SEQ ID NO: 44.

In other embodiments, the aforesaid antibody molecules comprise a heavy chain comprising the amino acid sequence of SEQ ID NO: 56 and a light chain comprising the amino acid sequence of SEQ ID NO: 60.

In other embodiments, the aforesaid antibody molecules comprise a heavy chain comprising the amino acid sequence of SEQ ID NO: 56 and a light chain comprising the amino acid sequence of SEQ ID NO: 88.

In other embodiments, the aforesaid antibody molecules comprise a heavy chain comprising the amino acid sequence of SEQ ID NO: 64 and a light chain comprising the amino acid sequence of SEQ ID NO: 68.

In other embodiments, the aforesaid antibody molecules comprise a heavy chain comprising the amino acid sequence of SEQ ID NO: 64 and a light chain comprising the amino acid sequence of SEQ ID NO: 88.

In other embodiments, the aforesaid antibody molecules comprise a heavy chain comprising the amino acid sequence of SEQ ID NO: 72 and a light chain comprising the amino acid sequence of SEQ ID NO: 68.

In other embodiments, the aforesaid antibody molecules comprise a heavy chain comprising the amino acid sequence of SEQ ID NO: 80 and a light chain comprising the amino acid sequence of SEQ ID NO: 84.

In other embodiments, the aforesaid antibody molecules comprise a heavy chain comprising the amino acid sequence of SEQ ID NO: 247 and a light chain comprising the amino acid sequence of SEQ ID NO: 84.

In other embodiments, the aforesaid antibody molecules comprise a heavy chain comprising the amino acid sequence of SEQ ID NO: 197 and a light chain comprising the amino acid sequence of SEQ ID NO: 36.

In other embodiments, the aforesaid antibody molecules comprise a heavy chain comprising the amino acid sequence of SEQ ID NO: 91 and a light chain comprising the amino acid sequence of SEQ ID NO: 44.

In other embodiments, the aforesaid antibodies comprise a heavy chain comprising the amino acid sequence of SEQ ID NO: 96 and a light chain comprising the amino acid sequence of SEQ ID NO: 68.

In other embodiments, the aforesaid antibody molecules are chosen from a Fab, F(ab')2, Fv, or a single chain Fv fragment (scFv).

In other embodiments, the aforesaid antibody molecules comprise a heavy chain constant region selected from IgG1, IgG2, IgG3, and IgG4.

In other embodiments, the aforesaid antibody molecules comprise a light chain constant region chosen from the light chain constant regions of kappa or lambda.

In other embodiments, the aforesaid antibody molecules comprise a human IgG4 heavy chain constant region with a mutation at position 228 of SEQ ID NO: 188 or 190 and a kappa light chain constant region.

In other embodiments, the aforesaid antibody molecules comprise a human IgG4 heavy chain constant region with a Serine to Proline mutation at position 228 of SEQ ID NO: 188 or 190 and a kappa light chain constant region.

In other embodiments, the aforesaid antibody molecules comprise a human IgG1 heavy chain constant region with an Asparagine to Alanine mutation at position 297 of SEQ ID NO: 192 and a kappa light chain constant region.

In other embodiments, the aforesaid antibody molecules comprise a human IgG1 heavy chain constant region with an Aspartate to Alanine mutation at position 265, and Proline to Alanine mutation at position 329 of SEQ ID NO: 193 and a kappa light chain constant region.

In other embodiments, the aforesaid antibody molecules comprise a human IgG1 heavy chain constant region with a Leucine to Alanine mutation at position 234 and Leucine to Alanine mutation at position 235 of SEQ ID NO: 194 and a kappa light chain constant region.

In other embodiments, the aforesaid antibody molecules are capable of binding to human PD-L1 with a dissociation constant ($K_D$) of less than about 0.2 nM.

In some embodiments, the aforesaid antibody molecules bind to human PD-L1 with a $K_D$ of less than about 2.5 nM, 2 nM, 1.5 nM, 1 nM, 0.5 nM, 0.2 nM, 0.15 nM, 0.1 nM, 0.05 nM, or 0.02 nM, e.g., about 0.2 nM to 0.1 nM, e.g., about 0.166 nM to 0.176 nM, e.g., about 0.171 nM, or e.g., about 0.1 nM to 1.5 nM, e.g., about 0.25 to 0.46 nM, e.g., about 0.137 nM, 0.931 nM, or 2.14 nM, e.g., as measured by a Biacore method.

In other embodiments, the aforesaid antibody molecules bind to cynomolgus PD-L1 with a $K_D$ of less than about 1 nM, 0.8 nM, 0.6 nM, 0.4 nM, 0.2 nM, 0.15 nM, 0.1 nM, 0.05 nM, or 0.02 nM, e.g., about 0.1 nM to 1 nM, e.g., about 0.2 nM to 0.8 nM, e.g., about 0.13 nM to 0.11 nM, e.g., about 0.124 nM, 0.369 nM, 0.431 nM, 0.735 nM, e.g., as measured by a Biacore method.

In other embodiments, the aforesaid antibody molecules bind to murine PD-L1 with a $K_D$ of less than about 100 nM, 60 nM, 10 nM, 1 nM, 0.5 nM, 0.2 nM, 0.15 nM, 0.1 nM, 0.05 nM, or 0.02 nM, e.g., about 0.13 nM to 0.11 nM, e.g., about 0.124 nM, 0.04 nM, 0.075 nM, or 77.4 nM, e.g., as measured by a Biacore method.

In other embodiments, the aforesaid antibody molecules bind to rat PD-L1 with a $K_D$ of less than about 15 nM, 10 nM, 5 nM, 1 nM, 0.5 nM, 0.2 nM, 0.15 nM, 0.1 nM, 0.05 nM, or 0.02 nM, e.g., about 0.1 nM to 3.5 nM, e.g., about 0.13 nM to 0.11 nM, e.g., about 0.124 nM, 0.04 nM, 0.075 nM, 0.431 nM, 1.36 nM, 6.14 nM, or 77.4 nM, e.g., as measured by a Biacore method. In certain embodiments, the aforesaid antibody molecules bind to both human PD-L1 and cynomolgus PD-L1 with similar $K_D$, e.g., in the nM range, e.g., as measured by a Biacore method.

In some embodiments, the aforesaid antibody molecules bind to 300.19 cells that express human PD-L1 (e.g., human PD-L1-transfected 300.19 cells) with a $K_D$ of less than about 0.5 nM, 0.4 nM, 0.3 nM, 0.2 nM, 0.1 nM, 0.075 nM, 0.05 nM, 0.025 nM, or 0.01 nM, e.g., about 0.285 nM, e.g., as measured by FACS analysis.

In some embodiments, the aforesaid antibody molecules bind to cells that express cynomolgus PD-L1 (e.g., cells transfected with cynomolgus PD-L1) with a $K_D$ of less than about 1 nM, 0.75 nM, 0.5 nM, 0.25 nM, or 0.01 nM, e.g., about 0.129 nM, e.g., as measured by FACS analysis.

In certain embodiments, the aforesaid antibody molecules are not cross-reactive with mouse or rat PD-L1. In other embodiments, the aforesaid antibodies are cross-reactive with rhesus PD-L1. For example, the cross-reactivity can be measured by a Biacore method or a binding assay using cells that expresses PD-L1 (e.g., human PD-L1-expressing 300.19 cells). In other embodiments, the aforesaid antibody molecules bind an extracellular Ig-like domain of PD-L1.

In other embodiments, the aforesaid antibody molecules are capable of reducing binding of PD-1 or B7-1 to PD-L1 or a cell that expresses PD-L1. In some embodiments, the aforesaid antibody molecules reduce (e.g., block) PD-L1 binding to a cell that expresses PD-L1 (e.g., human PD-L1-expressing 300.19 cells) with an IC50 of less than about 1.5 nM, 1 nM, 0.8 nM, 0.6 nM, 0.4 nM, 0.2 nM, or 0.1 nM, e.g., between about 0.2 nM and about 0.1 nM, e.g., about 0.15 nM or less, e.g., about 0.145 nM. In some embodiments, the aforesaid antibodies reduce (e.g., block) B7-1 binding to a cell that expresses PD-L1 (e.g., human PD-L1-expressing 300.19 cells) with an IC50 of less than about 2 nM, 1.5 nM, 1 nM, 0.5 nM, or 0.2 nM, e.g., between about 0.5 nM and about 0.01 nM, or about 0.2 nM or less, e.g., about 0.1 nM.

In other embodiments, the aforesaid antibody molecules are capable of enhancing an antigen-specific T cell response.

In some embodiments, the aforesaid antibody molecules increase the expression of IL-2 from cells activated by Staphylococcal enterotoxin B (SEB) (e.g., at 25 µg/mL) by at least about 2, 3, 4, 5, 6, 7, or 8-fold, e.g., about 2 to 3-fold, e.g., about 2 to 2.6-fold, e.g., about 2.39-fold, or e.g., about 2.4 to 6.4-fold, compared to the expression of IL-2 when an isotype control (e.g., IgG4) is used, e.g., as measured in a SEB T cell activation assay, e.g., using peripheral blood mononuclear cells (PMBCs), or a human whole blood ex vivo assay.

In some embodiments, the aforesaid antibody molecules increase the expression of IFN-γ from T cells activated by SEB (e.g., at 3 pg/mL) by at least about 2, 3, 4, 5, 6, 7, or 8-fold, e.g., about 0.5 to 4.5-fold, e.g., about 2.72-fold, or e.g., about 4 to 7-fold compared to the expression of IFN-γ when an isotype control (e.g., IgG4) is used, e.g., as measured in an IFN-γ activity assay.

In some embodiments, the aforesaid antibody molecules bind to PD-L1 with a Kd slower than $5\times10^{-4}$, $1\times10^{-4}$, $5\times10^{-5}$, or $1\times10^{-5}$ s$^{-1}$, e.g., about $6.33\times10^{-5}$ s$^{-1}$, e.g., as measured by a Biacore method. In some embodiments, the aforesaid antibody molecules bind to PD-L1 with a Ka faster than $1\times10^{4}$, $5\times10^{4}$, $1\times10^{5}$, or $5\times10^{5}$ M$^{-1}$ s$^{-1}$, e.g., about $3.07\times10^{4}$ M$^{-1}$ s$^{-1}$, e.g., as measured by a Biacore method.

In embodiments, the anti-PD-L1 antibody molecule is a monospecific antibody molecule or a bispecific antibody molecule. In embodiments, the anti-PD-L1 antibody molecule has a first binding specificity for PD-L1 and a second binding specificity for TIM-3, LAG-3, CEACAM (e.g., CEACAM-1, CEACAM-3, and/or CEACAM-5), PD-1 or PD-L2. In embodiments, the antibody molecule comprises an antigen binding fragment of an antibody, e.g., a half antibody or antigen binding fragment of a half antibody.

In another aspect, the invention provides an isolated nucleic acid molecule encoding any of the aforesaid antibody molecules, vectors and host cells thereof.

An isolated nucleic acid encoding the antibody heavy chain variable region or light chain variable region, or both, of any the aforesaid antibody molecules.

In one embodiment, the isolated nucleic acid encoding heavy chain CDRs 1-3, wherein said nucleic acid comprises a nucleotide sequence of SEQ ID NO: 104-108, 113-117, or 205-208.

In another embodiment, the isolated nucleic acid encoding light chain CDRs 1-3, wherein said nucleic acid comprises a nucleotide sequence of SEQ ID NO: 109-112, 118-123, 209-214, and 245-246.

In other embodiments, the aforesaid nucleic acid further comprises a nucleotide sequence encoding a heavy chain variable domain, wherein said nucleotide sequence is at least 85% identical to any of SEQ ID NO: 19, 31, 39, 47, 51, 55, 63, 71, 79, 90, 95, 100, 196, or 201.

In other embodiments, the aforesaid nucleic acid further comprises a nucleotide sequence encoding a heavy chain variable domain, wherein said nucleotide sequence comprises any of SEQ ID NO: 19, 31, 39, 47, 51, 55, 63, 71, 79, 90, 95, 100, 196, or 201.

In other embodiments, the aforesaid nucleic acid further comprises a nucleotide sequence encoding a heavy chain, wherein said nucleotide sequence is at least 85% identical to any of SEQ ID NO: 21, 33, 41, 49, 53, 57, 65, 73, 81, 92, 97, 101, 198, or 202.

In other embodiments, the aforesaid nucleic acid further comprises a nucleotide sequence encoding a heavy chain, wherein said nucleotide sequence comprises any of SEQ ID NO: 21, 33, 41, 49, 53, 57, 65, 73, 81, 92, 97, 101, 198, or 202.

In other embodiments, the aforesaid nucleic acid further comprises a nucleotide sequence encoding a light chain variable domain, wherein said nucleotide sequence is at least 85% identical to any of SEQ ID NO: 23, 27, 35, 43, 59, 67, 75, 83, 87, 93, 98, 102, 199, or 203.

In other embodiments, the aforesaid nucleic acid further comprises a nucleotide sequence encoding a light chain variable domain, wherein said nucleotide sequence comprises any of SEQ ID NO: 23, 27, 35, 43, 59, 67, 75, 83, 87, 93, 98, 102, 199, or 203.

In other embodiments, the aforesaid nucleic acid further comprises a nucleotide sequence encoding a light chain, wherein said nucleotide sequence is at least 85% identical to any of SEQ ID NO: 25, 29, 37, 45, 61, 69, 77, 85, 89, 94, 99, 103, 200, or 204.

In other embodiments, the aforesaid nucleic acid further comprises a nucleotide sequence encoding a light chain, wherein said nucleotide sequence comprises any of SEQ ID NO: 25, 29, 37, 45, 61, 69, 77, 85, 89, 94, 99, 103, 200, or 204.

In certain embodiments, one or more expression vectors and host cells comprising the aforesaid nucleic acids are provided.

A method of producing an antibody molecule or fragment thereof, comprising culturing the host cell as described herein under conditions suitable for gene expression is also provided.

Pharmaceutical Compositions and Kits

In another aspect, the present invention provides compositions, e.g., pharmaceutically acceptable compositions, which include an antibody molecule described herein, formulated together with a pharmaceutically acceptable carrier. As used herein, "pharmaceutically acceptable carrier" includes any and all solvents, dispersion media, isotonic and absorption delaying agents, and the like that are physiologically compatible. The carrier can be suitable for intravenous, intramuscular, subcutaneous, parenteral, rectal, spinal or epidermal administration (e.g. by injection or infusion).

The compositions of this invention may be in a variety of forms. These include, for example, liquid, semi-solid and solid dosage forms, such as liquid solutions (e.g., injectable and infusible solutions), dispersions or suspensions, liposomes and suppositories. The preferred form depends on the intended mode of administration and therapeutic application. Typical preferred compositions are in the form of injectable or infusible solutions. The preferred mode of administration is parenteral (e.g., intravenous, subcutaneous, intraperitoneal, intramuscular). In a preferred embodiment, the antibody is administered by intravenous infusion or injection. In another preferred embodiment, the antibody is administered by intramuscular or subcutaneous injection.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Therapeutic compositions typically should be sterile and stable under the conditions of manufacture and storage. The composition can be formulated as a solution, microemulsion, dispersion, liposome, or other ordered structure suitable to high antibody concentration. Sterile injectable solutions can be prepared by incorporating the active compound (i.e., antibody or antibody portion) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The antibody molecules can be administered by a variety of methods known in the art, although for many therapeutic applications, the preferred route/mode of administration is intravenous injection or infusion. For example, the antibody molecules can be administered by intravenous infusion at a rate of more than 20 mg/min, e.g., 20-40 mg/min, and typically, greater than or equal to 40 mg/min to reach a dose of about 35 to 440 mg/m$^2$, typically, about 70 to 310 mg/m$^2$, and more typically, about 110 to 130 mg/m$^2$. For example, the antibody molecules can be administered by intravenous infusion at a rate of less than 10 mg/min; typically less than or equal to 5 mg/min to reach a dose of about 1 to 100 mg/m$^2$, typically about 5 to 50 mg/m$^2$, about 7 to 25 mg/m$^2$ and more typically, about 10 mg/m$^2$. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

In certain embodiments, an antibody molecule can be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation. Therapeutic compositions can also be administered with medical devices known in the art.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

An exemplary, non-limiting range for a therapeutically or prophylactically effective amount of an antibody molecule is 0.1-30 mg/kg, more preferably 1-25 mg/kg. Dosages and therapeutic regimens of the anti-PD-L1 antibody molecule can be determined by a skilled artisan. In certain embodiments, the anti-PD-L1 antibody molecule is administered by injection (e.g., subcutaneously or intravenously) at a dose of about 1 to 40 mg/kg, e.g., 1 to 30 mg/kg, e.g., about 5 to 25 mg/kg, about 10 to 20 mg/kg, about 1 to 5 mg/kg, 1 to 10 mg/kg, 5 to 15 mg/kg, 10 to 20 mg/kg, 15 to 25 mg/kg, or about 3 mg/kg. The dosing schedule can vary from e.g., once a week to once every 2, 3, or 4 weeks. In one embodiment, the anti-PD-L1 antibody molecule is administered at a dose from about 10 to 20 mg/kg every other week. The antibody molecule can be administered by intravenous infusion at a rate of more than 20 mg/min, e.g., 20-40 mg/min, and typically greater than or equal to 40 mg/min to reach a dose of about 35 to 440 mg/m$^2$, typically about 70 to 310 mg/m$^2$, and more typically, about 110 to 130 mg/m$^2$. In embodiments, the infusion rate of about 110 to 130 mg/m$^2$ achieves a level of about 3 mg/kg. In other embodiments, the antibody molecule can be administered by intravenous infusion at a rate of less than 10 mg/min, e.g., less than or equal to 5 mg/min to reach a dose of about 1 to 100 mg/m$^2$, e.g., about 5 to 50 mg/m$^2$, about 7 to 25 mg/m$^2$, or, about 10 mg/m$^2$. In some embodiments, the antibody is infused over a period of about 30 min. The antibody molecule can be administered by intravenous infusion at a rate of less than 10 mg/min, preferably less than or equal to 5 mg/min to reach a dose of about 1 to 100 mg/m$^2$, preferably about 5 to 50 mg/m$^2$, about 7 to 25 mg/m$^2$, and more preferably, about 10 mg/m$^2$. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

The pharmaceutical compositions of the invention may include a "therapeutically effective amount" or a "prophylactically effective amount" of an antibody or antibody portion of the invention. A "therapeutically effective amount" refers to an amount effective, at dosages and for periods of time necessary, to achieve the desired therapeutic result. A therapeutically effective amount of the modified antibody or antibody fragment may vary according to factors such as the disease state, age, sex, and weight of the individual, and the ability of the antibody or antibody portion to elicit a desired response in the individual. A therapeutically effective amount is also one in which any toxic or detrimental effects of the modified antibody or antibody fragment is outweighed by the therapeutically beneficial effects. A "therapeutically effective dosage" preferably inhibits a measurable parameter, e.g., tumor growth rate by at least about 20%, more preferably by at least about 40%, even more preferably by at least about 60%, and still more preferably by at least about 80% relative to untreated subjects. The ability of a compound to inhibit a measurable parameter, e.g., cancer, can be evaluated in an animal model system predictive of efficacy in human tumors. Alternatively, this property of a composition can be evaluated by examining the ability of the compound to inhibit, such inhibition in vitro by assays known to the skilled practitioner.

A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Also within the scope of the invention is a kit comprising an antibody molecule described herein. The kit can include one or more other elements including: instructions for use; other reagents, e.g., a label, a therapeutic agent, or an agent useful for chelating, or otherwise coupling, an antibody to a label or therapeutic agent, or a radioprotective composition; devices or other materials for preparing the antibody for administration; pharmaceutically acceptable carriers; and devices or other materials for administration to a subject.

Uses of Anti-PD-L1 Antibody Molecules

The anti-PD-L1 antibody molecules disclosed herein have in vitro and in vivo diagnostic, as well as therapeutic and prophylactic utilities. For example, these molecules can be administered to cells in culture, in vitro or ex vivo, or to a subject, e.g., a human subject, to treat, prevent, and/or diagnose a variety of disorders, such as cancers and infectious disorders.

Accordingly, in one aspect, the invention provides a method of modifying an immune response in a subject comprising administering to the subject the antibody molecule described herein, such that the immune response in the subject is modified. In one embodiment, the immune response is enhanced, stimulated or up-regulated. In one embodiment, the antibody molecules enhance an immune response in a subject by blockade of PD-L1.

As used herein, the term "subject" is intended to include human and non-human animals. In one embodiment, the subject is a human subject, e.g., a human patient having a disorder or condition characterized by abnormal PD-L1 functioning. The term "non-human animals" includes mammals and non-mammals, such as non-human primates. In one embodiment, the subject is a human. In one embodiment, the subject is a human patient in need of enhancement of an immune response. In one embodiment, the subject is immunocompromised, e.g., the subject is undergoing, or has undergone a chemotherapeutic or radiation therapy. Alternatively, or in combination, the subject is, or is at risk of being, immunocompromised as a result of an infection. The methods and compositions described herein are suitable for treating human patients having a disorder that can be treated by augmenting the T-cell mediated immune response. For example, the methods and compositions described herein can enhance a number of immune activities. In one embodiment, the subject has increased number or activity of tumour-infiltrating T lymphocytes (TILs). In another embodiment, the subject has increased expression or activity of interferon-gamma (IFN-γ). In yet another embodiment, the subject has decreased PD-L1 expression or activity.

Therapeutic Uses

Blockade of PD-L1 by antibodies can enhance the immune response to cancerous cells in the patient. PD-L1 is typically not expressed in normal human cells, but is abundant in a variety of human cancers (Dong et al. (2002) *Nat Med* 8:787-9). The interaction between PD-1 and PD-L1 results in a decrease in tumor infiltrating lymphocytes, a decrease in T-cell receptor mediated proliferation, and immune evasion by the cancerous cells (Dong et al. (2003) *J Mol Med* 81:281-7; Blank et al. (2005) *Cancer Immunol Immunother.* 54:307-14); Konishi et al. (2004) *Clin. Cancer Res.* 10:5094-100). Immune suppression can be reversed by inhibiting the local interaction of PD-L1 to PD-1 and the effect is additive when the interaction of PD-L2 to PD-1 is blocked as well (Iwai et al. (2002) *PNAS* 99:12293-7; Brown et al. (2003) *J. Immunol.* 170:1257-66). An anti-PD-L1 antibody may be used alone to inhibit the growth of cancerous tumors. Alternatively, an anti-PD-L1 antibody may be used in conjunction with other immunogenic agents, standard cancer treatments, or other antibodies, as described herein. Thus, inhibition of PD-L1 can augment an immune response.

In one aspect, the invention relates to treatment of a subject in vivo using an anti-PD-L1 antibody molecule such that growth of cancerous tumors is inhibited or reduced. An anti-PD-L1 antibody may be used alone to inhibit the growth of cancerous tumors. Alternatively, an anti-PD-L1 antibody may be used in combination with one or more of: a standard of care treatment (e.g., for cancers or infectious disorders), another antibody or antigen-binding fragment thereof, an immunomodulator (e.g., an activator of a costimulatory molecule or an inhibitor of an inhibitory molecule); a vaccine, e.g., a therapeutic cancer vaccine; or other forms of cellular immunotherapy, as described below.

Accordingly, in one embodiment, the invention provides a method of inhibiting growth of tumor cells in a subject, comprising administering to the subject a therapeutically effective amount of an anti-PD-L1 antibody molecule described herein.

In one embodiment, the methods are suitable for the treatment of cancer in vivo. To achieve antigen-specific enhancement of immunity, the anti-PD-L1 antibody molecule can be administered together with an antigen of interest. When antibodies to PD-L1 are administered in combination with one or more agents, the combination can be administered in either order or simultaneously.

Types of Cancer; Theranostic Methods

In another aspect, a method of treating a subject, e.g., reducing or ameliorating, a hyperproliferative condition or disorder (e.g., a cancer), e.g., solid tumor, a soft tissue tumor, or a metastatic lesion, in a subject is provided. The method includes administering to the subject one or more anti-PD-L1 antibody molecules described herein, alone or in combination with other agents or therapeutic modalities.

As used herein, the term "cancer" is meant to include all types of cancerous growths or oncogenic processes, metastatic tissues or malignantly transformed cells, tissues, or organs, irrespective of histopathologic type or stage of invasiveness. Examples of cancerous disorders include, but are not limited to, solid tumors, hematological cancers, soft tissue tumors, and metastatic lesions.

Examples of solid tumors include malignancies, e.g., sarcomas, and carcinomas (including adenocarcinomas and squamous cell carcinomas), of the various organ systems, such as those affecting liver, lung, breast, lymphoid, gastrointestinal (e.g., colon), genitourinary tract (e.g., renal, urothelial cells), prostate and pharynx. Adenocarcinomas include malignancies such as most colon cancers, rectal cancer, renal-cell carcinoma, liver cancer, non-small cell carcinoma of the lung, cancer of the small intestine and cancer of the esophagus. Squamous cell carcinomas include malignancies, e.g., in the lung, esophagus, skin, head and neck region, oral cavity, anus, and cervix. In one embodiment, the cancer is a melanoma, e.g., an advanced stage melanoma. Metastatic lesions of the aforementioned cancers can also be treated or prevented using the methods and compositions of the invention.

Exemplary cancers whose growth can be inhibited using the antibodies molecules disclosed herein include cancers typically responsive to immunotherapy. Non-limiting examples of preferred cancers for treatment include lymphoma (e.g., diffuse large B-cell lymphoma, Hodgkin lymphoma, non-Hodgkin's lymphoma), breast cancer (e.g., metastic breast cancer), lung cancer (e.g., non-small cell lung cancer (NSCLC), e.g., stage IV or recurrent non-small cell lung cancer, a NSCLC adenocarcinoma, or a NSCLC squamous cell carcinoma), myeloma (e.g., multiple myeloma), leukemia (e.g., chronic myelogenous leukemia), skin cancer (e.g., melanoma (e.g., stage III or IV melanoma) or Merkel cell carcinoma), head and neck cancer (e.g., head and neck squamous cell carcinoma (HNSCC)), myelodysplastic syndrome, bladder cancer (e.g., transitional cell carcinoma), kidney cancer (e.g., renal cell cancer, e.g., clear-cell renal cell carcinoma, e.g., advanced or metastatic clear-cell renal cell carcinoma), and colon cancer. Additionally, refractory or recurrent malignancies can be treated using the antibody molecules described herein.

Examples of other cancers that can be treated include bone cancer, pancreatic cancer, skin cancer, cancer of the head or neck, cutaneous or intraocular malignant melanoma, uterine cancer, ovarian cancer, rectal cancer, anal cancer, gastro-esophageal, stomach cancer, testicular cancer, uterine cancer, carcinoma of the fallopian tubes, carcinoma of the endometrium, carcinoma of the cervix, carcinoma of the vagina, carcinoma of the vulva, Merkel cell cancer, Hodgkin lymphoma, non-Hodgkin lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, multiple myeloma, myelodisplastic syndromes, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos (e.g., mesothelioma), and combinations of said cancers.

Treatment of metastatic cancers, e.g., metastatic cancers that express PD-L1 (Iwai et al. (2005) *Int. Immunol.* 17:133-144) can be effected using the antibody molecules described herein. In one embodiment, the cancer expresses an elevated level of PD-L1, IFNγ and/or CD8.

PD-L1 signaling can contribute to elevated Bim expression in CD8+ T cells. Treatment of cancers, e.g., advanced melanomas, in patients that express high level of Bim (e.g., elevated Bim levels in PD-1+CD8+ T cells compared to PD-1-CD8+ T cells) can be effected using the antibody molecules described herein.

Animal models that can be used to test the efficacy of an anti-PD-L1 antibody in a monotherapy or combination therapy for cancer include, e.g., CT26 colon carcinoma model (Sakuishi et al. (2010) *J Exp Med.* 207(10): 2187-2194) and 5T33 myeloma model (Manning et al. (1992) *Br J Cancer.* 66(6): 1088-1093).

In one embodiment, the cancer expresses an elevated level of PD-L1, IFNγ and/or CD8.

While not wishing to be bound by theory, in some embodiments, a patient is more likely to respond to treatment with an immunomodulator (optionally in combination with one or more agents as described herein) if the patient has a cancer that highly expresses PD-L1, and/or the cancer is infiltrated by anti-tumor immune cells, e.g., TILs. The anti-tumor immune cells may be positive for CD8, PD-L1, and/or IFN-γ; thus levels of CD8, PD-L1, and/or IFN-γ can serve as a readout for levels of TILs in the microenvironment. In certain embodiments, the cancer microenvironment is referred to as triple-positive for PD-L1/CD8/IFN-γ.

Accordingly, in certain aspects, this application provides methods of determining whether a tumor sample is positive for one or more of PD-L1, CD8, and IFN-γ, and if the tumor sample is positive for one or more, e.g., two, or all three, of the markers, then administering to the patient a therapeutically effective amount of an anti-PD-L1 antibody molecule, optionally in combination with one or more other immunnomodulators or anti-cancer agents.

In the following indications, a large fraction of patients are triple-positive for PD-L1/CD8/IFN-γ: Lung cancer (squamous); lung cancer (adenocarcinoma); head and neck cancer; stomach cancer; NSCLC; HNSCC; gastric cancers (e.g., MSIhi and/or EBV+); CRC (e.g., MSIhi); nasopharyngeal cancer (NPC); cervical cancer (e.g., squamous); thyroid cancer e.g., papillary thyroid; melanoma; TN breast cancer; and DLBCL (Diffuse Large B-Cell Lymphoma). In breast cancer generally and in colon cancer generally, a moderate fraction of patients is triple-positive for PD-L1/CD8/IFN-γ. In the following indications, a small fraction of patients are triple-positive for PD-L1/CD8/IFN-γ: ER+ breast cancer, and pancreatic cancer. These findings are discussed further in Example 4. Regardless of whether a large or small fraction of patients is triple-positive for these markers, screening the patients for these markers allows one to identify a fraction of patients that has an especially high likelihood of responding favorably to therapy with a PD-L1 antibody (e.g., a blocking PD-L1 antibody), optionally in combination with one or more other immunomodulators (e.g., an anti-TIM-3 antibody molecule, an anti-LAG-3 antibody molecule, or an anti-PD-L1 antibody molecule) and/or anti-cancer agents, e.g., those listed in Table 6 and disclosed in the publications listed in Table 6.

In some embodiments, the cancer sample is classified as triple-positive for PD-L1/CD8/IFN-γ. This measurement can roughly be broken down into two thresholds: whether an individual cell is classified as positive, and whether the sample as a whole is classified as positive. First, one can measure, within an individual cell, the level of PD-L1, CD8, and/or IFN-γ. In some embodiments, a cell that is positive for one or more of these markers is a cell that has a higher level of the marker compared to a control cell or a reference value. For example, in some embodiments, a high level of PD-L1 in a given cell is a level higher than the level of PD-L1 in a corresponding non-cancerous tissue in the patient. As another example, in some embodiments, a high level of CD8 or IFN-γ in a given cell is a level of that protein typically seen in a TIL. Second, one can also measure the percentage of cells in the sample that are positive for PD-L1, CD8, and/or IFN-γ. (It is not necessary for a single cell to express all three markers.) In some embodiments, a triple positive sample is one that has a high percentage of cells, e.g., higher than a reference value or higher than a control sample, that are positive for these markers.

In other embodiments, one can measure the levels of PD-L1, CD8, and/or IFN-γ overall in the sample. In this case, a high level of CD8 or IFN-γ in the sample can be the level of that protein typically seen in a tumor infiltrated with TIL. Similarly, a high level of PD-L1 can be the level of that protein typically seen in a tumor sample, e.g., a tumor microenvironment.

The identification of subsets of patients that are triple-positive for PD-L1/CD8/IFN-γ, as shown in Example 4 herein, reveals certain sub-populations of patients that are likely to be especially responsive to PD-L1 antibody therapy. For instance, many IM-TN (immunomodulatory, triple negative) breast cancer patients are triple-positive for PD-L1/CD8/IFN-γ. IM-TN breast cancer is described in, e.g., Brian D. Lehmann et al., "Identification of human triple-negative breast cancer subtypes and preclinical models for selection of targeted therapies", *J Clin Invest*. Jul. 1, 2011; 121(7): 2750-2767. Triple-negative breast cancers are those that do not express estrogen receptor (ER), progesterone receptor (PR) and Her2/neu. These cancers are difficult to treat because they are typically not responsive to agents that target ER, PR, and Her2/neu. Triple-negative breast cancers can be further subdivided into different classes, one of which is immunomodulatory. As described in Lehmann et al., IM-TN breast cancer is enriched for factors involved in immune cell processes, for example, one or more of immune cell signaling (e.g., TH1/TH2 pathway, NK cell pathway, B cell receptor signaling pathway, DC pathway, and T cell receptor signaling), cytokine signaling (e.g., cytokine pathway, IL-12 pathway, and IL-7 pathway), antigen processing and presentation, signaling through core immune signal transduction pathways (e.g., NFKB, TNF, and JAK/STAT signaling), genes involved in T-cell function, immune transcription, interferon (IFN) response and antigen processing. Accordingly, in some embodiments, the cancer treated is a cancer that is, or is determined to be, positive for one or more marker of IM-TN breast cancer, e.g., a factor that promotes one or more of immune cell signaling (e.g., TH1/TH2 pathway, NK cell pathway, B cell receptor signaling pathway, DC pathway, and T cell receptor signaling), cytokine signaling (e.g., cytokine pathway, IL-12 pathway, and IL-7 pathway), antigen processing and presentation, signaling through core immune signal transduction pathways (e.g., NFKB, TNF, and JAK/STAT signaling), genes involved in T-cell function, immune transcription, interferon (IFN) response and antigen processing.

As another example, it is shown herein that a subset of colon cancer patients having high MSI (microsatellite instability) is also triple-positive for PD-L1/CD8/IFN-γ. Accordingly, in some embodiments, a PD-L1 antibody, e.g., a PD-L1 antibody as described herein, (optionally in combination with one or more immunomodulators such as a LAG-3 antibody, TIM-3 antibody, or PD-1 antibody, and one or more anti-cancer agents, e.g., an anti-cancer agent described in Table 6 or in a publication in Table 6) is administered to a patient who has, or who is identified as having, colon cancer with high MSI, thereby treating the cancer. In some embodiments, a cell with high MSI is a cell having MSI at a level higher than a reference value or a control cell, e.g., a non-cancerous cell of the same tissue type as the cancer.

As another example, it is shown herein that a subset of gastric cancer patients having high MSI, and/or which is EBV+, is also triple-positive for PD-L1/CD8/IFN-γ. Accordingly, in some embodiments, a PD-L1 antibody, e.g., a PD-L1 antibody as described herein, (optionally in combination with one or more immunomodulators such as a LAG-3 antibody, TIM-3 antibody, or PD-1 antibody, and one or more anti-cancer agents, e.g., an anti-cancer agent described in Table 6 or in a publication in Table 6) is administered to a patient who has, or who is identified as having, gastric cancer with high MSI and/or EBV+, thereby treating the cancer. In some embodiments, a cell with high MSI is a cell having MSI at a level higher than a reference value or a control cell, e.g., a non-cancerous cell of the same tissue type as the cancer.

Additionally disclosed herein are methods of assaying a cancer for PD-L1, and then treating the cancer with a PD-L1 antibody. As described in Example 5 herein, a cancer sample can be assayed for PD-L1 protein levels or mRNA levels. A sample having levels of PD-L1 (protein or mRNA) higher than a reference value or a control cell (e.g., a non-cancerous cell) can be classified as PD-L1 positive. Accordingly, in some embodiments, a PD-L1 antibody, e.g., a PD-L1 antibody as described herein, (optionally in combination with one or more anti-cancer agents) is administered to a patient who has, or who is identified as having, a cancer that is PD-L1 positive. The cancer may be, e.g., non-small cell lung (NSCLC) adenocarcinoma (ACA), NSCLC squamous cell carcinoma (SCC), or hepatocellular carcinoma (HCC).

In some embodiments, the methods herein involve using a PD-L1 antibody, e.g., a PD-L1 antibody as described herein, e.g., as a monotherapy, for treating a cancer that is (or is identified as being) positive for PD-L1. In some embodiments, the cancer is colorectal cancer (e.g., MSI-high), gastric cancer (e.g., MSI-high and/or EBV+), NPC, cervical cancer, breast cancer (e.g., TN breast cancer), and ovarian cancer. In some embodiments, the cancer is NSCLC, melanoma, or HNSCC. In some embodiments, the PD-L1 antibody is administered at a dose of, e.g., 1, 3, 10, or 20 mg/kg.

Based on, e.g, Example 4 herein, it was found that certain gastric cancers that are triple-positive for PD-L1/CD8/IFN-γ are also positive for PIK3CA. Accordingly, in some embodiments, a cancer can be treated with an anti-PD-1 antibody molecule (optionally in combination with one or more immunomodulators, e.g., an anti-LAG-3 antibody molecule, an anti-TIM-3 antibody molecule, or an anti-PD-1 antibody molecule) and an agent that inhibits PIK3CA. Exemplary agents in this category are described in Stein R C (September 2001). "Prospects for phosphoinositide 3-kinase inhibition as a cancer treatment". Endocrine-related Cancer 8 (3): 237-48 and Marone R, Cmiljanovic V, Giese B, Wymann M P (January 2008). "Targeting phosphoinositide 3-kinase: moving towards therapy". Biochimica et Biophysica Acta 1784 (1): 159-85.

Based on, e.g, Example 4 herein, CRC, e.g., a patient that has (or is identified as having) MSI-high CRC may be treated with a PD-L1 antibody, optionally in combination with a therapeutic that targets one or more of LAG-3, RNF43, and BRAF. For instance, these cancers may be treated with a PD-L1 antibody, optionally in combination with one or more therapeutics that target one or more of LAG-3, PD-1, RNF43, and BRAF. In embodiments, the one or more therapeutics include an immunomodulators such as an anti-LAG-3 antibody molecule, and an anti-cancer agent described in Table 6 or a publication listed in Table 6. LAG-3 inhibitors, e.g., antibodies, are described herein. RNF43 can be inhibited, e.g., with an antibody, small molecule (e.g., 2-(2',3-dimethyl-[2,4'-bipyridin]-5-yl)-N-(5-(pyrazin-2-yl)pyridin-2-yl)acetamide (Compound A28)), siRNA, or a Rspo ligand or derivative thereof. BRAF inhibitors (e.g., vemurafenib or dabrafenib) are described herein.

Based on, e.g, Example 4 herein, a patient that has (or is identified as having) a squamous cell lung cancer may be treated with a PD-L1 antibody molecule in combination with a therapeutic that targets LAG-3, e.g., a LAG-3 antibody molecule, and optionally with one or more anti-cancer agents, e.g., an anti-cancer agent described in Table 6 or in a publication in Table 6.

In some embodiments, a subject that has (or is identified as having) a squamous cell lung cancer may be treated with a PD-1 antibody, optionally in combination with a therapeutic that targets TIM-3, e.g., a TIM-3 antibody. TIM-3 inhibitors, e.g., antibodies, are described herein.

Based on, e.g, Example 4 herein, a patient that has (or is identified as having) a thyroid cancer may be treated with a PD-1 antibody molecule, optionally in combination with a therapeutic that targets BRAF, and optionally in combination with one or more immunomodulators, e.g., an anti-LAG-3 antibody molecule, an anti-TIM-3 antibody molecule, and an anti-PD-L1 antibody molecule. BRAF inhibitors (e.g., vemurafenib or dabrafenib) are described herein, e.g., in Table 6 and the publications listed in Table 6.

In some embodiments, the therapies here can be used to treat a patient that has (or is identified as having) a cancer associated with an infection, e.g., a viral or bacterial infection. Exemplary cancers include cervical cancer, anal cancer, HPV-associated head and neck squamous cell cancer, HPV-associated esophageal papillomas, HHV6-associated lymphomas, EBV-associated lymphomas (including Burkitt lymphoma), Gastric MALT lymphoma, other infection-associated MALT lymphomas, HCC, Kaposi's sarcoma.

In other embodiments, the cancer is a hematological malignancy or cancer including but is not limited to a leukemia or a lymphoma. For example, the anti-PD-L1 antibody molecule can be used to treat cancers and malignancies including, but not limited to, e.g., acute leukemias including but not limited to, e.g., B-cell acute lymphoid leukemia ("BALL"), T-cell acute lymphoid leukemia ("TALL"), acute lymphoid leukemia (ALL); one or more chronic leukemias including but not limited to, e.g., chronic myelogenous leukemia (CML), chronic lymphocytic leukemia (CLL); additional hematologic cancers or hematologic conditions including, but not limited to, e.g., B cell prolymphocytic leukemia, blastic plasmacytoid dendritic cell neoplasm, Burkitt's lymphoma, diffuse large B cell lymphoma, Follicular lymphoma, Hairy cell leukemia, small cell- or a large cell-follicular lymphoma, malignant lymphoproliferative conditions, MALT lymphoma, mantle cell lymphoma, Marginal zone lymphoma, multiple myeloma, myelodysplasia and myelodysplastic syndrome, non-Hodgkin's lymphoma, plasmablastic lymphoma, plasmacytoid dendritic cell neoplasm, Waldenstrom macroglobulinemia, and "preleukemia" which are a diverse collection of hematological conditions united by ineffective production (or dysplasia) of myeloid blood cells, and the like.

In one embodiment, the cancer is a breast cancer, e.g., a metastatic breast cancer, e.g., a breast cancer that does not express one, two or all of estrogen receptor, progesterone receptor, or Her2/neu, e.g., a triple negative breast cancer.

In another embodiment, the cancer is a lung cancer, e.g., a non-small cell lung cancer (e.g., squamous non-small cell lung cancer), e.g., locally advanced or metastic non-small cell lung cancer, e.g., stage IV or recurrent non-small cell lung cancer.

In yet another embodiment, the cancer is a skin cancer, e.g., Merkel cell carcinoma (MCC), e.g., metastatic Merkel cell carcinoma.

In one embodiment, the cancer is chosen from a lung cancer (e.g., a non-small cell lung cancer (NSCLC) (e.g., a NSCLC with squamous and/or non-squamous histology, a NSCLC adenocarcinoma, or a NSCLC squamous cell carcinoma)), a melanoma (e.g., an advanced melanoma), a renal cancer (e.g., a renal cell carcinoma, e.g., clear cell renal cell carcinoma), a liver cancer, a myeloma (e.g., a multiple myeloma), a prostate cancer, a breast cancer (e.g., a breast cancer that does not express one, two or all of estrogen receptor, progesterone receptor, or Her2/neu, e.g., a triple negative breast cancer), a colorectal cancer, a pancreatic cancer, a head and neck cancer (e.g., head and neck squamous cell carcinoma (HNSCC), anal cancer, gastroesophageal cancer, thyroid cancer, cervical cancer, a lymphoproliferative disease (e.g., a post-transplant lymphoproliferative disease) or a hematological cancer, T-cell lymphoma, a non-Hogdkin's lymphoma, or a leukemia (e.g., a myeloid leukemia).

In another embodiment, the cancer is chosen form a carcinoma (e.g., advanced or metastatic carcinoma), melanoma or a lung carcinoma, e.g., a non-small cell lung carcinoma.

In one embodiment, the cancer is a lung cancer, e.g., a non-small cell lung cancer.

In another embodiment, the cancer is a hepatocarcinoma, e.g., an advanced hepatocarcinoma, with or without a viral infection, e.g., a chronic viral hepatitis.

In another embodiment, the cancer is a prostate cancer, e.g., an advanced prostate cancer.

In yet another embodiment, the cancer is a myeloma, e.g., multiple myeloma.

In yet another embodiment, the cancer is a renal cancer, e.g., a renal cell carcinoma (RCC) (e.g., a metastatic RCC or clear cell renal cell carcinoma).

In one embodiment, the cancer is a melanoma, e.g., an advanced melanoma. In one embodiment, the cancer is an advanced or unresectable melanoma that does not respond to other therapies. In other embodiments, the cancer is a melanoma with a BRAF mutation (e.g., a BRAF V600 mutation). In yet other embodiments, the anti-PD-L1 antibody molecule is administered after treatment with an anti-CTLA-4 antibody (e.g., ipilimumab) with or without a BRAF inhibitor (e.g., vemurafenib or dabrafenib).

Methods and compositions disclosed herein are useful for treating metastatic lesions associated with the aforementioned cancers.

Combination of Anti-PD-L1 Antibodies with Cancer Vaccines

Antibody molecules to PD-L1 can be combined with an immunogenic agent, such as cancerous cells, purified tumor antigens (including recombinant proteins, peptides, and carbohydrate molecules), cells, and cells transfected with genes encoding immune stimulating cytokines (He et al. (2004) *J. Immunol.* 173:4919-28). Non-limiting examples of tumor vaccines that can be used include peptides of melanoma antigens, such as peptides of gp100, MAGE antigens, Trp-2, MART1 and/or tyrosinase, or tumor cells transfected to express the cytokine GM-CSF. DNA-based vaccines, RNA-based vaccines, and viral transduction-based vaccines. The cancer vaccine may be prophylactic or therapeutic.

PD-L1 blockade can be combined with a vaccination protocol. Many experimental strategies for vaccination against tumors have been devised (see Rosenberg, S., 2000, Development of Cancer Vaccines, ASCO Educational Book Spring: 60-62; Logothetis, C., 2000, ASCO Educational Book Spring: 300-302; Khayat, D. 2000, ASCO Educational Book Spring: 414-428; Foon, K. 2000, ASCO Educational Book Spring: 730-738; see also Restifo, N. and Sznol, M., Cancer Vaccines, Ch. 61, pp. 3023-3043 in DeVita, V. et al. (eds.), 1997, *Cancer*: Principles and Practice of Oncology. Fifth Edition). In one of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination (Dranoff et al. (1993) *Proc. Natl. Acad. Sci. U.S.A.* 90: 3539-43).

PD-L1 blockade can be used in conjunction with a collection of recombinant proteins and/or peptides expressed in a tumor in order to generate an immune response to these proteins. These proteins are normally viewed by the immune system as self antigens and are therefore tolerant to them. The tumor antigen may also include the protein telomerase, which is required for the synthesis of telomeres of chromosomes and which is expressed in more than 85% of human cancers and in only a limited number of somatic tissues (Kim, N et al. (1994) *Science* 266: 2011-2013). (These somatic tissues may be protected from immune attack by various means). Tumor antigen may also be "neo-antigens" expressed in cancer cells because of somatic mutations that alter protein sequence or create fusion proteins between two unrelated sequences (ie. bcr-abl in the Philadelphia chromosome), or idiotype from B cell tumors.

Other tumor vaccines may include the proteins from viruses implicated in human cancers such a Human Papilloma Viruses (HPV), Hepatitis Viruses (HBV and HCV), Kaposi's Herpes Sarcoma Virus (KHSV), and Epstein-Barr virus (EBV). Another form of tumor specific antigen which may be used in conjunction with PD-1 blockade is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (Suot, R & Srivastava, P (1995) *Science* 269: 1585-1588; Tamura, Y. et al. (1997) *Science* 278:117-120).

Dendritic cells (DC) are potent antigen presenting cells that can be used to prime antigen-specific responses. DC's can be produced ex vivo and loaded with various protein and peptide antigens as well as tumor cell extracts (Nestle, F. et al. (1998) *Nature Medicine* 4: 328-332). DCs may also be transduced by genetic means to express these tumor antigens as well. DCs have also been fused directly to tumor cells for the purposes of immunization (Kugler, A. et al. (2000) *Nature Medicine* 6:332-336). As a method of vaccination, DC immunization may be effectively combined with PD-1 blockade to activate more potent anti-tumor responses.

In another embodiment, the combination further includes an inhibitor or activator of an immune checkpoint modulator (e.g., a LAG-3 inhibitor (e.g., an anti-LAG-3 antibody molecule), a PD-1 inhibitor (e.g., an anti-PD-1 antibody molecule), a TIM-3 modulator (e.g., a TIM-3 activator or inhibitor, e.g., an anti-TIM-3 antibody molecule), or a CTLA-4 inhibitor (e.g., an anti-CTLA-4 antibody), or any combination thereof.

PD-L1 blockade may also be combined with a standard cancer treatment. PD-L1 blockade may be effectively combined with chemotherapeutic regimes. In these instances, it may be possible to reduce the dose of chemotherapeutic reagent administered (Mokyr, M. et al. (1998) *Cancer Research* 58: 5301-5304). In certain embodiments, the methods and compositions described herein are administered in combination with one or more of other antibody molecules, chemotherapy, other anti-cancer therapy (e.g., targeted anti-cancer therapies, or oncolytic drugs), cytotoxic agents, immune-based therapies (e.g., cytokines), surgical and/or radiation procedures. Exemplary cytotoxic agents that can be administered in combination with include anti-microtubule agents, topoisomerase inhibitors, anti-metabolites, mitotic inhibitors, alkylating agents, anthracyclines, vinca alkaloids, intercalating agents, agents capable of interfering with a signal transduction pathway, agents that promote apoptosis, proteosome inhibitors, and radiation (e.g., local or whole body irradiation).

Alternatively, or in combination with the aforesaid combinations, the methods and compositions described herein can be administered in combination with one or more of: an immunomodulator (e.g., an activator of a costimulatory molecule or an inhibitor of an inhibitory molecule); a vaccine, e.g., a therapeutic cancer vaccine; or other forms of cellular immunotherapy.

Exemplary non-limiting combinations and uses of the anti-PD-L1 antibody molecules include the following.

In certain embodiments, the anti-PD-L1 antibody molecule is administered in combination with a modulator of a costimulatory molecule or an inhibitory molecule, e.g., a co-inhibitory ligand or receptor.

In one embodiment, the anti-PD-L1 antibody molecule is administered in combination with a modulator, e.g., agonist, of a costimulatory molecule. In one embodiment, the agonist of the costimulatory molecule is chosen from an agonist (e.g., an agonistic antibody or antigen-binding fragment thereof, or soluble fusion) of OX40, CD2, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3 or CD83 ligand.

In another embodiment, the anti-PD-L1 antibody molecule is used in combination with a costimulatory molecule, e.g., an agonist associated with a positive signal that includes a costimulatory domain of CD28, CD27, ICOS and GITR.

Exemplary GITR agonists include, e.g., GITR fusion proteins and anti-GITR antibodies (e.g., bivalent anti-GITR antibodies), such as, a GITR fusion protein described in U.S. Pat. No. 6,111,090, European Patent No. 090505B1, U.S. Pat. No. 8,586,023, PCT Publication Nos.: WO 2010/003118 and 2011/090754, or an anti-GITR antibody described, e.g., in U.S. Pat. No. 7,025,962, European Patent No. 1947183B1, U.S. Pat. No. 7,812,135, U.S. Pat. No.

8,388,967, U.S. Pat. No. 8,591,886, European Patent No.: EP 1866339, PCT Publication No.: WO 2011/028683, PCT Publication No.: WO 2013/039954, PCT Publication No.: WO2005/007190, PCT Publication No.: WO 2007/133822, PCT Publication No.: WO2005/055808, PCT Publication No.: WO 99/40196, PCT Publication No.: WO 2001/03720, PCT Publication No.: WO99/20758, PCT Publication No.: WO2006/083289, PCT Publication No.: WO 2005/115451, U.S. Pat. No. 7,618,632, and PCT Publication No.: WO 2011/051726.

In one embodiment, the anti-PD-L1 antibody molecule is administered in combination with an inhibitor of an inhibitory molecule of an immune checkpoint molecule. It will be understood by those of ordinary skill in the art, that the term "immune checkpoints" means a group of molecules on the cell surface of CD4 and CD8 T cells. These molecules can effectively serve as "brakes" to down-modulate or inhibit an anti-tumor immune response. Immune checkpoint molecules include, but are not limited to, Programmed Death 1 (PD-1), Cytotoxic T-Lymphocyte Antigen 4 (CTLA-4), B7H1, B7H4, OX-40, CD137, CD40, and LAG-3, which directly inhibit immune cells. Immunotherapeutic agents which can act as immune checkpoint inhibitors useful in the methods of the present invention, include, but are not limited to, inhibitors of PD-1, PD-L2, CTLA-4, TIM-3, LAG-3, VISTA, BTLA, TIGIT, LAIR1, CD160, 2B4, CEACAM (e.g., CEACAM-1, CEACAM-3 and/or CEACAM-5), and/or TGFR beta. Inhibition of an inhibitory molecule can be performed by inhibition at the DNA, RNA or protein level. In embodiments, an inhibitory nucleic acid (e.g., a dsRNA, siRNA or shRNA), can be used to inhibit expression of an inhibitory molecule. In other embodiments, the inhibitor of an inhibitory signal is, a polypeptide e.g., a soluble ligand, or an antibody or antigen-binding fragment thereof, that binds to the inhibitory molecule.

In one embodiment, the inhibitor is a soluble ligand (e.g., a CTLA-4-Ig or a TIM-3-Ig), or an antibody or antibody fragment that binds to PD-1, PD-L2 or CTLA-4. For example, the anti-PD-L1 antibody molecule can be administered in combination with an anti-CTLA-4 antibody, e.g., ipilimumab, for example, to treat a cancer (e.g., a cancer chosen from: a melanoma, e.g., a metastatic melanoma; a lung cancer, e.g., a non-small cell lung carcinoma; or a prostate cancer). Exemplary anti-CTLA-4 antibodies include Tremelimumab (IgG2 monoclonal antibody available from Pfizer, formerly known as ticilimumab, CP-675, 206); and Ipilimumab (CTLA-4 antibody, also known as MDX-010, CAS No. 477202-00-9). In one embodiment, the anti-PD-L1 antibody molecule is administered after treatment, e.g., after treatment of a melanoma, with an anti-CTLA-4 antibody (e.g., ipilimumab) with or without a BRAF inhibitor (e.g., vemurafenib or dabrafenib). Exemplary doses that can be use include a dose of anti-PD-L1 antibody molecule of about 1 to 10 mg/kg, e.g., 3 mg/kg, and a dose of an anti-CTLA-4 antibody, e.g., ipilimumab, of about 3 mg/kg.

Immune inhibitory molecules, e.g., PD-L1 and LAG-3, can regulate, e.g., synergistically regulate, T-cell function to promote tumoral immune escape. In another embodiment, the anti-PD-L1 antibody molecule is administered in combination with an anti-LAG-3 antibody or an antigen-binding fragment thereof. In another embodiment, the anti-PD-L1 antibody molecule is administered in combination with an anti-TIM-3 antibody or antigen-binding fragment thereof. In yet other embodiments, the anti-PD-L1 antibody molecule is administered in combination with an anti-LAG-3 antibody and an anti-TIM-3 antibody, or antigen-binding fragments thereof. The combination of antibodies recited herein can be administered separately, e.g., as separate antibodies, or linked, e.g., as a bispecific or trispecific antibody molecule.

In some embodiments, the antibody molecule (e.g., mono-, bi- or trispecific antibody) for TIM-3, LAG-3 and/or PD-1 used in any of the methods disclosed herein includes an amino acid sequence, or is encoded by a nucleotide sequence as described herein (e.g., as disclosed in the section entitled "Inhibitors of Immune Checkpoint Molecules" starting on page 218 hereinbelow (including all publications mentioned therein).

In another embodiment, the anti-PD-L1 antibody molecule is administered in combination with a CEACAM inhibitor (e.g., CEACAM-1, CEACAM-3 and/or CEACAM-5 inhibitor), e.g., an anti-CEACAM antibody molecule. In another embodiment, the anti-PD-L1 antibody molecule is administered in combination with a CEACAM-1 inhibitor, e.g., an anti-CEACAM-1 antibody molecule. In another embodiment, the anti-PD-L1 antibody molecule is administered in combination with a CEACAM-5 inhibitor, e.g., an anti-CEACAM-5 antibody molecule. In one embodiment, a bispecific antibody that includes an anti-PD-L1 antibody molecule and an anti-TIM-3 or anti-LAG-3 antibody, or antigen-binding fragment thereof, is administered. In certain embodiments, the combination of antibodies recited herein is used to treat a cancer, e.g., a cancer as described herein (e.g., a solid tumor). The efficacy of the aforesaid combinations can be tested in animal models known in the art.

In one embodiment, the inhibitor of CEACAM (e.g., CEACAM-1 and/or CEACAM-5) is an anti-CEACAM antibody molecule. Without wishing to be bound by theory, CEACAM-1 has been described as a ligand and partner of TIM-3 (see e.g., WO 2014/022332). Synergistic in vivo effect of the combination of anti-TIM-3 and anti-CEACAM-1 antibodies have been detected in xenograft cancer models (see e.g., WO 2014/022332). Tumors are believed to use CEACAM-1 or CEACAM-5 to inhibit the immune system, as described in, e.g., Markel et al. *J Immunol.* 2002 Mar. 15; 168(6):2803-10; Markel et al. *J Immunol.* 2006 Nov. 1; 177(9):6062-71; Markel et al. *Immunology.* 2009 February; 126(2):186-200; Markel et al. *Cancer Immunol Immunother.* 2010 February; 59(2):215-30; Ortenberg et al. *Mol Cancer Ther.* 2012 June; 11(6):1300-10; Stern et al. *J Immunol.* 2005 Jun. 1; 174(11):6692-701; Zheng et al. *PLoS One.* 2010 Sep. 2; 5(9). pii: e12529. Thus, CEACAM inhibitors can be used with the other immunomodulators described herein (e.g., anti-PD-1 or anti-TIM-3 inhibitors) to enhance an immune response against a cancer, e.g., melanoma, lung cancer (e.g., NSCLC), bladder, colon or ovarian cancer, or other cancers as described herein. In one embodiment, the inhibitor of CEACAM is an anti-CEACAM-1 antibody as described in WO 2010/125571, WO 2013/82366 and WO 2014/022332, e.g., a monoclonal antibody 34B1, 26H7, and 5F4 or a recombinant form thereof, as described in, e.g., US 2004/0047858, U.S. Pat. No. 7,132,255 and WO 99/52552. In other embodiments, the anti-CEACAM antibody is an anti-CEACAM-1 and/or anti-CEACAM-5 antibody molecule as described in, e.g., WO 2010/125571, WO 2013/054331 and US 2014/0271618.

In some embodiments, the PD-L1 and LAG-3 immune inhibitory molecules (e.g., antibody molecules) are administered in combination with each other, e.g., to treat cancer. In some embodiments, the patient is a patient who progressed (e.g., experienced tumor growth) during therapy with a PD-1 inhibitor (e.g., an antibody molecule as described herein) and/or a PD-L1 inhibitor (e.g., antibody molecule). In some embodiments, therapy with the PD-L1 antibody molecule and/or PD-L1 antibody molecule is continued, and a LAG-3 immune inhibitory molecule (e.g., antibody) is added to the therapy.

In some embodiments, the PD-L1 and TIM-3 immune inhibitory molecules (e.g., antibody molecules) are administered in combination with each other, e.g., to treat cancer. In some embodiments, the patient is a patient who progressed (e.g., experienced tumor growth) during therapy with a PD-L1 inhibitor (e.g., an antibody molecule as described herein) and/or a PD-L1 inhibitor (e.g., antibody molecule). In some embodiments, therapy with the PD-1 antibody molecule and/or PD-L1 antibody molecule is continued, and a TIM-3 immune inhibitory molecule (e.g., antibody) is added to the therapy.

In other embodiments, the anti-PD-L1 antibody molecule is administered in combination with a cytokine, e.g., interleukin-2, -15, -12, or -21. In certain embodiments, the combination of anti-PD-L1 antibody molecule and cytokine described herein is used to treat a cancer, e.g., a cancer as described herein (e.g., a solid tumor or melanoma).

Exemplary immunomodulators that can be used in combination with anti-PD-L1 antibody molecules include, but are not limited to, e.g., afutuzumab (available from Roche®); pegfilgrastim (Neulasta®); lenalidomide (CC-5013, Revlimid®); thalidomide (Thalomid®), actimid (CC4047); and cytokines, e.g., IL-21 or IRX-2 (mixture of human cytokines including interleukin 1, interleukin 2, and interferon γ, CAS 951209-71-5, available from IRX Therapeutics).

In yet other embodiments, the anti-PD-L1 antibody molecule is used in combination with an indoleamine-pyrrole 2,3-dioxygenase (IDO) inhibitor (e.g., INCB24360) in a subject with advanced or metastatic cancer (e.g., a patient with metastic and recurrent NSCL cancer).

In other embodiments, the anti-PD-L1 antibody molecules are administered to a subject in conjunction with (e.g., before, simultaneously or following) one or more of: bone marrow transplantation, T cell ablative therapy using chemotherapy agents such as, fludarabine, external-beam radiation therapy (XRT), cyclophosphamide, and/or antibodies such as OKT3 or CAMPATH. In one embodiment, the anti-PD-L1 antibody molecules are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive the anti-PD-L1 antibody molecules. In an additional embodiment, the anti-PD-L1 antibody molecules are administered before or following surgery.

Another example of a combination is an anti-PD-L1 antibody in combination with decarbazine for the treatment of melanoma. Without being bound by theory, the combined use of PD-L1 blockade and chemotherapy is believed to be facilitated by cell death, that is a consequence of the cytotoxic action of most chemotherapeutic compounds, which can result in increased levels of tumor antigen in the antigen presentation pathway. Other combination therapies that may result in synergy with PD-L1 blockade through cell death are radiation, surgery, and hormone deprivation. Each of these protocols creates a source of tumor antigen in the host. Angiogenesis inhibitors may also be combined with PD-L1 blockade. Inhibition of angiogenesis leads to tumor cell death which may feed tumor antigen into host antigen presentation pathways.

PD-L1 blocking antibodies can also be used in combination with bispecific antibodies. Bispecific antibodies can be used to target two separate antigens. For example anti-Fc receptor/anti tumor antigen (e.g., Her-2/neu) bispecific antibodies have been used to target macrophages to sites of tumor. This targeting may more effectively activate tumor specific responses. The T cell arm of these responses would by augmented by the use of PD-L1 blockade. Alternatively, antigen may be delivered directly to DCs by the use of bispecific antibodies which bind to tumor antigen and a dendritic cell specific cell surface marker.

Tumors evade host immune surveillance by a large variety of mechanisms. Many of these mechanisms may be overcome by the inactivation of proteins which are expressed by the tumors and which are immunosuppressive. These include among others TGF-beta (Kehrl, J. et al. (1986) *J. Exp. Med.* 163: 1037-1050), IL-10 (Howard, M. & O'Garra, A. (1992) *Immunology Today* 13: 198-200), and Fas ligand (Hahne, M. et al. (1996) *Science* 274: 1363-1365). Antibodies or antigen-binding fragments thereof to each of these entities may be used in combination with anti-PD-L1 to counteract the effects of the immunosuppressive agent and favor tumor immune responses by the host.

Other antibodies which may be used to activate host immune responsiveness can be used in combination with anti-PD-L1. These include molecules on the surface of dendritic cells which activate DC function and antigen presentation. Anti-CD40 antibodies are able to substitute effectively for T cell helper activity (Ridge, J. et al. (1998) *Nature* 393: 474-478) and can be used in conjunction with PD-L1 antibodies (Ito, N. et al. (2000) *Immunobiology* 201 (5) 527-40). Antibodies to T cell costimulatory molecules such as CTLA-4 (e.g., U.S. Pat. No. 5,811,097), OX-40 (Weinberg, A. et al. (2000) *Immunol* 164: 2160-2169), 4-1BB (Melero, I. et al. (1997) *Nature Medicine* 3: 682-685 (1997), and ICOS (Hutloff, A. et al. (1999) *Nature* 397: 262-266) may also provide for increased levels of T cell activation.

Additional exemplary standard of care treatments are described in the section entitled "Combination Therapies" below.

In all of the methods described herein, PD-L1 blockade can be combined with other forms of immunotherapy such as cytokine treatment (e.g., interferons, GM-CSF, G-CSF, IL-2, IL-21), or bispecific antibody therapy, which provides for enhanced presentation of tumor antigens (see e.g., Holliger (1993) *Proc. Natl. Acad. Sci. USA* 90:6444-6448; Poljak (1994) *Structure* 2:1121-1123).

Methods of administering the antibody molecules are known in the art and are described below. Suitable dosages of the molecules used will depend on the age and weight of the subject and the particular drug used. Dosages and therapeutic regimens of the anti-PD-L1 antibody molecule can be determined by a skilled artisan. In certain embodiments, the anti-PD-L1 antibody molecule is administered by injection (e.g., subcutaneously or intravenously) at a dose of about 1 to 30 mg/kg, e.g., about 5 to 25 mg/kg, about 10 to 20 mg/kg, about 1 to 5 mg/kg, or about 3 mg/kg. In some embodiments, the anti-PD-L1 antibody molecule is administered at a dose of about 1 mg/kg, about 3 mg/kg, or 10 mg/kg, about 20 mg/kg, about 30 mg/kg, or about 40 mg/kg. In some embodiments, the anti-PD-L1 antibody molecule is administered at a dose of about 1-3 mg/kg, or about 3-10 mg/kg. In some embodiments, the anti-PD-L1 antibody molecule is administered at a dose of about 0.5-2, 2-4, 2-5, 5-15, or 5-20 mg/kg. The dosing schedule can vary from e.g., once a week to once every 2, 3, or 4 weeks. In one embodiment, the anti-PD-L1 antibody molecule is administered at a dose from about 10 to 20 mg/kg every other week.

The antibody molecules can be used unconjugated or conjugated to a second agent, e.g., a cytotoxic drug, radioisotope, or a protein, e.g., a protein toxin or a viral protein. This method includes: administering the antibody molecule, alone or conjugated to a cytotoxic drug, to a subject requiring such treatment. The antibody molecules can be used to deliver a variety of therapeutic agents, e.g., a cytotoxic moiety, e.g., a therapeutic drug, a radioisotope, molecules of plant, fungal, or bacterial origin, or biological proteins (e.g., protein toxins) or particles (e.g., a recombinant viral particles, e.g.; via a viral coat protein), or mixtures thereof.

Immunosuppression

Immunosuppression involves an act that reduces the activation or efficacy of the immune system. Some portions of the immune system itself have immuno-suppressive effects on other parts of the immune system, and immunosuppression may occur as an adverse reaction to treatment of other conditions.

Deliberately induced immunosuppression (e.g., by an immunosuppressant (e.g., an immunosuppressive drug or an environmental toxin), surgery (splenectomy), plasmapharesis, or radiation) can be performed to prevent the body from rejecting an organ transplant, treating graft-versus-host disease after a bone marrow transplant, or for the treatment of auto-immune diseases such as rheumatoid arthritis or Crohn's disease.

Non-deliberate immunosuppression can occur in, e.g., malnutrition, aging, many types of cancer (e.g., leukemia, lymphoma, multiple myeloma), and certain chronic infections e.g., Human Immunodeficiency virus (HIV). The unwanted effect in non-deliberate immunosuppression is immunodeficiency that results in increased susceptibility to pathogens e.g., bacteria and virus. Immunodeficiency can be a potential adverse effect of certain immunosuppressant drugs. As used herein, in some embodiments, the terms "immunosuppressed," "immunodificient" or "immunocompromised" may be used interchangeably.

Immunosuppression is one of the leading causes of death in septic patients. Neutrophils are classical components of innate immunology, but neutrophils might display antigen presenting function and inhibit lymphocyte proliferation by expressing PD-L1.

Accordingly, in one embodiment, the invention provides a method of inhibiting immunosuppression in a subject, comprising administering to the subject a therapeutically effective amount of an anti-PD-L1 antibody molecule described herein. In one embodiment, the methods are suitable for the treatment of sepsis.

In one aspect, a method of treating a subject, e.g., reducing or ameliorating, immunosuppression, in a subject is provided. In an embodiment, the subject is suffering from sepsis or is at risk of developing sepsis. In another embodiment, the subject has or is at risk of developing chronic infection (e.g., HIV) or cancer. In yet another embodiment, the subject is receiving or has received an anti-cancer therapy, e.g., chemotherapy or radiation therapy. The method includes administering to the subject one or more anti-PD-L1 antibody molecules described herein, alone or in combination with other agents or therapeutic modalities.

Additional Combination Therapies

The anti-PD-L1 antibody molecule can be used in combination with other therapies. For example, the combination therapy can include a composition of the present invention co-formulated with, and/or co-administered with, one or more additional therapeutic agents, e.g., one or more anti-cancer agents, cytotoxic or cytostatic agents, hormone treatment, vaccines, and/or other immunotherapies. In other embodiments, the antibody molecules are administered in combination with other therapeutic treatment modalities, including surgery, radiation, cryosurgery, and/or thermotherapy. Such combination therapies may advantageously utilize lower dosages of the administered therapeutic agents, thus avoiding possible toxicities or complications associated with the various monotherapies.

By "in combination with," it is not intended to imply that the therapy or the therapeutic agents must be administered at the same time and/or formulated for delivery together, although these methods of delivery are within the scope described herein. The anti-PD-L1 antibody molecules can be administered concurrently with, prior to, or subsequent to, one or more other additional therapies or therapeutic agents. The anti-PD-L1 antibody molecule and the other agent or therapeutic protocol can be administered in any order. In general, each agent will be administered at a dose and/or on a time schedule determined for that agent. In will further be appreciated that the additional therapeutic agent utilized in this combination may be administered together in a single composition or administered separately in different compositions. In general, it is expected that additional therapeutic agents utilized in combination be utilized at levels that do not exceed the levels at which they are utilized individually. In some embodiments, the levels utilized in combination will be lower than those utilized individually.

Immunomodulators

In certain embodiments, the immunomodulator used in combination with an anti-PD-L1 antibody molecule, or in the combinations disclosed herein (e.g., in combination with a therapeutic agent chosen from an antigen-presentation combination) is an inhibitor of an immune checkpoint molecule. In one embodiment, the immunomodulator is an inhibitor of PD-1, PD-L1, PD-L2, CTLA-4, TIM-3, LAG-3, CEACAM (e.g., CEACAM-1, -3 and/or -5), VISTA, BTLA, TIGIT, LAIR1, CD160, 2B4 and/or TGFR beta. In one embodiment, the inhibitor of an immune checkpoint molecule inhibits PD-1, PD-L1, LAG-3, TIM-3, CEACAM (e.g., CEACAM-1, -3 and/or -5), CTLA-4, or any combination thereof.

Inhibition of an inhibitory molecule can be performed at the DNA, RNA or protein level. In embodiments, an inhibitory nucleic acid (e.g., a dsRNA, siRNA or shRNA), can be used to inhibit expression of an inhibitory molecule. In other embodiments, the inhibitor of an inhibitory signal is, a polypeptide e.g., a soluble ligand (e.g., PD-1-Ig or CTLA-4 Ig), or an antibody or antigen-binding fragment thereof, that binds to the inhibitory molecule; e.g., an antibody or fragment thereof (also referred to herein as "an antibody molecule") that binds to PD-1, PD-L1, PD-L2, CEACAM (e.g., CEACAM-1, -3 and/or -5), CTLA-4, TIM-3, LAG-3, VISTA, BTLA, TIGIT, LAIR1, CD160, 2B4 and/or TGFR beta, or a combination thereof.

In certain embodiments, the antibody molecule is in the form of a bispecific or multispecific antibody molecule. In one embodiment, the bispecific antibody molecule has a first binding specificity to PD-1 or PD-L1 and a second binding specificity, e.g., a second binding specificity to TIM-3, CEACAM (e.g., CEACAM-1, -3 and/or -5), LAG-3, or PD-L2. In one embodiment, the bispecific antibody molecule binds to PD-1 or PD-L1 and TIM-3. In another embodiment, the bispecific antibody molecule binds to PD-1 or PD-L1 and LAG-3. In another embodiment, the bispecific antibody molecule binds to PD-1 or PD-L1 and CEACAM (e.g., CEACAM-1, -3 and/or -5). In another embodiment, the bispecific antibody molecule binds to PD-1 or PD-L1 and CEACAM-1. In still another embodiment, the bispecific antibody molecule binds to PD-1 or PD-L1 and CEACAM-3. In yet another embodiment, the bispecific antibody molecule binds to PD-1 or PD-L1 and CEACAM-5. In another embodiment, the bispecific antibody molecule binds to PD-1 or PD-L1. In yet another embodiment, the bispecific antibody molecule binds to PD-1 and PD-L2. In another embodiment, the bispecific antibody molecule binds to TIM-3 and LAG-3. In another embodiment, the bispecific antibody molecule binds to CEACAM (e.g., CEACAM-1, -3 and/or -5) and LAG-3. In another embodiment, the bispecific antibody molecule binds to CEACAM (e.g., CEACAM-1, -3 and/or -5) and TIM-3. Any combination of the aforesaid molecules can be made in a multispecific antibody molecule, e.g., a trispecific antibody that includes a first binding specificity to PD-1 or PD-1, and a second and third binding specificities to two or more of: TIM-3, CEACAM (e.g., CEACAM-1, -3 and/or -5), LAG-3, or PD-L2.

In certain embodiments, the immunomodulator is an inhibitor of PD-1, e.g., human PD-1 (e.g., an antibody molecule as described herein). In another embodiment, the immunomodulator is an inhibitor of PD-L1, e.g., human PD-L1. In one embodiment, the inhibitor of PD-1 or PD-L1 is an antibody molecule to PD-1 or PD-L1. The PD-1 or PD-L1 inhibitor can be administered alone, or in combination with other immunomodulators, e.g., in combination with an inhibitor of LAG-3, TIM-3, CEACAM (e.g., CEACAM-1, -3 and/or -5) or CTLA-4. In an exemplary embodiment, the inhibitor of PD-1 or PD-L1, e.g., the anti-PD-1 or PD-L1 antibody molecule, is administered in combination with a LAG-3 inhibitor, e.g., an anti-LAG-3 antibody molecule. In another embodiment, the inhibitor of PD-1 or PD-L1, e.g., the anti-PD-1 or PD-L1 antibody molecule, is administered in combination with a TIM-3 inhibitor, e.g., an anti-TIM-3 antibody molecule. In another embodiment, the inhibitor of PD-1 or PD-L1, e.g., the anti-PD-1 or PD-L1 antibody molecule, is administered in combination with a CEACAM inhibitor (e.g., CEACAM-1, -3 and/or -5 inhibitor), e.g., an anti-CEACAM antibody molecule. In another embodiment, the inhibitor of PD-1 or PD-L1, e.g., the anti-PD-1 or PD-L1 antibody molecule, is administered in combination with a CEACAM-1 inhibitor, e.g., an anti-CEACAM-1 antibody molecule. In another embodiment, the inhibitor of PD-1 or PD-L1, e.g., the anti-PD-1 or PD-L1 antibody molecule, is administered in combination with a CEACAM-5 inhibitor, e.g., an anti-CEACAM-5 antibody molecule. In yet other embodiments, the inhibitor of PD-1 or PD-L1, e.g., the anti-PD-1 antibody molecule, is administered in combination with a LAG-3 inhibitor, e.g., an anti-LAG-3 antibody molecule, and a TIM-3 inhibitor, e.g., an anti-TIM-3 antibody molecule. Other combinations of immunomodulators with a PD-1 inhibitor (e.g., one or more of PD-L2, CTLA-4, TIM-3, LAG-3, CEACAM (e.g., CEACAM-1, -3 and/or -5), VISTA, BTLA, TIGIT, LAIR1, CD160, 2B4 and/or TGFR) are also within the present invention. Any of the antibody molecules known in the art or disclosed herein can be used in the aforesaid combinations of inhibitors of checkpoint molecule.

In other embodiments, the immunomodulator is an inhibitor of CEACAM (e.g., CEACAM-1, -3 and/or -5), e.g., human CEACAM (e.g., CEACAM-1, -3 and/or -5). In one embodiment, the immunomodulator is an inhibitor of CEACAM-1, e.g., human CEACAM-1. In another embodiment, the immunomodulator is an inhibitor of CEACAM-3, e.g., human CEACAM-3. In another embodiment, the immunomodulator is an inhibitor of CEACAM-5, e.g., human CEACAM-5. In one embodiment, the inhibitor of CEACAM (e.g., CEACAM-1, -3 and/or -5) is an antibody molecule to CEACAM (e.g., CEACAM-1, -3 and/or -5). The CEACAM (e.g., CEACAM-1, -3 and/or -5) inhibitor can be administered alone, or in combination with other immunomodulators, e.g., in combination with an inhibitor of LAG-3, TIM-3, PD-1, PD-L1 or CTLA-4.

In other embodiments, the immunomodulator is an inhibitor of LAG-3, e.g., human LAG-3. In one embodiment, the inhibitor of LAG-3 is an antibody molecule to LAG-3. The LAG-3 inhibitor can be administered alone, or in combination with other immunomodulators, e.g., in combination with an inhibitor of CEACAM (e.g., CEACAM-1, -3 and/or -5), TIM-3, PD-1, PD-L1 or CTLA-4.

In other embodiments, the immunomodulator is an inhibitor of TIM-3, e.g., human TIM-3. In one embodiment, the inhibitor of TIM-3 is an antibody molecule to TIM-3. The TIM-3 inhibitor can be administered alone, or in combination with other immunomodulators, e.g., in combination with an inhibitor of CEACAM (e.g., CEACAM-1, -3 and/or -5), LAG-3, PD-1, PD-L1 or CTLA-4.

In certain embodiments, the immunomodulator used in the combinations disclosed herein (e.g., in combination with a therapeutic agent chosen from an antigen-presentation combination) is an activator or agonist of a costimulatory molecule. In one embodiment, the agonist of the costimulatory molecule is chosen from an agonist (e.g., an agonistic antibody or antigen-binding fragment thereof, or a soluble fusion) of OX40, CD2, CD27, CD28, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3, or CD83 ligand.

In other embodiments, the immunomodulator is a GITR agonist. In one embodiment, the GITR agonist is an antibody molecule to GITR. The GITR agonist can be administered alone, or in combination with other immunomodulators, e.g., in combination with an inhibitor of PD-1, PD-L1, CTLA-4, CEACAM (e.g., CEACAM-1, -3 and/or -5), TIM-3 or LAG-3. In some embodiments, the anti-GITR antibody molecule is a bispecific antibody that binds to GITR and PD-1, PD-L1, CTLA-4, CEACAM (e.g., CEACAM-1, -3 and/or -5), TIM-3 or LAG-3. In one exemplary embodiment, the anti-GITR antibody molecule is administered in combination with an anti-PD-1 antibody molecule (e.g., an anti-PD-1 molecule as described herein). The GITR antibody molecule and the anti-PD-1 antibody molecule may be in the form of separate antibody composition, or as a bispecific antibody molecule. In other embodiments, a GITR agonist can be administered in combination with other costimulatory molecule, e.g., an agonist of OX40, CD2, CD27, CD28, CDS, ICAM-1, LFA-1 (CD11a/CD18), ICOS (CD278), 4-1BB (CD137), CD30, CD40, BAFFR, HVEM, CD7, LIGHT, NKG2C, SLAMF7, NKp80, CD160, B7-H3, or CD83 ligand.

In other embodiments, the immunomodulator is an activator of a costimulatory molecule (e.g., an OX40 agonist). In one embodiment, the OX40 agonist is an antibody molecule to OX40. The OX40 agonist can be administered alone, or in combination with other immunomodulators, e.g., in combination with an inhibitor of PD-1, PD-L1, CTLA-4, CEACAM (e.g., CEACAM-1, -3 and/or -5), TIM-3 or LAG-3. In some embodiments, the anti-OX40 antibody molecule is a bispecific antibody that binds to GITR and PD-1, PD-L1, CTLA-4, CEACAM (e.g., CEACAM-1, -3 and/or -5), TIM-3 or LAG-3. In one exemplary embodiment, an OX40 antibody molecule is administered in combination with an anti-PD-1 antibody molecule (e.g., an anti-PD-1 molecule as described herein). The OX40 antibody molecule and the anti-PD-1 antibody molecule may be in the form of separate antibody composition, or as a bispecific antibody molecule. In other embodiments, the OX40 agonist can be administered in combination with other costimulatory molecule, e.g., an agonist of GITR, CD2, CD27, CD28, CDS, ICAM-1, LFA-1 (CD11a/CD18), ICOS (CD278), 4-1BB (CD137), CD30, CD40, BAFFR, HVEM, CD7, LIGHT, NKG2C, SLAMF7, NKp80, CD160, B7-H3, or CD83 ligand.

It is noted that only exemplary combinations of inhibitors of checkpoint inhibitors or agonists of costimulatory molecules are provided herein. Additional combinations of these agents are within the scope of the present invention.

In certain embodiments, the anti-PD-L1 molecules described herein are administered in combination with one or more other inhibitors of PD-1, PD-L1 and/or PD-L2 known in the art. The antagonist may be an antibody, an antigen binding fragment thereof, an immunoadhesin, a fusion protein, or oligopeptide. In some embodiments, the other anti-PD-1 antibody is chosen from MDX-1106, Merck 3475 or CT-011. In some embodiments, the PD-1 inhibitor is an immunoadhesin (e.g., an immunoadhesin comprising an extracellular or PD-1 binding portion of PD-L1 or PD-L2 fused to a constant region (e.g., an Fc region of an immunoglobulin sequence). In some embodiments, the PD-1 inhibitor is AMP-224. In some embodiments, the PD-L1 inhibitor is anti-PD-L1 antibody. In some embodiments, the anti-PD-L1 binding antagonist is chosen from YW243.55.S70, MPDL3280A, MEDI-4736, MSB-0010718C, or MDX-1105. MDX-1105, also known as BMS-936559, is an anti-PD-L1 antibody described in WO2007/005874. Antibody YW243.55.S70 (heavy and light chain variable region sequences shown in SEQ ID Nos. 20 and 21, respectively) is an anti-PD-L1 described in WO 2010/077634.

MDX-1106, also known as MDX-1106-04, ONO-4538 or BMS-936558, is an anti-PD-1 antibody described in WO2006/121168. Merck 3745, also known as MK-3475 or SCH-900475, is an anti-PD-1 antibody described in WO2009/114335. Pidilizumab (CT-011; Cure Tech) is a humanized IgG1k monoclonal antibody that binds to PD-1. Pidilizumab and other humanized anti-PD-1 monoclonal antibodies are disclosed in WO2009/101611. In other embodiments, the anti-PD-1 antibody is pembrolizumab. Pembrolizumab (Trade name Keytruda formerly lambrolizumab also known as MK-3475) disclosed, e.g., in Hamid, O. et al. (2013) *New England Journal of Medicine* 369 (2): 134-44. AMP-224 (B7-DCIg; Amplimmune; e.g., disclosed in WO2010/027827 and WO2011/066342), is a PD-L2 Fc fusion soluble receptor that blocks the interaction between PD-1 and B7-H1. Other anti-PD-1 antibodies include AMP 514 (Amplimmune), among others, e.g., anti-PD-1 antibodies disclosed in U.S. Pat. No. 8,609,089, US 2010028330, and/or US 20120114649.

In some embodiments, the other anti-PD-1 antibody is MDX-1106. Alternative names for MDX-1106 include MDX-1106-04, ONO-4538, BMS-936558 or Nivolumab. In some embodiments, the anti-PD-1 antibody is Nivolumab (CAS Registry Number: 946414-94-4). Nivolumab (also referred to as BMS-936558 or MDX1106; Bristol-Myers Squibb) is a fully human IgG4 monoclonal antibody which specifically blocks PD-1. Nivolumab (clone 5C4) and other human monoclonal antibodies that specifically bind to PD-1 are disclosed in U.S. Pat. No. 8,008,449 and WO2006/121168. Pembrolizumab or Lambrolizumab (also referred to as MK-3475; Merck) is a humanized IgG4 monoclonal antibody that binds to PD-1. Pembrolizumab and other humanized anti-PD-1 antibodies are disclosed in U.S. Pat. No. 8,354,509 and WO09/114335. MDPL3280A (Genentech/Roche) is a human Fc optimized IgG1 monoclonal antibody that binds to PD-L1. MDPL3280A and other human monoclonal antibodies to PD-L1 are disclosed in U.S. Pat. No. 7,943,743 and U.S Publication No. 20120039906. Other anti-PD-L1 binding agents include YW243.55.570 (heavy and light chain variable regions are shown in SEQ ID NOs 20 and 21 in WO2010/077634) and MDX-1105 (also referred to as BMS-936559, and, e.g., anti-PD-L1 binding agents disclosed in WO2007/005874). In some embodiments, the antibody molecule (e.g., mono-, bi- or trispecific antibody) for TIM-3, LAG-3 and/or PD-1 used in any of the methods and combinations disclosed herein includes an amino acid sequence, or is encoded by a nucleotide sequence as described herein (e.g., as disclosed in the section entitled "Inhibitors of Immune Checkpoint Molecules" starting on page 218 hereinbelow (including all publications mentioned therein).

Cancer Therapies

Exemplary combinations of anti-PD-L1 antibody molecules (alone or in combination with other stimulatory agents) and standard of care for cancer, include at least the following. In certain embodiments, the anti-PD-L1 antibody molecule, e.g., the anti-PD-L1 antibody molecule described herein, is used in combination with a standard of cancer care chemotherapeutic agent including, but not limited to, anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), vinorelbine (Navelbine®), Ibrutinib, idelalisib, and brentuximab vedotin.

Exemplary alkylating agents include, without limitation, nitrogen mustards, ethylenimine derivatives, alkyl sulfonates, nitrosoureas and triazenes): uracil mustard (Aminouracil Mustard®, Chlorethaminacil®, Demethyldopan®, Desmethyldopan®, Haemanthamine®, Nordopan®, Uracil nitrogen Mustard®, Uracillost®, Uracilmostaza®, Uramustin®, Uramustine®), chlormethine (Mustargen®), cyclophosphamide (Cytoxan®, Neosar®, Clafen®, Endoxan®, Procytox®, Revimmune™), ifosfamide (Mitoxana®), melphalan (Alkeran®), Chlorambucil (Leukeran®), pipobroman (Amedel®, Vercyte®), triethylenemelamine (Hemel®, Hexalen®, Hexastat®), triethylenethiophosphoramine, Temozolomide (Temodar®), thiotepa (Thioplex®), busulfan (Busilvex®, Myleran®), carmustine (BiCNU®), lomustine (CeeNU®), streptozocin (Zanosar®), and Dacarbazine (DTIC-Dome®). Additional exemplary alkylating agents include, without limitation, Oxaliplatin (Eloxatin®); Temozolomide (Temodar® and Temodal®); Dactinomycin (also known as actinomycin-D, Cosmegen®); Melphalan (also known as L-PAM, L-sarcolysin, and phenylalanine mustard, Alkeran®); Altretamine (also known as hexamethylmelamine (HMM, Hexalen®); Carmustine (BiCNU®); Bendamustine (Treanda®); Busulfan (Busulfex® and Myleran®); Carboplatin (Paraplatin®); Lomustine (also known as CCNU, CeeNU®); Cisplatin (also known as CDDP, Platinol® and Platinol®-AQ); Chlorambucil (Leukeran®); Cyclophosphamide (Cytoxan® and Neosar®); Dacarbazine (also known as DTIC, DIC and imidazole carboxamide, DTIC-Dome®); Altretamine (also known as hexamethylmelamine (HMM), Hexalen®); Ifosfamide (Ifex®); Prednumustine; Procarbazine (Matulane®); Mechlorethamine (also known as nitrogen mustard, mustine and mechloroethamine hydrochloride, Mustargen®); Streptozocin (Zanosar®); Thiotepa (also known as thiophosphoamide, TESPA and TSPA, Thioplex®); Cyclophosphamide (Endoxan®, Cytoxan®, Neosar®, Procytox®, Revimmune®); and Bendamustine HCl (Treanda®).

Exemplary anthracyclines include, e.g., doxorubicin (Adriamycin® and Rubex®); bleomycin (Lenoxane®); daunorubicin (dauorubicin hydrochloride, daunomycin, and rubidomycin hydrochloride, Cerubidine®); daunorubicin liposomal (daunorubicin citrate liposome, DaunoXome®); mitoxantrone (DHAD, Novantrone®); epirubicin (Ellence™); idarubicin (Idamycin®, Idamycin PFS®); mitomycin C (Mutamycin®); geldanamycin; herbimycin; ravidomycin; and desacetylravidomycin.

Exemplary vinca alkaloids that can be used in combination with the anti-PD-L1 antibody molecules, alone or in combination with another immunomodulator (e.g., an anti-LAG-3, anti-PD-1 or anti-TIM-3 antibody molecule), include, but are not limited to, vinorelbine tartrate (Navelbine®), Vincristine (Oncovin®), and Vindesine (Eldisine®)); vinblastine (also known as vinblastine sulfate, vincaleukoblastine and VLB, Alkaban-AQ® and Velban®); and vinorelbine (Navelbine®).

Exemplary proteosome inhibitors that can be used in combination with the anti-PD-L1 antibody molecules, alone or in combination with another immunomodulator (e.g., an anti-LAG-3, anti-PD-1 or anti-TIM-3 antibody molecule), include, but are not limited to, bortezomib (Velcade®); carfilzomib (PX-171-007, (S)-4-Methyl-N-((S)-1-(((S)-4-methyl-1-((R)-2-methyloxiran-2-yl)-1-oxopentan-2-yl) amino)-1-oxo-3-phenylpropan-2-yl)-2-((S)-2-(2-morpholinoacetamido)-4-phenylbutanamido)-pentanamide); marizomib (NPI-0052); ixazomib citrate (MLN-9708); delanzomib (CEP-18770); and O-Methyl-N-[(2-methyl-5-thiazolyl)carbonyl]-L-seryl-O-methyl-N-[(1S)-2-[(2R)-2-methyl-2-oxiranyl]-2-oxo-1-(phenylmethyl)ethyl]-L-serinamide (ONX-0912).

In some embodiments, the anti-PD-L1 antibody molecule, e.g., the anti-PD-L1 antibody molecule described herein, is used, alone or in combination with another immunomodulator (e.g., an anti-LAG-3, anti-PD-1 or anti-TIM-3 antibody molecule), in combination with a tyrosine kinase inhibitor (e.g., a receptor tyrosine kinase (RTK) inhibitor). Exemplary tyrosine kinase inhibitor include, but are not limited to, an epidermal growth factor (EGF) pathway inhibitor (e.g., an epidermal growth factor receptor (EGFR) inhibitor), a vascular endothelial growth factor (VEGF) pathway inhibitor (e.g., a vascular endothelial growth factor receptor (VEGFR) inhibitor (e.g., a VEGFR-1 inhibitor, a VEGFR-2 inhibitor, a VEGFR-3 inhibitor)), a platelet derived growth factor (PDGF) pathway inhibitor (e.g., a platelet derived growth factor receptor (PDGFR) inhibitor (e.g., a PDGFR-β inhibitor)), a RAF-1 inhibitor, a KIT inhibitor and a RET inhibitor. In some embodiments, the anti-cancer agent used in combination with the hedgehog inhibitor is selected from the group consisting of: axitinib (AG013736), bosutinib (SKI-606), cediranib (RECENTIN, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), alemtuzumab (CAMPATH®), gemtuzumab ozogamicin (MYLOTARG®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, XL228, AEE788, AG-490, AST-6, BMS-599626, CUDC-101, PD153035, pelitinib (EKB-569), vandetanib (zactima), WZ3146, WZ4002, WZ8040, ABT-869 (linifanib), AEE788, AP24534 (ponatinib), AV-951(tivozanib), axitinib, BAY 73-4506 (regorafenib), brivanib alaninate (BMS-582664), brivanib (BMS-540215), cediranib (AZD2171), CHIR-258 (dovitinib), CP 673451, CYC116, E7080, Ki8751, masitinib (AB1010), MGCD-265, motesanib diphosphate (AMG-706), MP-470, OSI-930, Pazopanib Hydrochloride, PD173074, Sorafenib Tosylate (Bay 43-9006), SU 5402, TSU-68(SU6668), vatalanib, XL880 (GSK1363089, EXEL-2880). Selected tyrosine kinase inhibitors are chosen from sunitinib, erlotinib, gefitinib, or sorafenib.

In certain embodiments, the anti-PD-L1 antibody molecule, e.g., the anti-PD-L1 antibody molecule described herein, is used, alone or in combination with another immunomodulator (e.g., an anti-LAG-3, anti-PD-1 or anti-TIM-3 antibody molecule), in combination with a Vascular Endothelial Growth Factor (VEGF) receptor inhibitors. Exemplary inhibitors of the VEGF/VEGFR are disclosed herein below, e.g., in the section entitled "Exemplary Agents used in the Combinations."

In some embodiments, the anti-PD-L1 antibody molecule, e.g., the anti-PD-L1 antibody molecule described herein, is used, alone or in combination with another immunomodulator (e.g., an anti-LAG-3, anti-PD-1 or anti-TIM-3 antibody molecule), in combination with a PI3K inhibitor. In one embodiment, the PI3K inhibitor is an inhibitor of delta and gamma isoforms of PI3K. Exemplary PI3K inhibitors that can be used in combination are described herein below, e.g., in the section entitled "Exemplary Agents used in the Combinations."

In some embodiments, the anti-PD-L1 antibody molecules described herein is used, alone or in combination with another immunomodulator (e.g., an anti-LAG-3, anti-PD-1 or anti-TIM-3 antibody molecule), in combination with a mTOR inhibitor, e.g., one or more mTOR inhibitors disclosed herein below, e.g., in the section entitled "Exemplary Agents used in the Combinations."

In some embodiments, the anti-PD-L1 antibody molecule, e.g., the anti-PD-L1 antibody molecule described herein, is used, alone or in combination with another immunomodulator (e.g., an anti-LAG-3, anti-PD-1 or anti-TIM-3 antibody molecule), in combination with a BRAF inhibitor, e.g., GSK2118436, RG7204, PLX4032, GDC-0879, PLX4720, and sorafenib tosylate (Bay 43-9006). In some embodiments, the combination includes a RAF inhibitor, e.g., debrafinib or N-{3-[5-(2-aminopyrimidin-4-yl)-2-tert-butyl-1,3-thiazol-4-yl]-2-fluorophenyl}-2,6-difluorobenzenesulfonamide.

In some embodiments, the anti-PD-L1 antibody molecule, e.g., the anti-PD-L1 antibody molecule described herein, is used, alone or in combination with another immunomodulator (e.g., an anti-LAG-3, anti-PD-1 or anti-TIM-3 antibody molecule), in combination with a MEK inhibitor. In some embodiments, the combination of the anti-PD-L1 antibody and the MEK inhibitor is used to treat a cancer (e.g., a cancer described herein). In some embodiments, the cancer treated with the combination is chosen from a melanoma, a colorectal cancer, a non-small cell lung cancer, an ovarian cancer, a breast cancer, a prostate cancer, a pancreatic cancer, a hematological malignancy or a renal cell carcinoma. In certain embodiments, the cancer includes a BRAF mutation (e.g., a BRAF V600E mutation), a BRAF wildtype, a KRAS wildtype or an activating KRAS mutation. The cancer may be at an early, intermediate or late stage.

Any MEK inhibitor can be used in combination including, but not limited to, ARRY-142886, G02442104 (also known as GSK1120212), RDEA436, RDEA119/BAY 869766, AS703026, G00039805 (also known as AZD-6244 or selumetinib), BIX 02188, BIX 02189, CI-1040 (PD-184352), PD0325901, PD98059, U0126, GDC-0973 (Methanone, [3,4-difluoro-2-[(2-fluoro-4-iodophenyl)amino]phenyl][3-hydroxy-3-(2S)-2-piperidinyl-1-azetidinyl]-), G-38963, G02443714 (also known as AS703206), or a pharmaceutically acceptable salt or solvate thereof. Additional examples of MEK inhibitors are disclosed in WO 2013/019906, WO 03/077914, WO 2005/121142, WO 2007/04415, WO 2008/024725 and WO 2009/085983, the contents of which are incorporated herein by reference. In some embodiments, the MEK inhibitor is trametinib or N-(3-{3-Cyclopropyl-5-[(2-fluoro-4-iodophenyl)amino]-6,8-dimethyl-2,4,7-trioxo-3,4,6,7-tetrahydropyrido[4,3-d]pyrimidin-1(2H)-yl}phenyl)acetamide.

In some embodiments, the anti-PD-L1 antibody molecule, e.g., the anti-PD-L1 antibody molecule described herein, is used, alone or in combination with another immunomodulator (e.g., an anti-LAG-3, anti-PD-1 or anti-TIM-3 antibody molecule), in combination with a JAK2 inhibitor, e.g., CEP-701, INCB18424, CP-690550 (tasocitinib).

In some embodiments, the pharmaceutical composition described herein is used, alone or in combination with another immunomodulator (e.g., an anti-LAG-3, anti-PD-L1 or anti-TIM-3 antibody molecule), in combination with paclitaxel or a paclitaxel agent, e.g., TAXOL®, protein-bound paclitaxel (e.g., ABRAXANE®). Exemplary paclitaxel agents include, but are not limited to, nanoparticle albumin-bound paclitaxel (ABRAXANE, marketed by Abraxis Bioscience), docosahexaenoic acid bound-paclitaxel (DHA-paclitaxel, Taxoprexin, marketed by Protarga), polyglutamate bound-paclitaxel (PG-paclitaxel, paclitaxel poliglumex, CT-2103, XYOTAX, marketed by Cell Therapeutic), the tumor-activated prodrug (TAP), ANG105 (Angiopep-2 bound to three molecules of paclitaxel, marketed by ImmunoGen), paclitaxel-EC-1 (paclitaxel bound to the erbB2-recognizing peptide EC-1; see Li et al., *Biopolymers* (2007) 87:225-230), and glucose-conjugated paclitaxel (e.g., 2'-paclitaxel methyl 2-glucopyranosyl succinate, see Liu et al., *Bioorganic & Medicinal Chemistry Letters* (2007) 17:617-620).

Radiation therapy can be administered through one of several methods, or a combination of methods, including without limitation external-beam therapy, internal radiation therapy, implant radiation, stereotactic radiosurgery, systemic radiation therapy, radiotherapy and permanent or temporary interstitial brachytherapy. The term "brachytherapy," refers to radiation therapy delivered by a spatially confined radioactive material inserted into the body at or near a tumor or other proliferative tissue disease site. The term is intended without limitation to include exposure to radioactive isotopes (e.g. At-211, I-131, I-125, Y-90, Re-186, Re-188, Sm-153, Bi-212, P-32, and radioactive isotopes of Lu). Suitable radiation sources for use as a cell conditioner of the present invention include both solids and liquids. By way of non-limiting example, the radiation source can be a radionuclide, such as I-125, I-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide(s), e.g., a solution of I-125 or I-131, or a radioactive fluid can be produced using a slurry of a suitable fluid containing small particles of solid radionuclides, such as Au-198, Y-90. Moreover, the radionuclide(s) can be embodied in a gel or radioactive micro spheres.

Anti-PD-L1 antibody molecules, alone or in combination with another immunomodulator (e.g., an anti-LAG-3, anti-PD-1 or anti-TIM-3 antibody molecule), can be administered in combination with one or more of the existing modalities for treating cancers, including, but not limited to: surgery; radiation therapy (e.g., external-beam therapy which involves three dimensional, conformal radiation therapy where the field of radiation is designed, local radiation (e.g., radiation directed to a preselected target or organ), or focused radiation). Focused radiation can be selected from the group consisting of stereotactic radiosurgery, fractionated stereotactic radiosurgery, and intensity-modulated radiation therapy. The focused radiation can have a radiation source selected from the group consisting of a particle beam (proton), cobalt-60 (photon), and a linear accelerator (x-ray), e.g., as described in WO 2012/177624.

In certain embodiments, the anti-PD-L1 antibody molecule, alone or in combination with another immunomodulator (e.g., an anti-LAG-3, anti-PD-1 or anti-TIM-3 antibody molecule), is administered in combination with an antibody against a Killer-cell Immunoglobulin-like Receptors (also referred to herein as an "anti-KIR antibody"), a pan-KIR antibody, or an anti-NKG2D antibody, and/or an anti-MICA antibody. In certain embodiments, the combination of anti-PD-L1 antibody molecule and anti-KIR antibody, pan-KIR antibody, or an anti-NKG2D antibody described herein is used to treat a cancer, e.g., a cancer as described herein (e.g., a solid tumor, e.g., an advanced solid tumor).

In one embodiment, the anti-PD-L1 antibody molecule, alone or in combination with another immunomodulator (e.g., an anti-LAG-3, anti-PD-1 or anti-TIM-3 antibody molecule), is administered in combination with a cellular immunotherapy (e.g., Provenge (e.g., Sipuleucel)), and optionally in combination with cyclophosphamide. In certain embodiments, the combination of anti-PD-L1 antibody molecule, Provenge and/or cyclophosphamide is used to treat a cancer, e.g., a cancer as described herein (e.g., a prostate cancer, e.g., an advanced prostate cancer).

In another embodiment, the anti-PD-L1 antibody molecule, alone or in combination with another immunomodulator (e.g., an anti-LAG-3, anti-PD-1 or anti-TIM-3 antibody molecule), is administered in combination with a vaccine, e.g., a dendritic cell renal carcinoma (DC-RCC) vaccine. In certain embodiments, the combination of anti-PD-L1 antibody molecule and the DC-RCC vaccine is used to treat a cancer, e.g., a cancer as described herein (e.g., a renal carcinoma, e.g., metastatic renal cell carcinoma (RCC) or clear cell renal cell carcinoma (CCRCC)).

In yet another embodiment, the anti-PD-L1 antibody molecule, alone or in combination with another immunomodulator (e.g., an anti-LAG-3, anti-PD-1 or anti-TIM-3 antibody molecule), is administered in combination with chemotherapy, and/or immunotherapy. For example, the anti-PD-L1 antibody molecule can be used to treat a myeloma, alone or in combination with one or more of: chemotherapy or other anti-cancer agents (e.g., thalidomide analogs, e.g., lenalidomide), an anti-TIM-3 antibody, tumor antigen-pulsed dendritic cells, fusions (e.g., electrofusions) of tumor cells and dendritic cells, or vaccination with immunoglobulin idiotype produced by malignant plasma cells. In one embodiment, the anti-PD-L1 antibody molecule is used in combination with an anti-TIM-3 antibody to treat a myeloma, e.g., a multiple myeloma.

In one embodiment, the anti-PD-L1 antibody molecule, alone or in combination with another immunomodulator (e.g., an anti-LAG-3, anti-PD-1 or anti-TIM-3 antibody molecule), is used in combination with chemotherapy to treat a lung cancer, e.g., non-small cell lung cancer. In one embodiment, the anti-PD-L1 antibody molecule is used with platinum doublet therapy to treat lung cancer.

In yet another embodiment, the anti-PD-L1 antibody molecule, alone or in combination with another immunomodulator (e.g., an anti-LAG-3, anti-PD-1 or anti-TIM-3 antibody molecule), is used to treat a renal cancer, e.g., renal cell carcinoma (RCC) (e.g., clear cell renal cell carcinoma (CCRCC) or metastatic RCC. The anti-PD-L1 antibody molecule can be administered in combination with one or more of: an immune-based strategy (e.g., interleukin-2 or interferon-α), a targeted agent (e.g., a VEGF inhibitor such as a monoclonal antibody to VEGF); a VEGF tyrosine kinase inhibitor such as sunitinib, sorafenib, axitinib and pazopanib; an RNAi inhibitor), or an inhibitor of a downstream mediator of VEGF signaling, e.g., an inhibitor of the mammalian target of rapamycin (mTOR), e.g., everolimus and temsirolimus.

An example of suitable therapeutics for use in combination with the anti-PD-L1 antibody molecules described herein, alone or in combination with another immunomodulator (e.g., an anti-LAG-3, anti-PD-1 or anti-TIM-3 antibody molecule), for treatment of pancreatic cancer includes, but is not limited to, a chemotherapeutic agent, e.g., paclitaxel or a paclitaxel agent (e.g., a paclitaxel formulation such as TAXOL, an albumin-stabilized nanoparticle paclitaxel formulation (e.g., ABRAXANE) or a liposomal paclitaxel formulation); gemcitabine (e.g., gemcitabine alone or in combination with AXP107-11); other chemotherapeutic agents such as oxaliplatin, 5-fluorouracil, capecitabine, rubitecan, epirubicin hydrochloride, NC-6004, cisplatin, docetaxel (e.g., TAXOTERE), mitomycin C, ifosfamide; interferon; tyrosine kinase inhibitor (e.g., EGFR inhibitor (e.g., erlotinib, panitumumab, cetuximab, nimotuzumab); HER2/neu receptor inhibitor (e.g., trastuzumab); dual kinase inhibitor (e.g., bosutinib, saracatinib, lapatinib, vandetanib); multikinase inhibitor (e.g., sorafenib, sunitinib, XL184, pazopanib); VEGF inhibitor (e.g., bevacizumab, AV-951, brivanib); radioimmunotherapy (e.g., XR303); cancer vaccine (e.g., GVAX, survivin peptide); COX-2 inhibitor (e.g., celecoxib); IGF-1 receptor inhibitor (e.g., AMG 479, MK-0646); mTOR inhibitor (e.g., everolimus, temsirolimus); IL-6 inhibitor (e.g., CNTO 328); cyclin-dependent kinase inhibitor (e.g., P276-00, UCN-01); Altered Energy Metabolism-Directed (AEMD) compound (e.g., CPI-613); HDAC inhibitor (e.g., vorinostat); TRAIL receptor 2 (TR-2) agonist (e.g., conatumumab); MEK inhibitor (e.g., AS703026, selumetinib, GSK1120212); Raf/MEK dual kinase inhibitor (e.g., R05126766); Notch signaling inhibitor (e.g., MK0752); monoclonal antibody-antibody fusion protein (e.g., L19IL2); curcumin; HSP90 inhibitor (e.g., tanespimycin, STA-9090); rIL-2; denileukin diftitox; topoisomerase 1 inhibitor (e.g., irinotecan, PEP02); statin (e.g., simvastatin); Factor VIIa inhibitor (e.g., PCI-27483); AKT inhibitor (e.g., RX-0201); hypoxia-activated prodrug (e.g., TH-302); metformin hydrochloride, gamma-secretase inhibitor (e.g., R04929097); ribonucleotide reductase inhibitor (e.g., 3-AP); immunotoxin (e.g., HuC242-DM4); PARP inhibitor (e.g., KU-0059436, veliparib); CTLA-4 inhbitor (e.g., CP-675,206, ipilimumab); AdV-tk therapy; proteasome inhibitor (e.g., bortezomib (Velcade), NPI-0052); thiazolidinedione (e.g., pioglitazone); NPC-1C; Aurora kinase inhibitor (e.g., R763/AS703569), CTGF inhibitor (e.g., FG-3019); siG12D LODER; and radiation therapy (e.g., tomotherapy, stereotactic radiation, proton therapy), surgery, and a combination thereof. In certain embodiments, a combination of paclitaxel or a paclitaxel agent, and gemcitabine can be used with the anti-PD-L1 antibody molecules described herein.

An example of suitable therapeutics for use in combination with the anti-PD-L1 antibody molecules, alone or in combination with another immunomodulator (e.g., an anti-LAG-3, anti-PD-1 or anti-TIM-3 antibody molecule), for treatment of small cell lung cancer includes, but is not limited to, a chemotherapeutic agent, e.g., etoposide, carboplatin, cisplatin, oxaliplatin, irinotecan, topotecan, gemcitabine, liposomal SN-38, bendamustine, temozolomide, belotecan, NK012, FR901228, flavopiridol); tyrosine kinase inhibitor (e.g., EGFR inhibitor (e.g., erlotinib, gefitinib, cetuximab, panitumumab); multikinase inhibitor (e.g., sorafenib, sunitinib); VEGF inhibitor (e.g., bevacizumab, vandetanib); cancer vaccine (e.g., GVAX); Bcl-2 inhibitor (e.g., oblimersen sodium, ABT-263); proteasome inhibitor (e.g., bortezomib (Velcade), NPI-0052), paclitaxel or a paclitaxel agent; docetaxel; IGF-1 receptor inhibitor (e.g., AMG 479); HGF/SF inhibitor (e.g., AMG 102, MK-0646); chloroquine; Aurora kinase inhibitor (e.g., MLN8237); radioimmunotherapy (e.g., TF2); HSP90 inhibitor (e.g., tanespimycin, STA-9090); mTOR inhibitor (e.g., everolimus); Ep-CAM-/CD3-bispecific antibody (e.g., MT110); CK-2 inhibitor (e.g., CX-4945); HDAC inhibitor (e.g., belinostat); SMO antagonist (e.g., BMS 833923); peptide cancer vaccine, and radiation therapy (e.g., intensity-modulated radiation therapy (IMRT), hypofractionated radiotherapy, hypoxia-guided radiotherapy), surgery, and combinations thereof.

An example of suitable therapeutics for use in combination with the anti-PD-L1 antibody molecules, alone or in combination with another immunomodulator (e.g., an anti-LAG-3, anti-PD-1 or anti-TIM-3 antibody molecule), for treatment of non-small cell lung cancer includes, but is not limited to, a chemotherapeutic agent, e.g., vinorelbine, cisplatin, docetaxel, pemetrexed disodium, etoposide, gemcitabine, carboplatin, liposomal SN-38, TLK286, temozolomide, topotecan, pemetrexed disodium, azacitidine, irinotecan, tegafur-gimeracil-oteracil potassium, sapacitabine); tyrosine kinase inhibitor (e.g., EGFR inhibitor (e.g., erlotinib, gefitinib, cetuximab, panitumumab, necitumumab, PF-00299804, nimotuzumab, RO5083945), MET inhibitor (e.g., PF-02341066, ARQ 197), PI3K kinase inhibitor (e.g., XL147, GDC-0941), Raf/MEK dual kinase inhibitor (e.g., RO5126766), PI3K/mTOR dual kinase inhibitor (e.g., XL765), SRC inhibitor (e.g., dasatinib), dual inhibitor (e.g., BIBW 2992, GSK1363089, ZD6474, AZD0530, AG-013736, lapatinib, MEHD7945A, linifanib), multikinase inhibitor (e.g., sorafenib, sunitinib, pazopanib, AMG 706, XL184, MGCD265, BMS-690514, R935788), VEGF inhibitor (e.g., endostar, endostatin, bevacizumab, cediranib, BIBF 1120, axitinib, tivozanib, AZD2171), cancer vaccine (e.g., BLP25 liposome vaccine, GVAX, recombinant DNA and adenovirus expressing L523S protein), Bcl-2 inhibitor (e.g., oblimersen sodium), proteasome inhibitor (e.g., bortezomib, carfilzomib, NPI-0052, MLN9708), paclitaxel or a paclitaxel agent, docetaxel, IGF-1 receptor inhibitor (e.g., cixutumumab, MK-0646, OSI 906, CP-751,871, BIIB022), hydroxychloroquine, HSP90 inhibitor (e.g., tanespimycin, STA-9090, AUY922, XL888), mTOR inhibitor (e.g., everolimus, temsirolimus, ridaforolimus), Ep-CAM-/CD3-bispecific antibody (e.g., MT110), CK-2 inhibitor (e.g., CX-4945), HDAC inhibitor (e.g., MS 275, LBH589, vorinostat, valproic acid, FR901228), DHFR inhibitor (e.g., pralatrexate), retinoid (e.g., bexarotene, tretinoin), antibody-drug conjugate (e.g., SGN-15), bisphosphonate (e.g., zoledronic acid), cancer vaccine (e.g., belagenpumatucel-L), low molecular weight heparin (LMWH) (e.g., tinzaparin, enoxaparin), GSK1572932A, melatonin, talactoferrin, dimesna, topoisomerase inhibitor (e.g., amrubicin, etoposide, karenitecin), nelfinavir, cilengitide, ErbB3 inhibitor (e.g., MM-121, U3-1287), survivin inhibitor (e.g., YM155, LY2181308), eribulin mesylate, COX-2 inhibitor (e.g., celecoxib), pegfilgrastim, Polo-like kinase 1 inhibitor (e.g., BI 6727), TRAIL receptor 2 (TR-2) agonist (e.g., CS-1008), CNGRC peptide (SEQ ID NO: 225)-TNF alpha conjugate, dichloroacetate (DCA), HGF inhibitor (e.g., SCH 900105), SAR240550, PPAR-gamma agonist (e.g., CS-7017), gamma-secretase inhibitor (e.g., R04929097), epigenetic therapy (e.g., 5-azacitidine), nitroglycerin, MEK inhibitor (e.g., AZD6244), cyclin-dependent kinase inhibitor (e.g., UCN-01), cholesterol-Fus1, antitubulin agent (e.g., E7389), farnesyl-OH-transferase inhibitor (e.g., lonafarnib), immunotoxin (e.g., BB-10901, SS1 (dsFv) PE38), fondaparinux, vascular-disrupting agent (e.g., AVE8062), PD-L1 inhibitor (e.g., MDX-1105, MDX-1106), beta-glucan, NGR-hTNF, EMD 521873, MEK inhibitor (e.g., GSK1120212), epothilone analog (e.g., ixabepilone), kinesin-spindle inhibitor (e.g., 4SC-205), telomere targeting agent (e.g., KML-001), P70 pathway inhibitor (e.g., LY2584702), AKT inhibitor (e.g., MK-2206), angiogenesis inhibitor (e.g., lenalidomide), Notch signaling inhibitor (e.g., OMP-21M18), radiation therapy, surgery, and combinations thereof.

An example of suitable therapeutics for use in combination with the anti-PD-L1 antibody molecules, alone or in combination with another immunomodulator (e.g., an anti-LAG-3, anti-PD-1 or anti-TIM-3 antibody molecule), for treatment of ovarian cancer includes, but is not limited to, a chemotherapeutic agent (e.g., paclitaxel or a paclitaxel agent; docetaxel; carboplatin; gemcitabine; doxorubicin; topotecan; cisplatin; irinotecan, TLK286, ifosfamide, olaparib, oxaliplatin, melphalan, pemetrexed disodium, SJG-136, cyclophosphamide, etoposide, decitabine); ghrelin antagonist (e.g., AEZS-130), immunotherapy (e.g., APC8024, oregovomab, OPT-821), tyrosine kinase inhibitor (e.g., EGFR inhibitor (e.g., erlotinib), dual inhibitor (e.g., E7080), multikinase inhibitor (e.g., AZD0530, JI-101, sorafenib, sunitinib, pazopanib), ON 01910.Na), VEGF inhibitor (e.g., bevacizumab, BIBF 1120, cediranib, AZD2171), PDGFR inhibitor (e.g., IMC-3G3), paclitaxel, topoisomerase inhibitor (e.g., karenitecin, Irinotecan), HDAC inhibitor (e.g., valproate, vorinostat), folate receptor inhibitor (e.g., farletuzumab), angiopoietin inhibitor (e.g., AMG 386), epothilone analog (e.g., ixabepilone), proteasome inhibitor (e.g., carfilzomib), IGF-1 receptor inhibitor (e.g., OSI 906, AMG 479), PARP inhibitor (e.g., veliparib, AG014699, iniparib, MK-4827), Aurora kinase inhibitor (e.g., MLN8237, ENMD-2076), angiogenesis inhibitor (e.g., lenalidomide), DHFR inhibitor (e.g., pralatrexate), radioimmunotherapeutic agnet (e.g., Hu3S193), statin (e.g., lovastatin), topoisomerase 1 inhibitor (e.g., NKTR-102), cancer vaccine (e.g., p53 synthetic long peptides vaccine, autologous OC-DC vaccine), mTOR inhibitor (e.g., temsirolimus, everolimus), BCR/ABL inhibitor (e.g., imatinib), ET-A receptor antagonist (e.g., ZD4054), TRAIL receptor 2 (TR-2) agonist (e.g., CS-1008), HGF/SF inhibitor (e.g., AMG 102), EGEN-001, Polo-like kinase 1 inhibitor (e.g., BI 6727), gamma-secretase inhibitor (e.g., R04929097), Wee-1 inhibitor (e.g., MK-1775), antitubulin agent (e.g., vinorelbine, E7389), immunotoxin (e.g., denileukin diftitox), SB-485232, vascular-disrupting agent (e.g., AVE8062), integrin inhibitor (e.g., EMD 525797), kinesin-spindle inhibitor (e.g., 4SC-205), revlimid, HER2 inhibitor (e.g., MGAH22), ErrB3 inhibitor (e.g., MM-121), radiation therapy; and combinations thereof.

In one exemplary embodiment, the anti-PD-L1 antibody molecule, alone or in combination with another immunomodulator (e.g., an anti-LAG-3, anti-PD-1 or anti-TIM-3 antibody molecule), is used to treat a myeloma, alone or in combination with one or more of: chemotherapy or other anti-cancer agents (e.g., thalidomide analogs, e.g., lenalidomide), HSCT (Cook, R. (2008) *J Manag Care Pharm.* 14(7 Suppl):19-25), an anti-TIM-3 antibody (Hallett, W H D et al. (2011) *J of American Society for Blood and Marrow Transplantation* 17(8):1133-145), tumor antigen-pulsed dendritic cells, fusions (e.g., electrofusions) of tumor cells and dendritic cells, or vaccination with immunoglobulin idiotype produced by malignant plasma cells (reviewed in Yi, Q. (2009) *Cancer J.* 15(6):502-10).

In yet another embodiment, the anti-PD-L1 antibody molecule, alone or in combination with another immunomodulator (e.g., an anti-LAG-3, anti-PD-1 or anti-TIM-3 antibody molecule), is used to treat a renal cancer, e.g., renal cell carcinoma (RCC) or metastatic RCC. The anti-PD-L1 antibody molecule can be administered in combination with one or more of: an immune-based strategy (e.g., interleukin-2 or interferon-α), a targeted agent (e.g., a VEGF inhibitor such as a monoclonal antibody to VEGF, e.g., bevacizumab (Rini, B. I. et al. (2010) *J. Clin. Oncol.* 28(13):2137-2143)); a VEGF tyrosine kinase inhibitor such as sunitinib, sorafenib, axitinib and pazopanib (reviewed in Pal. S. K. et al. (2014) *Clin. Advances in Hematology & Oncology* 12(2):90-99)); an RNAi inhibitor), or an inhibitor of a downstream mediator of VEGF signaling, e.g., an inhibitor of the mammalian target of rapamycin (mTOR), e.g., everolimus and temsirolimus (Hudes, G. et al. (2007) *N. Engl. J. Med.* 356(22):2271-2281, Motzer, R. J. et al. (2008) *Lancet* 372: 449-456).

An example of suitable therapeutics for use in combination with the anti-PD-L1 antibody molecules described herein, alone or in combination with another immunomodulator (e.g., an anti-LAG-3, anti-PD-1 or anti-TIM-3 antibody molecule), for treatment of chronic myelogenous leukemia (AML) according to the invention includes, but is not limited to, a chemotherapeutic (e.g., cytarabine, hydroxyurea, clofarabine, melphalan, thiotepa, fludarabine, busulfan, etoposide, cordycepin, pentostatin, capecitabine, azacitidine, cyclophosphamide, cladribine, topotecan), tyrosine kinase inhibitor (e.g., BCR/ABL inhibitor (e.g., imatinib, nilotinib), ON 01910.Na, dual inhibitor (e.g., dasatinib, bosutinib), multikinase inhibitor (e.g., DCC-2036, ponatinib, sorafenib, sunitinib, RGB-286638)), interferon alfa, steroids, apoptotic agent (e.g., omacetaxine mepesuccinat), immunotherapy (e.g., allogeneic CD4+ memory Th1-like T cells/microparticle-bound anti-CD3/anti-CD28, autologous cytokine induced killer cells (CIK), AHN-12), CD52 targeting agent (e.g., alemtuzumab), HSP90 inhibitor (e.g., tanespimycin, STA-9090, AUY922, XL888), mTOR inhibitor (e.g., everolimus), SMO antagonist (e.g., BMS 833923), ribonucleotide reductase inhibitor (e.g., 3-AP), JAK-2 inhibitor (e.g., INCB018424), Hydroxychloroquine, retinoid (e.g., fenretinide), cyclin-dependent kinase inhibitor (e.g., UCN-01), HDAC inhibitor (e.g., belinostat, vorinostat, JNJ-26481585), PARP inhibitor (e.g., veliparib), MDM2 antagonist (e.g., R05045337), Aurora B kinase inhibitor (e.g., TAK-901), radioimmunotherapy (e.g., actinium-225-labeled anti-CD33 antibody HuM195), Hedgehog inhibitor (e.g., PF-04449913), STAT3 inhibitor (e.g., OPB-31121), KB004, cancer vaccine (e.g., AG858), bone marrow transplantation, stem cell transplantation, radiation therapy, and combinations thereof.

An example of suitable therapeutics for use in combination with the anti-PD-L1 antibody molecules, alone or in combination with another immunomodulator (e.g., an anti-LAG-3, anti-PD-1 or anti-TIM-3 antibody molecule), for treatment of chronic lymphocytic leukemia (CLL) includes, but is not limited to, a chemotherapeutic agent (e.g., fludarabine, cyclophosphamide, doxorubicin, vincristine, chlorambucil, bendamustine, chlorambucil, busulfan, gemcitabine, melphalan, pentostatin, mitoxantrone, 5-azacytidine, pemetrexed disodium), tyrosine kinase inhibitor (e.g., EGFR inhibitor (e.g., erlotinib), BTK inhibitor (e.g., PCI-32765), multikinase inhibitor (e.g., MGCD265, RGB-286638), CD-20 targeting agent (e.g., rituximab, ofatumumab, R05072759, LFB-R603), CD52 targeting agent (e.g., alemtuzumab), prednisolone, darbepoetin alfa, lenalidomide, Bcl-2 inhibitor (e.g., ABT-263), immunotherapy (e.g., allogeneic CD4+ memory Th1-like T cells/ microparticle-bound anti-CD3/anti-CD28, autologous cytokine induced killer cells (CIK)), HDAC inhibitor (e.g., vorinostat, valproic acid, LBH589, JNJ-26481585, AR-42), XIAP inhibitor (e.g., AEG35156), CD-74 targeting agent (e.g., milatuzumab), mTOR inhibitor (e.g., everolimus), AT-101, immunotoxin (e.g., CAT-8015, anti-Tac(Fv)-PE38 (LMB-2)), CD37 targeting agent (e.g., TRU-016), radioimmunotherapy (e.g., 131-tositumomab), hydroxychloroquine, perifosine, SRC inhibitor (e.g., dasatinib), thalidomide, PI3K delta inhibitor (e.g., CAL-101), retinoid (e.g., fenretinide), MDM2 antagonist (e.g., R05045337), plerixafor, Aurora kinase inhibitor (e.g., MLN8237, TAK-901), proteasome inhibitor (e.g., bortezomib), CD-19 targeting agent (e.g., MEDI-551, MOR208), MEK inhibitor (e.g., ABT-348), JAK-2 inhibitor (e.g., INCB018424), hypoxia-activated prodrug (e.g., TH-302), paclitaxel or a paclitaxel agent, HSP90 inhibitor, AKT inhibitor (e.g., MK2206), HMG-CoA inhibitor (e.g., simvastatin), GNKG186, radiation therapy, bone marrow transplantation, stem cell transplantation, and a combination thereof.

An example of suitable therapeutics for use in combination with the anti-PD-L1 antibody molecules described herein, alone or in combination with another immunomodulator (e.g., an anti-LAG-3, anti-PD-1 or anti-TIM-3 antibody molecule), for treatment of acute lymphocytic leukemia (ALL) includes, but is not limited to, a chemotherapeutic agent (e.g., prednisolone, dexamethasone, vincristine, asparaginase, daunorubicin, cyclophosphamide, cytarabine, etoposide, thioguanine, mercaptopurine, clofarabine, liposomal annamycin, busulfan, etoposide, capecitabine, decitabine, azacitidine, topotecan, temozolomide), tyrosine kinase inhibitor (e.g., BCR/ABL inhibitor (e.g., imatinib, nilotinib), ON 01910.Na, multikinase inhibitor (e.g., sorafenib)), CD-20 targeting agent (e.g., rituximab), CD52 targeting agent (e.g., alemtuzumab), HSP90 inhibitor (e.g., STA-9090), mTOR inhibitor (e.g., everolimus, rapamycin), JAK-2 inhibitor (e.g., INCB018424), HER2/neu receptor inhibitor (e.g., trastuzumab), proteasome inhibitor (e.g., bortezomib), methotrexate, asparaginase, CD-22 targeting agent (e.g., epratuzumab, inotuzumab), immunotherapy (e.g., autologous cytokine induced killer cells (CIK), AHN-12), blinatumomab, cyclin-dependent kinase inhibitor (e.g., UCN-01), CD45 targeting agent (e.g., BC8), MDM2 antagonist (e.g., R05045337), immunotoxin (e.g., CAT-8015, DT2219ARL), HDAC inhibitor (e.g., JNJ-26481585), JVRS-100, paclitaxel or a paclitaxel agent, STAT3 inhibitor (e.g., OPB-31121), PARP inhibitor (e.g., veliparib), EZN-2285, radiation therapy, steroid, bone marrow transplantation, stem cell transplantation, or a combination thereof.

An example of suitable therapeutics for use in combination with the anti-PD-L1 antibody molecules described herein, alone or in combination with another immunomodulator (e.g., an anti-LAG-3, anti-PD-1 or anti-TIM-3 antibody molecule), for treatment of acute myeloid leukemia (AML) includes, but is not limited to, a chemotherapeutic agent (e.g., cytarabine, daunorubicin, idarubicin, clofarabine, decitabine, vosaroxin, azacitidine, clofarabine, ribavirin, CPX-351, treosulfan, elacytarabine, azacitidine), tyrosine kinase inhibitor (e.g., BCR/ABL inhibitor (e.g., imatinib, nilotinib), ON 01910.Na, multikinase inhibitor (e.g., midostaurin, SU 11248, quizartinib, sorafinib)), immunotoxin (e.g., gemtuzumab ozogamicin), DT388IL3 fusion protein, HDAC inhibitor (e.g., vorinostat, LBH589), plerixafor, mTOR inhibitor (e.g., everolimus), SRC inhibitor (e.g., dasatinib), HSP90 inhbitor (e.g., STA-9090), retinoid (e.g., bexarotene, Aurora kinase inhibitor (e.g., BI 811283), JAK-2 inhibitor (e.g., INCB018424), Polo-like kinase inhibitor (e.g., BI 6727), cenersen, CD45 targeting agent (e.g., BC8), cyclin-dependent kinase inhibitor (e.g., UCN-01), MDM2 antagonist (e.g., R05045337), mTOR inhibitor (e.g., everolimus), LY573636-sodium, ZRx-101, MLN4924, lenalidomide, immunotherapy (e.g., AHN-12), histamine dihydrochloride, radiation therapy, bone marrow transplantation, stem cell transplantation, and a combination thereof.

An example of suitable therapeutics for use in combination with the anti-PD-L1 antibody molecules described herein, alone or in combination with another immunomodulator (e.g., an anti-LAG-3, anti-PD-1 or anti-TIM-3 antibody molecule), for treatment of multiple myeloma (MM) includes, but is not limited to, a chemotherapeutic agent (e.g., melphalan, amifostine, cyclophosphamide, doxorubicin, clofarabine, bendamustine, fludarabine, adriamycin, SyB L-0501), thalidomide, lenalidomide, dexamethasone, prednisone, pomalidomide, proteasome inhibitor (e.g., bortezomib, carfilzomib, MLN9708), cancer vaccine (e.g., GVAX), CD-40 targeting agent (e.g., SGN-40, CHIR-12.12), perifosine, zoledronic acid, Immunotherapy (e.g., MAGE-A3, NY-ESO-1, HuMax-CD38), HDAC inhibitor (e.g., vorinostat, LBH589, AR-42), aplidin, cycline-dependent kinase inhibitor (e.g., PD-0332991, dinaciclib), arsenic trioxide, CB3304, HSP90 inhibitor (e.g., KW-2478), tyrosine kinase inhibitor (e.g., EGFR inhibitor (e.g., cetuximab), multikinase inhibitor (e.g., AT9283)), VEGF inhibitor (e.g., bevacizumab), plerixafor, MEK inhibitor (e.g., AZD6244), IPH2101, atorvastatin, immunotoxin (e.g., BB-10901), NPI-0052, radioimmunotherapeutic (e.g., yttrium Y 90 ibritumomab tiuxetan), STAT3 inhibitor (e.g., OPB-31121), MLN4924, Aurora kinase inhibitor (e.g., ENMD-2076), IMGN901, ACE-041, CK-2 inhibitor (e.g., CX-4945), radiation therapy, bone marrow transplantation, stem cell transplantation, and a combination thereof.

An example of suitable therapeutics for use in combination with the anti-PD-L1 antibody molecules, alone or in combination with another immunomodulator (e.g., an anti-LAG-3, anti-PD-1 or anti-TIM-3 antibody molecule), for treatment of prostate cancer includes, but is not limited to, a chemotherapeutic agent (e.g., docetaxel, carboplatin, fludarabine), abiraterone, hormonal therapy (e.g., flutamide, bicalutamide, nilutamide, cyproterone acetate, ketoconazole, aminoglutethimide, abarelix, degarelix, leuprolide, goserelin, triptorelin, buserelin), tyrosine kinase inhibitor (e.g., dual kinase inhibitor (e.g., lapatanib), multikinase inhibitor (e.g., sorafenib, sunitinib)), VEGF inhibitor (e.g., bevacizumab), TAK-700, cancer vaccine (e.g., BPX-101, PEP223), lenalidomide, TOK-001, IGF-1 receptor inhibitor (e.g., cixutumumab), TRC105, Aurora A kinase inhibitor (e.g., MLN8237), proteasome inhibitor (e.g., bortezomib), OGX-011, radioimmunotherapy (e.g., HuJ591-GS), HDAC inhibitor (e.g., valproic acid, SB939, LBH589), hydroxychloroquine, mTOR inhibitor (e.g., everolimus), dovitinib lactate, diindolylmethane, efavirenz, OGX-427, genistein, IMC-3G3, bafetinib, CP-675,206, radiation therapy, surgery, or a combination thereof.

An example of suitable therapeutics for use in combination with the anti-PD-L1 antibody molecules, alone or in combination with another immunomodulator (e.g., an anti-LAG-3, anti-PD-1 or anti-TIM-3 antibody molecule), for treatment of HNSCC includes, but is not limited to, one or both of Compound A8 as described herein (or a compound described in PCT Publication No. WO2010/029082) and cetuximab (e.g., Erbitux, marketed by BMS). In some embodiments, the therapeutic (e.g., the Compound A8 or compound related to A8) is a PI3K modulator, e.g., a PI3K inhibitor. In some embodiments, the therapeutic (e.g., cetuximab) modulates, e.g., inhibits, EGFR. In some embodiments, the cancer has, or is identified as having, elevated levels or activity of PI3K or EGFR compared to a control cell or reference value.

An example of suitable therapeutics for use in combination with the anti-PD-L1 antibody molecules, alone or in combination with another immunomodulator (e.g., an anti-LAG-3, anti-PD-1 or anti-TIM-3 antibody molecule), for treatment of gastric cancer, e.g., MSI-high and/or EBV+ gastric cancer, includes, but is not limited to, Compound A8 as described herein (or a compound described in PCT Publication No. WO2010/029082). In some embodiments, the therapeutic (e.g., the Compound A8 or compound related to A8) is a PI3K modulator, e.g., a PI3K inhibitor. In some embodiments, the cancer has, or is identified as having, elevated levels or activity of PI3K compared to a control cell or reference value.

An example of suitable therapeutics for use in combination with the anti-PD-L1 antibody molecules, alone or in combination with another immunomodulator (e.g., an anti-LAG-3, anti-PD-1 or anti-TIM-3 antibody molecule), for treatment of gastric cancer, e.g., MSI-high and/or RNF43-inactivated gastric cancer, includes, but is not limited to, Compound A28 as described herein (or a compound described in PCT Publication No. WO2010/101849). In some embodiments, the therapeutic (e.g., the Compound A28 or compound related to A28) is a modulator, e.g., inhibitor, of porcupine. In some embodiments, the cancer has, or is identified as having, elevated levels or activity of porcupine compared to a control cell or reference value.

An example of suitable therapeutics for use in combination with the anti-PD-L1 antibody molecules, alone or in combination with another immunomodulator (e.g., an anti-LAG-3, anti-PD-1 or anti-TIM-3 antibody molecule), for treatment of GI stromal tumor (GIST), includes, but is not limited to, Compound A16 as described herein (or a compound described in PCT Publication No. WO1999/003854). In some embodiments, the therapeutic (e.g., the Compound A16 or compound related to A16) is a modulator, e.g., inhibitor, of a tyrosine kinase. In some embodiments, the cancer has, or is determined to have, elevated levels or activity of a tyrosine kinase compared to a control cell or reference value.

An example of suitable therapeutics for use in combination with the anti-PD-L1 antibody molecules, alone or in combination with another immunomodulator (e.g., an anti-LAG-3, anti-PD-1 or anti-TIM-3 antibody molecule), for treatment of NSCLC, e.g., squamous or adenocarcinoma, includes, but is not limited to, one or both of Compound A17 as described herein (or a compound described in U.S. Pat. Nos. 7,767,675 and 8,420,645) and Compound A23 as described herein (or a compound described in PCT Publication No. WO2003/077914). In some embodiments, the compound (e.g., the Compound A17 or compound related to A17) modulates, e.g., inhibits, c-MET. In some embodiments, the compound (e.g., the Compound A23 or compound related to A23) modulates, e.g., inhibits, Alk. In some embodiments, the cancer has, or is determined to have, elevated levels or activity of one or both of c-MET or Alk compared to a control cell or reference value. In some embodiments, the cancer has, or is identified as having, a mutation in EGFR.

An example of suitable therapeutics for use in combination with the anti-PD-L1 antibody molecules, alone or in combination with another immunomodulator (e.g., an anti-LAG-3, anti-PD-1 or anti-TIM-3 antibody molecule), for treatment of melanoma (e.g., NRAS melanoma) includes, but is not limited to, one or both of Compound A24 as described herein (or a compound described in U.S. Pat. Nos. 8,415,355 and 8,685,980) and Compound A34 as described herein (or a compound described in PCT Publication No. WO2003/077914). In some embodiments, the compound (e.g., the Compound A24 or compound related to A24) modulates, e.g., inhibits, one or more of JAK and CDK4/6. In some embodiments, the compound (e.g., the Compound A34 or compound related to A34) modulates, e.g., inhibits, MEK. In some embodiments, the cancer has, or is identified as having, elevated levels or activity of one or more of JAK, CDK4/6, and MEK compared to a control cell or reference value.

An example of suitable therapeutics for use in combination with the anti-PD-L1 antibody molecules, alone or in combination with another immunomodulator (e.g., an anti-LAG-3, anti-PD-1 or anti-TIM-3 antibody molecule), for treatment of melanoma (e.g., NRAS melanoma) includes, but is not limited to, one or both of Compound A29 as described herein (or a compound described in PCT Publication No. WO2011/025927) and Compound A34 as described herein (or a compound described in PCT Publication No. WO2003/077914). In some embodiments, the compound (e.g., the Compound A29 or compound related to A29) modulates, e.g., inhibits, BRAF. In some embodiments, the compound (e.g., the Compound A34 or compound related to A34) modulates, e.g., inhibits, MEK. In some embodiments, the cancer has, or is identified as having, elevated levels or activity of one or both of BRAF and MEK compared to a control cell or reference value.

An example of suitable therapeutics for use in combination with the anti-PD-L1 antibody molecules, alone or in combination with another immunomodulator (e.g., an anti-LAG-3, anti-PD-1 or anti-TIM-3 antibody molecule), for treatment of squamous NSCLC includes, but is not limited to, Compound A5 as described herein (or a compound described in U.S. Pat. No. 8,552,002). In some embodiments, the compound (e.g., the Compound A5 or compound related to A5) modulates, e.g., inhibits, FGFR. In some embodiments, the cancer has, or is identified as having, elevated levels or activity of FGFR compared to a control cell or reference value.

An example of suitable therapeutics for use in combination with the anti-PD-L1 antibody molecules, alone or in combination with another immunomodulator (e.g., an anti-LAG-3, anti-PD-1 or anti-TIM-3 antibody molecule), for treatment of colorectal cancer includes, but is not limited to, one or both of Compound A29 as described herein (or a compound PCT Publication No. WO2011/025927) and cetuximab (e.g., Erbitux, marketed by BMS). In some embodiments, the therapeutic (e.g., the Compound A29 or compound related to A29) modulates, e.g., inhibits, BRAF. In some embodiments, the therapeutic (e.g., cetuximab) modulates, e.g., inhibits EGFR. In some embodiments, the cancer has, or is identified as having, elevated levels or activity of BRAF or EGFR compared to a control cell or reference value.

This disclosure also provides a method of treating cancer with Compound A8, cetuximab, and a PD-L1 antibody molecule (optionally in combination with a TIM-3 antibody molecule or LAG-3 antibody molecule). In some embodiments, the patient is first treated with Compound A8 and cetuximab. This treatment continues for an amount of time, e.g., a predetermined amount of time, e.g., about 1, 2, 4, 6, 8, 10, or 12 months. Next, the PD-L1 antibody molecule (optionally in combination with a TIM-3 antibody molecule or LAG-3 antibody molecule) is administered. The PD-L1 antibody can optionally be administered in combination with cetuximab.

In some embodiments, the patient is first treated with all three of Compound A8, cetuximab, and a PD-L1 antibody molecule (optionally in combination with a TIM-3 antibody molecule or LAG-3 antibody molecule). This treatment continues for an amount of time, e.g., a predetermined amount of time, e.g., about 6, 8, 10, or 12 months. Next, the Compound A8 and/or cetuximab can be tapered off, so that the maintenance phase involves treatment with the PD-L1 antibody molecule (e.g., as a monotherapy, or in combination with a TIM-3 antibody molecule or LAG-3 antibody molecule) but not Compound A8 or cetuximab.

In other embodiments, the three compounds (Compound A8, cetuximab, and a PD-L1 antibody molecule, optionally in combination with a TIM-3 antibody molecule or LAG-3 antibody molecule) are given sequentially at the outset of the treatment. For instance, Compound A8 and cetuximab can be given first, as described above. Next, the PD-L1 antibody molecule (optionally in combination with a TIM-3 antibody molecule or LAG-3 antibody molecule) is added to the regimen. Next, the Compound A8 and/or cetuximab can be tapered off as described above.

Exemplary doses for the three (or more) agent regimens are as follows. The PD-L1 antibody molecule can be administered, e.g., at a dose of about 1 to 40 mg/kg, e.g., 1 to 30 mg/kg, e.g., about 5 to 25 mg/kg, about 10 to 20 mg/kg, about 1 to 5 mg/kg, or about 3 mg/kg. In some embodiments, the Compound A8 is administered at a dose of approximately 200-300, 300-400, or 200-400 mg. In some embodiments, the cetuximab is administered at a 400 mg/m2 initial dose as a 120-minute intravenous infusion followed by 250 mg/m2 weekly infused over 60 minutes. In embodiments, one or more of the Compound A8, cetuximab, and PD-L1 antibody molecule is administered at a dose that is lower than the dose at which that agent is typically administered as a monotherapy, e.g., about 0-10%, 10-20%, 20-30%, 30-40%, 40-50%, 50-60%, 60-70%, 70-80%, or 80-90% lower than the dose at which that agent is typically administered as a monotherapy. In embodiments, the one or more of the Compound A8, cetuximab, and PD-L1 antibody molecule is administered at a dose that is lower than the dose of that agent recited in this paragraph, e.g., about 0-10%, 10-20%, 20-30%, 30-40%, 40-50%, 50-60%, 60-70%, 70-80%, or 80-90% lower than the dose of that agent recited in this paragraph. In certain embodiments, the concentration of the Compound A8 that is required to achieve inhibition, e.g., growth inhibition, is lower when the Compound A8 is administered in combination with one or both of the cetuximab and PD-L1 antibody molecule than when the Compound A8 is administered individually. In certain embodiments, the concentration of the cetuximab that is required to achieve inhibition, e.g., growth inhibition, is lower when the cetuximab is administered in combination with one or both of the Compound A8 and PD-L1 antibody molecule than when the cetuximab is administered individually. In certain embodiments, the concentration of the PD-L1 antibody molecule that is required to achieve inhibition, e.g., growth inhibition, is lower when the PD-L1 antibody molecule is administered in combination with one or both of the cetuximab and Compound A8 than when the PD-L1 antibody molecule is administered individually.

Additionally disclosed herein is a method of treating cancer with the anti-PD-L1 antibody molecules, alone or in combination with another immunomodulator (e.g., an anti-LAG-3, anti-PD-1 or anti-TIM-3 antibody molecule), and a targeted anti-cancer agent, e.g., an agent that targets one or more proteins. In some embodiments, the anti-PD-L1 antibody molecule (and optionally other immunomodulator(s)) are administered first, and the targeted anti-cancer agent is administered second. The length of time between administration of the anti-PD-L1 antibody molecule and the targeted anti-cancer agent can be, e.g., 10, 20, or 30 minutes, 1, 2, 4, 6, or 12 hours, or 1, 2, 3, 4, 5, 6, or 7 days, or any span of time within this range. In certain embodiments, the anti-PD-L1 antibody molecule is administered repeatedly over a period of time (e.g., 1, 2, 3, 4, 5, or 6 days, or 1, 2, 4, 8, 12, 16, or 20 weeks, or any span of time within this range) before the targeted anti-cancer agent is administered. In other embodiments, the anti-PD-L1 antibody molecule and the targeted anti-cancer agent are administered at substantially the same time.

Infectious Diseases

Other methods of the invention are used to treat patients that have been exposed to particular toxins or pathogens. Accordingly, another aspect of the invention provides a method of treating an infectious disease in a subject comprising administering to the subject an anti-PD-L1 antibody molecule, such that the subject is treated for the infectious disease.

In the treatment of infection (e.g., acute and/or chronic), administration of the anti-PD-L1 antibody molecules can be combined with conventional treatments in addition to or in lieu of stimulating natural host immune defenses to infection. Natural host immune defenses to infection include, but are not limited to inflammation, fever, antibody-mediated host defense, T-lymphocyte-mediated host defenses, including lymphokine secretion and cytotoxic T-cells (especially during viral infection), complement mediated lysis and opsonization (facilitated phagocytosis), and phagocytosis. The ability of the anti-PD-L1 antibody molecules to reactivate dysfunctional T-cells would be useful to treat chronic infections, in particular those in which cell-mediated immunity is important for complete recovery.

Similar to its application to tumors as discussed above, antibody mediated PD-L1 blockade can be used alone, or as an adjuvant, in combination with vaccines, to stimulate the immune response to pathogens, toxins, and self-antigens. Examples of pathogens for which this therapeutic approach may be particularly useful, include pathogens for which there is currently no effective vaccine, or pathogens for which conventional vaccines are less than completely effective. These include, but are not limited to HIV, Hepatitis (A, B, & C), Influenza, Herpes, *Giardia*, Malaria, Leishmania, *Staphylococcus aureus, Pseudomonas Aeruginosa*. PD-L1 blockade is particularly useful against established infections by agents such as HIV that present altered antigens over the course of the infections. These novel epitopes are recognized as foreign at the time of anti-human PD-L1 administration, thus provoking a strong T cell response that is not dampened by negative signals through PD-L1.

Viruses

For infections resulting from viral causes, the anti-PD-L1 antibody molecules can be combined by application simultaneous with, prior to or subsequent to application of standard therapies for treating viral infections. Such standard therapies vary depending upon type of virus, although in almost all cases, administration of human serum containing antibodies (e.g., IgA, IgG) specific to the virus can be effective.

Some examples of pathogenic viruses causing infections treatable by methods include HIV, hepatitis (A, B, or C), herpes virus (e.g., VZV, HSV-1, HAV-6, HSV-II, and CMV, Epstein Barr virus), adenovirus, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

In one embodiment, the infection is an influenza infection. Influenza infection can result in fever, cough, myalgia, headache and malaise, which often occur in seasonal epidemics. Influenza is also associated with a number of postinfectious disorders, such as encephalitis, myopericarditis, Goodpasture's syndrome, and Reye's syndrome. Influenza infection also suppresses normal pulmonary antibacterial defenses, such that patient's recovering from influenza have an increased risk of developing bacterial pneumonia. Influenza viral surface proteins show marked antigenic variation, resulting from mutation and recombination. Thus, cytolytic T lymphocytes are the host's primary vehicle for the elimination of virus after infection. Influenza is classified into three primary types: A, B and C. Influenza A is unique in that it infects both humans and many other animals (e.g., pigs, horses, birds and seals) and is the principal cause of pandemic influenza. Also, when a cell is infected by two different influenza A strains, the segmented RNA genomes of two parental virus types mix during replication to create a hybrid replicant, resulting in new epidemic strains. Influenza B does not replicate in animals and thus has less genetic variation and influenza C has only a single serotype.

Most conventional therapies are palliatives of the symptoms resulting from infection, while the host's immune response actually clears the disease. However, certain strains (e.g., influenza A) can cause more serious illness and death. Influenza A may be treated both clinically and prophylactically by the administration of the cyclic amines inhibitors amantadine and rimantadine, which inhibit viral replication. However, the clinical utility of these drugs is limited due to the relatively high incidence of adverse reactions, their narrow anti-viral spectrum (influenza A only), and the propensity of the virus to become resistant. The administration of serum IgG antibody to the major influenza surface proteins, hemagglutinin and neuraminidase can prevent pulmonary infection, whereas mucosal IgA is required to prevent infection of the upper respiratory tract and trachea. The most effective current treatment for influenza is vaccination with the administration of virus inactivated with formalin or β-propiolactone.

In another embodiment, the infection is a hepatitis infection, e.g., a Hepatitis B or C infection.

Hepatitis B virus (HB-V) is the most infectious known bloodborne pathogen. It is a major cause of acute and chronic hepatitis and hepatic carcinoma, as well as life-long, chronic infection. Following infection, the virus replicates in hepatocytes, which also then shed the surface antigen HBsAg. The detection of excessive levels of HBsAg in serum is used a standard method for diagnosing a hepatitis B infection. An acute infection may resolve or it can develop into a chronic persistent infection. Current treatments for chronic HBV include α-interferon, which increases the expression of class I human leukocyte antigen (HLA) on the surface of hepatocytes, thereby facilitating their recognition by cytotoxic T lymphocytes. Additionally, the nucleoside analogs ganciclovir, famciclovir and lamivudine have also shown some efficacy in the treatment of HBV infection in clinical trials. Additional treatments for HBV include pegylated α-interferon, adenfovir, entecavir and telbivudine. While passive immunity can be conferred through parental administration of anti-HBsAg serum antibodies, vaccination with inactivated or recombinant HBsAg also confers resistance to infection. The anti-PD-L1 antibody molecules may be combined with conventional treatments for hepatitis B infections for therapeutic advantage.

Hepatitis C virus (HC-V) infection may lead to a chronic form of hepatitis, resulting in cirrosis. While symptoms are similar to infections resulting from Hepatitis B, in distinct contrast to HB-V, infected hosts can be asymptomatic for 10-20 years. The anti-PD-L1 antibody molecule can be administered as a monotherapy, or combined with the standard of care for hepatitis C infection. For example, the anti-PD-L1 antibody molecule can be administered with one or more of Sovaldi (sofosbuvir) Olysio (simeprevir), plus ribavirin or pegylated interferon. Although regimens that include Incivek (telaprevir) or Victrelis (boceprevir) plus ribavirin and pegylated interferon are also approved, they are associated with increased side effects and longer duration of treatment and are therefore not considered preferred regimens.

Conventional treatment for HC-V infection includes the administration of a combination of α-interferon and ribavirin. A promising potential therapy for HC-V infection is the protease inhibitor telaprevir (VX-960). Additional treatments include: anti-PD-1 antibody (MDX-1106, Medarex), bavituximab (an antibody that binds anionic phospholipid phosphatidylserine in a B2-glycoprotein I dependent manner, Peregrine Pharmaceuticals), anti-HPV viral coat protein E2 antibod(y)(ies) (e.g., ATL 6865–Ab68+Ab65, XTL Pharmaceuticals) and Civacir® (polyclonal anti-HCV human immune globulin). The anti-PD-L1 antibodies of the invention may be combined with one or more of these treatments for hepatitis C infections for therapeutic advantage. Protease, polymerase and NS5A inhibitors which may be used in combination with the anti-PD-L1 antibody molecules to specifically treat Hepatitis C infection include those described in US 2013/0045202, incorporated herein by reference.

In another embodiment, the infection is a measles virus. After an incubation of 9-11 days, hosts infected with the measles virus develop fever, cough, coryza and conjunctivitis. Within 1-2 days, an erythematous, maculopapular rash develop, which quickly spreads over the entire body. Because infection also suppresses cellular immunity, the host is at greater risk for developing bacterial superinfections, including otitis media, pneumonia and postinfectious encephalomyelitis. Acute infection is associated with significant morbidity and mortality, especially in malnourished adolescents.

Treatment for measles includes the passive administration of pooled human IgG, which can prevent infection in non-immune subjects, even if given up to one week after exposure. However, prior immunization with live, attenuated virus is the most effective treatment and prevents disease in more than 95% of those immunized. As there is one serotype of this virus, a single immunization or infection typically results in protection for life from subsequent infection.

In a small proportion of infected hosts, measles can develop into SSPE, which is a chronic progressive neurologic disorder resulting from a persistent infection of the central nervous system. SSPE is caused by clonal variants of measles virus with defects that interfere with virion assembly and budding. For these patients, reactivation of T-cells with the anti-PD-L1 antibody molecules so as to facilitate viral clearance would be desirable.

In another embodiment, the infection is HIV. HIV attacks $CD4^+$ cells, including T-lymphocytes, monocyte-macrophages, follicular dendritic cells and Langerhan's cells, and $CD4^+$ helper/inducer cells are depleted. As a result, the host acquires a severe defect in cell-mediated immunity. Infection with HIV results in AIDS in at least 50% of individuals, and is transmitted via sexual contact, administration of infected blood or blood products, artificial insemination with infected semen, exposure to blood-containing needles or syringes and transmission from an infected mother to infant during childbirth.

A host infected with HIV may be asymptomatic, or may develop an acute illness that resembling mononucleosis—fever, headache, sore throat, malaise and rash. Symptoms can progress to progressive immune dysfunction, including persistent fever, night sweats, weight loss, unexplained diarrhea, eczema, psoriasis, seborrheic dermatitis, herpes zoster, oral candidiasis and oral hairy leukoplakia. Opportunistic infections by a host of parasites are common in patients whose infections develop into AIDS.

Treatments for HIV include antiviral therapies including nucleoside analogs, zidovudine (AST) either alone or in combination with didanosine or zalcitabine, dideoxyinosine, dideoxycytidine, lamidvudine, stavudine; reverse transcriptive inhibitors such as delavirdine, nevirapine, loviride, and proteinase inhibitors such as saquinavir, ritonavir, indinavir and nelfinavir. The anti-PD-L1 antibody molecules may be combined with conventional treatments for HIV infections for therapeutic advantage.

In another embodiment, the infection is a Cytomegalovirus (CMV). CMV infection is often associated with persistent, latent and recurrent infection. CMV infects and remains latent in monocytes and granulocyte-monocyte progenitor cells. The clinical symptoms of CMV include mononucleosis-like symptoms (i.e., fever, swollen glands, malaise), and a tendancy to develop allergic skin rashes to antibiotics. The virus is spread by direct contact. The virus is shed in the urine, saliva, semen and to a lesser extent in other body fluids. Transmission can also occur from an infected mother to her fetus or newborn and by blood transfusion and organ transplants. CMV infection results in general impairment of cellular immunity, characterized by impaired blastogenic responses to nonspecific mitogens and specific CMV antigens, diminished cytotoxic ability and elevation of CD8 lymphocyte number of $CD4^+$ lymphocytes.

Treatments of CMV infection include the anti-virals ganciclovir, foscarnet and cidovir, but these drugs are typically only prescribed in immunocompromised patients. The anti-PD-L1 antibody molecules may be combined with conventional treatments for cytomegalovirus infections for therapeutic advantage.

In another embodiment, the infection is Epstein-Barr virus (EBV). EBV can establish persistent and latent infections and primarily attacks B cells. Infection with EBV results in the clinical condition of infectious mononucleosis, which includes fever, sore throat, often with exudate, generalized lymphadenopathy and splenomegaly. Hepatitis is also present, which can develop into jaundice.

While typical treatments for EBV infections are palliative of symptoms, EBV is associated with the development of certain cancers such as Burkitt's lymphoma and nasopharyngeal cancer. Thus, clearance of viral infection before these complications result would be of great benefit. The anti-PD-L1 antibody molecules may be combined with conventional treatments for Epstein-Barr virus infections for therapeutic advantage.

In another embodiment, the infection is Herpes simplex virus (HSV). HSV is transmitted by direct contact with an infected host. A direct infection may be asymptomatic, but typically result in blisters containing infectious particles. The disease manifests as cycles of active periods of disease, in which lesions appear and disappear as the viral latently infect the nerve ganglion for subsequent outbreaks. Lesions may be on the face, genitals, eyes and/or hands. In some case, an infection can also cause encephalitis.

Treatments for herpes infections are directed primarily to resolving the symptomatic outbreaks, and include systemic antiviral medicines such as: acyclovir (e.g., Zovirax®), valaciclovir, famciclovir, penciclovir, and topical medications such as docosanol (Abreva®), tromantadine and zilactin. The clearance of latent infections of herpes would be of great clinical benefit. The anti-PD-L1 antibody molecules may be combined with conventional treatments for herpes virus infections for therapeutic advantage.

In another embodiment, the infection is Human T-lymphotrophic virus (HTLV-1, HTLV-2). HTLV is transmitted via sexual contact, breast feeding or exposure to contaminated blood. The virus activates a subset of $T_H$ cells called Th1 cells, resulting in their overproliferation and overproduction of Th1 related cytokines (e.g., IFN-γ and TNF-α). This in turn results in a suppression of Th2 lymphocytes and reduction of Th2 cytokine production (e.g., IL-4, IL-5, IL-10 and IL-13), causing a reduction in the ability of an infected host to mount an adequate immune response to invading organisms requiring a Th2-dependent response for clearance (e.g., parasitic infections, production of mucosal and humoral antibodies).

HTLV infections cause lead to opportunistic infections resulting in bronchiectasis, dermatitis and superinfections with *Staphylococcus* spp. and *Strongyloides* spp. resulting in death from polymicrobial sepsis. HTLV infection can also lead directly to adult T-cell leukemia/lymphoma and progressive demyelinating upper motor neuron disease known as HAM/TSP. The clearance of HTLV latent infections would be of great clinical benefit. The anti-PD-L1 antibody molecules may be combined with conventional treatments for HTLV infections for therapeutic advantage.

In another embodiment, the infection is Human papilloma virus (HPV). HPV primarily affects keratinocytes and occurs in two forms: cutaneous and genital. Transmission is believed to occur through direct contact and/or sexual activity. Both cutaneous and genital HPV infection, can result in warts and latent infections and sometimes recurring infections, which are controlled by host immunity which controls the symptoms and blocks the appearance of warts, but leaves the host capable of transmitting the infection to others.

Infection with HPV can also lead to certain cancers, such as cervical, anal, vulvar, penile and oropharynial cancer. There are no known cures for HPV infection, but current treatment is topical application of Imiquimod, which stimulates the immune system to attack the affected area. The clearance of HPV latent infections would be of great clinical benefit. The anti-PD-L1 antibodies of the invention may be combined with conventional treatments for HPV infections for therapeutic advantage.

Bacterial Infections

Some examples of pathogenic bacteria causing infections treatable by methods of the invention include syphilis, chlamydia, rickettsial bacteria, mycobacteria, staphylococci, streptococci, pneumonococci, meningococci and conococci, klebsiella, proteus, serratia, pseudomonas, legionella, diphtheria, salmonella, bacilli, cholera, tetanus, botulism, anthrax, plague, leptospirosis, and Lymes disease bacteria. The anti-PD-L1 antibody molecules can be used in combination with existing treatment modalities for the aforesaid infections. For example, Treatments for syphilis include penicillin (e.g., penicillin G.), tetracycline, doxycycline, ceftriaxone and azithromycin.

Lyme disease, caused by *Borrelia burgdorferi* is transmitted into humans through tick bites. The disease manifests initially as a localized rash, followed by flu-like symptoms including malaise, fever, headache, stiff neck and arthralgias. Later manifestations can include migratory and polyarticular arthritis, neurologic and cardiac involvement with cranial nerve palsies and radiculopathy, myocarditis and arrhythmias. Some cases of Lyme disease become persistent, resulting in irreversible damage analogous to tertiary syphilis. Current therapy for Lyme disease includes primarily the administration of antibiotics. Antibiotic-resistant strains may be treated with hydroxychloroquine or methotrexate. Antibiotic refractory patients with neuropathic pain can be treated with gabapentin. Minocycline may be helpful in late/chronic Lyme disease with neurological or other inflammatory manifestations.

Other forms of borreliois, such as those resulting from *B. recurentis, B. hermsii, B. turicatae, B. parikeri., B. hispanica, B. duttonii* and *B. persica*, as well leptospirosis (E.g., *L. interrogans*), typically resolve spontaneously unless blood titers reach concentrations to cause intrahepatic obstruction.

Fungi and Parasites

Some examples of pathogenic fungi causing infections treatable by methods of the invention include *Candida* (*albicans, krusei, glabrata, tropicalis*, etc.), *Cryptococcus neoformans, Aspergillus* (*fumigatus, niger*, etc.), Genus *Mucorales* (*mucor, absidia, rhizophus*), *Sporothrix schenkii, Blastomyces dermatitidis, Paracoccidioides brasiliensis, Coccidioides immitis* and *Histoplasma capsulatum*.

Some examples of pathogenic parasites causing infections treatable by methods described herein include *Entamoeba histolytica, Balantidium coli, Naegleriafowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi*, and *Nippostrongylus brasiliensis*.

Additional Combination Therapies

Combinations of anti-PD-L1 antibody molecules with one or more second therapeutics are provided herein. Many of the combinations in this section are useful in treating cancer, but other indications are also described. This section focuses on combinations of anti-PD-L1 antibody molecules, optionally in combination with one or more immunomodulators (e.g., an anti-TIM-3 antibody molecule, an anti-LAG-3 antibody molecule, or an anti-PD-L1 antibody molecule), with one or more of the agents described in Table 6. In the combinations herein below, in one embodiment, the anti-PD-1 antibody molecule comprises (i) a heavy chain variable region (VH) comprising a VHCDR1 amino acid sequence chosen from SEQ ID NO: 1, SEQ ID NO: 4 or SEQ ID NO: 195; a VHCDR2 amino acid sequence of SEQ ID NO: 2 or SEQ ID NO: 5; and a VHCDR3 amino acid sequence of SEQ ID NO: 3; and (ii) a light chain variable region (VL) comprising a VLCDR1 amino acid sequence of SEQ ID NO: 9 or SEQ ID NO: 12, a VLCDR2 amino acid sequence of SEQ ID NO: 10 or SEQ ID NO: 13, and a VLCDR3 amino acid sequence of SEQ ID NO: 11 or SEQ ID NO: 14.

In one embodiment, the anti-PD-L1 antibody molecule, e.g., an anti-PD-L1 antibody molecule as described herein, alone or in combination with one or more other immunomodulators, is used in combination with a PKC inhibitor, Sotrastaurin (Compound A1), or a compound disclosed in PCT Publication No. WO 2005/039549, to treat a disorder, e.g., a disorder described herein. In one embodiment, the PKC inhibitor is Sotrastaurin (Compound A1) or a compound disclosed in PCT Publication No. WO 2005/039549. In one embodiment, a PD-L1 antibody molecule is used in combination with Sotrastaurin (Compound A1), or a compound as described in PCT Publication No. WO 2005/039549, to treat a disorder such as a cancer, a melanoma, a non-Hodgkin lymphoma, an inflammatory bowel disease, transplant rejection, an ophthalmic disorder, or psoriasis.

In certain embodiments, Sotrastaurin (Compound A1) is administered at a dose of about 20 to 600 mg, e.g., about 200 to about 600 mg, about 50 mg to about 450 mg, about 100 mg to 400 mg, about 150 mg to 350 mg, or about 200 mg to 300 mg, e.g., about 50 mg, 100 mg, 150 mg, 200 mg, 300 mg, 400 mg, 500 mg, or 600 mg. The dosing schedule can vary from e.g., every other day to daily, twice or three times a day.

In one embodiment, the anti-PD-L1 antibody molecule, e.g., an anti-PD-L1 antibody molecule as described herein, alone or in combination with one or more other immunomodulators, is used in combination with a BCR-ABL inhibitor, TASIGNA (Compound A2), or a compound disclosed in PCT Publication No. WO 2004/005281, to treat a disorder, e.g., a disorder described herein. In one embodiment, the BCR-ABL inhibitor is TASIGNA, or a compound disclosed in PCT Publication No. WO 2004/005281. In one embodiment, a PD-L1 antibody molecule is used in combination with TASIGNA (Compound A2), or a compound as described in PCT Publication No. WO 2004/005281, to treat a disorder such as a lymphocytic leukemia, Parkinson's Disease, a neurologic cancer, a melanoma, a digestive/gastrointestinal cancer, a colorectal cancer, a myeloid leukemia, chronic myelogenous leukemia (CML), a head and neck cancer, or pulmonary hypertension.

In one embodiment, the BCR-ABL inhibitor or TASIGNA is administered at a dose of about 300 mg (e.g., twice daily, e.g., for newly diagnosed Ph+CML-CP), or about 400 mg, e.g., twice daily, e.g., for resistant or intolerant Ph+CML-CP and CML-AP). BCR-ABL inhibitor or a Compound A2 is administered at a dose of about 300-400 mg.

In another embodiment, the anti-PD-L1 antibody molecule, e.g., an anti-PD-L1 antibody molecule as described herein, alone or in combination with one or more other immunomodulators, is used in combination with an HSP90 inhibitor, such as 5-(2,4-dihydroxy-5-isopropylphenyl)-N-ethyl-4-(4-(morpholinomethyl)phenyl)isoxazole-3-carboxamide (Compound A3), or a compound disclosed in PCT Publication No. WO 2010/060937 or WO 2004/072051, to treat a disorder, e.g., a disorder described herein. In one embodiment, the HSP90 inhibitor is 5-(2,4-dihydroxy-5-isopropylphenyl)-N-ethyl-4-(4-(morpholinomethyl)phenyl)isoxazole-3-carboxamide (Compound A3), or a compound disclosed in PCT Publication No. WO 2010/060937 or WO 2004/072051. In one embodiment, a PD-L1 antibody molecule is used in combination with 5-(2,4-dihydroxy-5-isopropylphenyl)-N-ethyl-4-(4-(morpholinomethyl)phenyl)isoxazole-3-carboxamide (Compound A3), or a compound as described in PCT Publication No. WO 2010/060937 or WO 2004/072051, to treat a disorder such as a cancer, a multiple myeloma, a non-small cell lung cancer, a lymphoma, a gastric cancer, a breast cancer, a digestive/gastrointestinal cancer, a pancreatic cancer, a colorectal cancer, a solid tumor, or a hematopoiesis disorder.

In another embodiment, the anti-PD-L1 antibody molecule, e.g., an anti-PD-L1 antibody molecule as described herein, alone or in combination with one or more other immunomodulators, is used in combination with an inhibitor of PI3K and/or mTOR, Dactolisib (Compound A4) or 8-(6-Methoxy-pyridin-3-yl)-3-methyl-1-(4-piperazin-1-yl-3-trifluoromethyl-phenyl)-1,3-dihydro-imidazo[4,5-c]quinolin-2-one (Compound A41), or a compound disclosed in PCT Publication No. WO 2006/122806, to treat a disorder, e.g., a disorder described herein. In one embodiment, the PI3K and/or mTOR inhibitor is Dactolisib (Compound A4), 8-(6-Methoxy-pyridin-3-yl)-3-methyl-1-(4-piperazin-1-yl-3-trifluoromethyl-phenyl)-1,3-dihydro-imidazo[4,5-c]quinolin-2-one (Compound A41), or a compound disclosed in PCT Publication No. WO 2006/122806. In one embodiment, a PD-L1 antibody molecule is used in combination with Dactolisib (Compound A4), 8-(6-Methoxy-pyridin-3-yl)-3-methyl-1-(4-piperazin-1-yl-3-trifluoromethyl-phenyl)-1,3-dihydro-imidazo[4,5-c]quinolin-2-one (Compound A41), or a compound described in PCT Publication No. WO 2006/122806, to treat a disorder such as a cancer, a prostate cancer, a leukemia (e.g., lymphocytic leukemia), a breast cancer, a brain cancer, a bladder cancer, a pancreatic cancer, a renal cancer, a solid tumor, a digestive/gastrointestinal cancer, or a liver cancer.

In another embodiment, the anti-PD-L1 antibody molecule, e.g., an anti-PD-L1 antibody molecule as described herein, alone or in combination with one or more other immunomodulators, is used in combination with an FGFR inhibitor, 3-(2,6-dichloro-3,5-dimethoxyphenyl)-1-(6-((4-(4-ethylpiperazin-1-yl)phenyl)amino)pyrimidin-4-yl)-1-methylurea (Compound A5) or a compound disclosed in U.S. Pat. No. 8,552,002, to treat a disorder, e.g., a disorder described herein. In one embodiment, the FGFR inhibitor is 3-(2,6-dichloro-3,5-dimethoxyphenyl)-1-(6-((4-(4-ethylpiperazin-1-yl)phenyl)amino)pyrimidin-4-yl)-1-methylurea (Compound A5) or a compound disclosed in U.S. Pat. No. 8,552,002. In one embodiment, a PD-L1 antibody molecule is used in combination with Compound A5, or a compound as described in U.S. Pat. No. 8,552,002, to treat a disorder such as a digestive/gastrointestinal cancer, a hematological cancer, or a solid tumor.

In one embodiment, the FGFR inhibitor or 3-(2,6-dichloro-3,5-dimethoxyphenyl)-1-(6-((4-(4-ethylpiperazin-1-yl)phenyl)amino)pyrimidin-4-yl)-1-methylurea (Compound A5) is administered at a dose of about 100-125 mg (e.g., per day), e.g., about 100 mg or about 125 mg.

In another embodiment, the anti-PD-L1 antibody molecule, e.g., an anti-PD-L1 antibody molecule as described herein, alone or in combination with one or more other immunomodulators, is used in combination with a PI3K inhibitor, Buparlisib (Compound A6), or a compound disclosed in PCT Publication No. WO 2007/084786, to treat a disorder, e.g., a disorder described herein. In one embodiment, the PI3K inhibitor is Buparlisib (Compound A6) or a compound disclosed in PCT Publication No. WO 2007/084786. In one embodiment, a PD-L1 antibody molecule is used in combination with Buparlisib (Compound A6), or a compound disclosed in PCT Publication No. WO 2007/084786, to treat a disorder such as, a prostate cancer, a lung cancer (e.g., a non-small cell lung cancer (NSCLC)), a prostate cancer, a gastric cancer, a pancreatic cancer, an endocrine cancer, a leukemia, an ovarian cancer, a melanoma, a bladder cancer, a breast cancer, a female reproductive system cancer, a digestive/gastrointestinal cancer, a colorectal cancer, a glioblastoma multiforme (GBM), a solid tumor, a leukemia, a non-Hodgkin lymphoma, a hematopoiesis disorder, or a head and neck cancer.

In one embodiment, the PI3K inhibitor or Buparlisib (Compound A6) is administered at a dose of about 100 mg (e.g., per day).

In another embodiment, the anti-PD-L1 antibody molecule, e.g., an anti-PD-L1 antibody molecule as described herein, alone or in combination with one or more other immunomodulators, is used in combination with an FGFR inhibitor, 8-(2,6-difluoro-3,5-dimethoxyphenyl)-N-(4-((dimethylamino)methyl)-1H-imidazol-2-yl)quinoxaline-5-carboxamide (Compound A7) or a compound disclosed in PCT Publication No. WO 2009/141386 to treat a disorder, e.g., a disorder described herein. In one embodiment, the FGFR inhibitor is 8-(2,6-difluoro-3,5-dimethoxyphenyl)-N-(4-((dimethylamino)methyl)-1H-imidazol-2-yl)quinoxaline-5- carboxamide (Compound A7) or a compound disclosed in a PCT Publication No. WO 2009/141386. In one embodiment, the FGFR inhibitor is 8-(2,6-difluoro-3,5-dimethoxyphenyl)-N-(4-((dimethylamino)methyl)-1H-imidazol-2-yl)quinoxaline-5-carboxamide (Compound A7). In one embodiment, a PD-L1 antibody molecule is used in combination with 8-(2,6-difluoro-3,5-dimethoxyphenyl)-N-(4-((dimethylamino)methyl)-1H-imidazol-2-yl)quinoxaline-5-carboxamide (Compound A7), or a compound disclosed in PCT Publication No. WO 2009/141386, to treat a disorder such as a cancer characterized by angiogenesis, a digestive/gastrointestinal cancer; or a hematological cancer.

In one embodiment, the FGFR inhibitor or 8-(2,6-difluoro-3,5-dimethoxyphenyl)-N-(4-((dimethylamino)methyl)-1H-imidazol-2-yl)quinoxaline-5-carboxamide (Compound A7) is administered at a dose of e.g., from approximately 3 mg to approximately 5 g, more preferably from approximately 10 mg to approximately 1.5 g per person per day, optionally divided into 1 to 3 single doses which may, for example, be of the same size.

In another embodiment, the anti-PD-L1 antibody molecule, e.g., an anti-PD-L1 antibody molecule as described herein, alone or in combination with one or more other immunomodulators, is used in combination with a PI3K inhibitor, (S)-N1-(4-methyl-5-(2-(1,1,1-trifluoro-2-methylpropan-2-yl)pyridin-4-yl)thiazol-2-yl)pyrrolidine-1,2-dicarboxamide (Compound A8) or a compound disclosed PCT Publication No. WO 2010/029082 to treat a disorder, e.g., a disorder described herein. In one embodiment, the PI3K inhibitor is (S)-N1-(4-methyl-5-(2-(1,1,1-trifluoro-2-methylpropan-2-yl)pyridin-4-yl)thiazol-2-yl)pyrrolidine-1,2-dicarboxamide (Compound A8) or a compound disclosed PCT Publication No. WO 2010/029082. In one embodiment, a PD-L1 antibody molecule is used in combination with (S)-N1-(4-methyl-5-(2-(1,1,1-trifluoro-2-methylpropan-2-yl)pyridin-4-yl)thiazol-2-yl)pyrrolidine-1,2-dicarboxamide (Compound A8), or a compound disclosed PCT Publication No. WO 2010/029082, to treat a disorder such as a lung cancer (e.g., non-small cell lung cancer (NSCLC)), a prostate cancer, an endocrine cancer, an ovarian cancer, a melanoma, a bladder cancer, a female reproductive system cancer, a colorectal cancer, glioblastoma multiforme (GBM), a gastric cancer, a breast cancer, a pancreatic cancer, a digestive/gastrointestinal cancer, a solid tumor, leukemia, non-Hodgkin lymphoma; or a hematopoiesis disorder, and a head and neck cancer.

In one embodiment, the PI3K inhibitor or (S)-N1-(4-methyl-5-(2-(1,1,1-trifluoro-2-methylpropan-2-yl)pyridin-4-yl)thiazol-2-yl)pyrrolidine-1,2-dicarboxamide (Compound A8) is administered at a dose of about 150-300, 200-300, 200-400, or 300-400 mg (e.g., per day), e.g., about 200, 300, or 400 mg.

In another embodiment, the anti-PD-L1 antibody molecule, e.g., an anti-PD-L1 antibody molecule as described herein, alone or in combination with one or more other immunomodulators, is used in combination with an inhibitor of cytochrome P450 (e.g., a CYP17 inhibitor) or a compound disclosed in PCT Publication No. WO 2010/149755, to treat a disorder, e.g., a disorder described herein. In one embodiment, the cytochrome P450 inhibitor (e.g., the CYP17 inhibitor) is a compound disclosed in PCT Publication No. WO 2010/149755. In one embodiment, a PD-L1 antibody molecule is used in combination with a compound disclosed in PCT Publication No. WO 2010/149755, to treat prostate cancer.

In another embodiment, the anti-PD-L1 antibody molecule, e.g., an anti-PD-L1 antibody molecule as described herein, alone or in combination with one or more other immunomodulators, is used in combination with an HDM2 inhibitor, (S)-1-(4-chlorophenyl)-7-isopropoxy-6-methoxy-2-(4-(methyl(((1r,4S)-4-(4-methyl-3-oxopiperazin-1-yl)cyclohexyl)methyl)amino)phenyl)-1,2-dihydroisoquinolin-3(4H)-one (Compound A10) or a compound disclosed in PCT Publication No. WO 2011/076786 to treat a disorder, e.g., a disorder described herein). In one embodiment, the HDM2 inhibitor is (S)-1-(4-chlorophenyl)-7-isopropoxy-6-methoxy-2-(4-(methyl(((1r,4S)-4-(4-methyl-3-oxopiperazin-1-yl)cyclohexyl)methyl)amino)phenyl)-1,2-dihydroisoquinolin-3(4H)-one (Compound A10) or a compound disclosed in PCT Publication No. WO 2011/076786. In one embodiment, a PD-L1 antibody molecule is used in combination with (S)-1-(4-chlorophenyl)-7-isopropoxy-6-methoxy-2-(4-(methyl(((1r,4S)-4-(4-methyl-3-oxopiperazin-1-yl)cyclohexyl)methyl)amino)phenyl)-1,2-dihydroisoquinolin-3(4H)-one (Compound A10), or a compound disclosed in PCT Publication No. WO 2011/076786, to treat a disorder such as a solid tumor.

In one embodiment, the HDM2 inhibitor or (S)-1-(4-chlorophenyl)-7-isopropoxy-6-methoxy-2-(4-(methyl(((1r,4S)-4-(4-methyl-3-oxopiperazin-1-yl)cyclohexyl)methyl)amino)phenyl)-1,2-dihydroisoquinolin-3(4H)-one (Compound A10) is administered at a dose of about 400 to 700 mg, e.g., administered three times weekly, 2 weeks on and one week off. In some embodiments, the dose is about 400, 500, 600, or 700 mg; about 400-500, 500-600, or 600-700 mg, e.g., administered three times weekly.

In another embodiment, the anti-PD-L1 antibody molecule, e.g., an anti-PD-L1 antibody molecule as described herein, alone or in combination with one or more other immunomodulators, is used in combination with an iron chelating agent, Deferasirox (also known as EXJADE; Compound A11), or a compound disclosed in PCT Publication No. WO 1997/049395 to treat a disorder, e.g., a disorder described herein. In one embodiment, the iron chelating agent is Deferasirox or a compound disclosed in PCT Publication No. WO 1997/049395. In one embodiment, the iron chelating agent is Deferasirox (Compound A11). In one embodiment, a PD-L1 antibody molecule is used in combination with Deferasirox (Compound A11), or a compound disclosed in PCT Publication No. WO 1997/049395, to treat iron overload, hemochromatosis, or myelodysplasia.

In another embodiment, the anti-PD-L1 antibody molecule, e.g., an anti-PD-L1 antibody molecule as described herein, alone or in combination with one or more other immunomodulators, is used in combination with an aromatase inhibitor, Letrozole (also known as FEMARA; Compound A12), or a compound disclosed in U.S. Pat. No. 4,978,672 to treat a disorder, e.g., a disorder described herein. In one embodiment, the aromatase inhibitor is Letrozole (Compound A12) or a compound disclosed in U.S. Pat. No. 4,978,672. In one embodiment, a PD-L1 antibody molecule is used in combination with Letrozole (Compound A12), or a compound disclosed in U.S. Pat. No. 4,978,672, to treat a disorder such as a cancer, a leiomyosarcoma, an endometrium cancer, a breast cancer, a female reproductive system cancer, or a hormone deficiency.

In another embodiment, the anti-PD-L1 antibody molecule, e.g., an anti-PD-L1 antibody molecule as described herein, alone or in combination with one or more other immunomodulators, is used in combination with a PI3K inhibitor, e.g., a pan-PI3K inhibitor, (4S,5R)-3-(2'-amino-2-morpholino-4'-(trifluoromethyl)-[4,5'-bipyrimidin]-6-yl)-4-(hydroxymethyl)-5-methyloxazolidin-2-one (Compound A13) or a compound disclosed in PCT Publication No.

WO2013/124826 to treat a disorder, e.g., a disorder described herein. In one embodiment, the PI3K inhibitor is (4S,5R)-3-(2'-amino-2-morpholino-4'-(trifluoromethyl)-[4,5'-bipyrimidin]-6-yl)-4-(hydroxymethyl)-5-methyloxazolidin-2-one (Compound A13) or a compound disclosed in PCT Publication No. WO2013/124826. In one embodiment, a PD-L1 antibody molecule is used in combination with (4S,5R)-3-(2'-amino-2-morpholino-4'-(trifluoromethyl)-[4,5'-bipyrimidin]-6-yl)-4-(hydroxymethyl)-5-methyloxazolidin-2-one (Compound A13), or a compound disclosed in PCT Publication No. WO2013/124826, to treat a disorder such as a cancer or an advanced solid tumor.

In another embodiment, the anti-PD-L1 antibody molecule, e.g., an anti-PD-L1 antibody molecule as described herein, alone or in combination with one or more other immunomodulators, is used in combination with an inhibitor of p53 and/or a p53/Mdm2 interaction, (S)-5-(5-chloro-1-methyl-2-oxo-1,2-dihydropyridin-3-yl)-6-(4-chlorophenyl)-2-(2,4-dimethoxypyrimidin-5-yl)-1-isopropyl-5,6-dihydropyrrolo[3,4-d]imidazol-4(1H)-one (Compound A14), or a compound disclosed in PCT Publication No. WO2013/111105 to treat a disorder, e.g., a disorder described herein. In one embodiment, the p53 and/or a p53/Mdm2 interaction inhibitor is (S)-5-(5-chloro-1-methyl-2-oxo-1,2-dihydropyridin-3-yl)-6-(4-chlorophenyl)-2-(2,4-dimethoxypyrimidin-5-yl)-1-isopropyl-5,6-dihydropyrrolo[3,4-d]imidazol-4(1H)-one (Compound A14) or a compound disclosed in PCT Publication No. WO2013/111105. In one embodiment, a PD-L1 antibody molecule is used in combination with (S)-5-(5-chloro-1-methyl-2-oxo-1,2-dihydropyridin-3-yl)-6-(4-chlorophenyl)-2-(2,4-dimethoxypyrimidin-5-yl)-1-isopropyl-5,6-dihydropyrrolo[3,4-d]imidazol-4(1H)-one (Compound A14), or a compound disclosed in PCT Publication No. WO2013/111105, to treat a disorder such as a cancer or a soft tissue sarcoma.

In another embodiment, the anti-PD-L1 antibody molecule, e.g., an anti-PD-L1 antibody molecule as described herein, alone or in combination with one or more other immunomodulators, is used in combination with a CSF-1R tyrosine kinase inhibitor, 4-((2-(((1R,2R)-2-hydroxycyclohexyl)amino)benzo[d]thiazol-6-yl)oxy)-N-methylpicolinamide (Compound A15), or a compound disclosed in PCT Publication No. WO 2005/073224 to treat a disorder, e.g., a disorder described herein. In one embodiment, the CSF-1R tyrosine kinase inhibitor is 4-((2-(((1R,2R)-2-hydroxycyclohexyl)amino)benzo[d]thiazol-6-yl)oxy)-N-methylpicolinamide (Compound A15) or a compound disclosed in PCT Publication No. WO 2005/073224. In one embodiment, a PD-L1 antibody molecule is used in combination with 4-((2-(((1R,2R)-2-hydroxycyclohexyl)amino)benzo[d]thiazol-6-yl)oxy)-N-methylpicolinamide (Compound A15) or a compound disclosed in PCT Publication No. WO 2005/073224, to treat a disorder such as cancer.

In another embodiment, the anti-PD-L1 antibody molecule, e.g., an anti-PD-L1 antibody molecule as described herein, alone or in combination with one or more other immunomodulators, is used in combination with an apoptosis inducer and/or an angiogenesis inhibitor, such as Imatinib mesylate (also known as GLEEVEC; Compound A16) or a compound disclosed in PCT Publication No. WO1999/003854 to treat a disorder, e.g., a disorder described. In one embodiment, the apoptosis inducer and/or an angiogenesis inhibitor is Imatinib mesylate (Compound A16) or a compound disclosed in PCT Publication No. WO1999/003854. In one embodiment, a PD-L1 antibody molecule is used in combination with Imatinib mesylate (Compound A16), or a compound disclosed in PCT Publication No. WO1999/003854, to treat a disorder such as a cancer, a multiple myeloma, a prostate cancer, a non-small cell lung cancer, a lymphoma, a gastric cancer, a melanoma, a breast cancer, a pancreatic cancer, a digestive/gastrointestinal cancer, a colorectal cancer, a glioblastoma multiforme, a liver cancer, a head and neck cancer, asthma, multiple sclerosis, allergy, Alzheimer's dementia, amyotrophic lateral sclerosis, or rheumatoid arthritis.

In certain embodiments, Imatinib mesylate (Compound A16) is administered at a dose of about 100 to 1000 mg, e.g., about 200 mg to 800 mg, about 300 mg to 700 mg, or about 400 mg to 600 mg, e.g., about 200 mg, 300 mg, 400 mg, 500 mg, 600 mg, or 700 mg. The dosing schedule can vary from e.g., every other day to daily, twice or three times a day. In one embodiment, Imatinib mesylate is administered at an oral dose from about 100 mg to 600 mg daily, e.g., about 100 mg, 200 mg, 260 mg, 300 mg, 400 mg, or 600 mg daily.

In another embodiment, the anti-PD-L1 antibody molecule, e.g., an anti-PD-L1 antibody molecule as described herein, alone or in combination with one or more other immunomodulators, is used in combination with a JAK inhibitor, 2-fluoro-N-methyl-4-(7-(quinolin-6-ylmethyl)imidazo[1,2-b][1,2,4]triazin-2-yl)benzamide (Compound A17), or a dihydrochloric salt thereof, or a compound disclosed in PCT Publication No. WO 2007/070514, to treat a disorder, e.g., a disorder described herein. In one embodiment, the JAK inhibitor is 2-fluoro-N-methyl-4-(7-(quinolin-6-ylmethyl)imidazo[1,2-b][1,2,4]triazin-2-yl)benzamide (Compound A17), or a dihydrochloric salt thereof, or a compound disclosed in PCT Publication No. WO 2007/070514. In one embodiment, a PD-L1 antibody molecule is used in combination with 2-fluoro-N-methyl-4-(7-(quinolin-6-ylmethyl)imidazo[1,2-b][1,2,4]triazin-2-yl)benzamide (Compound A17), or a dihydrochloric salt thereof, or a compound disclosed in PCT Publication No. WO 2007/070514, to treat a disorder such as a solid tumor, e.g., a lung cancer (e.g., non-small cell lung cancer (NSCLC)), glioblastoma multiforme (GBM), a renal cancer, a liver cancer, a gastric cancer, colorectal cancer, myeloid leukemia, hematological cancer, autoimmune disease, non-Hodgkin lymphoma, or thrombocythemia. In some embodiments, the cancer has, or is identified as having, a c-MET mutation (e.g., a c-MET mutation or a c-MET amplification), In certain embodiments, Compound A17 is administered at an oral dose of about 100 to 1000 mg, e.g., about 200 mg to 900 mg, about 300 mg to 800 mg, or about 400 mg to 700 mg, e.g., about 400 mg, 500 mg or 600 mg. The dosing schedule can vary from e.g., every other day to daily, twice or three times a day. In one embodiment, Compound A17 is administered at an oral dose from about 400 to 600 mg twice a day.

In one embodiment, the JAK inhibitor or a 2-fluoro-N-methyl-4-(7-(quinolin-6-ylmethyl)imidazo[1,2-b][1,2,4]triazin-2-yl)benzamide (Compound A17), or a dihydrochloric salt thereof is administered at a dose of about 400-600 mg (e.g., per day), e.g., about 400, 500, or 600 mg, or about 400-500 or 500-600 mg.

In another embodiment, the anti-PD-L1 antibody molecule, e.g., an anti-PD-L1 antibody molecule as described herein, alone or in combination with one or more other immunomodulators, is used in combination with a JAK inhibitor, Ruxolitinib Phosphate (also known as JAKAFI; Compound A18) or a compound disclosed in PCT Publication No. WO 2007/070514 to treat a disorder, e.g., a disorder described herein. In one embodiment, the JAK inhibitor is Ruxolitinib Phosphate (Compound A18) or a compound disclosed in PCT Publication No. WO 2007/070514. In one embodiment, a PD-L1 antibody molecule is used in combination with Ruxolitinib Phosphate (Compound A18), or a compound disclosed in PCT Publication No. WO 2007/070514, to treat a disorder such as a prostate cancer, a lymphocytic leukemia, a multiple myeloma, a lymphoma (e.g., non-Hodgkin's lymphoma), a lung cancer, a leukemia (e.g., myeloid leukemia, lymphocytic leukemia), cachexia, a breast cancer, a pancreatic cancer, rheumatoid arthritis, psoriasis, a colorectal cancer, a myeloid leukemia, a hematological cancer, an autoimmune disease, a non-Hodgkin lymphoma, or thrombocythemia. In some embodiments, the cancer has, or is identified as having, a JAK mutation. In some embodiments, the JAK mutation is a JAK2 V617F mutation.

In one embodiment, the JAK inhibitor or Ruxolitinib Phosphate (Compound A18) is administered at a dose of about 15-25 mg, e.g., twice daily. In some embodiments, the dose is about 15, 20, or 25 mg, or about 15-20 or 20-25 mg.

In another embodiment, the anti-PD-L1 antibody molecule, e.g., an anti-PD-L1 antibody molecule as described herein, alone or in combination with one or more other immunomodulators, is used in combination with a deacetylase (DAC) inhibitor, Panobinostat (Compound A19), or a compound disclosed in PCT Publication No. WO 2014/072493 to treat a disorder, e.g., a disorder described herein. In one embodiment, the DAC inhibitor is Panobinostat (Compound A19) or a compound disclosed in PCT Publication No. WO 2014/072493. In one embodiment, a PD-L1 antibody molecule is used in combination with Panobinostat (Compound A19), a compound disclosed in PCT Publication No. WO 2014/072493, to treat a disorder such as a small cell lung cancer, a respiratory/thoracic cancer, a prostate cancer, a multiple myeloma, myelodysplastic syndrome, a bone cancer, a non-small cell lung cancer, an endocrine cancer, a lymphoma, a neurologic cancer, a leukemia, HIV/AIDS, an immune disorder, transplant rejection, a gastric cancer, a melanoma, a breast cancer, a pancreatic cancer, a colorectal cancer, a renal cancer, a glioblastoma multiforme, a myeloid leukemia, a hematological cancer, a renal cancer, a non-Hodgkin lymphoma, a head and neck cancer, multiple myeloma, myelodysplastic syndrome, lymphoma (e.g., non-Hodgkin lymphoma), or leukemia (e.g., myeloid leukemia), a hematopoiesis disorders, or a liver cancer.

In one embodiment, the DAC inhibitor or Panobinostat (Compound A19) is administered at a dose of about 20 mg (e.g., per day).

In another embodiment, the anti-PD-L1 antibody molecule, e.g., an anti-PD-L1 antibody molecule as described herein, alone or in combination with one or more other immunomodulators, is used in combination with an inhibitor of one or more of cytochrome P450 (e.g., 11B2), aldosterone or angiogenesis, Osilodrostat (Compound A20), or a compound disclosed in PCT Publication No. WO2007/024945 to treat a disorder, e.g., a disorder described herein. In one embodiment, the inhibitor of one or more of cytochrome P450 (e.g., 11B2), aldosterone or angiogenesis is Osilodrostat (Compound A20) or a compound disclosed in PCT Publication No. WO2007/024945. In one embodiment, a PD-L1 antibody molecule is used in combination with Osilodrostat (Compound A20), or a compound disclosed in PCT Publication No. WO2007/024945, to treat a disorder such as Cushing's syndrome, hypertension, or heart failure therapy.

In another embodiment, the anti-PD-L1 antibody molecule, e.g., an anti-PD-L1 antibody molecule as described herein, alone or in combination with one or more other immunomodulators, is used in combination with a IAP inhibitor, (S)-N-((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21) or a compound disclosed in U.S. Pat. No. 8,552,003 to treat a disorder, e.g., a disorder described herein. In one embodiment, the IAP inhibitor is (S)-N-((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21) or a compound disclosed in U.S. Pat. No. 8,552,003. In one embodiment, a PD-L1 antibody molecule is used in combination with (S)-N-((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21), or a compound disclosed in U.S. Pat. No. 8,552,003, to treat a disorder such as a multiple myeloma, a breast cancer, an ovarian cancer, a pancreatic cancer, or a hematopoiesis disorder.

In one embodiment, the IAP inhibitor or (S)-N-((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21) or a compound disclosed in U.S. Pat. No. 8,552,003 is administered at a dose of approximately 1800 mg, e.g., once weekly. In an embodiment, Compound A21 is administered at a dose (e.g., oral dose) of about 10-3000 mg, e.g., about 20-2400 mg, about 50-1800 mg, about 100-1500 mg, about 200-1200 mg, about 300-900 mg, e.g., about 600 mg, about 900 mg, about 1200 mg, about 1500 mg, about 1800 mg, about 2100 mg, or about 2400 mg. In an embodiment, Compound A21 is administered once a week or once every two weeks.

In one embodiment, in a combination therapy, Compound A21 is administered orally. In one embodiment, the anti-PD-L1 antibody molecule, e.g., an anti-PD-L1 antibody molecule as described herein is administered, e.g., intravenously, at least one, two, three, four, five, six, or seven days, e.g., three days, after Compound A21 is administered, e.g., orally. In one embodiment, the anti-PD-L1 antibody molecule, e.g., an anti-PD-L1 antibody molecule as described herein, is administered, e.g., intravenously, at least one, two, three, four, five, six, or seven days, e.g., three days, before Compound A21 is administered, e.g., orally. In yet another embodiment, the anti-PD-L1 antibody molecule, e.g., an anti-PD-L1 antibody molecule as described herein, is administered, e.g., intravenously, on the same day, as Compound A21 is administered, e.g., orally.

In another embodiment, the anti-PD-L1 antibody molecule, e.g., an anti-PD-L1 antibody molecule as described herein, alone or in combination with one or more other immunomodulators, is used in combination a Smoothened (SMO) inhibitor, Sonidegib phosphate (Compound A22), (R)-2-(5-(4-(6-benzyl-4,5-dimethylpyridazin-3-yl)-2-methylpiperazin-1-yl)pyrazin-2-yl)propan-2-ol (Compound A25), or a compound disclosed in PCT Publication No. WO 2007/131201 or WO 2010/007120 to treat a disorder, e.g., a disorder described herein. In one embodiment, the SMO inhibitor is Sonidegib phosphate (Compound A22), (R)-2-(5-(4-(6-benzyl-4,5-dimethylpyridazin-3-yl)-2-methylpiperazin-1-yl)pyrazin-2-yl)propan-2-ol (Compound A25), or a compound disclosed in PCT Publication No. WO 2007/131201 or WO 2010/007120. In one embodiment, a PD-L1 antibody molecule is used in combination with Sonidegib phosphate (Compound A22), (R)-2-(5-(4-(6-benzyl-4,5-dimethylpyridazin-3-yl)-2-methylpiperazin-1-yl)pyrazin-2-yl)propan-2-ol (Compound A25), or a compound disclosed in PCT Publication No. WO 2007/131201 or WO 2010/007120 to treat a disorder such as a cancer, a medulloblastoma, a small cell lung cancer, a prostate cancer, a basal cell carcinoma, a pancreatic cancer, or an inflammation.

In certain embodiments, Sonidegib phosphate (Compound A22) is administered at a dose of about 20 to 500 mg, e.g., about 40 mg to 400 mg, about 50 mg to 300 mg, or about 100 mg to 200 mg, e.g., about 50 mg, 100 mg, 150 mg, 200 mg, 250 mg, or 300 mg. The dosing schedule can vary from e.g., every other day to daily, twice or three times a day.

In another embodiment, the anti-PD-L1 antibody molecule, e.g., an anti-PD-L1 antibody molecule as described herein, alone or in combination with one or more other immunomodulators, is used in combination with an Alk inhibitor, ceritinib (also known as ZYKADIA; Compound A23) or a compound disclosed in PCT Publication No. WO 2007/131201 to treat a disorder, e.g., a disorder described herein. In one embodiment, the Alk inhibitor is ceritinib (Compound A23) or a compound disclosed in PCT Publication No. WO 2007/131201. In one embodiment, a PD-L1 antibody molecule is used in combination with ceritinib (Compound A23), or a compound disclosed in PCT Publication No. WO 2007/131201, to treat a disorder such as non-small cell lung cancer or solid tumors, e.g., a lung cancer (e.g., non-small cell lung cancer (NSCLC)), a lymphoma (e.g., an anaplastic large-cell lymphoma or non-Hodgkin lymphoma), an inflammatory myofibroblastic tumor (IMT), or a neuroblastoma. In some embodiments, the NSCLC is a stage IIIB or IV NSCLC, or a relapsed locally advanced or metastatic NSCLC. In some embodiments, the cancer (e.g., the lung cancer, lymphoma, inflammatory myofibroblastic tumor, or neuroblastoma) has, or is identified as having, an ALK rearrangement or translocation, e.g., an ALK fusion. In one embodiment, the ALK fusion is an EML4-ALK fusion, e.g., an EML4-ALK fusion described herein. In another embodiment, the ALK fusion is an ALK-ROS1 fusion. In certain embodiments, the cancer has progressed on, or is resistant or tolerant to, a ROS1 inhibitor, or an ALK inhibitor, e.g., an ALK inhibitor other than Compound A23. In some embodiments, the cancer has progressed on, or is resistant or tolerant to, crizotinib. In one embodiment, the subject is an ALK-naïve patient, e.g., a human patient. In another embodiment, the subject is a patient, e.g., a human patient, that has been pretreated with an ALK inhibitor. In another embodiment, the subject is a patient, e.g., a human patient, that has been pretreated with Compound A23.

In one embodiment, Compound A23 and the anti-PD-L1 antibody molecule, e.g., an anti-PD-L1 antibody molecule as described herein, are administered to an ALK-naïve patient. In another embodiment, Compound A23 and the anti-PD-L1 antibody molecule, e.g., an anti-PD-L1 antibody molecule as described herein, are administered to a patient that has been pretreated with an ALK inhibitor. In yet another embodiment, Compound A23 and the anti-PD-L1 antibody molecule, e.g., an anti-PD-L1 antibody molecule as described herein, are administered to a patient that has been pretreated with Compound A23.

In one embodiment, the Alk inhibitor or ceritinib (Compound A23) is administered at a dose of approximately 750 mg, e.g., once daily.

In certain embodiments, Compound A23 is administered at an oral dose of about 100 to 1000 mg, e.g., about 150 mg to 900 mg, about 200 mg to 800 mg, about 300 mg to 700 mg, or about 400 mg to 600 mg, e.g., about 150 mg, 300 mg, 450 mg, 600 mg or 750 mg. In one embodiment, Compound A23 is administered at an oral dose of about 750 mg or lower, e.g., about 600 mg or lower, e.g., about 450 mg or lower. In certain embodiments, Compound A23 is administered with food. In other embodiments, the dose is under fasting condition. The dosing schedule can vary from e.g., every other day to daily, twice or three times a day. In one embodiment, Compound A23 is administered daily. In one embodiment, Compound A23 is administered at an oral dose from about 150 mg to 750 mg daily, either with food or in a fasting condition. In one embodiment, Compound A23 is administered at an oral dose of about 750 mg daily, in a fasting condition. In one embodiment, Compound A23 is administered at an oral dose of about 750 mg daily, via capsule or tablet. In another embodiment, Compound A23 is administered at an oral dose of about 600 mg daily, via capsule or tablet. In one embodiment, Compound A23 is administered at an oral dose of about 450 mg daily, via capsule or tablet.

In one embodiment, Compound A23 is administered at a dose of about 450 mg and nivolumab is administered at a dose of about 3 mg/kg. In another embodiment, Compound A23 dose is 600 mg and the nivolumab dose is 3 mg/kg. In one embodiment, Compound A23 is administered with a low fat meal.

In another embodiment, the anti-PD-L1 antibody molecule, e.g., an anti-PD-L1 antibody molecule as described herein, alone or in combination with one or more other immunomodulators, is used in combination with a JAK and/or CDK4/6 inhibitor, 7-cyclopentyl-N,N-dimethyl-2-((5-(piperazin-1-yl)pyridin-2-yl)amino)-7H-pyrrolo[2,3-d]pyrimidine-6-carboxamide (Compound A24), or a compound disclosed in U.S. Pat. No. 8,415,355 or U.S. Pat. No. 8,685,980 to treat a disorder, e.g., a disorder described herein. In one embodiment, the JAK and/or CDK4/6 inhibitor is 7-cyclopentyl-N,N-dimethyl-2-((5-(piperazin-1-yl)pyridin-2-yl)amino)-7H-pyrrolo[2,3-d]pyrimidine-6-carboxamide (Compound A24) or a compound disclosed in U.S. Pat. No. 8,415,355 or U.S. Pat. No. 8,685,980. In one embodiment, a PD-L1 antibody molecule is used in combination with 7-cyclopentyl-N,N-dimethyl-2-((5-(piperazin-1-yl)pyridin-2-yl)amino)-7H-pyrrolo[2,3-d]pyrimidine-6-carboxamide (Compound A24), or a compound disclosed in U.S. Pat. No. 8,415,355 or U.S. Pat. No. 8,685,980, to treat a disorder such as a lymphoma, a neurologic cancer, a melanoma, a breast cancer, or a solid tumor e.g., a lung cancer (e.g., non-small cell lung cancer (NSCLC)).

In one embodiment, the JAK and/or CDK4/6 inhibitor or 7-cyclopentyl-N,N-dimethyl-2-((5-(piperazin-1-yl)pyridin-2-yl)amino)-7H-pyrrolo[2,3-d]pyrimidine-6-carboxamide (Compound A24) is administered at a dose of approximately 200-600 mg, e.g., per day. In one embodiment, the compound is administered at a dose of about 200, 300, 400, 500, or 600 mg, or about 200-300, 300-400, 400-500, or 500-600 mg.

In another embodiment, the antibody molecule, e.g., an anti-PD-L1 antibody molecule as described herein, alone or in combination with one or more other immunomodulators, is used in combination a prolactin receptor (PRLR) inhibitor, a human monoclonal antibody molecule (Compound A26) as disclosed in U.S. Pat. No. 7,867,493), to treat a disorder, e.g., a disorder described herein. In one embodiment, the PRLR inhibitor is a human monoclonal antibody (Compound A26) disclosed in U.S. Pat. No. 7,867,493. In one embodiment, a PD-L1 antibody molecule is used in combination with human monoclonal antibody molecule (Compound A26) described in U.S. Pat. No. 7,867,493 to treat a disorder such as, a cancer, a prostate cancer, or a breast cancer. Exemplary PRLR antibodies disclosed in U.S. Pat. No. 7,867,493 include chXHA.06.642, chXHA.06.275, he.06.642-1, he.06.642-2, he.06.275-1, he.06.275-2, he.06.275-3, he.06.275-4, XPA.06.128, XPA.06.129, XPA.06.130, XPA.06.131, XPA.06.141, XPA.06.147, XPA.06.148, XPA.06.158, XPA.06.159, XPA.06.163, XPA.06.167, XPA.06.171, XPA.06.178, XPA.06.181, XPA.06.192, XPA.06.202, XPA.06.203, XPA.06.206, XPA.06.207, XPA.06.210, XPA.06.212, XPA.06.217, XPA.06.219, XPA.06.229, XPA.06.233, XPA.06.235, XPA.06.239, XPA.06.145, XHA.06.567, XHA.06.642, XHA.06.983, XHA.06.275, XHA.06.189, or XHA.06.907.

In some embodiments, Compound A26 is an isolated antibody that binds the extracellular domain of PRLR and comprises (a) the Complementarily Determining Regions (CDRs) set forth at positions 24 through 38, positions 54 through 60, and positions 93 through 101 of the amino acid sequence of SEQ ID NO: 88, as disclosed in U.S. Pat. No. 7,867,493; and (b) the CDRs set forth at positions 31 through 35, positions 50 through 66, and 99 through 113 of SEQ ID NO: 90, as disclosed in U.S. Pat. No. 7,867,493.

In another embodiment, the anti-PD-L1 antibody molecule, e.g., an anti-PD-L1 antibody molecule as described herein, alone or in combination with one or more other immunomodulators, is used in combination with a PIM Kinase inhibitor, N-(4-((1R,3S,5S)-3-amino-5-methylcyclohexyl)pyridin-3-yl)-6-(2,6-difluorophenyl)-5-fluoropicolinamide (Compound A27) or a compound disclosed in PCT Publication No. WO 2010/026124 to treat a disorder, e.g., a disorder described herein. In one embodiment, the PIM Kinase inhibitor is N-(4-((1R,3S,5S)-3-amino-5-methylcyclohexyl)pyridin-3-yl)-6-(2,6-difluorophenyl)-5-fluoropicolinamide (Compound A27) or a compound disclosed in PCT Publication No. WO 2010/026124. In one embodiment, a PD-L1 antibody molecule is used in combination with N-(4-((1R,3S,55)-3-amino-5-methylcyclohexyl)pyridin-3-yl)-6-(2,6-difluorophenyl)-5-fluoropicolinamide (Compound A27), or a compound disclosed in PCT Publication No. WO 2010/026124, to treat a disorder such as a multiple myeloma, myelodysplastic syndrome, a myeloid leukemia, or a non-Hodgkin lymphoma.

In another embodiment, the anti-PD-L1 antibody molecule, e.g., an anti-PD-L1 antibody molecule as described herein, alone or in combination with one or more other immunomodulators, is used in combination a Wnt signaling inhibitor, 2-(2',3-dimethyl-[2,4'-bipyridin]-5-yl)-N-(5-(pyrazin-2-yl)pyridin-2-yl)acetamide (Compound A28) or a compound disclosed in PCT publication No. WO 2010/101849 to treat a disorder, e.g., a disorder described herein. In one embodiment, the Wnt signaling inhibitor is 2-(2',3-dimethyl-[2,4'-bipyridin]-5-yl)-N-(5-(pyrazin-2-yl)pyridin-2-yl)acetamide (Compound A28) or a compound disclosed in PCT publication No. WO 2010/101849. In one embodiment, the Wnt signaling inhibitor is 2-(2',3-dimethyl-[2,4'-bipyridin]-5-yl)-N-(5-(pyrazin-2-yl)pyridin-2-yl)acetamide (Compound A28). In one embodiment, a PD-L1 antibody molecule is used in combination with 2-(2',3-dimethyl-[2,4'-bipyridin]-5-yl)-N-(5-(pyrazin-2-yl)pyridin-2-yl)acetamide (Compound A28), or a compound disclosed in PCT publication No. WO 2010/101849, to treat a disorder such as a solid tumor (e.g., a head and neck cancer, a squamous cell carcinoma, a breast cancer, a pancreatic cancer, or a colon cancer).

In certain embodiments, 2-(2',3-dimethyl-[2,4'-bipyridin]-5-yl)-N-(5-(pyrazin-2-yl)pyridin-2-yl)acetamide (Compound A28) is administered at a dose of about 1 to 50 mg, e.g., about 2 mg to 45 mg, about 3 mg to 40 mg, about 5 mg to 35 mg, 5 mg to 10 mg, or about 10 mg to 30 mg, e.g., about 2 mg, 5 mg, 10 mg, 20 mg, 30 mg, or 40 mg. The dosing schedule can vary from e.g., every other day to daily, twice or three times a day.

In another embodiment, the anti-PD-L1 antibody molecule, e.g., an anti-PD-L1 antibody molecule as described herein, alone or in combination with one or more other immunomodulators, is used in combination with a BRAF inhibitor, Encorafenib (Compound A29), or a compound disclosed in PCT Publication No. WO 2011/025927 to treat a disorder, e.g., a disorder described herein. In one embodiment, the BRAF inhibitor is Encorafenib (Compound A29) or a compound disclosed in PCT Publication No. WO 2011/025927. In one embodiment, a PD-L1 antibody molecule is used in combination with Encorafenib (Compound A29), or a compound disclosed in PCT Publication No. WO 2011/025927, to treat a disorder such as a lung cancer (e.g., non-small cell lung cancer (NSCLC), a melanoma (e.g., advanced melanoma), a thyroid cancer (e.g, papillary thyroid cancer), or a colorectal cancer. In some embodiments, the cancer has, or is identified as having, a BRAF mutation (e.g., a BRAF V600E mutation), a BRAF wildtype, a KRAS wildtype or an activating KRAS mutation. The cancer may be at an early, intermediate or late stage.

In one embodiment, the BRAF inhibitor or Encorafenib (Compound A29) is administered at a dose of about 200-300, 200-400, or 300-400 mg, e.g., per day. In one embodiment, the compound is administered at a dose of about 200, about 300 or about 400 mg.

In another embodiment, the anti-PD-L1 antibody molecule, e.g., an anti-PD-L1 antibody molecule as described herein, alone or in combination with one or more other immunomodulators, is used in combination a CDK4/6 inhibitor, 7-cyclopentyl-N,N-dimethyl-2-((5-((1R,6S)-9-methyl-4-oxo-3,9-diazabicyclo[4.2.1]nonan-3-yl)pyridin-2-yl)amino)-7H-pyrrolo[2,3-d]pyrimidine-6-carboxamide (Compound A30), or a compound disclosed in PCT publication No. WO 2011/101409 to treat a disorder, e.g., a disorder described herein. In one embodiment, the CDK4/6 inhibitor is 7-cyclopentyl-N,N-dimethyl-2-((5-((1R,6S)-9-methyl-4-oxo-3,9-diazabicyclo[4.2.1]nonan-3-yl)pyridin-2-yl)amino)-7H-pyrrolo[2,3-d]pyrimidine-6-carboxamide (Compound A30) or a compound disclosed in PCT publication No. WO 2011/101409. In one embodiment, a PD-L1 antibody molecule is used in combination with 7-cyclopentyl-N,N-dimethyl-2-((5-((1R,6S)-9-methyl-4-oxo-3,9-diazabicyclo[4.2.1]nonan-3-yl)pyridin-2-yl)amino)-7H-pyrrolo[2,3-d]pyrimidine-6-carboxamide (Compound A30), or a compound disclosed in PCT publication No. WO 2011/101409, to treat a disorder such as a cancer, a mantle cell lymphoma, a liposarcoma, a non-small cell lung cancer, a melanoma, a squamous cell esophageal cancer, or a breast cancer.

In another embodiment, the anti-PD-L1 antibody molecule, e.g., an anti-PD-L1 antibody molecule as described herein, alone or in combination with one or more other immunomodulators, is used in combination with a HER3 inhibitor, Compound A31, or a compound disclosed in PCT Publication No. WO 2012/022814, to treat a disorder, e.g., a disorder described herein. In one embodiment, the HER3 inhibitor is Compound A31 or a compound disclosed in PCT Publication WO 2012/022814. In one embodiment, a PD-L1 antibody molecule is used in combination with Compound A31, or a compound disclosed in PCT Publication WO 2012/022814, to treat a disorder such as a gastric cancer, an esophageal cancer, a head and neck cancer, a squamous cell carcinoma, a stomach cancer, a breast cancer (e.g., metastatic breast cancer), or a digestive/gastrointestinal cancer.

In some embodiments, Compound A31 is a human monoclonal antibody molecule. In some embodiments, Compound A31 is an anti-HER3 monoclonal antibody or antigen binding fragment thereof, that comprises 1, 2, 3, 4, 5 or 6 CDRs according to Kabat or Chothia, a VH and/or VL, of any of the antibodies in Table 1 of U.S. Pat. No. 8,735,551. In one embodiment, the anti-HER3 monoclonal antibody or antigen binding fragment thereof comprises the VH of SEQ ID NO: 141 and VL of SEQ ID NO: 140, as described in U.S. Pat. No. 8,735,551.

In one embodiment, the HER3 inhibitor or Compound A31 is administered at a dose of about 3, 10, 20, or 40 mg/kg, e.g., once weekly (QW). In one embodiment, the compound is administered at a dose of about 3-10, 10-20, or 20-40 mg/kg.

In another embodiment, the anti-PD-L1 antibody molecule, e.g., an anti-PD-L1 antibody molecule as described herein, alone or in combination with one or more other immunomodulators, is used in combination an FGFR2 and/or FGFR4 inhibitor, Compound A32, or a compound disclosed in a publication PCT Publication No. WO 2014/160160 (e.g., an antibody molecule drug conjugate against an FGFR2 and/or FGFR4, e.g., mAb 12425), to treat a disorder, e.g., a disorder described herein. In one embodiment, the FGFR2 and/or FGFR4 inhibitor is Compound A32 or a compound disclosed in a publication PCT Publication No. WO 2014/160160. In one embodiment, a PD-L1 antibody molecule is used in combination with Compound A32, or a compound as described in Table 6, to treat a disorder such as a cancer, a gastric cancer, a breast cancer, a rhabdomyosarcoma, a liver cancer, an adrenal cancer, a lung cancer, an esophageal cancer, a colon cancer, or an endometrial cancer.

In some embodiments, Compound A32 is an antibody molecule drug conjugate against an FGFR2 and/or FGFR4, e.g., mAb 12425. In some embodiments, Compound A32 is an antibody molecule drug conjugate against an FGFR2 and/or FGFR4 that comprises 1, 2, 3, 4, 5, or 6 CDRs according to Kabat or Chothia, a VH and/or VL, of any of the antibodies in Table 1 of WO 2014/160160. In some embodiments, Compound A32 is an antibody molecule drug conjugate against an FGFR2 and/or FGFR4 that comprises a linker of N-succinimidyl-4-(maleimidomethyl)cyclohexanecarboxylate (SMCC) and a payload of $^{N2'}$-deacetyl-$N^{2'}$-(3-mercapto-1-oxopropyl)-maytansine (DM1). In some embodiments, Compound A32 is an antibody molecule drug conjugate having the following formula:

wherein Ab is an antibody or antigen binding fragment thereof comprising a heavy chain CDR1 of SEQ ID NO: 1, 21, 41, 61, 81, or 101, a heavy chain CDR2 of SEQ ID NO: 2, 22, 42, 62, 82, or 102, a heavy chain CDR3 of SEQ ID NO: 3, 23, 43, 63, 83, or 103 and a light chain CDR1 of SEQ ID NO: 11, 31, 51, 71, 91, or 111 a light chain CDR2 of SEQ ID NO: 12, 32, 52, 72, 92, or 112 a light chain CDR3 of SEQ ID NO: 13, 33, 53, 73, 93, or 113 wherein the CDR is defined in accordance with the Kabat definition; and n is 1 to 10, e.g., as disclosed in claim 29 of WO 2014/160160.

In another embodiment, the anti-PD-L1 antibody molecule, e.g., an anti-PD-L1 antibody molecule as described herein, alone or in combination with one or more other immunomodulators, is used in combination an M-CSF inhibitor, Compound A33, or a compound disclosed in PCT Publication No. WO 2004/045532 (e.g., an antibody molecule or Fab fragment against M-CSF), to treat a disorder, e.g., a disorder described herein. In one embodiment, the M-CSF inhibitor is Compound A33 or a compound disclosed in PCT Publication No. WO 2004/045532. In one embodiment, a PD-L1 antibody molecule is used in combination with Compound A33, or a compound as described in PCT Publication No. WO 2004/045532, to treat a disorder such as a cancer, a prostate cancer, a breast cancer, or pigmented villonodular synovitis (PVNS).

In some embodiments, Compound A33 is a monoclonal antibody molecule against M-CSF or a fragment (e.g., Fab fragment) thereof. In some embodiments, Compound A33 is a monoclonal antibody or Fab fragment that binds to the same epitope as monoclonal antibody 5H4 (ATCC Accession No. HB10027), e.g., as described in WO 2004/045532. In other embodiments, Compound A33 is a monoclonal antibody or Fab fragment thereof that competes with monoclonal antibody 5H4 (ATCC Accession No. HB10027) for binding to M-CSF, e.g., as described in WO 2004/045532. In some embodiments, Compound A33 is a monoclonal antibody or Fab fragment that comprises 1, 2, 3, 4, 5 or 6 CDRs of monoclonal antibody 5H4 (ATCC Accession No. HB10027), e.g., as described in WO 2004/045532. In embodiments, the M-CSF inhibitor or Compound A33 is administered at an average dose of about 10 mg/kg.

In another embodiment, the anti-PD-L1 antibody molecule, e.g., an anti-PD-L1 antibody molecule as described herein, alone or in combination with one or more other immunomodulators, is used in combination with a MEK inhibitor, Binimetinib (Compound A34), or a compound disclosed in PCT Publication No. WO 2003/077914 to treat

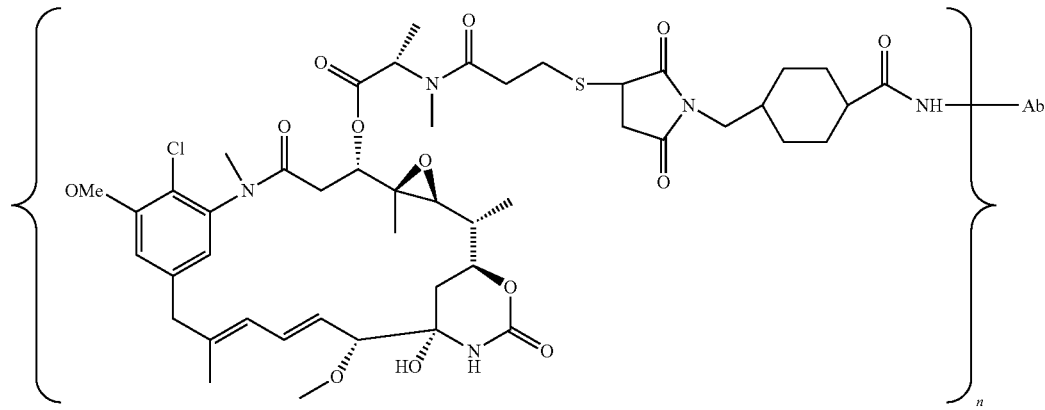

a disorder, e.g., a disorder described herein. In one embodiment, the MEK inhibitor is Binimetinib (Compound A34), or a compound disclosed in PCT Publication No. WO 2003/077914. In one embodiment, a PD-L1 antibody molecule is used in combination with Binimetinib (Compound A34), or a compound disclosed in PCT Publication No. WO 2003/077914, to treat a disorder such as a non-small cell lung cancer, a multisystem genetic disorder, a melanoma, an ovarian cancer, a breast cancer, a prostate cancer, a pancreatic cancer, a hematological malignancy or a renal cell carcinoma, a multisystem genetic disorder, a gastric cancer, a colorectal cancer, a digestive/gastrointestinal cancer, a rheumatoid arthritis, or a colorectal cancer. In some embodiments, the cancer has, or is identified as having, a KRAS mutation.

In one embodiment, the MEK inhibitor or Binimetinib (Compound A34) is administered at a dose of about 45 mg, e.g., twice daily.

In another embodiment, the anti-PD-L1 antibody molecule, e.g., an anti-PD-L1 antibody molecule as described herein, alone or in combination with one or more other immunomodulators, is used in combination an inhibitor of one or more of c-KIT, histamine release, Flt3 (e.g., FLK2/STK1) or PKC, Midostaurin (Compound A35) or a compound disclosed in PCT Publication No. WO 2003/037347 to treat a disorder, e.g., a disorder described herein. In one embodiment, the inhibitor is Midostaurin (Compound A35) or compound disclosed in PCT Publication No. WO 2003/037347. In one embodiment, the inhibitor of one or more of c-KIT, histamine release, Flt3 (e.g., FLK2/STK1) or PKC is Midostaurin. In one embodiment, a PD-L1 antibody molecule is used in combination with Midostaurin (Compound A35), or compound disclosed in PCT Publication No. WO 2003/037347, to treat a disorder such as a cancer, a colorectal cancer, a myeloid leukemia, myelodysplastic syndrome, an age-related mascular degeration, a diabetic complication, or a dermatologic disorder.

In another embodiment, the anti-PD-L1 antibody molecule, e.g., an anti-PD-L1 antibody molecule as described herein, alone or in combination with one or more other immunomodulators, is used in combination with a TOR inhibitor (e.g., mTOR inhibitor), Everolimus (also known as AFINITOR; Compound A36) or a Compound disclosed in PCT Publication No. WO 2014/085318 to treat a disorder, e.g., a disorder described herein). In one embodiment, the TOR inhibitor is Everolimus (Compound A36) or a Compound disclosed in PCT Publication No. WO 2014/085318. In one embodiment, a PD-L1 antibody molecule is used in combination with Everolimus (Compound A36) to treat a disorder such as an interstitial lung disease, a small cell lung cancer, a respiratory/thoracic cancer, a prostate cancer, a multiple myeloma, a sarcoma, an age-related macular degeneration, a bone cancer, tuberous sclerosis, a lung cancer (e.g., a non-small cell lung cancer (e.g., a NSCLC with squamous and/or non-squamous histology)), a melanoma (e.g., an advanced melanoma), a digestive/gastrointestinal cancer, a gastric cancer, a prostate cancer, a hematological malignancy, e.g., a lymphoma or leukemia, an endocrine cancer, a lymphoma, a neurologic disorders, an astrocytoma, a cervical cancer, a neurologic cancer, a leukemia, an immune disorders, transplant rejection, a gastric cancer, a melanoma, epilepsy, a breast cancer, or a bladder cancer.

In one embodiment, the TOR inhibitor or Everolimusis (Compound A36) administered at a dose of about 2.5-20 mg/day. In one embodiment, the compound is administered at a dose of about 2.5, 5, 10, or 20 mg/day, e.g., about 2.5-5, 5-10, or 10-20 mg/day.

In another embodiment, the anti-PD-L1 antibody molecule, e.g., an anti-PD-L1 antibody molecule as described herein, alone or in combination with one or more other immunomodulators, is used in combination an inhibitor of one or more of VEGFR-2, PDGFRbeta, KIT or Raf kinase C, 1-methyl-5-((2-(5-(trifluoromethyl)-1H-imidazol-2-yl)pyridin-4-yl)oxy)-N-(4-(trifluoromethyl)phenyl)-1H-benzo[d]imidazol-2-amine (Compound A37) or a compound disclosed in PCT Publication No. WO 2007/030377 to treat a disorder, e.g., a disorder described herein. In one embodiment, the inhibitor of one or more of VEGFR-2, PDGFRbeta, KIT or Raf kinase C is 1-methyl-5-((2-(5-(trifluoromethyl)-1H-imidazol-2-yl)pyridin-4-yl)oxy)-N-(4-(trifluoromethyl)phenyl)-1H-benzo[d]imidazol-2-amine (Compound A37) or a compound disclosed in PCT Publication No. WO 2007/030377. In one embodiment, a PD-L1 antibody molecule is used in combination with 1-methyl-5-((2-(5-(trifluoromethyl)-1H-imidazol-2-yl)pyridin-4-yl)oxy)-N-(4-(trifluoromethyl)phenyl)-1H-benzo[d]imidazol-2-amine (Compound A37), or a compound disclosed in PCT Publication No. WO 2007/030377, to treat a disorder such as a cancer, a melanoma, or a solid tumor.

In another embodiment, the anti-PD-L1 antibody molecule, e.g., an anti-PD-L1 antibody molecule as described herein, alone or in combination with one or more other immunomodulators, is used in combination a somatostatin agonist and/or growth hormone release inhibitor, Pasireotide diaspartate (also known as SIGNIFOR; Compound A38) or a compound disclosed in PCT Publication No. WO2002/010192 or U.S. Pat. No. 7,473,761 to treat a disorder, e.g., a disorder described herein. In one embodiment, the somatostatin agonist and/or growth hormone release inhibitor is Pasireotide diaspartate (Compound A38) or a compound disclosed in PCT Publication No. WO2002/010192 or U.S. Pat. No. 7,473,761. In one embodiment, a PD-L1 antibody molecule is used in combination with Pasireotide diaspartate (Compound A38), or a compound disclosed in PCT Publication No. WO2002/010192 or U.S. Pat. No. 7,473,761, to treat a disorder such as a prostate cancer, an endocrine cancer, a nurologic cancer, a skin cancer (e.g., a melanoma), a pancreatic cancer, a liver cancer, Cushing's syndrome, a gastrointestinal disorder, acromegaly, a liver and biliary tract disorder, or liver cirrhosis.

In another embodiment, the anti-PD-L1 antibody molecule, e.g., an anti-PD-L1 antibody molecule as described herein, alone or in combination with one or more other immunomodulators, is used in combination a signal transduction modulator and/or angiogenesis inhibitor, Dovitinib (Compound A39) or a compound disclosed in PCT Publication No. WO 2009/115562 to treat a disorder, e.g., a disorder described herein. In one embodiment, the signal transduction modulator and/or angiogenesis inhibitor is Dovitinib (Compound A39) or a compound disclosed in PCT Publication No. WO 2009/115562. In one embodiment, a PD-L1 antibody molecule is used in combination with Dovitinib (Compound A39), or a compound disclosed in PCT Publication No. WO 2009/115562, to treat a disorder such as a cancer, a respiratory/thoracic cancer, a multiple myeloma, a prostate cancer, a non-small cell lung cancer, an endocrine cancer, or a neurological genetic disorder.

In another embodiment, the anti-PD-L1 antibody molecule, e.g., an anti-PD-L1 antibody molecule as described herein, alone or in combination with one or more other immunomodulators, is used in combination with an EGFR inhibitor, (R,E)-N-(7-chloro-1-(1-(4-(dimethylamino)but-2-enoyl)azepan-3-yl)-1H-benzo[d]imidazol-2-yl)-2-methylisonicotinamide (Compound A40) or a compound disclosed in PCT Publication No. WO 2013/184757 to treat a disorder, e.g., a disorder described herein. In one embodiment, the EGFR inhibitor is (R,E)-N-(7-chloro-1-(1-(4-(dimethylamino)but-2-enoyl)azepan-3-yl)-1H-benzo[d]imidazol-2-yl)-2-methylisonicotinamide (Compound A40) or a compound disclosed in PCT Publication No. WO 2013/184757. In one embodiment, a PD-L1 antibody molecule is used in combination with (R,E)-N-(7-chloro-1-(1-(4-(dimethylamino)but-2-enoyl)azepan-3-yl)-1H-benzo[d]imidazol-2-yl)-2-methylisonicotinamide (Compound A40), or a compound disclosed in PCT Publication No. WO 2013/184757, to treat a disorder such as a cancer, e.g., a solid tumor. e.g., a lung cancer (e.g., non-small cell lung cancer (NSCLC)).

In one embodiment, the EGFR inhibitor or (R,E)-N-(7-chloro-1-(1-(4-(dimethylamino)but-2-enoyl)azepan-3-yl)-1H-benzo[d]imidazol-2-yl)-2-methylisonicotinamide (Compound A40) is administered at a dose of 150-250 mg, e.g., per day. In one embodiment, the compound is administered at a dose of about 150, 200, or 250 mg, or about 150-200 or 200-250 mg. In certain embodiments, Compound A40 is administered at an oral dose of about 50 to 500 mg, e.g., about 100 mg to 400 mg, about 150 mg to 350 mg, or about 200 mg to 300 mg, e.g., about 100 mg, 150 mg or 200 mg. The dosing schedule can vary from e.g., every other day to daily, twice or three times a day. In one embodiment, Compound A40 is administered at an oral dose from about 100 to 200 mg, e.g., about 150 mg, once a day.

In another embodiment, the anti-PD-L1 antibody molecule, e.g., an anti-PD-L1 antibody molecule as described herein, alone or in combination with one or more other immunomodulators, is used in combination an ALK inhibitor, $N^6$-(2-isopropoxy-5-methyl-4-(1-methylpiperidin-4-yl)phenyl)-$N^4$-(2-(isopropylsulfonyl)phenyl)-1H-pyrazolo[3,4-d]pyrimidine-4,6-diamine (Compound A42) or a compound disclosed in PCT Publication No. WO 2008/073687 to treat a disorder, e.g., a disorder described herein. In one embodiment, the ALK inhibitor is $N^6$-(2-isopropoxy-5-methyl-4-(1-methylpiperidin-4-yl)phenyl)-$N^4$-(2-(isopropylsulfonyl)phenyl)-1H-pyrazolo[3,4-d]pyrimidine-4,6-diamine (Compound A42) or a compound disclosed in PCT Publication No. WO 2008/073687. In one embodiment, a PD-L1 antibody molecule is used in combination with $N^6$-(2-isopropoxy-5-methyl-4-(1-methylpiperidin-4-yl)phenyl)-$N^4$-(2-(isopropylsulfonyl)phenyl)-1H-pyrazolo[3,4-d]pyrimidine-4,6-diamine (Compound A42), or a compound disclosed in PCT Publication No. WO 2008/073687, to treat a disorder such as a cancer, an anaplastic large-cell lymphoma (ALCL), a non-small cell lung carcinoma (NSCLC), or a neuroblastoma.

In another embodiment, the anti-PD-L1 antibody molecule, e.g., an anti-PD-L1 antibody molecule as described herein, alone or in combination with one or more other immunomodulators, is used in combination an IGF-1R inhibitor, 3-(4-(4-((5-chloro-4-((5-methyl-1H-pyrazol-3-yl)amino)pyrimidin-2-yl)amino)-5-fluoro-2-methylphenyl)piperidin-1-yl)thietane 1,1-dioxide (Compound A43), 5-chloro-$N^2$-(2-fluoro-5-methyl-4-(1-(tetrahydro-2H-pyran-4-yl)piperidin-4-yl)phenyl)-$N^4$-(5-methyl-1H-pyrazol-3-yl)pyrimidine-2,4-diamine (Compound A44), or 5-chloro-N2-(4-(1-ethylpiperidin-4-yl)-2-fluoro-5-methylphenyl)-$N^4$-(5-methyl-1H-pyrazol-3-yl)pyrimidine-2,4-diamine (Compound A45) or a compound disclosed in PCT Publication No. WO 2010/002655 to treat a disorder, e.g., a disorder described. In one embodiment, the IGF-1R inhibitor is 3-(4-(4-((5-chloro-4-((5-methyl-1H-pyrazol-3-yl)amino)pyrimidin-2-yl)amino)-5-fluoro-2-methylphenyl)piperidin-1-yl)thietane 1,1-dioxide (Compound A43), 5-chloro-$N^2$-(2-fluoro-5-methyl-4-(1-(tetrahydro-2H-pyran-4-yl)piperidin-4-yl)phenyl)-$N^4$-(5-methyl-1H-pyrazol-3-yl)pyrimidine-2,4-diamine (Compound A44), 5-chloro-N2-(4-(1-ethylpiperidin-4-yl)-2-fluoro-5-methylphenyl)-$N^4$-(5-methyl-1H-pyrazol-3-yl)pyrimidine-2,4-diamine (Compound A45), or a compound disclosed in PCT Publication No. WO 2010/002655. In one embodiment, a PD-L1 antibody molecule is used in combination with 3-(4-(4-((5-chloro-4-((5-methyl-1H-pyrazol-3-yl)amino)pyrimidin-2-yl)amino)-5-fluoro-2-methylphenyl)piperidin-1-yl)thietane 1,1-dioxide (Compound A43), 5-chloro-$N^2$-(2-fluoro-5-methyl-4-(1-(tetrahydro-2H-pyran-4-yl)piperidin-4-yl)phenyl)-$N^4$-(5-methyl-1H-pyrazol-3-yl)pyrimidine-2,4-diamine (Compound A44), 5-chloro-N2-(4-(1-ethylpiperidin-4-yl)-2-fluoro-5-methylphenyl)-$N^4$-(5-methyl-1H-pyrazol-3-yl)pyrimidine-2,4-diamine (Compound A45), or a compound disclosed in PCT Publication No. WO 2010/002655, to treat a disorder such as a cancer or a sarcoma.

In another embodiment, the anti-PD-L1 antibody molecule, e.g., an anti-PD-L1 antibody molecule as described herein, alone or in combination with one or more other immunomodulators, is used in combination a P-Glycoprotein 1 inhibitor, Valspodar (also known as AMDRAY; Compound A46) or a compound disclosed in EP 296122 to treat a disorder, e.g., a disorder described herein. In one embodiment, the P-Glycoprotein 1 inhibitor is Valspodar (Compound A46) or a compound disclosed in EP 296122. In one embodiment, a PD-L1 antibody molecule is used in combination with Valspodar (Compound A46), or a compound disclosed in EP 296122, to treat a disorder such as a cancer or a drug-resistant tumor.

In another embodiment, the anti-PD-L1 antibody molecule, e.g., an anti-PD-L1 antibody molecule as described herein, alone or in combination with one or more other immunomodulators, is used in combination one or more of a VEGFR inhibitor, Vatalanib succinate (Compound A47) or a compound disclosed in EP 296122 to treat a disorder, e.g., a disorder described herein. In one embodiment, the VEGFR inhibitor is Vatalanib succinate (Compound A47) or a compound disclosed in EP 296122. In one embodiment, a PD-L1 antibody molecule is used in combination with Vatalanib succinate (Compound A47), or a compound disclosed in EP 296122, to treat cancer.

In another embodiment, the anti-PD-L1 antibody molecule, e.g., an anti-PD-L1 antibody molecule as described herein, alone or in combination with one or more other immunomodulators, is used in combination with an IDH inhibitor or a compound disclosed in WO2014/141104 to treat a disorder, e.g., a disorder described herein. In one embodiment, the IDH inhibitor is Compound A48 or a compound disclosed in PCT Publication No. WO2014/141104. In one embodiment, a PD-L1 antibody molecule is used in combination with Compound A48 or a compound disclosed in WO2014/141104 to treat a disorder such as a cancer.

In another embodiment, the anti-PD-L1 antibody molecule, e.g., an anti-PD-L1 antibody molecule as described herein, alone or in combination with one or more other immunomodulators, is used in combination with a BCL-ABL inhibitor, (R)-N-(4-(chlorodifluoromethoxy)phenyl)-6-(3-hydroxypyrrolidin-1-yl)-5-(1H-pyrazol-5-yl)nicotinamide (Compound A49) or a compound disclosed in PCT Publication No. WO2013/171639, WO2013/171640, WO2013/171641, or WO2013/171642 to treat a disorder, e.g., a disorder described herein. In one embodiment, the BCL-ABL inhibitor is Compound A49 or a compound disclosed in PCT Publication No. WO2013/171639, WO2013/171640, WO2013/171641, or WO2013/171642. In one embodiment, a PD-L1 antibody molecule is used in combination with (R)-N-(4-(chlorodifluoromethoxy)phenyl)-6-(3-hydroxypyrrolidin-1-yl)-5-(1H-pyrazol-5-yl)nicotinamide (Compound A49) or a compound disclosed in PCT Publication No. WO2013/171639, WO2013/171640, WO2013/171641, or WO2013/171642 to treat a disorder such as a cancer.

In another embodiment, the anti-PD-L1 antibody molecule, e.g., an anti-PD-L1 antibody molecule as described herein, alone or in combination with one or more other immunomodulators, is used in combination with a c-RAF inhibitor or a compound disclosed in PCT Publication No. WO2014/151616 to treat a disorder, e.g., a disorder described herein. In one embodiment, the c-RAF inhibitor is Compound A50 or a compound disclosed in PCT Publication No. WO2014/151616. In one embodiment, a PD-L1 antibody molecule is used in combination with Compound A50 or a compound disclosed in PCT Publication No. WO2014/151616 to treat a disorder such as a cancer.

In another embodiment, the anti-PD-L1 antibody molecule, e.g., an anti-PD-L1 antibody molecule as described herein, alone or in combination with one or more other immunomodulators, is used in combination with an ERK1/2 ATP competitive inhibitor or a compound disclosed in International Patent Application No. PCT/US2014/062913 to treat a disorder, e.g., a disorder described herein. In one embodiment, the ERK1/2 ATP competitive inhibitor is Compound A51 or a compound disclosed in International Patent Application No. PCT/US2014/062913 or PCT Publication No. WO2015/066188. In one embodiment, a PD-L1 antibody molecule is used in combination with Compound A51 or a compound disclosed in International Patent Application No. PCT/US2014/062913 or PCT Publication No. WO2015/066188 to treat a disorder such as a cancer.

In some embodiments, the PD-L1 antibody molecule is administered in combination with one or more agents selected from, Compound A8, Compound A17, Compound A23, Compound A24, Compound A27, Compound A29, and Compound A33.

In some embodiments, a PD-L1 antibody molecule is administered in combination with an anti-cancer agent having a known activity in an immune cell assay, e.g., in one or more of a huMLR assay, a T cell proliferation assay, and a B-cell proliferation assay. Exemplary assays are described below. Based on the assay, an IC50 for can be calculated for each test agent. In embodiments, the anti-cancer agent has an IC50 of, e.g., 0-1 µM, 1-4 µM, or greater than 4 µM, e.g., 4-10 µM or 4-20 µM. In embodiments, the second therapeutic agent is chosen from one or more of: Compound A9, Compound A16, Compound A17, Compound A21, Compound A22, Compound A25, Compound A28, Compound A48, and Compound 49.

In some embodiments, the Compound A28 (or a compound related to Compound A28) is administered at a dose of approximately 5-10 or 10-30 mg. In some embodiments, the Compound A22 (or compound related to Compound A22) is administered at a dose of about 200 mg. In some embodiments, the Compound A17 (or compound related to Compound A17) is administered at a dose of approximately 400-600 mg. In some embodiments, the Compound A16 (or compound related to Compound A16) is administered at a dose of approximately 400-600 mg PO qDay. In some embodiments, the Compound A29 (or compound related to Compound A29) is administered at a dose of approximately 200-400 or 300-400 mg. In some embodiments, the Compound A24 (or compound related to Compound A24) is administered at a dose of approximately 200-600 mg. In some embodiments, the Compound A23 (ceritinib) (or compound related to ceritinib) is administered at a dose of approximately 750 mg once daily. In some embodiments, the Compound A8 (or compound related to Compound A8) is administered at a dose of approximately 200-400 or 300-400 mg. In some embodiments, the Compound A5 (or compound related to Compound A5) is administered at a dose of approximately 100-125 mg. In some embodiments, the Compound A6 (or compound related to Compound A6) is administered at a dose of about 100 mg. In some embodiments, the Compound A1 (or compound related to Compound A1) is administered at a dose of approximately 200-300 or 200-600 mg. In some embodiments, the Compound A40 (or compound related to Compound A40) is administered at a dose of approximately 150-250 mg. In embodiments, the Compound A10 (or compound related to Compound A10) is administered at a dose of approximately 400 to 700 mg, e.g., administered three times weekly, 2 weeks on and one week off. In embodiments, the BCR-ABL inhibitor is administered at a dose of approximately 20 mg bid-80 mg bid.

Exemplary huMLR assay and B or T cell proliferation assays are provided below.

Human Mixed Lymphocyte Reaction

The Mixed Lymphocyte Reaction (MLR) is a functional assay which measures the proliferative response of lymphocytes from one individual (the responder) to lymphocytes from another individual (the stimulator). To perform an allogeneic MLR, peripheral blood mononuclear cells (PBMC) from three donors were isolated from buffy-coats of unknown HLA type (Kantonspital Blutspendezentrum from Bern and Aarau, Switzerland). The cells were prepared at 2.105 in 0.2 mL of culture medium containing RPMI 1640 GlutaMAX™ with 10% fetal calf serum (FCS), 100 U penicillin/100 µg streptomycin, 50 µM 2-Mercaptoethanol. Individual 2-way reactions were set up by mixing PBMC from two different donors at a 1:1 ratio and co-cultures were done in triplicates in flat-bottomed 96-well tissue culture plates for 6 days at 37° C., 5% CO2, in presence or not of an 8-point concentration range of test compounds. Cells were pulsed with 3H-TdR (1 µCi/0.2 mL) for the last 16 h of culture and incorporated radioactivity was used as a measure of cell proliferation. The concentration that inhibited 50% of the maximal huMLR response (IC50) was calculated for each compound. Cyclosporine was used as a positive control of huMLR inhibition.

Human B Cell Proliferation Assay

PBMC were freshly isolated by Ficoll-Paque density gradient from human blood and subjected to negative B-cell isolation. B cells were resuspended in culture medium (RPMI 1640, HEPES, 10% FCS, 50 µg/mL gentamicine, 50 µM 2-Mercaptoethanol, 1×ITS (Insulin, Transferrin and Sodium Selenite), 1× Non-Essential Amino-Acids) at a concentration of 9.104 per well in a flat-bottom 96-well culture plate. B cell stimulation was performed by human anti-IgM antibody molecule (30 ug/mL) and IL-4 (75 ng/mL) or by CD40 ligand (3 ug/mL) and IL-4 (75 ng/mL) in presence or not of a 7-point concentration range of test compounds. After 72 h of culture at 37° C., 10% CO2, cells were pulsed with 3H-TdR (1 µCi/well) for the last 6 h of culture. B cells were then harvested and the incorporation of thymidine was measured using a scintillation counter. Of each duplicate treatment, the mean was calculated and these data were plotted in XLfit 4 to determine the respective IC50 values.

Human T Cell Proliferation Assay

PBMC were freshly isolated by Ficoll-Paque density gradient from human blood and subjected to negative isolation of T cells. T cells were prepared in culture medium (RPMI 1640, HEPES, 10% FCS, 50 µg/mL gentamicine, 50 µM 2-Mercaptoethanol, 1x ITS (Insulin, Transferrin and Sodium Selenite), 1x Non-Essential Amino-Acids) at a concentration of 8.104 per well in a flat-bottom 96-well culture plate. T cell stimulation was performed by human anti-CD3 antibody molecule (10 ug/mL) or by human anti-CD3 antibody molecule (5 µg/mL) and anti-CD28 antibody molecule (1 µg/mL) in presence or not of a 7-point concentration range of test compounds. After 72 h of culture at 37° C., 10% CO2, cells were pulsed with 3H-TdR (1 µCi/well) for the last 6 h of culture. Cell proliferation was measured by the incorporation of thymidine allowing IC50 determination for each tested compound.

Exemplary Combinations of Antigen-Presentation Combinations, Effector Cell Combinations and Anti-Tumor Immunosuppression Combinations Exemplary combinations of therapeutic agents from two or more of the antigen-presentation category (A), effector cell category (B), and anti-tumor immunosuppression category (C) are provided herein.

TABLE 7

Listing of Therapeutic Agents in Categories (A)-(C)

| | A = Antigen-Presentation | B = Effector Cell | C = Anti-tumor Immunosuppression |
|---|---|---|---|
| 1 | STING agonist | GITR agonist | PD-1 inhibitor |
| 2 | TLR agonist | PD-1 inhibitor | PD-L1 inhibitor |
| 3 | TIM-3 modulator | PD-L1 inhibitor | LAG-3 inhibitor |
| 4 | VEGFR inhibitor | IAP inhibitor | TEM-3 inhibitor |
| 5 | c-MET inhibitor | EGFR inhibitor | GITR inhibitor |
| 6 | TGFb inhibitor | mTOR inhibitor | CSF-1/1R inhibitor |
| 7 | IDO/TDO inhibitor | IL-15 agonist | IL-17 inhibitor |
| 8 | A2AR antagonist | CTLA-4 inhibitor | IL-1β inhibitor |
| 9 | Oncolytic viruses | Bispecific T-cell engagers | CXCR2 inhibitor |
| 10 | Scaffold vaccines | CD40 agonist | PI3K-γ, -δ inhibitor |
| 11 | Bispecific T-cell engagers | OX40 agonist | BAFF-R inhibitor |
| 12 | | CD27 agonist | MALT-1/BTK inhibitor |
| 13 | | | JAK inhibitor |
| 14 | | | CRTH2 inhibitor |
| 15 | | | VEGFR inhibitor |
| 16 | | | IL-15 agonist |
| 17 | | | Anti-TGFb inhibitor |
| 18 | | | IDO/TDO inhibitor |
| 19 | | | A2AR antagonist |
| 20 | | | CTLA-4 inhibitor |
| 21 | | | PFKFB3 inhibitor |

In some embodiments, the combinations of the present invention include one or more of the following:
A1B1, A1B2, A1B3, A1B4, A1B5, A1B6, A1B7, A1B8, A1B9, A1B10, A1B11, A1B12, A2B1, A2B2, A2B3, A2B4, A2B5, A2B6, A2B7, A2B8, A2B9, A2B10, A2B11, A2B12, A3B1, A3B2, A3B3, A3B4, A3B5, A3B6, A3B7, A3B8, A3B9, A3B10, A3B11, A3B12, A4B1, A4B2, A4B3, A4B4, A4B5, A4B6, A4B7, A4B8, A4B9, A4B10, A4B11, A4B12, A5B1, A5B2, A5B3, A5B4, A5B5, A5B6, A5B7, A5B8, A5B9, A5B10, A5B11, A5B12, A6B1, A6B2, A6B3, A6B4, A6B5, A6B6, A6B7, A6B8, A6B9, A6B10, A6B11, A6B12, A7B1, A7B2, A7B3, A7B4, A7B5, A7B6, A7B7, A7B8, A7B9, A7B10, A7B11, A7B12, A8B1, A8B2, A8B3, A8B4, A8B5, A8B6, A8B7, A8B8, A8B9, A8B10, A8B11, A8B12, A9B1, A9B2, A9B3, A9B4, A9B5, A9B6, A9B7, A9B8, A9B9, A9B10, A9B11, A9B12, A10B1, A10B2, A10B3, A10B4, A10B5, A10B6, A10B7, A10B8, A10B9, A10B10, A10B11, A10B12, A11B1, A11B2, A11B3, A11B4, A11B5, A11B6, A11B7, A11B8, A11B9, A11B10, A11B11, A11B12, A1C1, A1C2, A1C3, A1C4, A1C5, A1C6, A1C7, A1C8, A1C9, A1C10, A1C11, A1C12, A1C13, A1C14, A1C15, A1C16, A1C17, A1C18, A1C19, A1C20, A1C21, A2C1, A2C2, A2C3, A2C4, A2C5, A2C6, A2C7, A2C8, A2C9, A2C10, A2C11, A2C12, A2C13, A2C14, A2C15, A2C16, A2C17, A2C18, A2C19, A2C20, A2C21, A3C1, A3C2, A3C3, A3C4, A3C5, A3C6, A3C7, A3C8, A3C9, A3C10, A3C11, A3C12, A3C13, A3C14, A3C15, A3C16, A3C17, A3C18, A3C19, A3C20, A3C21, A4C1, A4C2, A4C3, A4C4, A4C5, A4C6, A4C7, A4C8, A4C9, A4C10, A4C11, A4C12, A4C13, A4C14, A4C15, A4C16, A4C17, A4C18, A4C19, A4C20, A4C21, A5C1, A5C2, A5C3, A5C4, A5C5, A5C6, A5C7, A5C8, A5C9, A5C10, A5C11, A5C12, A5C13, A5C14, A5C15, A5C16, A5C17, A5C18, A5C19, A5C20, A5C21, A6C1, A6C2, A6C3, A6C4, A6C5, A6C6, A6C7, A6C8, A6C9, A6C10, A6C11, A6C12, A6C13, A6C14, A6C15, A6C16, A6C17, A6C18, A6C19, A6C20, A6C21, A7C1, A7C2, A7C3, A7C4, A7C5, A7C6, A7C7, A7C8, A7C9, A7C10, A7C11, A7C12, A7C13, A7C14, A7C15, A7C16, A7C17, A7C18, A7C19, A7C20, A7C21, A8C1, A8C2, A8C3, A8C4, A8C5, A8C6, A8C7, A8C8, A8C9, A8C10, A8C11, A8C12, A8C13, A8C14, A8C15, A8C16, A8C17, A8C18, A8C19, A8C20, A8C21, A9C1, A9C2, A9C3, A9C4, A9C5, A9C6, A9C7, A9C8, A9C9, A9C10, A9C11, A9C12, A9C13, A9C14, A9C15, A9C16, A9C17, A9C18, A9C19, A9C20, A9C21, A10C1, A10C2, A10C3, A10C4, A10C5, A1006, A1007, A1008, A10C9, A10C10, A10C11, A10C12, A10C13, A10C14, A10C15, A10C16, A10C17, A10C18, A10C19, A10C20, A10C21, A11C1, A11C2, A11C3, A11C4, A1105, A1106, A11C7, A11C8, A11C9, A11C10, A11C11, A11C12, A11C13, A11C14, A11C15, A11C16, A11C17, A11C18, A11C19, A11C20, A11C21, B1C1, B1C2, B1C3, B1C4, B1C5, B1C6, B1C7, B1C8, B1C9, B1C10, B1C11, B1C12, B1C13, B1C14, B1C15, B1C16, B1C17, B1C18, B1C19, B1C20, B1C21, B2C1, B2C2, B2C3, B2C4, B2C5, B2C6, B2C7, B2C8, B2C9, B2C10, B2C11, B2C12, B2C13, B2C14, B2C15, B2C16, B2C17, B2C18, B2C19, B2C20, B2C21, B3C1, B3C2, B3C3, B3C4, B3C5, B3C6, B3C7, B3C8, B3C9, B3C10, B3C11, B3C12, B3C13, B3C14, B3C15, B3C16, B3C17, B3C18, B3C19, B3C20, B3C21, B4C1, B4C2, B4C3, B4C4, B4C5, B4C6, B4C7, B4C8, B4C9, B4C10, B4C11, B4C12, B4C13, B4C14, B4C15, B4C16, B4C17, B4C18, B4C19, B4C20, B4C21, B5C1, B5C2, B5C3, B5C4, B5C5, B5C6, B5C7, B5C8, B5C9, B5C10, B5C11, B5C12, B5C13, B5C14, B5C15, B5C16, B5C17, B5C18, B5C19, B5C20, B5C21, B6C1, B6C2, B6C3, B6C4, B6C5, B6C6, B6C7, B6C8, B6C9, B6C10, B6C11, B6C12, B6C13, B6C14, B6C15, B6C16, B6C17, B6C18, B6C19, B6C20, B6C21, B7C1, B7C2, B7C3, B7C4, B7C5, B7C6, B7C7, B7C8, B7C9, B7C10, B7C11, B7C12, B7C13, B7C14, B7C15, B7C16, B7C17, B7C18, B7C19, B7C20, B7C21, B8C1, B8C2, B8C3, B8C4, B8C5, B8C6, B8C7, B8C8, B8C9, B8C10, B8C11, B8C12, B8C13, B8C14, B8C15, B8C16, B8C17, B8C18, B8C19, B8C20, B8C21, B9C1, B9C2, B9C3, B9C4, B9C5, B9C6, B9C7, B9C8, B9C9, B9C10, B9C11, B9C12, B9C13, B9C14, B9C15, B9C16, B9C17, B9C18, B9C19, B9C20, B9C21, B10C1, B10C2, B10C3, B10C4, B1005, B1006, B1007, B1008, B10C9, B10C10, B10C11, B10C12, B10C13, B10C14, B10C15, B10C16, B10C17, B10C18, B10C19, B10C20, B10C21, B11C1, B11C2, B11C3, B11C4, B1105, B1106, B11C7, B11C8, B11C9, B11C10, B11C11, B11C12, B11C13, B11C14, B11C15, B11C16, B11C17, B11C18, B11C19, B11C20, B11C21, B12C1, B12C2, B12C3, B12C4, B12C5, B12C6, B12C7, B12C8, B12C9, B12C10, B12C11, B12C12, B12C13, B12C14, B12C15, B12C16, B12C17, B12C18, B12C19, B12C20, B12C21, A1B1C1, A1B1C2, A1B1C3, A1B1C4, A1B1C5, A1B1C6, A1B1C7, A1B1C8, A1B1C9, A1B1C10, A1B1C11, A1B1C12, A1B1C13, A1B1C14, A1B1C15, A1B1C16, A1B1C17, A1B1C18, A1B1C19, A1B1C20, A1B1C21, A1B2C1, A1B2C2, A1B2C3, A1B2C4, A1B2C5, A1B2C6, A1B2C7, A1B2C8, A1B2C9, A1B2C10, A1B2C11, A1B2C12, A1B2C13, A1B2C14, A1B2C15, A1B2C16, A1B2C17, A1B2C18, A1B2C19, A1B2C20, A1B2C21, A1B3C1, A1B3C2, A1B3C3, A1B3C4, A1B3C5, A1B3C6, A1B3C7, A1B3C8, A1B3C9, A1B3C10, A1B3C11, A1B3C12, A1B3C13, A1B3C14, A1B3C15, A1B3C16, A1B3C17, A1B3C18, A1B3C19, A1B3C20, A1B3C21, A1B4C1, A1B4C2, A1B4C3, A1B4C4, A1B4C5, A1B4C6, A1B4C7, A1B4C8, A1B4C9, A1B4C10, A1B4C11, A1B4C12, A1B4C13, A1B4C14, A1B4C15, A1B4C16, A1B4C17, A1B4C18, A1B4C19, A1B4C20, A1B4C21, A1B5C1, A1B5C2, A1B5C3, A1B5C4, A1B5C5, A1B5C6, A1B5C7, A1B5C8, A1B5C9, A1B5C10, A1B5C11, A1B5C12, A1B5C13, A1B5C14, A1B5C15, A1B5C16, A1B5C17, A1B5C18, A1B5C19, A1B5C20, A1B5C21, A1B6C1, A1B6C2, A1B6C3, A1B6C4, A1B6C5, A1B6C6, A1B6C7, A1B6C8, A1B6C9, A1B6C10, A1B6C11, A1B6C12, A1B6C13, A1B6C14, A1B6C15, A1B6C16, A1B6C17, A1B6C18, A1B6C19, A1B6C20, A1B6C21, A1B7C1, A1B7C2, A1B7C3, A1B7C4, A1B7C5, A1B7C6, A1B7C7, A1B7C8, A1B7C9, A1B7C10, A1B7C11, A1B7C12, A1B7C13, A1B7C14, A1B7C15, A1B7C16, A1B7C17, A1B7C18, A1B7C19, A1B7C20, A1B7C21, A1B8C1, A1B8C2, A1B8C3, A1B8C4, A1B8C5, A1B8C6, A1B8C7, A1B8C8, A1B8C9, A1B8C10, A1B8C11, A1B8C12, A1B8C13, A1B8C14, A1B8C15, A1B8C16, A1B8C17, A1B8C18, A1B8C19, A1B8C20, A1B8C21, A1B9C1, A1B9C2, A1B9C3, A1B9C4, A1B9C5, A1B9C6, A1B9C7, A1B9C8, A1B9C9, A1B9C10, A1B9C11, A1B9C12, A1B9C13, A1B9C14, A1B9C15, A1B9C16, A1B9C17, A1B9C18, A1B9C19, A1B9C20, A1B9C21, A1B10C1, A1B10C2, A1B10C3, A1B10C4, A1B1005, A1B1006, A1B1007, A1B1008, A1B10C9, A1B10C10, A1B10C11, A1B10C12, A1B10C13, A1B10C14, A1B10C15, A1B10C16, A1B10C17, A1B10C18, A1B10C19, A1B10C20, A1B10C21, A1B11C1, A1B11C2, A1B11C3, A1B11C4, A1B1105, A1B1106, A1B11C7, A1B11C8, A1B11C9, A1B11C10, A1B11C11, A1B11C12, A1B11C13, A1B11C14, A1B11C15, A1B11C16, A1B11C17, A1B11C18, A1B11C19, A1B11C20, A1B11C21, A1B12C1, A1B12C2, A1B12C3, A1B12C4, A1B12C5, A1B12C6, A1B12C7, A1B12C8, A1B12C9, A1B12C10, A1B12C11, A1B12C12, A1B12C13, A1B12C14, A1B12C15, A1B12C16, A1B12C17, A1B12C18, A1B12C19, A1B12C20, A1B12C21, A2B1C1, A2B1C2, A2B1C3, A2B1C4, A2B1C5, A2B1C6, A2B1C7, A2B1C8, A2B1C9, A2B1C10, A2B1C11, A2B1C12, A2B1C13, A2B1C14, A2B1C15, A2B1C16, A2B1C17, A2B1C18, A2B1C19, A2B1C20, A2B1C21, A2B2C1, A2B2C2, A2B2C3, A2B2C4, A2B2C5, A2B2C6, A2B2C7, A2B2C8, A2B2C9, A2B2C10, A2B2C11, A2B2C12, A2B2C13, A2B2C14, A2B2C15, A2B2C16, A2B2C17, A2B2C18, A2B2C19, A2B2C20, A2B2C21, A2B3C1, A2B3C2, A2B3C3, A2B3C4, A2B3C5, A2B3C6, A2B3C7, A2B3C8, A2B3C9, A2B3C10, A2B3C11, A2B3C12, A2B3C13, A2B3C14, A2B3C15, A2B3C16, A2B3C17, A2B3C18, A2B3C19, A2B3C20, A2B3C21, A2B4C1, A2B4C2, A2B4C3, A2B4C4, A2B4C5, A2B4C6, A2B4C7, A2B4C8, A2B4C9, A2B4C10, A2B4C11, A2B4C12, A2B4C13, A2B4C14, A2B4C15, A2B4C16, A2B4C17, A2B4C18, A2B4C19, A2B4C20, A2B4C21, A2B5C1, A2B5C2, A2B5C3, A2B5C4, A2B5C5, A2B5C6, A2B5C7, A2B5C8, A2B5C9, A2B5C10, A2B5C11, A2B5C12, A2B5C13, A2B5C14, A2B5C15, A2B5C16, A2B5C17, A2B5C18, A2B5C19, A2B5C20, A2B5C21, A2B6C1, A2B6C2, A2B6C3, A2B6C4, A2B6C5, A2B6C6, A2B6C7, A2B6C8, A2B6C9, A2B6C10, A2B6C11, A2B6C12, A2B6C13, A2B6C14, A2B6C15, A2B6C16, A2B6C17, A2B6C18, A2B6C19, A2B6C20, A2B6C21, A2B7C1, A2B7C2, A2B7C3, A2B7C4, A2B7C5, A2B7C6, A2B7C7, A2B7C8, A2B7C9, A2B7C10, A2B7C11, A2B7C12, A2B7C13, A2B7C14, A2B7C15, A2B7C16, A2B7C17, A2B7C18, A2B7C19, A2B7C20, A2B7C21, A2B8C1, A2B8C2, A2B8C3, A2B8C4, A2B8C5, A2B8C6, A2B8C7, A2B8C8, A2B8C9, A2B8C10, A2B8C11, A2B8C12, A2B8C13, A2B8C14, A2B8C15, A2B8C16, A2B8C17, A2B8C18, A2B8C19, A2B8C20, A2B8C21, A2B9C1, A2B9C2, A2B9C3, A2B9C4, A2B9C5, A2B9C6, A2B9C7, A2B9C8, A2B9C9, A2B9C10, A2B9C11, A2B9C12, A2B9C13, A2B9C14, A2B9C15, A2B9C16, A2B9C17, A2B9C18, A2B9C19, A2B9C20, A2B9C21, A2B10C1, A2B10C2, A2B10C3, A2B10C4, A2B1005, A2B1006, A2B1007, A2B1008, A2B10C9, A2B10C10, A2B10C11, A2B10C12, A2B10C13, A2B10C14, A2B10C15, A2B10C16, A2B10C17, A2B10C18, A2B10C19, A2B10C20, A2B10C21, A2B11C1, A2B11C2, A2B11C3, A2B11C4, A2B1105, A2B1106, A2B11C7, A2B11C8, A2B11C9, A2B11C10, A2B11C11, A2B11C12, A2B11C13, A2B11C14, A2B11C15, A2B11C16, A2B11C17, A2B11C18, A2B11C19, A2B11C20, A2B11C21, A2B12C1, A2B12C2, A2B12C3, A2B12C4, A2B12C5, A2B12C6, A2B12C7, A2B12C8, A2B12C9, A2B12C10, A2B12C11, A2B12C12, A2B12C13, A2B12C14, A2B12C15, A2B12C16, A2B12C17, A2B12C18, A2B12C19, A2B12C20, A2B12C21, A3B1C1, A3B1C2, A3B1C3, A3B1C4, A3B1C5, A3B1C6, A3B1C7, A3B1C8, A3B1C9, A3B1C10, A3B1C11, A3B1C12, A3B1C13, A3B1C14, A3B1C15, A3B1C16, A3B1C17, A3B1C18, A3B1C19, A3B1C20, A3B1C21, A3B2C1, A3B2C2, A3B2C3, A3B2C4, A3B2C5, A3B2C6, A3B2C7, A3B2C8, A3B2C9, A3B2C10, A3B2C11, A3B2C12, A3B2C13, A3B2C14, A3B2C15, A3B2C16, A3B2C17, A3B2C18, A3B2C19, A3B2C20, A3B2C21, A3B3C1, A3B3C2, A3B3C3, A3B3C4, A3B3C5, A3B3C6, A3B3C7, A3B3C8, A3B3C9, A3B3C10, A3B3C11, A3B3C12, A3B3C13, A3B3C14, A3B3C15, A3B3C16, A3B3C17, A3B3C18, A3B3C19, A3B3C20, A3B3C21, A3B4C1, A3B4C2, A3B4C3, A3B4C4, A3B4C5, A3B4C6, A3B4C7, A3B4C8, A3B4C9, A3B4C10, A3B4C11, A3B4C12, A3B4C13, A3B4C14, A3B4C15, A3B4C16, A3B4C17, A3B4C18, A3B4C19, A3B4C20, A3B4C21, A3B5C1, A3B5C2, A3B5C3, A3B5C4, A3B5C5, A3B5C6, A3B5C7, A3B5C8, A3B5C9, A3B5C10, A3B5C11, A3B5C12, A3B5C13, A3B5C14, A3B5C15, A3B5C16, A3B5C17, A3B5C18, A3B5C19, A3B5C20, A3B5C21, A3B6C1, A3B6C2, A3B6C3, A3B6C4, A3B6C5, A3B6C6, A3B6C7, A3B6C8, A3B6C9, A3B6C10, A3B6C11, A3B6C12, A3B6C13, A3B6C14, A3B6C15, A3B6C16, A3B6C17, A3B6C18, A3B6C19, A3B6C20, A3B6C21, A3B7C1, A3B7C2, A3B7C3, A3B7C4, A3B7C5, A3B7C6, A3B7C7, A3B7C8, A3B7C9, A3B7C10, A3B7C11, A3B7C12, A3B7C13, A3B7C14, A3B7C15, A3B7C16, A3B7C17, A3B7C18, A3B7C19, A3B7C20, A3B7C21, A3B8C1, A3B8C2, A3B8C3, A3B8C4, A3B8C5, A3B8C6, A3B8C7, A3B8C8, A3B8C9, A3B8C10, A3B8C11, A3B8C12, A3B8C13, A3B8C14, A3B8C15, A3B8C16, A3B8C17, A3B8C18, A3B8C19, A3B8C20, A3B8C21, A3B9C1, A3B9C2, A3B9C3, A3B9C4, A3B9C5, A3B9C6, A3B9C7, A3B9C8, A3B9C9, A3B9C10, A3B9C11, A3B9C12, A3B9C13, A3B9C14, A3B9C15, A3B9C16, A3B9C17, A3B9C18, A3B9C19, A3B9C20, A3B9C21, A3B10C1, A3B10C2, A3B10C3, A3B10C4, A3B1005, A3B1006, A3B1007, A3B1008, A3B10C9, A3B10C10, A3B10C11, A3B10C12, A3B10C13, A3B10C14, A3B10C15, A3B10C16, A3B10C17, A3B10C18, A3B10C19, A3B10C20, A3B10C21, A3B11C1, A3B11C2, A3B11C3, A3B11C4, A3B1105, A3B1106, A3B11C7, A3B11C8, A3B11C9, A3B11C10, A3B11C11, A3B11C12, A3B11C13, A3B11C14, A3B11C15, A3B11C16, A3B11C17, A3B11C18, A3B11C19, A3B11C20, A3B11C21, A3B12C1, A3B12C2, A3B12C3, A3B12C4, A3B12C5, A3B12C6, A3B12C7, A3B12C8, A3B12C9, A3B12C10, A3B12C11, A3B12C12, A3B12C13, A3B12C14, A3B12C15, A3B12C16, A3B12C17, A3B12C18, A3B12C19, A3B12C20, A3B12C21, A4B1C1, A4B1C2, A4B1C3, A4B1C4, A4B1C5, A4B1C6, A4B1C7, A4B1C8, A4B1C9, A4B1C10, A4B1C11, A4B1C12, A4B1C13, A4B1C14, A4B1C15, A4B1C16, A4B1C17, A4B1C18, A4B1C19, A4B1C20, A4B1C21, A4B2C1, A4B2C2, A4B2C3, A4B2C4, A4B2C5, A4B2C6, A4B2C7, A4B2C8, A4B2C9, A4B2C10, A4B2C11, A4B2C12, A4B2C13, A4B2C14, A4B2C15, A4B2C16, A4B2C17, A4B2C18, A4B2C19, A4B2C20, A4B2C21, A4B3C1, A4B3C2, A4B3C3, A4B3C4, A4B3C5, A4B3C6, A4B3C7, A4B3C8, A4B3C9, A4B3C10, A4B3C11, A4B3C12, A4B3C13, A4B3C14, A4B3C15, A4B3C16, A4B3C17, A4B3C18, A4B3C19, A4B3C20, A4B3C21, A4B4C1, A4B4C2, A4B4C3, A4B4C4, A4B4C5, A4B4C6, A4B4C7, A4B4C8, A4B4C9, A4B4C10, A4B4C11, A4B4C12, A4B4C13, A4B4C14, A4B4C15, A4B4C16, A4B4C17, A4B4C18, A4B4C19, A4B4C20, A4B4C21, A4B5C1, A4B5C2, A4B5C3, A4B5C4, A4B5C5, A4B5C6, A4B5C7, A4B5C8, A4B5C9, A4B5C10, A4B5C11, A4B5C12, A4B5C13, A4B5C14, A4B5C15, A4B5C16, A4B5C17, A4B5C18, A4B5C19, A4B5C20, A4B5C21, A4B6C1, A4B6C2, A4B6C3, A4B6C4, A4B6C5, A4B6C6, A4B6C7, A4B6C8, A4B6C9, A4B6C10, A4B6C11, A4B6C12, A4B6C13, A4B6C14, A4B6C15, A4B6C16, A4B6C17, A4B6C18, A4B6C19, A4B6C20, A4B6C21, A4B7C1, A4B7C2, A4B7C3, A4B7C4, A4B7C5, A4B7C6, A4B7C7, A4B7C8, A4B7C9, A4B7C10, A4B7C11, A4B7C12, A4B7C13, A4B7C14, A4B7C15, A4B7C16, A4B7C17, A4B7C18, A4B7C19, A4B7C20, A4B7C21, A4B8C1, A4B8C2, A4B8C3, A4B8C4, A4B8C5, A4B8C6, A4B8C7, A4B8C8, A4B8C9, A4B8C10, A4B8C11, A4B8C12, A4B8C13, A4B8C14, A4B8C15, A4B8C16, A4B8C17, A4B8C18, A4B8C19, A4B8C20, A4B8C21, A4B9C1, A4B9C2, A4B9C3, A4B9C4, A4B9C5, A4B9C6, A4B9C7, A4B9C8, A4B9C9, A4B9C10, A4B9C11, A4B9C12, A4B9C13, A4B9C14, A4B9C15, A4B9C16, A4B9C17, A4B9C18, A4B9C19, A4B9C20, A4B9C21, A4B10C1, A4B10C2, A4B10C3, A4B10C4, A4B1005, A4B1006, A4B1007, A4B1008, A4B10C9, A4B10C10, A4B10C11, A4B10C12, A4B10C13, A4B10C14, A4B10C15, A4B10C16, A4B10C17, A4B10C18, A4B10C19, A4B10C20, A4B10C21, A4B11C1, A4B11C2, A4B11C3, A4B11C4, A4B1105, A4B1106, A4B11C7, A4B11C8, A4B11C9, A4B11C10, A4B11C11, A4B11C12, A4B11C13, A4B11C14, A4B11C15, A4B11C16, A4B11C17, A4B11C18, A4B11C19, A4B11C20, A4B11C21, A4B12C1, A4B12C2, A4B12C3, A4B12C4, A4B12C5, A4B12C6, A4B12C7, A4B12C8, A4B12C9, A4B12C10, A4B12C11, A4B12C12, A4B12C13, A4B12C14, A4B12C15, A4B12C16, A4B12C17, A4B12C18, A4B12C19, A4B12C20, A4B12C21, A5B1C1, A5B1C2, A5B1C3, A5B1C4, A5B1C5, A5B1C6, A5B1C7, A5B1C8, A5B1C9, A5B1C10, A5B1C11, A5B1C12, A5B1C13, A5B1C14, A5B1C15, A5B1C16, A5B1C17, A5B1C18, A5B1C19, A5B1C20, A5B1C21, A5B2C1, A5B2C2, A5B2C3, A5B2C4, A5B2C5, A5B2C6, A5B2C7, A5B2C8, A5B2C9, A5B2C10, A5B2C11, A5B2C12, A5B2C13, A5B2C14, A5B2C15, A5B2C16, A5B2C17, A5B2C18, A5B2C19, A5B2C20, A5B2C21, A5B3C1, A5B3C2, A5B3C3, A5B3C4, A5B3C5, A5B3C6, A5B3C7, A5B3C8, A5B3C9, A5B3C10, A5B3C11, A5B3C12, A5B3C13, A5B3C14, A5B3C15, A5B3C16, A5B3C17, A5B3C18, A5B3C19, A5B3C20, A5B3C21, A5B4C1, A5B4C2, A5B4C3, A5B4C4, A5B4C5, A5B4C6, A5B4C7, A5B4C8, A5B4C9, A5B4C10, A5B4C11, A5B4C12, A5B4C13, A5B4C14, A5B4C15, A5B4C16, A5B4C17, A5B4C18, A5B4C19, A5B4C20, A5B4C21, A5B5C1, A5B5C2, A5B5C3, A5B5C4, A5B5C5, A5B5C6, A5B5C7, A5B5C8, A5B5C9, A5B5C10, A5B5C11, A5B5C12, A5B5C13, A5B5C14, A5B5C15, A5B5C16, A5B5C17, A5B5C18, A5B5C19, A5B5C20, A5B5C21, A5B6C1, A5B6C2, A5B6C3, A5B6C4, A5B6C5, A5B6C6, A5B6C7, A5B6C8, A5B6C9, A5B6C10, A5B6C11, A5B6C12, A5B6C13, A5B6C14, A5B6C15, A5B6C16, A5B6C17, A5B6C18, A5B6C19, A5B6C20, A5B6C21, A5B7C1, A5B7C2, A5B7C3, A5B7C4, A5B7C5, A5B7C6, A5B7C7, A5B7C8, A5B7C9, A5B7C10, A5B7C11, A5B7C12, A5B7C13, A5B7C14, A5B7C15, A5B7C16, A5B7C17, A5B7C18, A5B7C19, A5B7C20, A5B7C21, A5B8C1, A5B8C2, A5B8C3, A5B8C4, A5B8C5, A5B8C6, A5B8C7, A5B8C8, A5B8C9, A5B8C10, A5B8C11, A5B8C12, A5B8C13, A5B8C14, A5B8C15, A5B8C16, A5B8C17, A5B8C18, A5B8C19, A5B8C20, A5B8C21, A5B9C1, A5B9C2, A5B9C3, A5B9C4, A5B9C5, A5B9C6, A5B9C7, A5B9C8, A5B9C9, A5B9C10, A5B9C11, A5B9C12, A5B9C13, A5B9C14, A5B9C15, A5B9C16, A5B9C17, A5B9C18, A5B9C19, A5B9C20, A5B9C21, A5B10C1, A5B10C2, A5B10C3, A5B10C4, A5B1005, A5B1006, A5B1007, A5B1008, A5B10C9, A5B10C10, A5B10C11, A5B10C12, A5B10C13, A5B10C14, A5B10C15, A5B10C16, A5B10C17, A5B10C18, A5B10C19, A5B10C20, A5B10C21, A5B11C1, A5B11C2, A5B11C3, A5B11C4, A5B1105, A5B1106, A5B11C7, A5B11C8, A5B11C9, A5B11C10, A5B11C11, A5B11C12, A5B11C13, A5B11C14, A5B11C15, A5B11C16, A5B11C17, A5B11C18, A5B11C19, A5B11C20, A5B11C21, A5B12C1, A5B12C2, A5B12C3, A5B12C4, A5B12C5, A5B12C6, A5B12C7, A5B12C8, A5B12C9, A5B12C10, A5B12C11, A5B12C12, A5B12C13, A5B12C14, A5B12C15, A5B12C16, A5B12C17, A5B12C18, A5B12C19, A5B12C20, A5B12C21, A6B1C1, A6B1C2, A6B1C3, A6B1C4, A6B1C5, A6B1C6, A6B1C7, A6B1C8, A6B1C9, A6B1C10, A6B1C11, A6B1C12, A6B1C13, A6B1C14, A6B1C15, A6B1C16, A6B1C17, A6B1C18, A6B1C19, A6B1C20, A6B1C21, A6B2C1, A6B2C2, A6B2C3, A6B2C4, A6B2C5, A6B2C6, A6B2C7, A6B2C8, A6B2C9, A6B2C10, A6B2C11, A6B2C12, A6B2C13, A6B2C14, A6B2C15, A6B2C16, A6B2C17, A6B2C18, A6B2C19, A6B2C20, A6B2C21, A6B3C1, A6B3C2, A6B3C3, A6B3C4, A6B3C5, A6B3C6, A6B3C7, A6B3C8, A6B3C9, A6B3C10, A6B3C11, A6B3C12, A6B3C13, A6B3C14, A6B3C15, A6B3C16, A6B3C17, A6B3C18, A6B3C19, A6B3C20, A6B3C21, A6B4C1, A6B4C2, A6B4C3, A6B4C4, A6B4C5, A6B4C6, A6B4C7, A6B4C8, A6B4C9, A6B4C10, A6B4C11, A6B4C12, A6B4C13, A6B4C14, A6B4C15, A6B4C16, A6B4C17, A6B4C18, A6B4C19, A6B4C20, A6B4C21, A6B5C1, A6B5C2, A6B5C3, A6B5C4, A6B5C5, A6B5C6, A6B5C7, A6B5C8, A6B5C9, A6B5C10, A6B5C11, A6B5C12, A6B5C13, A6B5C14, A6B5C15, A6B5C16, A6B5C17, A6B5C18, A6B5C19, A6B5C20, A6B5C21, A6B6C1, A6B6C2, A6B6C3, A6B6C4, A6B6C5, A6B6C6, A6B6C7, A6B6C8, A6B6C9, A6B6C10, A6B6C11, A6B6C12, A6B6C13, A6B6C14, A6B6C15, A6B6C16, A6B6C17, A6B6C18, A6B6C19, A6B6C20, A6B6C21, A6B7C1, A6B7C2, A6B7C3, A6B7C4, A6B7C5, A6B7C6, A6B7C7, A6B7C8, A6B7C9, A6B7C10, A6B7C11, A6B7C12, A6B7C13, A6B7C14, A6B7C15, A6B7C16, A6B7C17, A6B7C18, A6B7C19, A6B7C20, A6B7C21, A6B8C1, A6B8C2, A6B8C3, A6B8C4, A6B8C5, A6B8C6, A6B8C7, A6B8C8, A6B8C9, A6B8C10, A6B8C11, A6B8C12, A6B8C13, A6B8C14, A6B8C15, A6B8C16, A6B8C17, A6B8C18, A6B8C19, A6B8C20, A6B8C21, A6B9C1, A6B9C2, A6B9C3, A6B9C4, A6B9C5, A6B9C6, A6B9C7, A6B9C8, A6B9C9, A6B9C10, A6B9C11, A6B9C12, A6B9C13, A6B9C14, A6B9C15, A6B9C16, A6B9C17, A6B9C18, A6B9C19, A6B9C20, A6B9C21, A6B10C1, A6B10C2, A6B10C3, A6B10C4, A6B1005, A6B1006, A6B1007, A6B1008, A6B10C9, A6B10C10, A6B10C11, A6B10C12, A6B10C13, A6B10C14, A6B10C15, A6B10C16, A6B10C17, A6B10C18, A6B10C19, A6B10C20, A6B10C21, A6B11C1, A6B11C2, A6B11C3, A6B11C4, A6B1105, A6B1106, A6B11C7, A6B11C8, A6B11C9, A6B11C10, A6B11C11, A6B11C12, A6B11C13, A6B11C14, A6B11C15, A6B11C16, A6B11C17, A6B11C18, A6B11C19, A6B11C20, A6B11C21, A6B12C1, A6B12C2, A6B12C3, A6B12C4, A6B12C5, A6B12C6, A6B12C7, A6B12C8, A6B12C9, A6B12C10, A6B12C11, A6B12C12, A6B12C13, A6B12C14, A6B12C15, A6B12C16, A6B12C17, A6B12C18, A6B12C19, A6B12C20, A6B12C21, A7B1C1, A7B1C2, A7B1C3, A7B1C4, A7B1C5, A7B1C6, A7B1C7, A7B1C8, A7B1C9, A7B1C10, A7B1C11, A7B1C12, A7B1C13, A7B1C14, A7B1C15, A7B1C16, A7B1C17, A7B1C18, A7B1C19, A7B1C20, A7B1C21, A7B2C1, A7B2C2, A7B2C3, A7B2C4, A7B2C5, A7B2C6, A7B2C7, A7B2C8, A7B2C9, A7B2C10, A7B2C11, A7B2C12, A7B2C13, A7B2C14, A7B2C15, A7B2C16, A7B2C17, A7B2C18, A7B2C19, A7B2C20, A7B2C21, A7B3C1, A7B3C2, A7B3C3, A7B3C4, A7B3C5, A7B3C6, A7B3C7, A7B3C8, A7B3C9, A7B3C10, A7B3C11, A7B3C12, A7B3C13, A7B3C14, A7B3C15, A7B3C16, A7B3C17, A7B3C18, A7B3C19, A7B3C20, A7B3C21, A7B4C1, A7B4C2, A7B4C3, A7B4C4, A7B4C5, A7B4C6, A7B4C7, A7B4C8, A7B4C9, A7B4C10, A7B4C11, A7B4C12, A7B4C13, A7B4C14, A7B4C15, A7B4C16, A7B4C17, A7B4C18, A7B4C19, A7B4C20, A7B4C21, A7B5C1, A7B5C2, A7B5C3, A7B5C4, A7B5C5, A7B5C6, A7B5C7, A7B5C8, A7B5C9, A7B5C10, A7B5C11, A7B5C12, A7B5C13, A7B5C14, A7B5C15, A7B5C16, A7B5C17, A7B5C18, A7B5C19, A7B5C20, A7B5C21, A7B6C1, A7B6C2, A7B6C3, A7B6C4, A7B6C5, A7B6C6, A7B6C7, A7B6C8, A7B6C9, A7B6C10, A7B6C11, A7B6C12, A7B6C13, A7B6C14, A7B6C15, A7B6C16, A7B6C17, A7B6C18, A7B6C19, A7B6C20, A7B6C21, A7B7C1, A7B7C2, A7B7C3, A7B7C4, A7B7C5, A7B7C6, A7B7C7, A7B7C8, A7B7C9, A7B7C10, A7B7C11, A7B7C12, A7B7C13, A7B7C14, A7B7C15, A7B7C16, A7B7C17, A7B7C18, A7B7C19, A7B7C20, A7B7C21, A7B8C1, A7B8C2, A7B8C3, A7B8C4, A7B8C5, A7B8C6, A7B8C7, A7B8C8, A7B8C9, A7B8C10, A7B8C11, A7B8C12, A7B8C13, A7B8C14, A7B8C15, A7B8C16, A7B8C17, A7B8C18, A7B8C19, A7B8C20, A7B8C21, A7B9C1, A7B9C2, A7B9C3, A7B9C4, A7B9C5, A7B9C6, A7B9C7, A7B9C8, A7B9C9, A7B9C10, A7B9C11, A7B9C12, A7B9C13, A7B9C14, A7B9C15, A7B9C16, A7B9C17, A7B9C18, A7B9C19, A7B9C20, A7B9C21, A7B10C1, A7B10C2, A7B10C3, A7B10C4, A7B1005, A7B1006, A7B1007, A7B1008, A7B10C9, A7B10C10, A7B10C11, A7B10C12, A7B10C13, A7B10C14, A7B10C15, A7B10C16, A7B10C17, A7B10C18, A7B10C19, A7B10C20, A7B10C21, A7B11C1, A7B11C2, A7B11C3, A7B11C4, A7B1105, A7B1106, A7B11C7, A7B11C8, A7B11C9, A7B11C10, A7B11C11, A7B11C12, A7B11C13, A7B11C14, A7B11C15, A7B11C16, A7B11C17, A7B11C18, A7B11C19, A7B11C20, A7B11C21, A7B12C1, A7B12C2, A7B12C3, A7B12C4, A7B12C5, A7B12C6, A7B12C7, A7B12C8, A7B12C9, A7B12C10, A7B12C11, A7B12C12, A7B12C13, A7B12C14, A7B12C15, A7B12C16, A7B12C17, A7B12C18, A7B12C19, A7B12C20, A7B12C21, A8B1C1, A8B1C2, A8B1C3, A8B1C4, A8B1C5, A8B1C6, A8B1C7, A8B1C8, A8B1C9, A8B1C10, A8B1C11, A8B1C12, A8B1C13, A8B1C14, A8B1C15, A8B1C16, A8B1C17, A8B1C18, A8B1C19, A8B1C20, A8B1C21, A8B2C1, A8B2C2, A8B2C3, A8B2C4, A8B2C5, A8B2C6, A8B2C7, A8B2C8, A8B2C9, A8B2C10, A8B2C11, A8B2C12, A8B2C13, A8B2C14, A8B2C15, A8B2C16, A8B2C17, A8B2C18, A8B2C19, A8B2C20, A8B2C21, A8B3C1, A8B3C2, A8B3C3, A8B3C4, A8B3C5, A8B3C6, A8B3C7, A8B3C8, A8B3C9, A8B3C10, A8B3C11, A8B3C12, A8B3C13, A8B3C14, A8B3C15, A8B3C16, A8B3C17, A8B3C18, A8B3C19, A8B3C20, A8B3C21, A8B4C1, A8B4C2, A8B4C3, A8B4C4, A8B4C5, A8B4C6, A8B4C7, A8B4C8, A8B4C9, A8B4C10, A8B4C11, A8B4C12, A8B4C13, A8B4C14, A8B4C15, A8B4C16, A8B4C17, A8B4C18, A8B4C19, A8B4C20, A8B4C21, A8B5C1, A8B5C2, A8B5C3, A8B5C4, A8B5C5, A8B5C6, A8B5C7, A8B5C8, A8B5C9, A8B5C10, A8B5C11, A8B5C12, A8B5C13, A8B5C14, A8B5C15, A8B5C16, A8B5C17, A8B5C18, A8B5C19, A8B5C20, A8B5C21, A8B6C1, A8B6C2, A8B6C3, A8B6C4, A8B6C5, A8B6C6, A8B6C7, A8B6C8, A8B6C9, A8B6C10, A8B6C11, A8B6C12, A8B6C13, A8B6C14, A8B6C15, A8B6C16, A8B6C17, A8B6C18, A8B6C19, A8B6C20, A8B6C21, A8B7C1, A8B7C2, A8B7C3, A8B7C4, A8B7C5, A8B7C6, A8B7C7, A8B7C8, A8B7C9, A8B7C10, A8B7C11, A8B7C12, A8B7C13, A8B7C14, A8B7C15, A8B7C16, A8B7C17, A8B7C18, A8B7C19, A8B7C20, A8B7C21, A8B8C1, A8B8C2, A8B8C3, A8B8C4, A8B8C5, A8B8C6, A8B8C7, A8B8C8, A8B8C9, A8B8C10, A8B8C11, A8B8C12, A8B8C13, A8B8C14, A8B8C15, A8B8C16, A8B8C17, A8B8C18, A8B8C19, A8B8C20, A8B8C21, A8B9C1, A8B9C2, A8B9C3, A8B9C4, A8B9C5, A8B9C6, A8B9C7, A8B9C8, A8B9C9, A8B9C10, A8B9C11, A8B9C12, A8B9C13, A8B9C14, A8B9C15, A8B9C16, A8B9C17, A8B9C18, A8B9C19, A8B9C20, A8B9C21, A8B10C1, A8B10C2, A8B10C3, A8B10C4, A8B1005, A8B1006, A8B1007, A8B1008, A8B10C9, A8B10C10, A8B10C11, A8B10C12, A8B10C13, A8B10C14, A8B10C15, A8B10C16, A8B10C17, A8B10C18, A8B10C19, A8B10C20, A8B10C21, A8B11C1, A8B11C2, A8B11C3, A8B11C4, A8B1105, A8B1106, A8B11C7, A8B11C8, A8B11C9, A8B11C10, A8B11C11, A8B11C12, A8B11C13, A8B11C14, A8B11C15, A8B11C16, A8B11C17, A8B11C18, A8B11C19, A8B11C20, A8B11C21, A8B12C1, A8B12C2, A8B12C3, A8B12C4, A8B12C5, A8B12C6, A8B12C7, A8B12C8, A8B12C9, A8B12C10, A8B12C11, A8B12C12, A8B12C13, A8B12C14, A8B12C15, A8B12C16, A8B12C17, A8B12C18, A8B12C19, A8B12C20, A8B12C21, A9B1C1, A9B1C2, A9B1C3, A9B1C4, A9B1C5, A9B1C6, A9B1C7, A9B1C8, A9B1C9, A9B1C10, A9B1C11, A9B1C12, A9B1C13, A9B1C14, A9B1C15, A9B1C16, A9B1C17, A9B1C18, A9B1C19, A9B1C20, A9B1C21, A9B2C1, A9B2C2, A9B2C3, A9B2C4, A9B2C5, A9B2C6, A9B2C7, A9B2C8, A9B2C9, A9B2C10, A9B2C11, A9B2C12, A9B2C13, A9B2C14, A9B2C15, A9B2C16, A9B2C17, A9B2C18, A9B2C19, A9B2C20, A9B2C21, A9B3C1, A9B3C2, A9B3C3, A9B3C4, A9B3C5, A9B3C6, A9B3C7, A9B3C8, A9B3C9, A9B3C10, A9B3C11, A9B3C12, A9B3C13, A9B3C14, A9B3C15, A9B3C16, A9B3C17, A9B3C18, A9B3C19, A9B3C20, A9B3C21, A9B4C1, A9B4C2, A9B4C3, A9B4C4, A9B4C5, A9B4C6, A9B4C7, A9B4C8, A9B4C9, A9B4C10, A9B4C11, A9B4C12, A9B4C13, A9B4C14, A9B4C15, A9B4C16, A9B4C17, A9B4C18, A9B4C19, A9B4C20, A9B4C21, A9B5C1, A9B5C2, A9B5C3, A9B5C4, A9B5C5, A9B5C6, A9B5C7, A9B5C8, A9B5C9, A9B5C10, A9B5C11, A9B5C12, A9B5C13, A9B5C14, A9B5C15, A9B5C16, A9B5C17, A9B5C18, A9B5C19, A9B5C20, A9B5C21, A9B6C1, A9B6C2, A9B6C3, A9B6C4, A9B6C5, A9B6C6, A9B6C7, A9B6C8, A9B6C9, A9B6C10, A9B6C11, A9B6C12, A9B6C13, A9B6C14, A9B6C15, A9B6C16, A9B6C17, A9B6C18, A9B6C19, A9B6C20, A9B6C21, A9B7C1, A9B7C2, A9B7C3, A9B7C4, A9B7C5, A9B7C6, A9B7C7, A9B7C8, A9B7C9, A9B7C10, A9B7C11, A9B7C12, A9B7C13, A9B7C14, A9B7C15, A9B7C16, A9B7C17, A9B7C18, A9B7C19, A9B7C20, A9B7C21, A9B8C1, A9B8C2, A9B8C3, A9B8C4, A9B8C5, A9B8C6, A9B8C7, A9B8C8, A9B8C9, A9B8C10, A9B8C11, A9B8C12, A9B8C13, A9B8C14, A9B8C15, A9B8C16, A9B8C17, A9B8C18, A9B8C19, A9B8C20, A9B8C21, A9B9C1, A9B9C2, A9B9C3, A9B9C4, A9B9C5, A9B9C6, A9B9C7, A9B9C8, A9B9C9, A9B9C10, A9B9C11, A9B9C12, A9B9C13, A9B9C14, A9B9C15, A9B9C16, A9B9C17, A9B9C18, A9B9C19, A9B9C20, A9B9C21, A9B10C1, A9B10C2, A9B10C3, A9B10C4, A9B10C5, A9B10C6, A9B10C7, A9B10C8, A9B10C9, A9B10C10, A9B10C11, A9B10C12, A9B10C13, A9B10C14, A9B10C15, A9B10C16, A9B10C17, A9B10C18, A9B10C19, A9B10C20, A9B10C21, A9B11C1, A9B11C2, A9B11C3, A9B11C4, A9B11C5, A9B11C6, A9B11C7, A9B11C8, A9B11C9, A9B11C10, A9B11C11, A9B11C12, A9B11C13, A9B11C14, A9B11C15, A9B11C16, A9B11C17, A9B11C18, A9B11C19, A9B11C20, A9B11C21, A9B12C1, A9B12C2, A9B12C3, A9B12C4, A9B12C5, A9B12C6, A9B12C7, A9B12C8, A9B12C9, A9B12C10, A9B12C11, A9B12C12, A9B12C13, A9B12C14, A9B12C15, A9B12C16, A9B12C17, A9B12C18, A9B12C19, A9B12C20, A9B12C21, A10B1C1, A10B1C2, A10B1C3, A10B1C4, A10B1C5, A10B1C6, A10B1C7, A10B1C8, A10B1C9, A10B1C10, A10B1C11, A10B1C12, A10B1C13, A10B1C14, A10B1C15, A10B1C16, A10B1C17, A10B1C18, A10B1C19, A10B1C20, A10B1C21, A10B2C1, A10B2C2, A10B2C3, A10B2C4, A10B2C5, A10B2C6, A10B2C7, A10B2C8, A10B2C9, A10B2C10, A10B2C11, A10B2C12, A10B2C13, A10B2C14, A10B2C15, A10B2C16, A10B2C17, A10B2C18, A10B2C19, A10B2C20, A10B2C21, A10B3C1, A10B3C2, A10B3C3, A10B3C4, A10B3C5, A10B3C6, A10B3C7, A10B3C8, A10B3C9, A10B3C10, A10B3C11, A10B3C12, A10B3C13, A10B3C14, A10B3C15, A10B3C16, A10B3C17, A10B3C18, A10B3C19, A10B3C20, A10B3C21, A10B4C1, A10B4C2, A10B4C3, A10B4C4, A10B4C5, A10B4C6, A10B4C7, A10B4C8, A10B4C9, A10B4C10, A10B4C11, A10B4C12, A10B4C13, A10B4C14, A10B4C15, A10B4C16, A10B4C17, A10B4C18, A10B4C19, A10B4C20, A10B4C21, A10B5C1, A10B5C2, A10B5C3, A10B5C4, A10B5C5, A10B5C6, A10B5C7, A10B5C8, A10B5C9, A10B5C10, A10B5C11, A10B5C12, A10B5C13, A10B5C14, A10B5C15, A10B5C16, A10B5C17, A10B5C18, A10B5C19, A10B5C20, A10B5C21, A10B6C1, A10B6C2, A10B6C3, A10B6C4, A10B6C5, A10B6C6, A10B6C7, A10B6C8, A10B6C9, A10B6C10, A10B6C11, A10B6C12, A10B6C13, A10B6C14, A10B6C15, A10B6C16, A10B6C17, A10B6C18, A10B6C19, A10B6C20, A10B6C21, A10B7C1, A10B7C2, A10B7C3, A10B7C4, A10B7C5, A10B7C6, A10B7C7, A10B7C8, A10B7C9, A10B7C10, A10B7C11, A10B7C12, A10B7C13, A10B7C14, A10B7C15, A10B7C16, A10B7C17, A10B7C18, A10B7C19, A10B7C20, A10B7C21, A10B8C1, A10B8C2, A10B8C3, A10B8C4, A10B8C5, A10B8C6, A10B8C7, A10B8C8, A10B8C9, A10B8C10, A10B8C11, A10B8C12, A10B8C13, A10B8C14, A10B8C15, A10B8C16, A10B8C17, A10B8C18, A10B8C19, A10B8C20, A10B8C21, A10B9C1, A10B9C2, A10B9C3, A10B9C4, A10B9C5, A10B9C6, A10B9C7, A10B9C8, A10B9C9, A10B9C10, A10B9C11, A10B9C12, A10B9C13, A10B9C14, A10B9C15, A10B9C16, A10B9C17, A10B9C18, A10B9C19, A10B9C20, A10B9C21, A10B10C1, A10B10C2, A10B10C3, A10B10C4, A10B10C5, A10B10C6, A10B10C7, A10B10C8, A10B10C9, A10B10C10, A10B10C11, A10B10C12, A10B10C13, A10B10C14, A10B10C15, A10B10C16, A10B10C17, A10B10C18, A10B10C19, A10B10C20, A10B10C21, A10B11C1, A10B11C2, A10B11C3, A10B11C4, A10B11C5, A10B11C6, A10B11C7, A10B11C8, A10B11C9, A10B11C10, A10B11C11, A10B11C12, A10B11C13, A10B11C14, A10B11C15, A10B11C16, A10B11C17, A10B11C18, A10B11C19, A10B11C20, A10B11C21, A10B12C1, A10B12C2, A10B12C3, A10B12C4, A10B12C5, A10B12C6, A10B12C7, A10B12C8, A10B12C9, A10B12C10, A10B12C11, A10B12C12, A10B12C13, A10B12C14, A10B12C15, A10B12C16, A10B12C17, A10B12C18, A10B12C19, A10B12C20, A10B12C21, A11B1C1, A11B1C2, A11B1C3, A11B1C4, A11B1C5, A11B1C6, A11B1C7, A11B1C8, A11B1C9, A11B1C10, A11B1C11, A11B1C12, A11B1C13, A11B1C14, A11B1C15, A11B1C16, A11B1C17, A11B1C18, A11B1C19, A11B1C20, A11B1C21, A11B2C1, A11B2C2, A11B2C3, A11B2C4, A11B2C5, A11B2C6, A11B2C7, A11B2C8, A11B2C9, A11B2C10, A11B2C11, A11B2C12, A11B2C13, A11B2C14, A11B2C15, A11B2C16, A11B2C17, A11B2C18, A11B2C19, A11B2C20, A11B2C21, A11B3C1, A11B3C2, A11B3C3, A11B3C4, A11B3C5, A11B3C6, A11B3C7, A11B3C8, A11B3C9, A11B3C10, A11B3C11, A11B3C12, A11B3C13, A11B3C14, A11B3C15, A11B3C16, A11B3C17, A11B3C18, A11B3C19, A11B3C20, A11B3C21, A11B4C1, A11B4C2, A11B4C3, A11B4C4, A11B4C5, A11B4C6, A11B4C7, A11B4C8, A11B4C9, A11B4C10, A11B4C11, A11B4C12, A11B4C13, A11B4C14, A11B4C15, A11B4C16, A11B4C17, A11B4C18, A11B4C19, A11B4C20, A11B4C21, A11B5C1, A11B5C2, A11B5C3, A11B5C4, A11B5C5, A11B5C6, A11B5C7, A11B5C8, A11B5C9, A11B5C10, A11B5C11, A11B5C12, A11B5C13, A11B5C14, A11B5C15, A11B5C16, A11B5C17, A11B5C18, A11B5C19, A11B5C20, A11B5C21, A11B6C1, A11B6C2, A11B6C3, A11B6C4, A11B6C5, A11B6C6, A11B6C7, A11B6C8, A11B6C9, A11B6C10, A11B6C11, A11B6C12, A11B6C13, A11B6C14, A11B6C15, A11B6C16, A11B6C17, A11B6C18, A11B6C19, A11B6C20, A11B6C21, A11B7C1, A11B7C2, A11B7C3, A11B7C4, A11B7C5, A11B7C6, A11B7C7, A11B7C8, A11B7C9, A11B7C10, A11B7C11, A11B7C12, A11B7C13, A11B7C14, A11B7C15, A11B7C16, A11B7C17, A11B7C18, A11B7C19, A11B7C20, A11B7C21, A11B8C1, A11B8C2, A11B8C3, A11B8C4, A11B8C5, A11B8C6, A11B8C7, A11B8C8, A11B8C9, A11B8C10, A11B8C11, A11B8C12, A11B8C13, A11B8C14, A11B8C15, A11B8C16, A11B8C17, A11B8C18, A11B8C19, A11B8C20, A11B8C21, A11B9C1, A11B9C2, A11B9C3, A11B9C4, A11B9C5, A11B9C6, A11B9C7, A11B9C8, A11B9C9, A11B9C10, A11B9C11, A11B9C12, A11B9C13, A11B9C14, A11B9C15, A11B9C16, A11B9C17, A11B9C18, A11B9C19, A11B9C20, A11B9C21, A11B10C1, A11B10C2, A11B10C3, A11B10C4, A11B1005, A11B1006, A11B1007, A11B1008, A11B10C9, A11B10C10, A11B10C11, A11B10C12, A11B10C13, A11B10C14, A11B10C15, A11B10C16, A11B10C17, A11B10C18, A11B10C19, A11B10C20, A11B10C21, A11B11C1, A11B11C2, A11B11C3, A11B11C4, A11B1105, A11B1106, A11B11C7, A11B11C8, A11B11C9, A11B11C10, A11B11C11, A11B11C12, A11B11C13, A11B11C14, A11B11C15, A11B11C16, A11B11C17, A11B11C18, A11B11C19, A11B11C20, A11B11C21, A11B12C1, A11B12C2, A11B12C3, A11B12C4, A11B12C5, A11B12C6, A11B12C7, A11B12C8, A11B12C9, A11B12C10, A11B12C11, A11B12C12, A11B12C13, A11B12C14, A11B12C15, A11B12C16, A11B12C17, A11B12C18, A11B12C19, A11B12C20, or A11B12C21.

Exemplary Agents Used in the Combinations

Described herein are methods and compositions that include a combination of one, two or more of: (i) an agent that enhances antigen (e.g., tumor antigen) presentation; (ii) an agent that enhances an effector cell response (e.g., B cell and/or T cell activation and/or mobilization); or (iii) an agent that decreases tumor immunosuppression, thereby treating the disorder, e.g., the hyperproliferative condition or disorder (e.g., the cancer).

In some embodiments, one or more of the agents of (i), (ii) and/or (iii) described herein can be used in combination with a PD-L1 inhibitor (e.g., an anti-PD-L1 antibody molecule as described herein).

Exemplary agents that can be used in these combinations are provided herein.

Exemplary STING Agonists

In an embodiment, the combination includes a STING agonist. In some embodiments, the combination is used to treat a cancer, e.g., a cancer described herein e.g., a solid tumor (e.g., a breast cancer, a squamous cell carcinoma, a melanoma, an ovarian cancer, a fallopian tube carcinoma, a peritoneal carcinoma, a soft tissue sarcoma, a melanoma, a breast cancer, an esophageal cancer, a head and neck cancer, an endometrial cancer, a cervical cancer, or a basal cell carcinoma), e.g., a hematologic malignancy (e.g., a leukemia (e.g., a chronic lymphocytic leukemia (CLL), or a lymphoma (e.g., a marginal zone B-cell lymphoma, a small lymphocytic lymphoma, a follicular lymphoma, Hodgkin lymphoma, non-Hodgkin lymphoma)).

In some embodiments, the STING agonist is cyclic dinucleotide, e.g., a cyclic dinucleotide comprising purine or pyrimidine nucleobases (e.g., adenosine, guanine, uracil, thymine, or cytosine nucleobases). In some embodiments, the nucleobases of the cyclic dinucleotide comprise the same nucleobase or different nucleobases.

In some embodiments, the STING agonist comprises an adenosine or a guanosine nucleobase. In some embodiments, the STING agonist comprises one adenosine nucleobase and one guanosine nucleobase. In some embodiments, the STING agonist comprises two adenosine nucleobases or two guanosine nucleobases.

In some embodiments, the STING agonist comprises a modified cyclic dinucleotide, e.g., comprising a modified nucleobase, a modified ribose, or a modified phosphate linkage. In some embodiments, the modified cyclic dinucleotide comprises a modified phosphate linkage, e.g., a thiophosphate.

In some embodiments, the STING agonist comprises a cyclic dinucleotide (e.g., a modified cyclic dinucleotide) with 2',5' or 3',5' phosphate linkages. In some embodiments, the STING agonist comprises a cyclic dinucleotide (e.g., a modified cyclic dinucleotide) with Rp or Sp stereochemistry around the phosphate linkages.

In some embodiments, the STING agonist is Rp,Rp dithio 2',3' c-di-AMP (e.g., Rp,Rp-dithio c-[A(2',5')pA(3',5')p]), or a cyclic dinucleotide analog thereof. In some embodiments, the STING agonist is a compound depicted in U.S. Patent Publication No. US2015/0056224 (e.g., a compound in FIG. 2c, e.g., compound 21 or compound 22). In some embodiments, the STING agonist is c-[G(2',5')pG(3',5')p], a dithio ribose O-substituted derivative thereof, or a compound depicted in FIG. 4 of PCT Publication Nos. WO 2014/189805 and WO 2014/189806. In some embodiments, the STING agonist is c-[A(2',5')pA(3',5')p] or a dithio ribose O-substituted derivative thereof, or is a compound depicted in FIG. 5 of PCT Publication Nos. WO 2014/189805 and WO 2014/189806. In some embodiments, the STING agonist is c-[G(2',5')pA(3',5')p], or a dithio ribose O-substituted derivative thereof, or is a compound depicted in FIG. 5 of PCT Publication Nos. WO 2014/189805 and WO 2014/189806. In some embodiments, the STING agonist is 2'-O-propargyl-cyclic-[A(2',5')pA(3',5')p] (2'-O-propargyl-ML-CDA) or a compound depicted in FIG. 7 of PCT Publication No. WO 2014/189806.

Other exemplary STING agonists are disclosed, e.g., in PCT Publication Nos. WO 2014/189805 and WO 2014/189806, and U.S. Publication No. 2015/0056225.

Exemplary TLR Agonists

In an embodiment, a combination described herein includes a Toll-like receptor (TLR) agonist. In some embodiments, the combination is used to treat a cancer, e.g., a cancer described herein, e.g., a solid tumor (e.g., a breast cancer, a squamous cell carcinoma, a melanoma, an ovarian cancer, a fallopian tube carcinoma, a peritoneal carcinoma, a soft tissue sarcoma, a melanoma, a breast cancer, an esophageal cancer, a head and neck cancer, an endometrial cancer, a cervical cancer, or a basal cell carcinoma), e.g., a hematologic malignancy (e.g., a leukemia (e.g., a chronic lymphocytic leukemia (CLL), or a lymphoma (e.g., a marginal zone B-cell lymphoma, a small lymphocytic lymphoma, a follicular lymphoma, Hodgkin lymphoma, non-Hodgkin lymphoma)).

TLRs are a family of pattern recognition receptors that were initially identified as sensors of the innate immune system that recognize microbial pathogens. In humans, the TLRs include TLR-1, TLR-2, TLR-3, TLR-4, TLR-5, TLR- 6, TLR-7, TLR-8, TLR-9, and TLR-10. TLR-1, -2, -4, -5, and -6, are expressed on the surface of cells and TLR-3, -7/8, and -9 are expressed with the ER compartment. Human dendritic cell subsets can be identified on the basis of distinct TLR expression patterns. The myeloid or "conventional" subset of human dendritic cells express TLRs 1-8 and the plasmacytoid subset of dendritic cells express only TLR-7 and TLR-9. Ligand binding to TLRs invokes a cascade of intra-cellular signaling pathways that induce the production of factors involved in inflammation and immunity. Upon stimulation, the myeloid subset and the plasmacytoid subset of human dendritic cells result in antigen-specific CD4+ and CD8+ T cell priming and activation of NK cells and T-cells, respectively.

In some embodiments, the TLR agonist is chosen from one or more of a TLR-1 agonist, a TLR-2 agonist, a TLR-3 agonist, a TLR-4 agonist, a TLR-5 agonist, a TLR-6 agonist, a TLR-7 agonist, a TLR-8 agonist, a TLR-9 agonist, a TLR-10 agonist, a TLR-1/2 agonist, a TLR-2/6 agonist, or a TLR-7/8 agonist. In one embodiment, the TLR agonist is a TLR7 agonist.

In some embodiments, the TLR agonist is imiquimod or 3-(2-Methylpropyl)-3,5,8-triazatricyclo[7.4.0.02,6]trideca-1 (9),2(6),4,7,10,12-hexaen-7-amine. Imiquimod or 3-(2-Methylpropyl)-3,5,8-triazatricyclo[7.4.0.02,6]trideca-1(9),2 (6),4,7,10,12-hexaen-7-amine can bind to and activate TLR-7 and/or TLR-8.

In some embodiments, the TLR agonist is 852A. 852A is disclosed, e.g., in Inglefield et al. *J Interferon Cytokine Res.* 2008; 28(4):253-63. 852A can bind to and activate TLR-7 and/or TLR-8.

In some embodiments, the TLR agonist is Bacille Calmette-Guérin (BCG). BCG can bind to and activate TLR-9.

In some embodiments, the TLR agonist is EMD 120108. EMD 120108 is a synthetic oligonucleotide containing phosphorothioate oligodeoxynucleotide. EMD 1201081 can bind to and activate TLR-9, e.g, in monocytes/macrophages, plasmacytoid dendritic cells (DCs) and B cells, initiating immune signaling pathways, activating B cells and inducing T-helper cell cytokine production.

In some embodiments, the TLR agonist is IMO-2055. IMO-2055 is a synthetic oligonucleotide containing unmethylated CpG dinucleotides. Mimicking unmethylated CpG sequences in bacterial DNA, IMO-2055 can bind to and activate TLR-9, e.g., in monocytes/macrophages, plasmacytoid dendritic cells (DCs) and B cells, initiating immune signaling pathways and activating B cells and DCs and inducing T-helper cell cytokine production.

Other exemplary TLR agonists that can be used in the combination include, e.g., TLR-1/2 agonists (e.g., Pam3Cys), TLR-2 agonists (e.g., CFA, MALP2, Pam2Cys, FSL-1, or Hib-OMPC), TLR-3 agonists (e.g., polyribosinic: polyribocytidic acid (Poly I:C), polyadenosine-polyuridylic acid (poly AU), polyinosinic-polycytidylic acid stabilized with poly-L-lysine and carboxymethylcellulose (Hiltonol®)), TLR-4 agonists (e.g., monophosphoryl lipid A (MPL), LPS, sialyl-Tn (STn)), TLR-5 agonists (e.g., bacterial flagellin), TLR-7 agonists (e.g., imiquimod), TLR-7/8 agonists (e.g., resiquimod or loxoribine), and TLR-9 agonists (e.g., unmethylated CpG dinucleotide (CpG-ODN)).

In another embodiment, the TLR agonist is used in combination with a GITR agonist, e.g., as described in WO2004060319, and International Publication No.: WO2014012479.

Exemplary VEGFR Inhibitors

In one embodiment, a combination described herein includes a vascular endothelial growth factor (VEGF) receptor inhibitor (e.g., an inhibitor of one or more of VEGFR (e.g., VEGFR-1, VEGFR-2, VEGFR-3) or VEGF). In some embodiments, the combination is used to treat a cancer, e.g., a cancer described herein, e.g., a solid tumor (e.g., a melanoma, a breast cancer, a colon cancer, an esophageal cancer, a gastrointestinal stromal tumor (GIST), a kidney cancer (e.g., a renal cell cancer), a liver cancer, a non-small cell lung cancer (NSCLC), an ovarian cancer, a pancreatic cancer, a prostate cancer, or a stomach cancer), e.g., a hematologic malignancy (e.g., a lymphoma).

In some embodiments, the VEGFR inhibitor is vatalanib succinate (Compound A47) or a compound disclosed in EP 296122.

In some embodiment, the VEGFR inhibitor is an inhibitor of one or more of VEGFR-2, PDGFRbeta, KIT or Raf kinase C, 1-methyl-5-((2-(5-(trifluoromethyl)-1H-imidazol-2-yl) pyridin-4-yl)oxy)-N-(4-(trifluoromethyl)phenyl)-1H-benzo [d]imidazol-2-amine (Compound A37) or a compound disclosed in PCT Publication No. WO 2007/030377.

Other exemplary VEGFR pathway inhibitors that can be used in the combinations disclosed herein include, e.g., bevacizumab (AVASTIN®), axitinib (INLYTA®); brivanib alaninate (BMS-582664, (S)-((R)-1-(4-(4-Fluoro-2-methyl-1H-indol-5-yloxy)-5-methylpyrrolo[2,1-f][1,2,4]triazin-6-yloxy)propan-2-yl)2-aminopropanoate); sorafenib (NEXAVAR®); pazopanib (VOTRIENT®); sunitinib malate (SUTENT®); cediranib (AZD2171, CAS 288383-20-1); vargatef (BIBF1120, CAS 928326-83-4); Foretinib (GSK1363089); telatinib (BAY57-9352, CAS 332012-40-5); apatinib (YN968D1, CAS 811803-05-1); imatinib (GLEEVEC®); ponatinib (AP24534, CAS 943319-70-8); tivozanib (AV951, CAS 475108-18-0); regorafenib (BAY73-4506, CAS 755037-03-7); vatalanib dihydrochloride (PTK787, CAS 212141-51-0); brivanib (BMS-540215, CAS 649735-46-6); vandetanib (CAPRELSA® or AZD6474); motesanib diphosphate (AMG706, CAS 857876-30-3, N-(2,3-dihydro-3,3-dimethyl-1H-indol-6-yl)-2-[(4-pyridinylmethyl)amino]-3-pyridinecarboxamide, described in PCT Publication No. WO 02/066470); dovitinib dilactic acid (TKI258, CAS 852433-84-2); linfanib (ABT869, CAS 796967-16-3); cabozantinib (XL184, CAS 849217-68-1); lestaurtinib (CAS 111358-88-4); N-[5-[[[5-(1,1-dimethylethyl)-2-oxazolyl]methyl]thio]-2-thiazolyl]-4-piperidinecarboxamide (BMS38703, CAS 345627-80-7); (3R,4R)-4-amino-1-((4-((3-methoxyphenyl)amino)pyrrolo [2,1-f][1,2,4]triazin-5-yl)methyl)piperidin-3-ol (BMS690514); N-(3,4-Dichloro-2-fluorophenyl)-6-methoxy-7-[[(3aα,5β,6aα)-octahydro-2-methylcyclopenta [c]pyrrol-5-yl]methoxy]-4-quinazolinamine (XL647, CAS 781613-23-8); 4-methyl-3-[[1-methyl-6-(3-pyridinyl)-1H-pyrazolo[3,4-d]pyrimidin-4-yl]amino]-N-[3-(trifluoromethyl)phenyl]-benzamide (BHG712, CAS 940310-85-0); aflibercept (EYLEA®), and endostatin (ENDOSTAR®).

Exemplary anti-VEGF antibodies that can be used in the combinations disclosed herein include, e.g., a monoclonal antibody that binds to the same epitope as the monoclonal anti-VEGF antibody A4.6.1 produced by hybridoma ATCC HB 10709; a recombinant humanized anti-VEGF monoclonal antibody generated according to Presta et al. (1997) Cancer Res. 57:4593-4599. In one embodiment, the anti-VEGF antibody is Bevacizumab (BV), also known as rhuMAb VEGF or AVASTIN®. It comprises mutated human IgG1 framework regions and antigen-binding complementarity-determining regions from the murine anti-hVEGF monoclonal antibody A.4.6.1 that blocks binding of human VEGF to its receptors. Bevacizumab and other humanized anti-VEGF antibodies are further described in U.S. Pat. No. 6,884,879 issued Feb. 26, 2005. Additional antibodies include the G6 or B20 series antibodies (e.g., G6-31, B20-4.1), as described in PCT Publication No. WO2005/012359, PCT Publication No. WO2005/044853, the contents of these patent applications are expressly incorporated herein by reference. For additional antibodies see U.S. Pat. Nos. 7,060,269, 6,582,959, 6,703,020, 6,054,297, WO98/45332, WO 96/30046, WO94/10202, EP 0666868B1, U.S. Patent Application Publication Nos. 2006009360, 20050186208, 20030206899, 20030190317, 20030203409, and 20050112126; and Popkov et al, *Journal of Immunological Methods* 288: 149-164 (2004). Other antibodies include those that bind to a functional epitope on human VEGF comprising of residues F17, M18, D19, Y21, Y25, Q89, 191, K101, E103, and C104 or, alternatively, comprising residues F17, Y21, Q22, Y25, D63, 183 and Q89.

Exemplary c-MET Inhibitors

In one embodiment, a combination described herein includes an inhibitor of c-MET. In some embodiments, the combination is used to treat a cancer, e.g., a cancer described herein, e.g., a solid tumor (e.g., a non-small cell lung cancer, a pancreatic cancer, a liver cancer, a thyroid cancer, a brain tumor (e.g., a glioblastoma), a kidney cancer (e.g., a renal cell carcinoma), a head and neck cancer (e.g., a head and neck squamous cell carcinoma).

In some embodiments, the c-MET inhibitor is Compound A17 or a compound described in U.S. Pat. Nos. 7,767,675 and 8,420,645). c-MET, a receptor tyrosine kinase overexpressed or mutated in many tumor cell types, plays key roles in tumor cell proliferation, survival, invasion, metastasis, and tumor angiogenesis. Inhibition of c-MET may induce cell death in tumor cells overexpressing c-MET protein or expressing constitutively activated c-MET protein.

In some embodiments, the c-MET inhibitor is JNJ-38877605. JNJ-38877605 is an orally available, small molecule inhibitor of c-Met. JNJ-38877605 selectively binds to c-MET, thereby inhibiting c-MET phosphorylation and disrupting c-Met signal transduction pathways.

In some embodiments, the c-Met inhibitor is AMG 208. AMG 208 is a selective small-molecule inhibitor of c-MET. AMG 208 inhibits the ligand-dependent and ligand-independent activation of c-MET, inhibiting its tyrosine kinase activity, which may result in cell growth inhibition in tumors that overexpress c-Met.

In some embodiments, the c-Met inhibitor is AMG 337. AMG 337 is an orally bioavailable inhibitor of c-Met. AMG 337 selectively binds to c-MET, thereby disrupting c-MET signal transduction pathways.

In some embodiments, the c-Met inhibitor is LY2801653. LY2801653 is an orally available, small molecule inhibitor of c-Met. LY2801653 selectively binds to c-MET, thereby inhibiting c-MET phosphorylation and disrupting c-Met signal transduction pathways.

In some embodiments, c-Met inhibitor is MSC2156119J. MSC2156119J is an orally bioavailable inhibitor of c-Met. MSC2156119J selectively binds to c-MET, which inhibits c-MET phosphorylation and disrupts c-Met-mediated signal transduction pathways.

In some embodiments, the c-MET inhibitor is capmatinib. Capmatinib is also known as INCB028060. Capmatinib is an orally bioavailable inhibitor of c-MET. Capmatinib selectively binds to c-Met, thereby inhibiting c-Met phosphorylation and disrupting c-Met signal transduction pathways.

In some embodiments, the c-MET inhibitor is crizotinib. Crizotinib is also known as PF-02341066. Crizotinib is an orally available aminopyridine-based inhibitor of the receptor tyrosine kinase anaplastic lymphoma kinase (ALK) and the c-Met/hepatocyte growth factor receptor (HGFR). Crizotinib, in an ATP-competitive manner, binds to and inhibits ALK kinase and ALK fusion proteins. In addition, crizotinib inhibits c-Met kinase, and disrupts the c-Met signaling pathway. Altogether, this agent inhibits tumor cell growth.

In some embodiments, the c-MET inhibitor is golvatinib. Golvatinib is an orally bioavailable dual kinase inhibitor of c-MET and VEGFR-2 with potential antineoplastic activity. Golvatinib binds to and inhibits the activities of both c-MET and VEGFR-2, which may inhibit tumor cell growth and survival of tumor cells that overexpress these receptor tyrosine kinases.

In some embodiments, the c-MET inhibitor is tivantinib. Tivantinib is also known as ARQ 197. Tivantinib is an orally bioavailable small molecule inhibitor of c-MET. Tivantinib binds to the c-MET protein and disrupts c-Met signal transduction pathways, which may induce cell death in tumor cells overexpressing c-MET protein or expressing constitutively activated c-Met protein.

Exemplary TGFb Inhibitors

In one embodiment, a combination described herein includes a transforming growth factor beta (TGF-β) inhibitor. In some embodiments, the combination is used to treat a cancer, e.g., a cancer described herein, e.g., a solid tumor (e.g., a brain cancer (e.g., a glioma), a melanoma, a kidney cancer (e.g., a renal cell carcinoma), a pleural malignant mesothelioma (e.g., a relapsed pleural malignant mesothelioma), or a breast cancer (e.g., a metastatic breast cancer)).

In some embodiments, the TGF-β inhibitor is fresolimumab (CAS Registry Number: 948564-73-6). Fresolimumab is also known as GC1008. Fresolimumab is a human monoclonal antibody that binds to and inhibits TGF-beta isoforms 1, 2 and 3.

The heavy chain of fresolimumab has the amino acid sequence of (SEQ ID NO: 300):
QVQLVQSGAEVKKPGSSVKVSCKASGYTFSSNVISWVRQAPGQGLEWMGG

VIPIVDIANYAQRFKGRVTITADESTSTTYMELSSLRSEDTAVYYCASTL

GLVLDAMDYWGQGTLVTVSSASTKGPSVFPLAPCSRSTSESTAALGCLVK

DYFPEPVTVSWNSGALTSGVHTFPAVLQSSGLYSLSSVVTVPSSSLGTKT

YTCNVDHKPSNTKVDKRVESKYGPPCPSCPAPEFLGGPSVFLFPPKPKDT

LMISRTPEVTCVVVDVSQEDPEVQFNWYVDGVEVHNAKTKPREEQFNSTY

RVVSVLTVLHQDWLNGKEYKCKVSNKGLPSSIEKTISKAKGQPREPQVYT

LPPSQEEMTKNQVSLTCLVKGFYPSDIAVEWESNGQPENNYKTTPPVLDS

DGSFFLYSRLTVDKSRWQEGNVFSCSVMHEALHNHYTQKSLSLSLGK.

The light chain of fresolimumab has the amino acid sequence of (SEQ ID NO: 301):
ETVLTQSPGTLSLSPGERATLSCRASQSLGSSYLAWYQQKPGQAPRLLIY

GASSRAPGIPDRFSGSGSGTDFTLTISRLEPEDFAVYYCQQYADSPITFG

QGTRLEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC.

Fresolimumab is disclosed, e.g., in WO 2006/086469, U.S. Pat. No. 8,383,780, and U.S. Pat. No. 8,591,901.

In some embodiments, the TGF-β inhibitor is XOMA 089. XOMA 089 is also known as XPA.42.089. XOMA 089 is a fully human monoclonal antibody that specifically binds and neutralizes TGF-beta 1 and 2 ligands.

```
The heavy chain variable region of XOMA 089 has
the amino acid sequence of (SEQ ID NO: 302):
QVQLVQSGAEVKKPGSSVKVSCKASGGTFSSYAISWVRQAPGQGLEWMG

GIIPIFGTANYAQKFQGRVTITADESTSTAYMELSSLRSEDTAVYYCAR

GLWEVRALPSVYWGQGTLVTVSS
(disclosed as SEQ ID NO: 6 in WO 2012/167143).

The light chain variable region of XOMA 089 has
the amino acid sequence of (SEQ ID NO: 303):
SYELTQPPSVSVAPGQTARITCGANDIGSKSVHWYQQKAGQAPVLVVSE

DIIRPSGIPERISGSNSGNTATLTISRVEAGDEADYYCQVWDRDSDQYV

FGTGTKVTVLG
(disclosed as SEQ ID NO: 8 in WO 2012/167143).
```

Exemplary IDO/TDO Inhibitors

In one embodiment, a combination described herein includes an inhibitor of indoleamine 2,3-dioxygenase (IDO) and/or tryptophan 2,3-dioxygenase (TDO). In some embodiments, the combination is used to treat a cancer, e.g., a cancer described herein, e.g., a solid tumor (e.g., melanoma, non-small cell lung cancer, colon cancer, squamous cell head and neck cancer, ovarian cancer, peritoneal cancer, fallopian tube cancer, breast cancer (e.g., metastatic or HER2-negative breast cancer)), e.g., a hematologic malignancy (e.g., a lymphoma, e.g., a non-Hodgkin lymphoma or a Hodgkin lymphoma (e.g., a diffuse large B-cell lymphoma (DLBCL))).

In some embodiments, the IDO/TDO inhibitor is chosen from (4E)-4-[(3-chloro-4-fluoroanilino)-nitrosomethylidene]-1,2,5-oxadiazol-3-amine (also known as INCB24360), indoximod (1-methyl-D-tryptophan), or α-cyclohexyl-5H-Imidazo[5,1-a]isoindole-5-ethanol (also known as NLG919).

In some embodiments, the IDO/TDO inhibitor is epacadostat (CAS Registry Number: 1204669-58-8). Epacadostat is also known as INCB24360 or INCB024360 (Incyte). Epacadostat is a potent and selective indoleamine 2,3-dioxygenase (IDO1) inhibitor with IC50 of 10 nM, highly selective over other related enzymes such as IDO2 or tryptophan 2,3-dioxygenase (TDO).

In some embodiments, the IDO/TDO inhibitor is indoximod (New Link Genetics). Indoximod, the D isomer of 1-methyl-tryptophan, is an orally administered small-molecule indoleamine 2,3-dioxygenase (IDO) pathway inhibitor that disrupts the mechanisms by which tumors evade immune-mediated destruction.

In some embodiments, the IDO/TDO inhibitor is NLG919 (New Link Genetics). NLG919 is a potent IDO (indoleamine-(2,3)-dioxygenase) pathway inhibitor with Ki/EC50 of 7 nM/75 nM in cell-free assays.

In some embodiments, the IDO/TDO inhibitor is F001287 (Flexus/BMS). F001287 is a small molecule inhibitor of indoleamine 2,3-dioxygenase 1 (IDO1).

Exemplary A2AR Antagonists

In one embodiment, a combination described herein includes an adenosine A2a receptor (A2aR) antagonist (e.g., an inhibitor of A2aR pathway, e.g., an adenosine inhibitor, e.g., an inhibitor of A2aR or CD-73). In some embodiments, the combination is used to treat a cancer, e.g., a cancer described herein.

In some embodiments, the A2aR antagonist is istradefylline (CAS Registry Number: 155270-99-8). Istradefylline is also known as KW-6002 or 8-[(E)-2-(3,4-dimethoxyphenyl)vinyl]-1,3-diethyl-7-methyl-3,7-dihydro-1H-purine-2,6-dione. Istradefylline is disclosed, e.g., in LeWitt et al. (2008) *Annals of Neurology* 63 (3): 295-302).

In some embodiments, the A2aR antagonist is tozadenant (Biotie). Tozadenant is also known as SYN115 or 4-hydroxy-N-(4-methoxy-7-morpholin-4-yl-1,3-benzothiazol-2-yl)-4-methylpiperidine-1-carboxamide. Tozadenant blocks the effect of endogenous adenosine at the A2a receptors, resulting in the potentiation of the effect of dopamine at the D2 receptor and inhibition of the effect of glutamate at the mGluR5 receptor. e.g., In some embodiments, the A2aR antagonist is preladenant (CAS Registry Number: 377727-87-2). Preladenant is also known as SCH 420814 or 2-(2-Furanyl)-7-[2-[4-[4-(2-methoxyethoxy)phenyl]-1-piperazinyl]ethyl]7H-pyrazolo[4,3-e][1,2,4]triazolo[1,5-c]pyrimidine-5-amine. Preladenant was developed as a drug that acted as a potent and selective antagonist at the adenosine A2A receptor.

In some embodiments, the A2aR antagonist is vipadenan. Vipadenan is also known as BIIB014, V2006, or 3-[(4-amino-3-methylphenyl)methyl]-7-(furan-2-yl)triazolo[4,5-d]pyrimidin-5-amine. e.g., In some embodiments, the A2aR antagonist is PBF-509 (Palobiofarma). e.g., In some embodiments, the A2aR antagonist, e.g., PBF-509 is administered at a daily dose of about 80 mg, 160 mg, or 240 mg.

Other exemplary A2aR antagonists include, e.g., ATL-444, MSX-3, SCH-58261, SCH-412,348, SCH-442,416, VER-6623, VER-6947, VER-7835, CGS-15943, or ZM-241,385.

In some embodiments, the A2aR antagonist is an A2aR pathway antagonist (e.g., a CD-73 inhibitor, e.g., an anti-CD73 antibody) is MEDI9447. MEDI9447 is a monoclonal antibody specific for CD73. Targeting the extracellular production of adenosine by CD73 may reduce the immunosuppressive effects of adenosine. MEDI9447 was reported to have a range of activities, e.g., inhibition of CD73 ectonucleotidase activity, relief from AMP-mediated lymphocyte suppression, and inhibition of syngeneic tumor growth. MEDI9447 can drive changes in both myeloid and lymphoid infiltrating leukocyte populations within the tumor microenvironment. These changes include, e.g., increases in CD8 effector cells and activated macrophages, as well as a reduction in the proportions of myeloid-derived suppressor cells (MDSC) and regulatory T lymphocytes.

Exemplary Oncolytic Viruses

In some embodiments, a combination as described herein includes an oncolytic virus. In embodiments, oncolytic viruses are capable of selectively replicating in and triggering the death of or slowing the growth of a cancer cell. In some cases, oncolytic viruses have no effect or a minimal effect on non-cancer cells. An oncolytic virus includes but is not limited to an oncolytic adenovirus, oncolytic Herpes Simplex Viruses, oncolytic retrovirus, oncolytic parvovirus, oncolytic vaccinia virus, oncolytic Sinbis virus, oncolytic influenza virus, or oncolytic RNA virus (e.g., oncolytic reovirus, oncolytic Newcastle Disease Virus (NDV), oncolytic measles virus, or oncolytic vesicular stomatitis virus (VSV)).

In some embodiments, the oncolytic virus is a virus, e.g., recombinant oncolytic virus, described in US2010/0178684 A1, which is incorporated herein by reference in its entirety. In some embodiments, a recombinant oncolytic virus comprises a nucleic acid sequence (e.g., heterologous nucleic acid sequence) encoding an inhibitor of an immune or inflammatory response, e.g., as described in US2010/0178684 A1, incorporated herein by reference in its entirety.

In embodiments, the recombinant oncolytic virus, e.g., oncolytic NDV, comprises a pro-apoptotic protein (e.g., apoptin), a cytokine (e.g., GM-CSF, CSF, interferon-gamma, interleukin-2 (IL-2), tumor necrosis factor-alpha), an immunoglobulin (e.g., an antibody against ED-B fibronectin), tumor associated antigen, a bispecific adapter protein (e.g., bispecific antibody or antibody fragment directed against NDV HN protein and a T cell co-stimulatory receptor, such as CD3 or CD28; or fusion protein between human IL-2 and single chain antibody directed against NDV HN protein). See, e.g., Zamarin et al. Future Microbiol. 7.3(2012):347-67, incorporated herein by reference in its entirety. In some embodiments, the oncolytic virus is a chimeric oncolytic NDV described in U.S. Pat. No. 8,591,881 B2, US 2012/0122185 A1, or US 2014/0271677 A1, each of which is incorporated herein by reference in their entireties.

In some embodiments, the oncolytic virus comprises a conditionally replicative adenovirus (CRAd), which is designed to replicate exclusively in cancer cells. See, e.g., Alemany et al. Nature Biotechnol. 18(2000):723-27. In some embodiments, an oncolytic adenovirus comprises one described in Table 1 on page 725 of Alemany et al., incorporated herein by reference in its entirety.

Exemplary oncolytic viruses include but are not limited to the following:

Group B Oncolytic Adenovirus (ColoAd1) (PsiOxus Therapeutics Ltd.) (see, e.g., Clinical Trial Identifier: NCT02053220);

ONCOS-102 (previously called CGTG-102), which is an adenovirus comprising granulocyte-macrophage colony stimulating factor (GM-CSF) (Oncos Therapeutics) (see, e.g., Clinical Trial Identifier: NCT01598129);

VCN-01, which is a genetically modified oncolytic human adenovirus encoding human PH20 hyaluronidase (VCN Biosciences, S.L.) (see, e.g., Clinical Trial Identifiers: NCT02045602 and NCT02045589);

Conditionally Replicative Adenovirus ICOVIR-5, which is a virus derived from wild-type human adenovirus serotype 5 (Had5) that has been modified to selectively replicate in cancer cells with a deregulated retinoblastoma/E2F pathway (Institut Català d'Oncologia) (see, e.g., Clinical Trial Identifier: NCT01864759);

Celyvir, which comprises bone marrow-derived autologous mesenchymal stem cells (MSCs) infected with ICOVIR5, an oncolytic adenovirus (Hospital Infantil Universitario Niño Jesùs, Madrid, Spain/Ramon Alemany) (see, e.g., Clinical Trial Identifier: NCT01844661);

CG0070, which is a conditionally replicating oncolytic serotype 5 adenovirus (Ad5) in which human E2F-1 promoter drives expression of the essential E1a viral genes, thereby restricting viral replication and cytotoxicity to Rb pathway-defective tumor cells (Cold Genesys, Inc.) (see, e.g., Clinical Trial Identifier: NCT02143804); or DNX-2401 (formerly named Delta-24-RGD), which is an adenovirus that has been engineered to replicate selectively in retinoblastoma (Rb)-pathway deficient cells and to infect cells that express certain RGD-binding integrins more efficiently (Clinica Universidad de Navarra, Universidad de Navarra/DNAtrix, Inc.) (see, e.g., Clinical Trial Identifier: NCT01956734).

In some embodiments, an oncolytic virus described herein is administering by injection, e.g., subcutaneous, intra-arterial, intravenous, intramuscular, intrathecal, or intraperitoneal injection. In embodiments, an oncolytic virus described herein is administered intratumorally, transdermally, transmucosally, orally, intranasally, or via pulmonary administration.

Exemplary Vaccines, e.g., Scaffold Vaccines

In one embodiment, a combination described herein includes a vaccine, e.g., a scaffold vaccine. In some embodiments, the combination is used to treat a cancer, e.g., a cancer described herein.

Cancer vaccines are disclosed, e.g., in PCT Publication Nos. WO 2007/070660 and WO 2012/167230, EP 1960009 B1, U.S. Pat. No. 8,067,237 and U.S. Pat. No. 8,932,583, and U.S. Publication No. US 2011/0020216. The components that can be used within cancer vaccines (e.g., implantable scaffold materials) are disclosed, e.g., in PCT Publication Nos. WO 2009/102465 and WO 2013/106852. Methods that can be used for administration of cancer vaccines are disclosed, e.g., in PCT Publication Nos. WO 2013/158673, WO 2012/048165, and WO 2012/149358.

In some embodiments, the cancer vaccine includes a macroporous scaffold comprising (i) cells or a cell recruitment composition, and (ii) a deployment signal capable of inducing or promoting migration of cells, and (iii) a bioactive composition coated or seeded onto/into the scaffold, which causes cells recruited into the scaffold to be modified. Migration of the modified cells can be promoted by the open, interconnected macropores and the deployment signal.

In some embodiments, the cancer vaccine induces an endogenous immune response to a cancer target via administration of a porous scaffold bearing a recruitment composition and a target antigen composition, wherein an endogenous antigen presenting cell is recruited into the scaffold to encounter antigen and where said cell resides until a deployment signal induces egress to a lymph node tissue outside the scaffold, thereby stimulating an endogenous immune response to said cancer target.

In some embodiments, the cancer vaccine is used to remove a target cell from a mammal using a scaffold composition.

In some embodiments, an in situ cancer vaccine is generated via recruitment of cancer cells to an implanted scaffold and destruction of the cells using a cytotoxic agent.

In some embodiments, a cytosine-guanosine oligonucleotide (CpG-ODN) is used as a component of a scaffold, which can effectively reprogram and deploy dendritic cells recruited to the scaffold, and generate an effective anti-tumor response.

In some embodiments, polyinosine-polycytidylic acid (poly I:C) and/or CpG ODN are used to exert a synergistic effect on tumor inhibition.

In some embodiments, porous rods comprising an immune cell recruitment compound (e.g. GM-CSF) and an immune cell activation compound (e.g. CpG ODN), and optionally comprising an antigen such as a tumor lysate, are used, e.g., to elicit an immune response to a vaccine antigen. In some embodiments, pores that facilitate recruitment or release of cells are formed in situ within hydrogels following hydrogel injection. In some embodiments, injectable shape memory porous hydrogel polymer is used for administration.

In other embodiments, the combinations disclosed herein include a cancer or tumor vaccine. Non-limiting examples of tumor vaccines that can be used include peptides of melanoma antigens, such as peptides of gp100, MAGE antigens, Trp-2, MART1 and/or tyrosinase, tumor cells transfected to express the cytokine GM-CSF, DNA-based vaccines, RNA-based vaccines, and viral transduction-based vaccines. The cancer vaccine may be prophylactic or therapeutic.

Many experimental strategies for vaccination against tumors have been devised (see Rosenberg, S., 2000, Development of Cancer Vaccines, ASCO Educational Book Spring: 60-62; Logothetis, C., 2000, ASCO Educational Book Spring: 300-302; Khayat, D. 2000, ASCO Educational Book Spring: 414-428; Foon, K. 2000, ASCO Educational Book Spring: 730-738; see also Restifo, N. and Sznol, M., *Cancer Vaccines*, Ch. 61, pp. 3023-3043 in DeVita, V. et al. (eds.), 1997, *Cancer*: Principles and Practice of Oncology. Fifth Edition). In one of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination (Dranoff et al. (1993) *Proc. Natl. Acad. Sci. U.S.A.* 90: 3539-43).

The combinations disclosed herein, e.g., PD-1 blockade, can be used in conjunction with a collection of recombinant proteins and/or peptides expressed in a tumor in order to generate an immune response to these proteins. These proteins are normally viewed by the immune system as self antigens and are therefore tolerant to them. The tumor antigen may also include the protein telomerase, which is required for the synthesis of telomeres of chromosomes and which is expressed in more than 85% of human cancers and in only a limited number of somatic tissues (Kim, N et al. (1994) *Science* 266: 2011-2013). (These somatic tissues may be protected from immune attack by various means). Tumor antigen may also be "neo-antigens" expressed in cancer cells because of somatic mutations that alter protein sequence or create fusion proteins between two unrelated sequences (ie. bcr-abl in the Philadelphia chromosome), or idiotype from B cell tumors.

Other tumor vaccines may include the proteins from viruses implicated in human cancers such a Human Papilloma Viruses (HPV), Hepatitis Viruses (HBV and HCV), Kaposi's Herpes Sarcoma Virus (KHSV), and Epstein-Barr virus (EBV). Another form of tumor specific antigen which may be used in conjunction with PD-1 blockade is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (Suot, R & Srivastava, P (1995) *Science* 269: 1585-1588; Tamura, Y. et al. (1997) *Science* 278:117-120).

Dendritic cells (DC) are potent antigen presenting cells that can be used to prime antigen-specific responses. DC's can be produced ex vivo and loaded with various protein and peptide antigens as well as tumor cell extracts (Nestle, F. et al. (1998) *Nature Medicine* 4: 328-332). DCs may also be transduced by genetic means to express these tumor antigens as well. DCs have also been fused directly to tumor cells for the purposes of immunization (Kugler, A. et al. (2000) *Nature Medicine* 6:332-336). As a method of vaccination, DC immunization may be effectively combined with other agent, e.g., PD-1 blockade, to activate more potent anti-tumor responses.

Exemplary Bispecific T-Cell Engagers

In one embodiment, a combination described herein includes a bispecific T-cell engager. In some embodiments, the combination is used to treat a cancer, e.g., a cancer described herein, e.g., a solid tumor (e.g., a gastrointestinal cancer, a melanoma, or a lung cancer) or a hematologic malignancy (e.g., a lymphoma (e.g., non-Hodgkin's lymphoma) or a leukemia (e.g., an acute lymphoblastic leukemia).

Bi-specific T-cell engagers (BiTE®) are a class of artificial bispecific monoclonal antibodies that can direct a host's immune system, e.g., the T cells' cytotoxic activity, against cancer cells. Bi-specific T-cell engagers can form a link between T cells and tumor cells, which causes T cells to exert cytotoxic activity on tumor cells by producing proteins like perforin and granzymes, independently of the presence of MHC I or co-stimulatory molecules. These proteins enter tumor cells and initiate the cell's apoptosis. This action mimics physiological processes observed during T cell attacks against tumor cells.

In some embodiments, the bi-specific T-cell engager is a fusion protein comprising two single-chain variable fragments (scFvs) of different antibodies. In some embodiments, one of the scFvs binds to T cells, e.g., via the CD3 receptor, and the other to a tumor cell, e.g., via a tumor specific molecule.

In some embodiments, the bi-specific T-cell engager is a bispecific antibody molecule of NKG2A and CD138, or a bispecific antibody molecule of CD3 and TCR. In some embodiments, the bispecific T-cell engager is a bispecific antibody molecule that binds to CD3 and a tumor antigen (e.g., EGFR, PSCA, PSMA, EpCAM, HER2 among others).

In some embodiments, the bi-specific T-cell engager is blinatumomab (CAS Registry Number: 853426-35-4). Blinatumomab is also known as MT103. Blinatumomab specifically targets a CD3 site for T cells and a CD19 site for B cells.

In some embodiments, the bi-specific T-cell engager is MT110. MT110 is a single-chain antibody that targets EpCAM and CD3. MT110 is disclosed, e.g., in Amann et al. *J Immunother.* 2009; 32(5):452-64.

In some embodiments, the bi-specific T-cell engager targets melanoma-associated chondroitin sulfate proteoglycan (MCSP). In some embodiments, the bi-specific T-cell engager targets CD33. In some embodiments the bi-specific T-cell engager comprises trastuzumab (targeting HER2/neu), cetuximab, or panitumumab (both targeting the EGF receptor), a functional fragment thereof. In some embodiments, the bi-specific T-cell engager targets CD66e and EphA2.

Exemplary GITR Agonist

In one embodiment, a combination described herein includes a GITR agonist. In some embodiments, the combination is used to treat a cancer, e.g., a cancer described herein, e.g., a solid tumor or a hematologic malignancy.

Exemplary GITR agonists include, e.g., GITR fusion proteins and anti-GITR antibodies (e.g., bivalent anti-GITR antibodies), such as, a GITR fusion protein described in U.S. Pat. No. 6,111,090, European Patent No. 0920505B1, U.S. Pat. No. 8,586,023, PCT Publication Nos.: WO 2010/003118 and 2011/090754, or an anti-GITR antibody described, e.g., in U.S. Pat. No. 7,025,962, European Patent No. 1947183B1, U.S. Pat. No. 7,812,135, U.S. Pat. No. 8,388,967, U.S. Pat. No. 8,591,886, European Patent No.: EP 1866339, PCT Publication No.: WO 2011/028683, U.S. Pat. No. 8,709,424, PCT Publication No.: WO 2013/039954, International Publication No.: WO2013/039954, U.S. Publication No.: US2014/0072566, International Publication NO.: WO2015/026684, PCT Publication No.: WO2005/007190, PCT Publication No.: WO 2007/133822, PCT Publication No.: WO2005/055808, PCT Publication No.: WO 99/40196, PCT Publication No.: WO 2001/03720, PCT Publication No.: WO99/20758, U.S. Pat. No. 6,689,607, PCT Publication No.: WO2006/083289, PCT Publication No.: WO 2005/115451, U.S. Pat. No. 7,618,632, PCT Publication No.: WO 2011/051726, International Publication No.: WO2004060319, and International Publication No.: WO2014012479.

In one embodiment, the GITR agonist is used in combination with a PD-1 inhibitor, e.g., as described in WO2015/026684.

In another embodiment, the GITR agonist is used in combination with a TLR agonist, e.g., as described in WO2004060319, and International Publication No.: WO2014012479.

Inhibitors of Immune Checkpoint Molecules

In one embodiment, the combinations disclosed herein include a PD-1 inhibitor, e.g., an anti-PD-1 antibody as described herein. In one embodiment, a combination of the PD-1 inhibitor includes a PD-L1 inhibitor, e.g., an anti-PD-L1 antibody molecule as described herein. In embodiments, the combination of the anti-PD-1 antibody and the anti-PD-L1 antibody are present as separate antibodies. In other embodiments, the anti-PD-1 antibody and the anti-PD-L1 antibody are present in the same antibody molecule, e.g., as a bispecific or multi-specific antibody molecule.

In other embodiments, the PD-1 inhibitor is an anti-PD-1 antibody chosen from Nivolumab, Pembrolizumab or Pidilizumab.

In some embodiments, the anti-PD-1 antibody is Nivolumab. Alternative names for Nivolumab include MDX-1106, MDX-1106-04, ONO-4538, or BMS-936558. In some embodiments, the anti-PD-1 antibody is Nivolumab (CAS Registry Number: 946414-94-4). Nivolumab is a fully human IgG4 monoclonal antibody which specifically blocks PD-1. Nivolumab (clone 5C4) and other human monoclonal antibodies that specifically bind to PD-1 are disclosed in U.S. Pat. No. 8,008,449 and WO2006/121168. In one embodiment, the inhibitor of PD-1 is Nivolumab, and having a sequence disclosed herein (or a sequence substantially identical or similar thereto, e.g., a sequence at least 85%, 90%, 95% identical or higher to the sequence specified).

The heavy and light chain amino acid sequences of Nivolumab are as follows:

Heavy chain
(SEQ ID NO: 304)
QVQLVESGGGVVQPGRSLRLDCKASGITFSNSGMHWVRQAPGKGLEWVAV
IWYDGSKRYYADSVKGRFTISRDNSKNTLFLQMNSLRAEDTAVYYCATND
DYWGQGTLVTVSSASTKGPSVFPLAPCSRSTSESTAALGCLVKDYFPEPV
TVSWNSGALTSGVHTFPAVLQSSGLYSLSSVVTVPSSSLGTKTYTCNVDH
KPSNTKVDKRVESKYGPPCPPCPAPEFLGGPSVFLFPPKPKDTLMISRTP
EVTCVVVDVSQEDPEVQFNWYVDGVEVHNAKTKPREEQFNSTYRVVSVLT
VLHQDWLNGKEYKCKVSNKGLPSSIEKTISKAKGQPREPQVYTLPPSQEE
MTKNQVSLTCLVKGFYPSDIAVEWESNGQPENNYKTTPPVLDSDGSFFLY
SRLTVDKSRWQEGNVFSCSVMHEALHNHYTQKSLSLSLGK Light chain
(SEQ ID NO: 305)
EIVLTQSPATLSLSPGERATLSCRASQSVSSYLAWYQQKPGQAPRLLIYD
ASNRATGIPARFSGSGSGTDFTLTISSLEPEDFAVYYCQQSSNWPRTFGQ
GTKVEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC In some embodiments, the anti-PD-1 antibody is Pembrolizumab. Pembrolizumab (also referred to as Lambrolizumab, MK-3475, MK03475, SCH-900475 or KEYTRUDA®; Merck) is a humanized IgG4 monoclonal antibody that binds to PD-1. Pembrolizumab and other humanized anti-PD-1 antibodies are disclosed in Hamid, O. et al. (2013) *New England Journal of Medicine* 369 (2): 134-44, U.S. Pat. No. 8,354,509 and WO2009/114335. The heavy and light chain amino acid sequences of Pembrolizumab are as follows:

Heavy chain
(SEQ ID NO: 306)

| | | | | | |
|---|---|---|---|---|---|
| QVQLVQSGVE | VKKPGASVKV | SCKASGYTFT | NYYMYWVRQA | PGQGLEWMGG | 50 |
| INPSNGGTNF | NEKFKNRVTL | TTDSSTTTAY | MELKSLQFDD | TAVYYCARRD | 100 |
| YRFDMGFDYW | GQGTTVTVSS | ASTKGPSVFP | LAPCSRSTSE | STAALGCLVK | 150 |
| DYFPEPVTVS | WNSGALTSGV | HTFPAVLQSS | GLYSLSSVVT | VPSSSLGTKT | 200 |
| YTCNVDHKPS | NTKVDKRVES | KYGPPCPPCP | APEFLGGPSV | FLFPPKPKDT | 250 |
| LMISRTPEVT | CVVVDVSQED | PEVQFNWYVD | GVEVHNAKTK | PREEQFNSTY | 300 |
| RVVSVLTVLH | QDWLNGKEYK | CKVSNKGLPS | SIEKTISKAK | GQPREPQVYT | 350 |
| LPPSQEEMTK | NQVSLTCLVK | GFYPSDIAVE | WESNGQPENN | YKTTPPVLDS | 400 |
| DGSFFLYSRL | TVDKSRWQEG | NVFSCSVMHE | ALHNHYTQKS | LSLSLGK | 447 |

Ligh chain
(SEQ ID NO: 307)

| | | | | | |
|---|---|---|---|---|---|
| EIVLTQSPAT | LSLSPGERAT | LSCRASKGVS | TSGYSYLHWY | QQKPGQAPRL | 50 |
| LIYLASYLES | GVPARFSGSG | SGTDFTLTIS | SLEPEDFAVY | YCQHSRDLPL | 100 |
| TFGGGTKVEI | KRTVAAPSVF | IFPPSDEQLK | SGTASVVCLL | NNFYPREAKV | 150 |
| QWKVDNALQS | GNSQESVTEQ | DSKDSTYSLS | STLTLSKADY | EKHKVYACEV | 200 |
| THQGLSSPVT | KSFNRGEC | | | | 218 |

In one embodiment, the inhibitor of PD-1 is Pembrolizumab disclosed in, e.g., U.S. Pat. No. 8,354,509 and WO 2009/114335, and having a sequence disclosed herein (or a sequence substantially identical or similar thereto, e.g., a sequence at least 85%, 90%, 95% identical or higher to the sequence specified).

In some embodiments, the anti-PD-1 antibody is Pidilizumab. Pidilizumab (CT-011; Cure Tech) is a humanized IgG1k monoclonal antibody that binds to PD-1. Pidilizumab and other humanized anti-PD-1 monoclonal antibodies are disclosed in WO2009/101611.

Other anti-PD-1 antibodies include AMP 514 (Amplimmune), among others, e.g., anti-PD-1 antibodies disclosed in U.S. Pat. No. 8,609,089, US 2010028330, and/or US 20120114649.

In some embodiments, the PD-1 inhibitor is an immunoadhesin (e.g., an immunoadhesin comprising an extracellular or PD-1 binding portion of PD-L1 or PD-L2 fused to a constant region (e.g., an Fc region of an immunoglobulin sequence). In some embodiments, the PD-1 inhibitor is AMP-224 (B7-DCIg; Amplimmune; e.g., disclosed in WO2010/027827 and WO2011/066342), is a PD-L2 Fc fusion soluble receptor that blocks the interaction between PD-1 and B7-H1.

Exemplary PD-L1 or PD-L2 Inhibitors

In some embodiments, the PD-L1 inhibitor is an antibody molecule, e.g., an anti-PD-L1 antibody molecule as described herein. In one embodiment, the anti-PD-L1 antibody molecule is chosen from an antibody molecule listed in the Summary section and the section entitled "Exemplary Anti-PD-L1 Antibody Molecules" disclosed herein.

In other embodiments, the PD-L1 inhibitor is chosen from YW243.55.570, MPDL3280A, MEDI-4736, MSB-0010718C, or MDX-1105.

In some embodiments, the anti-PD-L1 antibody is MSB0010718C. MSB0010718C (also referred to as A09-246-2; Merck Serono) is a monoclonal antibody that binds to PD-L1. Pembrolizumab and other humanized anti-PD-L1 antibodies are disclosed in WO2013/079174, and having a sequence disclosed herein (or a sequence substantially identical or similar thereto, e.g., a sequence at least 85%, 90%, 95% identical or higher to the sequence specified). The heavy and light chain amino acid sequences of MSB0010718C include at least the following:

```
Heavy chain (SEQ ID NO: 24 as disclosed in
WO2013/079174)
                                (SEQ ID NO: 308)
EVQLLESGGGLVQPGGSLRLSCAASGFTFSSYIMMWVRQAPGKGLEWVSS

IYPSGGITFYADKGRFTISRDNSKNTLYLQMNSLRAEDTAVYYCARIKLG

TVTTVDYWGQGTLVTSS

Light chain (SEQ ID NO: 25 as disclosed in
WO2013/079174)
                                (SEQ ID NO: 309)
QSALTQPASVSGSPGQSITISCTGTSSDVGGYNYVSWYQQHPGKAPKLMI

YDVSNRPSGVSNRFSGSKSGNTASLTISGLQAEDEADYYCSSYTSSSTRV

FGTGTKVTVL
```

In one embodiment, the PD-L1 inhibitor is YW243.55.S70. The YW243.55.S70 antibody is an anti-PD-L1 described in WO 2010/077634 (heavy and light chain variable region sequences shown in SEQ ID Nos. 20 and 21, respectively), and having a sequence disclosed therein (or a sequence substantially identical or similar thereto, e.g., a sequence at least 85%, 90%, 95% identical or higher to the sequence specified).

In one embodiment, the PD-L1 inhibitor is MDX-1105. MDX-1105, also known as BMS-936559, is an anti-PD-L1 antibody described in WO2007/005874, and having a sequence disclosed therein (or a sequence substantially identical or similar thereto, e.g., a sequence at least 85%, 90%, 95% identical or higher to the sequence specified).

In one embodiment, the PD-L1 inhibitor is MDPL3280A (Genentech/Roche). MDPL3280A is a human Fc optimized IgG1 monoclonal antibody that binds to PD-L1. MDPL3280A and other human monoclonal antibodies to PD-L1 are disclosed in U.S. Pat. No. 7,943,743 and U.S Publication No. 20120039906.

In other embodiments, the PD-L2 inhibitor is AMP-224. AMP-224 is a PD-L2 Fc fusion soluble receptor that blocks the interaction between PD-1 and B7-H1 (B7-DCIg; Amplimmune; e.g., disclosed in WO2010/027827 and WO2011/066342).

Exemplary LAG-3 Inhibitors

In one embodiment, the combinations disclosed herein include a LAG-3 inhibitor, e.g., an anti-LAG-3 antibody as described herein. In one embodiment, a combination of the LAG-3 inhibitor includes a PD-L1 inhibitor, e.g., an anti-PD-L1 antibody molecule as described herein. In embodiments, the combination of the anti-LAG-3 antibody and the anti-PD-L1 antibody are present as separate antibodies. In other embodiments, the anti-LAG-3 antibody and the anti-PD-L1 antibody are present in the same antibody molecule, e.g., as a bispecific or multi-specific antibody molecule.

In one embodiment, a combination described herein includes a LAG-3 inhibitor. In some embodiments, the combination is used to treat a cancer, e.g., a cancer described herein, e.g., a solid tumor or a hematologic malignancy.

In some embodiments, the anti-LAG-3 antibody is BMS-986016. BMS-986016 (also referred to as BMS986016; Bristol-Myers Squibb) is a monoclonal antibody that binds to LAG-3. BMS-986016 and other humanized anti-LAG-3 antibodies are disclosed in US 2011/0150892, WO2010/019570, and WO2014/008218.

Exemplary TIM-3 Inhibitors

In one embodiment, the combinations disclosed herein include a TIM-3 inhibitor, e.g., an anti-TIM-3 antibody as described herein. In one embodiment, a combination of the TIM-3 inhibitor includes a PD-L1 inhibitor, e.g., an anti-PD-L1 antibody molecule as described herein. In embodiments, the combination of the anti-TIM-3 antibody and the anti-PD-L1 antibody are present as separate antibodies. In other embodiments, the anti-TIM-3 antibody and the anti-PD-L1 antibody are present in the same antibody molecule, e.g., as a bispecific or multi-specific antibody molecule.

In one embodiment, a combination described herein includes a TIM-3 inhibitor. In some embodiments, the combination is used to treat a cancer, e.g., a cancer described herein, e.g., a solid tumor or a hematologic malignancy.

Exemplary anti-TIM-3 antibodies are disclosed in U.S. Pat. No. 8,552,156, WO 2011/155607, EP 2581113 and U.S Publication No. 2014/044728.

Exemplary CTLA-4 Inhibitors

In one embodiment, a combination described herein includes a CTLA-4 inhibitor. In some embodiments, the combination is used to treat a cancer, e.g., a cancer described herein, e.g., a solid tumor or a hematologic malignancy.

Exemplary anti-CTLA-4 antibodies include Tremelimumab (IgG2 monoclonal antibody available from Pfizer, formerly known as ticilimumab, CP-675,206); and Ipilimumab (CTLA-4 antibody, also known as MDX-010, CAS No. 477202-00-9).

In one embodiment, the combination includes an anti-PD-1 antibody molecule, e.g., as described herein, and an anti-CTLA-4 antibody, e.g., ipilimumab. Exemplary doses that can be use include a dose of anti-PD-1 antibody molecule of about 1 to 10 mg/kg, e.g., 3 mg/kg, and a dose of an anti-CTLA-4 antibody, e.g., ipilimumab, of about 3 mg/kg.

Other exemplary anti-CTLA-4 antibodies are disclosed, e.g., in U.S. Pat. No. 5,811,097.

Exemplary IAP Inhibitors

In one embodiment, a combination described herein includes an inhibitor of Inhibitor of Apoptosis Protein (IAP). In some embodiments, the combination is used to treat a cancer, e.g., a cancer described herein, e.g., a solid tumor (e.g., a breast cancer, an ovarian cancer, or a pancreatic cancer), e.g., a hematologic malignancy (e.g., a multiple myeloma).

In some embodiments, the IAP inhibitor is (S)-N-((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21) or a compound disclosed in U.S. Pat. No. 8,552,003.

In some embodiments, the IAP inhibitor, e.g., (S)-N-((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21) or a compound disclosed in U.S. Pat. No. 8,552,003, is administered at a dose of approximately 1800 mg, e.g., once weekly.

Exemplary EGFR Inhibitors

In one embodiment, a combination described herein includes an inhibitor of Epidermal Growth Factor Receptor (EGFR). In some embodiments, the combination is used to treat a cancer, e.g., a cancer described herein, e.g., a solid tumor (e.g., a lung cancer (e.g., a non-small cell lung cancer), a pancreatic cancer, a breast cancer, or a colon cancer).

In some embodiments, the EGFR inhibitor is (R,E)-N-(7-chloro-1-(1-(4-(dimethylamino)but-2-enoyl)azepan-3-yl)-1H-benzo[d]imidazol-2-yl)-2-methylisonicotinamide (Compound A40) or a compound disclosed in PCT Publication No. WO 2013/184757.

In some embodiments, the EGFR inhibitor, e.g., (R,E)-N-(7-chloro-1-(1-(4-(dimethylamino)but-2-enoyl)azepan-3-yl)-1H-benzo[d]imidazol-2-yl)-2-methylisonicotinamide (Compound A40) or a compound disclosed in PCT Publication No. WO 2013/184757, is administered at a dose of 150-250 mg, e.g., per day. In some embodiments, the EGFR inhibitor, e.g., (R,E)-N-(7-chloro-1-(1-(4-(dimethylamino)but-2-enoyl)azepan-3-yl)-1H-benzo[d]imidazol-2-yl)-2-methylisonicotinamide (Compound A40) or a compound disclosed in PCT Publication No. WO 2013/184757, is administered at a dose of about 150, 200, or 250 mg, or about 150-200 or 200-250 mg.

In some embodiments, the EGFR inhibitor is chosen from one of more of erlotinib, gefitinib, cetuximab, panitumumab, necitumumab, PF-00299804, nimotuzumab, or R05083945.

Exemplary mTOR Inhibitors

In one embodiment, a combination described herein includes an inhibitor of target of rapamycin (mTOR). In some embodiments, the combination is used to treat a cancer, e.g., a cancer described herein, e.g., a solid tumor (e.g., a prostate cancer, a breast cancer, a brain cancer, a bladder cancer, a renal cancer, or a liver cancer, a lung cancer (e.g., a small cell lung cancer or a non-small cell lung cancer), a respiratory/thoracic cancer, a sarcoma, a bone cancer, a non-small cell lung cancer, an endocrine cancer, an astrocytoma, a cervical cancer, a neurologic cancer, a gastric cancer, or a melanoma), e.g., a hematologic malignancy (e.g., a leukemia (e.g., lymphocytic leukemia), e.g., a lymphoma, or e.g., a multiple myeloma).

In some embodiments, the mTOR inhibitor is dactolisib (Compound A4) or 8-(6-Methoxy-pyridin-3-yl)-3-methyl-1-(4-piperazin-1-yl-3-trifluoromethyl-phenyl)-1,3-dihydro-imidazo[4,5-c]quinolin-2-one (Compound A41), or a compound disclosed in PCT Publication No. WO 2006/122806.

In some embodiments, the mTOR inhibitor is everolimus (also known as AFINITOR®; Compound A36) or a compound disclosed in PCT Publication No. WO 2014/085318.

In some embodiments, the mTOR inhibitor, e.g., everolimus (Compound A36) or a compound disclosed in PCT Publication No. WO 2014/085318, is administered at a dose of about 2.5-20 mg/day. In one embodiment, the TOR inhibitor, e.g., everolimus (Compound A36) or a compound disclosed in PCT Publication No. WO 2014/085318, is administered at a dose of about 2.5, 5, 10, or 20 mg/day, e.g., about 2.5-5, 5-10, or 10-20 mg/day.

In some embodiments, the mTOR inhibitor is chosen from one or more of rapamycin, temsirolimus (TORISEL®), AZD8055, BEZ235, BGT226, XL765, PF-4691502, GDC0980, SF1126, OSI-027, GSK1059615, KU-0063794, WYE-354, Palomid 529 (P529), PF-04691502, or PKI-587, ridaforolimus (formally known as deferolimus, (1R,2R,4S)-4-[(2R)-2 [(1R,9S,12S,15R,16E,18R,19R, 21R, 23S,24E, 26E,28Z,30S,32S,35R)-1,18-dihydroxy-19,30-dimethoxy-15,17,21,23,29,35-hexamethyl-2,3,10,14,20-pentaoxo-11, 36-dioxa-4-azatricyclo[30.3.1.04,9]hexatriaconta-16,24,26, 28-tetraen-12-yl]propyl]-2-methoxycyclohexyl dimethylphosphinate, also known as AP23573 and MK8669, and described in PCT Publication No. WO 03/064383); everolimus (AFINITOR® or RAD001); rapamycin (AY22989, SIROLIMUS®); simapimod (CAS Registry Number: 164301-51-3); (5-{2,4-Bis[(3S)-3-methylmorpholin-4-yl]pyrido[2,3-d]pyrimidin-7-yl}-2-methoxyphenyl)methanol (AZD8055); 2-Amino-8-[trans-4-(2-hydroxyethoxy)cyclohexyl]-6-(6-methoxy-3-pyridinyl)-4-methyl-pyrido[2,3-d]pyrimidin-7(8H)-one (PF04691502, CAS Registry Number: 1013101-36-4); N2-[1,4-dioxo-4-[[4-(4-oxo-8-phenyl-4H-1-benzopyran-2-yl)morpholinium-4-yl]methoxy]butyl]-L-arginylglycyl-L-α-aspartylL-serine inner salt (SF1126, CAS Registry Number: 936487-67-1), or XL765 (SAR245409).

Other exemplary mTOR Inhibitors include, but are not limited to, temsirolimus; ridaforolimus (1R,2R,4S)-4-[(2R)-2 [(1R,9S,12S,15R,16E,18R,19R, 21R, 23S,24E,26E, 28Z,30S,32S,35R)-1,18-dihydroxy-19,30-dimethoxy-15, 17,21,23,29,35-hexamethyl-2,3,10,14,20-pentaoxo-11,36-dioxa-4-azatricyclo[30.3.1.0$^{4,9}$]hexatriaconta-16,24,26,28-tetraen-12-yl]propyl]-2-methoxycyclohexyl dimethylphosphinate, also known as AP23573 and MK8669; everolimus (RAD001); rapamycin (AY22989); simapimod; (5-{2,4-bis[(3S)-3-methylmorpholin-4-yl]pyrido[2,3-d]pyrimidin-7-yl}-2-methoxyphenyl)methanol (AZD8055); 2-mmino-8-[trans-4-(2-hydroxyethoxy)cyclohexyl]-6-(6-methoxy-3-pyridinyl)-4-methyl-pyrido[2,3-d]pyrimidin-7(8H)-one (PF04691502); and N²-[1,4-dioxo-4-[[4-(4-oxo-8-phenyl-4H-1-benzopyran-2-yl)morpholinium-4-yl]methoxy]butyl]-L-arginylglycyl-L-α-aspartylL-serine-(SEQ ID NO: 360), inner salt (SF1126); and XL765.

Exemplary IL-15 Agonists

In one embodiment, a combination described herein includes an interleukin-15 (IL-15) agonist. In some embodiments, the combination is used to treat a cancer, e.g., a cancer described herein, e.g., a solid tumor (e.g., a refractory solid tumor), (e.g., a melanoma (e.g., a metastatic or advanced melanoma), a kidney cancer (e.g., a renal cell cancer), a non-small cell lung cancer, a squamous cell head and neck cancer, or a bladder cancer (e.g., a non-muscle invasive bladder cancer)), e.g., a hematologic malignancy (e.g., a leukemia, e.g., an acute myelogenous leukemia (e.g., a refractory or relapsed acute myelogenous leukemia), e.g., a lymphoma, e.g., a non-Hodgkin lymphoma (e.g., a relapsed/refractory indolent B cell non-Hodgkin lymphoma), e.g., or a multiple myeloma (e.g., a relapsed or refractory multiple myeloma)).

IL-15, secreted by mononuclear phagocytes (and some other cell types) following viral infection, regulates T and natural killer cell activation and proliferation. This cytokine induces activation of transcription activators STAT3, STAT5, and STAT6 via JAK kinase signal transduction pathways in mast cells, T cells, and dendritic epidermal T cells. IL-15 and interleukin-2 (IL-2) are structurally similar and share many biological activities; both may bind to common hematopoietin receptor subunits, negatively regulating each other's activity. CD8+ memory T cell number can be regulated by a balance between IL-15 and IL-2.

In some embodiments, the IL-15 agonist is a recombinant human IL-15 (rhIL-15), e.g., CYP0150 (Cytune). CYP0150 is a recombinant protein consisting of a human IL-15 linked to the Sushi+ domain of the human alpha chain receptor (transpresentation).

CYP0150 is disclosed, e.g., in PCT Publication No. WO 2007/046006. CYP0150 has the amino acid sequence of:

```
                                           (SEQ ID NO: 310)
MAPRRARGCRTLGLPALLLLLLLRPPATRGDYKDDDDKIEGRITCPPPMS

VEHADIWVKSYSLYSRERYICNSGFKRKAGTSSLTECVLNKATNVAHWTT

PSLKCIRDPALVHQRPAPPSGGSGGGGSGGGSGGGGSLQNWVNVISDLKK

IEDLIQSMHIDATLYTESDVHPSCKVTAMKCFLLELQVISLESGDASIHD

TVENLIILANNSLSSNGNVTESGCKECEELEEKNIKEFLQSFVHIVQMFI

NTS
(disclosed as SEQ ID NO: 60 in WO 2007/046006)
or
                                           (SEQ ID NO: 311)
MDSKGSSQKAGSRLLLLLVVSNLLLCQGVVSTTRDYKDDDDKIEGRNWVN

VISDLKKIEDLIQSMHIDATLYTESDVHPSCKVTAMKCFLLELQVISLES

GDASIHDTVENLIILANNSLSSNGNVTESGCKECEELEEKNIKEFLQSFV

HIVQMFINTSSGGGSGGGGSGGGGSGGGGSGGGSLQITCPPPMSVEHADI

WVKSYSLYSRERYICNSGFKRKAGTSSLTECVLNKATNVAHWTTPSLKCI

RDPALVHQRPAPP
(disclosed as SEQ ID NO: 62 in WO 2007/046006).
```

In some embodiments, the IL-15 agonist is ALT-803 (Altor BioScience). ALT-803 is an IL-15N72D:IL-15RαSu/Fc soluble complex, produced from a high-yield recombinant mammalian cell line that co-expresses IL-15N72D and IL-15RαSu/Fc fusion protein. The IL-15 mutant (N72D) has enhanced IL-15 biological activity (Zhu et al. 2009, *J Immunol.* 183:3598). The IL-15N72D mutant and the soluble domain of IL-15Rα can form stable heterodimeric complexes in solution and this complex exhibits increased biological activity (approximately 25-fold more active) compared to the non-complexed IL-15. ALT-803 is disclosed, e.g., in PCT Publication No. WO 2012/040323 and U.S. Pat. No. 8,507,222.

In some embodiments, the IL-15 agonist is hetIL-15 (Admune). HetIL-15 is a heterodimeric human IL-15 (IL-15/sIL-15Ra). HetIL-15 is disclosed, e.g., in PCT Publication Nos. WO 2009/002562 and WO 2014/066527.

Exemplary CD40 Agonists

In one embodiment, the combination includes a CD40 agonist. In some embodiments, the combination is used to treat a cancer, e.g., a cancer described herein, e.g., a solid tumor (e.g., a lung cancer, an esophageal carcinoma, a melanoma, or a renal cell carcinoma), e.g., a hematologic malignancy (e.g., a leukemia (e.g., a chronic lymphocytic leukemia (CLL)), e.g., a lymphoma (e.g., a non-Hodgkin's lymphoma), e.g., or a multiple myeloma).

In one embodiment, the CD40 agonist is ADC-1013 (Alligator/BioInvent). ADC-1013 is a fully human IgG agonistic monoclonal antibody against human CD40. CD40, an integral membrane protein found on the surface of B lymphocytes, is a member of the tumor necrosis factor receptor superfamily and is highly expressed in a number of cancers such as B-cell malignancies. CD40 agonists, e.g., anti-CD40 antibodies, are able to substitute effectively for T cell helper activity (Ridge, J. et al. (1998) *Nature* 393: 474-478).

ADC-1013 is disclosed, e.g., in PCT Publication No. WO 2015/091853. ADC-1013 clones include, e.g., 1136/1137, 1132/1133, 1148/1149, 1140/1135, 1134/1135, 1107/1108, 1142/1135, 1146/1147, and 1150/1151.

```
The heavy chain variable region of 1132/1133 has
the amino acid sequence of:
                                           (SEQ ID NO: 312)
EVQLLESGGGLVQPGGSLRLSCAASGFTFSSYAMSWVRQAPGKGLEWVSG

IGSYGGGTYYADSVKGRFTISRDNSKNTLYLQMNSLRAEDTAVYYCARYV

NFGMDYWGQGTLVTVSS
(disclosed as SEQ ID NO: 65 in WO 2015/091853).

The light chain variable region of 1132/1133 has
the amino acid sequence of:
                                           (SEQ ID NO: 313)
DIQMTQSPSSLSASVGDRVTITCRASQSISSYLNWYQQKPGKAPKLLIYA

ASSLQSGVPSRFSGSGSGTDFTLTISSLQPEDFATYYCQQYGRNPPTFGQ

GTKLEIK
(disclosed as SEQ ID NO: 66 in WO 2015/091853).
```

The heavy chain CDR1 of 1132/1133 has the amino acid sequence of: GFTFSSYA (SEQ ID NO: 314) (disclosed as SEQ ID NO: 13 in WO 2015/091853). The heavy chain CDR2 of 1132/1133 has the amino acid sequence of: IGSYGGGT (SEQ ID NO: 315) (disclosed as SEQ ID NO: 14 in WO 2015/091853). The heavy chain CDR3 of 1132/1133 has the amino acid sequence of: ARYVNFGMDY (SEQ ID NO: 316) (disclosed as SEQ ID NO: 15 in WO 2015/091853). The light chain CDR1 of 1132/1133 has the amino acid sequence of: QSISSY (SEQ ID NO: 317) (disclosed as SEQ ID NO: 16 in WO 2015/091853). The light chain CDR2 of 1132/1133 has the amino acid sequence of: AAS (SEQ ID NO: 289) (disclosed as SEQ ID NO: 17 in WO 2015/091853). The light chain CDR3 of 1132/1133 has the amino acid sequence of: QQYGRNPPT (SEQ ID NO: 318) (disclosed as SEQ ID NO: 18 in WO 2015/091853).

The heavy chain variable region of 1107/1108 has the amino acid sequence of:
(SEQ ID NO: 319)
EVQLLESGGGLVQPGGSLRLSCAASGFTFSSYAMSWVRQAPGKGLEWVSA

ISGSGGSTYYADSVKGRFTISRDNSKNTLYLQMNSLRAEDTAVYYCARRV

WGFDYWGQGTLVTVSS
(disclosed as SEQ ID NO: 79 in WO 2015/091853).

The light chain variable region of 1107/1108 has the amino acid sequence of (SEQ ID NO: 320):
DIQMTQSPSSLSASVGDRVTITCRASQSISSYLNWYQQKPGKAPKLLIYA

ASSLQSGVPSRFSGSGSGT DFTLTISSLQPEDFATYYCQQYGVYPFTFG

QGTKLEIK
(disclosed as SEQ ID NO: 80 in WO 2015/091853).

The heavy chain CDR1 of 1107/1108 has the amino acid sequence of: GFTFSSYA (SEQ ID NO: 314) (disclosed as SEQ ID NO: 55 in WO 2015/091853). The heavy chain CDR2 of 1107/1108 has the amino acid sequence of: ISGSGGST (SEQ ID NO: 321) (disclosed as SEQ ID NO: 56 in WO 2015/091853). The heavy chain CDR3 of 1107/1108 has the amino acid sequence of: ARRVWGFDY (SEQ ID NO: 322) (disclosed as SEQ ID NO: 57 in WO 2015/091853). The light chain CDR1 of 1107/1108 has the amino acid sequence of: QSISSY (SEQ ID NO: 317) (disclosed as SEQ ID NO: 58 in WO 2015/091853). The light chain CDR2 of 1107/1108 has the amino acid sequence of: AAS (SEQ ID NO: 289) (disclosed as SEQ ID NO: 59 in WO 2015/091853). The light chain CDR3 of 1107/1108 has the amino acid sequence of: QQYGVYPFT (SEQ ID NO: 323) (disclosed as SEQ ID NO: 60 in WO 2015/091853).

In some embodiments, the CD40 agonist is ISF35. ISF35 is a chimeric CD154. ISF is disclosed in PCT Publication Nos. WO 2003/099340 and WO 2008/070743.

In some embodiments, the CD40 agonist is dacetuzumab. Dacetuzumab is also known as SGN-40 or huS2C6. Dacetuzumab is a humanized monoclonal antibody that targets CD40. Dacetuzumab is disclosed, e.g., in Advani et al. *J Clin Oncol.* 2009; 27(26):4371-7; and Khubchandani et al. *Curr Opin Investig Drugs.* 2009; 10(6):579-87.

In some embodiments, the CD40 agonist is lucatumumab (CAS Registry Number: 903512-50-5). Lucatumumab is also known as CHIR-12.12 or HCD-122. Lucatumumab binds to and inhibits CD40, thereby inhibiting CD40 ligand-induced cell proliferation and triggering cell lysis via antibody-dependent cellular cytotoxicity (ADCC) in cells overexpressing CD40. Lucatumumab is disclosed, e.g., in Tai et al. *Cancer Res.* 2005; 65(13):5898-906.

Anti-CD40 antibodies are able to substitute effectively for T cell helper activity (Ridge, J. et al. (1998) Nature 393: 474-478) and can be used in conjunction with PD-1 antibodies (Ito, N. et al. (2000) Immunobiology 201 (5) 527-40).

Exemplary OX40 Agonists

In one embodiment, a combination described herein includes an OX40 agonist. In some embodiments, the combination is used to treat a cancer, e.g., a cancer described herein, e.g., a solid tumor (e.g., a breast cancer, a melanoma, a head and neck cancer, or a prostate cancer), e.g., a hematologic malignancy (e.g., a lymphoma (e.g., a B-cell lymphoma)).

OX40, also known as CD134, is a cell surface glycoprotein and member of the tumor necrosis factor (TNF) receptor superfamily, is expressed on T-lymphocytes and provides a co-stimulatory signal for the proliferation and survival of activated T-cells. OX40 activation can induce proliferation of effector T-lymphocytes, which promotes an immune response against the tumor cells that express tumor-associated antigens (TAAs).

In some embodiments, the OX40 agonist is chosen from mAb 106-222, humanized 106-222 (Hu106), mAb 119-122, or humanized 119-122 (Hu119).

MAb 106-222, humanized 106-222 (Hu106), mAb 119-122, and humanized 119-122 (Hu119) are disclosed, e.g., in PCT Publication No. WO 2012/027328 and U.S. Pat. No. 9,006,399. The amino acid sequence of the heavy chain variable region of mAb 106-222 is disclosed as SEQ ID NO: 4 in WO 2012/027328. The amino acid sequence of the light chain variable region of mAb 106-222 is disclosed as SEQ ID NO: 10 in WO 2012/027328. The amino acid sequence of the heavy chain variable region of humanized 106-222 (Hu106) is disclosed as SEQ ID NO: 5 in WO 2012/027328. The amino acid sequence of the light chain variable region of humanized 106-222 (Hu106) is disclosed as SEQ ID NO: 11 in WO 2012/027328. The amino acid sequence of the heavy chain variable region of mAb 119-122 is disclosed as SEQ ID NO: 16 in WO 2012/027328. The amino acid sequence of the light chain variable region of mAb 119-122 is disclosed as SEQ ID NO: 22 in WO 2012/027328. The amino acid sequence of the heavy chain variable region of humanized 119-122 (Hu119) is disclosed as SEQ ID NO: 17 in WO 2012/027328. The amino acid sequence of the light chain variable region of humanized 119-122 (Hu119) is disclosed as SEQ ID NO: 23 in WO 2012/027328.

In some embodiments, the OX40 agonist is a humanized monoclonal antibody disclosed in U.S. Pat. No. 7,959,925 and PCT Publication No. WO 2006/121810.

In some embodiments, the OX40 agonist is chosen from MEDI6469, MEDI0562, or MEDI6383. MEDI6469 is a murine monoclonal antibody against OX40. MEDI0562 is a humanized monoclonal antibody against OX40. MEDI6383 is a monoclonal antibody against OX40.

In some embodiments, the OX40 agonist, e.g., MEDI6469, is administered intravenously at a dose of approximately 0.4 mg/kg, e.g., every other day.

Other exemplary anti-OX-40 antibodies are disclosed, e.g., in Weinberg, A. et al. (2000) *Immunol* 164: 2160-2169).

Exemplary CD27 Agonists

In one embodiment, a combination described herein includes a CD27 agonist. In some embodiments, the combination is used to treat a cancer, e.g., a cancer described herein, e.g., a solid tumor (e.g., a melanoma, a renal cell carcinoma, a hormone-refractory prostate adenocarcinoma, an ovarian cancer, a breast cancer, a colorectal adenocarcinoma, or a non-small cell lung cancer), e.g., a hematologic malignancy (e.g., a lymphoma (e.g., a Hodgkin's lymphoma, a Burkett's lymphoma, a mantle cell lymphoma, a primary lymphoma of the central nervous system, or a marginal zone B-cell lymphoma), or a leukemia (e.g., a chronic lymphocytic leukemia (CLL)).

In one embodiment, the CD27 agonist is Varlilumab (CAS Registry Number: 1393344-72-3). Varlilumab is also known as CDX-1127 (Celldex) or 1F5. Varlilumab is a fully human monoclonal antibody (mAb) that targets CD27, molecule in the activation pathway of lymphocytes. CDX-1127 is an agonist anti-CD27 mAb that can activate human T cells in the context of T cell receptor stimulation and therefore mediate anti-tumor effects. CDX-1127 can also provide direct therapeutic effects against tumors with CD27 expression.

Varlilumab is disclosed, e.g., in Vitale et al., *Clin Cancer Res.* 2012; 18(14):3812-21, WO 2008/051424, and U.S. Pat. No. 8,481,029.

In one embodiment, the CD27 agonist is BION-1402 (BioNovion). BION-1402 is also known as hCD27.15. BION-1402 is an anti-human CD27 monoclonal antibody. BION-1402 can stimulate the proliferation and/or survival of CD27+ cells. BION-1402 can activate human CD27 more effectively than its ligand CD70, which results in a significantly increased effect on proliferation of CD8+ and CD4+ T-cells.

BION-1402 is disclosed, e.g., as hCD27.15 in WO 2012/004367. This antibody is produced by hybridoma hCD27.15, which was deposited with the ATCC in on Jun. 2, 2010 under number PTA-11008.

```
The heavy chain variable region of hCD27.15 has
the amino acid sequence of:
                                    (SEQ ID NO: 324)
EVRLQQSGADLVKPGASVKLSCASGFIIKATYMHWVRQRPEQGLEWIGRI

DPANGE KYDPKFQVKAITADTSSSTAYLQLNSLTSDDTAVYYCARYAWY

FDVWGAGTTVTVSSAKTTPPXVYPXXPGS
(disclosed as SEQ ID NO: 3 in WO 2012/004367).

The light chain variable region of hCD27.15 has
the amino acid sequence of:
                                    (SEQ ID NO: 325)
DIQMTQSPASLSASVGDTVTITCRASENIYSFLAWYHQKQGRSPQLLVYH

AKTLAEGVPSRFSGSGSGTQFSLKINSLQAEDFGSYYCQHYYGSPLTFGA

GTKLEVKRADAAPTVSIFPPSSEELSL
(disclosed as SEQ ID NO: 4 in WO 2012/004367).

The heavy chain CDR1 of hCD27.15 has the amino
acid sequence of:
                                    (SEQ ID NO: 326)
GFIIKATYMH
(disclosed as SEQ ID NO: 5 in WO 2012/004367).
```

The heavy chain CDR2 of hCD27.15 has the amino acid sequence of: RIDPANGETKYDPKFQV (SEQ ID NO: 327) (disclosed as SEQ ID NO: 6 in WO 2012/004367). The heavy chain CDR3 of hCD27.15 has the amino acid sequence of: YAWYFDV (SEQ ID NO: 328) (disclosed as SEQ ID NO: 7 in WO 2012/004367). The light chain CDR1 of hCD27.15 has the amino acid sequence of: RASENIYSFLA (SEQ ID NO: 329) (disclosed as SEQ ID NO: 8 in WO 2012/004367). The light chain CDR2 of hCD27.15 has the amino acid sequence of: HAKTLAE (SEQ ID NO: 330) (disclosed as SEQ ID NO: 9 in WO 2012/004367). The light chain CDR3 of hCD27.15 has the amino acid sequence of: QHYYGSPLT (SEQ ID NO: 331) (disclosed as SEQ ID NO: 10 in WO 2012/004367).

Exemplary CSF-1/1R Binding Agents

In one embodiment, a combination described herein includes a CSF-1/1R binding agent. In some embodiments, the combination is used to treat a cancer, e.g., a cancer described herein, e.g., a solid tumor (e.g., a prostate cancer, a breast cancer, or pigmented villonodular synovitis (PVNS)).

In some embodiments, the CSF-1/1R binding agent is an inhibitor of macrophage colony-stimulating factor (M-CSF).

In another embodiment, the CSF-1/1R binding agent is a CSF-1R tyrosine kinase inhibitor, 4-((2-(((1R,2R)-2-hydroxycyclohexyl)amino)benzo[d]thiazol-6-yl)oxy)-N-methylpicolinamide (Compound A15), or a compound disclosed in PCT Publication No. WO 2005/073224.

In some embodiments, the CSF-1/1R binding agent is an M-CSF inhibitor, Compound A33, or a binding agent to CSF-1 disclosed in PCT Publication No. WO 2004/045532 or PCT Publication No WO 2005/068503 including RX1 or 5H4 (e.g., an antibody molecule or Fab fragment against M-CSF).

In some embodiments, the CSF-1/1R binding agent, e.g., an M-CSF inhibitor, Compound A33, or a compound disclosed in PCT Publication No. WO 2004/045532 (e.g., an antibody molecule or Fab fragment against M-CSF), is administered at an average dose of about 10 mg/kg. In some embodiments, the CSF-1/1R binding agent is a CSF1R inhibitor or 4-(2-((1R, 2R)-2-hydroxycyclohexylamino)benzothiazol-6-yloxy)-N-methylpicolinamide. 4-(2-((1R,2R)-2-hydroxycyclohexylamino)benzothiazol-6-yloxy)-N-methylpicolinamide is disclosed as example 157 at page 117 of PCT Publication No. WO 2007/121484.

In some embodiments, the CSF-1/1R binding agent is pexidartinib (CAS Registry Number 1029044-16-3). Pexidrtinib is also known as PLX3397 or 5-45-chloro-1H-pyrrolo[2,3-b]pyridin-3-yl)methyl)-N-((6-(trifluoromethyl)pyridin-3-yl)methyl)pyridin-2-amine. Pexidartinib is a small-molecule receptor tyrosine kinase (RTK) inhibitor of KIT, CSF1R and FLT3. FLT3, CSF1R and FLT3 are overexpressed or mutated in many cancer cell types and play major roles in tumor cell proliferation and metastasis. PLX3397 can bind to and inhibit phosphorylation of stem cell factor receptor (KIT), colony-stimulating factor-1 receptor (CSF1R) and FMS-like tyrosine kinase 3 (FLT3), which may result in the inhibition of tumor cell proliferation and down-modulation of macrophages, osteoclasts and mast cells involved in the osteolytic metastatic disease. In some embodiments, the CSF-1/1R binding agent, e.g., pexidartinib, is used in combination with a PD-1 inhibitor, e.g., an anti-PD-1 antibody molecule described herein.

In some embodiments, the CSF-1/1R binding agent is emactuzumab. Emactuzumab is also known as RG7155 or RO5509554. Emactuzumab is a humanized IgG1 mAb targeting CSF1R. In some embodiments, the CSF-1/1R binding agent, e.g., pexidartinib, is used in combination with a PD-L1 inhibitor, e.g., an anti-PD-L1 antibody molecule described herein. In some embodiments, the CSF-1/1R binding agent is FPA008. FPA008 is a humanized mAb that inhibits CSF1R. In some embodiments, the CSF-1/1R binding agent, e.g., FPA008, is used in combination with a PD-1 inhibitor, e.g., an anti-PD-1 antibody molecule described herein.

Exemplary IL-17 Inhibitors

In one embodiment, a combination described herein includes an interleukine-17 (IL-17) inhibitor. In some embodiments, the combination is used to treat a cancer, e.g., a cancer described herein, e.g., a solid tumor, e.g., breast cancer, lung cancer, or colon cancer.

In some embodiments, the IL-17 inhibitor is secukinumab (CAS Registry Numbers: 875356-43-7 (heavy chain) and 875356-44-8 (light chain)). Secukinumab is also known as AIN457 and COSENTYX®. Secukinumab is a recombinant human monoclonal IgG1/κ antibody that binds specifically to IL-17A. It is expressed in a recombinant Chinese Hamster Ovary (CHO) cell line.

Secukinumab is described, e.g., in WO 2006/013107, U.S. Pat. No. 7,807,155, U.S. Pat. No. 8,119,131, U.S. Pat. No. 8,617,552, and EP 1776142.

The heavy chain variable region of secukinumab
has the amino acid sequence of (SEQ ID NO: 332):
EVQLVESGGGLVQPGGSLRLSCAASGFTFSNYWMNWVRQAPGKGLEWVAA

INQDGSEKYYVGSVKGRFTISRDNAKNSLYLQMNSLRVEDTAVYYCVRDY

YDILTDYYIHYWYFDLWGRGTLVTVSS
(disclosed as SEQ ID NO: 8 in WO 2006/013107).

The light chain variable region of secukinumab
has the amino acid sequence of (SEQ ID NO: 333):
EVQLVESGGGLVQPGGSLRLSCAASGFTFSNYWMNWVRQAPGKGLEWVAA

INQDGSEKYYVGSVKGRFTISRDNAKNSLYLQMNSLRVEDTAVYYCVRDY

YDILTDYYIHYWYFDLWGRGTLVTVSS
(disclosed as SEQ ID NO: 10 in WO 2006/013107).

The heavy chain CDR1 of secukinumab has the amino acid sequence of NYWMN (SEQ ID NO: 334) (disclosed as SEQ ID NO: 1 in WO 2006/013107). The heavy chain CDR2 of secukinumab has the amino acid sequence of AINQDG-SEKYYVGSVKG (SEQ ID NO: 335) (disclosed as SEQ ID NO: 2 in WO 2006/013107). The heavy chain CDR3 of secukinumab has the amino acid sequence of DYYDILT-DYYIHYWYFDL (SEQ ID NO: 336) (disclosed as SEQ ID NO: 3 in WO 2006/013107). The light chain CDR1 of secukinumab has the amino acid sequence of RASQSVSS-SYLA (SEQ ID NO: 337) (disclosed as SEQ ID NO: 4 in WO 2006/013107). The light chain CDR2 of secukinumab has the amino acid sequence of GASSRAT (SEQ ID NO: 338) (disclosed as SEQ ID NO: 5 in WO 2006/013107). The light chain CDR3 of secukinumab has the amino acid sequence of QQYGSSPCT (SEQ ID NO: 361) (disclosed as SEQ ID NO: 6 in WO 2006/013107).

In some embodiments, the IL-17 inhibitor is CJM112. CJM112 is also known as XAB4. CJM112 is a fully human monoclonal antibody that targets IL-17A.

CJM112 is disclosed, e.g., in WO 2014/122613.

The heavy chain of CJM112 has the amino acid
sequence of (SEQ ID NO: 339):
EVQLVESGGDLVQPGGSLRLSCAASGFTFSSYWMSWVRQAPGKGLEWVAN

IKQDGSEKYYVDSVKGRFTISRDNAKNSLYLQMNSLRAEDTAVYYCARDR

GSLYYWGQGTLVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKRVEPKSCDKTHTCPPCPAPELLGGPSVFLFPPKPKDTL

MISRTPEVTCVVVDVSHEDPEVKFNWYVDGVEVHNAKTKPREEQYNSTYR

VVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSD

GSFFLYSKLTVDKSRWQQGNVFSCSVMHEALHNHYTQKSLSLSPGK
(disclosed as SEQ ID NO: 14 in WO 2014/122613).

The light chain of CJM112 has the amino acid
sequence of (SEQ ID NO: 340):
AIQLTQSPSSLSASVGDRVTITCRPSQGINWELAWYQQKPGKAPKLLIYD

ASSLEQGVPSRFSGSGSGTDFTLTISSLQPEDFATYYCQQFNSYPLTFGG

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC
(disclosed as SEQ ID NO: 44 in WO 2014/122613).

In some embodiments, the IL-17 inhibitor is ixekizumab (CAS Registry Number: 1143503-69-8). Ixekizumab is also known as LY2439821. Ixekizumab is a humanized IgG4 monoclonal antibody that targets IL-17A.

Ixekizumab is described, e.g., in WO 2007/070750, U.S. Pat. No. 7,838,638, and U.S. Pat. No. 8,110,191.

The heavy chain variable region of ixekizumab has
the amino acid sequence of (SEQ ID NO: 341):
QVQLVQSGAEVKKPGSSVKVSCKASGYSFTDYHIHWVRQAPGQGLEWMGV

INPMYGTTDYNQRFKGRVTITADESTSTAYMELSSLRSEDTAVYYCARYD

YFTGTGVYWGQGTLVTVSS
(disclosed as SEQ ID NO: 118 in WO 2007/070750).

The light chain variable region of ixekizumab has
the amino acid sequence of (SEQ ID NO: 342):
DIVMTQTPLSLSVTPGQPASISCRSSRSLVHSRGNTYLHWYLQKPGQSPQ

LLIYKVSNRFIGVPDRFSGSGSGTDFTLKISRVEAEDVGVYYCSQSTHLP

FTFGQGTKLEIK
(disclosed as SEQ ID NO: 241 in WO 2007/070750).

In some embodiments, the IL-17 inhibitor is brodalumab (CAS Registry Number: 1174395-19-7). Brodalumab is also known as AMG 827 or AM-14. Brodalumab binds to the interleukin-17 receptor A (IL-17RA) and prevents IL-17 from activating the receptor.

Brodalumab is disclosed, e.g., in WO 2008/054603, U.S. Pat. No. 7,767,206, U.S. Pat. No. 7,786,284, U.S. Pat. No. 7,833,527, U.S. Pat. No. 7,939,070, U.S. Pat. No. 8,435,518, U.S. Pat. No. 8,545,842, U.S. Pat. No. 8,790,648, and U.S. Pat. No. 9,073,999. The heavy chain CDR1 of brodalumab has the amino acid sequence of RYGIS (SEQ ID NO: 343) (as disclosed as SEQ ID NO: 146 in WO 2008/054603). The heavy chain CDR2 of brodalumab has the amino acid sequence of WISTYSGNTNYAQKLQG (SEQ ID NO: 344) (as disclosed as SEQ ID NO: 147 in WO 2008/054603). The heavy chain CDR3 of brodalumab has the amino acid sequence of RQLYFDY (SEQ ID NO: 345) (as disclosed as SEQ ID NO: 148 in WO 2008/054603). The light chain CDR1 of brodalumab has the amino acid sequence of RASQSVSSNLA (SEQ ID NO: 346) (as disclosed as SEQ ID NO: 224 in WO 2008/054603). The heavy chain CDR2 of brodalumab has the amino acid sequence of DASTRAT (SEQ ID NO: 347) (as disclosed as SEQ ID NO: 225 in WO 2008/054603). The heavy chain CDR3 of brodalumab has the amino acid sequence of QQYDNWPLT (SEQ ID NO: 348) (as disclosed as SEQ ID NO: 226 in WO 2008/054603).

Exemplary IL-1β Inhibitors

In one embodiment, a combination described herein includes an interleukine-1 beta (IL-1β) inhibitor. In some embodiments, the combination is used to treat a cancer, e.g., a cancer described herein, e.g., a hematologic malignancy (e.g., a lymphoma (e.g., Hodgkin lymphoma), a leukemia (e.g., an acute or chronic leukemia), or a multiple myeloma).

In some embodiments, the IL-1β inhibitor is canakinumab. Canakinumab is also known as ACZ885 or ILARIS®. Canakinumab is a human monoclonal IgG1/κ antibody that neutralizes the bioactivity of human IL-1β.

Canakinumab is disclosed, e.g., in WO 2002/16436, U.S. Pat. No. 7,446,175, and EP 1313769.

The heavy chain variable region of canakinumab has the amino acid sequence of (SEQ ID NO: 349):
MEFGLSWVFLVALLRGVQCQVQLVESGGGVVQPGRSLRLSCAASGFTFS

VYGMNWVRQAPGKGLEWVAIIWYDGDNQYYADSVKGRFTISRDNSKNTL

YLQMNGLRAEDTAVYYCARDLRTGPFDYWGQGTLVTVSS
(disclosed as SEQ ID NO: 1 in U.S. Pat. No. 7,446,175).

The light chain variable region of canakinumab has the amino acid sequence of (SEQ ID NO: 350):
MLPSQLIGFLLLWVPASRGEIVLTQSPDFQSVTPKEKVTITCRASQSIGS

SLHWYQQKPDQSPKLLIKYASQSFSGVPSRFSGSGSGTDFTLTINSLEAE

DAAAYYCHQSSSLPFTFGPGTKVDIK
(disclosed as SEQ ID NO: 2 in U.S. Pat. No. 7,446,175).

Exemplary CXCR2 Inhibitors

In one embodiment, a combination described herein includes an inhibitor of chemokine (C-X-C motif) receptor 2 (CXCR2) inhibitor. In some embodiments, the combination is used to treat a cancer, e.g., a cancer described herein, e.g., a solid tumor, e.g., a breast cancer, a metastatic sarcoma, a pancreatic cancer, a melanoma, a renal cell carcinoma (RCC), a non-small cell lung cancer (NSCLC), or a pediatric tumor (e.g., a rhabdomyosarcoma).

In some embodiments, the CXCR2 inhibitor is danirixin (CAS Registry Number: 954126-98-8). Danirixin is also known as GSK1325756 or 1-(4-chloro-2-hydroxy-3-piperidin-3-ylsulfonylphenyl)-3-(3-fluoro-2-methylphenyl)urea. Danirixin is disclosed, e.g., in Miller et al. *Eur J Drug Metab Pharmacokinet* (2014) 39:173-181; and Miller et al. *BMC Pharmacology and Toxicology* (2015), 16:18.

In some embodiments, the CXCR2 inhibitor is reparixin (CAS Registry Number: 266359-83-5). Reparixin is also known as repertaxin or (2R)-2-[4-(2-methylpropyl)phenyl]-N-methylsulfonylpropanamide. Reparixin is a non-competitive allosteric inhibitor of CXCR1/2. Reparixin is disclosed, e.g., in Zarbock et al. *British Journal of Pharmacology* (2008), 1-8.

In some embodiments, the CXCR2 inhibitor is navarixin. Navarixin is also known as MK-7123, SCH 527123, PS291822, or 2-hydroxy-N,N-dimethyl-3-[[2-[[(1R)-1-(5-methylfuran-2-yl)propyl]amino]-3,4-dioxocyclobuten-1-yl]amino]benzamide. Navarixin is disclosed, e.g., in Ning et al. *Mol Cancer Ther.* 2012; 11(6):1353-64.

Exemplary PI3K-γ, -δ Inhibitors

In one embodiment, a combination described herein includes an inhibitor of phosphatidylinositol-4,5-bisphosphate 3-kinase (PI3K), e.g., phosphatidylinositol-4,5-bisphosphate 3-kinase gamma and/or delta (PI3K-γ,δ). In some embodiments, the combination is used to treat a cancer, e.g., a cancer described herein, e.g., a solid tumor (e.g., a prostate cancer, a breast cancer, a brain cancer, a bladder cancer, a pancreatic cancer, a renal cancer, a solid tumor, a liver cancer, a non-small cell lung cancer, an endocrine cancer, an ovarian cancer, a melanoma, a female reproductive system cancer, a digestive/gastrointestinal cancer, a glioblastoma multiforme, a head and neck cancer, or a colon cancer), e.g., a hematologic malignancy (e.g., a leukemia (e.g., a lymphocytic leukemia, e.g., chronic lymphocytic leukemia (CLL) (e.g., relapsed CLL)),e.g., a lymphoma (e.g., non-Hodgkin lymphoma (e.g., relapsed follicular B-cell non-Hodgkin lymphoma (FL) or relapsed small lymphocytic lymphoma (SLL)), or e.g., a multiple myeloma).

In some embodiments, the PI3K inhibitor is an inhibitor of delta and gamma isoforms of PI3K. Exemplary PI3K inhibitors that can be used in combination are described in, e.g., WO 2010/036380, WO 2010/006086, WO 09/114870, WO 05/113556, GSK 2126458, GDC-0980, GDC-0941, Sanofi XL147, XL756, XL147, PF-46915032, BKM 120, CAL-101, CAL 263, SF1126, PX-886, and a dual PI3K inhibitor (e.g., Novartis BEZ235).

In some embodiments, the PI3K-γ,δ inhibitor is idelalisib (CAS Registry Number: 870281-82-6). Idelalisib is also known as ZYDELIG®, GS-1101, CAL-101, or 5-Fluoro-3-phenyl-2-[(1S)-1-(7H-purin-6-ylamino)propyl]-4(3H)-quinazolinone. Idelalisib blocks P110δ, the delta isoform of PI3K. Idelalisib is disclosed, e.g., in Wu et al. *Journal of Hematology & Oncology* (2013) 6: 36.

In some embodiments, the PI3K-γ,-δ inhibitor is dactolisib (Compound A4) or 8-(6-Methoxy-pyridin-3-yl)-3-methyl-1-(4-piperazin-1-yl-3-trifluoromethyl-phenyl)-1,3-dihydro-imidazo[4,5-c]quinolin-2-one (Compound A41), or a compound disclosed in PCT Publication No. WO 2006/122806.

In some embodiments, the PI3K-γ,-δ inhibitor is buparlisib (Compound A6) or a compound disclosed in PCT Publication No. WO 2007/084786.

In one embodiment, the PI3K-γ,δ inhibitor, e.g., buparlisib (Compound A6) or a compound disclosed in PCT Publication No. WO 2007/084786, is administered at a dose of about 100 mg (e.g., per day).

Other exemplary PI3K-γ,-δ inhibitors that can be used in the combination include, e.g., pictilisib (GDC-0941), LY294002, pilaralisib (XL147), PI-3065, PI-103, VS-5584 (SB2343), CZC24832, duvelisib (IPI-145, INK1197), TG100-115, CAY10505, GSK1059615, PF-04691502, AS-605240, voxtalisib (SAR245409, XL765), IC-87114, omipalisib (GSK2126458, GSK458), TG100713, gedatolisib (PF-05212384, PKI-587), PKI-402, XL147 analogue, PIK-90, PIK-293, PIK-294, 3-Methyladenine (3-MA), AS-252424, AS-604850, or apitolisib (GDC-0980, RG7422).

In some embodiments, the PI3K inhibitor is Compound A8 or a compound described in PCT Publication No. WO2010/029082.

In some embodiments, the PI3K inhibitor is a pan-PI3K inhibitor, (4S,5R)-3-(2'-amino-2-morpholino-4'-(trifluoromethyl)-[4,5'-bipyrimidin]-6-yl)-4-(hydroxymethyl)-5-methyloxazolidin-2-one (Compound A13) or a compound disclosed in PCT Publication No. WO2013/124826.

Exemplary PI3K-γ, -δ inhibitors include, but are not limited to, duvelisib and idelalisib. Idelalisib (also called GS-1101 or CAL-101; Gilead) is a small molecule that blocks the delta isoform of PI3K. The structure of idelalisib (5-Fluoro-3-phenyl-2-[(1S)-1-(7H-purin-6-ylamino)propyl]-4(3H)-quinazolinone) is shown below.

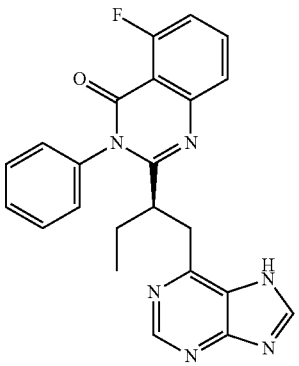 [SMILES: CC[C@H](Cc1ncnc2nc[nH]c12)c1nc2cccc(F)c2c(=O)n1-c1ccccc1]

Duvelisib (also called IPI-145; Infinity Pharmaceuticals and Abbvie) is a small molecule that blocks PI3K-δ,γ. The structure of duvelisib (8-Chloro-2-phenyl-3-[(1S)-1-(9H-purin-6-ylamino)ethyl]-1(2H)-isoquinolinone) is shown below.

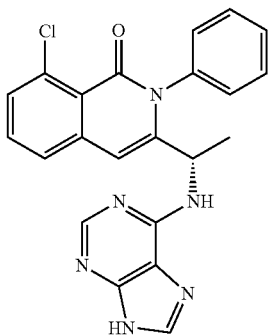 [SMILES: C[C@H](Nc1ncnc2[nH]cnc12)c1cc2cccc(Cl)c2c(=O)n1-c1ccccc1]

In one embodiment, the inhibitor is a dual phosphatidylinositol 3-kinase (PI3K) and mTOR inhibitor selected from 2-Amino-8-[trans-4-(2-hydroxyethoxy)cyclohexyl]-6-(6-methoxy-3-pyridinyl)-4-methyl-pyrido[2,3-d]pyrimidin-7(8H)-one (PF-04691502); N-[4-[[4-(Dimethylamino)-1-piperidinyl]carbonyl]phenyl]-N-[4-(4,6-di-4-morpholinyl-1,3,5-triazin-2-yl)phenyl]urea (PF-05212384, PKI-587); 2-Methyl-2-{4-[3-methyl-2-oxo-8-(quinolin-3-yl)-2,3-dihydro-1H-imidazo[4,5-c]quinolin-1-yl]phenyl}propanenitrile (BEZ-235); apitolisib (GDC-0980, RG7422); 2,4-Difluoro-N-{2-(methyloxy)-5-[4-(4-pyridazinyl)-6-quinolinyl]-3-pyridinyl}benzenesulfonamide (GSK2126458); 8-(6-methoxypyridin-3-yl)-3-methyl-1-(4-(piperazin-1-yl)-3-(trifluoromethyl)phenyl)-1H-imidazo[4,5-c]quinolin-2(3H)-one Maleic acid (NVP-BGT226); 3-[4-(4-Morpholinylpyrido[3',2':4,5]furo[3,2-d]pyrimidin-2-yl]phenol (PI-103); 5-(9-isopropyl-8-methyl-2-morpholino-9H-purin-6-yl)pyrimidin-2-amine (VS-5584, SB2343); or N-[2-[(3,5-Dimethoxyphenyl)amino]quinoxalin-3-yl]-4-[(4-methyl-3-methoxyphenyl)carbonyl]aminophenylsulfonamide (XL765).

Exemplary BAFF-R Inhibitors

In one embodiment, a combination described herein includes a B-cell-activating factor receptor (BAFF-R) inhibitor. In some embodiments, the combination is used to treat a cancer, e.g., a cancer described herein, e.g., a hematologic malignancy, e.g., a leukemia (e.g., chronic lymphocytic leukemia (CLL), e.g., relapsed or refractory chronic lymphocytic leukemia).

In one embodiment, the BAFF-R inhibitor is VAY736. VAY736 is a fully human combinatorial antibody library (HuCAL)-derived monoclonal antibody targeting BAFF-R. BAFF-R, also known as tumor necrosis factor receptor superfamily member 13C, is overexpressed in certain tumor cell types and autoimmune diseases. VAY736 has both anti-inflammatory and antineoplastic activities. In cancer cells, BAFF-R plays a key role in B-cell proliferation and survival. VAY736 targets and binds to BAFF-R, which inhibits both BAFF/BAFF-R interaction and BAFF-R-mediated signaling. This may decrease cell growth in tumor cells expressing BAFF-R.

VAY736 is disclosed, e.g., in U.S. Pat. No. 8,106,163. The heavy chain CDR1 of VAY736 has the amino acid sequence of GDSVSSNSAAWG (SEQ ID NO: 351) (disclosed as SEQ ID NO: 3 in U.S. Pat. No. 8,106,163). The heavy chain CDR2 of VAY736 has the amino acid sequence of RIYYR-SKWYNSYAVSVKS (SEQ ID NO: 352) (disclosed as SEQ ID NO: 10 in U.S. Pat. No. 8,106,163). The heavy chain CDR3 of VAY736 has the amino acid sequence of YDWVP-KIGVFDS (SEQ ID NO: 362) (disclosed as SEQ ID NO: 17 in U.S. Pat. No. 8,106,163). The light chain CDR1 of VAY736 has the amino acid sequence of RASQFISSSYLS (SEQ ID NO: 353) (disclosed as SEQ ID NO: 24 in U.S. Pat. No. 8,106,163). The light chain CDR2 of VAY736 has the amino acid sequence of LLIYGSSSRAT (SEQ ID NO: 354) (disclosed as SEQ ID NO: 31 in U.S. Pat. No. 8,106,163). The light chain CDR3 of VAY736 has the amino acid sequence of QQLYSSPM (SEQ ID NO: 355) (disclosed as SEQ ID NO: 38 in U.S. Pat. No. 8,106,163).

```
The heavy chain variable region of VAY736 has the
amino acid sequence of (SEQ ID NO: 356):
QVQLQQSGPGLVKPSQTLSLTCAISGDSVSSNSAAWGWIRQSPGRGLEWL

GRIYYRSKWYNSYAVSVKSRITINPDTSKNQFSLQLNSVTPEDTAVYYCA

RYDWVPKIGVFDSWGQGTLVTVSS
(disclosed as SEQ ID NO: 52 in U.S. Pat. No.
8,106,163).

The light chain variable region of VAY736 has the
amino acid sequence of (SEQ ID NO: 357):
DIVLTQSPATLSLSPGERATLSCRASQFISSSYLSWYQQKPGQAPRLLIY

GSSSRATGVPARFSGSGSGTDFTLTISSLEPEDFAVYYCQQLYSSPMTFG

QGTKVEIKRT
(disclosed as SEQID NO: 45 in U.S. Pat. No.
8,106,163).

The heavy chain of VAY736 has the amino acid
sequence of (SEQ ID NO: 358):
QVQLQQSGPGLVKPSQTLSLTCAISGDSVSSNSAAWGWIRQSPGRGLEWL

GRIYYRSKWYNSYAVSVKSRITINPDTSKNQFSLQLNSVTPEDTAVYYCA

RYDWVPKIGVFDSWGQGTLVTVSSASTKGPSVFPLAPSSKSTSGGTAALG

CLVKDYFPEPVTVSWNSGALTSGVHTFPAVLQSSGLYSLSSVVTVPSSSL

GTQTYICNVNHKPSNTKVDKRVEPKSCDKTHTCPPCPAPELLGGPSVFLF

PPKPKDTLMISRTPEVTCVVVDVSHEDPEVKFNWYVDGVEVHNAKTKPRE

EQYNSTYRVVSVLTVLHQDWLNGKEYKCKVSNKALPAPIEKTISKAKGQP

REPQVYTLPPSREEMTKNQVSLTCLVKGFYPSDIAVEWESNGQPENNYKT

TPPVLDSDGSFFLYSKLTVDKSRWQQGNVFSCSVMHEALHNHYTQKSLSL

SPGK
(disclosed as SEQ ID NO: 75 in U.S. Pat. No.
8,106,163).

The light chain variable region of VAY736 has the
amino acid sequence of (SEQ ID NO: 359):
DIVLTQSPATLSLSPGERATLSCRASQFISSSYLSWYQQKPGQAPRLLIY

GSSSRATGVPARFSGSGSGTDFTLTISSLEPEDFAVYYCQQLYSSPMTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC
(disclosed as SEQ ID NO: 71 in U.S. Pat. No.
8,106,163).
```

Exemplary MALT-1/BTK Inhibitors

In one embodiment, a combination described herein includes an inhibitor of MALT-1 and/or BTK. In some embodiments, the combination is used to treat a cancer, e.g., a cancer described herein.

Exemplary MALT-1/BTK inhibitors include, but are not limited to, (S)-1-(6-(2H-1,2,3-triazol-2-yl)-5-(trifluoromethyl)pyridin-3-yl)-3-(2-chloro-7-(1-methoxyethyl)pyrazolo[1,5-a]pyrimidin-6-yl)urea, (S)-1-(2-chloro-7-(1-methoxyethyl)pyrazolo[1,5-a]pyrimidin-6-yl)-3-(2-(trifluoromethyl)pyridin-4-yl)urea, (S)-1-(2-chloro-7-(1-methoxyethyl)pyrazolo[1,5-a]pyrimidin-6-yl)-3-(1-methyl-2-oxo-5-(trifluoromethyl)-1,2-dihydropyridin-3-yl)urea, (R)-1-(6-(2H-1,2,3-triazol-2-yl)-5-(trifluoromethyl)pyridin-3-yl)-3-(2-chloro-7-(1-methoxy-2-methylpropyl)pyrazolo[1,5-a]pyrimidin-6-yl)urea, (R)-1-(5-chloro-6-(2H-1,2,3-triazol-2-yl)pyridin-3-yl)-3-(2-chloro-7-(1-methoxy-2-methylpropyl)pyrazolo[1,5-a]pyrimidin-6-yl)urea, (S)-1-(7-(1-methoxyethyl)-2-methylpyrazolo[1,5-a]pyrimidin-6-yl)-3-(2-(trifluoromethyl)pyridin-4-yl)urea, (S)-1-(2-fluoro-7-(1-methoxyethyl)pyrazolo[1,5-a]pyrimidin-6-yl)-3-(2-(trifluoromethyl)pyridin-4-yl)urea, (S)-1-(2-chloro-7-(1-methoxyethyl)pyrazolo[1,5-a]pyrimidin-6-yl)-3-(5-cyanopyridin-3-yl)urea, Exemplary BTK inhibitors include, but are not limited to, ibrutinib (PCI-32765); GDC-0834; RN-486; CGI-560; CGI-1764; HM-71224; CC-292; ONO-4059; CNX-774; or LFM-A13. In one embodiment, the BTK inhibitor does not reduce or inhibit the kinase activity of interleukin-2-inducible kinase (ITK), e.g., is selected from GDC-0834; RN-486; CGI-560; CGI-1764; HM-71224; CC-292; ONO-4059; CNX-774; or LFM-A13.

In one embodiment, the kinase inhibitor is a BTK inhibitor, e.g., ibrutinib (PCI-32765). The structure of ibrutinib (1-[(3R)-3-[4-Amino-3-(4-phenoxyphenyl)-1H-pyrazolo[3,4-d]pyrimidin-1-yl]piperidin-1-yl]prop-2-en-1-one) is shown below.

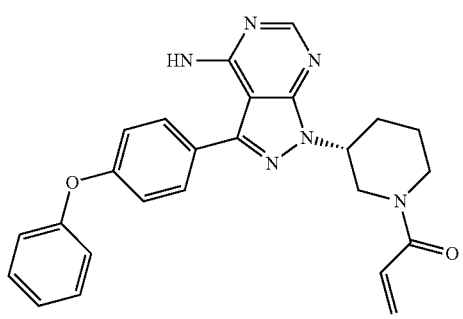 [SMILES: C=CC(=O)N1CCC[C@@H](n2nc(-c3ccc(Oc4ccccc4)cc3)c3c(N)ncnc32)C1]

In other embodiments, the BTK inhibitor is a BTK inhibitor described in International Application WO/2015/079417, which is herein incorporated by reference in its entirety. For instance, in some embodiments, the BTK inhibitor is a compound of formula (I) or a pharmaceutically acceptable salt thereof;

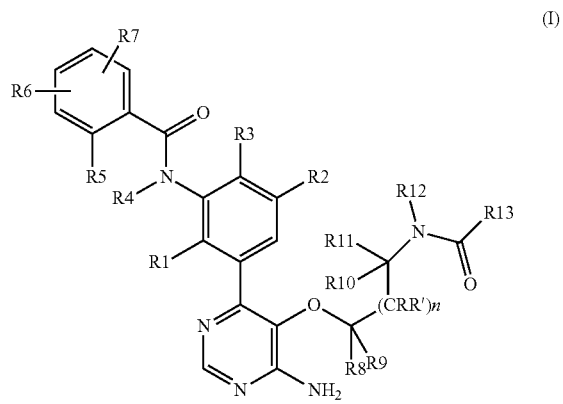

wherein,

R1 is hydrogen, C1-C6 alkyl optionally substituted by hydroxy;

R2 is hydrogen or halogen;

R3 is hydrogen or halogen;

R4 is hydrogen;

R5 is hydrogen or halogen;

or R4 and R5 are attached to each other and stand for a bond, —CH2-, —CH2-CH2-, —CH═CH—, —CH═CH—CH2-; —CH2-CH═CH—; or —CH2-CH2-CH2-;

R6 and R7 stand independently from each other for H, C1-C6 alkyl optionally substituted by hydroxyl, C3-C6 cycloalkyl optionally substituted by halogen or hydroxy, or halogen;

R8, R9, R, R', R10 and R11 independently from each other stand for H, or C1-C6 alkyl optionally substituted by C1-C6 alkoxy; or any two of R8, R9, R, R', R10 and R11 together with the carbon atom to which they are bound may form a 3-6 membered saturated carbocyclic ring;

R12 is hydrogen or C1-C6 alkyl optionally substituted by halogen or C1-C6 alkoxy;

or R12 and any one of R8, R9, R, R', R10 or R11 together with the atoms to which they are bound may form a 4, 5, 6 or 7 membered azacyclic ring, which ring may optionally be substituted by halogen, cyano, hydroxyl, C1-C6 alkyl or C1-C6 alkoxy;

n is 0 or 1; and

R13 is C2-C6 alkenyl optionally substituted by C1-C6 alkyl, C1-C6 alkoxy or N,N-di-C1-C6 alkyl amino; C2-C6 alkynyl optionally substituted by C1-C6 alkyl or C1-C6 alkoxy; or C2-C6 alkylenyl oxide optionally substituted by C1-C6 alkyl.

In some embodiments, the BTK inhibitor of Formula I is chosen from: N-(3-(5-((1-Acryloylazetidin-3-yl)oxy)-6-aminopyrimidin-4-yl)-5-fluoro-2-methylphenyl)-4-cyclopropyl-2-fluorobenzamide; (E)-N-(3-(6-Amino-5-((1-(but-2-enoyl)azetidin-3-yl)oxy)pyrimidin-4-yl)-5-fluoro-2-methylphenyl)-4-cyclopropyl-2-fluorobenzamide; N-(3-(6-Amino-5-((1-propioloylazetidin-3-yl)oxy)pyrimidin-4-yl)-5-fluoro-2-methylphenyl)-4-cyclopropyl-2-fluorobenzamide; N-(3-(6-Amino-5-((1-(but-2-ynoyl)azetidin-3-yl)oxy)pyrimidin-4-yl)-5-fluoro-2-methylphenyl)-4-cyclopropyl-2-fluorobenzamide; N-(3-(5-((1-Acryloylpiperidin-4-yl)oxy)-6-aminopyrimidin-4-yl)-5-fluoro-2-methylphenyl)-4-cyclopropyl-2-fluorobenzamide; N-(3-(6-Amino-5-(2-(N-methylacrylamido)ethoxy)pyrimidin-4-yl)-5-fluoro-2-methylphenyl)-4-cyclopropyl-2-fluorobenzamide; (E)-N-(3-(6-Amino-5-(2-(N-methylbut-2- enamido)ethoxy)pyrimidin-4-yl)-5-fluoro-2-methylphenyl)-4-cyclopropyl-2-fluorobenzamide; N-(3-(6-Amino-5-(2-(N-methylpropiolamido)ethoxy)pyrimidin-4-yl)-5-fluoro-2-methylphenyl)-4-cyclopropyl-2-fluorobenzamide; (E)-N-(3-(6-Amino-5-(2-(4-methoxy-N-methylbut-2-enamido)ethoxy)pyrimidin-4-yl)-5-fluoro-2-methylphenyl)-4-cyclopropyl-2-fluorobenzamide; N-(3-(6-Amino-5-(2-(N-methylbut-2-ynamido)ethoxy)pyrimidin-4-yl)-5-fluoro-2-methylphenyl)-4-cyclopropyl-2-fluorobenzamide; N-(2-((4-Amino-6-(3-(4-cyclopropyl-2-fluorobenzamido)-5-fluoro-2-methylphenyl)pyrimidin-5-yl)oxy)ethyl)-N-methyloxirane-2-carboxamide; N-(2-((4-Amino-6-(3-(6-cyclopropyl-8-fluoro-1-oxoisoquinolin-2(1H)-yl)phenyl)pyrimidin-5-yl)oxy)ethyl)-N-methylacrylamide; N-(3-(5-(2-Acrylamidoethoxy)-6-aminopyrimidin-4-yl)-5-fluoro-2-methylphenyl)-4-cyclopropyl-2-fluorobenzamide; N-(3-(6-Amino-5-(2-(N-ethylacrylamido)ethoxy)pyrimidin-4-yl)-5-fluoro-2-methylphenyl)-4-cyclopropyl-2-fluorobenzamide; N-(3-(6-Amino-5-(2-(N-(2-fluoroethyl)acrylamido)ethoxy)pyrimidin-4-yl)-5-fluoro-2-methylphenyl)-4-cyclopropyl-2-fluorobenzamide; N-(3-(5-((1-Acrylamidocyclopropyl)methoxy)-6-aminopyrimidin-4-yl)-5-fluoro-2-methylphenyl)-4-cyclopropyl-2-fluorobenzamide; (S)-N-(3-(5-(2-Acrylamidopropoxy)-6-aminopyrimidin-4-yl)-5-fluoro-2-methylphenyl)-4-cyclopropyl-2-fluorobenzamide; (S)-N-(3-(6-Amino-5-(2-(but-2-ynamido)propoxy)pyrimidin-4-yl)-5-fluoro-2-methylphenyl)-4-cyclopropyl-2-fluorobenzamide; (S)-N-(3-(6-Amino-5-(2-(N-methylacrylamido)propoxy)pyrimidin-4-yl)-5-fluoro-2-methylphenyl)-4-cyclopropyl-2-fluorobenzamide; (S)-N-(3-(6-Amino-5-(2-(N-methylbut-2-ynamido)propoxy)pyrimidin-4-yl)-5-fluoro-2-methylphenyl)-4-cyclopropyl-2-fluorobenzamide; N-(3-(6-Amino-5-(3-(N-methylacrylamido)propoxy)pyrimidin-4-yl)-5-fluoro-2-methylphenyl)-4-cyclopropyl-2-fluorobenzamide; (S)-N-(3-(5-((1-Acryloylpyrrolidin-2-yl)methoxy)-6-aminopyrimidin-4-yl)-5-fluoro-2-methylphenyl)-4-cyclopropyl-2-fluorobenzamide; (S)-N-(3-(6-Amino-5-((1-(but-2-ynoyl)pyrrolidin-2-yl)methoxy)pyrimidin-4-yl)-5-fluoro-2-methylphenyl)-4-cyclopropyl-2-fluorobenzamide; (S)-2-(3-(5-((1-Acryloylpyrrolidin-2-yl)methoxy)-6-aminopyrimidin-4-yl)-5-fluoro-2-(hydroxymethyl)phenyl)-6-cyclopropyl-3,4-dihydroisoquinolin-1(2H)-one; N-(2-((4-Amino-6-(3-(6-cyclopropyl-1-oxo-3,4-dihydroisoquinolin-2(1H)-yl)-5-fluoro-2-(hydroxymethyl)phenyl)pyrimidin-5-yl)oxy)ethyl)-N-methylacrylamide; N-(3-(5-(((2S,4R)-1-Acryloyl-4-methoxypyrrolidin-2-yl)methoxy)-6-aminopyrimidin-4-yl)-5-fluoro-2-methylphenyl)-4-cyclopropyl-2-fluorobenzamide; N-(3-(6-Amino-5-(((2S,4R)-1-(but-2-ynoyl)-4-methoxypyrrolidin-2-yl)methoxy)pyrimidin-4-yl)-5-fluoro-2-methylphenyl)-4-cyclopropyl-2-fluorobenzamide; 2-(3-(5-(((2S,4R)-1-Acryloyl-4-methoxypyrrolidin-2-yl)methoxy)-6-aminopyrimidin-4-yl)-5-fluoro-2-(hydroxymethyl)phenyl)-6-cyclopropyl-3,4-dihydroisoquinolin-1(2H)-one; N-(3-(5-(((2S,4S)-1-Acryloyl-4-methoxypyrrolidin-2-yl)methoxy)-6-aminopyrimidin-4-yl)-5-fluoro-2-methylphenyl)-4-cyclopropyl-2-fluorobenzamide; N-(3-(6-Amino-5-(((2S,4S)-1-(but-2-ynoyl)-4-methoxypyrrolidin-2-yl)methoxy)pyrimidin-4-yl)-5-fluoro-2-methylphenyl)-4-cyclopropyl-2-fluorobenzamide; N-(3-(5-(((2S,4R)-1-Acryloyl-4-fluoropyrrolidin-2-yl)methoxy)-6-aminopyrimidin-4-yl)-5-fluoro-2-methylphenyl)-4-cyclopropyl-2-fluorobenzamide; N-(3-(6-Amino-5-(((2S,4R)-1-(but-2-ynoyl)-4-fluoropyrrolidin-2-yl)methoxy)pyrimidin-4-yl)-5-fluoro-2-methylphenyl)-4-cyclopropyl-2-fluorobenzamide; (S)-N-(3-(5-((1-Acryloylazetidin-2-yl)methoxy)-6-aminopyrimidin-4-yl)-5-fluoro-2-methylphenyl)-4-cyclopropyl-2-fluorobenzamide; (S)-N-(3-(6-Amino-5-((1-propioloylazetidin-2-yl)methoxy)pyrimidin-4-yl)-5-fluoro-2-methylphenyl)-4-cyclopropyl-2-fluorobenzamide; (S)-2-(3-(5-((1-Acryloylazetidin-2-yl)methoxy)-6-aminopyrimidin-4-yl)-5-fluoro-2-(hydroxymethyl)phenyl)-6-cyclopropyl-3,4-dihydroisoquinolin-1(2H)-one; (R)-N-(3-(5-((1-Acryloylazetidin-2-yl)methoxy)-6-aminopyrimidin-4-yl)-5-fluoro-2-methylphenyl)-4-cyclopropyl-2-fluorobenzamide; (R)-N-(3-(5-((1-Acryloylpiperidin-3-yl)methoxy)-6-aminopyrimidin-4-yl)-5-fluoro-2-methylphenyl)-4-cyclopropyl-2-fluorobenzamide; N-(3-(5-(((2R,3S)-1-Acryloyl-3-methoxypyrrolidin-2-yl)methoxy)-6-aminopyrimidin-4-yl)-5-fluoro-2-methylphenyl)-4-cyclopropyl-2-fluorobenzamide; N-(3-(5-(((2S,4R)-1-Acryloyl-4-cyanopyrrolidin-2-yl)methoxy)-6-aminopyrimidin-4-yl)-5-fluoro-2-methylphenyl)-4-cyclopropyl-2-fluorobenzamide; or N-(3-(5-(((2S,4S)-1-Acryloyl-4-cyanopyrrolidin-2-yl)methoxy)-6-aminopyrimidin-4-yl)-5-fluoro-2-methylphenyl)-4-cyclopropyl-2-fluorobenzamide.

Unless otherwise provided, the chemical terms used above in describing the BTK inhibitor of Formula I are used according to their meanings as set out in International Application WO/2015/079417, which is herein incorporated by reference in its entirety.

Exemplary JAK Inhibitors

In one embodiment, a combination described herein includes an inhibitor of Janus kinase (JAK). In some embodiments, the combination is used to treat a cancer, e.g., a cancer described herein, e.g., a solid tumor (e.g., a colon cancer, a prostate cancer, a lung cancer, a breast cancer, or a pancreatic cancer), e.g., a hematologic malignancy (e.g., a leukemia (e.g., a myeloid leukemia or a lymphocytic leukemia), e.g., a lymphoma (e.g., a non-Hodgkin lymphoma), or e.g., a multiple myeloma.

In some embodiments, the JAK inhibitor is 2-fluoro-N-methyl-4-(7-(quinolin-6-ylmethyl)imidazo[1,2-b][1,2,4]triazin-2-yl)benzamide (Compound A17), or a dihydrochloric salt thereof, or a compound disclosed in PCT Publication No. WO 2007/070514.

In some embodiments, the JAK inhibitor, e.g., 2-fluoro-N-methyl-4-(7-(quinolin-6-ylmethyl)imidazo[1,2-b][1,2,4]triazin-2-yl)benzamide (Compound A17), or a dihydrochloric salt thereof, or a compound disclosed in PCT Publication No. WO 2007/070514, is administered at a dose of about 400-600 mg (e.g., per day), e.g., about 400, 500, or 600 mg, or about 400-500 or 500-600 mg.

In some embodiment, the JAK inhibitor is ruxolitinib phosphate (also known as JAKAFI; Compound A18) or a compound disclosed in PCT Publication No. WO 2007/070514.

In one embodiment, the JAK inhibitor, e.g., ruxolitinib phosphate (also known as JAKAFI; Compound A18) or a compound disclosed in PCT Publication No. WO 2007/070514, is administered at a dose of about 15-25 mg, e.g., twice daily. In some embodiments, the dose is about 15, 20, or 25 mg, or about 15-20 or 20-25 mg.

Exemplary CRTH2 Inhibitors

In one embodiment, a combination described herein includes an inhibitor of chemoattractant receptor homologous to the T helper 2 cell (CRTH2). In some embodiments, the combination is used to treat a cancer, e.g., a cancer described herein.

In some embodiments, the CRTH2 inhibitor is QAV680 (CAS Registry Number: 872365-16-7). QAV680 is also known as fevipiprant and 2-[2-methyl-1-[(4-methylsulfonylphenyl)methyl]pyrrolo[2,3-b]pyridin-3-yl]acetic acid.

QAV680 is disclosed, e.g., in Sandham et al. *Bioorg Med Chem.* 2013; 21(21):6582-91. QAW039 is also known as [1-(4-Methanesulfonyl-2-trifluoromethyl-benzyl)-2-methyl-1H-pyrrolo[2,3-b]pyridin-3-yl]-acetic acid. QAW039 is disclosed, e.g., in Sykes et al. European Respiratory Journal Sep. 1, 2014 vol. 44 no. Suppl 58 P4074.

In some embodiments, the CRTH2 inhibitor is QAW039 (CAS Number: 872365-14-5).

Other CRTH2 inhibitors that can be used in the combination include, e.g., AZD1981, ARRY-502, setipiprant (ACT-453859), and ACT-129968.

Exemplary PFKFB3 Inhibitors

In one embodiment, a combination described herein includes an inhibitor of 6-phosphofructo-2-kinase/fructose-2,6-biphosphatase 3 (PFKFB3). In some embodiments, the combination is used to treat a cancer, e.g., a cancer described herein, e.g., a solid tumor (e.g., an advanced solid tumor).

In some embodiments, the PFKFB3 inhibitor is PFK-158. PFK-158 is also known as ACT-PFK-158 or (E)-1-(pyridyn-4-yl)-3-(7-(trifluoromethyl)quinolin-2-yl)-prop-2-en-1-one. PFK-158 is a derivative of 3-(3-pyridinyl)-1-[4-pyridinyl]-2-propen-1-one (3P0). PFKFB3, which catalyzes the conversion of fructose-6-phosphate to fructose-2,6-bisphosphate, is highly expressed and active in human cancer cells and plays a key role in increasing both glycolytic flux in and proliferation of cancer cells. PFKFB3 inhibitors, e.g., PFK-158, can bind to and inhibit the activity of PFKFB3, which leads to the inhibition of both the glycolytic pathway in and glucose uptake by cancer cells. This prevents the production of macromolecules and energy that causes the enhanced cellular proliferation in cancer cells as compared to that of normal, healthy cells. Depriving cancer cells of nutrients and energy leads to the inhibition of cancer cell growth.

PFK158 is disclosed, e.g., at page 5 of WO 2013/148228.

In some embodiments, the PFKFB3 inhibitor has the following structure:

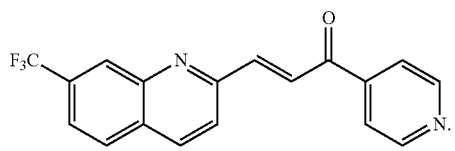 [SMILES: O=C(/C=C/c1ccc2ccc(C(F)(F)F)cc2n1)c1ccncc1]

Down-Modulators of the Immune System

In an alternative embodiment, the anti-PD-L1 antibody molecules disclosed herein are used to produce anti-idiotypic peptides or antibodies (Wallmann, J. et al. (2010) "Anti-Ids in Allergy: Timeliness of a Classic Concept," *World Allergy Organiz. J.* 3(6):195-201; Nardi, M. et al. (2000) "Antiidiotype Antibody Against Platelet Anti-Gpiiia Contributes To The Regulation Of Thrombocytopenia In HIV-1-ITP Patients," *J. Exp. Med.* 191(12):2093-2100) or mimetics (Zang, Y. C. et al. (2003) "Human Anti-Idiotypic T Cells Induced By TCR Peptides Corresponding To A Common CDR3 Sequence Motif In Myelin Basic Protein-Reactive T Cells," *Int. Immunol.* 15(9):1073-1080; Loiarro, M. et al. (Epub 2010 Apr. 8) "Targeting TLR/IL-1R Signalling In Human Diseases," *Mediators Inflamm.* 2010:674363) of B7-H1 or PD-1.

Down-modulation of the immune system is desirable in the treatment of inflammatory and auto-immune diseases, and graft vs. host disease (GvHD). Examples of autoimmune disorders that may be treated by administering the antibodies of the present invention include, but are not limited to, alopecia greata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, discoid lupus, essential mixed cryoglobulinemia, fibromyalgia-fibromyositis, glomerulonephritis, Graves' disease, Guillain-Barre, Hashimoto's thyroiditis, idiopathic pulmonary fibrosis, idiopathic thrombocytopenia purpura (ITP), IgA neuropathy, juvenile arthritis, lichen planus, lupus erthematosus, Meniere's disease, mixed connective tissue disease, multiple sclerosis, Neuromyelitis optica (NMO), type 1 or immune-mediated diabetes mellitus, myasthenia gravis, pemphigus vulgaris, pernicious anemia, polyarteritis nodosa, polychrondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, Rheumatoid arthritis, sarcoidosis, scleroderma, Sjogren's syndrome, stiff-man syndrome, systemic lupus erythematosus, lupus erythematosus, takayasu arteritis, temporal arteristis/giant cell arteritis, transverse myelitis, ulcerative colitis, uveitis, vasculitides such as dermatitis herpetiformis vasculitis, vitiligo, and Wegener's granulomatosis.

Examples of inflammatory disorders which can be prevented, treated or managed in accordance with the methods of the invention include, but are not limited to, asthma, encephilitis, inflammatory bowel disease, chronic obstructive pulmonary disease (COPD), allergic disorders, septic shock, pulmonary fibrosis, undifferentiated spondyloarthropathy, undifferentiated arthropathy, arthritis, inflammatory osteolysis, and chronic inflammation resulting from chronic viral or bacterial infections.

Thus, the antibodies and antigen-binding fragments of the present invention have utility in the treatment of inflammatory and autoimmune diseases.

Diagnostic Uses

In one aspect, the present invention provides a diagnostic method for detecting the presence of a PD-L1 protein in vitro (e.g., in a biological sample, such as a tissue biopsy, e.g., from a cancerous tissue) or in vivo (e.g., in vivo imaging in a subject). The method includes: (i) contacting the sample with an antibody molecule described herein, or administering to the subject, the antibody molecule; (optionally) (ii) contacting a reference sample, e.g., a control sample (e.g., a control biological sample, such as plasma, tissue, biopsy) or a control subject)); and (iii) detecting formation of a complex between the antibody molecule, and the sample or subject, or the control sample or subject, wherein a change, e.g., a statistically significant change, in the formation of the complex in the sample or subject relative to the control sample or subject is indicative of the presence of PD-L1 in the sample. The antibody molecule can be directly or indirectly labeled with a detectable substance to facilitate detection of the bound or unbound antibody. Suitable detectable substances include various enzymes, prosthetic groups, fluorescent materials, luminescent materials and radioactive materials, as described above and described in more detail below.

The term "sample," as it refers to samples used for detecting polypeptides includes, but is not limited to, cells, cell lysates, proteins or membrane extracts of cells, body fluids, or tissue samples.

Complex formation between the antibody molecule and PD-L1 can be detected by measuring or visualizing either the binding molecule bound to the PD-L1 antigen or unbound binding molecule. Conventional detection assays can be used, e.g., an enzyme-linked immunosorbent assays (ELISA), a radioimmunoassay (RIA) or tissue immunohistochemistry. Alternative to labeling the antibody molecule, the presence of PD-L1 can be assayed in a sample by a competition immunoassay utilizing standards labeled with a detectable substance and an unlabeled antibody molecule. In this assay, the biological sample, the labeled standards and the antibody molecule are combined and the amount of labeled standard bound to the unlabeled binding molecule is determined. The amount of PD-L1 in the sample is inversely proportional to the amount of labeled standard bound to the antibody molecule.

Alternatively, or in combination with the methods described herein, a method for evaluating a subject's status of immune cell (e.g., T cell) activation (e.g., evaluating a subject's likely responsiveness to an immunomodulator therapy) is disclosed. The method includes determining the level and/or distribution of T cell activation in the subject. In one embodiment, the level and/or distribution of T activation includes a measure of the level and/or distribution of one or more of: CD8, PD-L1, or other checkpoint inhibitor (e.g., one or more of PD-1, LAG-3, TIM-3, CEACAM (e.g., CEACAM-1, -3 and/or -5), or CTLA-4), or any combination thereof. For example, the level and/or distribution of CD8-expressing cells can be evaluated as a marker for activated T cells. In other embodiments, the level and/or distribution of cells expressing PD-L1, or other checkpoint inhibitor can be evaluated. The subject can be evaluated prior to, during, or after, administration of the immunomodulator therapy. In one embodiment, the subject is evaluated prior to the immunomodulator therapy (e.g., the checkpoint molecule inhibitor therapy), e.g., prior to an initial treatment, or prior to a treatment after a treatment interval. In one embodiment, an elevated level of one or more of CD8, PD-L1, or other checkpoint inhibitor in the subject (e.g., relative to a reference, e.g., control) is indicative of increased responsiveness of the subject to the therapy (also referred to herein as a positive immune activation status). In another embodiment, a decreased level of one or more of CD8, PD-L1, or other checkpoint inhibitor in the subject (e.g., relative to a reference, e.g., control) is indicative of decreased responsiveness of the subject to the therapy (also referred to herein as a negative immune activation status). The method can, optionally, include administration of the immunomodulator therapy as described herein (e.g., a checkpoint molecule inhibitor therapy as described herein), if the subject is determined to have a positive immune activation status.

In one embodiment, the immunomodulator therapy includes an activator of a costimulatory molecule, e.g., one or more activators as described herein (e.g., an agonist of a GITR molecule as described herein). In other embodiments, the immunomodulator therapy includes an inhibitor of an immune checkpoint molecule, e.g., one or more inhibitors of checkpoint inhibitor as described herein (e.g., an inhibitor of one or more of PD-L1, PD-1, TIM-3, or CTLA-4, as described herein). In one embodiment, the immunomodulator therapy includes an anti-PD-L1 antibody molecule as described herein. In other embodiments, the immunomodulator therapy includes a combination of an activator of a costimulatory molecule and an inhibitor of a checkpoint inhibitor.

In some embodiments, the level and/or distribution of the CD8, PD-L1, or other checkpoint inhibitor is determined in vivo, e.g., non-invasively (e.g., by detecting an antibody to a T cell marker detectably labeled using a suitable imaging technique, e.g., positron emission tomography (PET) scan). For example, target antibody-PET or immune-PET (e.g., an anti-CD8 PET or an anti-PD-L1 PET) can be used to detect the level and/or distribution (e.g., tumor localization) of the target CD8- or PD-L1-expressing cells in vivo. Techniques for antibody imaging (e.g., antibody-PET imaging) are known in the art, e.g., as described by Lamberts, L. E. et al. (2015) *J. Clin. Oncol.* 33 (DOI: 10.1200/JCO.2014.57.8278); Tavare, R. et al. (2014) *PNAS* 111(3): 1108-1113; Pampaloni et al., *J Clin Oncol* 32:5s, 2014 (suppl; abstr 3084); and Boerman and Oyen (2011) *The Journal of Nuclear Medicine* 52 (8):1171-72; U.S. Pat. No. 5,192,525, U.S. Pat. No. 5,219,548, U.S. Pat. No. 5,399,338, U.S. Pat. No. 6,096,874, U.S. Pat. No. 7,338,651, U.S. Pat. No. 7,410,943, U.S. Pat. No. 7,747,308, U.S. Pat. No. 7,754,884, U.S. Pat. No. 7,848,557, U.S. Pat. No. 7,894,649, U.S. Pat. No. 8,090,175, U.S. Pat. No. 8,188,116, U.S. Pat. No. 8,287,471, U.S. Pat. No. 8,323,621, U.S. Pat. No. 8,372,868, U.S. Pat. No. 8,532,739, U.S. Pat. No. 8,679,483, U.S. Pat. No. 8,771,966, and U.S. Pat. No. 8,841,320; U.S. Patent Application Publication Nos. US 2002/122806, US 2003/129579, US 2004/096915, US 2004/096915, US 2005/215883, US 2006/193773, US 2007/258888, US 2008/004521, US 2008/031823, US 2008/119718, US 2008/130825, US 2008/146914, US 2008/200806, US 2008/230703, US 2008/241074, US 2008/241873, US 2010/034735, US 2010/092384, US 2010/258138, US 2010/278739, US 2010/324130, US 2011/014120, US 2011/064652, US 2011/116703, US 2012/052010, US 2013/136688, US 2013/157289, US 2013/177502, US 2015/185204, US 2015/190534, and US 2015/217006; International Patent Application Publication Nos. WO 92/19213, WO 9640616, WO 2002/035232, WO 2002/047537, WO 2003/020701, WO 2003/034068, WO 2005/012335, WO 2005/046733, WO 2005/077263, WO 2006/074129, WO 2006/100562, WO 2006/147379, WO 2007/092115, WO 2008/023251, WO 2008/057166, WO 2008/115854, WO 2008/143706, WO 2009/121631, WO 2010/127054, WO 2011/153346, WO 2015/085179, WO 2015/100498, WO 2015/103039, and WO 92/06068; and European Patent Nos. EP 0551434 B1, EP 1330652 B1, and EP 1861713 B1; all of which are incorporated herein by reference.

In one embodiment, the level and/or distribution of CD8 is determined in vivo, e.g., by detecting an anti-CD8 antibody detectably labeled with a PET reagent, e.g., conjugated to 5-2-(4-isothiocyanatobenzyl)-1,4,7-triazacyclononane-1, 4,7-triacetic acid for $^{64}$Cu radiolabeling, e.g., as described in Tavare, R. et al. (2014) *PNAS* 111(3):1108-1113. In another embodiment, the level and/or distribution of PD-1 or PD-L1 is determined in vivo, e.g., by detecting an anti-PD-1 or anti-PD-L1 antibody detectably labeled with a PET reagent, e.g., $^{18}$F-fluorodeoxyglucose (FDG), e.g., as described in Pampaloni et al., *J Clin Oncol* 32:5s, 2014 (suppl; abstr 3084). In yet another embodiment, the level and/or distribution of CTLA-4 is determined in vivo, e.g., by detecting an anti-CTLA-4 antibody detectably labeled with a PET reagent, e.g., as described in WO 2009/121631.

In other embodiments, the level of the CD8, PD-L1, or other checkpoint inhibitor is determined in a sample (e.g., a tumor biopsy) acquired from the subject (e.g., using immunohistochemical techniques).

Also within the scope of the invention are detection reagents. For example, immuno-PET reagents that include an anti-PD-L1 antibody molecule as described herein.

Exemplary labeling reagents include, but are not limited to, bromine-76 ($^{76}$Br), calcium-47 ($^{47}$Ca), carbon-11 ($^{11}$C), carbon-14 ($^{14}$C), chromium-51 ($^{51}$Cr), cobalt-57 ($^{57}$Co), cobalt-58 ($^{58}$Co), copper-64 ($^{64}$Cu), erbium-169 ($^{169}$Er), fluorine-18 ($^{18}$F), fluorodeoxyglucose ($^{18}$F-FDG), gallium-67 ($^{67}$Ga), gallium-68 ($^{68}$Ga), hydrogen-3 ($^{3}$H), indium-111 ($^{111}$In), iodine-123 ($^{123}$I), iodine-124 ($^{124}$I), iodine-125 ($^{125}$I), iodine-131 ($^{131}$I), iron-59 ($^{59}$Fe), krypton-81m ($^{81m}$Kr), lutetium-177 ($^{177}$Lu), nitrogen-13 ($^{13}$N), oxygen-15 ($^{15}$O), phosphorus-32 ($^{32}$P), samarium-153 ($^{153}$Sm), selenium-75 (75Se), strontium-89 ($^{89}$Sr), thallium-201 ($^{201}$Tl), sodium-22 ($^{22}$Na), sodium-24 ($^{24}$Na), technetium 99m ($^{99}$mTc), xenon-133 ($^{133}$Xe), yttrium-86 ($^{86}$Y), yttrium-88 ($^{88}$Y), Yttrium-90 ($^{90}$Y), and zirconium-89 ($^{89}$Zr). Additional exemplary labeling reagents and their applications in immune-PET are described, e.g., in Lamberts, L. E. et al. (2015) *J. Clin. Oncol.* 33 (DOI: 10.1200/JCO.2014.57.8278) and Boerman and Oyen (2011) *The Journal of Nuclear Medicine* 52 (8):1171-72.

Nucleic Acids

The invention also features nucleic acids comprising nucleotide sequences that encode heavy and light chain variable regions and CDRs or hypervariable loops of the anti-PD-L1 antibody molecules, as described herein. For example, the invention features a first and second nucleic acid encoding heavy and light chain variable regions, respectively, of an anti-PD-L1 antibody molecule chosen from one or more of the antibody molecules disclosed herein. The nucleic acid can comprise a nucleotide sequence as set forth in the tables herein, or a sequence substantially identical thereto (e.g., a sequence at least about 85%, 90%, 95%, 99% or more identical thereto, or which differs by no more than 3, 6, 15, 30, or 45 nucleotides from the sequences shown in the tables herein.

In certain embodiments, the nucleic acid can comprise a nucleotide sequence encoding at least one, two, or three CDRs or hypervariable loops from a heavy chain variable region having an amino acid sequence as set forth in the tables herein, or a sequence substantially homologous thereto (e.g., a sequence at least about 85%, 90%, 95%, 99% or more identical thereto, and/or having one or more substitutions, e.g., conserved substitutions). In other embodiments, the nucleic acid can comprise a nucleotide sequence encoding at least one, two, or three CDRs or hypervariable loops from a light chain variable region having an amino acid sequence as set forth in the tables herein, or a sequence substantially homologous thereto (e.g., a sequence at least about 85%, 90%, 95%, 99% or more identical thereto, and/or having one or more substitutions, e.g., conserved substitutions). In yet another embodiment, the nucleic acid can comprise a nucleotide sequence encoding at least one, two, three, four, five, or six CDRs or hypervariable loops from heavy and light chain variable regions having an amino acid sequence as set forth in the tables herein, or a sequence substantially homologous thereto (e.g., a sequence at least about 85%, 90%, 95%, 99% or more identical thereto, and/or having one or more substitutions, e.g., conserved substitutions).

In certain embodiments, the nucleic acid can comprise a nucleotide sequence encoding at least one, two, or three CDRs or hypervariable loops from a heavy chain variable region having the nucleotide sequence as set forth in the tables herein, a sequence substantially homologous thereto (e.g., a sequence at least about 85%, 90%, 95%, 99% or more identical thereto, and/or capable of hybridizing under the stringency conditions described herein). In another embodiment, the nucleic acid can comprise a nucleotide sequence encoding at least one, two, or three CDRs or hypervariable loops from a light chain variable region having the nucleotide sequence as set forth in the tables herein, or a sequence substantially homologous thereto (e.g., a sequence at least about 85%, 90%, 95%, 99% or more identical thereto, and/or capable of hybridizing under the stringency conditions described herein). In yet another embodiment, the nucleic acid can comprise a nucleotide sequence encoding at least one, two, three, four, five, or six CDRs or hypervariable loops from heavy and light chain variable regions having the nucleotide sequence as set forth in the tables herein, or a sequence substantially homologous thereto (e.g., a sequence at least about 85%, 90%, 95%, 99% or more identical thereto, and/or capable of hybridizing under the stringency conditions described herein).

In another aspect, the application features host cells and vectors containing the nucleic acids described herein. The nucleic acids may be present in a single vector or separate vectors present in the same host cell or separate host cell, as described in more detail hereinbelow.

Vectors

Further provided herein are vectors comprising nucleotide sequences encoding an antibody molecule described herein. In one embodiment, the vectors comprise nucleotides encoding an antibody molecule described herein. In one embodiment, the vectors comprise the nucleotide sequences described herein. The vectors include, but are not limited to, a virus, plasmid, cosmid, lambda phage or a yeast artificial chromosome (YAC).

Numerous vector systems can be employed. For example, one class of vectors utilizes DNA elements which are derived from animal viruses such as, for example, bovine papilloma virus, polyoma virus, adenovirus, vaccinia virus, baculovirus, retroviruses (Rous Sarcoma Virus, MMTV or MOMLV) or SV40 virus. Another class of vectors utilizes RNA elements derived from RNA viruses such as Semliki Forest virus, Eastern Equine Encephalitis virus and Flaviviruses.

Additionally, cells which have stably integrated the DNA into their chromosomes may be selected by introducing one or more markers which allow for the selection of transfected host cells. The marker may provide, for example, prototropy to an auxotrophic host, biocide resistance (e.g., antibiotics), or resistance to heavy metals such as copper, or the like. The selectable marker gene can be either directly linked to the DNA sequences to be expressed, or introduced into the same cell by cotransformation. Additional elements may also be needed for optimal synthesis of mRNA. These elements may include splice signals, as well as transcriptional promoters, enhancers, and termination signals.

Once the expression vector or DNA sequence containing the constructs has been prepared for expression, the expression vectors may be transfected or introduced into an appropriate host cell. Various techniques may be employed to achieve this, such as, for example, protoplast fusion, calcium phosphate precipitation, electroporation, retroviral transduction, viral transfection, gene gun, lipid based transfection or other conventional techniques. In the case of protoplast fusion, the cells are grown in media and screened for the appropriate activity.

Methods and conditions for culturing the resulting transfected cells and for recovering the antibody molecule produced are known to those skilled in the art, and may be varied or optimized depending upon the specific expression vector and mammalian host cell employed, based upon the present description.

Cells

The invention also provides host cells comprising a nucleic acid encoding an antibody molecule as described herein.

In one embodiment, the host cells are genetically engineered to comprise nucleic acids encoding the antibody molecule.

In one embodiment, the host cells are genetically engineered by using an expression cassette. The phrase "expression cassette," refers to nucleotide sequences, which are capable of affecting expression of a gene in hosts compatible with such sequences. Such cassettes may include a promoter, an open reading frame with or without introns, and a termination signal. Additional factors necessary or helpful in effecting expression may also be used, such as, for example, an inducible promoter.

The invention also provides host cells comprising the vectors described herein.

The cell can be, but is not limited to, a eukaryotic cell, a bacterial cell, an insect cell, or a human cell. Suitable eukaryotic cells include, but are not limited to, Vero cells, HeLa cells, COS cells, CHO cells, HEK293 cells, BHK cells and MDCKII cells. Suitable insect cells include, but are not limited to, Sf9 cells.

TABLE 1

| | | | |
|---|---|---|---|
| BAP058HC | | | |
| SEQ ID NO: 1 (Kabat) | HCDR1 | SYWMY | |
| SEQ ID NO: 2 (Kabat) | HCDR2 | RIDPNSGSTKYNEKFKN | |
| SEQ ID NO: 3 (Kabat) | HCDR3 | DYRKGLYAMDY | |
| SEQ ID NO: 4 (Chothia) | HCDR1 | GYTFTSY | |
| SEQ ID NO: 5 (Chothia) | HCDR2 | DPNSGS | |
| SEQ ID NO: 3 (Chothia) | HCDR3 | DYRKGLYAMDY | |
| SEQ ID NO: 6 | VH | QVHLQQPGAELVKPGASVKLSCKASGYTFTSYWMYWV KQGPGRGLEWIGRIDPNSGSTKYNEKFKNKATLTVDK SSSTAYMQLSSLTSEDSAVYYCARDYRKGLYAMDYWG QGTSVTVSS | |
| SEQ ID NO: 7 | DNA VH | CAGGTCCACCTGCAGCAGCCTGGGGCTGAGCTTGTGA AGCCTGGGGCTTCAGTGAAGCTGTCCTGCAAGGCTTC TGGCTACACCTTCACCAGTTACTGGATGTACTGGGTG AAACAGGGGCCTGGACGAGGCCTTGAGTGGATTGGAA GGATTGATCCTAATAGTGGGAGTACTAAGTACAATGA GAAGTTCAAGAACAAGGCCACACTGACTGTAGACAAA TCCTCCAGCACAGCCTACATGCAGCTCAGCAGCCTGA CATCTGAGGACTCTGCGGTCTATTATTGTGCAAGGGA CTATAGAAAGGGGCTCTATGCTATGGACTACTGGGGT CAAGGAACCTCAGTCACCGTCTCCTCA | |
| BAP058 LC | | | |
| SEQ ID NO: 9 (Kabat) | LCDR1 | KASQDVGTAVA | |
| SEQ ID NO: 10 (Kabat) | LCDR2 | WASTRHT | |
| SEQ ID NO: 11 (Kabat) | LCDR3 | QQYNSYPLT | |
| SEQ ID NO: 12 (Chothia) | LCDR1 | SQDVGTA | |
| SEQ ID NO: 13 (Chothia) | LCDR2 | WAS | |
| SEQ ID NO: 14 (Chothia) | LCDR3 | YNSYPL | |
| SEQ ID NO: 8 | VL | DIVMTQSHKFMSTSVGDRVSITCKASQDVGTAVAWYQ QKPGQSPKLLIYWASTRHTGVPDRFTGSGSGTDFTLT ISNVQSEDLADYFCQQYNSYPLTFGAGSKLELK | |
| SEQ ID NO: 15 | DNA VL | GACATTGTGATGACCCAGTCTCACAAATTCATGTCCA CATCAGTAGGAGACAGGGTCAGCATCACCTGCAAGGC CAGTCAGGATGTGGGTACTGCTGTAGCCTGGTATCAA CAGAAACCAGGGCAATCTCCTAAACTACTGATTTACT GGGCATCCACCCGGCACACTGGAGTCCCTGATCGCTT CACAGGCAGTGGATCTGGGACAGATTTCACTCTCACC ATTAGCAATGTGCAGTCTGAAGACTTGGCAGATTATT TCTGTCAGCAGTATAACAGCTATCCTCTCACGTTCGG TGCTGGGTCCAAGCTGGAGCTGAAA | |
| BAP058-chi HC | | | |
| SEQ ID NO: 1 (Kabat) | HCDR1 | SYWMY | |
| SEQ ID NO: 2 (Kabat) | HCDR2 | RIDPNSGSTKYNEKFKN | |

TABLE 1-continued

| | | |
|---|---|---|
| SEQ ID NO: 3 (Kabat) | HCDR3 | DYRKGLYAMDY |
| SEQ ID NO: 4 (Chothia) | HCDR1 | GYTFTSY |
| SEQ ID NO: 5 (Chothia) | HCDR2 | DPNSGS |
| SEQ ID NO: 3 (Chothia) | HCDR3 | DYRKGLYAMDY |
| SEQ ID NO: 16 | VH | EVQLQQSGAELVKPGASVKLSCKASGYTFTSYWMYWV KQGPGRGLEWIGRIDPNSGSTKYNEKFKNKATLTVDK SSSTAYMQLSSLTSEDSAVYYCARDYRKGLYAMDYWG QGTTVTVSS |

BAP058-chi LC

| | | |
|---|---|---|
| SEQ ID NO: 9 (Kabat) | LCDR1 | KASQDVGTAVA |
| SEQ ID NO: 10 (Kabat) | LCDR2 | WASTRHT |
| SEQ ID NO: 11 (Kabat) | LCDR3 | QQYNSYPLT |
| SEQ ID NO: 12 (Chothia) | LCDR1 | SQDVGTA |
| SEQ ID NO: 13 (Chothia) | LCDR2 | WAS |
| SEQ ID NO: 14 (Chothia) | LCDR3 | YNSYPL |
| SEQ ID NO: 17 | VL | DIMMTQSHKFMSTSVGDRVSITCKASQDVGTAVAWYQ QKPGQSPKLLIYWASTRHTGVPDRFTGSGSGTDFTLT ISNVQSEDLADYFCQQYNSYPLTFGQGTKVEIK |

BAP058-hum01-HC

| | | |
|---|---|---|
| SEQ IDNO: 1 (Kabat) | HCDR1 | SYWMY |
| SEQ IDNO: 2 (Kabat) | HCDR2 | RIDPNSGSTKYNEKFKN |
| SEQ IDNO: 3 (Kabat) | HCDR3 | DYRKGLYAMDY |
| SEQ IDNO: 4 (Chothia) | HCDR1 | GYTFTSY |
| SEQ IDNO: 5 (Chothia) | HCDR2 | DPNSGS |
| SEQ IDNO: 3 (Chothia) | HCDR3 | DYRKGLYAMDY |
| SEQ IDNO: 18 | VH | QVQLVQSGAEVKKPGASVKVSCKASGYTFTSYWMYWV RQATGQGLEWMGRIDPNSGSTKYNEKFKNRFTISRDD SKNTAYLQMNSLKTEDTAVYYCARDYRKGLYAMDYWG QGTTVTVSS |
| SEQ IDNO: 19 | DNA VH | CAGGTTCAGCTGGTGCAGTCTGGAGCTGAGGTGAAGA AGCCTGGGGCCTCAGTGAAGGTCTCCTGCAAGGCTTC TGGCTACACCTTCACCAGTTACTGGATGTACTGGGTG CGACAGGCCACTGGACAAGGGCTTGAGTGGATGGGTA GGATTGATCCTAATAGTGGGAGTACTAAGTACAATGA GAAGTTCAAGAACAGATTCACCATCTCCAGAGATGAT TCAAAGAACACGGCGTATCTGCAAATGAACAGCCTGA AAACCGAGGACACGGCCGTGTATTACTGTGCAAGGGA CTATAGAAAGGGGCTCTATGCTATGGACTACTGGGGC CAGGGCACCACCGTGACCGTGTCCTCC |
| SEQ IDNO: 20 | Heavy Chain | QVQLVQSGAEVKKPGASVKVSCKASGYTFTSYWMYWV RQATGQGLEWMGRIDPNSGSTKYNEKFKNRFTISRDD SKNTAYLQMNSLKTEDTAVYYCARDYRKGLYAMDYWG QGTTVTVSSASTKGPSVFPLAPCSRSTSESTAALGCL VKDYFPEPVTVSWNSGALTSGVHTFPAVLQSSGLYSL SSVVTVPSSSLGTKTYTCNVDHKPSNTKVDKRVESKY GPPCPPCPAPEFLGGPSVFLFPPKPKDTLMISRTPEV TCVVVDVSQEDPEVQFNWYVDGVEVHNAKTKPREEQF NSTYRVVSVLTVLHQDWLNGKEYKCKVSNKGLPSSIE KTISKAKGQPREPQVYTLPPSQEEMTKNQVSLTCLVK GFYPSDIAVEWESNGQPENNYKTTPPVLDSDGSFFLY SRLTVDKSRWQEGNVFSCSVMHEALHNHYTQKSLSLS LGK |
| SEQ IDNO: 21 | DNA Heavy Chain | CAGGTTCAGCTGGTGCAGTCTGGAGCTGAGGTGAAGA AGCCTGGGGCCTCAGTGAAGGTCTCCTGCAAGGCTTC TGGCTACACCTTCACCAGTTACTGGATGTACTGGGTG CGACAGGCCACTGGACAAGGGCTTGAGTGGATGGGTA GGATTGATCCTAATAGTGGGAGTACTAAGTACAATGA |

TABLE 1 -continued

```
                    GAAGTTCAAGAACAGATTCACCATCTCCAGAGATGAT
                    TCAAAGAACACGGCGTATCTGCAAATGAACAGCCTGA
                    AAACCGAGGACACGGCCGTGTATTACTGTGCAAGGGA
                    CTATAGAAAGGGGCTCTATGCTATGGACTACTGGGGC
                    CAGGGCACCACCGTGACCGTGTCCTCCGCTTCCACCA
                    AGGGCCCATCCGTCTTCCCCCTGGCGCCCTGCTCCAG
                    GAGCACCTCCGAGAGCACAGCCGCCCTGGGCTGCCTG
                    GTCAAGGACTACTTCCCCGAACCGGTGACGGTGTCGT
                    GGAACTCAGGCGCCCTGACCAGCGGCGTGCACACCTT
                    CCCGGCTGTCCTACAGTCCTCAGGACTCTACTCCCTC
                    AGCAGCGTGGTGACCGTGCCCTCCAGCAGCTTGGGCA
                    CGAAGACCTACACCTGCAACGTAGATCACAAGCCCAG
                    CAACACCAAGGTGGACAAGAGAGTTGAGTCCAAATAT
                    GGTCCCCCATGCCCACCGTGCCCAGCACCTGAGTTCC
                    TGGGGGGACCATCAGTCTTCCTGTTCCCCCCAAAACC
                    CAAGGACACTCTCATGATCTCCCGGACCCCTGAGGTC
                    ACGTGCGTGGTGGTGGACGTGAGCCAGGAAGACCCCG
                    AGGTCCAGTTCAACTGGTACGTGGATGGCGTGGAGGT
                    GCATAATGCCAAGACAAAGCCGCGGGAGGAGCAGTTC
                    AACAGCACGTACCGTGTGGTCAGCGTCCTCACCGTCC
                    TGCACCAGGACTGGCTGAACGGCAAGGAGTACAAGTG
                    CAAGGTGTCCAACAAAGGCCTCCCGTCCTCCATCGAG
                    AAAACCATCTCCAAAGCCAAAGGGCAGCCCCGAGAGC
                    CACAGGTGTACACCCTGCCCCCATCCCAGGAGGAGAT
                    GACCAAGAACCAGGTCAGCCTGACCTGCCTGGTCAAA
                    GGCTTCTACCCCAGCGACATCGCCGTGGAGTGGGAGA
                    GCAATGGGCAGCCGGAGAACAACTACAAGACCACGCC
                    TCCCGTGCTGGACTCCGACGGCTCCTTCTTCCTCTAC
                    AGCAGGCTAACCGTGGACAAGAGCAGGTGGCAGGAGG
                    GGAATGTCTTCTCATGCTCCGTGATGCATGAGGCTCT
                    GCACAACCACTACACACAGAAGAGCCTCTCCCTGTCT
                    CTGGGTAAA
```

| | BAP058-hum01-LC | |
|---|---|---|
| SEQ ID NO: 9 (Kabat) | LCDR1 | KASQDVGTAVA |
| SEQ ID NO: 10 (Kabat) | LCDR2 | WASTRHT |
| SEQ ID NO: 11 (Kabat) | LCDR3 | QQYNSYPLT |
| SEQ ID NO: 12 (Chothia) | LCDR1 | SQDVGTA |
| SEQ ID NO: 13 (Chothia) | LCDR2 | WAS |
| SEQ ID NO: 14 (Chothia) | LCDR3 | YNSYPL |
| SEQ ID NO: 22 | VL | DIVMTQTPLSLPVTPGEPASISCKASQDVGTAVAWYL<br>QKPGQSPQLLIYWASTRHTGIPARFSGSGSGTEFTLT<br>ISSLQSEDFAVYYCQQYNSYPLTFGQGTKVEIK |
| SEQ ID NO: 23 | DNA VL | GATATTGTGATGACCCAGACTCCACTCTCCCTGCCCG<br>TCACCCCTGGAGAGCCGGCCTCCATCTCCTGCAAGGC<br>CAGTCAGGATGTGGGTACTGCTGTAGCCTGGTACCTG<br>CAGAAGCCAGGGCAGTCTCCACAGCTCCTGATCTATT<br>GGGCATCCACCCGGCACACTGGGATCCCAGCCAGGTT<br>CAGTGGCAGTGGGTCTGGGACAGAGTTCACTCTCACC<br>ATCAGCAGCCTGCAGTCTGAAGATTTTGCAGTTTATT<br>ACTGTCAGCAGTATAACAGCTATCCTCTCACGTTCGG<br>CCAAGGGACCAAGGTGGAAATCAAA |
| SEQ ID NO: 24 | Light Chain | DIVMTQTPLSLPVTPGEPASISCKASQDVGTAVAWYL<br>QKPGQSPQLLIYWASTRHTGIPARFSGSGSGTEFTLT<br>ISSLQSEDFAVYYCQQYNSYPLTFGQGTKVEIKRTVA<br>APSVFIFPPSDEQLKSGTASVVCLLNNFYPREAKVQW<br>KVDNALQSGNSQESVTEQDSKDSTYSLSSTLTLSKAD<br>YEKHKVYACEVTHQGLSSPVTKSFNRGEC |
| SEQ ID NO: 25 | DNA Light Chain | GATATTGTGATGACCCAGACTCCACTCTCCCTGCCCG<br>TCACCCCTGGAGAGCCGGCCTCCATCTCCTGCAAGGC<br>CAGTCAGGATGTGGGTACTGCTGTAGCCTGGTACCTG<br>CAGAAGCCAGGGCAGTCTCCACAGCTCCTGATCTATT<br>GGGCATCCACCCGGCACACTGGGATCCCAGCCAGGTT<br>CAGTGGCAGTGGGTCTGGGACAGAGTTCACTCTCACC<br>ATCAGCAGCCTGCAGTCTGAAGATTTTGCAGTTTATT<br>ACTGTCAGCAGTATAACAGCTATCCTCTCACGTTCGG<br>CCAAGGGACCAAGGTGGAAATCAAACGTACGGTGGCT<br>GCACCATCTGTCTTCATCTTCCCGCCATCTGATGAGC<br>AGTTGAAATCTGGAACTGCCTCTGTTGTGTGCCTGCT<br>GAATAACTTCTATCCCAGAGAGGCCAAAGTACAGTGG |

TABLE 1 -continued

AAGGTGGATAACGCCCTCCAATCGGGTAACTCCCAGG
AGAGTGTCACAGAGCAGGACAGCAAGGACAGCACCTA
CAGCCTCAGCAGCACCCTGACGCTGAGCAAAGCAGAC
TACGAGAAACACAAAGTCTACGCCTGCGAAGTCACCC
ATCAGGGCCTGAGCTCGCCCGTCACAAAGAGCTTCAA
CAGGGGAGAGTGT

| | BAP058-hum02-HC | |
|---|---|---|
| SEQ ID NO: 1 (Kabat) | HCDR1 | SYWMY |
| SEQ ID NO: 2 (Kabat) | HCDR2 | RIDPNSGSTKYNEKFKN |
| SEQ ID NO: 3 (Kabat) | HCDR3 | DYRKGLYAMDY |
| SEQ ID NO: 4 (Chothia) | HCDR1 | GYTFTSY |
| SEQ ID NO: 5 (Chothia) | HCDR2 | DPNSGS |
| SEQ ID NO: 3 (Chothia) | HCDR3 | DYRKGLYAMDY |
| SEQ ID NO: 18 | VH | QVQLVQSGAEVKKPGASVKVSCKASGYTFTSYWMYWV RQATGQGLEWMGRIDPNSGSTKYNEKFKNRFTISRDD SKNTAYLQMNSLKTEDTAVYYCARDYRKGLYAMDYWG QGTTVTVSS |
| SEQ ID NO: 19 | DNA VH | CAGGTTCAGCTGGTGCAGTCTGGAGCTGAGGTGAAGA AGCCTGGGGCCTCAGTGAAGGTCTCCTGCAAGGCTTC TGGCTACACCTTCACCAGTTACTGGATGTACTGGGTG CGACAGGCCACTGGACAAGGGCTTGAGTGGATGGGTA GGATTGATCCTAATAGTGGGAGTACTAAGTACAATGA GAAGTTCAAGAACAGATTCACCATCTCCAGAGATGAT TCAAAGAACACGGCGTATCTGCAAATGAACAGCCTGA AAACCGAGGACACGGCCGTGTATTACTGTGCAAGGGA CTATAGAAAGGGGCTCTATGCTATGGACTACTGGGGC CAGGGCACCACCGTGACCGTGTCCTCC |
| SEQ ID NO: 20 | Heavy Chain | QVQLVQSGAEVKKPGASVKVSCKASGYTFTSYWMYWV RQATGQGLEWMGRIDPNSGSTKYNEKFKNRFTISRDD SKNTAYLQMNSLKTEDTAVYYCARDYRKGLYAMDYWG QGTTVTVSSASTKGPSVFPLAPCSRSTSESTAALGCL VKDYFPEPVTVSWNSGALTSGVHTFPAVLQSSGLYSL SSVVTVPSSSLGTKTYTCNVDHKPSNTKVDKRVESKY GPPCPPCPAPEFLGGPSVFLFPPKPKDTLMISRTPEV TCVVVDVSQEDPEVQFNWYVDGVEVHNAKTKPREEQF NSTYRVVSVLTVLHQDWLNGKEYKCKVSNKGLPSSIE KTISKAKGQPREPQVYTLPPSQEEMTKNQVSLTCLVK GFYPSDIAVEWESNGQPENNYKTTPPVLDSDGSFFLY SRLTVDKSRWQEGNVFSCSVMHEALHNHYTQKSLSLS LGK |
| SEQ ID NO: 21 | DNA Heavy Chain | CAGGTTCAGCTGGTGCAGTCTGGAGCTGAGGTGAAGA AGCCTGGGGCCTCAGTGAAGGTCTCCTGCAAGGCTTC TGGCTACACCTTCACCAGTTACTGGATGTACTGGGTG CGACAGGCCACTGGACAAGGGCTTGAGTGGATGGGTA GGATTGATCCTAATAGTGGGAGTACTAAGTACAATGA GAAGTTCAAGAACAGATTCACCATCTCCAGAGATGAT TCAAAGAACACGGCGTATCTGCAAATGAACAGCCTGA AAACCGAGGACACGGCCGTGTATTACTGTGCAAGGGA CTATAGAAAGGGGCTCTATGCTATGGACTACTGGGGC CAGGGCACCACCGTGACCGTGTCCTCCGCTTCCACCA AGGGCCCATCCGTCTTCCCCCTGGCGCCCTGCTCCAG GAGCACCTCCGAGAGCACAGCCGCCCTGGGCTGCCTG GTCAAGGACTACTTCCCCGAACCGGTGACGGTGTCGT GGAACTCAGGCGCCCTGACCAGCGGCGTGCACACCTT CCCGGCTGTCCTACAGTCCTCAGGACTCTACTCCCTC AGCAGCGTGGTGACCGTGCCCTCCAGCAGCTTGGGCA CGAAGACCTACACCTGCAACGTAGATCACAAGCCCAG CAACACCAAGGTGGACAAGAGAGTTGAGTCCAAATAT GGTCCCCCATGCCCACCGTGCCCAGCACCTGAGTTCC TGGGGGGACCATCAGTCTTCCTGTTCCCCCCAAAACC CAAGGACACTCTCATGATCTCCCGGACCCCTGAGGTC ACGTGCGTGGTGGTGGACGTGAGCCAGGAAGACCCCG AGGTCCAGTTCAACTGGTACGTGGATGGCGTGGAGGT GCATAATGCCAAGACAAAGCCGCGGGAGGAGCAGTTC AACAGCACGTACCGTGTGGTCAGCGTCCTCACCGTCC TGCACCAGGACTGGCTGAACGGCAAGGAGTACAAGTG CAAGGTGTCCAACAAAGGCCTCCCGTCCTCCATCGAG AAAACCATCTCCAAAGCCAAAGGGCAGCCCCGAGAGC CACAGGTGTACACCCTGCCCCCATCCCAGGAGGAGAT |

TABLE 1 -continued

| | | | |
|---|---|---|---|
| | | | GACCAAGAACCAGGTCAGCCTGACCTGCCTGGTCAAA<br>GGCTTCTACCCCAGCGACATCGCCGTGGAGTGGGAGA<br>GCAATGGGCAGCCGGAGAACAACTACAAGACCACGCC<br>TCCCGTGCTGGACTCCGACGGCTCCTTCTTCCTCTAC<br>AGCAGGCTAACCGTGGACAAGAGCAGGTGGCAGGAGG<br>GGAATGTCTTCTCATGCTCCGTGATGCATGAGGCTCT<br>GCACAACCACTACACACAGAAGAGCCTCTCCCTGTCT<br>CTGGGTAAA |

BAP058-hum02-LC

| | | |
|---|---|---|
| SEQ ID NO: 9 (Kabat) | LCDR1 | KASQDVGTAVA |
| SEQ ID NO: 10 (Kabat) | LCDR2 | WASTRHT |
| SEQ ID NO: 11 (Kabat) | LCDR3 | QQYNSYPLT |
| SEQ ID NO: 12 (Chothia) | LCDR1 | SQDVGTA |
| SEQ ID NO: 13 (Chothia) | LCDR2 | WAS |
| SEQ ID NO: 14 (Chothia) | LCDR3 | YNSYPL |
| SEQ ID NO: 26 | VL | DIQMTQSPSSLSASVGDRVTITCKASQDVGTAVAWYL<br>QKPGQSPQLLIYWASTRHTGVPSRFSGSGSGTDFTLT<br>ISSLQPEDFATYYCQQYNSYPLTFGQGTKVEIK |
| SEQ ID NO: 27 | DNA VL | GACATCCAGATGACCCAGTCTCCATCCTCCCTGTCTG<br>CATCTGTAGGAGACAGAGTCACCATCACTTGCAAGGC<br>CAGTCAGGATGTGGGTACTGCTGTAGCCTGGTACCTG<br>CAGAAGCCAGGGCAGTCTCCACAGCTCCTGATCTATT<br>GGGCATCCACCCGGCACACTGGGGTCCCATCAAGGTT<br>CAGCGGCAGTGGATCTGGGACAGATTTCACTCTCACC<br>ATCAGCAGCCTGCAGCCTGAAGATTTTGCAACTTATT<br>ACTGTCAGCAGTATAACAGCTATCCTCTCACGTTCGG<br>CCAAGGGACCAAGGTGGAAATCAAA |
| SEQ ID NO: 28 | Light Chain | DIQMTQSPSSLSASVGDRVTITCKASQDVGTAVAWYL<br>QKPGQSPQLLIYWASTRHTGVPSRFSGSGSGTDFTLT<br>ISSLQPEDFATYYCQQYNSYPLTFGQGTKVEIKRTVA<br>APSVFIFPPSDEQLKSGTASVVCLLNNFYPREAKVQW<br>KVDNALQSGNSQESVTEQDSKDSTYSLSSTLTLSKAD<br>YEKHKVYACEVTHQGLSSPVTKSFNRGEC |
| SEQ ID NO: 29 | DNA Light Chain | GACATCCAGATGACCCAGTCTCCATCCTCCCTGTCTG<br>CATCTGTAGGAGACAGAGTCACCATCACTTGCAAGGC<br>CAGTCAGGATGTGGGTACTGCTGTAGCCTGGTACCTG<br>CAGAAGCCAGGGCAGTCTCCACAGCTCCTGATCTATT<br>GGGCATCCACCCGGCACACTGGGGTCCCATCAAGGTT<br>CAGCGGCAGTGGATCTGGGACAGATTTCACTCTCACC<br>ATCAGCAGCCTGCAGCCTGAAGATTTTGCAACTTATT<br>ACTGTCAGCAGTATAACAGCTATCCTCTCACGTTCGG<br>CCAAGGGACCAAGGTGGAAATCAAACGTACGGTGGCT<br>GCACCATCTGTCTTCATCTTCCCGCCATCTGATGAGC<br>AGTTGAAATCTGGAACTGCCTCTGTTGTGTGCCTGCT<br>GAATAACTTCTATCCCAGAGAGGCCAAAGTACAGTGG<br>AAGGTGGATAACGCCCTCCAATCGGGTAACTCCCAGG<br>AGAGTGTCACAGAGCAGGACAGCAAGGACAGCACCTA<br>CAGCCTCAGCAGCACCCTGACGCTGAGCAAAGCAGAC<br>TACGAGAAACACAAAGTCTACGCCTGCGAAGTCACCC<br>ATCAGGGCCTGAGCTCGCCCGTCACAAAGAGCTTCAA<br>CAGGGGAGAGTGT |

BAP058-hum03-HC

| | | |
|---|---|---|
| SEQ ID NO: 1 (Kabat) | HCDR1 | SYWMY |
| SEQ ID NO: 2 (Kabat) | HCDR2 | RIDPNSGSTKYNEKFKN |
| SEQ ID NO: 3 (Kabat) | HCDR3 | DYRKGLYAMDY |
| SEQ ID NO: 4 (Chothia) | HCDR1 | GYTFTSY |
| SEQ ID NO: 5 (Chothia) | HCDR2 | DPNSGS |
| SEQ ID NO: 3 (Chothia) | HCDR3 | DYRKGLYAMDY |
| SEQ ID NO: 30 | VH | EVQLVQSGAEVKKPGATVKISCKVSGYTFTSYWMYWV<br>RQATGQGLEWMGRIDPNSGSTKYNEKFKNRVTITADK |

TABLE 1-continued

| | | |
|---|---|---|
| | | STSTAYMELSSLRSEDTAVYYCARDYRKGLYAMDYWG<br>QGTTVTVSS |
| SEQ ID NO: 31 | DNA VH | GAGGTCCAGCTGGTACAGTCTGGGGCTGAGGTGAAGA<br>AGCCTGGGGCTACAGTGAAAATCTCCTGCAAGGTTTC<br>TGGCTACACCTTCACCAGTTACTGGATGTACTGGGTG<br>CGACAGGCCACTGGACAAGGGCTTGAGTGGATGGGTA<br>GGATTGATCCTAATAGTGGGAGTACTAAGTACAATGA<br>GAAGTTCAAGAACAGAGTCACGATTACCGCGGACAAA<br>TCCACGAGCACAGCCTACATGGAGCTGAGCAGCCTGA<br>GATCTGAGGACACGGCCGTGTATTACTGTGCAAGGGA<br>CTATAGAAAGGGGCTCTATGCTATGGACTACTGGGGC<br>CAGGGCACCACCGTGACCGTGTCCTCC |
| SEQ ID NO: 32 | Heavy<br>Chain | EVQLVQSGAEVKKPGATVKISCKVSGYTFTSYWMYWV<br>RQATGQGLEWMGRIDPNSGSTKYNEKFKNRVTITADK<br>STSTAYMELSSLRSEDTAVYYCARDYRKGLYAMDYWG<br>QGTTVTVSSASTKGPSVFPLAPCSRSTSESTAALGCL<br>VKDYFPEPVTVSWNSGALTSGVHTFPAVLQSSGLYSL<br>SSVVTVPSSSLGTKTYTCNVDHKPSNTKVDKRVESKY<br>GPPCPPCPAPEFLGGPSVFLFPPKPKDTLMISRTPEV<br>TCVVVDVSQEDPEVQFNWYVDGVEVHNAKTKPREEQF<br>NSTYRVVSVLTVLHQDWLNGKEYKCKVSNKGLPSSIE<br>KTISKAKGQPREPQVYTLPPSQEEMTKNQVSLTCLVK<br>GFYPSDIAVEWESNGQPENNYKTTPPVLDSDGSFFLY<br>SRLTVDKSRWQEGNVFSCSVMHEALHNHYTQKSLSLS<br>LGK |
| SEQ ID NO: 33 | DNA Heavy<br>Chain | GAGGTCCAGCTGGTACAGTCTGGGGCTGAGGTGAAGA<br>AGCCTGGGGCTACAGTGAAAATCTCCTGCAAGGTTTC<br>TGGCTACACCTTCACCAGTTACTGGATGTACTGGGTG<br>CGACAGGCCACTGGACAAGGGCTTGAGTGGATGGGTA<br>GGATTGATCCTAATAGTGGGAGTACTAAGTACAATGA<br>GAAGTTCAAGAACAGAGTCACGATTACCGCGGACAAA<br>TCCACGAGCACAGCCTACATGGAGCTGAGCAGCCTGA<br>GATCTGAGGACACGGCCGTGTATTACTGTGCAAGGGA<br>CTATAGAAAGGGGCTCTATGCTATGGACTACTGGGGC<br>CAGGGCACCACCGTGACCGTGTCCTCCGCTTCCACCA<br>AGGGCCCATCCGTCTTCCCCCTGGCGCCCTGCTCCAG<br>GAGCACCTCCGAGAGCACAGCCGCCCTGGGCTGCCTG<br>GTCAAGGACTACTTCCCCGAACCGGTGACGGTGTCGT<br>GGAACTCAGGCGCCCTGACCAGCGGCGTGCACACCTT<br>CCCGGCTGTCCTACAGTCCTCAGGACTCTACTCCCTC<br>AGCAGCGTGGTGACCGTGCCCTCCAGCAGCTTGGGCA<br>CGAAGACCTACACCTGCAACGTAGATCACAAGCCCAG<br>CAACACCAAGGTGGACAAGAGAGTTGAGTCCAAATAT<br>GGTCCCCCATGCCCACCGTGCCCAGCACCTGAGTTCC<br>TGGGGGGACCATCAGTCTTCCTGTTCCCCCCAAAACC<br>CAAGGACACTCTCATGATCTCCCGGACCCCTGAGGTC<br>ACGTGCGTGGTGGTGGACGTGAGCCAGGAAGACCCCG<br>AGGTCCAGTTCAACTGGTACGTGGATGGCGTGGAGGT<br>GCATAATGCCAAGACAAAGCCGCGGGAGGAGCAGTTC<br>AACAGCACGTACCGTGTGGTCAGCGTCCTCACCGTCC<br>TGCACCAGGACTGGCTGAACGGCAAGGAGTACAAGTG<br>CAAGGTGTCCAACAAAGGCCTCCCGTCCTCCATCGAG<br>AAAACCATCTCCAAAGCCAAAGGGCAGCCCCGAGAGC<br>CACAGGTGTACACCCTGCCCCCATCCCAGGAGGAGAT<br>GACCAAGAACCAGGTCAGCCTGACCTGCCTGGTCAAA<br>GGCTTCTACCCCAGCGACATCGCCGTGGAGTGGGAGA<br>GCAATGGGCAGCCGGAGAACAACTACAAGACCACGCC<br>TCCCGTGCTGGACTCCGACGGCTCCTTCTTCCTCTAC<br>AGCAGGCTAACCGTGGACAAGAGCAGGTGGCAGGAGG<br>GGAATGTCTTCTCATGCTCCGTGATGCATGAGGCTCT<br>GCACAACCACTACACACAGAAGAGCCTCTCCCTGTCT<br>CTGGGTAAA |

| BAP058-hum03-LC | | |
|---|---|---|
| SEQ ID NO: 9 (Kabat) | LCDR1 | KASQDVGTAVA |
| SEQ ID NO: 10 (Kabat) | LCDR2 | WASTRHT |
| SEQ ID NO: 11 (Kabat) | LCDR3 | QQYNSYPLT |
| SEQ ID NO: 12 (Chothia) | LCDR1 | SQDVGTA |
| SEQ ID NO: 13 (Chothia) | LCDR2 | WAS |
| SEQ ID NO: 14 (Chothia) | LCDR3 | YNSYPL |

TABLE 1 -continued

| SEQ ID NO: 34 | VL | EIVLTQSPDFQSVTPKEKVTITCKASQDVGTAVAWYL QKPGQSPQLLIYWASTRHTGVPDRFSGSGSGTDFTLK ISRVEAEDVGVYYCQQYNSYPLTFGQGTKVEIK |
| --- | --- | --- |
| SEQ ID NO: 35 | DNA VL | GAAATTGTGCTGACTCAGTCTCCAGACTTTCAGTCTG TGACTCCAAAGGAGAAAGTCACCATCACCTGCAAGGC CAGTCAGGATGTGGGTACTGCTGTAGCCTGGTACCTG CAGAAGCCAGGGCAGTCTCCACAGCTCCTGATCTATT GGGCATCCACCCGGCACACTGGGGTCCCAGACAGGTT CAGTGGCAGTGGGTCAGGCACTGATTTCACACTGAAA ATCAGCAGGGTGGAGGCTGAGGATGTTGGAGTTTATT ACTGTCAGCAGTATAACAGCTATCCTCTCACGTTCGG CCAAGGGACCAAGGTGGAAATCAAA |
| SEQ ID NO: 36 | Light Chain | EIVLTQSPDFQSVTPKEKVTITCKASQDVGTAVAWYL QKPGQSPQLLIYWASTRHTGVPDRFSGSGSGTDFTLK ISRVEAEDVGVYYCQQYNSYPLTFGQGTKVEIKRTVA APSVFIFPPSDEQLKSGTASVVCLLNNFYPREAKVQW KVDNALQSGNSQESVTEQDSKDSTYSLSSTLTLSKAD YEKHKVYACEVTHQGLSSPVTKSFNRGEC |
| SEQ ID NO: 37 | DNA Light Chain | GAAATTGTGCTGACTCAGTCTCCAGACTTTCAGTCTG TGACTCCAAAGGAGAAAGTCACCATCACCTGCAAGGC CAGTCAGGATGTGGGTACTGCTGTAGCCTGGTACCTG CAGAAGCCAGGGCAGTCTCCACAGCTCCTGATCTATT GGGCATCCACCCGGCACACTGGGGTCCCAGACAGGTT CAGTGGCAGTGGGTCAGGCACTGATTTCACACTGAAA ATCAGCAGGGTGGAGGCTGAGGATGTTGGAGTTTATT ACTGTCAGCAGTATAACAGCTATCCTCTCACGTTCGG CCAAGGGACCAAGGTGGAAATCAAACGTACGGTGGCT GCACCATCTGTCTTCATCTTCCCGCCATCTGATGAGC AGTTGAAATCTGGAACTGCCTCTGTTGTGTGCCTGCT GAATAACTTCTATCCCAGAGAGGCCAAAGTACAGTGG AAGGTGGATAACGCCCTCCAATCGGGTAACTCCCAGG AGAGTGTCACAGAGCAGGACAGCAAGGACAGCACCTA CAGCCTCAGCAGCACCCTGACGCTGAGCAAAGCAGAC TACGAGAAACACAAAGTCTACGCCTGCGAAGTCACCC ATCAGGGCCTGAGCTCGCCCGTCACAAAGAGCTTCAA CAGGGGAGAGTGT |

| BAP058-hum04-HC | | |
| --- | --- | --- |
| SEQ ID NO: 1 (Kabat) | HCDR1 | SYWMY |
| SEQ ID NO: 2 (Kabat) | HCDR2 | RIDPNSGSTKYNEKFKN |
| SEQ ID NO: 3 (Kabat) | HCDR3 | DYRKGLYAMDY |
| SEQ ID NO: 4 (Chothia) | HCDR1 | GYTFTSY |
| SEQ ID NO: 5 (Chothia) | HCDR2 | DPNSGS |
| SEQ ID NO: 3 (Chothia) | HCDR3 | DYRKGLYAMDY |
| SEQ ID NO: 38 | VH | EVQLVQSGAEVKKPGESLRISCKGSGYTFTSYWMYWV RQAPGQGLEWMGRIDPNSGSTKYNEKFKNRVTISVDT SKNQFSLKLSSVTAADTAVYYCARDYRKGLYAMDYWG QGTTVTVSS |
| SEQ ID NO: 39 | DNA VH | GAAGTGCAGCTGGTGCAGTCTGGAGCAGAGGTGAAAA AGCCCGGGGAGTCTCTGAGGATCTCCTGTAAGGGTTC TGGCTACACCTTCACCAGTTACTGGATGTACTGGGTG CGACAGGCCCCTGGACAAGGGCTTGAGTGGATGGGTA GGATTGATCCTAATAGTGGGAGTACTAAGTACAATGA GAAGTTCAAGAACAGAGTCACCATATCAGTAGACACG TCCAAGAACCAGTTCTCCCTGAAGCTGAGCTCTGTGA CCGCCGCGGACACGGCTGTGTATTACTGCGCAAGGGA CTATAGAAAGGGGCTCTATGCTATGGACTACTGGGGC CAGGGCACCACCGTGACCGTGTCCTCC |
| SEQ ID NO: 40 | Heavy Chain | EVQLVQSGAEVKKPGESLRISCKGSGYTFTSYWMYWV RQAPGQGLEWMGRIDPNSGSTKYNEKFKNRVTISVDT SKNQFSLKLSSVTAADTAVYYCARDYRKGLYAMDYWG QGTTVTVSSASTKGPSVFPLAPCSRSTSESTAALGCL VKDYFPEPVTVSWNSGALTSGVHTFPAVLQSSGLYSL SSVVTVPSSSLGTKTYTCNVDHKPSNTKVDKRVESKY GPPCPPCPAPEFLGGPSVFLFPPKPKDTLMISRTPEV TCVVVDVSQEDPEVQFNWYVDGVEVHNAKTKPREEQF NSTYRVVSVLTVLHQDWLNGKEYKCKVSNKGLPSSIE KTISKAKGQPREPQVYTLPPSQEEMTKNQVSLTCLVK |

TABLE 1 -continued

| | | |
|---|---|---|
| | | GFYPSDIAVEWESNGQPENNYKTTPPVLDSDGSFFLY<br>SRLTVDKSRWQEGNVFSCSVMHEALHNHYTQKSLSLS<br>LGK |
| SEQ ID NO: 41 | DNA Heavy<br>Chain | GAAGTGCAGCTGGTGCAGTCTGGAGCAGAGGTGAAAA<br>AGCCCGGGGAGTCTCTGAGGATCCTGTAAGGGTTC<br>TGGCTACACCTTCACCAGTTACTGGATGTACTGGGTG<br>CGACAGGCCCCTGGACAAGGGCTTGAGTGGATGGGTA<br>GGATTGATCCTAATAGTGGGAGTACTAAGTACAATGA<br>GAAGTTCAAGAACAGAGTCACCATATCAGTAGACACG<br>TCCAAGAACCAGTTCTCCCTGAAGCTGAGCTCTGTGA<br>CCGCCGCGGACACGGCTGTGTATTACTGTGCAAGGGA<br>CTATAGAAAGGGGCTCTATGCTATGGACTACTGGGGC<br>CAGGGCACCACCGTGACCGTGTCCTCCGCTTCCACCA<br>AGGGCCCATCCGTCTTCCCCCTGGCGCCCTGCTCCAG<br>GAGCACCTCCGAGAGCACAGCCGCCCTGGGCTGCCTG<br>GTCAAGGACTACTTCCCCGAACCGGTGACGGTGTCGT<br>GGAACTCAGGCGCCCTGACCAGCGGCGTGCACACCTT<br>CCCGGCTGTCCTACAGTCCTCAGGACTCTACTCCCTC<br>AGCAGCGTGGTGACCGTGCCCTCCAGCAGCTTGGGCA<br>CGAAGACCTACACCTGCAACGTAGATCACAAGCCCAG<br>CAACACCAAGGTGGACAAGAGAGTTGAGTCCAAATAT<br>GGTCCCCCATGCCCACCGTGCCCAGCACCTGAGTTCC<br>TGGGGGGACCATCAGTCTTCCTGTTCCCCCCAAAACC<br>CAAGGACACTCTCATGATCTCCCGGACCCCTGAGGTC<br>ACGTGCGTGGTGGTGGACGTGAGCCAGGAAGACCCCG<br>AGGTCCAGTTCAACTGGTACGTGGATGGCGTGGAGGT<br>GCATAATGCCAAGACAAAGCCGCGGGAGGAGCAGTTC<br>AACAGCACGTACCGTGTGGTCAGCGTCCTCACCGTCC<br>TGCACCAGGACTGGCTGAACGGCAAGGAGTACAAGTG<br>CAAGGTGTCCAACAAAGGCCTCCCGTCCTCCATCGAG<br>AAAACCATCTCCAAAGCCAAAGGGCAGCCCCGAGAGC<br>CACAGGTGTACACCCTGCCCCCATCCCAGGAGGAGAT<br>GACCAAGAACCAGGTCAGCCTGACCTGCCTGGTCAAA<br>GGCTTCTACCCCAGCGACATCGCCGTGGAGTGGGAGA<br>GCAATGGGCAGCCGGAGAACAACTACAAGACCACGCC<br>TCCCGTGCTGGACTCCGACGGCTCCTTCTTCCTCTAC<br>AGCAGGCTAACCGTGGACAAGAGCAGGTGGCAGGAGG<br>GGAATGTCTTCTCATGCTCCGTGATGCATGAGGCTCT<br>GCACAACCACTACACACAGAAGAGCCTCTCCCTGTCT<br>CTGGGTAAA |

| BAP058-hum04-LC | | |
|---|---|---|
| SEQ ID NO: 9 (Kabat) | LCDR1 | KASQDVGTAVA |
| SEQ ID NO: 10 (Kabat) | LCDR2 | WASTRHT |
| SEQ ID NO: 11 (Kabat) | LCDR3 | QQYNSYPLT |
| SEQ ID NO: 12 (Chothia) | LCDR1 | SQDVGTA |
| SEQ ID NO: 13 (Chothia) | LCDR2 | WAS |
| SEQ ID NO: 14 (Chothia) | LCDR3 | YNSYPL |
| SEQ ID NO: 42 | VL | EIVLTQSPDFQSVTPKEKVTITCKASQDVGTAVAWYL<br>QKPGQSPQLLIYWASTRHTGVPSRFSGSGSGTDFTFT<br>ISSLQPEDIATYYCQQYNSYPLTFGQGTKVEIK |
| SEQ ID NO: 43 | DNA VL | GAAATTGTGCTGACTCAGTCTCCAGACTTTCAGTCTG<br>TGACTCCAAAGGAGAAAGTCACCATCACCTGCAAGGC<br>CAGTCAGGATGTGGGTACTGCTGTAGCCTGGTACCTG<br>CAGAAGCCAGGGCAGTCTCCACAGCTCCTGATCTATT<br>GGGCATCCACCCGGCACACTGGGGTCCCATCAAGGTT<br>CAGTGGAAGTGGATCTGGGACAGATTTTACTTTCACC<br>ATCAGCAGCCTGCAGCCTGAAGATATTGCAACATATT<br>ACTGTCAGCAGTATAACAGCTATCCTCTCACGTTCGG<br>CCAAGGGACCAAGGTGGAAATCAAA |
| SEQ ID NO: 44 | Light<br>Chain | EIVLTQSPDFQSVTPKEKVTITCKASQDVGTAVAWYL<br>QKPGQSPQLLIYWASTRHTGVPSRFSGSGSGTDFTFT<br>ISSLQPEDIATYYCQQYNSYPLTFGQGTKVEIKRTVA<br>APSVFIFPPSDEQLKSGTASVVCLLNNFYPREAKVQW<br>KVDNALQSGNSQESVTEQDSKDSTYSLSSTLTLSKAD<br>YEKHKVYACEVTHQGLSSPVTKSFNRGEC |
| SEQ ID NO: 45 | DNA Light<br>Chain | GAAATTGTGCTGACTCAGTCTCCAGACTTTCAGTCTG<br>TGACTCCAAAGGAGAAAGTCACCATCACCTGCAAGGC<br>CAGTCAGGATGTGGGTACTGCTGTAGCCTGGTACCTG |

TABLE 1 -continued

CAGAAGCCAGGGCAGTCTCCACAGCTCCTGATCTATT
GGGCATCCACCCGGCACACTGGGGTCCCATCAAGGTT
CAGTGGAAGTGGATCTGGGACAGATTTTACTTTCACC
ATCAGCAGCCTGCAGCCTGAAGATATTGCAACATATT
ACTGTCAGCAGTATAACAGCTATCCTCTCACGTTCGG
CCAAGGGACCAAGGTGGAAATCAAACGTACGGTGGCT
GCACCATCTGTCTTCATCTTCCCGCCATCTGATGAGC
AGTTGAAATCTGGAACTGCCTCTGTTGTGTGCCTGCT
GAATAACTTCTATCCCAGAGAGGCCAAAGTACAGTGG
AAGGTGGATAACGCCCTCCAATCGGGTAACTCCCAGG
AGAGTGTCACAGAGCAGGACAGCAAGGACAGCACCTA
CAGCCTCAGCAGCACCCTGACGCTGAGCAAAGCAGAC
TACGAGAAACACAAGTCTACGCCTGCGAAGTCACCC
ATCAGGGCCTGAGCTCGCCCCGTCACAAAGAGCTTCAA
CAGGGGAGAGTGT

| | BAP058-hum05-HC | |
|---|---|---|
| SEQ ID NO: 1 (Kabat) | HCDR1 | SYWMY |
| SEQ ID NO: 2 (Kabat) | HCDR2 | RIDPNSGSTKYNEKFKN |
| SEQ ID NO: 3 (Kabat) | HCDR3 | DYRKGLYAMDY |
| SEQ ID NO: 4 (Chothia) | HCDR1 | GYTFTSY |
| SEQ ID NO: 5 (Chothia) | HCDR2 | DPNSGS |
| SEQ ID NO: 3 (Chothia) | HCDR3 | DYRKGLYAMDY |
| SEQ ID NO: 46 | VH | EVQLVQSGAEVKKPGATVKISCKVSGYTFTSYWMYWI
RQSPSRGLEWLGRIDPNSGSTKYNEKFKNRLTISKDT
SKNQVVLTMTNMDPVDTATYYCARDYRKGLYAMDYWG
QGTTVTVSS |
| SEQ ID NO: 47 | DNA VH | GAGGTCCAGCTGGTACAGTCTGGGGCTGAGGTGAAGA
AGCCTGGGGCTACAGTGAAAATCTCCTGCAAGGTTTC
TGGCTACACCTTCACCAGTTACTGGATGTACTGGATC
AGGCAGTCCCCATCGAGAGGCCTTGAGTGGCTGGGTA
GGATTGATCCTAATAGTGGGAGTACTAAGTACAATGA
GAAGTTCAAGAACAGACTCACCATCTCCAAGGACACC
TCCAAAAACCAGGTGGTCCTTACAATGACCAACATGG
ACCCTGTGGACACAGCCACGTATTACTGTGCAAGGGA
CTATAGAAAGGGGCTCTATGCTATGGACTACTGGGGC
CAGGGCACCACCGTGACCGTGTCCTCC |
| SEQ ID NO: 48 | Heavy Chain | EVQLVQSGAEVKKPGATVKISCKVSGYTFTSYWMYWI
RQSPSRGLEWLGRIDPNSGSTKYNEKFKNRLTISKDT
SKNQVVLTMTNMDPVDTATYYCARDYRKGLYAMDYWG
QGTTVTVSSASTKGPSVFPLAPCSRSTSESTAALGCL
VKDYFPEPVTVSWNSGALTSGVHTFPAVLQSSGLYSL
SSVVTVPSSSLGTKTYTCNVDHKPSNTKVDKRVESKY
GPPCPPCPAPEFLGGPSVFLFPPKPKDTLMISRTPEV
TCVVVDVSQEDPEVQFNWYVDGVEVHNAKTKPREEQF
NSTYRVVSVLTVLHQDWLNGKEYKCKVSNKGLPSSIE
KTISKAKGQPREPQVYTLPPSQEEMTKNQVSLTCLVK
GFYPSDIAVEWESNGQPENNYKTTPPVLDSDGSFFLY
SRLTVDKSRWQEGNVFSCSVMHEALHNHYTQKSLSLS
LGK |
| SEQ ID NO: 49 | DNA Heavy Chain | GAGGTCCAGCTGGTACAGTCTGGGGCTGAGGTGAAGA
AGCCTGGGGCTACAGTGAAAATCTCCTGCAAGGTTTC
TGGCTACACCTTCACCAGTTACTGGATGTACTGGATC
AGGCAGTCCCCATCGAGAGGCCTTGAGTGGCTGGGTA
GGATTGATCCTAATAGTGGGAGTACTAAGTACAATGA
GAAGTTCAAGAACAGACTCACCATCTCCAAGGACACC
TCCAAAAACCAGGTGGTCCTTACAATGACCAACATGG
ACCCTGTGGACACAGCCACGTATTACTGTGCAAGGGA
CTATAGAAAGGGGCTCTATGCTATGGACTACTGGGGC
CAGGGCACCACCGTGACCGTGTCCTCCGCTTCCACCA
AGGGCCCATCCGTCTTCCCCCTGGCGCCCTGCTCCAG
GAGCACCTCCGAGAGCACAGCCGCCCTGGGCTGCCTG
GTCAAGGACTACTTCCCCGAACCGGTGACGGTGTCGT
GGAACTCAGGCGCCCTGACCAGCGGCGTGCACACCTT
CCCGGCTGTCCTACAGTCCTCAGGACTCTACTCCCTC
AGCAGCGTGGTGACCGTGCCCTCCAGCAGCTTGGGCA
CGAAGACCTACACCTGCAACGTAGATCACAAGCCCAG
CAACACCAAGGTGGACAAGAGAGTTGAGTCCAAATAT
GGTCCCCCATGCCCACCGTGCCCAGCACCTGAGTTCC
TGGGGGGACCATCAGTCTTCCTGTTCCCCCCAAAACC |

TABLE 1 -continued

| | | | |
|---|---|---|---|
| | | | CAAGGACACTCTCATGATCTCCCGGACCCCTGAGGTC ACGTGCGTGGTGGTGGACGTGAGCCAGGAAGACCCCG AGGTCCAGTTCAACTGGTACGTGGATGGCGTGGAGGT GCATAATGCCAAGACAAAGCCGCGGGAGGAGCAGTTC AACAGCACGTACCGTGTGGTCAGCGTCCTCACCGTCC TGCACCAGGACTGGCTGAACGGCAAGGAGTACAAGTG CAAGGTGTCCAACAAAGGCCTCCCGTCCTCCATCGAG AAAACCATCTCCAAAGCCAAAGGGCAGCCCCGAGAGC CACAGGTGTACACCCTGCCCCCATCCCAGGAGGAGAT GACCAAGAACCAGGTCAGCCTGACCTGCCTGGTCAAA GGCTTCTACCCCAGCGACATCGCCGTGGAGTGGGAGA GCAATGGGCAGCCGGAGAACAACTACAAGACCACGCC TCCCGTGCTGGACTCCGACGGCTCCTTCTTCCTCTAC AGCAGGCTAACCGTGGACAAGAGCAGGTGGCAGGAGG GGAATGTCTTCTCATGCTCCGTGATGCATGAGGCTCT GCACAACCACTACACACAGAAGAGCCTCTCCCTGTCT CTGGGTAAA |

| BAP058-hum05-LC | | | |
|---|---|---|---|
| SEQ ID NO: 9 (Kabat) | LCDR1 | KASQDVGTAVA | |
| SEQ ID NO: 10 (Kabat) | LCDR2 | WASTRHT | |
| SEQ ID NO: 11 (Kabat) | LCDR3 | QQYNSYPLT | |
| SEQ ID NO: 12 (Chothia) | LCDR1 | SQDVGTA | |
| SEQ ID NO: 13 (Chothia) | LCDR2 | WAS | |
| SEQ ID NO: 14 (Chothia) | LCDR3 | YNSYPL | |
| SEQ ID NO: 42 | VL | EIVLTQSPDFQSVTPKEKVTITCKASQDVGTAVAWYL QKPGQSPQLLIYWASTRHTGVPSRFSGSGSGTDFTFT ISSLQPEDIATYYCQQYNSYPLTFGQGTKVEIK | |
| SEQ ID NO: 43 | DNA VL | GAAATTGTGCTGACTCAGTCTCCAGACTTTCAGTCTG TGACTCCAAAGGAGAAAGTCACCATCACCTGCAAGGC CAGTCAGGATGTGGGTACTGCTGTAGCCTGGTACCTG CAGAAGCCAGGGCAGTCTCCACAGCTCCTGATCTATT GGGCATCCACCCGGCACACTGGGGTCCCATCAAGGTT CAGTGGAAGTGGATCTGGGACAGATTTTACTTTCACC ATCAGCAGCCTGCAGCCTGAAGATATTGCAACATATT ACTGTCAGCAGTATAACAGCTATCCTCTCACGTTCGG CCAAGGGACCAAGGTGGAAATCAAA | |
| SEQ ID NO: 44 | Light Chain | EIVLTQSPDFQSVTPKEKVTITCKASQDVGTAVAWYL QKPGQSPQLLIYWASTRHTGVPSRFSGSGSGTDFTFT ISSLQPEDIATYYCQQYNSYPLTFGQGTKVEIKRTVA APSVFIFPPSDEQLKSGTASVVCLLNNFYPREAKVQW KVDNALQSGNSQESVTEQDSKDSTYSLSSTLTLSKAD YEKHKVYACEVTHQGLSSPVTKSFNRGEC | |
| SEQ ID NO: 45 | DNA Light Chain | GAAATTGTGCTGACTCAGTCTCCAGACTTTCAGTCTG TGACTCCAAAGGAGAAAGTCACCATCACCTGCAAGGC CAGTCAGGATGTGGGTACTGCTGTAGCCTGGTACCTG CAGAAGCCAGGGCAGTCTCCACAGCTCCTGATCTATT GGGCATCCACCCGGCACACTGGGGTCCCATCAAGGTT CAGTGGAAGTGGATCTGGGACAGATTTTACTTTCACC ATCAGCAGCCTGCAGCCTGAAGATATTGCAACATATT ACTGTCAGCAGTATAACAGCTATCCTCTCACGTTCGG CCAAGGGACCAAGGTGGAAATCAAACGTACGGTGGCT GCACCATCTGTCTTCATCTTCCCGCCATCTGATGAGC AGTTGAAATCTGGAACTGCCTCTGTTGTGTGCCTGCT GAATAACTTCTATCCCAGAGAGGCCAAAGTACAGTGG AAGGTGGATAACGCCCTCCAATCGGGTAACTCCCAGG AGAGTGTCACAGAGCAGGACAGCAAGGACAGCACCTA CAGCCTCAGCAGCACCCTGACGCTGAGCAAAGCAGAC TACGAGAAACACAAAGTCTACGCCTGCGAAGTCACCC ATCAGGGCCTGAGCTCGCCCGTCACAAAGAGCTTCAA CAGGGGAGAGTGT | |

| BAP058-hum06-HC | | | |
|---|---|---|---|
| SEQ ID NO: 1 (Kabat) | HCDR1 | SYWMY | |
| SEQ ID NO: 2 (Kabat) | HCDR2 | RIDPNSGSTKYNEKFKN | |
| SEQ ID NO: 3 (Kabat) | HCDR3 | DYRKGLYAMDY | |

TABLE 1-continued

| SEQ ID NO: 4 (Chothia) | HCDR1 | GYTFTSY |
|---|---|---|
| SEQ ID NO: 5 (Chothia) | HCDR2 | DPNSGS |
| SEQ ID NO: 3 (Chothia) | HCDR3 | DYRKGLYAMDY |
| SEQ ID NO: 50 | VH | EVQLVQSGAEVKKPGESLRISCKGSGYTFTSYWMYWI<br>RQPPGKGLEWIGRIDPNSGSTKYNEKFKNRVTITADK<br>STSTAYMELSSLRSEDTAVYYCARDYRKGLYAMDYWG<br>QGTTVTVSS |
| SEQ ID NO: 51 | DNA VH | GAAGTGCAGCTGGTGCAGTCTGGAGCAGAGGTGAAAA<br>AGCCCGGGGAGTCTCTGAGGATCTCCTGTAAGGGTTC<br>TGGCTACACCTTCACCAGTTACTGGATGTACTGGATC<br>CGCCAGCCCCCAGGGAAGGGGCTGGAGTGGATTGTA<br>GGATTGATCCTAATAGTGGGAGTACTAAGTACAATGA<br>GAAGTTCAAGAACAGAGTCACGATTACCGCGGACAAA<br>TCCACGAGCACAGCCTACATGGAGCTGAGCAGCCTGA<br>GATCTGAGGACACGGCCGTGTATTACTGTGCAAGGGA<br>CTATAGAAAGGGGCTCTATGCTATGGACTACTGGGGC<br>CAGGGCACCACCGTGACCGTGTCCTCC |
| SEQ ID NO: 52 | Heavy Chain | EVQLVQSGAEVKKPGESLRISCKGSGYTFTSYWMYWI<br>RQPPGKGLEWIGRIDPNSGSTKYNEKFKNRVTITADK<br>STSTAYMELSSLRSEDTAVYYCARDYRKGLYAMDYWG<br>QGTTVTVSSASTKGPSVFPLAPCSRSTSESTAALGCL<br>VKDYFPEPVTVSWNSGALTSGVHTFPAVLQSSGLYSL<br>SSVVTVPSSSLGTKTYTCNVDHKPSNTKVDKRVESKY<br>GPPCPPCPAPEFLGGPSVFLFPPKPKDTLMISRTPEV<br>TCVVVDVSQEDPEVQFNWYVDGVEVHNAKTKPREEQF<br>NSTYRVVSVLTVLHQDWLNGKEYKCKVSNKGLPSSIE<br>KTISKAKGQPREPQVYTLPPSQEEMTKNQVSLTCLVK<br>GFYPSDIAVEWESNGQPENNYKTTPPVLDSDGSFFLY<br>SRLTVDKSRWQEGNVFSCSVMHEALHNHYTQKSLSLS<br>LGK |
| SEQ ID NO: 53 | DNA Heavy Chain | GAAGTGCAGCTGGTGCAGTCTGGAGCAGAGGTGAAAA<br>AGCCCGGGGAGTCTCTGAGGATCTCCTGTAAGGGTTC<br>TGGCTACACCTTCACCAGTTACTGGATGTACTGGATC<br>CGCCAGCCCCCAGGGAAGGGGCTGGAGTGGATTGTA<br>GGATTGATCCTAATAGTGGGAGTACTAAGTACAATGA<br>GAAGTTCAAGAACAGAGTCACGATTACCGCGGACAAA<br>TCCACGAGCACAGCCTACATGGAGCTGAGCAGCCTGA<br>GATCTGAGGACACGGCCGTGTATTACTGTGCAAGGGA<br>CTATAGAAAGGGGCTCTATGCTATGGACTACTGGGGC<br>CAGGGCACCACCGTGACCGTGTCCTCCGCTTCCACCA<br>AGGGCCCATCCGTCTTCCCCCTGGCGCCCTGCTCCAG<br>GAGCACCTCCGAGAGCACAGCCGCCCTGGGCTGCCTG<br>GTCAAGGACTACTTCCCCGAACCGGTGACGGTGTCGT<br>GGAACTCAGGCGCCCTGACCAGCGGCGTGCACACCTT<br>CCCGGCTGTCCTACAGTCCTCAGGACTCTACTCCCTC<br>AGCAGCGTGGTGACCGTGCCCTCCAGCAGCTTGGGCA<br>CGAAGACCTACACCTGCAACGTAGATCACAAGCCCAG<br>CAACACCAAGGTGGACAAGAGAGTTGAGTCCAAATAT<br>GGTCCCCCATGCCCACCGTGCCCAGCACCTGAGTTCC<br>TGGGGGGACCATCAGTCTTCCTGTTCCCCCCAAAACC<br>CAAGGACACTCTCATGATCTCCCGGACCCCTGAGGTC<br>ACGTGCGTGGTGGTGGACGTGAGCCAGGAAGACCCCG<br>AGGTCCAGTTCAACTGGTACGTGGATGGCGTGGAGGT<br>GCATAATGCCAAGACAAAGCCGCGGGAGGAGCAGTTC<br>AACAGCACGTACCGTGTGGTCAGCGTCCTCACCGTCC<br>TGCACCAGGACTGGCTGAACGGCAAGGAGTACAAGTG<br>CAAGGTGTCCAACAAAGGCCTCCCGTCCTCCATCGAG<br>AAAACCATCTCCAAAGCCAAAGGGCAGCCCCGAGAGC<br>CACAGGTGTACACCCTGCCCCCATCCCAGGAGGAGAT<br>GACCAAGAACCAGGTCAGCCTGACCTGCCTGGTCAAA<br>GGCTTCTACCCCAGCGACATCGCCGTGGAGTGGGAGA<br>GCAATGGGCAGCCGGAGAACAACTACAAGACCACGCC<br>TCCCGTGCTGGACTCCGACGGCTCCTTCTTCCTCTAC<br>AGCAGGCTAACCGTGGACAAGAGCAGGTGGCAGGAGG<br>GGAATGTCTTCTCATGCTCCGTGATGCATGAGGCTCT<br>GCACAACCACTACACACAGAAGAGCCTCTCCCTGTCT<br>CTGGGTAAA |

| BAP058-hum06-LC | | |
|---|---|---|
| SEQ ID NO: 9 (Kabat) | LCDR1 | KASQDVGTAVA |
| SEQ ID NO: 10 (Kabat) | LCDR2 | WASTRHT |

TABLE 1 -continued

| SEQ ID NO: 11 (Kabat) | LCDR3 | QQYNSYPLT |
|---|---|---|
| SEQ ID NO: 12 (Chothia) | LCDR1 | SQDVGTA |
| SEQ ID NO: 13 (Chothia) | LCDR2 | WAS |
| SEQ ID NO: 14 (Chothia) | LCDR3 | YNSYPL |
| SEQ ID NO: 42 | VL | EIVLTQSPDFQSVTPKEKVTITCKASQDVGTAVAWYL QKPGQSPQLLIYWASTRHTGVPSRFSGSGSGTDFTFT ISSLQPEDIATYYCQQYNSYPLTFGQGTKVEIK |
| SEQ ID NO: 43 | DNA VL | GAAATTGTGCTGACTCAGTCTCCAGACTTTCAGTCTG TGACTCCAAAGGAGAAAGTCACCATCACCTGCAAGGC CAGTCAGGATGTGGGTACTGCTGTAGCCTGGTACCTG CAGAAGCCAGGGCAGTCTCCACAGCTCCTGATCTATT GGGCATCCACCCGGCACACTGGGGTCCCATCAAGGTT CAGTGGAAGTGGATCTGGGACAGATTTTACTTTCACC ATCAGCAGCCTGCAGCCTGAAGATATTGCAACATATT ACTGTCAGCAGTATAACAGCTATCCTCTCACGTTCGG CCAAGGGACCAAGGTGGAAATCAAA |
| SEQ ID NO: 44 | Light Chain | EIVLTQSPDFQSVTPKEKVTITCKASQDVGTAVAWYL QKPGQSPQLLIYWASTRHTGVPSRFSGSGSGTDFTFT ISSLQPEDIATYYCQQYNSYPLTFGQGTKVEIKRTVA APSVFIFPPSDEQLKSGTASVVCLLNNFYPREAKVQW KVDNALQSGNSQESVTEQDSKDSTYSLSSTLTLSKAD YEKHKVYACEVTHQGLSSPVTKSFNRGEC |
| SEQ ID NO: 45 | DNA Light Chain | GAAATTGTGCTGACTCAGTCTCCAGACTTTCAGTCTG TGACTCCAAAGGAGAAAGTCACCATCACCTGCAAGGC CAGTCAGGATGTGGGTACTGCTGTAGCCTGGTACCTG CAGAAGCCAGGGCAGTCTCCACAGCTCCTGATCTATT GGGCATCCACCCGGCACACTGGGGTCCCATCAAGGTT CAGTGGAAGTGGATCTGGGACAGATTTTACTTTCACC ATCAGCAGCCTGCAGCCTGAAGATATTGCAACATATT ACTGTCAGCAGTATAACAGCTATCCTCTCACGTTCGG CCAAGGGACCAAGGTGGAAATCAAACGTACGGTGGCT GCACCATCTGTCTTCATCTTCCCGCCATCTGATGAGC AGTTGAAATCTGGAACTGCCTCTGTTGTGTGCCTGCT GAATAACTTCTATCCCAGAGAGGCCAAAGTACAGTGG AAGGTGGATAACGCCCTCCAATCGGGTAACTCCCAGG AGAGTGTCACAGAGCAGGACAGCAAGGACAGCACCTA CAGCCTCAGCAGCACCCTGACGCTGAGCAAAGCAGAC TACGAGAAACACAAAGTCTACGCCTGCGAAGTCACCC ATCAGGGCCTGAGCTCGCCCGTCACAAAGAGCTTCAA CAGGGGAGAGTGT |
| BAP058-hum07-HC | | |
| SEQ ID NO: 1 (Kabat) | HCDR1 | SYWMY |
| SEQ ID NO: 2 (Kabat) | HCDR2 | RIDPNSGSTKYNEKFKN |
| SEQ ID NO: 3 (Kabat) | HCDR3 | DYRKGLYAMDY |
| SEQ ID NO: 4 (Chothia) | HCDR1 | GYTFTSY |
| SEQ ID NO: 5 (Chothia) | HCDR2 | DPNSGS |
| SEQ ID NO: 3 (Chothia) | HCDR3 | DYRKGLYAMDY |
| SEQ ID NO: 54 | VH | QVQLVQSGAEVKKPGASVKVSCKASGYTFTSYWMYWI RQSPSRGLEWLGRIDPNSGSTKYNEKFKNRFTISRDD SKNTAYLQMNSLKTEDTAVYYCARDYRKGLYAMDYWG QGTTVTVSS |
| SEQ ID NO: 55 | DNA VH | CAGGTTCAGCTGGTGCAGTCTGGAGCTGAGGTGAAGA AGCCTGGGGCCTCAGTGAAGGTCTCCTGCAAGGCTTC TGGCTACACCTTCACCAGTTACTGGATGTACTGGATC AGGCAGTCCCCATCGAGAGGCCTTGAGTGGCTGGGTA GGATTGATCCTAATAGTGGGAGTACTAAGTACAATGA GAAGTTCAAGAACAGATTCACCATCTCCAGAGATGAT TCAAAGAACACGGCGTATCTGCAAATGAACAGCCTGA AAACCGAGGACACGGCCGTGTATTACTGTGCAAGGGA CTATAGAAAGGGGCTCTATGCTATGGACTACTGGGGC CAGGGCACCACCGTGACCGTGTCCTCC |
| SEQ ID NO: 56 | Heavy Chain | QVQLVQSGAEVKKPGASVKVSCKASGYTFTSYWMYWI RQSPSRGLEWLGRIDPNSGSTKYNEKFKNRFTISRDD |

TABLE 1 -continued

|  |  |  |
|---|---|---|
|  |  | SKNTAYLQMNSLKTEDTAVYYCARDYRKGLYAMDYWG<br>QGTTVTVSSASTKGPSVFPLAPCSRSTSESTAALGCL<br>VKDYFPEPVTVSWNSGALTSGVHTFPAVLQSSGLYSL<br>SSVVTVPSSSLGTKTYTCNVDHKPSNTKVDKRVESKY<br>GPPCPPCPAPEFLGGPSVFLFPPKPKDTLMISRTPEV<br>TCVVVDVSQEDPEVQFNWYVDGVEVHNAKTKPREEQF<br>NSTYRVVSVLTVLHQDWLNGKEYKCKVSNKGLPSSIE<br>KTISKAKGQPREPQVYTLPPSQEEMTKNQVSLTCLVK<br>GFYPSDIAVEWESNGQPENNYKTTPPVLDSDGSFFLY<br>SRLTVDKSRWQEGNVFSCSVMHEALHNHYTQKSLSLS<br>LGK |
| SEQ ID NO: 57 | DNA Heavy<br>Chain | CAGGTTCAGCTGGTGCAGTCTGGAGCTGAGGTGAAGA<br>AGCCTGGGGCCTCAGTGAAGGTCTCCTGCAAGGCTTC<br>TGGCTACACCTTCACCAGTTACTGGATGTACTGGATC<br>AGGCAGTCCCCATCGAGAGGCCTTGAGTGGCTGGGTA<br>GGATTGATCCTAATAGTGGGAGTACTAAGTACAATGA<br>GAAGTTCAAGAACAGATTCACCATCTCCAGAGATGAT<br>TCAAAGAACACGGCGTATCTGCAAATGAACAGCCTGA<br>AAACCGAGGACACGGCCGTGTATTACTGTGCAAGGGA<br>CTATAGAAAGGGGCTCTATGCTATGGACTACTGGGGC<br>CAGGGCACCACCGTGACCGTGTCCTCCGCTTCCACCA<br>AGGGCCCATCCGTCTTCCCCCTGGCGCCCTGCTCCAG<br>GAGCACCTCCGAGAGCACAGCCGCCCTGGGCTGCCTG<br>GTCAAGGACTACTTCCCCGAACCGGTGACGGTGTCGT<br>GGAACTCAGGCGCCCTGACCAGCGGCGTGCACACCTT<br>CCCGGCTGTCCTACAGTCCTCAGGACTCTACTCCCTC<br>AGCAGCGTGGTGACCGTGCCCTCCAGCAGCTTGGGCA<br>CGAAGACCTACACCTGCAACGTAGATCACAAGCCCAG<br>CAACACCAAGGTGGACAAGAGAGTTGAGTCCAAATAT<br>GGTCCCCCATGCCCACCGTGCCCAGCACCTGAGTTCC<br>TGGGGGGACCATCAGTCTTCCTGTTCCCCCCAAAACC<br>CAAGGACACTCTCATGATCTCCCGGACCCCTGAGGTC<br>ACGTGCGTGGTGGTGGACGTGAGCCAGGAAGACCCCG<br>AGGTCCAGTTCAACTGGTACGTGGATGGCGTGGAGGT<br>GCATAATGCCAAGACAAAGCCGCGGGAGGAGCAGTTC<br>AACAGCACGTACCGTGTGGTCAGCGTCCTCACCGTCC<br>TGCACCAGGACTGGCTGAACGGCAAGGAGTACAAGTG<br>CAAGGTGTCCAACAAAGGCCTCCCGTCCTCCATCGAG<br>AAAACCATCTCCAAAGCCAAAGGGCAGCCCCGAGAGC<br>CACAGGTGTACACCCTGCCCCCATCCCAGGAGGAGAT<br>GACCAAGAACCAGGTCAGCCTGACCTGCCTGGTCAAA<br>GGCTTCTACCCCAGCGACATCGCCGTGGAGTGGGAGA<br>GCAATGGGCAGCCGGAGAACAACTACAAGACCACGCC<br>TCCCGTGCTGGACTCCGACGGCTCCTTCTTCCTCTAC<br>AGCAGGCTAACCGTGGACAAGAGCAGGTGGCAGGAGG<br>GGAATGTCTTCTCATGCTCCGTGATGCATGAGGCTCT<br>GCACAACCACTACACACAGAAGAGCCTCTCCCTGTCT<br>CTGGGTAAA |
| BAP058-hum07-LC |  |  |
| SEQ ID NO: 9 (Kabat) | LCDR1 | KASQDVGTAVA |
| SEQ ID NO: 10 (Kabat) | LCDR2 | WASTRHT |
| SEQ ID NO: 11 (Kabat) | LCDR3 | QQYNSYPLT |
| SEQ ID NO: 12 (Chothia) | LCDR1 | SQDVGTA |
| SEQ ID NO: 13 (Chothia) | LCDR2 | WAS |
| SEQ ID NO: 14 (Chothia) | LCDR3 | YNSYPL |
| SEQ ID NO: 58 | VL | EIVLTQSPATLSLSPGERATLSCKASQDVGTAVAWYL<br>QKPGQSPQLLIYWASTRHTGIPPRFSGSGYGTDFTLT<br>INNIESEDAAYYFCQQYNSYPLTFGQGTKVEIK |
| SEQ ID NO: 59 | DNA VL | GAAATTGTGTTGACACAGTCTCCAGCCACCCTGTCTT<br>TGTCTCCAGGGGAAAGAGCCACCCTCTCCTGCAAGGC<br>CAGTCAGGATGTGGGTACTGCTGTAGCCTGGTACCTG<br>CAGAAGCCAGGGCAGTCTCCACAGCTCCTGATCTATT<br>GGGCATCCACCCGGCACACTGGGATCCCACCTCGATT<br>CAGTGGCAGCGGGTATGGAACAGATTTTACCCTCACA<br>ATTAATAACATAGAATCTGAGGATGCTGCATATTACT<br>TCTGTCAGCAGTATAACAGCTATCCTCTCACGTTCGG<br>CCAAGGGACCAAGGTGGAAATCAAA |
| SEQ ID NO: 60 | Light<br>Chain | EIVLTQSPATLSLSPGERATLSCKASQDVGTAVAWYL<br>QKPGQSPQLLIYWASTRHTGIPPRFSGSGYGTDFTLT |

TABLE 1 -continued

| | | |
|---|---|---|
| | | INNIESEDAAYYFCQQYNSYPLTFGQGTKVEIKRTVA<br>APSVFIFPPSDEQLKSGTASVVCLLNNFYPREAKVQW<br>KVDNALQSGNSQESVTEQDSKDSTYSLSSTLTLSKAD<br>YEKHKVYACEVTHQGLSSPVTKSFNRGEC |
| SEQ ID NO: 61 | DNA Light Chain | GAAATTGTGTTGACACAGTCTCCAGCCACCCTGTCTT<br>TGTCTCCAGGGGAAAGAGCCACCCTCTCCTGCAAGGC<br>CAGTCAGGATGTGGGTACTGCTGTAGCCTGGTACCTG<br>CAGAAGCCAGGGCAGTCTCCACAGCTCCTGATCTATT<br>GGGCATCCACCCGGCACACTGGGATCCCACCTCGATT<br>CAGTGGCAGCGGGTATGGAACAGATTTTACCCTCACA<br>ATTAATAACATAGAATCTGAGGATGCTGCATATTACT<br>TCTGTCAGCAGTATAACAGCTATCCTCTCACGTTCGG<br>CCAAGGGACCAAGGTGGAAATCAAACGTACGGTGGCT<br>GCACCATCTGTCTTCATCTTCCCGCCATCTGATGAGC<br>AGTTGAAATCTGGAACTGCCTCTGTTGTGTGCCTGCT<br>GAATAACTTCTATCCCAGAGAGGCCAAAGTACAGTGG<br>AAGGTGGATAACGCCCTCCAATCGGGTAACTCCCAGG<br>AGAGTGTCACAGAGCAGGACAGCAAGGACAGCACCTA<br>CAGCCTCAGCAGCACCCTGACGCTGAGCAAAGCAGAC<br>TACGAGAAACACAAAGTCTACGCCTGCGAAGTCACCC<br>ATCAGGGCCTGAGCTCGCCCGTCACAAAGAGCTTCAA<br>CAGGGGAGAGTGT |
| | BAP058-hum08-HC | |
| SEQ ID NO: 1 (Kabat) | HCDR1 | SYWMY |
| SEQ ID NO: 2 (Kabat) | HCDR2 | RIDPNSGSTKYNEKFKN |
| SEQ ID NO: 3 (Kabat) | HCDR3 | DYRKGLYAMDY |
| SEQ ID NO: 4 (Chothia) | HCDR1 | GYTFTSY |
| SEQ ID NO: 5 (Chothia) | HCDR2 | DPNSGS |
| SEQ ID NO: 3 (Chothia) | HCDR3 | DYRKGLYAMDY |
| SEQ ID NO: 62 | VH | EVQLVQSGAEVKKPGESLRISCKGSYTFTSYWMYWV<br>RQARGQRLEWIGRIDPNSGSTKYNEKFKNRLTISKDT<br>SKNQVVLTMTNMDPVDTATYYCARDYRKGLYAMDYWG<br>QGTTVTVSS |
| SEQ ID NO: 63 | DNA VH | GAAGTGCAGCTGGTGCAGTCTGGAGCAGAGGTGAAAA<br>AGCCCGGGGAGTCTCTGAGGATCTCCTGTAAGGGTTC<br>TGGCTACACCTTCACCAGTTACTGGATGTACTGGGTG<br>CGACAGGCTCGTGGACAACGCCTTGAGTGGATAGGTA<br>GGATTGATCCTAATAGTGGGAGTACTAAGTACAATGA<br>GAAGTTCAAGAACAGACTCACCATCTCCAAGGACACC<br>TCCAAAAACCAGGTGGTCCTTACAATGACCAACATGG<br>ACCCTGTGGACACAGCCACGTATTACTGTGCAAGGGA<br>CTATAGAAAGGGGCTCTATGCTATGGACTACTGGGGC<br>CAGGGCACCACCGTGACCGTGTCCTCC |
| SEQ ID NO: 64 | Heavy Chain | EVQLVQSGAEVKKPGESLRISCKGSYTFTSYWMYWV<br>RQARGQRLEWIGRIDPNSGSTKYNEKFKNRLTISKDT<br>SKNQVVLTMTNMDPVDTATYYCARDYRKGLYAMDYWG<br>QGTTVTVSSASTKGPSVFPLAPCSRSTSESTAALGCL<br>VKDYFPEPVTVSWNSGALTSGVHTFPAVLQSSGLYSL<br>SSVVTVPSSSLGTKTYTCNVDHKPSNTKVDKRVESKY<br>GPPCPPCPAPEFLGGPSVFLFPPKPKDTLMISRTPEV<br>TCVVVDVSQEDPEVQFNWYVDGVEVHNAKTKPREEQF<br>NSTYRVVSVLTVLHQDWLNGKEYKCKVSNKGLPSSIE<br>KTISKAKGQPREPQVYTLPPSQEEMTKNQVSLTCLVK<br>GFYPSDIAVEWESNGQPENNYKTTPPVLDSDGSFFLY<br>SRLTVDKSRWQEGNVFSCSVMHEALHNHYTQKSLSLS<br>LGK |
| SEQ ID NO: 65 | DNA Heavy Chain | GAAGTGCAGCTGGTGCAGTCTGGAGCAGAGGTGAAAA<br>AGCCCGGGGAGTCTCTGAGGATCTCCTGTAAGGGTTC<br>TGGCTACACCTTCACCAGTTACTGGATGTACTGGGTG<br>CGACAGGCTCGTGGACAACGCCTTGAGTGGATAGGTA<br>GGATTGATCCTAATAGTGGGAGTACTAAGTACAATGA<br>GAAGTTCAAGAACAGACTCACCATCTCCAAGGACACC<br>TCCAAAAACCAGGTGGTCCTTACAATGACCAACATGG<br>ACCCTGTGGACACAGCCACGTATTACTGTGCAAGGGA<br>CTATAGAAAGGGGCTCTATGCTATGGACTACTGGGGC<br>CAGGGCACCACCGTGACCGTGTCCTCCGCTTCCACCA<br>AGGGCCCATCCGTCTTCCCCCTGGCGCCCTGCTCCAG<br>GAGCACCTCCGAGAGCACAGCCGCCCTGGGCTGCCTG |

TABLE 1 -continued

GTCAAGGACTACTTCCCCGAACCGGTGACGGTGTCGT
GGAACTCAGGCGCCCTGACCAGCGGCGTGCACACCTT
CCCGGCTGTCCTACAGTCCTCAGGACTCTACTCCCTC
AGCAGCGTGGTGACCGTGCCCTCCAGCAGCTTGGGCA
CGAAGACCTACACCTGCAACGTAGATCACAAGCCCAG
CAACACCAAGGTGGACAAGAGAGTTGAGTCCAAATAT
GGTCCCCCATGCCCACCGTGCCCAGCACCTGAGTTCC
TGGGGGGACCATCAGTCTTCCTGTTCCCCCCAAAACC
CAAGGACACTCTCATGATCTCCCGGACCCCTGAGGTC
ACGTGCGTGGTGGTGGACGTGAGCCAGGAAGACCCCG
AGGTCCAGTTCAACTGGTACGTGGATGGCGTGGAGGT
GCATAATGCCAAGACAAAGCCGCGGGAGGAGCAGTTC
AACAGCACGTACCGTGTGGTCAGCGTCCTCACCGTCC
TGCACCAGGACTGGCTGAACGGCAAGGAGTACAAGTG
CAAGGTGTCCAACAAAGGCCTCCCGTCCTCCATCGAG
AAAACCATCTCCAAAGCCAAAGGGCAGCCCCGAGAGC
CACAGGTGTACACCCTGCCCCCATCCCAGGAGGAGAT
GACCAAGAACCAGGTCAGCCTGACCTGCCTGGTCAAA
GGCTTCTACCCCAGCGACATCGCCGTGGAGTGGGAGA
GCAATGGGCAGCCGGAGAACAACTACAAGACCACGCC
TCCCGTGCTGGACTCCGACGGCTCCTTCTTCCTCTAC
AGCAGGCTAACCGTGGACAAGAGCAGGTGGCAGGAGG
GGAATGTCTTCTCATGCTCCGTGATGCATGAGGCTCT
GCACAACCACTACACACAGAAGAGCCTCTCCCTGTCT
CTGGGTAAA

| | | BAP058-hum08-LC | |
|---|---|---|---|
| SEQ ID NO: 9 | (Kabat) | LCDR1 | KASQDVGTAVA |
| SEQ ID NO: 10 | (Kabat) | LCDR2 | WASTRHT |
| SEQ ID NO: 11 | (Kabat) | LCDR3 | QQYNSYPLT |
| SEQ ID NO: 12 | (Chothia) | LCDR1 | SQDVGTA |
| SEQ ID NO: 13 | (Chothia) | LCDR2 | WAS |
| SEQ ID NO: 14 | (Chothia) | LCDR3 | YNSYPL |
| SEQ ID NO: 66 | | VL | DVVMTQSPLSLPVTLGQPASISCKASQDVGTAVAWYQ QKPGQAPRLLIYWASTRHTGVPSRFSGSGSGTEFTLT ISSLQPDDFATYYCQQYNSYPLTFGQGTKVEIK |
| SEQ ID NO: 67 | | DNA VL | GATGTTGTGATGACTCAGTCTCCACTCTCCCTGCCCG TCACCCTTGGACAGCCGGCCTCCATCTCCTGCAAGGC CAGTCAGGATGTGGGTACTGCTGTAGCCTGGTACCAG CAGAAACCTGGCCAGGCTCCCAGGCTCCTCATCTATT GGGCATCCACCCGGCACACTGGGGTCCCATCAAGGTT CAGCGGCAGTGGATCTGGGACAGAATTCACTCTCACC ATCAGCAGCCTGCAGCCTGATGATTTTGCAACTTATT ACTGTCAGCAGTATAACAGCTATCCTCTCACGTTCGG CCAAGGGACCAAGGTGGAAATCAAA |
| SEQ ID NO: 68 | | Light Chain | DVVMTQSPLSLPVTLGQPASISCKASQDVGTAVAWYQ QKPGQAPRLLIYWASTRHTGVPSRFSGSGSGTEFTLT ISSLQPDDFATYYCQQYNSYPLTFGQGTKVEIKRTVA APSVFIFPPSDEQLKSGTASVVCLLNNFYPREAKVQW KVDNALQSGNSQESVTEQDSKDSTYSLSSTLTLSKAD YEKHKVYACEVTHQGLSSPVTKSFNRGEC |
| SEQ ID NO: 69 | | DNA Light Chain | GATGTTGTGATGACTCAGTCTCCACTCTCCCTGCCCG TCACCCTTGGACAGCCGGCCTCCATCTCCTGCAAGGC CAGTCAGGATGTGGGTACTGCTGTAGCCTGGTACCAG CAGAAACCTGGCCAGGCTCCCAGGCTCCTCATCTATT GGGCATCCACCCGGCACACTGGGGTCCCATCAAGGTT CAGCGGCAGTGGATCTGGGACAGAATTCACTCTCACC ATCAGCAGCCTGCAGCCTGATGATTTTGCAACTTATT ACTGTCAGCAGTATAACAGCTATCCTCTCACGTTCGG CCAAGGGACCAAGGTGGAAATCAAACGTACGGTGGCT GCACCATCTGTCTTCATCTTCCCGCCATCTGATGAGC AGTTGAAATCTGGAACTGCCTCTGTTGTGTGCCTGCT GAATAACTTCTATCCCAGAGAGGCCAAAGTACAGTGG AAGGTGGATAACGCCCTCCAATCGGGTAACTCCCAGG AGAGTGTCACAGAGCAGGACAGCAAGGACAGCACCTA CAGCCTCAGCAGCACCCTGACGCTGAGCAAAGCAGAC TACGAGAAACACAAAGTCTACGCCTGCGAAGTCACCC ATCAGGGCCTGAGCTCGCCCGTCACAAAGAGCTTCAA CAGGGGAGAGTGT |

TABLE 1 -continued

BAP058-hum09-HC

| SEQ ID NO: 1 (Kabat) | HCDR1 | SYWMY |
|---|---|---|
| SEQ ID NO: 2 (Kabat) | HCDR2 | RIDPNSGSTKYNEKFKN |
| SEQ ID NO: 3 (Kabat) | HCDR3 | DYRKGLYAMDY |
| SEQ ID NO: 4 (Chothia) | HCDR1 | GYTFTSY |
| SEQ ID NO: 5 (Chothia) | HCDR2 | DPNSGS |
| SEQ ID NO: 3 (Chothia) | HCDR3 | DYRKGLYAMDY |
| SEQ ID NO: 50 | VH | EVQLVQSGAEVKKPGESLRISCKGSYTFTSYWMYWI RQPPGKGLEWIGRIDPNSGSTKYNEKFKNRVTITADK STSTAYMELSSLRSEDTAVYYCARDYRKGLYAMDYWG QGTTVTVSS |
| SEQ ID NO: 51 | DNA VH | GAAGTGCAGCTGGTGCAGTCTGGAGCAGAGGTGAAAA AGCCCGGGGAGTCTCTGAGGATCTCCTGTAAGGGTTC TGGCTACACCTTCACCAGTTACTGGATGTACTGGATC CGCCAGCCCCCAGGGAAGGGGCTGGAGTGGATTGGTA GGATTGATCCTAATAGTGGGAGTACTAAGTACAATGA GAAGTTCAAGAACAGAGTCACGATTACCGCGGACAAA TCCACGAGCACAGCCTACATGGAGCTGAGCAGCCTGA GATCTGAGGACACGGCCGTGTATTACTGTGCAAGGGA CTATAGAAAGGGGCTCTATGCTATGGACTACTGGGGC CAGGGCACCACCGTGACCGTGTCCTCC |
| SEQ ID NO: 52 | Heavy Chain | EVQLVQSGAEVKKPGESLRISCKGSYTFTSYWMYWI RQPPGKGLEWIGRIDPNSGSTKYNEKFKNRVTITADK STSTAYMELSSLRSEDTAVYYCARDYRKGLYAMDYWG QGTTVTVSSASTKGPSVFPLAPCSRSTSESTAALGCL VKDYFPEPVTVSWNSGALTSGVHTFPAVLQSSGLYSL SSVVTVPSSSLGTKTYTCNVDHKPSNTKVDKRVESKY GPPCPPCPAPEFLGGPSVFLFPPKPKDTLMISRTPEV TCVVVDVSQEDPEVQFNWYVDGVEVHNAKTKPREEQF NSTYRVVSVLTVLHQDWLNGKEYKCKVSNKGLPSSIE KTISKAKGQPREPQVYTLPPSQEEMTKNQVSLTCLVK GFYPSDIAVEWESNGQPENNYKTTPPVLDSDGSFFLY SRLTVDKSRWQEGNVFSCSVMHEALHNHYTQKSLSLS LGK |
| SEQ ID NO: 53 | DNA Heavy Chain | GAAGTGCAGCTGGTGCAGTCTGGAGCAGAGGTGAAAA AGCCCGGGGAGTCTCTGAGGATCTCCTGTAAGGGTTC TGGCTACACCTTCACCAGTTACTGGATGTACTGGATC CGCCAGCCCCCAGGGAAGGGGCTGGAGTGGATTGGTA GGATTGATCCTAATAGTGGGAGTACTAAGTACAATGA GAAGTTCAAGAACAGAGTCACGATTACCGCGGACAAA TCCACGAGCACAGCCTACATGGAGCTGAGCAGCCTGA GATCTGAGGACACGGCCGTGTATTACTGTGCAAGGGA CTATAGAAAGGGGCTCTATGCTATGGACTACTGGGGC CAGGGCACCACCGTGACCGTGTCCTCCGCTTCCACCA AGGGCCCATCCGTCTTCCCCCTGGCGCCCTGCTCCAG GAGCACCTCCGAGAGCACAGCCGCCCTGGGCTGCCTG GTCAAGGACTACTTCCCCGAACCGGTGACGGTGTCGT GGAACTCAGGCGCCCTGACCAGCGGCGTGCACACCTT CCCGGCTGTCCTACAGTCCTCAGGACTCTACTCCCTC AGCAGCGTGGTGACCGTGCCCTCCAGCAGCTTGGGCA CGAAGACCTACACCTGCAACGTAGATCACAAGCCCAG CAACACCAAGGTGGACAAGAGAGTTGAGTCCAAATAT GGTCCCCCATGCCCACCGTGCCCAGCACCTGAGTTCC TGGGGGGACCATCAGTCTTCCTGTTCCCCCCAAAACC CAAGGACACTCTCATGATCTCCCGGACCCCTGAGGTC ACGTGCGTGGTGGTGGACGTGAGCCAGGAAGACCCCG AGGTCCAGTTCAACTGGTACGTGGATGGCGTGGAGGT GCATAATGCCAAGACAAAGCCGCGGGAGGAGCAGTTC AACAGCACGTACCGTGTGGTCAGCGTCCTCACCGTCC TGCACCAGGACTGGCTGAACGGCAAGGAGTACAAGTG CAAGGTGTCCAACAAAGGCCTCCCGTCCTCCATCGAG AAAACCATCTCCAAAGCCAAAGGGCAGCCCCGAGAGC CACAGGTGTACACCCTGCCCCCATCCCAGGAGGAGAT GACCAAGAACCAGGTCAGCCTGACCTGCCTGGTCAAA GGCTTCTACCCCAGCGACATCGCCGTGGAGTGGGAGA GCAATGGGCAGCCGGAGAACAACTACAAGACCACGCC TCCCGTGCTGGACTCCGACGGCTCCTTCTTCCTCTAC AGCAGGCTAACCGTGGACAAGAGCAGGTGGCAGGAGG GGAATGTCTTCTCATGCTCCGTGATGCATGAGGCTCT GCACAACCACTACACACAGAAGAGCCTCTCCCTGTCT |

TABLE 1 -continued

| | | CTGGGTAAA |
|---|---|---|
| | BAP058-hum09-LC | |
| SEQ ID NO: 9 (Kabat) | LCDR1 | KASQDVGTAVA |
| SEQ ID NO: 10 (Kabat) | LCDR2 | WASTRHT |
| SEQ ID NO: 11 (Kabat) | LCDR3 | QQYNSYPLT |
| SEQ ID NO: 12 (Chothia) | LCDR1 | SQDVGTA |
| SEQ ID NO: 13 (Chothia) | LCDR2 | WAS |
| SEQ ID NO: 14 (Chothia) | LCDR3 | YNSYPL |
| SEQ ID NO: 22 | VL | DIVMTQTPLSLPVTPGEPASISCKASQDVGTAVAWYL QKPGQSPQLLIYWASTRHTGIPARFSGSGSGTEFTLT ISSLQSEDFAVYYCQQYNSYPLTFGQGTKVEIK |
| SEQ ID NO: 23 | DNA VL | GATATTGTGATGACCCAGACTCCACTCTCCCTGCCCG TCACCCCTGGAGAGCCGGCCTCCATCTCCTGCAAGGC CAGTCAGGATGTGGGTACTGCTGTAGCCTGGTACCTG CAGAAGCCAGGGCAGTCTCCACAGCTCCTGATCTATT GGGCATCCACCCGGCACACTGGGATCCCAGCCAGGTT CAGTGGCAGTGGGTCTGGGACAGAGTTCACTCTCACC ATCAGCAGCCTGCAGTCTGAAGATTTTGCAGTTTATT ACTGTCAGCAGTATAACAGCTATCCTCTCACGTTCGG CCAAGGGACCAAGGTGGAAATCAAA |
| SEQ ID NO: 24 | Light Chain | DIVMTQTPLSLPVTPGEPASISCKASQDVGTAVAWYL QKPGQSPQLLIYWASTRHTGIPARFSGSGSGTEFTLT ISSLQSEDFAVYYCQQYNSYPLTFGQGTKVEIKRTVA APSVFIFPPSDEQLKSGTASVVCLLNNFYPREAKVQW KVDNALQSGNSQESVTEQDSKDSTYSLSSTLTLSKAD YEKHKVYACEVTHQGLSSPVTKSFNRGEC |
| SEQ ID NO: 25 | DNA Light Chain | GATATTGTGATGACCCAGACTCCACTCTCCCTGCCCG TCACCCCTGGAGAGCCGGCCTCCATCTCCTGCAAGGC CAGTCAGGATGTGGGTACTGCTGTAGCCTGGTACCTG CAGAAGCCAGGGCAGTCTCCACAGCTCCTGATCTATT GGGCATCCACCCGGCACACTGGGATCCCAGCCAGGTT CAGTGGCAGTGGGTCTGGGACAGAGTTCACTCTCACC ATCAGCAGCCTGCAGTCTGAAGATTTTGCAGTTTATT ACTGTCAGCAGTATAACAGCTATCCTCTCACGTTCGG CCAAGGGACCAAGGTGGAAATCAAACGTACGGTGGCT GCACCATCTGTCTTCATCTTCCCGCCATCTGATGAGC AGTTGAAATCTGGAACTGCCTCTGTTGTGTGCCTGCT GAATAACTTCTATCCCAGAGAGGCCAAAGTACAGTGG AAGGTGGATAACGCCCTCCAATCGGGTAACTCCCAGG AGAGTGTCACAGAGCAGGACAGCAAGGACAGCACCTA CAGCCTCAGCAGCACCCTGACGCTGAGCAAAGCAGAC TACGAGAAACACAAAGTCTACGCCTGCGAAGTCACCC ATCAGGGCCTGAGCTCGCCCGTCACAAAGAGCTTCAA CAGGGGAGAGTGT |
| | BAP058-hum10-HC | |
| SEQ ID NO: 1 (Kabat) | HCDR1 | SYWMY |
| SEQ ID NO: 2 (Kabat) | HCDR2 | RIDPNSGSTKYNEKFKN |
| SEQ ID NO: 3 (Kabat) | HCDR3 | DYRKGLYAMDY |
| SEQ ID NO: 4 (Chothia) | HCDR1 | GYTFTSY |
| SEQ ID NO: 5 (Chothia) | HCDR2 | DPNSGS |
| SEQ ID NO: 3 (Chothia) | HCDR3 | DYRKGLYAMDY |
| SEQ ID NO: 70 | VH | QITLKESGPTLVKPTQTLTLTCTFSGYTFTSYWMYWV RQAPGKGLEWVSRIDPNSGSTKYNEKFKNRVTITADK STSTAYMELSSLRSEDTAVYYCARDYRKGLYAMDYWG QGTTVTVSS |
| SEQ ID NO: 71 | DNA VH | CAGATCACCTTGAAGGAGTCTGGTCCTACGCTGGTGA AACCCACACAGACCCTCACGCTGACCTGCACCTTCTC TGGCTACACCTTCACCAGTTACTGGATGTACTGGGTC CGCCAGGCTCCAGGGAAGGGGCTGGAGTGGGTCAGTA GGATTGATCCTAATAGTGGGAGTACTAAGTACAATGA |

TABLE 1 -continued

| | | |
|---|---|---|
| | | GAAGTTCAAGAACAGAGTCACGATTACCGCGGACAAA<br>TCCACGAGCACAGCCTACATGGAGCTGAGCAGCCTGA<br>GATCTGAGGACACGGCCGTGTATTACTGTGCAAGGGA<br>CTATAGAAAGGGGCTCTATGCTATGGACTACTGGGGC<br>CAGGGCACCACCGTGACCGTGTCCTCC |
| SEQ ID NO: 72 | Heavy<br>Chain | QITLKESGPTLVKPTQTLTLTCTFSGYTFTSYWMYWV<br>RQAPGKGLEWVSRIDPNSGSTKYNEKFKNRVTITADK<br>STSTAYMELSSLRSEDTAVYYCARDYRKGLYAMDYWG<br>QGTTVTVSSASTKGPSVFPLAPCSRSTSESTAALGCL<br>VKDYFPEPVTVSWNSGALTSGVHTFPAVLQSSGLYSL<br>SSVVTVPSSSLGTKTYTCNVDHKPSNTKVDKRVESKY<br>GPPCPPCPAPEFLGGPSVFLFPPKPKDTLMISRTPEV<br>TCVVVDVSQEDPEVQFNWYVDGVEVHNAKTKPREEQF<br>NSTYRVVSVLTVLHQDWLNGKEYKCKVSNKGLPSSIE<br>KTISKAKGQPREPQVYTLPPSQEEMTKNQVSLTCLVK<br>GFYPSDIAVEWESNGQPENNYKTTPPVLDSDGSFFLY<br>SRLTVDKSRWQEGNVFSCSVMHEALHNHYTQKSLSLS<br>LGK |
| SEQ ID NO: 73 | DNA Heavy<br>Chain | CAGATCACCTTGAAGGAGTCTGGTCCTACGCTGGTGA<br>AACCCACACAGACCCTCACGCTGACCTGCACCTTCTC<br>TGGCTACACCTTCACCAGTTACTGGATGTACTGGGTC<br>CGCCAGGCTCCAGGGAAGGGGCTGGAGTGGGTCAGTA<br>GGATTGATCCTAATAGTGGGAGTACTAAGTACAATGA<br>GAAGTTCAAGAACAGAGTCACGATTACCGCGGACAAA<br>TCCACGAGCACAGCCTACATGGAGCTGAGCAGCCTGA<br>GATCTGAGGACACGGCCGTGTATTACTGTGCAAGGGA<br>CTATAGAAAGGGGCTCTATGCTATGGACTACTGGGGC<br>CAGGGCACCACCGTGACCGTGTCCTCCGCTTCCACCA<br>AGGGCCCATCCGTCTTCCCCCTGGCGCCCTGCTCCAG<br>GAGCACCTCCGAGAGCACAGCCGCCCTGGGCTGCCTG<br>GTCAAGGACTACTTCCCCGAACCGGTGACGGTGTCGT<br>GGAACTCAGGCGCCCTGACCAGCGGCGTGCACACCTT<br>CCCGGCTGTCCTACAGTCCTCAGGACTCTACTCCCTC<br>AGCAGCGTGGTGACCGTGCCCTCCAGCAGCTTGGGCA<br>CGAAGACCTACACCTGCAACGTAGATCACAAGCCCAG<br>CAACACCAAGGTGGACAAGAGAGTTGAGTCCAAATAT<br>GGTCCCCCATGCCCACCGTGCCCAGCACCTGAGTTCC<br>TGGGGGGACCATCAGTCTTCCTGTTCCCCCCAAAACC<br>CAAGGACACTCTCATGATCTCCCGGACCCCTGAGGTC<br>ACGTGCGTGGTGGTGGACGTGAGCCAGGAAGACCCCG<br>AGGTCCAGTTCAACTGGTACGTGGATGGCGTGGAGGT<br>GCATAATGCCAAGACAAAGCCGCGGGAGGAGCAGTTC<br>AACAGCACGTACCGTGTGGTCAGCGTCCTCACCGTCC<br>TGCACCAGGACTGGCTGAACGGCAAGGAGTACAAGTG<br>CAAGGTGTCCAACAAAGGCCTCCCGTCCTCCATCGAG<br>AAAACCATCTCCAAAGCCAAAGGGCAGCCCCGAGAGC<br>CACAGGTGTACACCCTGCCCCCATCCCAGGAGGAGAT<br>GACCAAGAACCAGGTCAGCCTGACCTGCCTGGTCAAA<br>GGCTTCTACCCCAGCGACATCGCCGTGGAGTGGGAGA<br>GCAATGGGCAGCCGGAGAACAACTACAAGACCACGCC<br>TCCCGTGCTGGACTCCGACGGCTCCTTCTTCCTCTAC<br>AGCAGGCTAACCGTGGACAAGAGCAGGTGGCAGGAGG<br>GGAATGTCTTCTCATGCTCCGTGATGCATGAGGCTCT<br>GCACAACCACTACACACAGAAGAGCCTCTCCCTGTCT<br>CTGGGTAAA |

| BAP058-hum10-LC | | |
|---|---|---|
| SEQ ID NO: 9 (Kabat) | LCDR1 | KASQDVGTAVA |
| SEQ ID NO: 10 (Kabat) | LCDR2 | WASTRHT |
| SEQ ID NO: 11 (Kabat) | LCDR3 | QQYNSYPLT |
| SEQ ID NO: 12 (Chothia) | LCDR1 | SQDVGTA |
| SEQ ID NO: 13 (Chothia) | LCDR2 | WAS |
| SEQ ID NO: 14 (Chothia) | LCDR3 | YNSYPL |
| SEQ ID NO: 66 | VL | DVVMTQSPLSLPVTLGQPASISCKASQDVGTAVAWYQ<br>QKPGQAPRLLIYWASTRHTGVPSRFSGSGSGTEFTLT<br>ISSLQPDDFATYYCQQYNSYPLTFGQGTKVEIK |
| SEQ ID NO: 67 | DNA VL | GATGTTGTGATGACTCAGTCTCCACTCTCCCTGCCCG<br>TCACCCTTGGACAGCCGGCCTCCATCTCCTGCAAGGC<br>CAGTCAGGATGTGGGTACTGCTGTAGCCTGGTACCAG<br>CAGAAACCTGGCCAGGCTCCCAGGCTCCTCATCTATT |

TABLE 1 -continued

| | | |
|---|---|---|
| | | GGGCATCCACCCGGCACACTGGGGTCCCATCAAGGTT<br>CAGCGGCAGTGGATCTGGGACAGAATTCACTCTCACC<br>ATCAGCAGCCTGCAGCCTGATGATTTTGCAACTTATT<br>ACTGTCAGCAGTATAACAGCTATCCTCTCACGTTCGG<br>CCAAGGGACCAAGGTGGAAATCAAA |
| SEQ ID NO: 68 | Light<br>Chain | DVVMTQSPLSLPVTLGQPASISCKASQDVGTAVAWYQ<br>QKPGQAPRLLIYWASTRHTGVPSRFSGSGSGTEFTLT<br>ISSLQPDDFATYYCQQYNSYPLTFGQGTKVEIKRTVA<br>APSVFIFPPSDEQLKSGTASVVCLLNNFYPREAKVQW<br>KVDNALQSGNSQESVTEQDSKDSTYSLSSTLTLSKAD<br>YEKHKVYACEVTHQGLSSPVTKSFNRGEC |
| SEQ ID NO: 69 | DNA Light<br>Chain | GATGTTGTGATGACTCAGTCTCCACTCTCCCTGCCCG<br>TCACCCTTGGACAGCCGGCCTCCATCTCCTGCAAGGC<br>CAGTCAGGATGTGGGTACTGCTGTAGCCTGGTACCAG<br>CAGAAACCTGGCCAGGCTCCCAGGCTCCTCATCTATT<br>GGGCATCCACCCGGCACACTGGGGTCCCATCAAGGTT<br>CAGCGGCAGTGGATCTGGGACAGAATTCACTCTCACC<br>ATCAGCAGCCTGCAGCCTGATGATTTTGCAACTTATT<br>ACTGTCAGCAGTATAACAGCTATCCTCTCACGTTCGG<br>CCAAGGGACCAAGGTGGAAATCAAACGTACGGTGGCT<br>GCACCATCTGTCTTCATCTTCCCGCCATCTGATGAGC<br>AGTTGAAATCTGGAACTGCCTCTGTTGTGTGCCTGCT<br>GAATAACTTCTATCCCAGAGAGGCCAAAGTACAGTGG<br>AAGGTGGATAACGCCCTCCAATCGGGTAACTCCCAGG<br>AGAGTGTCACAGAGCAGGACAGCAAGGACAGCACCTA<br>CAGCCTCAGCAGCACCCTGACGCTGAGCAAAGCAGAC<br>TACGAGAAACACAAAGTCTACGCCTGCGAAGTCACCC<br>ATCAGGGCCTGAGCTCGCCCGTCACAAAGAGCTTCAA<br>CAGGGGAGAGTGT |

| BAP058-hum11-HC | | |
|---|---|---|
| SEQ ID NO: 1 (Kabat) | HCDR1 | SYWMY |
| SEQ ID NO: 2 (Kabat) | HCDR2 | RIDPNSGSTKYNEKFKN |
| SEQ ID NO: 3 (Kabat) | HCDR3 | DYRKGLYAMDY |
| SEQ ID NO: 4 (Chothia) | HCDR1 | GYTFTSY |
| SEQ ID NO: 5 (Chothia) | HCDR2 | DPNSGS |
| SEQ ID NO: 3 (Chothia) | HCDR3 | DYRKGLYAMDY |
| SEQ ID NO: 30 | VH | EVQLVQSGAEVKKPGATVKISCKVSGYTFTSYWMYWV<br>RQATGQGLEWMGRIDPNSGSTKYNEKFKNRVTITADK<br>STSTAYMELSSLRSEDTAVYYCARDYRKGLYAMDYWG<br>QGTTVTVSS |
| SEQ ID NO: 31 | DNA VH | GAGGTCCAGCTGGTACAGTCTGGGGCTGAGGTGAAGA<br>AGCCTGGGGCTACAGTGAAAATCTCCTGCAAGGTTTC<br>TGGCTACACCTTCACCAGTTACTGGATGTACTGGGTG<br>CGACAGGCCACTGGACAAGGGCTTGAGTGGATGGGTA<br>GGATTGATCCTAATAGTGGGAGTACTAAGTACAATGA<br>GAAGTTCAAGAACAGAGTCACGATTACCGCGGACAAA<br>TCCACGAGCACAGCCTACATGGAGCTGAGCAGCCTGA<br>GATCTGAGGACACGGCCGTGTATTACTGTGCAAGGGA<br>CTATAGAAAGGGGCTCTATGCTATGGACTACTGGGGC<br>CAGGGCACCACCGTGACCGTGTCCTCC |
| SEQ ID NO: 32 | Heavy<br>Chain | EVQLVQSGAEVKKPGATVKISCKVSGYTFTSYWMYWV<br>RQATGQGLEWMGRIDPNSGSTKYNEKFKNRVTITADK<br>STSTAYMELSSLRSEDTAVYYCARDYRKGLYAMDYWG<br>QGTTVTVSSASTKGPSVFPLAPCSRSTSESTAALGCL<br>VKDYFPEPVTVSWNSGALTSGVHTFPAVLQSSGLYSL<br>SSVVTVPSSSLGTKTYTCNVDHKPSNTKVDKRVESKY<br>GPPCPPCPAPEFLGGPSVFLFPPKPKDTLMISRTPEV<br>TCVVVDVSQEDPEVQFNWYVDGVEVHNAKTKPREEQF<br>NSTYRVVSVLTVLHQDWLNGKEYKCKVSNKGLPSSIE<br>KTISKAKGQPREPQVYTLPPSQEEMTKNQVSLTCLVK<br>GFYPSDIAVEWESNGQPENNYKTTPPVLDSDGSFFLY<br>SRLTVDKSRWQEGNVFSCSVMHEALHNHYTQKSLSLS<br>LGK |
| SEQ ID NO: 33 | DNA Heavy<br>Chain | GAGGTCCAGCTGGTACAGTCTGGGGCTGAGGTGAAGA<br>AGCCTGGGGCTACAGTGAAAATCTCCTGCAAGGTTTC<br>TGGCTACACCTTCACCAGTTACTGGATGTACTGGGTG<br>CGACAGGCCACTGGACAAGGGCTTGAGTGGATGGGTA<br>GGATTGATCCTAATAGTGGGAGTACTAAGTACAATGA |

TABLE 1 -continued

GAAGTTCAAGAACAGAGTCACGATTACCGCGGACAAA
TCCACGAGCACAGCCTACATGGAGCTGAGCAGCCTGA
GATCTGAGGACACGGCCGTGTATTACTGTGCAAGGGA
CTATAGAAAGGGGCTCTATGCTATGGACTACTGGGGC
CAGGGCACCACCGTGACCGTGTCCTCCGCTTCCACCA
AGGGCCCATCCGTCTTCCCCCTGGCGCCCTGCTCCAG
GAGCACCTCCGAGAGCACAGCCGCCCTGGGCTGCCTG
GTCAAGGACTACTTCCCCGAACCGGTGACGGTGTCGT
GGAACTCAGGCGCCCTGACCAGCGGCGTGCACACCTT
CCCGGCTGTCCTACAGTCCTCAGGACTCTACTCCCTC
AGCAGCGTGGTGACCGTGCCCTCCAGCAGCTTGGGCA
CGAAGACCTACACCTGCAACGTAGATCACAAGCCCAG
CAACACCAAGGTGGACAAGAGAGTTGAGTCCAAATAT
GGTCCCCCATGCCCACCGTGCCCAGCACCTGAGTTCC
TGGGGGGACCATCAGTCTTCCTGTTCCCCCCAAAACC
CAAGGACACTCTCATGATCTCCCGGACCCCTGAGGTC
ACGTGCGTGGTGGTGGACGTGAGCCAGGAAGACCCCG
AGGTCCAGTTCAACTGGTACGTGGATGGCGTGGAGGT
GCATAATGCCAAGACAAAGCCGCGGGAGGAGCAGTTC
AACAGCACGTACCGTGTGGTCAGCGTCCTCACCGTCC
TGCACCAGGACTGGCTGAACGGCAAGGAGTACAAGTG
CAAGGTGTCCAACAAAGGCCTCCCGTCCTCCATCGAG
AAAACCATCTCCAAAGCCAAAGGGCAGCCCCGAGAGC
CACAGGTGTACACCCTGCCCCCATCCCAGGAGGAGAT
GACCAAGAACCAGGTCAGCCTGACCTGCCTGGTCAAA
GGCTTCTACCCCAGCGACATCGCCGTGGAGTGGGAGA
GCAATGGGCAGCCGGAGAACAACTACAAGACCACGCC
TCCCGTGCTGGACTCCGACGGCTCCTTCTTCCTCTAC
AGCAGGCTAACCGTGGACAAGAGCAGGTGGCAGGAGG
GGAATGTCTTCTCATGCTCCGTGATGCATGAGGCTCT
GCACAACCACTACACACAGAAGAGCCTCTCCCTGTCT
CTGGGTAAA

| BAP058-hum11-LC | | |
|---|---|---|
| SEQ ID NO: 9 (Kabat) | LCDR1 | KASQDVGTAVA |
| SEQ ID NO: 10 (Kabat) | LCDR2 | WASTRHT |
| SEQ ID NO: 11 (Kabat) | LCDR3 | QQYNSYPLT |
| SEQ ID NO: 12 (Chothia) | LCDR1 | SQDVGTA |
| SEQ ID NO: 13 (Chothia) | LCDR2 | WAS |
| SEQ ID NO: 14 (Chothia) | LCDR3 | YNSYPL |
| SEQ ID NO: 66 | VL | DVVMTQSPLSLPVTLGQPASISCKASQDVGTAVAWYQ QKPGQAPRLLIYWASTRHTGVPSRFSGSGSGTEFTLT ISSLQPDDFATYYCQQYNSYPLTFGQGTKVEIK |
| SEQ ID NO: 67 | DNA VL | GATGTTGTGATGACTCAGTCTCCACTCTCCCTGCCCG TCACCCTTGGACAGCCGGCCTCCATCTCCTGCAAGGC CAGTCAGGATGTGGGTACTGCTGTAGCCTGGTACCAG CAGAAACCTGGCCAGGCTCCCAGGCTCCTCATCTATT GGGCATCCACCCGGCACACTGGGGTCCCATCAAGGTT CAGCGGCAGTGGATCTGGGACAGAATTCACTCTCACC ATCAGCAGCCTGCAGCCTGATGATTTTGCAACTTATT ACTGTCAGCAGTATAACAGCTATCCTCTCACGTTCGG CCAAGGGACCAAGGTGGAAATCAAA |
| SEQ ID NO: 68 | Light Chain | DVVMTQSPLSLPVTLGQPASISCKASQDVGTAVAWYQ QKPGQAPRLLIYWASTRHTGVPSRFSGSGSGTEFTLT ISSLQPDDFATYYCQQYNSYPLTFGQGTKVEIKRTVA APSVFIFPPSDEQLKSGTASVVCLLNNFYPREAKVQW KVDNALQSGNSQESVTEQDSKDSTYSLSSTLTLSKAD YEKHKVYACEVTHQGLSSPVTKSFNRGEC |
| SEQ ID NO: 69 | DNA Light Chain | GATGTTGTGATGACTCAGTCTCCACTCTCCCTGCCCG TCACCCTTGGACAGCCGGCCTCCATCTCCTGCAAGGC CAGTCAGGATGTGGGTACTGCTGTAGCCTGGTACCAG CAGAAACCTGGCCAGGCTCCCAGGCTCCTCATCTATT GGGCATCCACCCGGCACACTGGGGTCCCATCAAGGTT CAGCGGCAGTGGATCTGGGACAGAATTCACTCTCACC ATCAGCAGCCTGCAGCCTGATGATTTTGCAACTTATT ACTGTCAGCAGTATAACAGCTATCCTCTCACGTTCGG CCAAGGGACCAAGGTGGAAATCAAACGTACGGTGGCT GCACCATCTGTCTTCATCTTCCCGCCATCTGATGAGC AGTTGAAATCTGGAACTGCCTCTGTTGTGTGCCTGCT GAATAACTTCTATCCCAGAGAGGCCAAAGTACAGTGG |

TABLE 1 -continued

AAGGTGGATAACGCCCTCCAATCGGGTAACTCCCAGG
AGAGTGTCACAGAGCAGGACAGCAAGGACAGCACCTA
CAGCCTCAGCAGCACCCTGACGCTGAGCAAAGCAGAC
TACGAGAAACACAAAGTCTACGCCTGCGAAGTCACCC
ATCAGGGCCTGAGCTCGCCCGTCACAAAGAGCTTCAA
CAGGGGAGAGTGT

| | BAP058-hum12-HC | |
|---|---|---|
| SEQ ID NO: 1 (Kabat) | HCDR1 | SYWMY |
| SEQ ID NO: 2 (Kabat) | HCDR2 | RIDPNSGSTKYNEKFKN |
| SEQ ID NO: 3 (Kabat) | HCDR3 | DYRKGLYAMDY |
| SEQ ID NO: 4 (Chothia) | HCDR1 | GYTFTSY |
| SEQ ID NO: 5 (Chothia) | HCDR2 | DPNSGS |
| SEQ ID NO: 3 (Chothia) | HCDR3 | DYRKGLYAMDY |
| SEQ ID NO: 38 | VH | EVQLVQSGAEVKKPGESLRISCKGSGYTFTSYWMYWV RQAPGQGLEWMGRIDPNSGSTKYNEKFKNRVTISVDT SKNQFSLKLSSVTAADTAVYYCARDYRKGLYAMDYWG QGTTVTVSS |
| SEQ ID NO: 39 | DNA VH | GAAGTGCAGCTGGTGCAGTCTGGAGCAGAGGTGAAAA AGCCCGGGGAGTCTCTGAGGATCTCCTGTAAGGGTTC TGGCTACACCTTCACCAGTTACTGGATGTACTGGGTG CGACAGGCCCCTGGACAAGGGCTTGAGTGGATGGGTA GGATTGATCCTAATAGTGGGAGTACTAAGTACAATGA GAAGTTCAAGAACAGAGTCACCATATCAGTAGACACG TCCAAGAACCAGTTCTCCCTGAAGCTGAGCTCTGTGA CCGCCGCGGACACGGCTGTGTATTACTGTGCAAGGGA CTATAGAAAGGGGCTCTATGCTATGGACTACTGGGGC CAGGGCACCACCGTGACCGTGTCCTCC |
| SEQ ID NO: 40 | Heavy Chain | EVQLVQSGAEVKKPGESLRISCKGSGYTFTSYWMYWV RQAPGQGLEWMGRIDPNSGSTKYNEKFKNRVTISVDT SKNQFSLKLSSVTAADTAVYYCARDYRKGLYAMDYWG QGTTVTVSSASTKGPSVFPLAPCSRSTSESTAALGCL VKDYFPEPVTVSWNSGALTSGVHTFPAVLQSSGLYSL SSVVTVPSSSLGTKTYTCNVDHKPSNTKVDKRVESKY GPPCPPCPAPEFLGGPSVFLFPPKPKDTLMISRTPEV TCVVVDVSQEDPEVQFNWYVDGVEVHNAKTKPREEQF NSTYRVVSVLTVLHQDWLNGKEYKCKVSNKGLPSSIE KTISKAKGQPREPQVYTLPPSQEEMTKNQVSLTCLVK GFYPSDIAVEWESNGQPENNYKTTPPVLDSDGSFFLY SRLTVDKSRWQEGNVFSCSVMHEALHNHYTQKSLSLS LGK |
| SEQ ID NO: 41 | DNA Heavy Chain | GAAGTGCAGCTGGTGCAGTCTGGAGCAGAGGTGAAAA AGCCCGGGGAGTCTCTGAGGATCTCCTGTAAGGGTTC TGGCTACACCTTCACCAGTTACTGGATGTACTGGGTG CGACAGGCCCCTGGACAAGGGCTTGAGTGGATGGGTA GGATTGATCCTAATAGTGGGAGTACTAAGTACAATGA GAAGTTCAAGAACAGAGTCACCATATCAGTAGACACG TCCAAGAACCAGTTCTCCCTGAAGCTGAGCTCTGTGA CCGCCGCGGACACGGCTGTGTATTACTGTGCAAGGGA CTATAGAAAGGGGCTCTATGCTATGGACTACTGGGGC CAGGGCACCACCGTGACCGTGTCCTCCGCTTCCACCA AGGGCCCATCCGTCTTCCCCCTGGCGCCCTGCTCCAG GAGCACCTCCGAGAGCACAGCCGCCCTGGGCTGCCTG GTCAAGGACTACTTCCCCGAACCGGTGACGGTGTCGT GGAACTCAGGCGCCCTGACCAGCGGCGTGCACACCTT CCCGGCTGTCCTACAGTCCTCAGGACTCTACTCCCTC AGCAGCGTGGTGACCGTGCCCTCCAGCAGCTTGGGCA CGAAGACCTACACCTGCAACGTAGATCACAAGCCCAG CAACACCAAGGTGGACAAGAGAGTTGAGTCCAAATAT GGTCCCCCATGCCCACCGTGCCCAGCACCTGAGTTCC TGGGGGGACCATCAGTCTTCCTGTTCCCCCCAAAACC CAAGGACACTCTCATGATCTCCCGGACCCCTGAGGTC ACGTGCGTGGTGGTGGACGTGAGCCAGGAAGACCCCG AGGTCCAGTTCAACTGGTACGTGGATGGCGTGGAGGT GCATAATGCCAAGACAAAGCCGCGGGAGGAGCAGTTC AACAGCACGTACCGTGTGGTCAGCGTCCTCACCGTCC TGCACCAGGACTGGCTGAACGGCAAGGAGTACAAGTG CAAGGTGTCCAACAAAGGCCTCCCGTCCTCCATCGAG AAAACCATCTCCAAAGCCAAAGGGCAGCCCCGAGAGC CACAGGTGTACACCCTGCCCCCATCCCAGGAGGAGAT |

TABLE 1 -continued

|  |  |  | GACCAAGAACCAGGTCAGCCTGACCTGCCTGGTCAAA<br>GGCTTCTACCCCAGCGACATCGCCGTGGAGTGGGAGA<br>GCAATGGGCAGCCGGAGAACAACTACAAGACCACGCC<br>TCCCGTGCTGGACTCCGACGGCTCCTTCTTCCTCTAC<br>AGCAGGCTAACCGTGGACAAGAGCAGGTGGCAGGAGG<br>GGAATGTCTTCTCATGCTCCGTGATGCATGAGGCTCT<br>GCACAACCACTACACACAGAAGAGCCTCTCCCTGTCT<br>CTGGGTAAA |
| --- | --- | --- | --- |
|  | BAP058-hum12-LC |  |  |
| SEQ ID NO: 9 (Kabat) | LCDR1 | KASQDVGTAVA |  |
| SEQ ID NO: 10 (Kabat) | LCDR2 | WASTRHT |  |
| SEQ ID NO: 11 (Kabat) | LCDR3 | QQYNSYPLT |  |
| SEQ ID NO: 12 (Chothia) | LCDR1 | SQDVGTA |  |
| SEQ ID NO: 13 (Chothia) | LCDR2 | WAS |  |
| SEQ ID NO: 14 (Chothia) | LCDR3 | YNSYPL |  |
| SEQ ID NO: 74 | VL | DIQMTQSPSSLSASVGDRVTITCKASQDVGTAVAWYQ<br>QKPGQAPRLLIYWASTRHTGVPSRFSGSGSGTDFTFT<br>ISSLQPEDIATYYCQQYNSYPLTFGQGTKVEIK |  |
| SEQ ID NO: 75 | DNA VL | GACATCCAGATGACCCAGTCTCCATCCTCCCTGTCTG<br>CATCTGTAGGAGACAGAGTCACCATCACTTGCAAGGC<br>CAGTCAGGATGTGGGTACTGCTGTAGCCTGGTACCAG<br>CAGAAACCTGGCCAGGCTCCCAGGCTCCTCATCTATT<br>GGGCATCCACCCGGCACACTGGGGTCCCATCAAGGTT<br>CAGTGGAAGTGGATCTGGGACAGATTTTACTTTCACC<br>ATCAGCAGCCTGCAGCCTGAAGATATTGCAACATATT<br>ACTGTCAGCAGTATAACAGCTATCCTCTCACGTTCGG<br>CCAAGGGACCAAGGTGGAAATCAAA |  |
| SEQ ID NO: 76 | Light Chain | DIQMTQSPSSLSASVGDRVTITCKASQDVGTAVAWYQ<br>QKPGQAPRLLIYWASTRHTGVPSRFSGSGSGTDFTFT<br>ISSLQPEDIATYYCQQYNSYPLTFGQGTKVEIKRTVA<br>APSVFIFPPSDEQLKSGTASVVCLLNNFYPREAKVQW<br>KVDNALQSGNSQESVTEQDSKDSTYSLSSTLTLSKAD<br>YEKHKVYACEVTHQGLSSPVTKSFNRGEC |  |
| SEQ ID NO: 77 | DNA Light Chain | GACATCCAGATGACCCAGTCTCCATCCTCCCTGTCTG<br>CATCTGTAGGAGACAGAGTCACCATCACTTGCAAGGC<br>CAGTCAGGATGTGGGTACTGCTGTAGCCTGGTACCAG<br>CAGAAACCTGGCCAGGCTCCCAGGCTCCTCATCTATT<br>GGGCATCCACCCGGCACACTGGGGTCCCATCAAGGTT<br>CAGTGGAAGTGGATCTGGGACAGATTTTACTTTCACC<br>ATCAGCAGCCTGCAGCCTGAAGATATTGCAACATATT<br>ACTGTCAGCAGTATAACAGCTATCCTCTCACGTTCGG<br>CCAAGGGACCAAGGTGGAAATCAAACGTACGGTGGCT<br>GCACCATCTGTCTTCATCTTCCCGCCATCTGATGAGC<br>AGTTGAAATCTGGAACTGCCTCTGTTGTGTGCCTGCT<br>GAATAACTTCTATCCCAGAGAGGCCAAAGTACAGTGG<br>AAGGTGGATAACGCCCTCCAATCGGGTAACTCCCAGG<br>AGAGTGTCACAGAGCAGGACAGCAAGGACAGCACCTA<br>CAGCCTCAGCAGCACCCTGACGCTGAGCAAAGCAGAC<br>TACGAGAAACACAAAGTCTACGCCTGCGAAGTCACCC<br>ATCAGGGCCTGAGCTCGCCCGTCACAAAGAGCTTCAA<br>CAGGGGAGAGTGT |  |
|  | BAP058-hum13-HC |  |  |
| SEQ ID NO: 1 (Kabat) | HCDR1 | SYWMY |  |
| SEQ ID NO: 2 (Kabat) | HCDR2 | RIDPNSGSTKYNEKFKN |  |
| SEQ ID NO: 3 (Kabat) | HCDR3 | DYRKGLYAMDY |  |
| SEQ ID NO: 4 (Chothia) | HCDR1 | GYTFTSY |  |
| SEQ ID NO: 5 (Chothia) | HCDR2 | DPNSGS |  |
| SEQ ID NO: 3 (Chothia) | HCDR3 | DYRKGLYAMDY |  |
| SEQ ID NO: 78 | VH | EVQLVQSGAEVKKPGATVKISCKVSGYTFTSYWMYWV<br>RQARGQRLEWIGRIDPNSGSTKYNEKFKNRFTISRDN |  |

TABLE 1 -continued

| | | |
|---|---|---|
| | | SKNTLYLQMNSLRAEDTAVYYCARDYRKGLYAMDYWG<br>QGTTVTVSS |
| SEQ ID NO: 79 | DNA VH | GAGGTCCAGCTGGTACAGTCTGGGGCTGAGGTGAAGA<br>AGCCTGGGGCTACAGTGAAAATCTCCTGCAAGGTTTC<br>TGGCTACACCTTCACCAGTTACTGGATGTACTGGGTG<br>CGACAGGCTCGTGGACAACGCCTTGAGTGGATAGGTA<br>GGATTGATCCTAATAGTGGGAGTACTAAGTACAATGA<br>GAAGTTCAAGAACAGATTCACCATCTCCAGAGACAAT<br>TCCAAGAACACGCTGTATCTTCAAATGAACAGCCTGA<br>GAGCCGAGGACACGGCCGTGTATTACTGTGCAAGGGA<br>CTATAGAAAGGGGCTCTATGCTATGGACTACTGGGGC<br>CAGGGCACCACCGTGACCGTGTCCTCC |
| SEQ ID NO: 247 | Heavy<br>Chain | EVQLVQSGAEVKKPGATVKISCKVSGYTFTSYWMYWV<br>RQARGQRLEWIGRIDPNSGSTKYNEKFKNRFTISRDN<br>SKNTLYLQMNSLRAEDTAVYYCARDYRKGLYAMDYWG<br>QGTTVTVSSASTKGPSVFPLAPCSRSTSESTAALGCL<br>VKDYFPEPVTVSWNSGALTSGVHTFPAVLQSSGLYSL<br>SSVVTVPSSSLGTKTYTCNVDHKPSNTKVDKRVESKY<br>GPPCPPCPAPEFLGGPSVFLFPPKPKDTLMISRTPEV<br>TCVVVDVSQEDPEVQFNWYVDGVEVHNAKTKPREEQF<br>NSTYRVVSVLTVLHQDWLNGKEYKCKVSNKGLPSSIE<br>KTISKAKGQPREPQVYTLPPSQEEMTKNQVSLTCLVK<br>GFYPSDIAVEWESNGQPENNYKTTPPVLDSDGSFFLY<br>SRLTVDKSRWQEGNVFSCSVMHEALHNHYTQKSLSLS<br>LGK |
| SEQ ID NO: 81 | DNA Heavy<br>Chain | GAGGTCCAGCTGGTACAGTCTGGGGCTGAGGTGAAGA<br>AGCCTGGGGCTACAGTGAAAATCTCCTGCAAGGTTTC<br>TGGCTACACCTTCACCAGTTACTGGATGTACTGGGTG<br>CGACAGGCTCGTGGACAACGCCTTGAGTGGATAGGTA<br>GGATTGATCCTAATAGTGGGAGTACTAAGTACAATGA<br>GAAGTTCAAGAACAGATTCACCATCTCCAGAGACAAT<br>TCCAAGAACACGCTGTATCTTCAAATGAACAGCCTGA<br>GAGCCGAGGACACGGCCGTGTATTACTGTGCAAGGGA<br>CTATAGAAAGGGGCTCTATGCTATGGACTACTGGGGC<br>CAGGGCACCACCGTGACCGTGTCCTCCGCTTCCACCA<br>AGGGCCCATCCGTCTTCCCCCTGGCGCCCTGCTCCAG<br>GAGCACCTCCGAGAGCACAGCCGCCCTGGGCTGCCTG<br>GTCAAGGACTACTTCCCCGAACCGGTGACGGTGTCGT<br>GGAACTCAGGCGCCCTGACCAGCGGCGTGCACACCTT<br>CCCGGCTGTCCTACAGTCCTCAGGACTCTACTCCCTC<br>AGCAGCGTGGTGACCGTGCCCTCCAGCAGCTTGGGCA<br>CGAAGACCTACACCTGCAACGTAGATCACAAGCCCAG<br>CAACACCAAGGTGGACAAGAGAGTTGAGTCCAAATAT<br>GGTCCCCCATGCCCACCGTGCCCAGCACCTGAGTTCC<br>TGGGGGGACCATCAGTCTTCCTGTTCCCCCCAAAACC<br>CAAGGACACTCTCATGATCTCCCGGACCCCTGAGGTC<br>ACGTGCGTGGTGGTGGACGTGAGCCAGGAAGACCCCG<br>AGGTCCAGTTCAACTGGTACGTGGATGGCGTGGAGGT<br>GCATAATGCCAAGACAAAGCCGCGGGAGGAGCAGTTC<br>AACAGCACGTACCGTGTGGTCAGCGTCCTCACCGTCC<br>TGCACCAGGACTGGCTGAACGGCAAGGAGTACAAGTG<br>CAAGGTGTCCAACAAAGGCCTCCCGTCCTCCATCGAG<br>AAAACCATCTCCAAAGCCAAAGGGCAGCCCCGAGAGC<br>CACAGGTGTACACCCTGCCCCCATCCCAGGAGGAGAT<br>GACCAAGAACCAGGTCAGCCTGACCTGCCTGGTCAAA<br>GGCTTCTACCCCAGCGACATCGCCGTGGAGTGGGAGA<br>GCAATGGGCAGCCGGAGAACAACTACAAGACCACGCC<br>TCCCGTGCTGGACTCCGACGGCTCCTTCTTCCTCTAC<br>AGCAGGCTAACCGTGGACAAGAGCAGGTGGCAGGAGG<br>GGAATGTCTTCTCATGCTCCGTGATGCATGAGGCTCT<br>GCACAACCACTACACACAGAAGAGCCTCTCCCTGTCT<br>CTGGGTAAA |

| BAP058-hum13-LC | | |
|---|---|---|
| SEQ ID NO: 9 (Kabat) | LCDR1 | KASQDVGTAVA |
| SEQ ID NO: 10 (Kabat) | LCDR2 | WASTRHT |
| SEQ ID NO: 11 (Kabat) | LCDR3 | QQYNSYPLT |
| SEQ ID NO: 12 (Chothia) | LCDR1 | SQDVGTA |
| SEQ ID NO: 13 (Chothia) | LCDR2 | WAS |
| SEQ ID NO: 14 (Chothia) | LCDR3 | YNSYPL |

TABLE 1 -continued

| SEQ ID NO: 82 | VL | AIQLTQSPSSLSASVGDRVTITCKASQDVGTAVAWYL<br>QKPGQSPQLLIYWASTRHTGVPSRFSGSGSGTDFTFT<br>ISSLEAEDAATYYCQQYNSYPLTFGQGTKVEIK |
|---|---|---|
| SEQ ID NO: 83 | DNA VL | GCCATCCAGTTGACCCAGTCTCCATCCTCCCTGTCTG<br>CATCTGTAGGAGACAGAGTCACCATCACTTGCAAGGC<br>CAGTCAGGATGTGGGTACTGCTGTAGCCTGGTACCTG<br>CAGAAGCCAGGGCAGTCTCCACAGCTCCTGATCTATT<br>GGGCATCCACCCGGCACACTGGGGTCCCCTCGAGGTT<br>CAGTGGCAGTGGATCTGGGACAGATTTCACCTTTACC<br>ATCAGTAGCCTGGAAGCTGAAGATGCTGCAACATATT<br>ACTGTCAGCAGTATAACAGCTATCCTCTCACGTTCGG<br>CCAAGGGACCAAGGTGGAAATCAAA |
| SEQ ID NO: 84 | Light Chain | AIQLTQSPSSLSASVGDRVTITCKASQDVGTAVAWYL<br>QKPGQSPQLLIYWASTRHTGVPSRFSGSGSGTDFTFT<br>ISSLEAEDAATYYCQQYNSYPLTFGQGTKVEIKRTVA<br>APSVFIFPPSDEQLKSGTASVVCLLNNFYPREAKVQW<br>KVDNALQSGNSQESVTEQDSKDSTYSLSSTLTLSKAD<br>YEKHKVYACEVTHQGLSSPVTKSFNRGEC |
| SEQ ID NO: 85 | DNA Light Chain | GCCATCCAGTTGACCCAGTCTCCATCCTCCCTGTCTG<br>CATCTGTAGGAGACAGAGTCACCATCACTTGCAAGGC<br>CAGTCAGGATGTGGGTACTGCTGTAGCCTGGTACCTG<br>CAGAAGCCAGGGCAGTCTCCACAGCTCCTGATCTATT<br>GGGCATCCACCCGGCACACTGGGGTCCCCTCGAGGTT<br>CAGTGGCAGTGGATCTGGGACAGATTTCACCTTTACC<br>ATCAGTAGCCTGGAAGCTGAAGATGCTGCAACATATT<br>ACTGTCAGCAGTATAACAGCTATCCTCTCACGTTCGG<br>CCAAGGGACCAAGGTGGAAATCAAACGTACGGTGGCT<br>GCACCATCTGTCTTCATCTTCCCGCCATCTGATGAGC<br>AGTTGAAATCTGGAACTGCCTCTGTTGTGTGCCTGCT<br>GAATAACTTCTATCCCAGAGAGGCCAAAGTACAGTGG<br>AAGGTGGATAACGCCCTCCAATCGGGTAACTCCCAGG<br>AGAGTGTCACAGAGCAGGACAGCAAGGACAGCACCTA<br>CAGCCTCAGCAGCACCCTGACGCTGAGCAAAGCAGAC<br>TACGAGAAACACAAAGTCTACGCCTGCGAAGTCACCC<br>ATCAGGGCCTGAGCTCGCCCGTCACAAAGAGCTTCAA<br>CAGGGGAGAGTGT |
| BAP058-hum14-HC | | |
| SEQ ID NO: 1 (Kabat) | HCDR1 | SYWMY |
| SEQ ID NO: 2 (Kabat) | HCDR2 | RIDPNSGSTKYNEKFKN |
| SEQ ID NO: 3 (Kabat) | HCDR3 | DYRKGLYAMDY |
| SEQ ID NO: 4 (Chothia) | HCDR1 | GYTFTSY |
| SEQ ID NO: 5 (Chothia) | HCDR2 | DPNSGS |
| SEQ ID NO: 3 (Chothia) | HCDR3 | DYRKGLYAMDY |
| SEQ ID NO: 18 | VH | QVQLVQSGAEVKKPGASVKVSCKASGYTFTSYWMYWV<br>RQATGQGLEWMGRIDPNSGSTKYNEKFKNRFTISRDD<br>SKNTAYLQMNSLKTEDTAVYYCARDYRKGLYAMDYWG<br>QGTTVTVSS |
| SEQ ID NO: 19 | DNA VH | CAGGTTCAGCTGGTGCAGTCTGGAGCTGAGGTGAAGA<br>AGCCTGGGGCCTCAGTGAAGGTCTCCTGCAAGGCTTC<br>TGGCTACACCTTCACCAGTTACTGGATGTACTGGGTG<br>CGACAGGCCACTGGACAAGGGCTTGAGTGGATGGGTA<br>GGATTGATCCTAATAGTGGGAGTACTAAGTACAATGA<br>GAAGTTCAAGAACAGATTCACCATCTCCAGAGATGAT<br>TCAAAGAACACGGCGTATCTGCAAATGAACAGCCTGA<br>AAACCGAGGACACGGCCGTGTATTACTGTGCAAGGGA<br>CTATAGAAAGGGGCTCTATGCTATGGACTACTGGGGC<br>CAGGGCACCACCGTGACCGTGTCCTCC |
| SEQ ID NO: 20 | Heavy Chain | QVQLVQSGAEVKKPGASVKVSCKASGYTFTSYWMYWV<br>RQATGQGLEWMGRIDPNSGSTKYNEKFKNRFTISRDD<br>SKNTAYLQMNSLKTEDTAVYYCARDYRKGLYAMDYWG<br>QGTTVTVSSASTKGPSVFPLAPCSRSTSESTAALGCL<br>VKDYFPEPVTVSWNSGALTSGVHTFPAVLQSSGLYSL<br>SSVVTVPSSSLGTKTYTCNVDHKPSNTKVDKRVESKY<br>GPPCPPCPAPEFLGGPSVFLFPPKPKDTLMISRTPEV<br>TCVVVDVSQEDPEVQFNWYVDGVEVHNAKTKPREEQF<br>NSTYRVVSVLTVLHQDWLNGKEYKCKVSNKGLPSSIE<br>KTISKAKGQPREPQVYTLPPSQEEMTKNQVSLTCLVK |

TABLE 1 -continued

| | | |
|---|---|---|
| | | GFYPSDIAVEWESNGQPENNYKTTPPVLDSDGSFFLY<br>SRLTVDKSRWQEGNVFSCSVMHEALHNHYTQKSLSLS<br>LGK |
| SEQ ID NO: 21 | DNA Heavy<br>Chain | CAGGTTCAGCTGGTGCAGTCTGGAGCTGAGGTGAAGA<br>AGCCTGGGGCCTCAGTGAAGGTCTCCTGCAAGGCTTC<br>TGGCTACACCTTCACCAGTTACTGGATGTACTGGGTG<br>CGACAGGCCACTGGACAAGGGCTTGAGTGGATGGGTA<br>GGATTGATCCTAATAGTGGGAGTACTAAGTACAATGA<br>GAAGTTCAAGAACAGATTCACCATCTCCAGAGATGAT<br>TCAAAGAACACGGCGTATCTGCAAATGAACAGCCTGA<br>AAACCGAGGACACGGCCGTGTATTACTGTGCAAGGGA<br>CTATAGAAAGGGGCTCTATGCTATGGACTACTGGGGC<br>CAGGGCACCACCGTGACCGTGTCCTCCGCTTCCACCA<br>AGGGCCCATCCGTCTTCCCCCTGGCGCCCTGCTCCAG<br>GAGCACCTCCGAGAGCACAGCCGCCCTGGGCTGCCTG<br>GTCAAGGACTACTTCCCCGAACCGGTGACGGTGTCGT<br>GGAACTCAGGCGCCCTGACCAGCGGCGTGCACACCTT<br>CCCGGCTGTCCTACAGTCCTCAGGACTCTACTCCCTC<br>AGCAGCGTGGTGACCGTGCCCTCCAGCAGCTTGGGCA<br>CGAAGACCTACACCTGCAACGTAGATCACAAGCCCAG<br>CAACACCAAGGTGGACAAGAGAGTTGAGTCCAAATAT<br>GGTCCCCCATGCCCACCGTGCCCAGCACCTGAGTTCC<br>TGGGGGGACCATCAGTCTTCCTGTTCCCCCCAAAACC<br>CAAGGACACTCTCATGATCTCCCGGACCCCTGAGGTC<br>ACGTGCGTGGTGGTGGACGTGAGCCAGGAAGACCCCG<br>AGGTCCAGTTCAACTGGTACGTGGATGGCGTGGAGGT<br>GCATAATGCCAAGACAAAGCCGCGGGAGGAGCAGTTC<br>AACAGCACGTACCGTGTGGTCAGCGTCCTCACCGTCC<br>TGCACCAGGACTGGCTGAACGGCAAGGAGTACAAGTG<br>CAAGGTGTCCAACAAAGGCCTCCCGTCCTCCATCGAG<br>AAAACCATCTCCAAAGCCAAAGGGCAGCCCCGAGAGC<br>CACAGGTGTACACCCTGCCCCCATCCCAGGAGGAGAT<br>GACCAAGAACCAGGTCAGCCTGACCTGCCTGGTCAAA<br>GGCTTCTACCCCAGCGACATCGCCGTGGAGTGGGAGA<br>GCAATGGGCAGCCGGAGAACAACTACAAGACCACGCC<br>TCCCGTGCTGGACTCCGACGGCTCCTTCTTCCTCTAC<br>AGCAGGCTAACCGTGGACAAGAGCAGGTGGCAGGAGG<br>GGAATGTCTTCTCATGCTCCGTGATGCATGAGGCTCT<br>GCACAACCACTACACACAGAAGAGCCTCTCCCTGTCT<br>CTGGGTAAA |

| BAP058-hum14-LC | | |
|---|---|---|
| SEQ ID NO: 9 (Kabat) | LCDR1 | KASQDVGTAVA |
| SEQ ID NO: 10 (Kabat) | LCDR2 | WASTRHT |
| SEQ ID NO: 11 (Kabat) | LCDR3 | QQYNSYPLT |
| SEQ ID NO: 12 (Chothia) | LCDR1 | SQDVGTA |
| SEQ ID NO: 13 (Chothia) | LCDR2 | WAS |
| SEQ ID NO: 14 (Chothia) | LCDR3 | YNSYPL |
| SEQ ID NO: 86 | VL | EIVLTQSPDFQSVTPKEKVTITCKASQDVGTAVAWYQ<br>QKPGQAPRLLIYWASTRHTGVPSRFSGSGSGTEFTLT<br>ISSLQPDDFATYYCQQYNSYPLTFGQGTKVEIK |
| SEQ ID NO: 87 | DNA VL | GAAATTGTGCTGACTCAGTCTCCAGACTTTCAGTCTG<br>TGACTCCAAAGGAGAAAGTCACCATCACCTGCAAGGC<br>CAGTCAGGATGTGGGTACTGCTGTAGCCTGGTACCAG<br>CAGAAACCTGGCCAGGCTCCCAGGCTCCTCATCTATT<br>GGGCATCCACCCGGCACACTGGGGTCCCATCAAGGTT<br>CAGCGGCAGTGGATCTGGGACAGAATTCACTCTCACC<br>ATCAGCAGCCTGCAGCCTGATGATTTTGCAACTTATT<br>ACTGTCAGCAGTATAACAGCTATCCTCTCACGTTCGG<br>CCAAGGGACCAAGGTGGAAATCAAA |
| SEQ ID NO: 88 | Light<br>Chain | EIVLTQSPDFQSVTPKEKVTITCKASQDVGTAVAWYQ<br>QKPGQAPRLLIYWASTRHTGVPSRFSGSGSGTEFTLT<br>ISSLQPDDFATYYCQQYNSYPLTFGQGTKVEIKRTVA<br>APSVFIFPPSDEQLKSGTASVVCLLNNFYPREAKVQW<br>KVDNALQSGNSQESVTEQDSKDSTYSLSSTLTLSKAD<br>YEKHKVYACEVTHQGLSSPVTKSFNRGEC |
| SEQ ID NO: 89 | DNA Light<br>Chain | GAAATTGTGCTGACTCAGTCTCCAGACTTTCAGTCTG<br>TGACTCCAAAGGAGAAAGTCACCATCACCTGCAAGGC<br>CAGTCAGGATGTGGGTACTGCTGTAGCCTGGTACCAG |

TABLE 1 -continued

CAGAAACCTGGCCAGGCTCCCAGGCTCCTCATCTATT
GGGCATCCACCCGGCACACTGGGGTCCCATCAAGGTT
CAGCGGCAGTGGATCTGGGACAGAATTCACTCTCACC
ATCAGCAGCCTGCAGCCTGATGATTTTGCAACTTATT
ACTGTCAGCAGTATAACAGCTATCCTCTCACGTTCGG
CCAAGGGACCAAGGTGGAAATCAAACGTACGGTGGCT
GCACCATCTGTCTTCATCTTCCCGCCATCTGATGAGC
AGTTGAAATCTGGAACTGCCTCTGTTGTGTGCCTGCT
GAATAACTTCTATCCCAGAGAGGCCAAAGTACAGTGG
AAGGTGGATAACGCCCTCCAATCGGGTAACTCCCAGG
AGAGTGTCACAGAGCAGGACAGCAAGGACAGCACCTA
CAGCCTCAGCAGCACCCTGACGCTGAGCAAAGCAGAC
TACGAGAAACACAAAGTCTACGCCTGCGAAGTCACCC
ATCAGGGCCTGAGCTCGCCCGTCACAAAGAGCTTCAA
CAGGGGAGAGTGT

| | BAP058-hum15-HC | |
|---|---|---|
| SEQ ID NO: 1 (Kabat) | HCDR1 | SYWMY |
| SEQ ID NO: 2 (Kabat) | HCDR2 | RIDPNSGSTKYNEKFKN |
| SEQ ID NO: 3 (Kabat) | HCDR3 | DYRKGLYAMDY |
| SEQ ID NO: 4 (Chothia) | HCDR1 | GYTFTSY |
| SEQ ID NO: 5 (Chothia) | HCDR2 | DPNSGS |
| SEQ ID NO: 3 (Chothia) | HCDR3 | DYRKGLYAMDY |
| SEQ ID NO: 50 | VH | EVQLVQSGAEVKKPGESLRISCKGSYTFTSYWMYWI RQPPGKGLEWIGRIDPNSGSTKYNEKFKNRVTITADK STSTAYMELSSLRSEDTAVYYCARDYRKGLYAMDYWG QGTTVTVSS |
| SEQ ID NO: 51 | DNA VH | GAAGTGCAGCTGGTGCAGTCTGGAGCAGAGGTGAAAA AGCCCGGGGAGTCTCTGAGGATCTCCTGTAAGGGTTC TGGCTACACCTTCACCAGTTACTGGATGTACTGGATC CGCCAGCCCCCAGGGAAGGGGCTGGAGTGGATTGGTA GGATTGATCCTAATAGTGGGAGTACTAAGTACAATGA GAAGTTCAAGAACAGAGTCACGATTACCGCGGACAAA TCCACGAGCACAGCCTACATGGAGCTGAGCAGCCTGA GATCTGAGGACACGGCCGTGTATTACTGTGCAAGGGA CTATAGAAAGGGGCTCTATGCTATGGACTACTGGGGC CAGGGCACCACCGTGACCGTGTCCTCC |
| SEQ ID NO: 52 | Heavy Chain | EVQLVQSGAEVKKPGESLRISCKGSYTFTSYWMYWI RQPPGKGLEWIGRIDPNSGSTKYNEKFKNRVTITADK STSTAYMELSSLRSEDTAVYYCARDYRKGLYAMDYWG QGTTVTVSSASTKGPSVFPLAPCSRSTSESTAALGCL VKDYFPEPVTVSWNSGALTSGVHTFPAVLQSSGLYSL SSVVTVPSSSLGTKTYTCNVDHKPSNTKVDKRVESKY GPPCPPCPAPEFLGGPSVFLFPPKPKDTLMISRTPEV TCVVVDVSQEDPEVQFNWYVDGVEVHNAKTKPREEQF NSTYRVVSVLTVLHQDWLNGKEYKCKVSNKGLPSSIE KTISKAKGQPREPQVYTLPPSQEEMTKNQVSLTCLVK GFYPSDIAVEWESNGQPENNYKTTPPVLDSDGSFFLY SRLTVDKSRWQEGNVFSCSVMHEALHNHYTQKSLSLS LGK |
| SEQ ID NO: 53 | DNA Heavy Chain | GAAGTGCAGCTGGTGCAGTCTGGAGCAGAGGTGAAAA AGCCCGGGGAGTCTCTGAGGATCTCCTGTAAGGGTTC TGGCTACACCTTCACCAGTTACTGGATGTACTGGATC CGCCAGCCCCCAGGGAAGGGGCTGGAGTGGATTGGTA GGATTGATCCTAATAGTGGGAGTACTAAGTACAATGA GAAGTTCAAGAACAGAGTCACGATTACCGCGGACAAA TCCACGAGCACAGCCTACATGGAGCTGAGCAGCCTGA GATCTGAGGACACGGCCGTGTATTACTGTGCAAGGGA CTATAGAAAGGGGCTCTATGCTATGGACTACTGGGGC CAGGGCACCACCGTGACCGTGTCCTCCGCTTCCACCA AGGGCCCATCCGTCTTCCCCCTGGCGCCCTGCTCCAG GAGCACCTCCGAGAGCACAGCCGCCCTGGGCTGCCTG GTCAAGGACTACTTCCCCGAACCGGTGACGGTGTCGT GGAACTCAGGCGCCCTGACCAGCGGCGTGCACACCTT CCCGGCTGTCCTACAGTCCTCAGGACTCTACTCCCTC AGCAGCGTGGTGACCGTGCCCTCCAGCAGCTTGGGCA CGAAGACCTACACCTGCAACGTAGATCACAAGCCCAG CAACACCAAGGTGGACAAGAGAGTTGAGTCCAAATAT GGTCCCCCATGCCCACCGTGCCCAGCACCTGAGTTCC TGGGGGGACCATCAGTCTTCCTGTTCCCCCCAAAACC |

TABLE 1-continued

```
                           CAAGGACACTCTCATGATCTCCCGGACCCCTGAGGTC
                           ACGTGCGTGGTGGTGGACGTGAGCCAGGAAGACCCCG
                           AGGTCCAGTTCAACTGGTACGTGGATGGCGTGGAGGT
                           GCATAATGCCAAGACAAAGCCGCGGGAGGAGCAGTTC
                           AACAGCACGTACCGTGTGGTCAGCGTCCTCACCGTCC
                           TGCACCAGGACTGGCTGAACGGCAAGGAGTACAAGTG
                           CAAGGTGTCCAACAAAGGCCTCCCGTCCTCCATCGAG
                           AAAACCATCTCCAAAGCCAAAGGGCAGCCCCGAGAGC
                           CACAGGTGTACACCCTGCCCCCATCCCAGGAGGAGAT
                           GACCAAGAACCAGGTCAGCCTGACCTGCCTGGTCAAA
                           GGCTTCTACCCCAGCGACATCGCCGTGGAGTGGGAGA
                           GCAATGGGCAGCCGGAGAACAACTACAAGACCACGCC
                           TCCCGTGCTGGACTCCGACGGCTCCTTCTTCCTCTAC
                           AGCAGGCTAACCGTGGACAAGAGCAGGTGGCAGGAGG
                           GGAATGTCTTCTCATGCTCCGTGATGCATGAGGCTCT
                           GCACAACCACTACACACAGAAGAGCCTCTCCCTGTCT
                           CTGGGTAAA
```

| | BAP058-hum15-LC | | |
|---|---|---|---|
| SEQ ID NO: 9 (Kabat) | LCDR1 | KASQDVGTAVA | |
| SEQ ID NO: 10 (Kabat) | LCDR2 | WASTRHT | |
| SEQ ID NO: 11 (Kabat) | LCDR3 | QQYNSYPLT | |
| SEQ ID NO: 12 (Chothia) | LCDR1 | SQDVGTA | |
| SEQ ID NO: 13 (Chothia) | LCDR2 | WAS | |
| SEQ ID NO: 14 (Chothia) | LCDR3 | YNSYPL | |
| SEQ ID NO: 86 | VL | EIVLTQSPDFQSVTPKEKVTITCKASQDVGTAVAWYQ QKPGQAPRLLIYWASTRHTGVPSRFSGSGSGTEFTLT ISSLQPDDFATYYCQQYNSYPLTFGQGTKVEIK | |
| SEQ ID NO: 87 | DNA VL | GAAATTGTGCTGACTCAGTCTCCAGACTTTCAGTCTG TGACTCCAAAGGAGAAAGTCACCATCACCTGCAAGGC CAGTCAGGATGTGGGTACTGCTGTAGCCTGGTACCAG CAGAAACCTGGCCAGGCTCCCAGGCTCCTCATCTATT GGGCATCCACCCGGCACACTGGGGTCCCATCAAGGTT CAGCGGCAGTGGATCTGGGACAGAATTCACTCTCACC ATCAGCAGCCTGCAGCCTGATGATTTTGCAACTTATT ACTGTCAGCAGTATAACAGCTATCCTCTCACGTTCGG CCAAGGGACCAAGGTGGAAATCAAA | |
| SEQ ID NO: 88 | Light Chain | EIVLTQSPDFQSVTPKEKVTITCKASQDVGTAVAWYQ QKPGQAPRLLIYWASTRHTGVPSRFSGSGSGTEFTLT ISSLQPDDFATYYCQQYNSYPLTFGQGTKVEIKRTVA APSVFIFPPSDEQLKSGTASVVCLLNNFYPREAKVQW KVDNALQSGNSQESVTEQDSKDSTYSLSSTLTLSKAD YEKHKVYACEVTHQGLSSPVTKSFNRGEC | |
| SEQ ID NO: 89 | DNA Light Chain | GAAATTGTGCTGACTCAGTCTCCAGACTTTCAGTCTG TGACTCCAAAGGAGAAAGTCACCATCACCTGCAAGGC CAGTCAGGATGTGGGTACTGCTGTAGCCTGGTACCAG CAGAAACCTGGCCAGGCTCCCAGGCTCCTCATCTATT GGGCATCCACCCGGCACACTGGGGTCCCATCAAGGTT CAGCGGCAGTGGATCTGGGACAGAATTCACTCTCACC ATCAGCAGCCTGCAGCCTGATGATTTTGCAACTTATT ACTGTCAGCAGTATAACAGCTATCCTCTCACGTTCGG CCAAGGGACCAAGGTGGAAATCAAACGTACGGTGGCT GCACCATCTGTCTTCATCTTCCCGCCATCTGATGAGC AGTTGAAATCTGGAACTGCCTCTGTTGTGTGCCTGCT GAATAACTTCTATCCCAGAGAGGCCAAAGTACAGTGG AAGGTGGATAACGCCCTCCAATCGGGTAACTCCCAGG AGAGTGTCACAGAGCAGGACAGCAAGGACAGCACCTA CAGCCTCAGCAGCACCCTGACGCTGAGCAAAGCAGAC TACGAGAAACACAAAGTCTACGCCTGCGAAGTCACCC ATCAGGGCCTGAGCTCGCCCGTCACAAAGAGCTTCAA CAGGGGAGAGTGT | |

| | BAP058-hum16-HC | | |
|---|---|---|---|
| SEQ ID NO: 1 (Kabat) | HCDR1 | SYWMY | |
| SEQ ID NO: 2 (Kabat) | HCDR2 | RIDPNSGSTKYNEKFKN | |
| SEQ ID NO: 3 (Kabat) | HCDR3 | DYRKGLYAMDY | |

TABLE 1 -continued

| SEQ ID NO: 4 (Chothia) | HCDR1 | GYTFTSY |
|---|---|---|
| SEQ ID NO: 5 (Chothia) | HCDR2 | DPNSGS |
| SEQ ID NO: 3 (Chothia) | HCDR3 | DYRKGLYAMDY |
| SEQ ID NO: 54 | VH | QVQLVQSGAEVKKPGASVKVSCKASGYTFTSYWMYWI<br>RQSPSRGLEWLGRIDPNSGSTKYNEKFKNRFTISRDD<br>SKNTAYLQMNSLKTEDTAVYYCARDYRKGLYAMDYWG<br>QGTTVTVSS |
| SEQ ID NO: 55 | DNA VH | CAGGTTCAGCTGGTGCAGTCTGGAGCTGAGGTGAAGA<br>AGCCTGGGGCCTCAGTGAAGGTCTCCTGCAAGGCTTC<br>TGGCTACACCTTCACCAGTTACTGGATGTACTGGATC<br>AGGCAGTCCCCATCGAGAGGCCTTGAGTGGCTGGGTA<br>GGATTGATCCTAATAGTGGGAGTACTAAGTACAATGA<br>AGAGTTCAAGAACAGGATTCACCATCTCCAGAGATGAT<br>TCAAAGAACACGGCGTATCTGCAAATGAACAGCCTGA<br>AAACCGAGGACACGGCCGTGTATTACTGTGCAAGGGA<br>CTATAGAAAGGGGCTCTATGCTATGGACTACTGGGGC<br>CAGGGCACCACCGTGACCGTGTCCTCC |
| SEQ ID NO: 56 | Heavy<br>Chain | QVQLVQSGAEVKKPGASVKVSCKASGYTFTSYWMYWI<br>RQSPSRGLEWLGRIDPNSGSTKYNEKFKNRFTISRDD<br>SKNTAYLQMNSLKTEDTAVYYCARDYRKGLYAMDYWG<br>QGTTVTVSSASTKGPSVFPLAPCSRSTSESTAALGCL<br>VKDYFPEPVTVSWNSGALTSGVHTFPAVLQSSGLYSL<br>SSVVTVPSSSLGTKTYTCNVDHKPSNTKVDKRVESKY<br>GPPCPPCPAPEFLGGPSVFLFPPKPKDTLMISRTPEV<br>TCVVVDVSQEDPEVQFNWYVDGVEVHNAKTKPREEQF<br>NSTYRVVSVLTVLHQDWLNGKEYKCKVSNKGLPSSIE<br>KTISKAKGQPREPQVYTLPPSQEEMTKNQVSLTCLVK<br>GFYPSDIAVEWESNGQPENNYKTTPPVLDSDGSFFLY<br>SRLTVDKSRWQEGNVFSCSVMHEALHNHYTQKSLSLS<br>LGK |
| SEQ ID NO: 57 | DNA Heavy<br>Chain | CAGGTTCAGCTGGTGCAGTCTGGAGCTGAGGTGAAGA<br>AGCCTGGGGCCTCAGTGAAGGTCTCCTGCAAGGCTTC<br>TGGCTACACCTTCACCAGTTACTGGATGTACTGGATC<br>AGGCAGTCCCCATCGAGAGGCCTTGAGTGGCTGGGTA<br>GGATTGATCCTAATAGTGGGAGTACTAAGTACAATGA<br>AGAGTTCAAGAACAGGATTCACCATCTCCAGAGATGAT<br>TCAAAGAACACGGCGTATCTGCAAATGAACAGCCTGA<br>AAACCGAGGACACGGCCGTGTATTACTGTGCAAGGGA<br>CTATAGAAAGGGGCTCTATGCTATGGACTACTGGGGC<br>CAGGGCACCACCGTGACCGTGTCCTCCGCTTCCACCA<br>AGGGCCCATCCGTCTTCCCCCTGGCGCCCTGCTCCAG<br>GAGCACCTCCGAGAGCACAGCCGCCCTGGGCTGCCTG<br>GTCAAGGACTACTTCCCCGAACCGGTGACGGTGTCGT<br>GGAACTCAGGCGCCCTGACCAGCGGCGTGCACACCTT<br>CCCGGCTGTCCTACAGTCCTCAGGACTCTACTCCCTC<br>AGCAGCGTGGTGACCGTGCCCTCCAGCAGCTTGGGCA<br>CGAAGACCTACACCTGCAACGTAGATCACAAGCCCAG<br>CAACACCAAGGTGGACAAGAGAGTTGAGTCCAAATAT<br>GGTCCCCCATGCCCACCGTGCCCAGCACCTGAGTTCC<br>TGGGGGGACCATCAGTCTTCCTGTTCCCCCCAAAACC<br>CAAGGACACTCTCATGATCTCCCGGACCCCTGAGGTC<br>ACGTGCGTGGTGGTGGACGTGAGCCAGGAAGACCCCG<br>AGGTCCAGTTCAACTGGTACGTGGATGGCGTGGAGGT<br>GCATAATGCCAAGACAAAGCCGCGGGAGGAGCAGTTC<br>AACAGCACGTACCGTGTGGTCAGCGTCCTCACCGTCC<br>TGCACCAGGACTGGCTGAACGGCAAGGAGTACAAGTG<br>CAAGGTGTCCAACAAAGGCCTCCCGTCCTCCATCGAG<br>AAAACCATCTCCAAAGCCAAAGGGCAGCCCCGAGAGC<br>CACAGGTGTACACCCTGCCCCCATCCCAGGAGGAGAT<br>GACCAAGAACCAGGTCAGCCTGACCTGCCTGGTCAAA<br>GGCTTCTACCCCAGCGACATCGCCGTGGAGTGGGAGA<br>GCAATGGGCAGCCGGAGAACAACTACAAGACCACGCC<br>TCCCGTGCTGGACTCCGACGGCTCCTTCTTCCTCTAC<br>AGCAGGCTAACCGTGGACAAGAGCAGGTGGCAGGAGG<br>GGAATGTCTTCTCATGCTCCGTGATGCATGAGGCTCT<br>GCACAACCACTACACACAGAAGAGCCTCTCCCTGTCT<br>CTGGGTAAA |

BAP058-hum16-LC

| SEQ ID NO: 9 (Kabat) | LCDR1 | KASQDVGTAVA |
|---|---|---|
| SEQ ID NO: 10 (Kabat) | LCDR2 | WASTRHT |

TABLE 1 -continued

| SEQ ID NO: 11 (Kabat) | LCDR3 | QQYNSYPLT |
|---|---|---|
| SEQ ID NO: 12 (Chothia) | LCDR1 | SQDVGTA |
| SEQ ID NO: 13 (Chothia) | LCDR2 | WAS |
| SEQ ID NO: 14 (Chothia) | LCDR3 | YNSYPL |
| SEQ ID NO: 86 | VL | EIVLTQSPDFQSVTPKEKVTITCKASQDVGTAVAWYQQKPGQAPRLLIYWASTRHTGVPSRFSGSGSGTEFTLTISSLQPDDFATYYCQQYNSYPLTFGQGTKVEIK |
| SEQ ID NO: 87 | DNA VL | GAAATTGTGCTGACTCAGTCTCCAGACTTTCAGTCTGTGACTCCAAAGGAGAAAGTCACCATCACCTGCAAGGCCAGTCAGGATGTGGGTACTGCTGTAGCCTGGTACCAGCAGAAACCTGGCCAGGCTCCCAGGCTCCTCATCTATTGGGCATCCACCCGGCACACTGGGGTCCCATCAAGGTTCAGCGGCAGTGGATCTGGGACAGAATTCACTCTCACCATCAGCAGCCTGCAGCCTGATGATTTTGCAACTTATTACTGTCAGCAGTATAACAGCTATCCTCTCACGTTCGGCCAAGGGACCAAGGTGGAAATCAAA |
| SEQ ID NO: 88 | Light Chain | EIVLTQSPDFQSVTPKEKVTITCKASQDVGTAVAWYQQKPGQAPRLLIYWASTRHTGVPSRFSGSGSGTEFTLTISSLQPDDFATYYCQQYNSYPLTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| SEQ ID NO: 89 | DNA Light Chain | GAAATTGTGCTGACTCAGTCTCCAGACTTTCAGTCTGTGACTCCAAAGGAGAAAGTCACCATCACCTGCAAGGCCAGTCAGGATGTGGGTACTGCTGTAGCCTGGTACCAGCAGAAACCTGGCCAGGCTCCCAGGCTCCTCATCTATTGGGCATCCACCCGGCACACTGGGGTCCCATCAAGGTTCAGCGGCAGTGGATCTGGGACAGAATTCACTCTCACCATCAGCAGCCTGCAGCCTGATGATTTTGCAACTTATTACTGTCAGCAGTATAACAGCTATCCTCTCACGTTCGGCCAAGGGACCAAGGTGGAAATCAAACGTACGGTGGCTGCACCATCTGTCTTCATCTTCCCGCCATCTGATGAGCAGTTGAAATCTGGAACTGCCTCTGTTGTGTGCCTGCTGAATAACTTCTATCCCAGAGAGGCCAAAGTACAGTGGAAGGTGGATAACGCCCTCCAATCGGGTAACTCCCAGGAGAGTGTCACAGAGCAGGACAGCAAGGACAGCACCTACAGCCTCAGCAGCACCCTGACGCTGAGCAAAGCAGACTACGAGAAACACAAAGTCTACGCCTGCGAAGTCACCCATCAGGGCCTGAGCTCGCCCGTCACAAAGAGCTTCAACAGGGGAGAGTGT |

| BAP058-hum17-HC | | |
|---|---|---|
| SEQ ID NO: 1 (Kabat) | HCDR1 | SYWMY |
| SEQ ID NO: 2 (Kabat) | HCDR2 | RIDPNSGSTKYNEKFKN |
| SEQ ID NO: 3 (Kabat) | HCDR3 | DYRKGLYAMDY |
| SEQ ID NO: 4 (Chothia) | HCDR1 | GYTFTSY |
| SEQ ID NO: 5 (Chothia) | HCDR2 | DPNSGS |
| SEQ ID NO: 3 (Chothia) | HCDR3 | DYRKGLYAMDY |
| SEQ ID NO: 62 | VH | EVQLVQSGAEVKKPGESLRISCKGSGYTFTSYWMYWVRQARGQRLEWIGRIDPNSGSTKYNEKFKNRLTISKDTSKNQVVLTMTNMDPVDTATYYCARDYRKGLYAMDYWGQGTTVTVSS |
| SEQ ID NO: 63 | DNA VH | GAAGTGCAGCTGGTGCAGTCTGGAGCAGAGGTGAAAAAGCCCGGGGAGTCTCTGAGGATCTCCTGTAAGGGTTCTGGCTACACCTTCACCAGTTACTGGATGTACTGGGTGCGACAGGCTCGTGGACAACGCCTTGAGTGGATAGGTAGGATTGATCCTAATAGTGGGAGTACTAAGTACAATGAGAAGTTCAAGAACAGACTCACCATCTCCAAGGACACCTCCAAAAACCAGGTGGTCCTTACAATGACCAACATGGACCCTGTGGACACAGCCACGTATTACTGTGCAAGGGACTATAGAAAGGGGCTCTATGCTATGGACTACTGGGGCCAGGGCACCACCGTGACCGTGTCCTCC |
| SEQ ID NO: 64 | Heavy Chain | EVQLVQSGAEVKKPGESLRISCKGSGYTFTSYWMYWVRQARGQRLEWIGRIDPNSGSTKYNEKFKNRLTISKDT |

TABLE 1 -continued

|  |  |  | SKNQVVLTMTNMDPVDTATYYCARDYRKGLYAMDYWG<br>QGTTVTVSSASTKGPSVFPLAPCSRSTSESTAALGCL<br>VKDYFPEPVTVSWNSGALTSGVHTFPAVLQSSGLYSL<br>SSVVTVPSSSLGTKTYTCNVDHKPSNTKVDKRVESKY<br>GPPCPPCPAPEFLGGPSVFLFPPKPKDTLMISRTPEV<br>TCVVVDVSQEDPEVQFNWYVDGVEVHNAKTKPREEQF<br>NSTYRVVSVLTVLHQDWLNGKEYKCKVSNKGLPSSIE<br>KTISKAKGQPREPQVYTLPPSQEEMTKNQVSLTCLVK<br>GFYPSDIAVEWESNGQPENNYKTTPPVLDSDGSFFLY<br>SRLTVDKSRWQEGNVFSCSVMHEALHNHYTQKSLSLS<br>LGK |
|---|---|---|---|
| SEQ ID NO: 65 |  | DNA Heavy<br>Chain | GAAGTGCAGCTGGTGCAGTCTGGAGCAGAGGTGAAAA<br>AGCCCGGGGAGTCTCTGAGGATCCTGTAAGGGTTC<br>TGGCTACACCTTCACCAGTTACTGGATGTACTGGGTG<br>CGACAGGCTCGTGGACAACGCCTTGAGTGGATAGGTA<br>GGATTGATCCTAATAGTGGGAGTACTAAGTACAATGA<br>GAAGTTCAAGAACAGACTCACCATCTCCAAGGACACC<br>TCCAAAAACCAGGTGGTCCTTACAATGACCAACATGG<br>ACCCTGTGGACACAGCCACGTATTACTGTGCAAGGGA<br>CTATAGAAAGGGGCTCTATGCTATGGACTACTGGGGC<br>CAGGGCACCACCGTGACCGTGTCCTCCGCTTCCACCA<br>AGGGCCCATCCGTCTTCCCCCTGGCGCCCTGCTCCAG<br>GAGCACCTCCGAGAGCACAGCCGCCCTGGGCTGCCTG<br>GTCAAGGACTACTTCCCCGAACCGGTGACGGTGTCGT<br>GGAACTCAGGCGCCCTGACCAGCGGCGTGCACACCTT<br>CCCGGCTGTCCTACAGTCCTCAGGACTCTACTCCCTC<br>AGCAGCGTGGTGACCGTGCCCTCCAGCAGCTTGGGCA<br>CGAAGACCTACACCTGCAACGTAGATCACAAGCCCAG<br>CAACACCAAGGTGGACAAGAGAGTTGAGTCCAAATAT<br>GGTCCCCCATGCCCACCGTGCCCAGCACCTGAGTTCC<br>TGGGGGGACCATCAGTCTTCCTGTTCCCCCCAAAACC<br>CAAGGACACTCTCATGATCTCCCGGACCCCTGAGGTC<br>ACGTGCGTGGTGGTGGACGTGAGCCAGGAAGACCCCG<br>AGGTCCAGTTCAACTGGTACGTGGATGGCGTGGAGGT<br>GCATAATGCCAAGACAAAGCCGCGGGAGGAGCAGTTC<br>AACAGCACGTACCGTGTGGTCAGCGTCCTCACCGTCC<br>TGCACCAGGACTGGCTGAACGGCAAGGAGTACAAGTG<br>CAAGGTGTCCAACAAAGGCCTCCCGTCCTCCATCGAG<br>AAAACCATCTCCAAAGCCAAAGGGCAGCCCCGAGAGC<br>CACAGGTGTACACCCTGCCCCCATCCCAGGAGGAGAT<br>GACCAAGAACCAGGTCAGCCTGACCTGCCTGGTCAAA<br>GGCTTCTACCCCAGCGACATCGCCGTGGAGTGGGAGA<br>GCAATGGGCAGCCGGAGAACAACTACAAGACCACGCC<br>TCCCGTGCTGGACTCCGACGGCTCCTTCTTCCTCTAC<br>AGCAGGCTAACCGTGGACAAGAGCAGGTGGCAGGAGG<br>GGAATGTCTTCTCATGCTCCGTGATGCATGAGGCTCT<br>GCACAACCACTACACACAGAAGAGCCTCTCCCTGTCT<br>CTGGGTAAA |
|  | BAP058-hum17-LC |  |  |
| SEQ ID NO: 9 | (Kabat) | LCDR1 | KASQDVGTAVA |
| SEQ ID NO: 10 | (Kabat) | LCDR2 | WASTRHT |
| SEQ ID NO: 11 | (Kabat) | LCDR3 | QQYNSYPLT |
| SEQ ID NO: 12 | (Chothia) | LCDR1 | SQDVGTA |
| SEQ ID NO: 13 | (Chothia) | LCDR2 | WAS |
| SEQ ID NO: 14 | (Chothia) | LCDR3 | YNSYPL |
| SEQ ID NO: 86 |  | VL | EIVLTQSPDFQSVTPKEKVTITCKASQDVGTAVAWYQ<br>QKPGQAPRLLIYWASTRHTGVPSRFSGSGSGTEFTLT<br>ISSLQPDDFATYYCQQYNSYPLTFGQGTKVEIK |
| SEQ ID NO: 87 |  | DNA VL | GAAATTGTGCTGACTCAGTCTCCAGACTTTCAGTCTG<br>TGACTCCAAAGGAGAAAGTCACCATCACCTGCAAGGC<br>CAGTCAGGATGTGGGTACTGCTGTAGCCTGGTACCAG<br>CAGAAACCTGGCCAGGCTCCCAGGCTCCTCATCTATT<br>GGGCATCCACCCGGCACACTGGGGTCCCATCAAGGTT<br>CAGCGGCAGTGGATCTGGGACAGAATTCACTCTCACC<br>ATCAGCAGCCTGCAGCCTGATGATTTTGCAACTTATT<br>ACTGTCAGCAGTATAACAGCTATCCTCTCACGTTCGG<br>CCAAGGGACCAAGGTGGAAATCAAA |
| SEQ ID NO: 88 |  | Light<br>Chain | EIVLTQSPDFQSVTPKEKVTITCKASQDVGTAVAWYQ<br>QKPGQAPRLLIYWASTRHTGVPSRFSGSGSGTEFTLT |

TABLE 1 -continued

| | | |
|---|---|---|
| | | ISSLQPDDFATYYCQQYNSYPLTFGQGTKVEIKRTVA<br>APSVFIFPPSDEQLKSGTASVVCLLNNFYPREAKVQW<br>KVDNALQSGNSQESVTEQDSKDSTYSLSSTLTLSKAD<br>YEKHKVYACEVTHQGLSSPVTKSFNRGEC |
| SEQ ID NO: 89 | DNA Light Chain | GAAATTGTGCTGACTCAGTCTCCAGACTTTCAGTCTG<br>TGACTCCAAAGGAGAAAGTCACCATCACCTGCAAGGC<br>CAGTCAGGATGTGGGTACTGCTGTAGCCTGGTACCAG<br>CAGAAACCTGGCCAGGCTCCCAGGCTCCTCATCTATT<br>GGGCATCCACCCGGCACACTGGGGTCCCATCAAGGTT<br>CAGCGGCAGTGGATCTGGGACAGAATTCACTCTCACC<br>ATCAGCAGCCTGCAGCCTGATGATTTTGCAACTTATT<br>ACTGTCAGCAGTATAACAGCTATCCTCTCACGTTCGG<br>CCAAGGGACCAAGGTGGAAATCAAACGTACGGTGGCT<br>GCACCATCTGTCTTCATCTTCCCGCCATCTGATGAGC<br>AGTTGAAATCTGGAACTGCCTCTGTTGTGTGCCTGCT<br>GAATAACTTCTATCCCAGAGAGGCCAAAGTACAGTGG<br>AAGGTGGATAACGCCCTCCAATCGGGTAACTCCCAGG<br>AGAGTGTCACAGAGCAGGACAGCAAGGACAGCACCTA<br>CAGCCTCAGCAGCACCCTGACGCTGAGCAAAGCAGAC<br>TACGAGAAACACAAAGTCTACGCCTGCGAAGTCACCC<br>ATCAGGGCCTGAGCTCGCCCGTCACAAAGAGCTTCAA<br>CAGGGGAGAGTGT |
| BAP058-Clone K HC | | |
| SEQ ID NO: 1 (Kabat) | HCDR1 | SYWMY |
| SEQ ID NO: 2 (Kabat) | HCDR2 | RIDPNSGSTKYNEKFKN |
| SEQ ID NO: 3 (Kabat) | HCDR3 | DYRKGLYAMDY |
| SEQ ID NO: 4 (Chothia) | HCDR1 | GYTFTSY |
| SEQ ID NO: 5 (Chothia) | HCDR2 | DPNSGS |
| SEQ ID NO: 3 (Chothia) | HCDR3 | DYRKGLYAMDY |
| SEQ ID NO: 30 | VH | EVQLVQSGAEVKKPGATVKISCKVSGYTFTSYWMYWV<br>RQATGQGLEWMGRIDPNSGSTKYNEKFKNRVTITADK<br>STSTAYMELSSLRSEDTAVYYCARDYRKGLYAMDYWG<br>QGTTVTVSS |
| SEQ ID NO: 196 | DNA VH | GAAGTGCAGCTGGTGCAGTCTGGCGCCGAAGTGAAGA<br>AACCCGGCGCTACCGTGAAGATCTCCTGCAAGGTGTC<br>CGGCTACACCTTCACCAGCTACTGGATGTACTGGGTG<br>CGACAGGCTACCGGCCAGGGCCTGGAATGGATGGGCA<br>GAATCGACCCCAACTCCGGCTCCACCAAGTACAACGA<br>GAAGTTCAAGAACCGCGTGACCATCACCGCCGACAAG<br>TCCACCTCCACCGCCTACATGGAACTGTCCTCCCTGC<br>GGAGCGAGGACACCGCCGTGTACTACTGCGCCAGAGA<br>CTACCGGAAGGGCCTGTACGCCATGGACTATTGGGGC<br>CAGGGCACCACCGTGACCGTGTCCTCT |
| SEQ ID NO: 197 | Heavy Chain | EVQLVQSGAEVKKPGATVKISCKVSGYTFTSYWMYWV<br>RQATGQGLEWMGRIDPNSGSTKYNEKFKNRVTITADK<br>STSTAYMELSSLRSEDTAVYYCARDYRKGLYAMDYWG<br>QGTTVTVSSASTKGPSVFPLAPCSRSTSESTAALGCL<br>VKDYFPEPVTVSWNSGALTSGVHTFPAVLQSSGLYSL<br>SSVVTVPSSSLGTKTYTCNVDHKPSNTKVDKRVESKY<br>GPPCPPCPAPEFLGGPSVFLFPPKPKDTLMISRTPEV<br>TCVVVDVSQEDPEVQFNWYVDGVEVHNAKTKPREEQF<br>NSTYRVVSVLTVLHQDWLNGKEYKCKVSNKGLPSSIE<br>KTISKAKGQPREPQVYTLPPSQEEMTKNQVSLTCLVK<br>GFYPSDIAVEWESNGQPENNYKTTPPVLDSDGSFFLY<br>SRLTVDKSRWQEGNVFSCSVMHEALHNHYTQKSLSLS<br>LG |
| SEQ ID NO: 198 | DNA Heavy Chain | GAAGTGCAGCTGGTGCAGTCTGGCGCCGAAGTGAAGA<br>AACCCGGCGCTACCGTGAAGATCTCCTGCAAGGTGTC<br>CGGCTACACCTTCACCAGCTACTGGATGTACTGGGTG<br>CGACAGGCTACCGGCCAGGGCCTGGAATGGATGGGCA<br>GAATCGACCCCAACTCCGGCTCCACCAAGTACAACGA<br>GAAGTTCAAGAACCGCGTGACCATCACCGCCGACAAG<br>TCCACCTCCACCGCCTACATGGAACTGTCCTCCCTGC<br>GGAGCGAGGACACCGCCGTGTACTACTGCGCCAGAGA<br>CTACCGGAAGGGCCTGTACGCCATGGACTATTGGGGC<br>CAGGGCACCACCGTGACCGTGTCCTCTGCTTCCACCA<br>AGGGCCCAAGCGTGTTCCCCCTGGCCCCCTGCTCCAG<br>AAGCACCAGCGAGAGCACAGCCGCCCTGGGCTGCCTG |

TABLE 1 -continued

|  |  |  |
|---|---|---|
|  |  | GTGAAGGACTACTTCCCCGAGCCCGTGACCGTGTCCT<br>GGAACAGCGGAGCCCTGACCAGCGGCGTGCACACCTT<br>CCCCGCCGTGCTGCAGAGCAGCGGCCTGTACAGCCTG<br>AGCAGCGTGGTGACCGTGCCCAGCAGCAGCCTGGGCA<br>CCAAGACCTACACCTGTAACGTGGACCACAAGCCCAG<br>CAACACCAAGGTGGACAAGAGGGTGGAGAGCAAGTAC<br>GGCCCACCCTGCCCCCCTGCCCAGCCCCCGAGTTCC<br>TGGGCGGACCCAGCGTGTTCCTGTTCCCCCCCAAGCC<br>CAAGGACACCCTGATGATCAGCAGAACCCCCGAGGTG<br>ACCTGTGTGGTGGTGGACGTGTCCCAGGAGGACCCCG<br>AGGTCCAGTTCAACTGGTACGTGGACGGCGTGGAGGT<br>GCACAACGCCAAGACCAAGCCCAGAGAGGAGCAGTTT<br>AACAGCACCTACCGGGTGGTGTCCGTGCTGACCGTGC<br>TGCACCAGGACTGGCTGAACGGCAAAGAGTACAAGTG<br>TAAGGTCTCCAACAAGGGCCTGCCAAGCAGCATCGAA<br>AAGACCATCAGCAAGGCCAAGGGCCAGCCTAGAGAGC<br>CCCAGGTCTACACCCTGCCACCCAGCCAAGAGGAGAT<br>GACCAAGAACCAGGTGTCCCTGACCTGTCTGGTGAAG<br>GGCTTCTACCCAAGCGACATCGCCGTGGAGTGGGAGA<br>GCAACGGCCAGCCCGAGAACAACTACAAGACCACCCC<br>CCCAGTGCTGGACAGCGACGGCAGCTTCTTCCTGTAC<br>AGCAGGCTGACCGTGGACAAGTCCAGATGGCAGGAGG<br>GCAACGTCTTTAGCTGCTCCGTGATGCACGAGGCCCT<br>GCACAACCACTACACCCAGAAGAGCCTGAGCCTGTCC<br>CTGGGCTGATGAATTC |
|  | BAP058-Clone K LC |  |
| SEQ ID NO: 9 (Kabat) | LCDR1 | KASQDVGTAVA |
| SEQ ID NO: 10 (Kabat) | LCDR2 | WASTRHT |
| SEQ ID NO: 11 (Kabat) | LCDR3 | QQYNSYPLT |
| SEQ ID NO: 12 (Chothia) | LCDR1 | SQDVGTA |
| SEQ ID NO: 13 (Chothia) | LCDR2 | WAS |
| SEQ ID NO: 14 (Chothia) | LCDR3 | YNSYPL |
| SEQ ID NO: 34 | VL | EIVLTQSPDFQSVTPKEKVTITCKASQDVGTAVAWYL<br>QKPGQSPQLLIYWASTRHTGVPDRFSGSGSGTDFTLK<br>ISRVEAEDVGVYYCQQYNSYPLTFGQGTKVEIK |
| SEQ ID NO: 199 | DNA VL | GAGATCGTGCTGACCCAGTCCCCCGACTTCCAGTCCG<br>TGACCCCAAAGAAAAAGTGACCATCACATGCAAGGC<br>CTCCCAGGACGTGGGCACCGCCGTGGCTTGGTATCTG<br>CAGAAGCCTGGCCAGTCCCCTCAGCTGCTGATCTACT<br>GGGCCTCTACCAGACACACCGGCGTGCCCGACAGATT<br>CTCCGGCTCTGGCTCTGGCACCGACTTCACCCTGAAG<br>ATCTCCCGGGTGGAAGCCGAGGATGTGGGCGTGTACT<br>ACTGCCAGCAGTACAACTCCTACCCCCTGACCTTCGG<br>CCAGGGCACCAAGGTGGAAATCAAG |
| SEQ ID NO: 36 | Light Chain | EIVLTQSPDFQSVTPKEKVTITCKASQDVGTAVAWYL<br>QKPGQSPQLLIYWASTRHTGVPDRFSGSGSGTDFTLK<br>ISRVEAEDVGVYYCQQYNSYPLTFGQGTKVEIKRTVA<br>APSVFIFPPSDEQLKSGTASVVCLLNNFYPREAKVQW<br>KVDNALQSGNSQESVTEQDSKDSTYSLSSTLTLSKAD<br>YEKHKVYACEVTHQGLSSPVTKSFNRGEC |
| SEQ ID NO: 200 | DNA Light Chain | GAGATCGTGCTGACCCAGTCCCCCGACTTCCAGTCCG<br>TGACCCCAAAGAAAAAGTGACCATCACATGCAAGGC<br>CTCCCAGGACGTGGGCACCGCCGTGGCTTGGTATCTG<br>CAGAAGCCTGGCCAGTCCCCTCAGCTGCTGATCTACT<br>GGGCCTCTACCAGACACACCGGCGTGCCCGACAGATT<br>CTCCGGCTCTGGCTCTGGCACCGACTTCACCCTGAAG<br>ATCTCCCGGGTGGAAGCCGAGGATGTGGGCGTGTACT<br>ACTGCCAGCAGTACAACTCCTACCCCCTGACCTTCGG<br>CCAGGGCACCAAGGTGGAAATCAAGCGTACGGTGGCC<br>GCTCCCAGCGTGTTCATCTTCCCCCCAAGCGACGAGC<br>AGCTGAAGAGCGGCACCGCCAGCGTGGTGTGTCTGCT<br>GAACAACTTCTACCCCAGGGAGGCCAAGGTGCAGTGG<br>AAGGTGGACAACGCCCTGCAGAGCGGCAACAGCCAGG<br>AGAGCGTCACCGAGCAGGACAGCAAGGACTCCACCTA<br>CAGCCTGAGCAGCACCCTGACCCTGAGCAAGGCCGAC<br>TACGAGAAGCACAAGGTGTACGCCTGTGAGGTGACCC<br>ACCAGGGCCTGTCCAGCCCCGTGACCAAGAGCTTCAA<br>CAGGGGCGAGTGCTGATGAATTC |

TABLE 1 -continued

BAP058-Clone L HC

| | | |
|---|---|---|
| SEQ ID NO: 1 (Kabat) | HCDR1 | SYWMY |
| SEQ ID NO: 2 (Kabat) | HCDR2 | RIDPNSGSTKYNEKFKN |
| SEQ ID NO: 3 (Kabat) | HCDR3 | DYRKGLYAMDY |
| SEQ ID NO: 4 (Chothia) | HCDR1 | GYTFTSY |
| SEQ ID NO: 5 (Chothia) | HCDR2 | DPNSGS |
| SEQ ID NO: 3 (Chothia) | HCDR3 | DYRKGLYAMDY |
| SEQ ID NO: 38 | VH | EVQLVQSGAEVKKPGESLRISCKGSGYTFTSYWMYWV RQAPGQGLEWMGRIDPNSGSTKYNEKFKNRVTISVDT SKNQFSLKLSSVTAADTAVYYCARDYRKGLYAMDYWG QGTTVTVSS |
| SEQ ID NO: 90 | DNA VH | GAAGTGCAGCTGGTGCAGTCAGGCGCCGAAGTGAAGA AGCCCGGCGAGTCACTGAGAATTAGCTGTAAAGGTTC AGGCTACACCTTCACTAGCTACTGGATGTACTGGGTC CGACAGGCCCCAGGGCAAGGCCTGGAGTGGATGGGTA GAATCGACCCTAATAGCGGCTCTACTAAGTATAACGA GAAGTTTAAGAATAGAGTGACTATTAGCGTGGACACC TCTAAGAATCAGTTTAGCCTGAAGCTGTCTAGCGTGA CCGCCGCTGACACCGCCGTCTACTACTGCGCTAGAGA CTATAGAAAGGGCCTGTACGCTATGGACTACTGGGGT CAAGGCACTACCGTGACCGTGTCTTCA |
| SEQ ID NO: 91 | Heavy Chain | EVQLVQSGAEVKKPGESLRISCKGSGYTFTSYWMYWV RQAPGQGLEWMGRIDPNSGSTKYNEKFKNRVTISVDT SKNQFSLKLSSVTAADTAVYYCARDYRKGLYAMDYWG QGTTVTVSSASTKGPSVFPLAPCSRSTSESTAALGCL VKDYFPEPVTVSWNSGALTSGVHTFPAVLQSSGLYSL SSVVTVPSSSLGTKTYTCNVDHKPSNTKVDKRVESKY GPPCPPCPAPEFLGGPSVFLFPPKPKDTLMISRTPEV TCVVVDVSQEDPEVQFNWYVDGVEVHNAKTKPREEQF NSTYRVVSVLTVLHQDWLNGKEYKCKVSNKGLPSSIE KTISKAKGQPREPQVYTLPPSQEEMTKNQVSLTCLVK GFYPSDIAVEWESNGQPENNYKTTPPVLDSDGSFFLY SRLTVDKSRWQEGNVFSCSVMHEALHNHYTQKSLSLS LG |
| SEQ ID NO: 92 | DNA Heavy Chain | GAAGTGCAGCTGGTGCAGTCAGGCGCCGAAGTGAAGA AGCCCGGCGAGTCACTGAGAATTAGCTGTAAAGGTTC AGGCTACACCTTCACTAGCTACTGGATGTACTGGGTC CGACAGGCCCCAGGGCAAGGCCTGGAGTGGATGGGTA GAATCGACCCTAATAGCGGCTCTACTAAGTATAACGA GAAGTTTAAGAATAGAGTGACTATTAGCGTGGACACC TCTAAGAATCAGTTTAGCCTGAAGCTGTCTAGCGTGA CCGCCGCTGACACCGCCGTCTACTACTGCGCTAGAGA CTATAGAAAGGGCCTGTACGCTATGGACTACTGGGGT CAAGGCACTACCGTGACCGTGTCTTCAGCTAGCACTA AGGGCCCGTCCGTGTTCCCCCTGGCACCTTGTAGCCG GAGCACTAGCGAATCCACCGCTGCCCTCGGCTGCCTG GTCAAGGATTACTTCCCGGAGCCCGTGACCGTGTCCT GGAACAGCGGAGCCCTGACCTCCGGAGTGCACACCTT CCCCGCTGTGCTGCAGAGCTCCGGGCTGTACTCGCTG TCGTCGGTGGTCACGGTGCCTTCATCTAGCCTGGGTA CCAAGACCTACACTTGCAACGTGGACCACAAGCCTTC CAACACTAAGGTGGACAAGCGCGTCGAATCGAAGTAC GGCCCACCGTGCCCGCCTTGTCCCGCGCCGGAGTTCC TCGGCGGTCCCTCGGTCTTTCTGTTCCCACCGAAGCC CAAGGACACTTTGATGATTTCCCGCACCCCTGAAGTG ACATGCGTGGTCGTGGACGTGTCACAGGAAGATCCGG AGGTGCAGTTCAATTGGTACGTGGATGGCGTCGAGGT GCACAACGCCAAAACCAAGCCGAGGGAGGAGCAGTTC AACTCCACTTACCGCGTCGTGTCCGTGCTGACGGTGC TGCATCAGGACTGGCTGAACGGGAAGGAGTACAAGTG CAAAGTGTCCAACAAGGGACTTCCTAGCTCAATCGAA AAGACCATCTCGAAAGCCAAGGGACAGCCCCGGGAAC CCCAAGTGTATACCCTGCCACCGAGCCAGGAAGAAAT GACTAAGAACCAAGTCTCATTGACTTGCCTTGTGAAG GGCTTCTACCCATCGGATATCGCCGTGGAATGGGAGT CCAACGGCCAGCCGGAAAACAACTACAAGACCACCCC TCCCGTGCTGGACTCAGACGGATCCTTCTTCCTCTAC TCGCGGCTGACCGTGGATAAGAGCAGATGGCAGGAGG GAAATGTGTTCAGCTGTTCTGTGATGCATGAAGCCCT |

TABLE 1 -continued

| | | | |
|---|---|---|---|
| | | | GCACAACCACTACACTCAGAAGTCCCTGTCCCTCTCC CTGGGA |

| BAP058-Clone L LC | | | |
|---|---|---|---|
| SEQ ID NO: 9 (Kabat) | LCDR1 | | KASQDVGTAVA |
| SEQ ID NO: 10 (Kabat) | LCDR2 | | WASTRHT |
| SEQ ID NO: 11 (Kabat) | LCDR3 | | QQYNSYPLT |
| SEQ ID NO: 12 (Chothia) | LCDR1 | | SQDVGTA |
| SEQ ID NO: 13 (Chothia) | LCDR2 | | WAS |
| SEQ ID NO: 14 (Chothia) | LCDR3 | | YNSYPL |
| SEQ ID NO: 42 | | VL | EIVLTQSPDFQSVTPKEKVTITCKASQDVGTAVAWYL QKPGQSPQLLIYWASTRHTGVPSRFSGSGSGTDFTFT ISSLQPEDIATYYCQQYNSYPLTFGQGTKVEIK |
| SEQ ID NO: 93 | | DNA VL | GAGATCGTCCTGACTCAGTCACCCGACTTTCAGTCAG TGACCCCTAAAGAGAAAGTCACTATCACCTGTAAAGC CTCTCAGGACGTGGGCACCGCCGTGGCCTGGTATCTG CAGAAGCCTGGTCAATCACCTCAGCTGCTGATCTACT GGGCCTCTACTAGACACACCGGCGTGCCCTCTAGGTT TAGCGGTAGCGGTAGTGGCACCGACTTCACCTTCACT ATCTCTTCACTGCAGCCCGAGGATATCGCTACCTACT ACTGTCAGCAGTATAATAGCTACCCCCTGACCTTCGG TCAAGGCACTAAGGTCGAGATTAAG |
| SEQ ID NO: 44 | | Light Chain | EIVLTQSPDFQSVTPKEKVTITCKASQDVGTAVAWYL QKPGQSPQLLIYWASTRHTGVPSRFSGSGSGTDFTFT ISSLQPEDIATYYCQQYNSYPLTFGQGTKVEIKRTVA APSVFIFPPSDEQLKSGTASVVCLLNNFYPREAKVQW KVDNALQSGNSQESVTEQDSKDSTYSLSSTLTLSKAD YEKHKVYACEVTHQGLSSPVTKSFNRGEC |
| SEQ ID NO: 94 | | DNA Light Chain | GAGATCGTCCTGACTCAGTCACCCGACTTTCAGTCAG TGACCCCTAAAGAGAAAGTCACTATCACCTGTAAAGC CTCTCAGGACGTGGGCACCGCCGTGGCCTGGTATCTG CAGAAGCCTGGTCAATCACCTCAGCTGCTGATCTACT GGGCCTCTACTAGACACACCGGCGTGCCCTCTAGGTT TAGCGGTAGCGGTAGTGGCACCGACTTCACCTTCACT ATCTCTTCACTGCAGCCCGAGGATATCGCTACCTACT ACTGTCAGCAGTATAATAGCTACCCCCTGACCTTCGG TCAAGGCACTAAGGTCGAGATTAAGCGTACGGTGGCC GCTCCCAGCGTGTTCATCTTCCCCCCCAGCGACGAGC AGCTGAAGAGCGGCACCGCCAGCGTGGTGTGCCTGCT GAACAACTTCTACCCCCGGGAGGCCAAGGTGCAGTGG AAGGTGGACAACGCCCTGCAGAGCGGCAACAGCCAGG AGAGCGTCACCGAGCAGGACAGCAAGGACTCCACCTA CAGCCTGAGCAGCACCCTGACCCTGAGCAAGGCCGAC TACGAGAAGCATAAGGTGTACGCCTGCGAGGTGACCC ACCAGGGCCTGTCCAGCCCCGTGACCAAGAGCTTCAA CAGGGGCGAGTGC |

| BAP058-Clone M HC | | | |
|---|---|---|---|
| SEQ ID NO: 1 (Kabat) | HCDR1 | | SYWMY |
| SEQ ID NO: 2 (Kabat) | HCDR2 | | RIDPNSGSTKYNEKFKN |
| SEQ ID NO: 3 (Kabat) | HCDR3 | | DYRKGLYAMDY |
| SEQ ID NO: 4 (Chothia) | HCDR1 | | GYTFTSY |
| SEQ ID NO: 5 (Chothia) | HCDR2 | | DPNSGS |
| SEQ ID NO: 3 (Chothia) | HCDR3 | | DYRKGLYAMDY |
| SEQ ID NO: 50 | | VH | EVQLVQSGAEVKKPGESLRISCKGSYTFTSYWMYWI RQPPGKGLEWIGRIDPNSGSTKYNEKFKNRVTITADK STSTAYMELSSLRSEDTAVYYCARDYRKGLYAMDYWG QGTTVTVSS |
| SEQ ID NO: 201 | | DNA VH | GAAGTGCAGCTGGTGCAGTCTGGCGCCGAAGTGAAGA AGCCTGGCGAGTCCCTGCGGATCTCCTGCAAGGGCTC CGGCTACACCTTCACCAGCTACTGGATGTACTGGATC CGGCAGCCCCCTGGCAAGGGCCTGGAATGGATCGGCA |

TABLE 1 -continued

|  |  |  |
|---|---|---|
|  |  | GAATCGACCCCAACTCCGGCTCCACCAAGTACAACGA<br>GAAGTTCAAGAACCGCGTGACCATCACCGCCGACAAG<br>TCCACCTCCACCGCCTACATGGAACTGTCCTCCCTGA<br>GATCCGAGGACACCGCCGTGTACTACTGCGCCAGAGA<br>CTACCGGAAGGGCCTGTACGCCATGGACTATTGGGGC<br>CAGGGCACCACCGTGACCGTGTCCTCT |
| SEQ ID NO: 260 | Heavy<br>Chain | EVQLVQSGAEVKKPGESLRISCKGSGYTFTSYWMYWI<br>RQPPGKGLEWIGRIDPNSGSTKYNEKFKNRVTITADK<br>STSTAYMELSSLRSEDTAVYYCARDYRKGLYAMDYWG<br>QGTTVTVSSASTKGPSVFPLAPCSRSTSESTAALGCL<br>VKDYFPEPVTVSWNSGALTSGVHTFPAVLQSSGLYSL<br>SSVVTVPSSSLGTKTYTCNVDHKPSNTKVDKRVESKY<br>GPPCPPCPAPEFLGGPSVFLFPPKPKDTLMISRTPEV<br>TCVVVDVSQEDPEVQFNWYVDGVEVHNAKTKPREEQF<br>NSTYRVVSVLTVLHQDWLNGKEYKCKVSNKGLPSSIE<br>KTISKAKGQPREPQVYTLPPSQEEMTKNQVSLTCLVK<br>GFYPSDIAVEWESNGQPENNYKTTPPVLDSDGSFFLY<br>SRLTVDKSRWQEGNVFSCSVMHEALHNHYTQKSLSLS<br>LG |
| SEQ ID NO: 202 | DNA Heavy<br>Chain | GAAGTGCAGCTGGTGCAGTCTGGCGCCGAAGTGAAGA<br>AGCCTGGCGAGTCCCTGCGGATCTCCTGCAAGGGCTC<br>CGGCTACACCTTCACCAGCTACTGGATGTACTGGATC<br>CGGCAGCCCCCTGGCAAGGGCCTGGAATGGATCGGCA<br>GAATCGACCCCAACTCCGGCTCCACCAAGTACAACGA<br>GAAGTTCAAGAACCGCGTGACCATCACCGCCGACAAG<br>TCCACCTCCACCGCCTACATGGAACTGTCCTCCCTGA<br>GATCCGAGGACACCGCCGTGTACTACTGCGCCAGAGA<br>CTACCGGAAGGGCCTGTACGCCATGGACTATTGGGGC<br>CAGGGCACCACCGTGACCGTGTCCTCTGCTTCTACCA<br>AGGGCCCAAGCGTGTTCCCCCTGGCCCCCTGCTCCAG<br>AAGCACCAGCGAGAGCACAGCCGCCCTGGGCTGCCTG<br>GTGAAGGACTACTTCCCCGAGCCCGTGACCGTGTCCT<br>GGAACAGCGGAGCCCTGACCAGCGGCGTGCACACCTT<br>CCCCGCCGTGCTGCAGAGCAGCGGCCTGTACAGCCTG<br>AGCAGCGTGGTGACCGTGCCCAGCAGCAGCCTGGGCA<br>CCAAGACCTACACCTGTAACGTGGACCACAAGCCCAG<br>CAACACCAAGGTGGACAAGAGGGTGGAGAGCAAGTAC<br>GGCCCCACCCTGCCCCCCCTGCCCAGCCCCCGAGTTCC<br>TGGGCGGACCCAGCGTGTTCCTGTTCCCCCCCAAGCC<br>CAAGGACACCCTGATGATCAGCAGAACCCCCGAGGTG<br>ACCTGTGTGGTGGTGGACGTGTCCCAGGAGGACCCCG<br>AGGTCCAGTTCAACTGGTACGTGGACGGCGTGGAGGT<br>GCACAACGCCAAGACCAAGCCCAGAGAGGAGCAGTTT<br>AACAGCACCTACCGGGTGGTGTCCGTGCTGACCGTGC<br>TGCACCAGGACTGGCTGAACGGCAAAGAGTACAAGTG<br>TAAGGTCTCCAACAAGGGCCTGCCAAGCAGCATCGAA<br>AAGACCATCAGCAAGGCCAAGGGCCAGCCTAGAGAGC<br>CCCAGGTCTACACCCTGCCCACCCAGCCAAGAGGAGAT<br>GACCAAGAACCAGGTGTCCCTGACCTGTCTGGTGAAG<br>GGCTTCTACCCAAGCGACATCGCCGTGGAGTGGGAGA<br>GCAACGGCCAGCCCGAGAACAACTACAAGACCACCCC<br>CCCAGTGCTGGACAGCGACGGCAGCTTCTTCCTGTAC<br>AGCAGGCTGACCGTGGACAAGTCCAGATGGCAGGAGG<br>GCAACGTCTTTAGCTGCTCCGTGATGCACGAGGCCCT<br>GCACAACCACTACACCCAGAAGAGCCTGAGCCTGTCC<br>CTGGGCTGATGAATTC |

| BAP058-Clone M LC |
|---|

| SEQ ID NO: 9 (Kabat) | LCDR1 | KASQDVGTAVA |
| SEQ ID NO: 10 (Kabat) | LCDR2 | WASTRHT |
| SEQ ID NO: 11 (Kabat) | LCDR3 | QQYNSYPLT |
| SEQ ID NO: 12 (Chothia) | LCDR1 | SQDVGTA |
| SEQ ID NO: 13 (Chothia) | LCDR2 | WAS |
| SEQ ID NO: 14 (Chothia) | LCDR3 | YNSYPL |
| SEQ ID NO: 42 | VL | EIVLTQSPDFQSVTPKEKVTITCKASQDVGTAVAWYL<br>QKPGQSPQLLIYWASTRHTGVPSRFSGSGSGTDFTFT<br>ISSLQPEDIATYYCQQYNSYPLTFGQGTKVEIK |
| SEQ ID NO: 203 | DNA VL | GAGATCGTGCTGACCCAGTCCCCCGACTTCCAGTCCG<br>TGACCCCCAAAGAAAAAGTGACCATCACATGCAAGGC<br>CTCCCAGGACGTGGGCACCGCCGTGGCTTGGTATCTG |

TABLE 1 -continued

| | | |
|---|---|---|
| | | CAGAAGCCTGGCCAGTCCCCTCAGCTGCTGATCTACT GGGCCTCTACCAGACACACCGGCGTGCCCTCCAGATT CTCCGGCTCTGGCTCTGGCACCGACTTTACCTTCACC ATCTCCAGCCTGCAGCCCGAGGATATCGCCACCTACT ACTGCCAGCAGTACAACTCCTACCCCCTGACCTTCGG CCAGGGCACCAAGGTGGAAATCAAG |
| SEQ ID NO: 44 | Light Chain | EIVLTQSPDFQSVTPKEKVTITCKASQDVGTAVAWYL QKPGQSPQLLIYWASTRHTGVPSRFSGSGSGTDFTFT ISSLQPEDIATYYCQQYNSYPLTFGQGTKVEIKRTVA APSVFIFPPSDEQLKSGTASVVCLLNNFYPREAKVQW KVDNALQSGNSQESVTEQDSKDSTYSLSSTLTLSKAD YEKHKVYACEVTHQGLSSPVTKSFNRGEC |
| SEQ ID NO: 204 | DNA Light Chain | GAGATCGTGCTGACCCAGTCCCCCGACTTCCAGTCCG TGACCCCCAAAGAAAAAGTGACCATCACATGCAAGGC CTCCCAGGACGTGGGCACCGCCGTGGCTTGGTATCTG CAGAAGCCTGGCCAGTCCCCTCAGCTGCTGATCTACT GGGCCTCTACCAGACACACCGGCGTGCCCTCCAGATT CTCCGGCTCTGGCTCTGGCACCGACTTTACCTTCACC ATCTCCAGCCTGCAGCCCGAGGATATCGCCACCTACT ACTGCCAGCAGTACAACTCCTACCCCCTGACCTTCGG CCAGGGCACCAAGGTGGAAATCAAGCGTACGGTGGCC GCTCCCAGCGTGTTCATCTTCCCCCCAAGCGACGAGC AGCTGAAGAGCGGCACCGCCAGCGTGGTGTGTCTGCT GAACAACTTCTACCCCAGGGAGGCCAAGGTGCAGTGG AAGGTGGACAACGCCCTGCAGAGCGGCAACAGCCAGG AGAGCGTCACCGAGCAGGACAGCAAGGACTCCACCTA CAGCCTGAGCAGCACCCTGACCCTGAGCAAGGCCGAC TACGAGAAGCACAAGGTGTACGCCTGTGAGGTGACCC ACCAGGGCCTGTCCAGCCCCGTGACCAAGAGCTTCAA CAGGGGCGAGTGCTGATGAATTC |
| BAP058-Clone N HC | | |
| SEQ ID NO: 1 (Kabat) | HCDR1 | SYWMY |
| SEQ ID NO: 2 (Kabat) | HCDR2 | RIDPNSGSTKYNEKFKN |
| SEQ ID NO: 3 (Kabat) | HCDR3 | DYRKGLYAMDY |
| SEQ ID NO: 4 (Chothia) | HCDR1 | GYTFTSY |
| SEQ ID NO: 5 (Chothia) | HCDR2 | DPNSGS |
| SEQ ID NO: 3 (Chothia) | HCDR3 | DYRKGLYAMDY |
| SEQ ID NO: 30 | VH | EVQLVQSGAEVKKPGATVKISCKVSGYTFTSYWMYWV RQATGQGLEWMGRIDPNSGSTKYNEKFKNRVTITADK STSTAYMELSSLRSEDTAVYYCARDYRKGLYAMDYWG QGTTVTVSS |
| SEQ ID NO: 95 | DNA VH | GAAGTGCAGCTGGTGCAGTCAGGCGCCGAAGTGAAGA AACCCGGCGCTACCGTGAAGATTAGCTGTAAAGTCTC AGGCTACACCTTCACTAGCTACTGGATGTACTGGGTC CGACAGGCTACCGGTCAAGGCCTGGAGTGGATGGGTA GAATCGACCCTAATAGCGGCTCTACTAAGTATAACGA GAAGTTTAAGAATAGAGTGACTATCACCGCCGATAAG TCTACTAGCACCGCCTATATGGAACTGTCTAGCCTGA GATCAGAGGACACCGCCGTCTACTACTGCGCTAGAGA CTATAGAAAGGGCCTGTACGCTATGGACTACTGGGGT CAAGGCACTACCGTGACCGTGTCTTCA |
| SEQ ID NO: 96 | Heavy Chain | EVQLVQSGAEVKKPGATVKISCKVSGYTFTSYWMYWV RQATGQGLEWMGRIDPNSGSTKYNEKFKNRVTITADK STSTAYMELSSLRSEDTAVYYCARDYRKGLYAMDYWG QGTTVTVSSASTKGPSVFPLAPCSRSTSESTAALGCL VKDYFPEPVTVSWNSGALTSGVHTFPAVLQSSGLYSL SSVVTVPSSSLGTKTYTCNVDHKPSNTKVDKRVESKY GPPCPPCPAPEFLGGPSVFLFPPKPKDTLMISRTPEV TCVVVDVSQEDPEVQFNWYVDGVEVHNAKTKPREEQF NSTYRVVSVLTVLHQDWLNGKEYKCKVSNKGLPSSIE KTISKAKGQPREPQVYTLPPSQEEMTKNQVSLTCLVK GFYPSDIAVEWESNGQPENNYKTTPPVLDSDGSFFLY SRLTVDKSRWQEGNVFSCSVMHEALHNHYTQKSLSLS LG |
| SEQ ID NO: 97 | DNA Heavy Chain | GAAGTGCAGCTGGTGCAGTCAGGCGCCGAAGTGAAGA AACCCGGCGCTACCGTGAAGATTAGCTGTAAAGTCTC AGGCTACACCTTCACTAGCTACTGGATGTACTGGGTC |

TABLE 1 -continued

CGACAGGCTACCGGTCAAGGCCTGGAGTGGATGGGTA
GAATCGACCCTAATAGCGGCTCTACTAAGTATAACGA
GAAGTTTAAGAATAGAGTGACTATCACCGCCGATAAG
TCTACTAGCACCGCCTATATGGAACTGTCTAGCCTGA
GATCAGAGGACACCGCCGTCTACTACTGCGCTAGAGA
CTATAGAAAGGGCCTGTACGCTATGGACTACTGGGGT
CAAGGCACTACCGTGACCGTGTCTTCAGCTAGCACTA
AGGGCCCGTCCGTGTTCCCCCTGGCACCTTGTAGCCG
GAGCACTAGCGAATCCACCGCTGCCCTCGGCTGCCTG
GTCAAGGATTACTTCCCGGAGCCCGTGACCGTGTCCT
GGAACAGCGGAGCCCTGACCTCCGGAGTGCACACCTT
CCCCGCTGTGCTGCAGAGCTCCGGGCTGTACTCGCTG
TCGTCGGTGGTCACGGTGCCTTCATCTAGCCTGGGTA
CCAAGACCTACACTTGCAACGTGGACCACAAGCCTTC
CAACACTAAGGTGGACAAGCGCGTCGAATCGAAGTAC
GGCCCACCGTGCCCGCCTTGTCCCGCGCCGGAGTTCC
TCGGCGGTCCCTCGGTCTTTCTGTTCCCACCGAAGCC
CAAGGACACTTTGATGATTTCCCGCACCCCTGAAGTG
ACATGCGTGGTCGTGGACGTGTCACAGGAAGATCCGG
AGGTGCAGTTCAATTGGTACGTGGATGGCGTCGAGGT
GCACAACGCCAAAACCAAGCCGAGGGAGGAGCAGTTC
AACTCCACTTACCGCGTCGTGTCCGTGCTGACGGTGC
TGCATCAGGACTGGCTGAACGGGAAGGAGTACAAGTG
CAAAGTGTCCAACAAGGGACTTCCTAGCTCAATCGAA
AAGACCATCTCGAAAGCCAAGGGACAGCCCCGGGAAC
CCCAAGTGTATACCCTGCCACCGAGCCAGGAAGAAAT
GACTAAGAACCAAGTCTCATTGACTTGCCTTGTGAAG
GGCTTCTACCCATCGGATATCGCCGTGGAATGGGAGT
CCAACGGCCAGCCGGAAAACAACTACAAGACCACCCC
TCCGGTGCTGGACTCAGACGGATCCTTCTTCCTCTAC
TCGCGGCTGACCGTGGATAAGAGCAGATGGCAGGAGG
GAAATGTGTTCAGCTGTTCTGTGATGCATGAAGCCCT
GCACAACCACTACACTCAGAAGTCCCTGTCCCTCTCC
CTGGGA

| BAP058-Clone N LC | | |
|---|---|---|
| SEQ ID NO: 9 (Kabat) | LCDR1 | KASQDVGTAVA |
| SEQ ID NO: 10 (Kabat) | LCDR2 | WASTRHT |
| SEQ ID NO: 11 Kabat) | LCDR3 | QQYNSYPLT |
| SEQ ID NO: 12 (Chothia) | LCDR1 | SQDVGTA |
| SEQ ID NO: 13 (Chothia) | LCDR2 | WAS |
| SEQ ID NO: 14 (Chothia) | LCDR3 | YNSYPL |
| SEQ ID NO: 66 | VL | DVVMTQSPLSLPVTLGQPASISCKASQDVGTAVAWYQ QKPGQAPRLLIYWASTRHTGVPSRFSGSGSGTEFTLT ISSLQPDDFATYYCQQYNSYPLTFGQGTKVEIK |
| SEQ ID NO: 98 | DNA VL | GACGTCGTGATGACTCAGTCACCCCTGAGCCTGCCCG TGACCCTGGGGCAGCCCGCCTCTATTAGCTGTAAAGC CTCTCAGGACGTGGGCACCGCCGTGGCCTGGTATCAG CAGAAGCCAGGGCAAGCCCCTAGACTGCTGATCTACT GGGCCTCTACTAGACACACCGGCGTGCCCTCTAGGTT TAGCGGTAGCGGTAGTGGCACCGAGTTCACCCTGACT ATCTCTTCACTGCAGCCCGACGACTTCGCTACCTACT ACTGTCAGCAGTATAATAGCTACCCCCTGACCTTCGG TCAAGGCACTAAGGTCGAGATTAAG |
| SEQ ID NO: 68 | Light Chain | DVVMTQSPLSLPVTLGQPASISCKASQDVGTAVAWYQ QKPGQAPRLLIYWASTRHTGVPSRFSGSGSGTEFTLT ISSLQPDDFATYYCQQYNSYPLTFGQGTKVEIKRTVA APSVFIFPPSDEQLKSGTASVVCLLNNFYPREAKVQW KVDNALQSGNSQESVTEQDSKDSTYSLSSTLTLSKAD YEKHKVYACEVTHQGLSSPVTKSFNRGEC |
| SEQ ID NO: 99 | DNA Light Chain | GACGTCGTGATGACTCAGTCACCCCTGAGCCTGCCCG TGACCCTGGGGCAGCCCGCCTCTATTAGCTGTAAAGC CTCTCAGGACGTGGGCACCGCCGTGGCCTGGTATCAG CAGAAGCCAGGGCAAGCCCCTAGACTGCTGATCTACT GGGCCTCTACTAGACACACCGGCGTGCCCTCTAGGTT TAGCGGTAGCGGTAGTGGCACCGAGTTCACCCTGACT ATCTCTTCACTGCAGCCCGACGACTTCGCTACCTACT ACTGTCAGCAGTATAATAGCTACCCCCTGACCTTCGG TCAAGGCACTAAGGTCGAGATTAAGCGTACGGTGGCC GCTCCCAGCGTGTTCATCTTCCCCCCCAGCGACGAGC |

TABLE 1 -continued

AGCTGAAGAGCGGCACCGCCAGCGTGGTGTGCCTGCT
GAACAACTTCTACCCCGGGAGGCCAAGGTGCAGTGG
AAGGTGGACAACGCCCTGCAGAGCGGCAACAGCCAGG
AGAGCGTCACCGAGCAGGACAGCAAGGACTCCACCTA
CAGCCTGAGCAGCACCCTGACCCTGAGCAAGGCCGAC
TACGAGAAGCATAAGGTGTACGCCTGCGAGGTGACCC
ACCAGGGCCTGTCCAGCCCCGTGACCAAGAGCTTCAA
CAGGGGCGAGTGC

| | | BAP058-Clone O HC |
|---|---|---|
| SEQ ID NO: 1 (Kabat) | HCDR1 | SYWMY |
| SEQ ID NO: 2 (Kabat) | HCDR2 | RIDPNSGSTKYNEKFKN |
| SEQ ID NO: 3 (Kabat) | HCDR3 | DYRKGLYAMDY |
| SEQ ID NO: 4 (Chothia) | HCDR1 | GYTFTSY |
| SEQ ID NO: 5 (Chothia) | HCDR2 | DPNSGS |
| SEQ ID NO: 3 (Chothia) | HCDR3 | DYRKGLYAMDY |
| SEQ ID NO: 78 | VH | EVQLVQSGAEVKKPGATVKISCKVSGYTFTSYWMYWV RQARGQRLEWIGRIDPNSGSTKYNEKFKNRFTISRDN SKNTLYLQMNSLRAEDTAVYYCARDYRKGLYAMDYWG QGTTVTVSS |
| SEQ ID NO: 100 | DNA VH | GAAGTGCAGCTGGTGCAGTCAGGCGCCGAAGTGAAGA AACCCGGCGCTACCGTGAAGATTAGCTGTAAAGTCTC AGGCTACACCTTCACTAGCTACTGGATGTACTGGGTC CGACAGGCTAGAGGGCAAAGACTGGAGTGGATCGGTA GAATCGACCCTAATAGCGGCTCTACTAAGTATAACGA GAAGTTTAAGAATAGGTTCACTATTAGTAGGGATAAC TCTAAGAACACCCTGTACCTGCAGATGAATAGCCTGA GAGCCGAGGACACCGCCGTCTACTACTGCGCTAGAGA CTATAGAAAGGGCCTGTACGCTATGGACTACTGGGGT CAAGGCACTACCGTGACCGTGTCTTCA |
| SEQ ID NO: 80 | Heavy Chain | EVQLVQSGAEVKKPGATVKISCKVSGYTFTSYWMYWV RQARGQRLEWIGRIDPNSGSTKYNEKFKNRFTISRDN SKNTLYLQMNSLRAEDTAVYYCARDYRKGLYAMDYWG QGTTVTVSSASTKGPSVFPLAPCSRSTSESTAALGCL VKDYFPEPVTVSWNSGALTSGVHTFPAVLQSSGLYSL SSVVTVPSSSLGTKTYTCNVDHKPSNTKVDKRVESKY GPPCPPCPAPEFLGGPSVFLFPPKPKDTLMISRTPEV TCVVVDVSQEDPEVQFNWYVDGVEVHNAKTKPREEQF NSTYRVVSVLTVLHQDWLNGKEYKCKVSNKGLPSSIE KTISKAKGQPREPQVYTLPPSQEEMTKNQVSLTCLVK GFYPSDIAVEWESNGQPENNYKTTPPVLDSDGSFFLY SRLTVDKSRWQEGNVFSCSVMHEALHNHYTQKSLSLS LG |
| SEQ ID NO: 101 | DNA Heavy Chain | GAAGTGCAGCTGGTGCAGTCAGGCGCCGAAGTGAAGA AACCCGGCGCTACCGTGAAGATTAGCTGTAAAGTCTC AGGCTACACCTTCACTAGCTACTGGATGTACTGGGTC CGACAGGCTAGAGGGCAAAGACTGGAGTGGATCGGTA GAATCGACCCTAATAGCGGCTCTACTAAGTATAACGA GAAGTTTAAGAATAGGTTCACTATTAGTAGGGATAAC TCTAAGAACACCCTGTACCTGCAGATGAATAGCCTGA GAGCCGAGGACACCGCCGTCTACTACTGCGCTAGAGA CTATAGAAAGGGCCTGTACGCTATGGACTACTGGGGT CAAGGCACTACCGTGACCGTGTCTTCAGCTAGCACTA AGGGCCCGTCCGTGTTCCCCCTGGCACCTTGTAGCCG GAGCACTAGCGAATCCACCGCTGCCCTCGGCTGCCTG GTCAAGGATTACTTCCCGGAGCCCGTGACCGTGTCCT GGAACAGCGGAGCCCTGACCTCCGGAGTGCACACCTT CCCCGCTGTGCTGCAGAGCTCCGGGCTGTACTCGCTG TCGTCGGTGGTCACGGTGCCTTCATCTAGCCTGGGTA CCAAGACCTACACTTGCAACGTGGACCACAAGCCTTC CAACACTAAGGTGGACAAGCGCGTCGAATCGAAGTAC GGCCCACCGTGCCCGCCTTGTCCCGCGCCGGAGTTCC TCGGCGGTCCCTCGGTCTTTCTGTTCCCACCGAAGCC CAAGGACACTTTGATGATTTCCCGCACCCCTGAAGTG ACATGCGTGGTCGTGGACGTGTCACAGGAAGATCCGG AGGTGCAGTTCAATTGGTACGTGGATGGCGTCGAGGT GCACAACGCCAAAACCAAGCCGAGGGAGGAGCAGTTC AACTCCACTTACCGCGTCGTGTCCGTGCTGACGGTGC TGCATCAGGACTGGCTGAACGGGAAGGAGTACAAGTG CAAAGTGTCCAACAAGGGACTTCCTAGCTCAATCGAA |

TABLE 1 -continued

|  |  |  |
|---|---|---|
|  |  | AAGACCATCTCGAAAGCCAAGGGACAGCCCCGGGAAC<br>CCCAAGTGTATACCCTGCCACCGAGCCAGGAAGAAAT<br>GACTAAGAACCAAGTCTCATTGACTTGCCTTGTGAAG<br>GGCTTCTACCCATCGGATATCGCCGTGGAATGGGAGT<br>CCAACGGCCAGCCGGAAAACAACTACAAGACCACCCC<br>TCCGGTGCTGGACTCAGACGGATCCTTCTTCCTCTAC<br>TCGCGGCTGACCGTGGATAAGAGCAGATGGCAGGAGG<br>GAAATGTGTTCAGCTGTTCTGTGATGCATGAAGCCCT<br>GCACAACCACTACACTCAGAAGTCCCTGTCCCTCTCC<br>CTGGGA |

BAP058-Clone O LC

| SEQ ID NO: 9 (Kabat) | LCDR1 | KASQDVGTAVA |
|---|---|---|
| SEQ ID NO: 10 (Kabat) | LCDR2 | WASTRHT |
| SEQ ID NO: 11 (Kabat) | LCDR3 | QQYNSYPLT |
| SEQ ID NO: 12 (Chothia) | LCDR1 | SQDVGTA |
| SEQ ID NO: 13 (Chothia) | LCDR2 | WAS |
| SEQ ID NO: 14 (Chothia) | LCDR3 | YNSYPL |
| SEQ ID NO: 82 | VL | AIQLTQSPSSLSASVGDRVTITCKASQDVGTAVAWYL<br>QKPGQSPQLLIYWASTRHTGVPSRFSGSGSGTDFTFT<br>ISSLEAEDAATYYCQQYNSYPLTFGQGTKVEIK |
| SEQ ID NO: 102 | DNA VL | GCTATTCAGCTGACTCAGTCACCTAGTAGCCTGAGCG<br>CTAGTGTGGGCGATAGAGTGACTATCACCTGTAAAGC<br>CTCTCAGGACGTGGGCACCGCCGTGGCCTGGTATCTG<br>CAGAAGCCTGGTCAATCACCTCAGCTGCTGATCTACT<br>GGGCCTCTACTAGACACACCGGCGTGCCCTCTAGGTT<br>TAGCGGTAGCGGTAGTGGCACCGACTTCACCTTCACT<br>ATCTCTTCACTGGAAGCCGAGGACGCCGCTACCTACT<br>ACTGTCAGCAGTATAATAGCTACCCCCTGACCTTCGG<br>TCAAGGCACTAAGGTCGAGATTAAG |
| SEQ ID NO: 84 | Light Chain | AIQLTQSPSSLSASVGDRVTITCKASQDVGTAVAWYL<br>QKPGQSPQLLIYWASTRHTGVPSRFSGSGSGTDFTFT<br>ISSLEAEDAATYYCQQYNSYPLTFGQGTKVEIKRTVA<br>APSVFIFPPSDEQLKSGTASVVCLLNNFYPREAKVQW<br>KVDNALQSGNSQESVTEQDSKDSTYSLSSTLTLSKAD<br>YEKHKVYACEVTHQGLSSPVTKSFNRGEC |
| SEQ ID NO: 103 | DNA Light Chain | GCTATTCAGCTGACTCAGTCACCTAGTAGCCTGAGCG<br>CTAGTGTGGGCGATAGAGTGACTATCACCTGTAAAGC<br>CTCTCAGGACGTGGGCACCGCCGTGGCCTGGTATCTG<br>CAGAAGCCTGGTCAATCACCTCAGCTGCTGATCTACT<br>GGGCCTCTACTAGACACACCGGCGTGCCCTCTAGGTT<br>TAGCGGTAGCGGTAGTGGCACCGACTTCACCTTCACT<br>ATCTCTTCACTGGAAGCCGAGGACGCCGCTACCTACT<br>ACTGTCAGCAGTATAATAGCTACCCCCTGACCTTCGG<br>TCAAGGCACTAAGGTCGAGATTAAGCGTACGGTGGCC<br>GCTCCCAGCGTGTTCATCTTCCCCCCAGCGACGAGC<br>AGCTGAAGAGCGGCACCGCCAGCGTGGTGTGCCTGCT<br>GAACAACTTCTACCCCCGGGAGGCCAAGGTGCAGTGG<br>AAGGTGGACAACGCCCTGCAGAGCGGCAACAGCCAGG<br>AGAGCGTCACCGAGCAGGACAGCAAGGACTCCACCTA<br>CAGCCTGAGCAGCACCCTGACCCTGAGCAAGGCCGAC<br>TACGAGAAGCATAAGGTGTACGCCTGCGAGGTGACCC<br>ACCAGGGCCTGTCCAGCCCCGTGACCAAGAGCTTCAA<br>CAGGGGCGAGTGC |

BAP058 HC

| SEQ ID NO: 104 (Kabat) | HCDR1 | agttactggatgtac |
|---|---|---|
| SEQ ID NO: 105 (Kabat) | HCDR2 | aggattgatcctaatagtgggagtactaagtacaatg<br>agaagttcaagaac |
| SEQ ID NO: 106 (Kabat) | HCDR3 | gactatagaaaggggctctatgctatggactac |
| SEQ ID NO: 107 (Chothia) | HCDR1 | ggctacaccttcaccagttac |
| SEQ ID NO: 108 (Chothia) | HCDR2 | gatcctaatagtgggagt |

TABLE 1 -continued

| | | |
|---|---|---|
| SEQ ID NO: 106 (Chothia) | HCDR3 | gactatagaaaggggctctatgctatggactac |
| BAP058 LC | | |
| SEQ ID NO: 245 (Kabat) | LCDR1 | aaggccagtcaggatgtgggtactgctgtagcc |
| SEQ ID NO: 246 (Kabat) | LCDR2 | tgggcatccacccggcacact |
| SEQ ID NO: 109 (Kabat) | LCDR3 | cagcagtataacagctatcctctcacg |
| SEQ ID NO: 110 (Chothia) | LCDR1 | agtcaggatgtgggtactgct |
| SEQ ID NO: 111 (Chothia) | LCDR2 | tgggcatcc |
| SEQ ID NO: 112 (Chothia) | LCDR3 | tataacagctatcctctc |
| BAP058-chi HC | | |
| SEQ ID NO: (Kabat) | HCDR1 | |
| SEQ ID NO: (Kabat) | HCDR2 | |
| SEQ ID NO: (Kabat) | HCDR3 | |
| SEQ ID NO: (Chothia) | HCDR1 | |
| SEQ ID NO: (Chothia) | HCDR2 | |
| SEQ ID NO: (Chothia) | HCDR3 | |
| BAP058-chi LC | | |
| SEQ ID NO: (Kabat) | LCDR1 | |
| SEQ ID NO: (Kabat) | LCDR2 | |
| SEQ ID NO: (Kabat) | LCDR3 | |
| SEQ ID NO: (Chothia) | LCDR1 | |
| SEQ ID NO: (Chothia) | LCDR2 | |
| SEQ ID NO: (Chothia) | LCDR3 | |
| BAP058-hum01-HC | | |
| SEQ ID NO: 104 (Kabat) | HCDR1 | agttactggatgtac |
| SEQ ID NO: 105 (Kabat) | HCDR2 | aggattgatcctaatagtgggagtactaagtacaatgagaagttcaagaac |
| SEQ ID NO: 106 (Kabat) | HCDR3 | gactatagaaaggggctctatgctatggactac |
| SEQ ID NO: 107 (Chothia) | HCDR1 | ggctacaccttcaccagttac |
| SEQ ID NO: 108 (Chothia) | HCDR2 | gatcctaatagtgggagt |
| SEQ ID NO: 106 (Chothia) | HCDR3 | gactatagaaaggggctctatgctatggactac |
| BAP058-hum01-LC | | |
| SEQ ID NO: 245 (Kabat) | LCDR1 | aaggccagtcaggatgtgggtactgctgtagcc |
| SEQ ID NO: 246 (Kabat) | LCDR2 | tgggcatccacccggcacact |
| SEQ ID NO: 109 (Kabat) | LCDR3 | cagcagtataacagctatcctctcacg |
| SEQ ID NO: 110 (Chothia) | LCDR1 | agtcaggatgtgggtactgct |
| SEQ ID NO: 111 (Chothia) | LCDR2 | tgggcatcc |

TABLE 1 -continued

| | | |
|---|---|---|
| SEQ ID NO: 112 (Chothia) | LCDR3 | tataacagctatcctctc |

BAP058-hum02-HC

| | | |
|---|---|---|
| SEQ ID NO: 104 (Kabat) | HCDR1 | agttactggatgtac |
| SEQ ID NO: 105 (Kabat) | HCDR2 | aggattgatcctaatagtgggagtactaagtacaatg agaagttcaagaac |
| SEQ ID NO: 106 (Kabat) | HCDR3 | gactatagaaaggggctctatgctatggactac |
| SEQ ID NO: 107 (Chothia) | HCDR1 | ggctacaccttcaccagttac |
| SEQ ID NO: 108 (Chothia) | HCDR2 | gatcctaatagtgggagt |
| SEQ ID NO: 106 (Chothia) | HCDR3 | gactatagaaaggggctctatgctatggactac |

BAP058-hum02-LC

| | | |
|---|---|---|
| SEQ ID NO: 245 (Kabat) | LCDR1 | aaggccagtcaggatgtgggtactgctgtagcc |
| SEQ ID NO: 246 (Kabat) | LCDR2 | tgggcatccacccggcacact |
| SEQ ID NO: 109 (Kabat) | LCDR3 | cagcagtataacagctatcctctcacg |
| SEQ ID NO: 110 (Chothia) | LCDR1 | agtcaggatgtgggtactgct |
| SEQ ID NO: 111 (Chothia) | LCDR2 | tgggcatcc |
| SEQ ID NO: 112 (Chothia) | LCDR3 | tataacagctatcctctc |

BAP058-hum03-HC

| | | |
|---|---|---|
| SEQ ID NO: 104 (Kabat) | HCDR1 | agttactggatgtac |
| SEQ ID NO: 105 (Kabat) | HCDR2 | aggattgatcctaatagtgggagtactaagtacaatg |

| | | |
|---|---|---|
| ----- | PAGE 305 | agaagttcaagaac |
| | HCDR3 | gactatagaaaggggctctatgctatggactac |
| | HCDR1 | ggctacaccttcaccagttac |
| | HCDR2 | gatcctaatagtgggagt |
| | HCDR3 | gactatagaaaggggctctatgctatggactac |
| | LCDR1 | aaggccagtcaggatgtgggtactgctgtagcc |
| | LCDR2 | tgggcatccacccggcacact |
| | LCDR3 | cagcagtataacagctatcctctcacg |
| | LCDR1 | agtcaggatgtgggtactgct |
| | LCDR2 | tgggcatcc |
| | LCDR3 | tataacagctatcctctc |
| | HCDR1 | agtactggatgtac |
| | HCDR2 | aggattgatcctaatagtgggagtactaagtacaatg agaagttcaagaac |
| | HCDR3 | gactatagaaaggggctctatgctatggactac |
| | HCDR1 | ggctacaccttcaccagttac |
| | HCDR2 | gatcctaatagtgggagt |
| | HCDR3 | gactatagaaaggggctctatgctatggactac |
| | LCDR1 | aaggccagtcaggatgtgggtactgctgtagcc |
| | LCDR2 | tgggcatccacccggcacact |
| | LCDR3 | cagcagtataacagctatcctctcacg |
| | LCDR1 | agtcaggatgtgggtactgct |
| | LCDR2 | tgggcatcc |
| | LCDR3 | tataacagctatcctctc |
| | HCDR1 | agttactggatgtac |
| | HCDR2 | aggattgatcctaatagtgggagtactaagtacaatg aggagttcaagaac |
| | HCDR3 | gactatagaaaggggctctatgctatggactac |
| | HCDR1 | ggctacaccttcaccagttac |
| | HCDR2 | gatcctaatagtgggagt |
| | HCDR3 | gactatagaaaggggctctatgctatggactac |
| | LCDR1 | aaggccagtcaggatgtgggtactgctgtagcc |
| | LCDR2 | tgggcatccacccggcacact |
| | LCDR3 | cagcagtataacagctatcctctcacg |
| | LCDR1 | agtcaggatgtgggtactgct |
| | LCDR2 | tgggcatcc |

TABLE 1 -continued

| | | | |
|---|---|---|---|
| 306 | | LCDR3 | tataacagctatcctctc |
| | | HCDR1 | agttactggatgtac |
| | | HCDR2 | aggattgatcctaatagtgggagtactaagtacaatgagaagttcaagaac |
| | | HCDR3 | gactatagaaaggggctctatgctatggactac |
| | | HCDR1 | ggctacaccttcaccagttac |
| | | HCDR2 | gatcctaatagtgggagt |
| | | HCDR3 | gactatagaaaggggctctatgctatggactac |
| | | LCDR1 | aaggccagtcaggatgtgggtactgctgtagcc |
| | | LCDR2 | tgggcatccacccggcacact |
| | | LCDR3 | cagcagtataacagctatcctctcacg |
| | | LCDR1 | agtcaggatgtgggtactgct |
| | | LCDR2 | tgggcatcc |
| | | LCDR3 | tataacagctatcctctc |
| | | HCDR1 | agttactggatgtac |
| | | HCDR2 | aggattgatcctaatagtgggagtactaagtacaatgagaagttcaagaac |
| | | HCDR3 | gactatagaaaggggctctatgctatggactac |
| | | HCDR1 | ggctacaccttcaccagttac |
| | | HCDR2 | gatcctaatagtgggagt |
| | | HCDR3 | gactatagaaaggggctctatgctatggactac |
| | | LCDR1 | aaggccagtcaggatgtgggtactgctgtagcc |
| | | LCDR2 | tgggcatccacccggcacact |
| | | LCDR3 | cagcagtataacagctatcctctcacg |
| | | LCDR1 | agtcaggatgtgggtactgct |
| | | LCDR2 | tgggcatcc |
| | | LCDR3 | tataacagctatcctctc |
| | | HCDR1 | agttactggatgtac |
| | | HCDR2 | aggattgatcctaatagtgggagtactaagtacaatgagaagttcaagaac |
| | | HCDR3 | gactatagaaaggggctctatgctatggactac |
| | | HCDR1 | ggctacaccttcaccagttac |
| | | HCDR2 | gatcctaatagtgggagt |
| | | HCDR3 | gactatagaaaggggctctatgctatggactac |
| | | LCDR1 | aaggccagtcaggatgtgggtactgctgtagcc |
| 307 | | LCDR2 | |
| | | LCDR3 | |
| | | LCDR1 | |
| | | LCDR2 | |
| | | LCDR3 | |
| | | HCDR1 | |
| | | HCDR2 | |
| | | HCDR3 | |
| | | HCDR1 | |
| | | HCDR2 | |
| | | HCDR3 | |
| | | HCDR1 | |
| | | HCDR2 | |
| | | HCDR3 | |
| | | HCDR1 | |
| | | HCDR2 | |
| | | HCDR3 | |
| | | BAP058-Clone L LC | |
| SEQ ID NO: 118 (Kabat) | | LCDR1 | aaagcctctcaggacgtgggcaccgccgtggcc |
| SEQ ID NO: 119 (Kabat) | | LCDR2 | tgggcctctactagacacacc |
| SEQ ID NO: 120 (Kabat) | | LCDR3 | cagcagtataatagctaccccctgacc |
| SEQ ID NO: 121 (Chothia) | | LCDR1 | tctcaggacgtgggcaccgcc |
| SEQ ID NO: 122 (Chothia) | | LCDR2 | tgggcctct |
| SEQ ID NO: 123 (Chothia) | | LCDR3 | tataatagctacccctg |
| | | BAP058-Clone M HC | |
| SEQ ID NO: 113 (Kabat) | | HCDR1 | agctactggatgtac |
| SEQ ID NO: 205 (Kabat) | | HCDR2 | agaatcgaccccaactccggctccaccaagtacaacgagaagttcaagaac |
| SEQ ID NO: 206 (Kabat) | | HCDR3 | gactaccggaagggcctgtacgccatggactat |

TABLE 1 -continued

| | | |
|---|---|---|
| SEQ ID NO: 207 (Chothia) | HCDR1 | ggctacaccttcaccagctac |
| SEQ ID NO: 208 (Chothia) | HCDR2 | gaccccaactccggctcc |
| SEQ ID NO: 206 (Chothia) | HCDR3 | gactaccggaagggcctgtacgccatggactat |

BAP058-Clone M LC

| | | |
|---|---|---|
| SEQ ID NO: 209 (Kabat) | LCDR1 | aaggcctcccaggacgtgggcaccgccgtggct |
| SEQ ID NO: 210 (Kabat) | LCDR2 | tgggcctctaccagacacacc |
| SEQ ID NO: 211 (Kabat) | LCDR3 | cagcagtacaactcctaccccctgacc |
| SEQ ID NO: 212 (Chothia) | LCDR1 | tcccaggacgtgggcaccgcc |
| SEQ ID NO: 213 (Chothia) | LCDR2 | tgggcctct |
| SEQ ID NO: 214 (Chothia) | LCDR3 | tacaactcctaccccctg |

BAP058-Clone N HC

| | | |
|---|---|---|
| SEQ ID NO: 113 (Kabat) | HCDR1 | agctactggatgtac |
| SEQ ID NO: 114 (Kabat) | HCDR2 | agaatcgaccctaatagcggctctactaagtataacgagaagtttaagaat |
| SEQ ID NO: 115 (Kabat) | HCDR3 | gactatagaaagggcctgtacgctatggactac |
| SEQ ID NO: 116 (Chothia) | HCDR1 | ggctacaccttcactagctac |
| SEQ ID NO: 117 (Chothia) | HCDR2 | gaccctaatagcggctct |
| SEQ ID NO: 115 (Chothia) | HCDR3 | gactatagaaagggcctgtacgctatggactac |

BAP058-Clone N LC

| | | |
|---|---|---|
| SEQ ID NO: 118 (Kabat) | LCDR1 | aaagcctctcaggacgtgggcaccgccgtggcc |
| SEQ ID NO: 119 (Kabat) | LCDR2 | tgggcctctactagacacacc |
| SEQ ID NO: 120 (Kabat) | LCDR3 | cagcagtataatagctaccccctgacc |
| SEQ ID NO: 121 (Chothia) | LCDR1 | tctcaggacgtgggcaccgcc |
| SEQ ID NO: 122 (Chothia) | LCDR2 | tgggcctct |
| SEQ ID NO: 123 (Chothia) | LCDR3 | tataatagctaccccctg |

BAP058-Clone O HC

| | | |
|---|---|---|
| SEQ ID NO: 113 (Kabat) | HCDR1 | agctactggatgtac |
| SEQ ID NO: 114 (Kabat) | HCDR2 | agaatcgaccctaatagcggctctactaagtataacgagaagtttaagaat |
| SEQ ID NO: 115 (Kabat) | HCDR3 | gactatagaaagggcctgtacgctatggactac |
| SEQ ID NO: 116 (Chothia) | HCDR1 | ggctacaccttcactagctac |
| SEQ ID NO: 117 (Chothia) | HCDR2 | gaccctaatagcggctct |
| SEQ ID NO: 115 (Chothia) | HCDR3 | gactatagaaagggcctgtacgctatggactac |

TABLE 1 -continued

BAP058-Clone O LC

| | | | |
|---|---|---|---|
| SEQ ID NO: 118 (Kabat) | LCDR1 | aaagcctctcaggacgtgggcaccgccgtggcc | |
| SEQ ID NO: 119 (Kabat) | LCDR2 | tgggcctctactagacacacc | |
| SEQ ID NO: 120 (Kabat) | LCDR3 | cagcagtataatagctaccccctgacc | |
| SEQ ID NO: 121 (Chothia) | LCDR1 | tctcaggacgtgggcaccgcc | |
| SEQ ID NO: 122 (Chothia) | LCDR2 | tgggcctct | |
| SEQ ID NO: 123 (Chothia) | LCDR3 | tataatagctaccccctg | |

Amino acid and nucleotide sequences for murine, chimeric and humanized antibody molecules. The antibody molecules include murine mAb BAP058, chimeric mAb BAP058-chi, and humanized mAbs BAP058-hum01 to BAP058-hum17 and BAP058-Clone-K to BAP058-Clone-O. The amino acid and nucleotide sequences of the heavy and light chain CDRs, the heavy and light chain variable regions, and the heavy and light chains are shown.

TABLE 2

Amino acid and nucleotide sequences of the heavy and light chain framework regions for humanized mAbs BAP058-hum01 to BAP058-hum17 and BAP058-Clone-K to BAP058-Clone-O

| | Amino Acid Sequence | Nucleotide Sequence |
|---|---|---|
| VHFW1 (type a) | QVQLVQSGAEVKKPGASVKVSCKAS (SEQ ID NO: 124) | CAGGTTCAGCTGGTGCAGTCTGGAGCTGAGGTGAAGAA GCCTGGGGCCTCAGTGAAGGTCTCCTGCAAGGCTTCT (SEQ ID NO: 125) |
| VHFW1 (type b) | EVQLVQSGAEVKKPGESLRISCKGS (SEQ ID NO: 126) | GAAGTGCAGCTGGTGCAGTCTGGAGCAGAGGTGAAAAA GCCCGGGGAGTCTCTGAGGATCTCCTGTAAGGGTTCT (SEQ ID NO: 127) GAAGTGCAGCTGGTGCAGTCAGGCGCCGAAGTGAAGAA GCCCGGCGAGTCACTGAGAATTAGCTGTAAAGGTTCA (SEQ ID NO: 215) GAAGTGCAGCTGGTGCAGTCTGGCGCCGAAGTGAAGAA GCCTGGCGAGTCCCTGCGGATCTCCTGCAAGGGCTCC (SEQ ID NO: 216) |
| VHFW1 (type c) | EVQLVQSGAEVKKPGATVKISCKVS (SEQ ID NO: 128) | GAGGTCCAGCTGGTACAGTCTGGGGCTGAGGTGAAGAA GCCTGGGGCTACAGTGAAAATCTCCTGCAAGGTTTCT (SEQ ID NO: 129) GAAGTGCAGCTGGTGCAGTCTGGCGCCGAAGTGAAGAA ACCCGGCGCTACCGTGAAGATCTCCTGCAAGGTGTCC (SEQ ID NO: 217) GAAGTGCAGCTGGTGCAGTCAGGCGCCGAAGTGAAGAA ACCCGGCGCTACCGTGAAGATTAGCTGTAAAGTCTCA (SEQ ID NO: 218) |
| VHFW1 (type d) | QITLKESGPTLVKPTQTLTLTCTFS (SEQ ID NO: 130) | CAGATCACCTTGAAGGAGTCTGGTCCTACGCTGGTGAA ACCCACACAGACCCTCACGCTGACCTGCACCTTCTCT (SEQ ID NO: 131) |
| VHFW2 (type a) | WVRQATGQGLEWMG (SEQ ID NO: 132) | TGGGTGCGACAGGCCACTGGACAAGGGCTTGAGTGGAT GGGT (SEQ ID NO: 133) TGGGTGCGACAGGCTACCGGCCAGGGCCTGGAATGGAT GGGC (SEQ ID NO: 219) TGGGTCCGACAGGCTACCGGTCAAGGCCTGGAGTGGAT GGGT (SEQ ID NO: 220) |
| VHFW2 (type a') | WVRQAPGQGLEWMG (SEQ ID NO: 134) | TGGGTGCGACAGGCCCCTGGACAAGGGCTTGAGTGGAT GGGT (SEQ ID NO: 135) TGGGTCCGACAGGCCCCAGGGCAAGGCCTGGAGTGGAT GGGT (SEQ ID NO: 221) |

TABLE 2 -continued

Amino acid and nucleotide sequences of the heavy and light chain framework regions for humanized mAbs BAP058-hum01 to BAP058-hum17 and BAP058-Clone-K to BAP058-Clone-O

| | Amino Acid Sequence | Nucleotide Sequence |
|---|---|---|
| VHFW2 (type b) | WIRQPPGKGLEWIG (SEQ ID NO: 136) | TGGATCCGCCAGCCCCCAGGGAAGGGGCTGGAGTGGAT TGGT (SEQ ID NO: 137) TGGATCCGGCAGCCCCCTGGCAAGGGCCTGGAATGGAT CGGC (SEQ ID NO: 222) |
| VHFW2 (type c) | WIRQSPSRGLEWLG (SEQ ID NO: 138) | TGGATCAGGCAGTCCCCATCGAGAGGCCTTGAGTGGCT GGGT (SEQ ID NO: 139) |
| VHFW2 (type d) | WVRQARGQRLEWIG (SEQ ID NO: 140) | TGGGTGCGACAGGCTCGTGGACAACGCCTTGAGTGGAT AGGT (SEQ ID NO: 141) TGGGTCCGACAGGCTAGAGGGCAAAGACTGGAGTGGAT CGGT (SEQ ID NO: 223) |
| VHFW2 (type e) | WVRQAPGKGLEWVS (SEQ ID NO: 142) | TGGGTCCGCCAGGCTCCAGGGAAGGGGCTGGAGTGGGT CAGT (SEQ ID NO: 143) |
| VHFW3 (type a) | RFTISRDDSKNTAYLQMNSLKTEDTAVY YCAR (SEQ ID NO: 144) | AGATTCACCATCTCCAGAGATGATTCAAAGAACACGGC GTATCTGCAAATGAACAGCCTGAAAACCGAGGACACGG CCGTGTATTACTGTGCAAGG (SEQ ID NO: 145) |
| VHFW3 (type b) | RVTITADKSTSTAYMELSSLRSEDTAVY YCAR (SEQ ID NO: 146) | AGAGTCACGATTACCGCGGACAAATCCACGAGCACAGC CTACATGGAGCTGAGCAGCCTGAGATCTGAGGACACGG CCGTGTATTACTGTGCAAGG (SEQ ID NO: 147) CGCGTGACCATCACCGCCGACAAGTCCACCTCCACCGC CTACATGGAACTGTCCTCCCTGCGGAGCGAGGACACCG CCGTGTACTACTGCGCCAGA (SEQ ID NO: 224) CGCGTGACCATCACCGCCGACAAGTCCACCTCCACCGC CTACATGGAACTGTCCTCCCTGAGATCCGAGGACACCG CCGTGTACTACTGCGCCAGA (SEQ ID NO: 225) AGAGTGACTATCACCGCCGATAAGTCTACTAGCACCGC CTATATGGAACTGTCTAGCCTGAGATCAGAGGACACCG CCGTCTACTACTGCGCTAGA (SEQ ID NO: 226) |
| VHFW3 (type c) | RVTISVDTSKNQFSLKLSSVTAADTAVY YCAR (SEQ ID NO: 148) | AGAGTCACCATATCAGTAGACACGTCCAAGAACCAGTT CTCCCTGAAGCTGAGCTCTGTGACCGCCGCGGACACGG CTGTGTATTACTGTGCAAGG (SEQ ID NO: 149) AGAGTGACTATTAGCGTGGACACCTCTAAGAATCAGTT TAGCCTGAAGCTGTCTAGCGTGACCGCCGCTGACACCG CCGTCTACTACTGCGCTAGA (SEQ ID NO: 227) |
| VHFW3 (type d) | RLTISKDTSKNQVVLTMTNMDPVDTATY YCAR (SEQ ID NO: 150) | AGACTCACCATCTCCAAGGACACCTCCAAAAACCAGGT GGTCCTTACAATGACCAACATGGACCCTGTGGACACAG CCACGTATTACTGTGCAAGG (SEQ ID NO: 151) |
| VHFW3 (type e) | RFTISRDNSKNTLYLQMNSLRAEDTAVY YCAR (SEQ ID NO: 152) | AGATTCACCATCTCCAGAGACAATTCCAAGAACACGCT GTATCTTCAAATGAACAGCCTGAGAGCCGAGGACACGG CCGTGTATTACTGTGCAAGG (SEQ ID NO: 153) AGGTTCACTATTAGTAGGGATAACTCTAAGAACACCCT GTACCTGCAGATGAATAGCCTGAGAGCCGAGGACACCG CCGTCTACTACTGCGCTAGA (SEQ ID NO: 228) |
| VHFW4 | WGQGTTVTVSS (SEQ ID NO: 154) | TGGGGCCAGGGCACCACCGTGACCGTGTCCTCC (SEQ ID NO: 155) TGGGGCCAGGGCACCACCGTGACCGTGTCCTCT (SEQ ID NO: 229) TGGGGTCAAGGCACTACCGTGACCGTGTCTTCA (SEQ ID NO: 230) |

TABLE 2 -continued

Amino acid and nucleotide sequences of the heavy and light chain framework regions for humanized mAbs BAP058-hum01 to BAP058-hum17 and BAP058-Clone-K to BAP058-Clone-O

| | Amino Acid Sequence | Nucleotide Sequence |
|---|---|---|
| VLFW1 (type a) | EIVLTQSPDFQSVTPKEKVTITC (SEQ ID NO: 156) | GAAATTGTGCTGACTCAGTCTCCAGACTTTCAGTCTGT GACTCCAAAGGAGAAAGTCACCATCACCTGC (SEQ ID NO: 157) GAGATCGTGCTGACCCAGTCCCCCGACTTCCAGTCCGT GACCCCCAAAGAAAAAGTGACCATCACATGC (SEQ ID NO: 231) GAGATCGTCCTGACTCAGTCACCCGACTTTCAGTCAGT GACCCCTAAAGAGAAAGTCACTATCACCTGT (SEQ ID NO: 232) |
| VLFW1 (type b) | DVVMTQSPLSLPVTLGQPASISC (SEQ ID NO: 158) | GATGTTGTGATGACTCAGTCTCCACTCTCCCTGCCCGT CACCCTTGGACAGCCGGCCTCCATCTCCTGC (SEQ ID NO: 159) GACGTCGTGATGACTCAGTCACCCCTGAGCCTGCCCGT GACCCTGGGGCAGCCCGCCTCTATTAGCTGT (SEQ ID NO: 233) |
| VLFW1 (type c) | DIVMTQTPLSLPVTPGEPASISC (SEQ ID NO: 160) | GATATTGTGATGACCCAGACTCCACTCTCCCTGCCCGT CACCCCTGGAGAGCCGGCCTCCATCTCCTGC (SEQ ID NO: 161) |
| VLFW1 (type d) | DIQMTQSPSSLSASVGDRVTITC (SEQ ID NO: 162) | GACATCCAGATGACCCAGTCTCCATCCTCCCTGTCTGC ATCTGTAGGAGACAGAGTCACCATCACTTGC (SEQ ID NO: 163) |
| VLFW1 (type e) | EIVLTQSPATLSLSPGERATLSC (SEQ ID NO: 164) | GAAATTGTGTTGACACAGTCTCCAGCCACCCTGTCTTT GTCTCCAGGGGAAAGAGCCACCCTCTCCTGC (SEQ ID NO: 165) |
| VLFW1 (type f) | AIQLTQSPSSLSASVGDRVTITC (SEQ ID NO: 166) | GCCATCCAGTTGACCCAGTCTCCATCCTCCCTGTCTGC ATCTGTAGGAGACAGAGTCACCATCACTTGC (SEQ ID NO: 167) GCTATTCAGCTGACTCAGTCACCTAGTAGCCTGAGCGC TAGTGTGGGCGATAGAGTGACTATCACCTGT (SEQ ID NO: 234) |
| VLFW2 (type a) | WYQQKPGQAPRLLIY (SEQ ID NO: 168) | TGGTACCAGCAGAAACCTGGCCAGGCTCCCAGGCTCCT CATCTAT (SEQ ID NO: 169) TGGTATCAGCAGAAGCCAGGGCAAGCCCCTAGACTGCT GATCTAC (SEQ ID NO: 235) |
| VLFW2 (type c) | WYLQKPGQSPQLLIY (SEQ ID NO: 170) | TGGTACCTGCAGAAGCCAGGGCAGTCTCCACAGCTCCT GATCTAT (SEQ ID NO: 171) TGGTATCTGCAGAAGCCTGGCCAGTCCCCTCAGCTGCT GATCTAC (SEQ ID NO: 236) TGGTATCTGCAGAAGCCTGGTCAATCACCTCAGCTGCT GATCTAC (SEQ ID NO: 237) |
| VLFW3 (type a) | GVPSRFSGSGSGTEFTLTISSLQPDDFA TYYC (SEQ ID NO: 172) | GGGGTCCCATCAAGGTTCAGCGGCAGTGGATCTGGGAC AGAATTCACTCTCACCATCAGCAGCCTGCAGCCTGATG ATTTTGCAACTTATTACTGT (SEQ ID NO: 173) GGCGTGCCCTCTAGGTTTAGCGGTAGCGGTAGTGGCAC CGAGTTCACCCTGACTATCTCTTCACTGCAGCCCGACG ACTTCGCTACCTACTACTGT (SEQ ID NO: 238) |
| VLFW3 (type b) | GVPSRFSGSGSGTDFTFTISSLQPEDIA TYYC (SEQ ID NO: 174) | GGGGTCCCATCAAGGTTCAGTGGAAGTGGATCTGGGAC AGATTTTACTTTCACCATCAGCAGCCTGCAGCCTGAAG ATATTGCAACATATTACTGT (SEQ ID NO: 175) GGCGTGCCCTCTAGGTTTAGCGGTAGCGGTAGTGGCAC CGACTTCACCTTCACTATCTCTTCACTGCAGCCCGAGG ATATCGCTACCTACTACTGT (SEQ ID NO: 239) GGCGTGCCCTCCAGATTCTCCGGCTCTGGCTCTGGCAC CGACTTTACCTTCACCATCTCCAGCCTGCAGCCCGAGG ATATCGCCACCTACTACTGC (SEQ ID NO: 240) |

TABLE 2 -continued

Amino acid and nucleotide sequences of the heavy and light chain framework regions for humanized mAbs BAP058-hum01 to BAP058-hum17 and BAP058-Clone-K to BAP058-Clone-O

| | Amino Acid Sequence | Nucleotide Sequence |
|---|---|---|
| VLFW3 (type c) | GIPARFSGSGSGTEFTLTISSLQSEDFA VYYC (SEQ ID NO: 176) | GGGGATCCCAGCCAGGTTCAGTGGCAGTGGGTCTGGGAC AGAGTTCACTCTCACCATCAGCAGCCTGCAGTCTGAAG ATTTTGCAGTTTATTACTGT (SEQ ID NO: 177) |
| VLFW3 (type d) | GVPSRFSGSGSGTDFTLTISSLQPEDFA TYYC (SEQ ID NO: 178) | GGGGTCCCATCAAGGTTCAGCGGCAGTGGATCTGGGAC AGATTTCACTCTCACCATCAGCAGCCTGCAGCCTGAAG ATTTTGCAACTTATTACTGT (SEQ ID NO: 179) |
| VLFW3 (type e) | GVPDRFSGSGSGTDFTLKISRVEAEDVG VYYC (SEQ ID NO: 180) | GGGGTCCCAGACAGGTTCAGTGGCAGTGGGTCAGGCAC TGATTTCACACTGAAAATCAGCAGGGTGGAGGCTGAGG ATGTTGGAGTTTATTACTGT (SEQ ID NO: 181) GGCGTGCCCGACAGATTCTCCGGCTCTGGCTCTGGCAC CGACTTCACCCTGAAGATCTCCCGGGTGGAAGCCGAGG ATGTGGGCGTGTACTACTGC (SEQ ID NO: 241) |
| VLFW3 (type f) | GIPPRFSGSGYGTDFTLTINNIESEDAA YYFC (SEQ ID NO: 182) | GGGATCCCACCTCGATTCAGTGGCAGCGGGTATGGAAC AGATTTTACCCTCACAATTAATAACATAGAATCTGAGG ATGCTGCATATTACTTCTGT (SEQ ID NO: 183) |
| VLFW3 (type g) | GVPSRFSGSGSGTDFTFTISSLEAEDAA TYYC (SEQ ID NO: 184) | GGGGTCCCCTCGAGGTTCAGTGGCAGTGGATCTGGGAC AGATTTCACCTTTACCATCAGTAGCCTGGAAGCTGAAG ATGCTGCAACATATTACTGT (SEQ ID NO: 185) GGCGTGCCCTCTAGGTTTAGCGGTAGCGGTAGTGGCAC CGACTTCACCTTCACTATCTCTTCACTGGAAGCCGAGG ACGCCGCTACCTACTACTGT (SEQ ID NO: 242) |
| VLFW4 | FGQGTKVEIK (SEQ ID NO: 186) | TTCGGCCAAGGGACCAAGGTGGAAATCAAA (SEQ ID NO: 187) TTCGGCCAGGGCACCAAGGTGGAAATCAAG (SEQ ID NO: 243) TTCGGTCAAGGCACTAAGGTCGAGATTAAG (SEQ ID NO: 244) |

TABLE 3

Constant region amino acid sequences of human IgG heavy chains and human kappa light chain HC IgG4 (S228P) mutant constant region amino acid sequence (EU Numbering)
ASTKGPSVFP LAPCSRSTSE STAALGCLVK DYFPEPVTVS WNSGALTSGV
HTFPAVLQSS GLYSLSSVVT VPSSSLGTKT YTCNVDHKPS NTKVDKRVES
KYGPPCPPCP APEFLGGPSV FLFPPKPKDT LMISRTPEVT CVVVDVSQED
PEVQFNWYVD GVEVHNAKTK PREEQFNSTY RVVSVLTVLH QDWLNGKEYK
CKVSNKGLPS SIEKTISKAK GQPREPQVYT LPPSQEEMTK NQVSLTCLVK
GFYPSDIAVE WESNGQPENN YKTTPPVLDS DGSFFLYSRL TVDKSRWQEG
NVFSCSVMHE ALHNHYTQKS LSLSLGK (SEQ ID NO: 188)

LC Human kappa constant region amino acid sequence
RTVAAPSVFI FPPSDEQLKS GTASVVCLLN NFYPREAKVQ WKVDNALQSG
NSQESVTEQD SKDSTYSLSS TLTLSKADYE KHKVYACEVT HQGLSSPVTK
SFNRGEC (SEQ ID NO: 189)

HC IgG4 (S228P) mutant constant region amino acid sequence lacing C-terminal lysine (K) (EU Numbering)
ASTKGPSVFP LAPCSRSTSE STAALGCLVK DYFPEPVTVS WNSGALTSGV
HTFPAVLQSS GLYSLSSVVT VPSSSLGTKT YTCNVDHKPS NTKVDKRVES
KYGPPCPPCP APEFLGGPSV FLFPPKPKDT LMISRTPEVT CVVVDVSQED
PEVQFNWYVD GVEVHNAKTK PREEQFNSTY RVVSVLTVLH QDWLNGKEYK
CKVSNKGLPS SIEKTISKAK GQPREPQVYT LPPSQEEMTK NQVSLTCLVK
GFYPSDIAVE WESNGQPENN YKTTPPVLDS DGSFFLYSRL TVDKSRWQEG
NVFSCSVMHE ALHNHYTQKS LSLSLG (SEQ ID NO: 190)

TABLE 3 -continued

Constant region amino acid sequences of human IgG heavy chains and human kappa light chain

```
HC IgG1 wild type
    ASTKGPSVFP LAPSSKSTSG GTAALGCLVK DYFPEPVTVS WNSGALTSGV
    HTFPAVLQSS GLYSLSSVVT VPSSSLGTQT YICNVNHKPS NTKVDKRVEP
    KSCDKTHTCP PCPAPELLGG PSVFLFPPKP KDTLMISRTP EVTCVVVDVS
    HEDPEVKFNW YVDGVEVHNA KTKPREEQYN STYRVVSVLT VLHQDWLNGK
    EYKCKVSNKA LPAPIEKTIS KAKGQPREPQ VYTLPPSREE MTKNQVSLTC
    LVKGFYPSDI AVEWESNGQP ENNYKTTPPV LDSDGSFFLY SKLTVDKSRW
    QQGNVFSCSV MHEALHNHYT QKSLSLSPGK (SEQ ID NO: 191)

HC IgG1 (N297A) mutant constant region amino acid sequence
    (EU Numbering)
    ASTKGPSVFP LAPSSKSTSG GTAALGCLVK DYFPEPVTVS WNSGALTSGV
    HTFPAVLQSS GLYSLSSVVT VPSSSLGTQT YICNVNHKPS NTKVDKRVEP
    KSCDKTHTCP PCPAPELLGG PSVFLFPPKP KDTLMISRTP EVTCVVVDVS
    HEDPEVKFNW YVDGVEVHNA KTKPREEQYA STYRVVSVLT VLHQDWLNGK
    EYKCKVSNKA LPAPIEKTIS KAKGQPREPQ VYTLPPSREE MTKNQVSLTC
    LVKGFYPSDI AVEWESNGQP ENNYKTTPPV LDSDGSFFLY SKLTVDKSRW
    QQGNVFSCSV MHEALHNHYT QKSLSLSPGK (SEQ ID NO: 192)

HC IgG1 (D265A, P329A) mutant constant region amino acid sequence
    (EU Numbering)
    ASTKGPSVFP LAPSSKSTSG GTAALGCLVK DYFPEPVTVS WNSGALTSGV
    HTFPAVLQSS GLYSLSSVVT VPSSSLGTQT YICNVNHKPS NTKVDKRVEP
    KSCDKTHTCP PCPAPELLGG PSVFLFPPKP KDTLMISRTP EVTCVVVAVS
    HEDPEVKFNW YVDGVEVHNA KTKPREEQYN STYRVVSVLT VLHQDWLNGK
    EYKCKVSNKA LAAPIEKTIS KAKGQPREPQ VYTLPPSREE MTKNQVSLTC
    LVKGFYPSDI AVEWESNGQP ENNYKTTPPV LDSDGSFFLY SKLTVDKSRW
    QQGNVFSCSV MHEALHNHYT QKSLSLSPGK (SEQ ID NO: 193)

HC IgG1 (L234A, L235A) mutant constant region amino acid sequence
    (EU Numbering)
    ASTKGPSVFP LAPSSKSTSG GTAALGCLVK DYFPEPVTVS WNSGALTSGV
    HTFPAVLQSS GLYSLSSVVT VPSSSLGTQT YICNVNHKPS NTKVDKRVEP
    KSCDKTHTCP PCPAPEAAGG PSVFLFPPKP KDTLMISRTP EVTCVVVDVS
    HEDPEVKFNW YVDGVEVHNA KTKPREEQYN STYRVVSVLT VLHQDWLNGK
    EYKCKVSNKA LPAPIEKTIS KAKGQPREPQ VYTLPPSREE MTKNQVSLTC
    LVKGFYPSDI AVEWESNGQP ENNYKTTPPV LDSDGSFFLY SKLTVDKSRW
    QQGNVFSCSV MHEALHNHYT QKSLSLSPGK (SEQ ID NO: 194)
```

Table 4. See Examples.
Table 5. See Examples.
Table 6. Selected therapeutic agents that can be administered in combination with the anti-PD-L1 antibody molecules, e.g., as a single agent or in combination with other immunomodulators described herein. Each publication listed in this Table is herein incorporated by reference in its entirety, including all structural formulae therein.

| Compound Designation | Generic Name Tradename | Compound Structure | Patents/Patent Application Publications |
|---|---|---|---|
| A1 | Sotrastaurin | [chemical structure] | EP 1682103<br>US 2007/142401<br>WO 2005/039549 |

-continued

| Compound Designation | Generic Name Tradename | Compound Structure | Patents/Patent Application Publications |
|---|---|---|---|
| A2 | Nilotinib HCl monohydrate TASIGNA ® | HCl·H₂O | WO 2004/005281 U.S. Pat. No. 7,169,791 |
| A3 | | 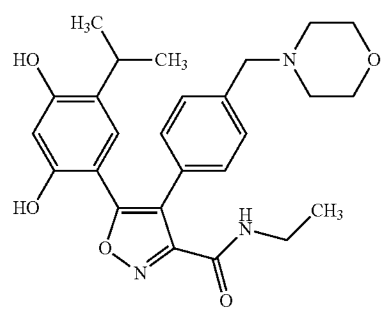 [SMILES: CCNC(=O)c1noc(-c2cc(C(C)C)c(O)cc2O)c1-c1ccc(CN2CCOCC2)cc1] | WO 2010/060937 WO 2004/072051 EP 1611112 U.S. Pat. No. 8,450,310 |
| A4 | Dactolisib | 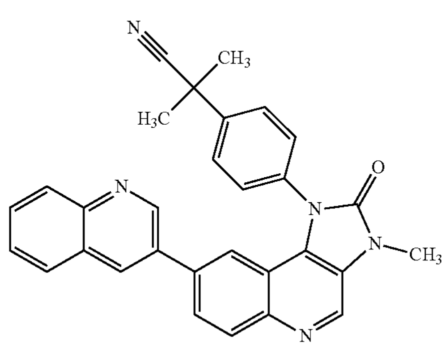 [SMILES: Cn1c(=O)n(-c2ccc(C(C)(C)C#N)cc2)c2c3cc(-c4cnc5ccccc5c4)ccc3ncc21] | WO 2006/122806 |

-continued
| Compound Designation | Generic Name Tradename | Compound Structure | Patents/Patent Application Publications |
|---|---|---|---|
| A5 | | 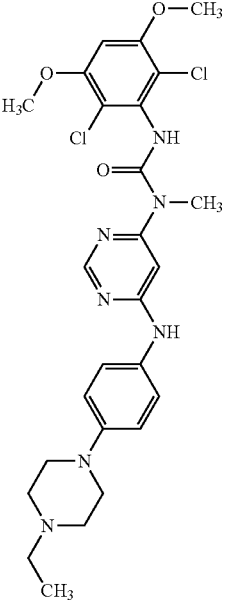 | U.S. Pat. No. 8,552,002 |
| A6 | Buparlisib | 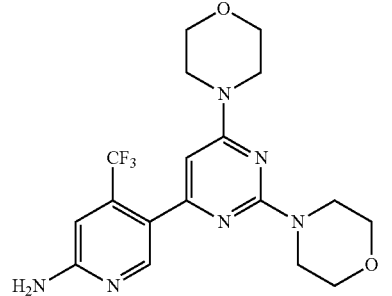 [SMILES: Nc1cc(C(F)(F)F)c(-c2cc(N3CCOCC3)nc(N3CCOCC3)n2)cn1] | WO 2007/084786 |
| A7 | | 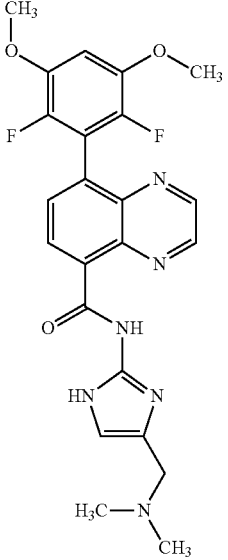 [SMILES: COc1cc(OC)c(F)c(-c2ccc(C(=O)Nc3nc(CN(C)C)c[nH]3)c3nccnc23)c1F] | WO 2009/141386 US 2010/0105667 |

-continued

| Compound Designation | Generic Name Tradename | Compound Structure | Patents/Patent Application Publications |
|---|---|---|---|
| A8 | | 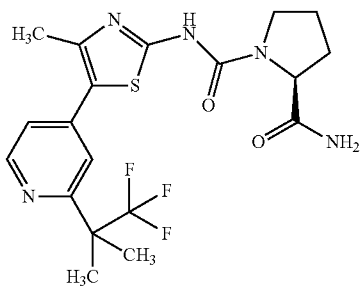 [SMILES: Cc1nc(NC(=O)N2CCC[C@H]2C(N)=O)sc1-c1ccnc(C(C)(C)C(F)(F)F)c1] | WO 2010/029082 |
| A9 | | CYP17 inhibitor | WO 2010/149755 U.S. Pat. No. 8,263,635 B2 EP 2445903 B1 |
| A10 | | 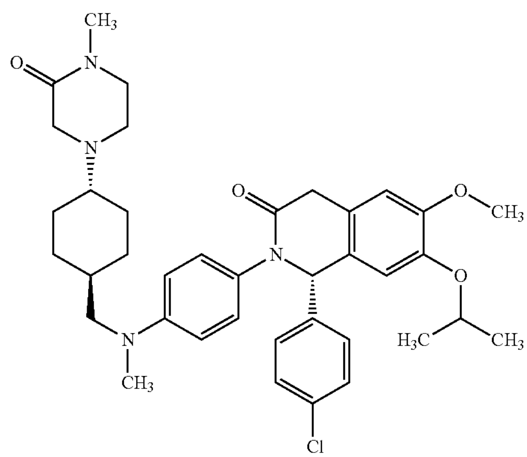 [SMILES: COc1cc2c(cc1OC(C)C)[C@H](c1ccc(Cl)cc1)N(c1ccc(N(C)C[C@H]3CC[C@H](N4CCN(C)C(=O)C4)CC3)cc1)C(=O)C2] | WO 2011/076786 |
| A11 | Deferasirox EXJADE ® | 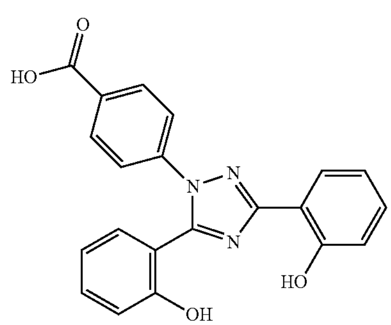 [SMILES: O=C(O)c1ccc(-n2nc(-c3ccccc3O)nc2-c2ccccc2O)cc1] | WO 1997/049395 |
| A12 | Letrozole FEMARA ® | 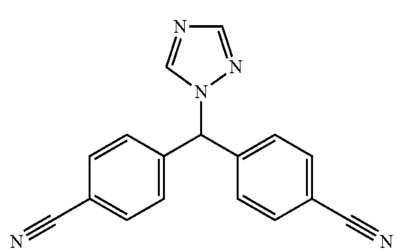 [SMILES: N#Cc1ccc(C(c2ccc(C#N)cc2)n2cncn2)cc1] | U.S. Pat. No. 4,978,672 |

-continued

| Compound Designation | Generic Name Tradename | Compound Structure | Patents/Patent Application Publications |
|---|---|---|---|
| A13 | | 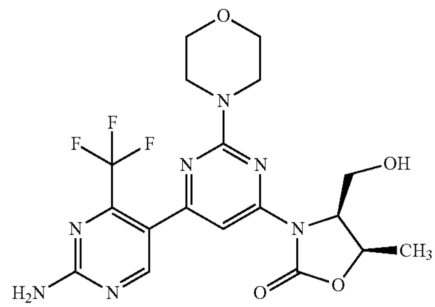 [SMILES: C[C@H]1OC(=O)N(c2cc(-c3cnc(N)nc3C(F)(F)F)nc(N3CCOCC3)n2)[C@H]1CO] | WO 2013/124826<br>US 2013/0225574 |
| A14 | | 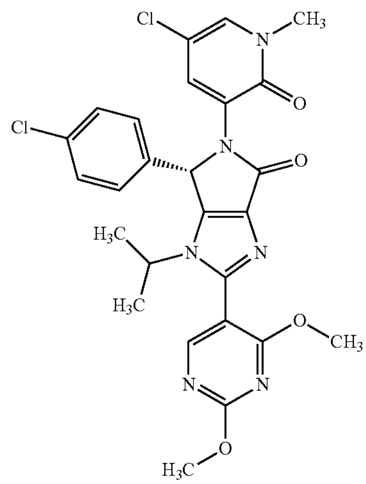 [SMILES: COc1ncc(-c2nc3c(n2C(C)C)[C@H](c2ccc(Cl)cc2)N(c2cc(Cl)cn(C)c2=O)C3=O)c(OC)n1] | WO 2013/111105 |
| A15 | | 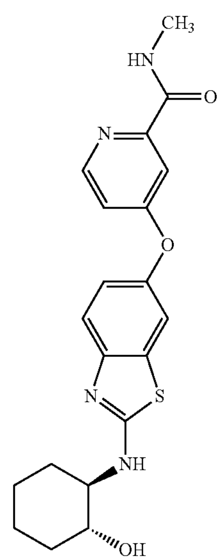 [SMILES: CNC(=O)c1cc(Oc2ccc3nc(N[C@@H]4CCCC[C@H]4O)sc3c2)ccn1] | WO 2005/073224 |

| Compound Designation | Generic Name Tradename | Compound Structure | Patents/Patent Application Publications |
|---|---|---|---|
| A16 | Imatinib mesylate GLEEVEC ® | 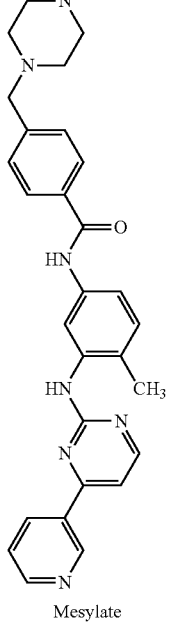<br>Mesylate | WO 1999/003854 |
| A17 | | 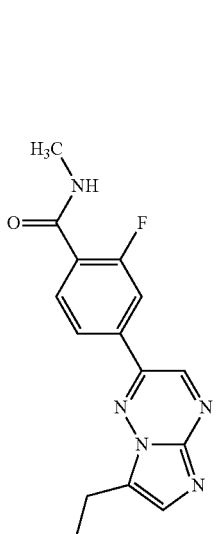<br>Dihydrochloric salt | EP 2099447<br>U.S. Pat. No. 7,767,675<br>U.S. Pat. No. 8,420,645 |

-continued

| Compound Designation | Generic Name Tradename | Compound Structure | Patents/Patent Application Publications |
|---|---|---|---|
| A18 | Ruxolitinib Phosphate JAKAFI ® | (structure shown) H₃PO₄ | WO 2007/070514 EP 2474545 U.S. Pat. No. 7,598,257 WO 2014/018632 |
| A19 | Panobinostat | (structure shown) | WO 2014/072493 WO 2002/022577 EP 1870399 |
| A20 | Osilodrostat | (structure shown) | WO 2007/024945 |
| A21 | | (structure shown) | WO 2008/016893 EP 2051990 U.S. Pat. No. 8,546,336 |

| Compound Designation | Generic Name Tradename | Compound Structure | Patents/Patent Application Publications |
|---|---|---|---|
| A22 | Sonidegib phosphate | 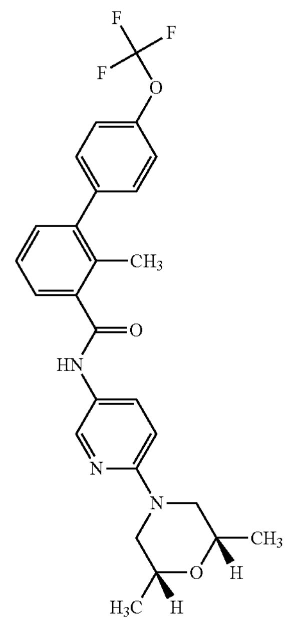 [SMILES: Cc1c(C(=O)Nc2ccc(N3C[C@@H](C)O[C@@H](C)C3)nc2)cccc1-c1ccc(OC(F)(F)F)cc1] | WO 2007/131201 EP 2021328 U.S. Pat. No. 8,178,563 |
| A23 | ceritinib ZYKADIA ™ | 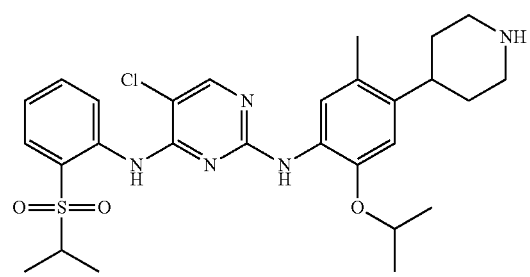 | WO 2008/073687 U.S. Pat. No. 8,039,479 |
| A24 | | 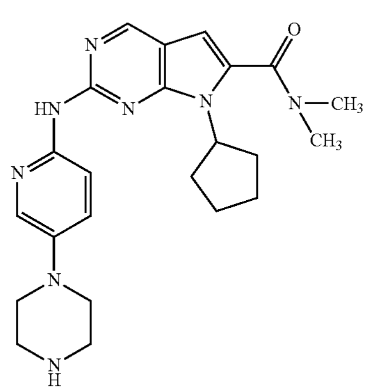 [SMILES: CN(C)C(=O)c1cc2cnc(Nc3ccc(N4CCNCC4)cn3)nc2n1C1CCCC1] | U.S. Pat. No. 8,415,355 U.S. Pat. No. 8,685,980 |

-continued
| Compound Designation | Generic Name Tradename | Compound Structure | Patents/Patent Application Publications |
|---|---|---|---|
| A25 | | 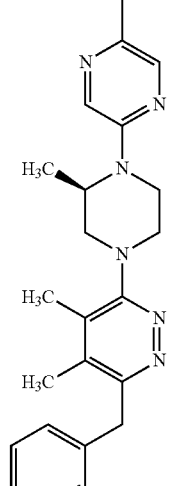 | WO 2010/007120 |
| A26 | | Human monoclonal antibody to PRLR | U.S. Pat. No. 7,867,493 |
| A27 | | 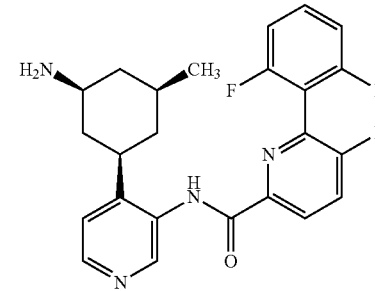 | WO 2010/026124<br>EP 2344474<br>US 2010/0056576<br>WO2008/106692 |
| A28 | | 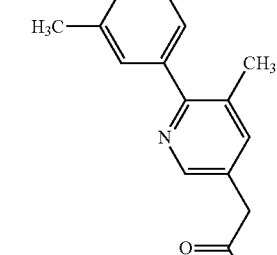 | WO 2010/101849 |

-continued

| Compound Designation | Generic Name Tradename | Compound Structure | Patents/Patent Application Publications |
|---|---|---|---|
| A29 | Encorafenib | *(structure shown)* | WO 2011/025927 |
| A30 | | *(structure shown)* | WO 2011/101409 |
| A31 | | Human monoclonal antibody to HER3 | WO 2012/022814<br>EP 2606070<br>U.S. Pat. No. 8,735,551 |
| A32 | | Antibody Drug Conjugate (ADC) | WO 2014/160160<br>Ab: 12425 (see Table 1, paragraph [00191])<br>Linker: SMCO (see paragraph [00117])<br>Payload: DM1 (see paragraph [00111]<br>See also Claim 29 |
| A33 | | Monoclonal antibody or Fab to M-CSF | WO 2004/045532 |
| A34 | Binimetinib | *(structure shown)* | WO 2003/077914 |

-continued
| Compound Designation | Generic Name Tradename | Compound Structure | Patents/Patent Application Publications |
|---|---|---|---|
| A35 | Midostaurin | 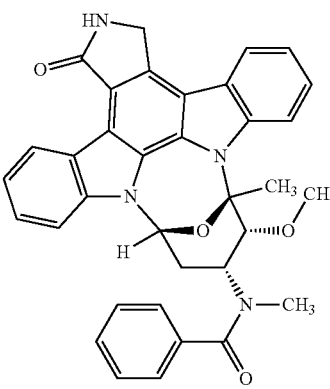 | WO 2003/037347<br>EP 1441737<br>US 2012/252785 |
| A36 | Everolimus<br>AFINITOR ® | 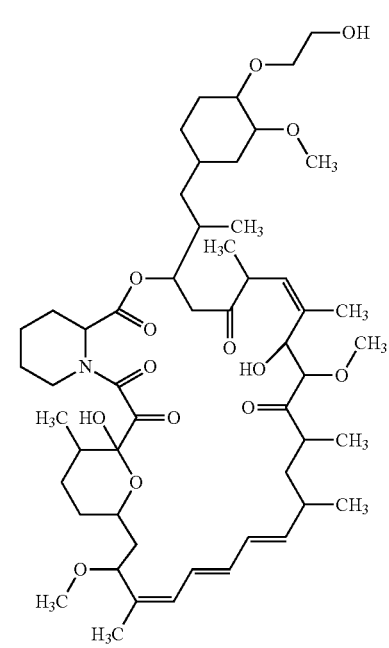 [SMILES: COC1CC2CCC(C)C(O)(O2)C(=O)C(=O)N2CCCCC2C(=O)OC(C(C)CC2CCC(OCCO)C(OC)C2)CC(=O)C(C)/C=C(/C)C(O)C(OC)C(=O)C(C)CC(C)/C=C/C=C/C=C\1C] | WO 2014/085318 |

| Compound Designation | Generic Name Tradename | Compound Structure | Patents/Patent Application Publications |
|---|---|---|---|
| A37 | | 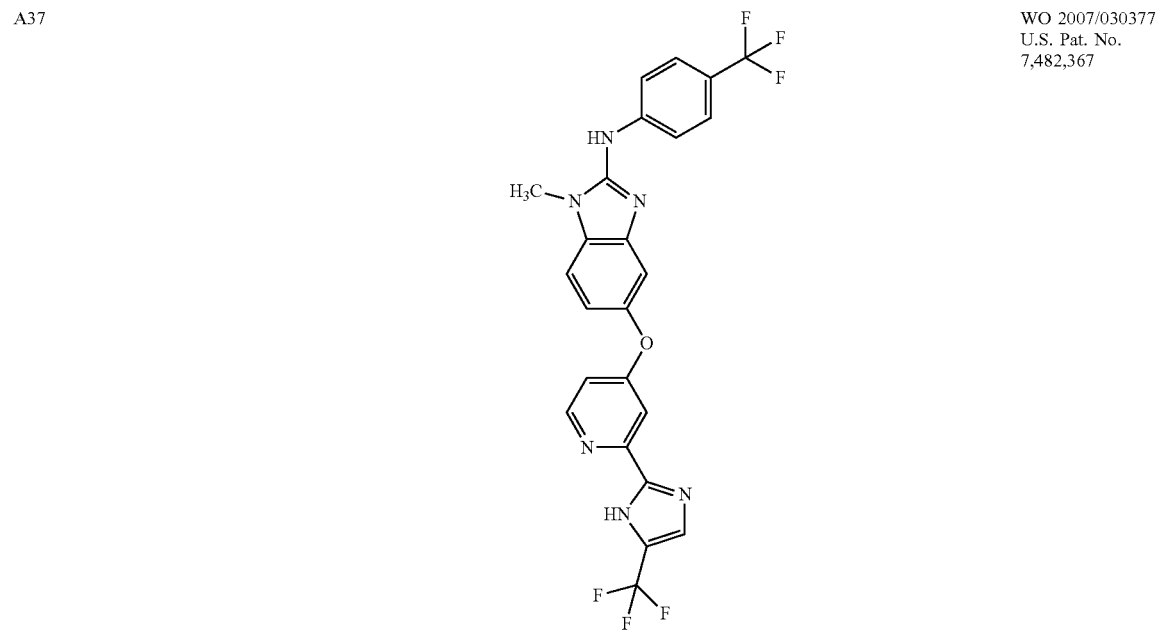 | WO 2007/030377 U.S. Pat. No. 7,482,367 |
| A38 | Pasireotide diaspartate SIGNIFOR ® | 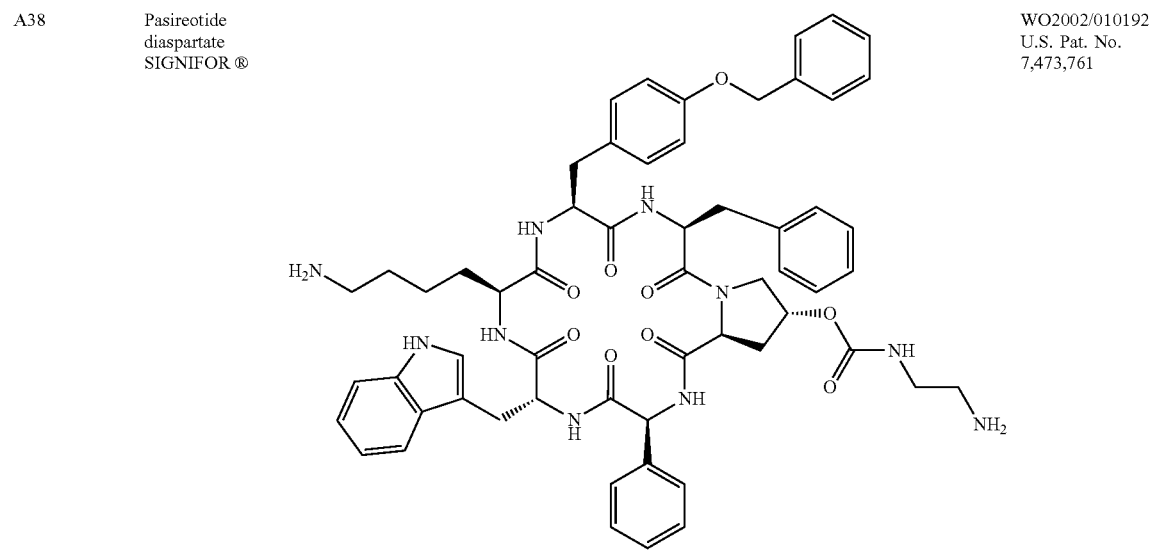 | WO2002/010192 U.S. Pat. No. 7,473,761 |

| Compound Designation | Generic Name Tradename | Compound Structure | Patents/Patent Application Publications |
|---|---|---|---|
| A39 | Dovitinib | 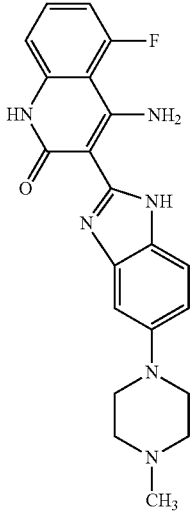 [SMILES: CN1CCN(c2ccc3[nH]c(-c4c(N)c5c(F)cccc5[nH]c4=O)nc3c2)CC1] | WO 2009/115562<br>U.S. Pat. No. 8,563,556 |
| A40 | | 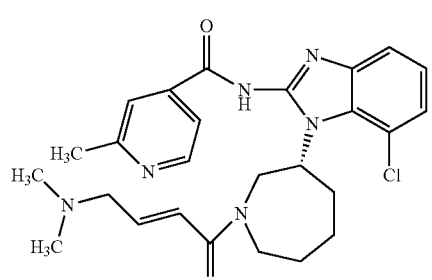 | WO 2013/184757 |
| A41 | | 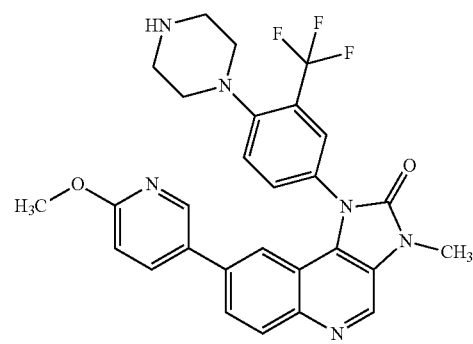 | WO 2006/122806 |

-continued
| Compound Designation | Generic Name Tradename | Compound Structure | Patents/Patent Application Publications |
|---|---|---|---|
| A42 | | 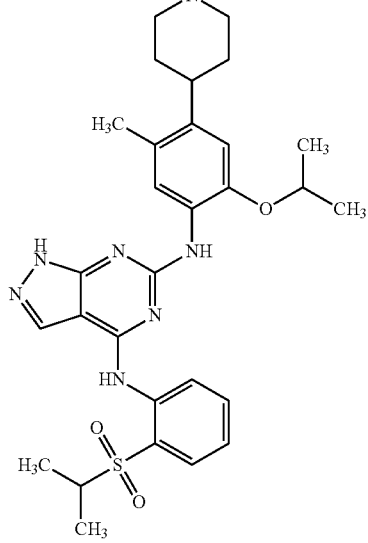 | WO 2008/073687 U.S. Pat. No. 8,372,858 |
| A43 | | 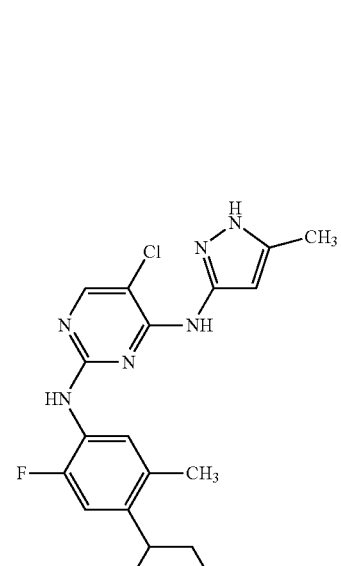 | WO 2010/002655 U.S. Pat. No. 8,519,129 |

-continued
| Compound Designation | Generic Name Tradename | Compound Structure | Patents/Patent Application Publications |
|---|---|---|---|
| A44 | | 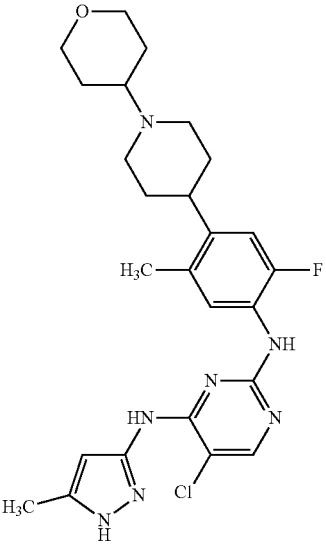 [SMILES: Cc1cc(Nc2nc(Nc3cc(C)c(C4CCN(C5CCOCC5)CC4)cc3F)ncc2Cl)n[nH]1] | WO 2010/002655 U.S. Pat. No. 8,519,129 |
| A45 | | 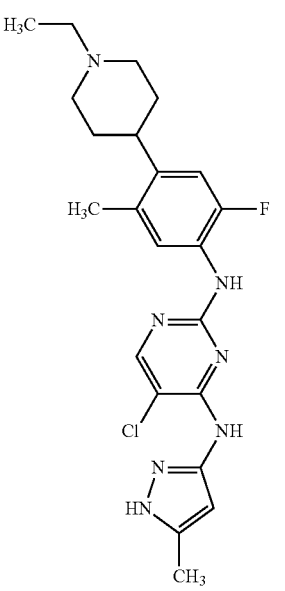 [SMILES: CCN1CCC(c2cc(F)c(Nc3ncc(Cl)c(Nc4cc(C)[nH]n4)n3)cc2C)CC1] | WO 2010/002655 |

-continued

| Compound Designation | Generic Name Tradename | Compound Structure | Patents/Patent Application Publications |
|---|---|---|---|
| A46 | Valspodar AMDRAY ™ | 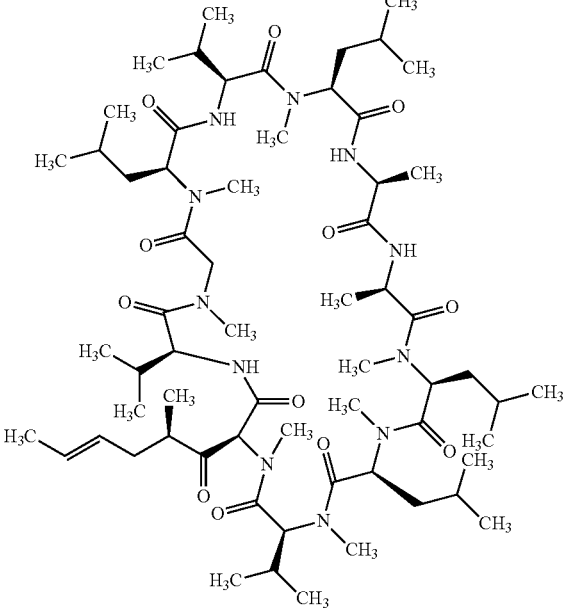 [SMILES: C/C=C/C[C@@H](C)C(=O)[C@H]1C(=O)N[C@@H](C(C)C)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C] | EP 296122 |
| A47 | Vatalanib succinate | 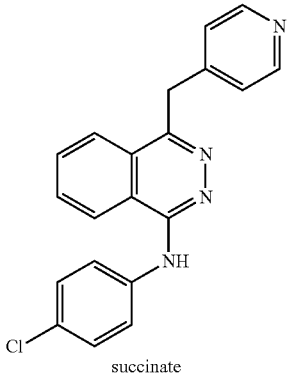 succinate | WO 98/35958 |
| A48 | | IDH inhibitor | WO2014/141104 |
| A49 | | BCR-ABL inhibitor 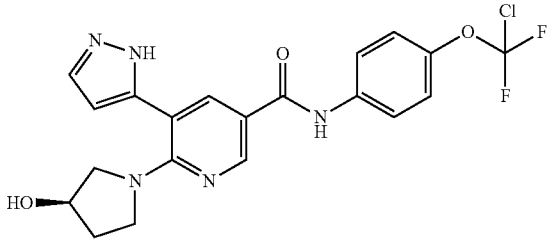 [SMILES: O=C(Nc1ccc(OC(F)(F)Cl)cc1)c1cnc(N2CC[C@@H](O)C2)c(-c2ccn[nH]2)c1] | WO2013/171639 WO2013/171640 WO2013/171641 WO2013/171642 |
| A50 | | cRAF inhibitor | WO2014/151616 |
| A51 | | ERK1/2 ATP competitive inhibitor | PCT/US2014/062913 WO2015066188 A1 |

EXAMPLES

The Examples below are set forth to aid in the understanding of the inventions but are not intended to, and should not be construed to limit its scope in any way.

Example 1: Humanization of Anti-PD-L1 Antibody, BAP058

Murine anti-PD-L1 monoclonal antibody BAP058 was humanized. The sequences and test samples of seventeen humanized BAP058 clones with unique variable region sequences were obtained. These clones were further analyzed for their biological functions (e.g., antigen binding and ligand blocking), structural features, and transient expression in CHO cells.

Example 1.1: Humanization Technology and Process

Humanization of BAP058 was performed using a combinatorial library of human germline variable region frameworks (FWs). The technology entails transferring the murine CDRs in frame to a library of human variable regions (VRs) that had been constructed by randomly combining human germ line FW1, FW2 and FW3 sequences. Only one FW4 sequence was used, which is WGQGTTVTVSS (SEQ ID NO: 154) for the heavy chain (HC) (Kabat human HC subgroup I, No. 21) and FGQGTKVEIK (SEQ ID NO: 186) for the light chain (LC) (Kabat human κ subgroup I, No. 5). The library of VR sequences was fused to human constant region (CR) sequences, human IgG4(S228P) of HC and human κ CR of LC, and the resulting library of whole IgG mAbs was expressed in CHO cells for screening. Screening was performed with tissue culture supernatants measuring binding avidity on antigen-expressing cells in a whole cell ELISA format or on FACS.

The humanization process was performed in a stepwise manner starting with the construction and expression of the appropriate chimeric mAb (murine VR, IgG4(S228P), human κ), which can serve as a comparator for the screening of the humanized clones. The constant region amino acid sequences for human IgG4(S228P) heavy chain and human kappa light chain are shown in Table 3.

Humanization of the VR of LC and HC were performed in two independent steps. The library of humanized LC (huLC) was paired with the chimeric HC (murine VR, IgG4(S228P)) and the resulting "half-humanized" mAbs were screened for binding activity by ELISA. The huLC of clones with adequate binding activity (≥binding of chimeric mAb) were selected. Analogously, the library of humanized HC (huHC) was paired with the chimeric LC (murine VR, human κ) and screened for binding activity by ELISA. The huHC of clones with appropriate binding activity (≥binding of chimeric mAb) were selected.

The variable regions of the selected huLC and huHC were then sequenced to identify the huLC and huHC with unique sequences (some clones from the initial selection process may share the same LC or HC). The unique huLC and huHC were then randomly combined to form a small library of humanized mAbs (humAbs), which was expressed in CHO cells and screened on antigen-expressing cells in an ELISA and FACS format. Clones with binding activities that were equal or better than the binding of the chimeric comparator mAb are the final product of the humanization process.

Example 1.2: Sequence of Murine mAb BAP058

The LC and HC variable region sequences of murine anti-PD-L1 mAb were determined. The sequences obtained from two independent analyses were identical and are shown in FIG. 1.

Germline analysis was performed and part of the result is shown in FIG. 2 as an amino acid sequence alignment. For the light chain, the V-gene is 99.28% identical to mIGKV6-23*01F (277/279 nts) and the J-gene is 97.06% identical to mIGKJ5*01F (33/34 nts). For the heavy chain, the V-gene is 96.88% identical to mIGHV1-72*01F (279/288 nts), the J-gene is 92.45% identical to mIGHJ4*01F, and the D-gene is mIGHD2-5*01F.

Example 1.3: Construction of Chimeric Antibody

A chimeric antibody was prepared by cloning the HC and LC variable domains into a mammalian expression vector in frame with a either a secretion signal and a human kappa constant region (LC) or a secretion signal and a human IgG4 constant domain (HC). The resulting antibody was empty vector were transfected into CHO—S cells. Cell culture supernatant was collected at 48 hours post transfection and the concentration of the recombinant clones in the supernatant was determined by quantitation ELISA. IgG in the cell culture supernatant was captured on the plate with anti-human-IgG Fc antibody. Bound IgG was detected with anti-human-IgG conjugated with HRP. Concentration of the IgG was calculated using commercial available human IgG4 as standard.

Binding of the recombinant clone to human PD-L1 was tested using the 300.19 cell line expressing huPD-L1 on the cell surface and FACS analysis. The result indicated that the chimera bound well to the antigen.

The amino acid sequences of the heavy and light chains for chimeric mAb BAP058-chi are shown in Table 1. The nucleotide sequences of the heavy and light chains for chimeric mAb BAP058-chi are shown in Table 1.

Example 1.4: Humanized Antibody Clones

As shown in FIG. 3, the process of humanization yielded seventeen clones with binding affinities comparable to that of the chimeric antibody. In addition to binding data, for each clone, the VR sequences were provided along with a sample of the mAb. The samples had been prepared by transient transfections of CHO cells and were concentrated tissue culture supernatants. The antibody concentrations in the solutions had been determined by an IgG4-specific ELISA.

As shown in FIG. 4, the seventeen unique clones are combinations of nine unique HC sequences and nine unique LC sequences. For the HC and LC FW regions, four to seven different germ line sequences were used by the 17 humanized clones. The amino acid and nucleotide sequences of the heavy and light chain variable domains for the humanized BAP058 clones are shown in Table 1. The amino acid and nucleotide sequences of the heavy and light chain CDRs of the humanized BAP058 clones are also shown in Table 1.

FIG. 4 indicates that the samples varied in the concentration of the mAb, ranging from 0.5 µg/mL to 47.6 µg/mL. These numbers were representative of several transient expression experiments.

Example 1.5: Analysis of Humanized Clones

Example 1.5.1: Analysis of Binding Activity and Binding Specificity

The binding activity and specificity was measured in a competition binding assay using a constant concentration of Alexa 488-labeled murine BAP058, serial dilutions of the test antibodies, and PD-L1-expressing 300.19 cells. Incubations with the mAb mixtures having different concentration ratios of test mAb to labeled mAb was at 4° C. for 30 min. Bound labeled murine mAb was then quantified using a FACS machine. The experiment was performed twice. The results are shown in FIG. 5. Fluorescence intensity is plotted the ratio of concentrations of test mAb over labelled murine BAP058. FIG. 6 lists ratios for the $IC_{50}$ value for each mAb. The ratio for the murine parent mAb was close to 1 (actual value is 1.34), which indicates that the labelled murine BAP058 mAb had not lost binding affinity.

The ratios of the test mAbs were in the range from 1.3 to 4.64, suggesting that the binding strength could vary by about threefold between the different clones. These results correlated well with semi-quantitative ranking derived from FACS data in FIGS. 3 and 5. Human BAP058 clones with a high ranking number (poorer binders) had a high ratio in the competition binding assay.

Example 1.5.2: Sequence Analysis

Based on structural features, the seventeen humanized mAbs were divided into six groups and ranked from 1-17. The results are shown in FIG. 6.

Example 1.5.3: Selection of Humanized Clones

FIG. 6 summarizes the data which was considered for the selection of humanized clones. Expression data ($2^{nd}$ column), the diversity in the composition of the variable regions ($3^{rd}$ column), relative rankings in binding studies ($4^{th}$ and $5^{th}$ columns), and structural analysis ($6^{th}$ column), were considered.

Selected clones were produced in higher amounts (0.5 mg; transient expression in CHO cells) and purified by Protein A affinity chromatography. Samples were shown to be endotoxin-free.

Example 1.5.4: Blocking of Binding of PD-1-Ig to PD-L1-Transfected 300.19 Cells The six preferred human BAP058 mAbs were tested for their capacity to block PD-1-Ig binding to PD-L1-expressing 300.19 cells. In a competition binding experiment, PD-L1-expressing 300.19 cells were incubated with mixtures of a constant concentration of PE-labelled PD-1-Ig (0.7 µg/mL) and increasing concentrations of test mAbs at 4° C. for 4 hours. Bound fluorescence was then measured using FACS and $IC_{50}$ values determined using Prism software.

All human BAP058 mAbs and the murine BAP058 mAb yielded similar competition binding curves. The $IC_{50}$ values vary over a narrow range from 0.29 nM to 0.33. The murine BAP058 parent mAb shows an $IC_{50}$ value of 0.30 nm. The results are shown in FIG. 7.

Summary and Conclusions

Murine anti-PD-L1 monoclonal antibody, BAP058, was humanized. The technology entails the cloning of the murine CDRs in-frame into an ordered library of human germ line variable region frameworks, expressing the library of cloned variable regions as intact IgG4(S228P) humanized mAbs in CHO cells, and selecting clones that bind with comparable or higher affinity to the target as the parent mAb. Therefore, the murine CDRs were asked to select proper human germline framework sequences that preserve their conformations and thus the binding affinity and specificity of the parent murine mAb. The sequences and test samples of seventeen humanized mAbs with unique variable region sequences were obtained, which had passed a binding test with PD-L1-transfected 300.19 cells. These clones were further analyzed for their biological functions (e.g., binding and blocking of the interaction with PD-1), structural features, and transient expression in CHO cells.

Example 2: Expression of Humanized Anti-PD-L1 Antibody, BAP058

Five humanized clones described in Example 1 were selected for evaluation of expression in Chinese Hamster Ovary (CHO) cells.

Single gene vectors (SGVs) were constructed using Lonza's GS Xceed vectors (IgG4proΔk for heavy chain and Kappa for light chain). The SGVs were amplified and transiently co-transfected into CHOK1SV GS-KO cells for expression at a volume of 2.8 L.

Expression cultures were harvested Day 6 post-transfection and clarified by centrifugation and sterile filtration. The clarified cell culture supernatant was purified using one-step Protein A chromatography. Product quality analysis in the form of SE-HPLC, SDS-PAGE, IEF, and LAL was carried out using purified material at a concentration of 1 mg/ml including an antibody as a control sample.

Example 2.1: Vector Construction

The sequences of the light and heavy chain variable domain encoding regions were synthesised by GeneArt AG. Light chain variable domain encoding regions were sub-cloned into pXC-Kappa and heavy chain variable domain encoding regions into pXC-IgG4pro AK vectors respectively using the N-terminal restriction site Hind III and the C-terminal restriction sites BsiWI (light chain) and ApaI (heavy chain). 5 µg of lyophilised shuttle vectors, were resuspended in 50 µl endotoxin free, sterile water. 1 µg of DNA was digested with the relevant restriction enzymes in a total volume of 50 µl and samples were incubated for 2 hours at 37° C. 8.3 µl of 6×DNA loading buffer was added and samples electrophoresed at 120 V for 40 min on a 1% w/v agarose gel stained with ethidium bromide. 10 µl Lonza SimplyLoad Tandem DNA ladder was used as reference ladder.

The relevant fragments were gel-extracted using a QIAquick gel extraction kit (QIAGEN, 28704) according to manufacturer's instructions. Ligations were performed using Roche's quick ligation kit with a 1:12 ratio of vector backbone to insert DNA, 1 µl T4 quick ligase, 10 µl of 2× T4 quick ligation buffer, reaction volume adjusted to 21 µl with endotoxin-free, sterile water when necessary and samples were incubated at room temperature for 10 minutes. 10 µl aliquots of the ligation reactions were used to transform One Shot Top 10 Chemically Competent *Escherichia coli* cells (Invitrogen, C404003) using the heat-shock method according to manufacturer's instructions. Cells were spread onto ampicillin-containing (50 µg/ml) Luria Bertani agar plates (Select APS LB Broth base, BD 292438 and Bactiological Agar, Sigma Aldrich A5306) and incubated overnight at 37° C. until bacterial colonies were evident.

Single bacterial colonies were picked into 15 ml Luria Bertani (LB) medium (Select APS LB Broth base, BD 292438), containing 50 µg/ml ampicillin and incubated at 37° C. for 6 hours with shaking. Vector DNA was isolated from 10 ml of these growth cultures using the QIAGEN miniprep system and eluted in 30 µl EB buffer. Positive clones were identified by digestion with HindIII and EcoRI and confirmed by nucleotide sequencing and nucleotide sequencing of the gene of interest.

Example 2.2: DNA Amplification

A single bacterial colony was picked into 15 ml Luria Bertani (LB) medium containing 50 µg/ml ampicillin and incubated at 37° C. overnight with shaking at 220 rpm. The resulting starter culture was used to inoculate 1 L Luria Bertani (LB) medium containing 50 μg/ml ampicillin and incubated at 37° C. overnight with shaking at 220 rpm. Vector DNA was isolated using the QIAGEN Plasmid Plus Gigaprep system (QIAGEN, 12991). In all instances, DNA concentration was measured using a Nanodrop 1000 spectrophotometer (Thermo-Scientific) and adjusted to 1 mg/ml with EB buffer (10 mM Tris-C1, pH 8.5). DNA quality for the single gene vectors was assessed by measuring the absorbance ratio A260/A280 and was found to be between 1.88 and 1.90. DNA concentration was adjusted to 1 mg/ml with EB buffer.

Example 2.3: Culture of CHOK1SV GS-KO Cells

CHOK1SV GS-KO cells were cultured in CD-CHO media (Invitrogen, 10743-029) supplemented with 6 mM glutamine (Invitrogen, 25030-123). Cells were incubated in a shaking incubator at 36.5° C., 5% $CO_2$, 85% humidity, 140 rpm. Cells were routinely sub-cultured every 3-4 days, seeding at $2 \times 10^5$ cells/ml and were propagated in order to have sufficient cells available for transfection. Cells were discarded by passage 20.

Example 2.4: Transient Transfections of CHOK1SV GS-KO Cells

Transient transfections were performed using CHOK1SV GS-KO cells which had been in culture a minimum two weeks. Cells were sub-cultured 24 h prior to transfection and cell viability was >99% at the time of transfection.

All transfections were carried out via electroporation using a Gene Pulse MXCell (Bio-Rad), a plate based system for electroporation. For each transfection, viable cells were resuspended in pre-warmed media to $2.86 \times 10^7$ cells/ml. 80 μg DNA (1:1 ratio of heavy and light chain SGVs) and 700 μl cell suspension were aliquotted into each cuvette/well. Cells were electroporated at 300 V, 1300 μF. Transfected cells were transferred to pre-warmed media in Erlenmeyer flasks and the cuvette/wells rinsed twice with pre-warmed media which was also transferred to the flasks. Transfected cell cultures were incubated in a shaking incubator at 36.5° C., 5% $CO_2$, 85% humidity, 140 rpm for 6 days. Cell viability and viable cell concentrations were measured at the time of harvest using a Vicell automated cell counter. Upon harvest of the cell culture, the cell density and viability ($>7.72 \times 10^6$ cell/ml; >92.5% on Day 6) was found to be within typically observed range.

Example 2.5: Protein A Affinity Chromatography

Cell culture supernatant was harvested and clarified by centrifugation at 2000 rpm for 10 min, then filtered through a 0.22 μm PES membrane filter. Clarified supernatant was purified using a pre-packed 5 ml HiTrap MabSelect SuRE column (GE Healthcare, 11-0034-94) on an AKTA purifier (10 ml/min). The column was equilibrated with 50 mM sodium phosphate, 125 mM sodium chloride, pH 7.0 (equilibration buffer) for 5 column volumes (CVs). After sample loading, the column was washed with 2 CVs of equilibration buffer followed by 3 CVs of 50 mM sodium phosphate, 1 M sodium chloride pH 7.0 and a repeat wash of 2 CVs of equilibration buffer. The product was then eluted with 10 mM sodium formate, pH 3.5 over 5 to 15 CVs. Protein containing, eluted fractions were immediately pH adjusted to pH 7.2 and filtered through a 0.2 μm filter. Once eluted, the pH of the elution fractions was adjusted to pH 7.4. The product was then concentrated using Amicon Ultra-4 Centrifugal Filter Unit (30 k Da MWCO) (UFC903024), to between 5 and 10 mg/ml.

A single protein-containing peak was observed during the elution phase. This peak was shown to contain the mAb, when analyzed by SE-HPLC and SDS-PAGE. Post concentrating protein yield is shown in Table 4. The clones expressed transiently in a range from 8.25 to 13.21 mg/L. The BAP058 antibody variants displayed a slow elution profile (tailing) under the standard elution conditions (10 mM sodium formate, pH 3.5 for 5 column volumes), requiring an additional 5 to 10 column volumes of elution buffer for the UV signal to drop to below 50 mAU.

TABLE 4

Summary of yield, titre, monomer content and endotoxin levels

| Product | Yield* (mg) | Titre* (mg/L) | Monomer Content (%) | Endotoxin levels (EU/mg) |
|---|---|---|---|---|
| Clone K | 37.0 | 13.21 | 86.23 | 0.191 |
| Clone L | 29.4 | 12.25 | 98.04 | 0.084 |
| Clone M | 25.0 | 8.92 | 84.57 | 0.193 |
| Clone N | 19.8 | 8.25 | 91.48 | 0.122 |
| Clone O | 25.74 | 9.19 | 93.70 | <0.050 |

*Post Protein A purification

Example 2.6: SE-HPLC Analysis

Duplicate samples of Protein A purified antibodies were analysed by SE-HPLC on an Agilent 1200 series HPLC system, using a Zorbax GF-250 4 μm 9.4 mm ID×250 mm column (Agilent). Aliquots of sample at a concentration of 1 mg/ml were filtered through a 0.2 μm filter prior to injection. 80 μl aliquots were injected respectively and run at 1 ml/min for 15 minutes. Soluble aggregate levels were analysed using Chemstation (Agilent) software.

Chromatography profiles with retention time showing the percentage of the overall detected peak areas were obtained for the tested antibodies and a control IgG4 antibody. The products show a single protein peak at approximately 9.05 to 9.07 min comparable to the human IgG4 antibody control (about 9.03 min) and consistent with a monomeric antibody Varying amounts (up to 15.4%) of higher molecular weight impurities, consistent with soluble aggregates, were detected at retention times between 8.29 and 8.45 min. All products displayed a similar retention profile but with varying monomeric levels detected in the range of 84.6-98.0% of total protein content. Clones K and M showed the highest amount of impurities with retention times consistent for dimeric antibodies (soluble aggregates) of approximately 15%, while Clone L showed the least (1.96%).

Example 2.7: SDS-PAGE Analysis

Reduced and non-reduced samples of Protein A purified antibody were prepared for analysis by mixing with NuPage 4×LDS sample buffer (Invitrogen, NP0007) and NuPage 10× sample reducing agent (Invitrogen, NP0009), and incubated at 70° C., 10 min. For non-reduced samples, the reducing agent and heat incubation were omitted. Samples were electrophoresed on 1.5 mm NuPage 4-12% Bis-Tris Novex pre-cast gels (Invitrogen, NP0335PK2) with NuPage MES SDS running buffer under denaturing conditions. 10 μl aliquots of SeeBlue Plus 2 pre-stained molecular weight standard (Invitrogen, LC5925) and a control IgG4 antibody at 1 mg/ml were included on the gel. 1 µl of each sample at 1 mg/ml were loaded onto the gel. Once electrophoresed, gels were stained with InstantBlue (TripleRed, ISB01L) for 30 min at room temperature. Images of the stained gels were analysed on a BioSpectrum Imaging System (UVP).

The analysis confirms the presence of the antibodies. Under non-reducing conditions, a predominant protein band greater 98 kDa is observed comparable with the control IgG4 antibody. The control IgG4 antibody displays an additional fainter band corresponding to a heavy plus light chain half-antibody at approximately 70 kDa under non-reducing conditions. This is expected for the control antibody. Two bands were observed under reducing conditions consistent with the size of heavy (close to the position of the 49 kDa marker) and light chains (close to the position of the 28 kDa marker) and comparable with the bands found for the control IgG4 antibody.

Example 2.8: Iso-Electric Focussing (IEF) Analysis

Non-reduced samples of Protein A purified antibody were electrophoresed as described below.

5 µg of Protein A purified samples were electrophoresed on a 1.0 mm Novex pH 3-10 gradient gel (Invitrogen, EC66552BOX) using manufacturers recommended running conditions. A 10 µl aliquot of IEF pH 3-10 markers (Invitrogen, 39212-01) was included on the gel. Once electrophoresed, gels were fixed with 10% TCA solution for 30 min and then stained with InstantBlue (TripleRed, ISB01L) over night at room temperature. Images of the stained gels were analysed on a BioSpectrum Imaging System (UVP).

As shown in Table 5, the test clones showed charge isoforms greater than pH 7.8. The detected charge isoforms were slightly more basic than the theoretically calculated isoelectric points (pIs) for these antibodies which were predicted to be between 7.72 and 8.21. This general shift to more basic charge isoforms suggests the presence of post-translational modifications such as glycosylation on the molecules. Clones K and M, L and N, show comparable charge isoforms, consistent with their theoretically calculated pI being the same for both pairs (7.72 for K and M, 7.87 for L and N). The pI for Clone O was not possible to accurately detect, as it did not descend from the well in which it was loaded. The predicted isoelectric point for Clone O is 8.21 which is close to the detection limit (8.3) of this assay. Since the general trend appears to be a slight increase in the measured pI when compared to the predicted pI, this would suggest the actual pI is likely to be around 8.6 falling outside the detection limit. The control IgG4 antibody behaved as expected.

TABLE 5

Charge isoforms as detected by Novex IEF analysis

| Product | pI of predominant charge isoform* | Acidic charge isoforms* | Basic charge isoforms* |
|---|---|---|---|
| Clone K | 8.0 | 2x; 7.8 to 7.9 | 2x 8.2 to 8.3 |
| Clone L | 8.2 | 2x; 7.9 to 8.0 | 8.3 |
| Clone M | 8.0 | 2x 7.8 to 7.9 | 8.1 |
| Clone N | 8.3 | 2x 8.1 to 8.2 | 8.4 |
| Clone O | >8.3 | N/D | N/D |

*pI readings are estimated from the staining positions correlated against the IEF 3-10 marker.

Example 2.9: Endotoxin Analysis

Endotoxin levels of purified proteins were measured (at 1 mg/ml) using an Endosafe-PTS instrument, a cartridge based method based on the LAL assay (Charles River).

As shown in Table 4, the endotoxin content was found to range from 0.05 to 0.191 EU/mg.

Conclusion

GS single gene expression vectors for selected humanized anti-PD-L1 mAbs were constructed and used to transiently transfect CHOK1SV GS-KO cells. 2.4 to 2.8 liters of expression culture were incubated under standard conditions for 6 days and the resulting cell culture supernatant purified using Protein A chromatography. Post-purification and concentrating titres are indicated in Table 4 and were found to be ranging from 8.25 to 13.21 mg/L. The final yields ranged from 19.8 to 37 mg.

SDS-PAGE analysis indicated good levels of purity after the initial Protein A purification and buffer exchange while SE-HPLC analysis indicated the presence of soluble aggregates (up to 15.43%) in the products being predominantly consistent with dimeric antibody. Clones M and K showed elevated amounts of these higher molecular weight impurities (15.4% and 13.8% respectively).

Iso-electric focussing detected a number of charge isoforms for all mAbs. Clones K to N showed isoforms generally more basic when based on the theoretically calculated pI for these molecules indicating some level of post translation modification. The pI for Clone O could not be quantified accurately due to the measured pI exceeding the detection range of the gel.

The endotoxin levels for all samples were measured prior to provision of samples and found to be below 0.191 EU/mg.

Example 3: Characterization of Murine and Humanized Anti-PD-L1 Antibodies

Example 3.1: Characterization of Humanized Anti-PD-L1 Antibody

Binding Affinity and Specificity

The binding of an exemplary humanized anti-PD-L1 antibody on human PD-L1 protein was measured using Biacore method. The results are: Ka=$3.07 \times 10^5$ $M^{-1}s^{-1}$; Kd=$4.55 \times 10^{-5}$ $s^{-1}$; $K_D$=0.171 nM.

The binding of an exemplary humanized anti-PD-L1 antibody on cynomolgus PD-L1 protein was measured using Biacore method. The results are: Ka=$9.51 \times 10^5$ $M^{-1}$ $s^{-1}$; Kd=$4.55 \times 10^{-5}$ $s^{-1}$; $K_D$=0.124 nM.

The binding of an exemplary humanized anti-PD-L1 antibody on mouse PD-L1 protein was measured using Biacore method. The results are: Ka=$8.30 \times 10^6$ $M^{-1}s^{-1}$; Kd=$1.67 \times 10^{-4}$ $s^{-1}$; $K_D$=0.0202 nM.

The binding of an exemplary humanized anti-PD-L1 antibody on rat PD-L1 protein was measured using Biacore method. The results are: Ka=$9.45 \times 10^6$ $M^{-1}s^{-1}$; Kd=$1.23 \times 10^{-4}$ $S^{-1}$; $K_D$=0.168 nM.

The binding of the same humanized anti-PD-L1 antibody on human PD-L1-expressing 300.19 cells was measured using FACS analysis. The result shows that the anti-PD-L1 antibody (human IgG4) binds to human PD-L1 with a $K_D$ of 0.285 nM.

The binding of the same humanized anti-PD-L1 antibody on cynomolgus PD-L1-expressing 300.19 cells was measured using FACS analysis. The result shows that the anti-PD-L1 antibody (human IgG4) binds to human PD-L1 with a $K_D$ of 1.29 nM.

These results show that the exemplary anti-PD-L1 antibody binds with high affinity to human, mouse, rat and cynomolgus PD-L1.

Blocking of Interactions Between PD-1,1 and its Ligands

The ability of the exemplary humanized anti-PD-L1 antibody to block the interactions between PD-L1 and both of its known ligands, PD-1 and B7-1 was examined. The results show that the anti-PD-L1 antibody blocked the binding of PD-1 and B7-1 on human PD-L1-expressing 300.19 cells compared to human IgG4 isotype control and no antibody control. The anti-PD-L1 antibody blocked PD-1 binding on the 300.19 cells with an IC50 of 0.145 nM. The same antibody blocked B7-1 binding on the 300.19 cells with an IC50 of 0.1 nM.

Cellular Activity

The ability of the exemplary humanized anti-PD-L1 antibody to enhance the Staphylococcal enterotoxin B (SEB)-stimulated expression of IL-2 and IFNγ was tested in human whole blood ex vivo assay. Diluted human whole blood was incubated with the anti-PD-L1 antibody in the presence or absence of SEB at 37° C. for 48 hours prior to IFNγ and IL-2 measurement. The result shows that the anti-PD-L1 antibody increased SEB-stimulated IFNγ expression by 2.72±0.84 fold and increased IL-2 expression by 2.39±0.96 fold compared to a human IgG4 isotype control (25 μg/ml SEB; n=5 donors).

Example 4: Patient Selection Based on PD-L1/CD8/IFN-γ Status

Figure 10:
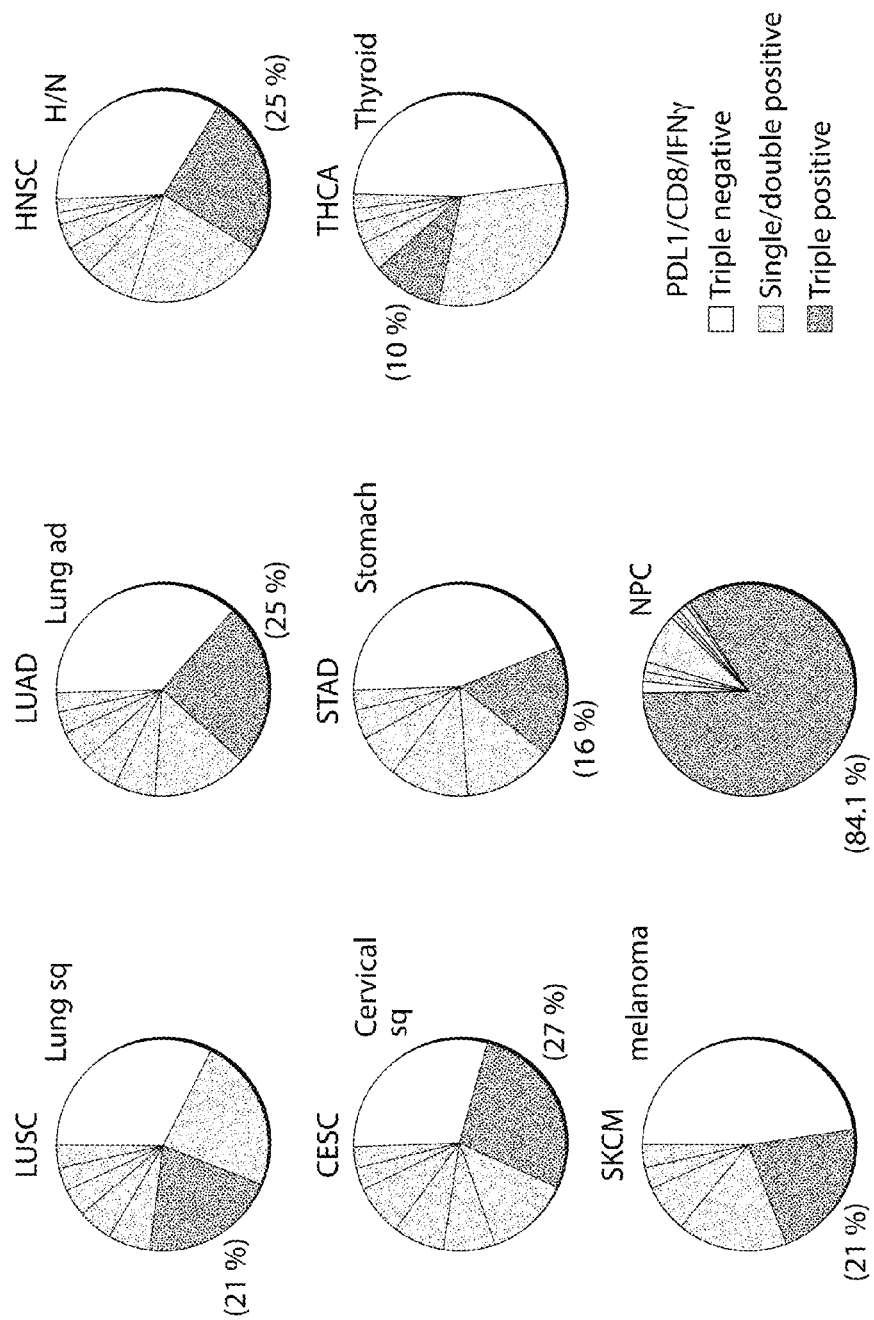
FIG. 10 shows exemplary cancers having relatively high proportions of patients that are triple-positive for PD-L1/CD8/IFN-γ.

For each of several types of cancer, samples from multiple patients were tested for PD-L1/CD8/IFN-γ status. Each sample was classified as: triple-negative for PD-L1/CD8/IFN-γ, single or double positive for these markers, or triple-positive for these markers. FIG. 10 shows that in this experiment, within a population of patients, the following types of cancer are frequently triple-positive for PD-L1/CD8/IFN-γ: Lung cancer (squamous), lung cancer (adenocarcinoma), head and neck cancer, cervical cancer (squamous), stomach cancer, thyroid cancer, melanoma, and nasopharyngeal cancer. Patients having these types of cancer are good candidates for therapy with anti PD-1 antibodies and combination therapies as described herein. The likelihood of successful treatment can be further boosted by determining which patients are triple-positive for PD-L1/CD8/IFN-γ, and treating the triple-positive patients with anti PD-L1 antibodies and combination therapies as described herein.

Figure 11:
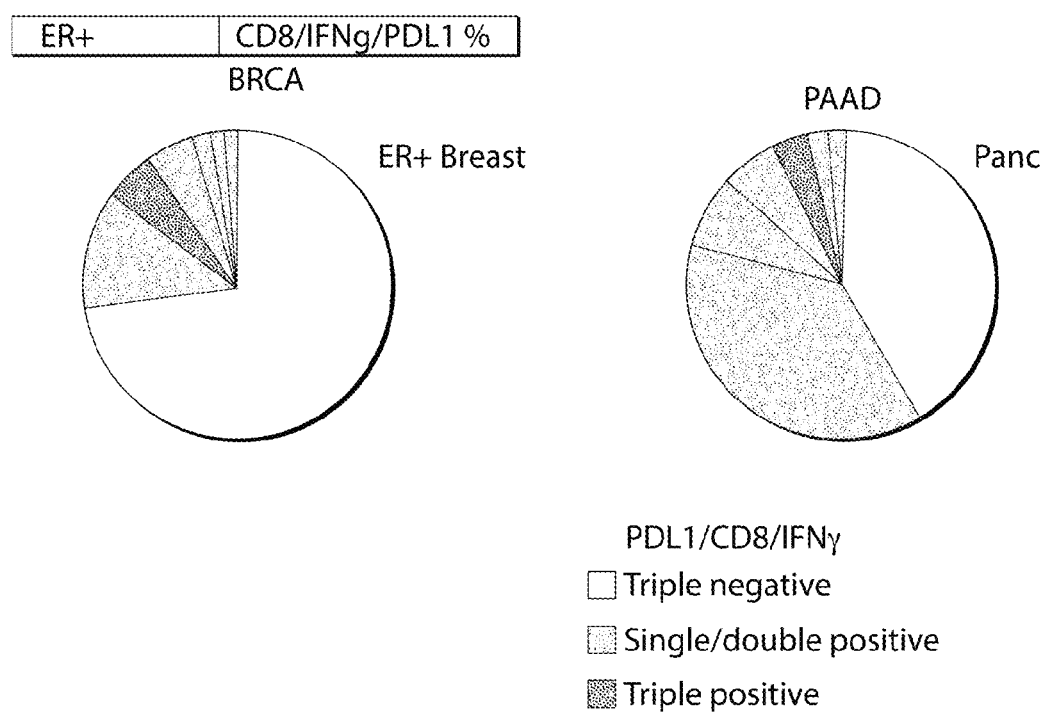
FIG. 11 shows exemplary ER+ breast cancer and pancreatic cancer having relatively low proportions for patients that are triple positive for PD-L1/CD8/IFN-γ.

FIG. 11 shows that within a population of patients, the following types of cancer are rarely triple positive for PD-L1/CD8/IFN-γ: ER+ breast cancer and pancreatic cancer. Notably, even in cancers that are generally not positive for PD-L1/CD8/IFN-γ, one can increase the likelihood of successful treatment by determining which patients are triple-positive for PD-L1/CD8/IFN-γ, and treating the triple-positive patients with anti PD-L1 antibodies and combination therapies as described herein.

Figure 12:
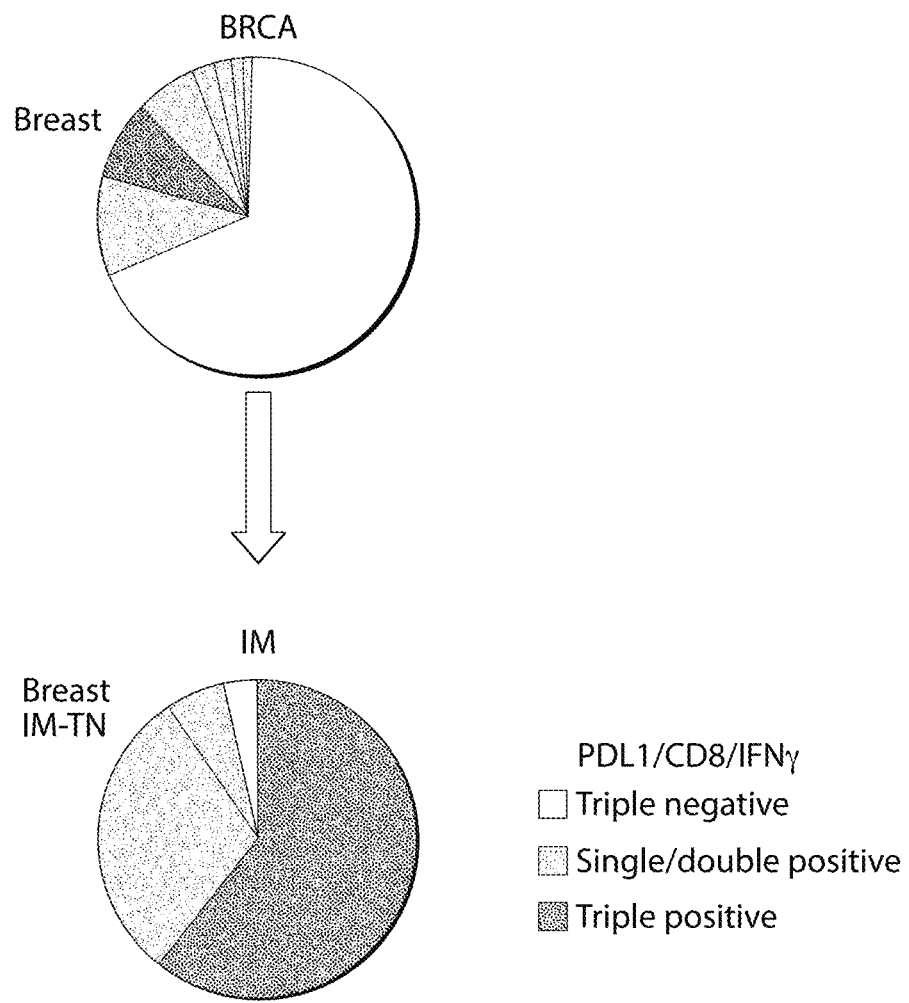
FIG. 12 shows the proportion of exemplary breast cancer patients that are triple positive for PD-L1/CD8/IFN-γ.

FIG. 12 shows the proportion of breast cancer patients that are triple positive for PD-L1/CD8/IFN-γ. Considering breast cancer in general, the proportion of triple-positives is somewhat low. However, when one focuses only on IM-TN breast cancer, it can be seen that a much larger percentage of patients is triple positive for PD-L1/CD8/IFN-γ. IM-TN breast cancer is particularly difficult to treat with conventional therapies. The discovery that IM-TN breast cancer is often triple-positive for PD-L1/CD8/IFN-γ opens up new avenues of therapy for this cancer with anti PD-L1 antibodies and combination therapies as described herein.

Figure 13:
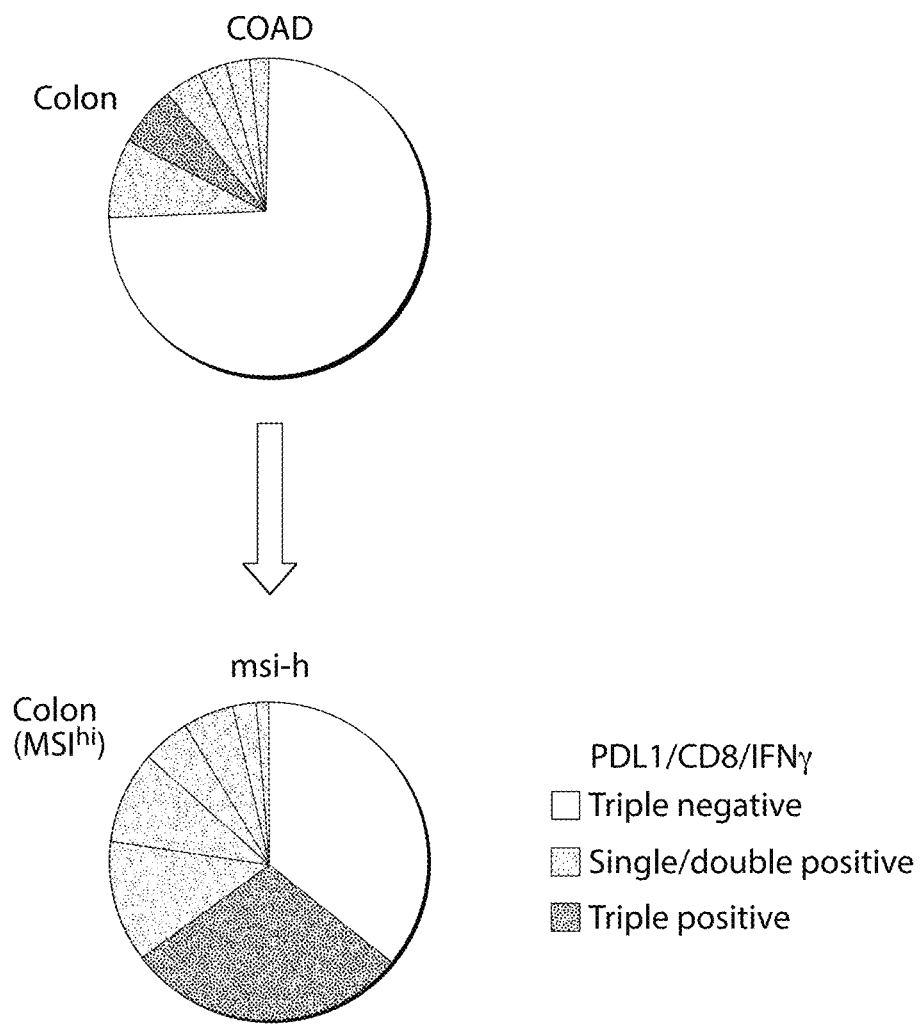
FIG. 13 shows the proportion of exemplary colon cancer patients that are triple positive for PD-L1/CD8/IFN-γ.

FIG. 13 shows the proportion of colon cancer patients that are triple positive for PD-L1/CD8/IFN-γ. Considering colon cancer in general, the proportion of triple-positive is somewhat low. However, when one focuses only on MSI-high (high microsatellite instability) breast cancer, it can be seen that a much larger percentage of patients is triple positive for PD-L1/CD8/IFN-γ. MSI levels can be assayed using, e.g., commercially available PCR-based methods.

Gastric cancer samples were tested for levels of PD-L1/CD8/IFN-γ (data not shown). It was found that in MSI-high or EBV+ gastric cancers, about 49% were positive for PD-L1, and a high proportion of the PD-L1-positive cells were triple positive for PD-L1/CD8/IFN-γ. It was also found that a proportion of PD-L1-positive cells and PD-L1/CD8/IFN-γ positive cells were also positive for PIK3CA. This finding suggests that these cancers may be treated with a PD-1 antibody, optionally in combination with a PIK3 therapeutic.

MSI-high CRC samples were tested for a combination of markers (data not shown). It was found that in MSI-high CRC samples, a high proportion of the PD-L1/CD8/IFN-γ samples are also positive for LAG-3, PD-1 (also called PDCD1), RNF43, and BRAF. This finding suggests that these cancers may be treated with a PD-1 antibody, optionally in combination with a therapeutic that targets one or more of LAG-3, PDCD1, RNF43, and BRAF.

Squamous cell lung cancers were tested for a combination of markers (data not shown). It was found that in squamous cell lung cancer samples, a high proportion of the PD-L1/CD8/IFN-γ samples are also positive for LAG-3. This finding suggests that these cancers may be treated with a PD-1 antibody, optionally in combination with a therapeutic that targets LAG-3, e.g., a LAG-3 antibody.

Papillary thyroid cancers were tested for a combination of markers including the BRAF V600E mutation (data not shown). It was found that a high proportion of thyroid cancer samples that are positive for PD-L1 are also positive for BRAF V600E. This finding suggests that these cancers may be treated with a PD-L1 antibody, optionally in combination with a therapeutic that targets BRAF.

Example 5: Patient Selection Based on PD-L1 Status

To enable broad examination of cancer indications for PD-1/PD-L1 based therapies, we evaluated PD-L1 expression at both the protein and mRNA level in human cancers including both lung and hepatic tumors.

PD-L1 protein expression was evaluated in a set of formalin-fixed paraffin-embedded non-small cell lung (NSCLC) adenocarcinoma (ACA), NSCLC squamous cell carcinoma (SCC), and hepatocellular carcinoma (HCC) tumors by immunohistochemistry (IHC). PD-L1 expression was scored semi-quantitatively by a manual histo-score (H-score) methodology based on staining intensity and percentage of positive tumor cells. In our IHC analysis, PD-L1 positivity (PD-L1+) was defined as an H-score ≥20. In parallel, PD-L1 mRNA expression data was examined from The Cancer Genome Atlas (TCGA) in these same indications (503 NSCLC ACA, 489 NSCLC SCC, and 191 HCC) and analyzed by comparing the expression in matched normal tissues from TCGA.

With RNAseq analysis, data was calculated as log 2 (RPKM+0.1) after RSEM normalization, utilizing OmicSoft RNASeq pipelines across TCGA tumor indications. The expression of PD-L1 is elevated in NSCLC ACA and SCC, relative to that in HCC. By overlaying the distributions and comparing the expression levels across all indications in TCGA, we ranked overexpression profiles for PD-L1 and found the TCGA HCC cohort to have much reduced PD-L1 mRNA levels, with a median level of −0.8 compared to 1.3 for ACA and 1.5 for SCC, which amounts to more than a 2-fold change of median level expression. With RNAseq, our analysis defines 50% of NSCLC adenocarcinoma, 54% of NSCLC squamous cell carcinoma, and 6% of HCC as high expressers for PD-L1.

Tumor cell PD-L1 protein expression was measured in 45 lung adenocarcinoma (ACA) samples, 47 lung squamous cell carcinoma (SCC) samples, and 36 hepatocellular carcinoma (HCC) samples. 16/45 (35.6%) lung ACA, 21/47 (44.7%) lung SCC were PD-L1 positive. In contrast, PD-L1 positivity was seen in only 2/36 (5.6%) HCC samples.

In summary, with IHC and RNAseq analysis in large and independent human NSCLC and HCC sample sets, we have found PD-L1 expression to be more enriched in NSCLC than in HCC. Within NSCLC, there are comparable findings between adenocarcinoma and squamous cell carcinomas. Importantly, amongst the large number of samples (128 for IHC and 1183 for RNAseq) in the 3 indications, very good concordance is observed between protein- and mRNA-based analyses. Our finding thus establishes the basis for large scale mRNA-based data mining in TCGA for indications and patient segments that may be enriched for responses to PD-1/PD-L1-based immune therapies.

Example 6: Effects of Targeted Agents on PD-L1 Modulation

This example evaluates the effects of selected therapeutic agents (e.g., a cMET inhibitor, a MEK inhibitor, a bRAF inhibitor, and an ALK inhibitor) on PD-L1 (CD274) modulation. Compound A17 can be prepared as disclosed in Example 21 of U.S. Pat. No. 8,420,645. The following compounds: Compound A18 (ruxolitinib phosphate), Compound A23 (ceritinib), Compound A34 (Binimetinib), and Compound A29 (Encorafenib) are available from Novartis AG, Basel, Switzerland. Selected therapeutic agents were examined by real time PCR and flow cytometry on PD-L1 levels. Significant inhibition of PD-L1 by Compound A17, Compound A18, Compound A34, Compound A29, and Compound A23 on tumor cells was observed.

Compound A17 Downregulation of PD-L1 Protein in Non-Small Cell Lung Cancer Cells PD-L1 (CD274) expression was analyzed in cancer cell lines treated with Compound A17. Cells were obtained from ATCC and cultured in vitro following ATCC directions. The cell lines used were previously characterized by the Cancer Cell Line Encyclopedia Project (http://www.broadinstitute.org/ccle/home).

Cells plated in six-well culture plates were treated with the Compound A17 at different concentrations (10 nM, 100 nM, and 1000 nM) for 24, 48 and 72 hours. Equal amount of vehicle (DMSO) was used as a control. Cells were washed with PBS and then harvested using a cell scraper.

For each reaction, 0.5-1×10⁶ cells were stained with 20 μL of anti-human monoclonal PD-L1-PE antibody, clone M1H1 (BD) for 30-60 minutes at 4° C. Cells were washed twice and data was acquired using a Canto II with FACSDiva software (BD Bioscience). Data analysis was performed using FlowJo software (Tree Star). Mean fluorescence intensity (MFI) was determined by gating on single cells. Unstained cells were used as a gating control.

Figure 14:
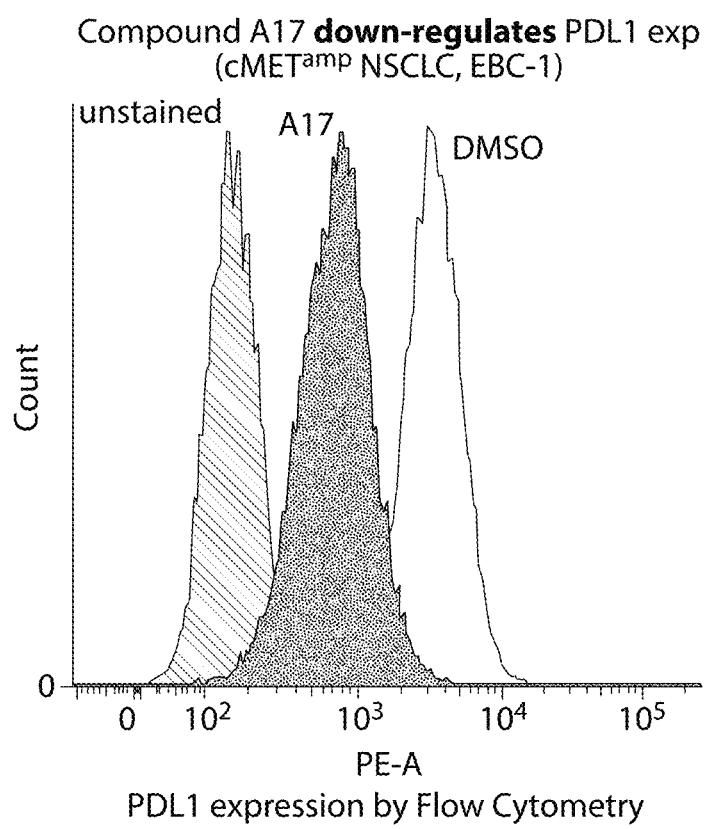
FIG. 14 shows a graphical representation of flow cytometry of PD-L1 surface expression in EBC-1 cells in vitro with or without Compound A17 treatment. EBC-1 cells are non-small cell lung cancer cells with a cMET amplification.
Figure 15:
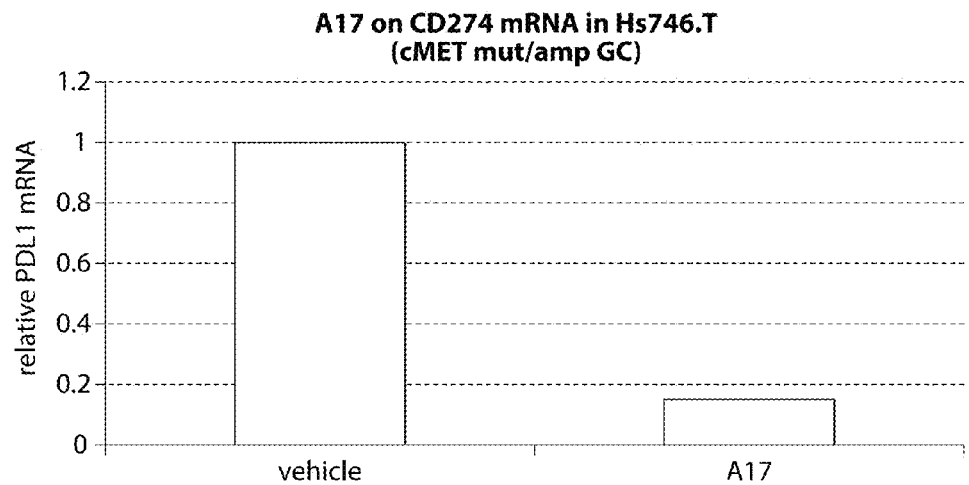
FIG. 15 shows a graphical representation of PD-L1 mRNA expression in Hs.746.T cells in a tumor xenograft model with or without Compound A17 treatment. Hs.746.T cells are gastric cancer cells with a c-MET amplification and a c-MET mutation.

In vitro treatment of EBC-1 cells (Non-Small Cell Lung Cancer (NSCLC) with cMET amplification) with Compound A17 led to significant downregulation of surface expression of PD-L1 as observed by flow cytometry (FIG. 14). The results presented herein suggest that Compound A17 functions as a PD-L1/PD-1 inhibitor.

Compound A17, Compound A34, Compound A18, Compound A29, and Compound A23 Downregulate PD-L1 mRNA TaqMan RT PCR assays were developed to detect changes of expression levels of PD-L1 (CD274) in cell lines and xenograft tumors. mRNA was isolated from frozen cell pellets or tumor fragments using the Qiagen RNeasy Mini kit. Isolated RNA was frozen at −80° C. RNA quality was checked and RNA was quantified using a 2100 Agilent Bioanalyzer following the protocol for the Agilent RNA 6000 Nano Kit. cDNA was prepared using a High Capacity RNA- to cDNA Kit (Applied Biosystems).

Real-time PCR reactions were carried out in 20 μl total volume, including 10 μl of Universal PCR master mix (Applied Biosystems), 1 μl of human PD-L1 (CD274) probe/primer set (Applied Biosystems), and 8 μl of cDNA. Each sample was run in triplicate. The amount of cDNA produced from 25-50 ng of RNA in the reverse transcription reaction was used in each PCR reaction. Due to difference in mRNA levels between PD-L1 and GAPDH, the two real-time PCR reactions were done in separate tubes using same amount of cDNA. The real-time PCR reaction was run on the C1000 Thermal Cycle (BioRad) with the cycle program as follows: a 10 minute incubation at 95° C. followed by 40 cycles of 95° C. for 15 seconds and 60° C. for 1 minute. After the reaction was complete, the PD-L1 average Ct was normalized relative to each Ct value from the GAPDH reference reaction. Each normalized logarithmic value was then converted into a linear value.

Figure 16:
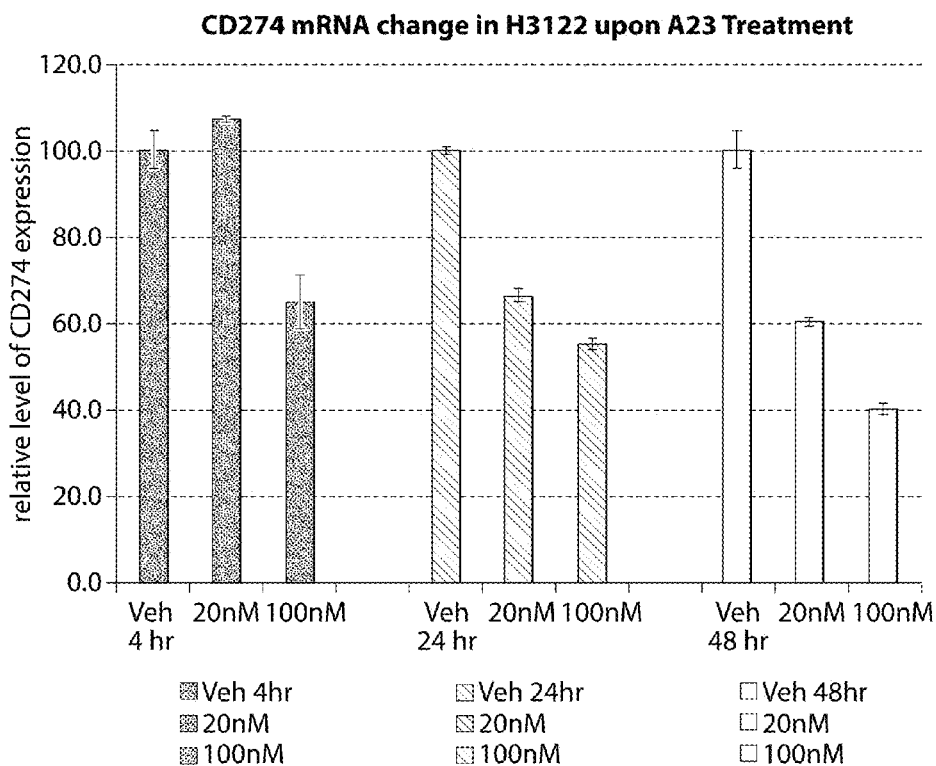
FIG. 16 shows a graphical representation of PD-L1 mRNA expression in H3122 cells in vitro with or without Compound A23. H3122 cells are non-small cell lung cancer (NSCLC) cells with an ALK translocation.
Figure 17:
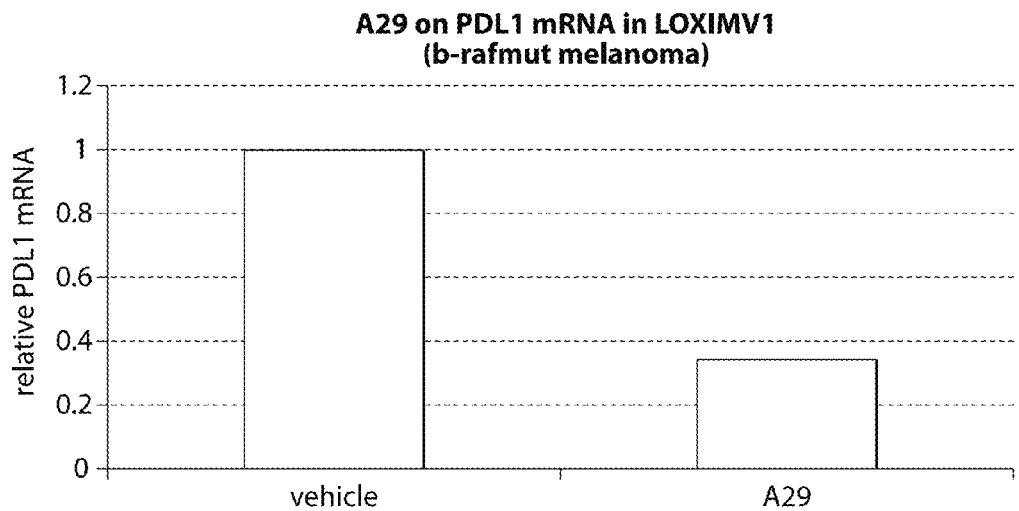
FIG. 17 shows a graphical representation of PD-L1 mRNA expression in LOXIMV1 cells (BRAF mutant melanoma cells) in a tumor xenograft model with or without Compound A29 treatment.
Figure 18:
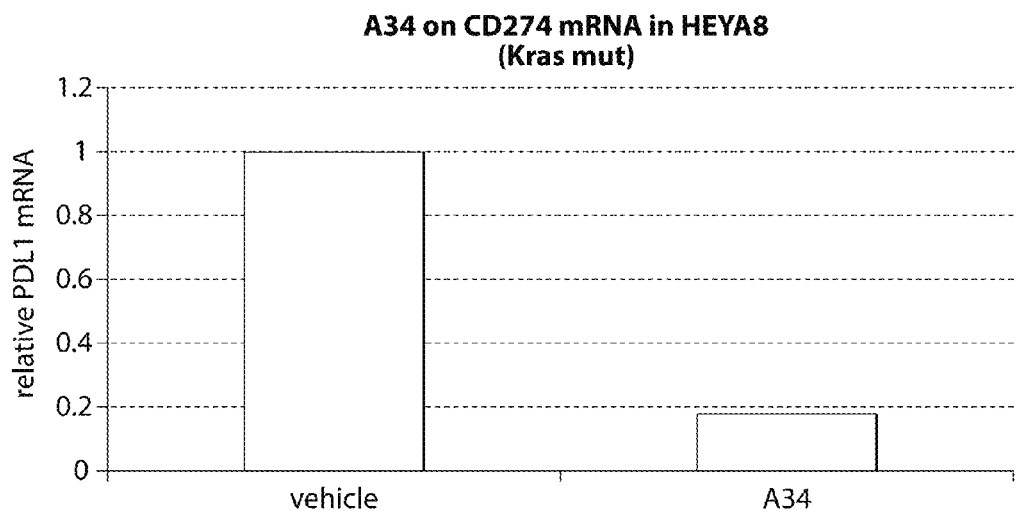
FIG. 18 shows a graphical representation of PD-L1 mRNA expression in HEYA8 cells (KRAS mutant ovarian cancer cells) in a tumor xenograft model with or without Compound A34 treatment.
Figure 19:
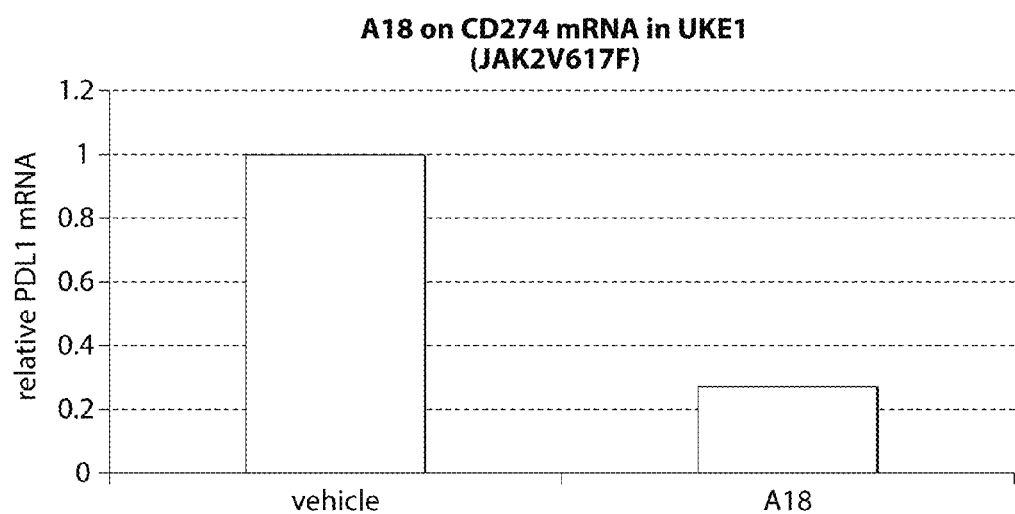
FIG. 19 shows a graphical representation of PD-L1 mRNA expression in UKE-1 cells (JAK2 V617F mutant myeloproliferative neoplasm cells) in a tumor xenograft model with or without Compound A18 treatment.

Inhibition of PD-L1 expression (mRNA) by Compound A17 was observed in a Hs.746.T tumor (gastric cancer cell with cMET amplification & mutation) xenograft (FIG. 16). Inhibition of PD-L1 mRNA by Compound A23 was observed in H3122 (Non-Small Cell Lung Cancer (NSCLC) with ALK translocation) in vitro (FIG. 17). Downregulation of PD-L1 mRNA by Compound A29, and Compound A34 was observed in tumor xenograft models bearing LOXIMV1 (BRAF mutant melanoma, FIG. 18) and HEYA8 (KRAF mutant ovarian cancer, FIG. 19) tumors, respectively. Downregulation of PD-L1 mRNA by Compound A18 was observed in tumor xenograft models bearing UKE-1 (Myeloproliferative Neoplasm (MPN) line with JAK2V617F mutation, FIG. 19).

The results presented herein demonstrate a role of Compound A17, Compound A34, Compound A18, Compound A29, and Compound A23 in the regulation of immunecheckpoint molecules on cancer. The observed inhibition of PD-L1 expression by these agents suggests that these targeted agents may have immune-modulatory activities, in addition to their effects on cancer signaling. Thus, the results presented herein suggest that administration of targeted agents with inhibitors of immunecheckpoint inhibitors such as PD-1, PD-L1, LAG-3 and/or TIM-3 will achieve a more potent reversal of the immunecheckpoint-mediated immune suppression.

Example 7: Mixed Lymphocyte Reaction with Monocyte Derived Dendritic Cells and Allogeneic CD4+ T Cells Peripheral blood mononuclear cells (PBMCs) were isolated from Buffy coats by standard procedures using a Ficoll gradient. The CD14+ monocyte fraction of the PBMCs was isolated by negative selection using the EasySep monocyte enrichment kit from StemCell following the supplier's instructions. In order to differentiate the monocytes into dendritic cells (DCs), the media was supplemented with 100 ng/ml human GM-CSF (BTP30538 produced at Novartis or commercially available from R&D) and 80 ng/ml human IL4 (BTP30884 produced at Novartis) and cells were incubated for 7 days at 37° C. and 5% $CO_2$. On day 7 of the monocyte-derived DC cultures, CD4+T lymphocytes were freshly enriched from PBMCs derived from a buffy coat obtained from a different donor (i.e., allogeneic). The CD4+ T cell fraction was isolated by negative selection using the Easysep CD4+ T cell enrichment kit from StemCell according to the manufacturer's instructions. DCs and the allogeneic enriched CD4+ T cells were then plated in U-bottomed 96-well plates at a ratio of 1:10 ($10^4$ DC and $10^5$ CD4 T cells/well) in the presence of the indicated antibodies and in triplicates. The tested antibodies included a control anti-chicken lysozyme huIgG4 (ACE14834). The co-cultures were then incubated for 5 days at 37° C. and 5% $CO_2$. On day 5, 100 µl of the supernatant was collected and stored at −20° C. for subsequent cytokine analysis. Stimulation Indexes (SI) for proliferation and IFNγ release in each experiment and for each antibody concentration tested were calculated by dividing the mean value of each readout measured for the test antibodies divided by the mean value measured for the human IgG4 anti-chicken lysozyme control antibody ACE14834. IFNγ and in the co-culture supernatants were measured by standard ELISA using commercially available ELISA kits.

Figure 21:
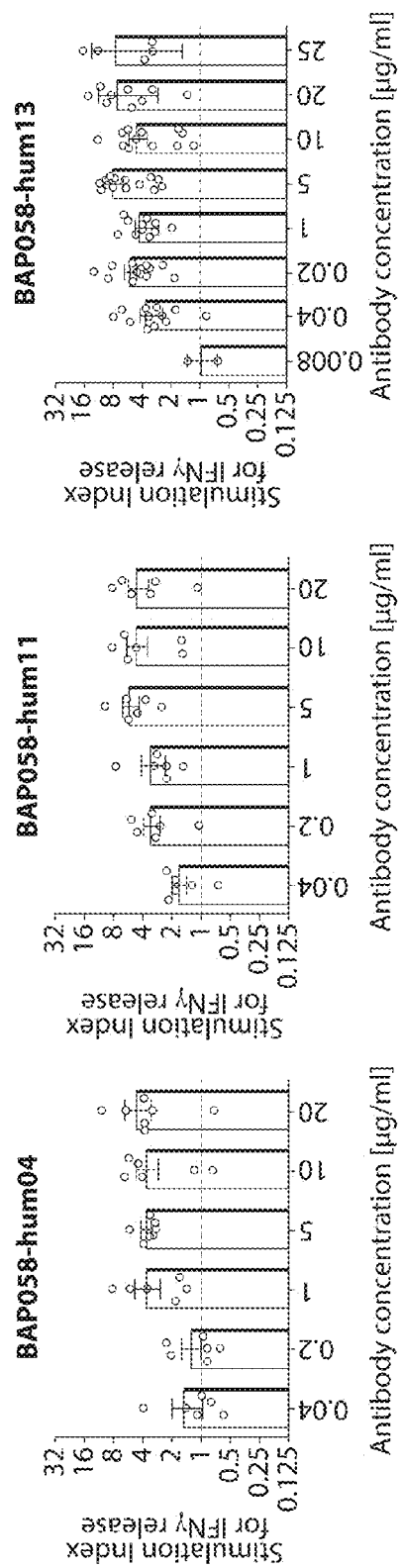
FIG. 21 depicts the effect of exemplary anti-PD-L1 antibodies on stimulation of IFN-γ release from co-cultures of dendritic cells and CD4+ T cells.

Exemplary anti-PD-L1 antibodies displayed a pronounced effect on the levels of IFNγ detectable in the supernatants collected on day 5 of the co-culture. As shown in FIG. 21, antibody treatment led to a dose-dependent increase in IFNγ release by an average factor of ~4-7 times the levels observed with an isotype control antibody at doses ranging between 0.04 µg/ml and 20 µg/ml.

Example 8: Superantigen T Cell Stimulation Assay

PBMCs were isolated from Buffy coats by standard procedures using a Ficoll gradient and resuspended at $2\times10^6$ cells/mL in T-cell culture Media. 200,000 cells/well were added to a 96-well round bottomed plate. SEB (Staph Enterotoxin B) was then added at 1 ng/mL final concentration. Test antibodies or human IgG4 isotype control were added at a final concentration of 25 ug/mL and the plate was incubated at 37° C., 5% $CO_2$ for 4 days. Supernatants were collected to measure IL-2 cytokine by MSD following the manufacturer's protocol. Data are shown from 5 human donors.

Figure 22:
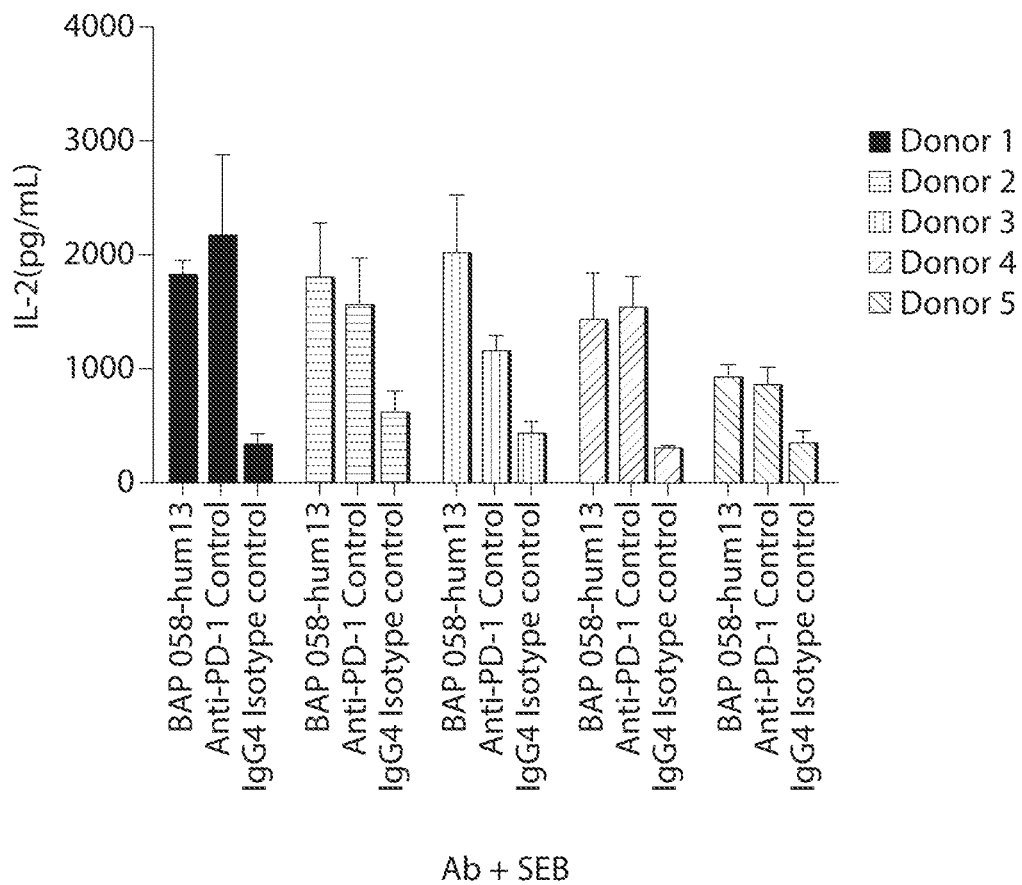
FIG. 22 depicts the effect of exemplary anti-PD-L1 antibodies on SEB-induced IL-2 secretion by T cells.

As shown in FIG. 22, exemplary anti-PD-L1 antibodies enhanced SEB-induced IL-2 secretion by T cells as compared to an isotype control Ab in all donors, with an average fold stimulation of 4.4±2.0 (n=5). Anti-PD-1 antibodies were used as a positive control in this assay and showed a similar effect to anti-PD-L1 antibodies.

Example 9: Cross Species Binding of Anti-PD-L1 Antibodies as Assessed by Biacore Anti-human Fab specific antibody was immobilized on CM5 chip (GE Cat: 28-9583-25). Immobilization was done at 25° C. using a flow rate of 10 µl/min. IgG was diluted at 2.5 µg/ml, capture for 30 sec, at flow rate of 100/min. Test antibody was captured on Flow cell FC2, FC3 and FC4. PD-L1 (rat, human, mouse or cyno) was flowed over: start concentration of PD-L1 are 100 nM 2-fold dilution: 100, 50, 25, 12.5, 6.25, 3.12, 1.56 and 0 nM. Run Biacore Wizards Kinetic/Affinity: association time 120 sec, dissociation 600 sec. (Running buffer HBS-EP+BSA 0.25 mg/ml, Regeneration buffer: 10 mM glycine HCl pH 2.1). Data analyses were done with Biacore T-100 Evaluation software version 2, fit on 1:1. The results are shown in Table 8.

TABLE 8

| Binding affinities of exemplary anti-PD-L1 antibodies to PD-L1 measured by Biacore | | | |
|---|---|---|---|
| Species | BAP058-hum13 | BAP058-hum11 | BAP058-hum04 |
| Human PD-L1 | 0.137 ± .035 nM | 0.931 ± .477 nM | 2.14 ± .289 nM |
| Monkey PD-L1 | 0.431 ± .289 nM | 0.735 ± .126 nM | 0.369 ± .175 nM |
| Mouse PD-L1 | 0.040 ± .007 nM | 0.075 ± .031 nM | 77.4 ± 18.5 nM |
| Rat PD-L1 | 0.431 ± .451 nM | 1.36 ± 2.02 nM | 6.14 ± 8.12 nM |

INCORPORATION BY REFERENCE

All publications, patents, and Accession numbers mentioned herein are hereby incorporated by reference in their entirety as if each individual publication or patent was specifically and individually indicated to be incorporated by reference.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

What is claimed is:

1. An antibody molecule capable of binding to human Programmed Death-Ligand 1 (PD-L1), comprising:
   (a) a heavy chain variable region (VH) comprising a VHCDR1 amino acid sequence of SEQ ID NO: 4; a VHCDR2 amino acid sequence of SEQ ID NO: 5, and a VHCDR3 amino acid sequence of SEQ ID NO: 3; and a light chain variable region (VL) comprising a VLCDR1 amino acid sequence of SEQ ID NO: 12, a VLCDR2 amino acid sequence of SEQ ID NO: 13, and a VLCDR3 amino acid sequence of SEQ ID NO: 14;
   (b) a VH comprising a VHCDR1 amino acid sequence of SEQ ID NO: 1; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 9, a VLCDR2 amino acid sequence of SEQ ID NO: 10, and a VLCDR3 amino acid sequence of SEQ ID NO: 11;
   (c) a VH comprising a VHCDR1 amino acid sequence of SEQ ID NO: 195; a VHCDR2 amino acid sequence of SEQ ID NO: 5, and a VHCDR3 amino acid sequence of SEQ ID NO: 3; and a VL comprising a VLCDR1 amino acid sequence of SEQ ID NO: 12, a VLCDR2 amino acid sequence of SEQ ID NO: 13, and a VLCDR3 amino acid sequence of SEQ ID NO: 14; or
   (d) a VH comprising a VHCDR1 amino acid sequence of SEQ ID NO: 195; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 9, a VLCDR2 amino acid sequence of SEQ ID NO: 10, and a VLCDR3 amino acid sequence of SEQ ID NO: 11.

2. The antibody molecule of claim 1, which comprises a VH comprising the amino acid sequence of SEQ ID NO: 18, 30, 38, 46, 50, 54, 62, 70, or 78, a VL comprising the amino acid sequence of SEQ ID NO: 22, 26, 34, 42, 58, 66, 74, 82, or 86, or both.

3. The antibody molecule of claim 1, which comprises:
   (a) a VH comprising the amino acid sequence of SEQ ID NO: 18 and a VL comprising the amino acid sequence of SEQ ID NO: 22;
   (b) a VH comprising the amino acid sequence of SEQ ID NO: 18 and a VL comprising the amino acid sequence of SEQ ID NO: 26;
   (c) a VH comprising the amino acid sequence of SEQ ID NO: 18 and a VL comprising the amino acid sequence of SEQ ID NO: 86;
   (d) a VH comprising the amino acid sequence of SEQ ID NO: 30 and a VL comprising the amino acid sequence of SEQ ID NO: 34;
   (e) a VH comprising the amino acid sequence of SEQ ID NO: 30 and a VL comprising the amino acid sequence of SEQ ID NO: 66;
   (f) a VH comprising the amino acid sequence of SEQ ID NO: 38 and a VL comprising the amino acid sequence of SEQ ID NO: 42;
   (g) a VH comprising the amino acid sequence of SEQ ID NO: 38 and a VL comprising the amino acid sequence of SEQ ID NO: 74;
   (h) a VH comprising the amino acid sequence of SEQ ID NO: 46 and a VL comprising the amino acid sequence of SEQ ID NO: 42;
   (i) a VH comprising the amino acid sequence of SEQ ID NO: 50 and a VL comprising the amino acid sequence of SEQ ID NO: 42;
   (j) a VH comprising the amino acid sequence of SEQ ID NO: 50 and a VL comprising the amino acid sequence of SEQ ID NO: 22;
   (k) a VH comprising the amino acid sequence of SEQ ID NO: 50 and a VL comprising the amino acid sequence of SEQ ID NO: 86;
   (l) a VH comprising the amino acid sequence of SEQ ID NO: 54 and a VL comprising the amino acid sequence of SEQ ID NO: 58;

(m) a VH comprising the amino acid sequence of SEQ ID NO: 54 and a VL comprising the amino acid sequence of SEQ ID NO: 86;
(n) a VH comprising the amino acid sequence of SEQ ID NO: 62 and a VL comprising the amino acid sequence of SEQ ID NO: 66;
(o) a VH comprising the amino acid sequence of SEQ ID NO: 62 and a VL comprising the amino acid sequence of SEQ ID NO: 86;
(p) a VH comprising the amino acid sequence of SEQ ID NO: 70 and a VL comprising the amino acid sequence of SEQ ID NO: 66; or
(q) a VH comprising the amino acid sequence of SEQ ID NO: 78 and a VL comprising the amino acid sequence of SEQ ID NO: 82.

4. The antibody molecule of claim 1, which comprises:
(a) a heavy chain comprising the amino acid sequence of SEQ ID NO: 20 and a light chain comprising the amino acid sequence of SEQ ID NO: 24;
(b) a heavy chain comprising the amino acid sequence of SEQ ID NO: 20 and a light chain comprising the amino acid sequence of SEQ ID NO: 28;
(c) a heavy chain comprising the amino acid sequence of SEQ ID NO: 20 and a light chain comprising the amino acid sequence of SEQ ID NO: 88;
(d) a heavy chain comprising the amino acid sequence of SEQ ID NO: 32 and a light chain comprising the amino acid sequence of SEQ ID NO: 36;
(e) a heavy chain comprising the amino acid sequence of SEQ ID NO: 32 and a light chain comprising the amino acid sequence of SEQ ID NO: 68;
(f) a heavy chain comprising the amino acid sequence of SEQ ID NO: 40 and a light chain comprising the amino acid sequence of SEQ ID NO: 44;
(g) a heavy chain comprising the amino acid sequence of SEQ ID NO: 40 and a light chain comprising the amino acid sequence of SEQ ID NO: 76;
(h) a heavy chain comprising the amino acid sequence of SEQ ID NO: 48 and a light chain comprising the amino acid sequence of SEQ ID NO: 44;
(i) a heavy chain comprising the amino acid sequence of SEQ ID NO: 52 and a light chain comprising the amino acid sequence of SEQ ID NO: 44;
(j) a heavy chain comprising the amino acid sequence of SEQ ID NO: 52 and a light chain comprising the amino acid sequence of SEQ ID NO: 24
(k) a heavy chain comprising the amino acid sequence of SEQ ID NO: 52 and a light chain comprising the amino acid sequence of SEQ ID NO: 88;
(l) a heavy chain comprising the amino acid sequence of SEQ ID NO: 56 and a light chain comprising the amino acid sequence of SEQ ID NO: 60;
(m) a heavy chain comprising the amino acid sequence of SEQ ID NO: 56 and a light chain comprising the amino acid sequence of SEQ ID NO: 88;
(n) a heavy chain comprising the amino acid sequence of SEQ ID NO: 64 and a light chain comprising the amino acid sequence of SEQ ID NO: 68;
(o) a heavy chain comprising the amino acid sequence of SEQ ID NO: 64 and a light chain comprising the amino acid sequence of SEQ ID NO: 88;
(p) a heavy chain comprising the amino acid sequence of SEQ ID NO: 72 and a light chain comprising the amino acid sequence of SEQ ID NO: 68;
(q) a heavy chain comprising the amino acid sequence of SEQ ID NO: 80 and a light chain comprising the amino acid sequence of SEQ ID NO: 84;
(r) a heavy chain comprising the amino acid sequence of SEQ ID NO: 197 and a light chain comprising the amino acid sequence of SEQ ID NO: 36;
(s) a heavy chain comprising the amino acid sequence of SEQ ID NO: 91 and a light chain comprising the amino acid sequence of SEQ ID NO: 44;
(t) a heavy chain comprising the amino acid sequence of SEQ ID NO: 96 and a light chain comprising the amino acid sequence of SEQ ID NO: 68;
(u) a heavy chain comprising the amino acid sequence of SEQ ID NO: 247 and a light chain comprising the amino acid sequence of SEQ ID NO: 84; or
(v) a heavy chain comprising the amino acid sequence of SEQ ID NO: 260 and a light chain comprising the amino acid sequence of SEQ ID NO: 44.

5. The antibody molecule of claim 1, wherein the VH comprises the amino acid sequence of SEQ ID NO: 30 and the VL comprises the amino acid sequence of SEQ ID NO: 66.

6. The antibody molecule of claim 1, wherein the VH comprises the amino acid sequence of SEQ ID NO: 78 and the VL comprising the amino acid sequence of SEQ ID NO: 82.

7. The antibody molecule of claim 1, wherein the heavy chain comprises the amino acid sequence of SEQ ID NO: 96 and a light chain comprises the amino acid sequence of SEQ ID NO: 68.

8. The antibody molecule of claim 1, wherein the heavy chain comprises the amino acid sequence of SEQ ID NO: 80 and the light chain comprises the amino acid sequence of SEQ ID NO: 84.

9. A pharmaceutical composition comprising the antibody molecule of claim 1 and a pharmaceutically acceptable carrier, excipient or stabilizer.

10. A pharmaceutical composition comprising the antibody molecule of claim 5 and a pharmaceutically acceptable carrier, excipient or stabilizer.

11. A pharmaceutical composition comprising the antibody molecule of claim 6 and a pharmaceutically acceptable carrier, excipient or stabilizer.

12. A pharmaceutical composition comprising the antibody molecule of claim 7 and a pharmaceutically acceptable carrier, excipient or stabilizer.

13. A pharmaceutical composition comprising the antibody molecule of claim 8 and a pharmaceutically acceptable carrier, excipient or stabilizer.

14. The antibody molecule of claim 1, which is a Fab, F(ab')2, Fv, or a single chain Fv fragment (scFv).

15. The antibody molecule of claim 1, which comprises a heavy chain constant region of IgG1, IgG2, IgG3, or IgG4 and/or a light chain constant region of kappa or lambda.

16. The antibody molecule of claim 15, which comprises a kappa light chain constant region and:
(a) a human IgG4 heavy chain constant region comprising SEQ ID NO:188 or 190 or a human IgG4 heavy chain constant region comprising Proline at the position corresponding to amino acid 108 of SEQ ID NO:188;
(b) a human IgG1 heavy chain constant region comprising SEQ ID NO:192 or a human IgG1 heavy chain constant region comprising Alanine at the position corresponding to amino acid 180 of SEQ ID NO:191;
(c) a human IgG1 heavy chain constant region comprising SEQ ID NO:193 or a human IgG1 heavy chain constant region comprising Alanine at the positions corresponding to amino acid 148 and 212 of SEQ ID NO:191; or
(d) a human IgG1 heavy chain constant region comprising SEQ ID NO:194 or a human IgG1 heavy chain constant region comprising Alanine at the positions corresponding to amino acid 117 and 118 of SEQ ID NO:191.

17. The antibody molecule of claim 1, which has one or more of the following properties:
    (a) is capable of binding to human PD-L1 with a dissociation constant ($K_D$) of less than about 0.2 nM;
    (b) binds an extracellular domain of PD-L1;
    (c) is capable of reducing binding of PD-1 to PD-L1; or
    (d) is capable of enhancing an antigen-specific T cell response.

18. The antibody molecule of claim 1, wherein said antibody molecule is a humanized antibody molecule, a monospecific antibody molecule or a bispecific antibody molecule.

19. The antibody molecule of claim 18, wherein said antibody molecule is a bispecific antibody molecule and has a first binding specificity for PD-L1 and a second binding specificity for TIM-3, LAG-3, CEACAM-1, CEACAM-5, PD-1 or PD-L2.

20. A nucleic acid molecule comprising a first nucleotide sequence that encodes a heavy chain variable region (VH), or a second nucleotide sequence that encodes a light chain variable region (VL), or both, of an antibody molecule capable of binding to human Programmed Death Ligand-1 (PD-L1), wherein the antibody molecule comprises:
    (a) a VH comprising a VHCDR1 amino acid sequence of SEQ ID NO: 4; a VHCDR2 amino acid sequence of SEQ ID NO: 5, and a VHCDR3 amino acid sequence of SEQ ID NO: 3; and a VL comprising a VLCDR1 amino acid sequence of SEQ ID NO: 12, a VLCDR2 amino acid sequence of SEQ ID NO: 13, and a VLCDR3 amino acid sequence of SEQ ID NO: 14;
    (b) a VH comprising a VHCDR1 amino acid sequence of SEQ ID NO: 1; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 9, a VLCDR2 amino acid sequence of SEQ ID NO: 10, and a VLCDR3 amino acid sequence of SEQ ID NO: 11;
    (c) a VH comprising a VHCDR1 amino acid sequence of SEQ ID NO: 195; a VHCDR2 amino acid sequence of SEQ ID NO: 5, and a VHCDR3 amino acid sequence of SEQ ID NO: 3; and a VL comprising a VLCDR1 amino acid sequence of SEQ ID NO: 12, a VLCDR2 amino acid sequence of SEQ ID NO: 13, and a VLCDR3 amino acid sequence of SEQ ID NO: 14; or
    (d) a VH comprising a VHCDR1 amino acid sequence of SEQ ID NO: 195; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 9, a VLCDR2 amino acid sequence of SEQ ID NO: 10, and a VLCDR3 amino acid sequence of SEQ ID NO: 11.

21. An expression vector comprising the nucleic acid molecule of claim 20.

22. An isolated host cell comprising the nucleic acid molecule of claim 20.

23. A method of producing an antibody molecule or fragment thereof, comprising culturing the host cell of claim 22 under conditions suitable for gene expression, wherein said host cell comprises said first nucleotide sequence that encodes a VH and said second nucleotide sequence that encodes a VL.

24. The nucleic acid molecule of claim 20, wherein the first nucleotide sequence encodes a VH comprising the amino acid sequence of SEQ ID NO: 30 or comprises the nucleotide sequence of SEQ ID NO: 95; and/or wherein the second nucleotide sequence encodes a VL comprising the amino acid sequence of SEQ ID NO: 66 or comprises the nucleotide sequence of SEQ ID NO: 98.

25. The nucleic acid molecule of claim 20, wherein the first nucleotide sequence encodes a VH comprising the amino acid sequence of SEQ ID NO: 78 or comprises the nucleotide sequence of SEQ ID NO: 100; and/or wherein the second nucleotide sequence encodes a VL comprising the amino acid sequence of SEQ ID NO: 82 or comprises the nucleotide sequence of SEQ ID NO: 102.

26. The nucleic acid molecule of claim 20, wherein the first nucleotide sequence encodes a heavy chain comprising the amino acid sequence of SEQ ID NO: 80 or comprises a heavy chain nucleotide sequence of SEQ ID NO: 101; and/or wherein the second nucleotide sequence encodes a light chain comprising the amino acid sequence of SEQ ID NO: 84 or comprises a light chain nucleotide sequence of SEQ ID NO: 103.

27. The nucleic acid molecule of claim 20, wherein the first nucleotide sequence encodes a heavy chain comprising the amino acid sequence of SEQ ID NO: 96 or comprises a heavy chain nucleotide sequence of SEQ ID NO: 97; and/or wherein the second nucleotide sequence encodes a light chain comprising the amino acid sequence of SEQ ID NO: 68 or comprises a light chain nucleotide sequence of SEQ ID NO: 99.

* * * * *

SEQUENCE LISTING

```
<160> NUMBER OF SEQ ID NOS: 362

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 1

Ser Tyr Trp Met Tyr
1               5

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Ile Asp Pro Asn Ser Gly Ser Thr Lys Tyr Asn Glu Lys Phe Lys
1               5                   10                  15

Asn

<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Asp Tyr Arg Lys Gly Leu Tyr Ala Met Asp Tyr
1               5                   10

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Tyr Thr Phe Thr Ser Tyr
1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Asp Pro Asn Ser Gly Ser
1               5

<210> SEQ ID NO 6
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Gln Val His Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr

```
                20                  25                  30
Trp Met Tyr Trp Val Lys Gln Gly Pro Gly Arg Gly Leu Glu Trp Ile
            35                  40                  45

Gly Arg Ile Asp Pro Asn Ser Gly Ser Thr Lys Tyr Asn Glu Lys Phe
    50                  55                  60

Lys Asn Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Asp Tyr Arg Lys Gly Leu Tyr Ala Met Asp Tyr Trp Gly Gln
                100                 105                 110

Gly Thr Ser Val Thr Val Ser Ser
                115                 120

<210> SEQ ID NO 7
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
caggtccacc tgcagcagcc tggggctgag cttgtgaagc ctggggcttc agtgaagctg      60
tcctgcaagg cttctggcta caccttcacc agttactgga tgtactgggt gaaacagggg     120
cctggacgag gccttgagtg gattggaagg attgatccta atagtgggag tactaagtac     180
aatgagaagt tcaagaacaa ggccacactg actgtagaca atcctccag cacagcctac      240 atgcagctca gcagcctgac atctgaggac tctgcggtct attattgtgc aagggactat     300
agaaaggggc tctatgctat ggactactgg ggtcaaggaa cctcagtcac cgtctcctca     360

<210> SEQ ID NO 8
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Thr Ala
                20                  25                  30

Val Ala Trp Tyr Gln Gln Lys Pro Gly Gln Ser Pro Lys Leu Leu Ile
            35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Asn Ser Tyr Pro Leu
                85                  90                  95

Thr Phe Gly Ala Gly Ser Lys Leu Glu Leu Lys
                100                 105

<210> SEQ ID NO 9
<211> LENGTH: 11
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 9

Lys Ala Ser Gln Asp Val Gly Thr Ala Val Ala
1               5                   10

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Trp Ala Ser Thr Arg His Thr
1               5

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gln Gln Tyr Asn Ser Tyr Pro Leu Thr
1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ser Gln Asp Val Gly Thr Ala
1               5

<210> SEQ ID NO 13
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Trp Ala Ser
1

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Tyr Asn Ser Tyr Pro Leu
1               5
```

<210> SEQ ID NO 15
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
gacattgtga tgacccagtc tcacaaattc atgtccacat cagtaggaga cagggtcagc      60
atcacctgca aggccagtca ggatgtgggt actgctgtag cctggtatca acagaaacca     120
gggcaatctc ctaaactact gatttactgg gcatccaccc ggcacactgg agtccctgat     180
cgcttcacag gcagtggatc tgggacagat ttcactctca ccattagcaa tgtgcagtct     240
gaagacttgg cagattattt ctgtcagcag tataacagct atcctctcac gttcggtgct     300
gggtccaagc tggagctgaa a                                              321

<210> SEQ ID NO 16
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Glu Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Ser Tyr
                20                  25                  30

Trp Met Tyr Trp Val Lys Gln Gly Pro Gly Arg Gly Leu Glu Trp Ile
            35                  40                  45

Gly Arg Ile Asp Pro Asn Ser Gly Ser Thr Lys Tyr Asn Glu Lys Phe
        50                  55                  60

Lys Asn Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Asp Tyr Arg Lys Gly Leu Tyr Ala Met Asp Tyr Trp Gly Gln
            100                 105                 110

Gly Thr Thr Val Thr Val Ser Ser
        115                 120

<210> SEQ ID NO 17
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Asp Ile Met Met Thr Gln Ser His Lys Phe Met Ser Thr Ser Val Gly
1               5                   10                  15

Asp Arg Val Ser Ile Thr Cys Lys Ala Ser Gln Asp Val Gly Thr Ala
                20                  25                  30

Val Ala Trp Tyr Gln Gln Lys Pro Gly Gln Ser Pro Lys Leu Leu Ile
            35                  40                  45

-continued

Tyr Trp Ala Ser Thr Arg His Thr Gly Val Pro Asp Arg Phe Thr Gly
            50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Asn Ser Tyr Pro Leu
                85                  90                  95

Thr Phe Gly Gln Gly Thr Lys Val Glu Ile Lys
            100                 105

<210> SEQ ID NO 18
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Met Tyr Trp Val Arg Gln Ala Thr Gly Gln Gly Leu Glu Trp Met
            35                  40                  45

Gly Arg Ile Asp Pro Asn Ser Gly Ser Thr Lys Tyr Asn Glu Lys Phe
    50                  55                  60

Lys Asn Arg Phe Thr Ile Ser Arg Asp Asp Ser Lys Asn Thr Ala Tyr
65                  70                  75                  80

Leu Gln Met Asn Ser Leu Lys Thr Glu Asp Thr Ala Val Tyr Tyr Cys
                85                  90                  95

Ala Arg Asp Tyr Arg Lys Gly Leu Tyr Ala Met Asp Tyr Trp Gly Gln
                100                 105                 110

Gly Thr Thr Val Thr Val Ser Ser
            115                 120

<210> SEQ ID NO 19
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
caggttcagc tggtgcagtc tggagctgag gtgaagaagc ctggggcctc agtgaaggtc      60
tcctgcaagg cttctggcta caccttcacc agttactgga tgtactgggt gcgacaggcc    120
actggacaag gcttgagtg gatgggtagg attgatccta atagtgggag tactaagtac     180
aatgagaagt tcaagaacag attcaccatc tccagagatg attcaaagaa cacggcgtat    240
ctgcaaatga acagcctgaa aaccgaggac acggccgtgt attactgtgc aagggactat    300 agaaagggc tctatgctat ggactactgg ggccagggca ccaccgtgac cgtgtcctcc    360

<210> SEQ ID NO 20
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Tyr Trp Val Arg Gln Ala Thr Gly Gln Gly Leu Glu Trp Met
        35                  40                  45

Gly Arg Ile Asp Pro Asn Ser Gly Ser Thr Lys Tyr Asn Glu Lys Phe
    50                  55                  60

Lys Asn Arg Phe Thr Ile Ser Arg Asp Asp Ser Lys Asn Thr Ala Tyr
65                  70                  75                  80

Leu Gln Met Asn Ser Leu Lys Thr Glu Asp Thr Ala Val Tyr Tyr Cys
                85                  90                  95

Ala Arg Asp Tyr Arg Lys Gly Leu Tyr Ala Met Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 21
<211> LENGTH: 1341
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
caggttcagc tggtgcagtc tggagctgag gtgaagaagc ctggggcctc agtgaaggtc     60
tcctgcaagg cttctggcta caccttcacc agttactgga tgtactgggt gcgacaggcc    120
actggacaag gcttgagtg gatgggtagg attgatccta atagtgggag tactaagtac    180
aatgagaagt tcaagaacag attcaccatc tccagagatg attcaaagaa cacggcgtat    240
ctgcaaatga acagcctgaa aaccgaggac acggccgtgt attactgtgc aagggactat    300 agaaagggc tctatgctat ggactactgg ggccagggca ccaccgtgac cgtgtcctcc    360
gcttccacca agggcccatc cgtcttcccc ctggcgccct gctccaggag cacctccgag    420
agcacagccg ccctgggctg cctggtcaag gactacttcc ccgaaccggt gacggtgtcg    480
tggaactcag gcgccctgac cagcggcgtg cacaccttcc cggctgtcct acagtcctca    540
ggactctact ccctcagcag cgtggtgacc gtgccctcca gcagcttggg cacgaagacc    600
tacacctgca acgtagatca caagcccagc aacaccaagg tggacaagag agttgagtcc    660
aaatatggtc cccatgccc accgtgccca gcacctgagt tcctgggggg accatcagtc    720
ttcctgttcc ccccaaaacc caaggacact ctcatgatct cccggacccc tgaggtcacg    780
tgcgtggtgg tggacgtgag ccaggaagac cccgaggtcc agttcaactg gtacgtggat    840
ggcgtggagg tgcataatgc caagacaaag ccgcgggagg agcagttcaa cagcacgtac    900
cgtgtggtca gcgtcctcac cgtcctgcac caggactggc tgaacggcaa ggagtacaag    960
tgcaaggtgt ccaacaaagg cctcccgtcc tccatcgaga aaaccatctc caaagccaaa    1020
gggcagcccc gagagccaca ggtgtacacc ctgcccccat cccaggagga gatgaccaag    1080
aaccaggtca gcctgacctg cctggtcaaa ggcttctacc ccagcgacat cgccgtggag    1140
tgggagagca atgggcagcc ggagaacaac tacaagacca cgcctcccgt gctggactcc    1200
gacggctcct tcttcctcta cagcaggcta accgtggaca agagcaggtg gcaggagggg    1260
aatgtcttct catgctccgt gatgcatgag gctctgcaca accactacac acagaagagc    1320
ctctccctgt ctctgggtaa a                                              1341

<210> SEQ ID NO 22
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Asp Ile Val Met Thr Gln Thr Pro Leu Ser Leu Pro Val Thr Pro Gly
1               5                   10                  15

Glu Pro Ala Ser Ile Ser Cys Lys Ala Ser Gln Asp Val Gly Thr Ala

```
                    20                  25                  30

Val Ala Trp Tyr Leu Gln Lys Pro Gly Gln Ser Pro Gln Leu Leu Ile
            35                  40                  45

Tyr Trp Ala Ser Thr Arg His Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Ser Tyr Pro Leu
                85                  90                  95

Thr Phe Gly Gln Gly Thr Lys Val Glu Ile Lys
            100                 105

<210> SEQ ID NO 23
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23
gatattgtga tgacccagac tccactctcc ctgcccgtca cccctggaga gccggcctcc     60
atctcctgca aggccagtca ggatgtgggt actgctgtag cctggtacct gcagaagcca    120
gggcagtctc cacagctcct gatctattgg gcatccaccc ggcacactgg gatcccagcc    180
aggttcagtg gcagtgggtc tgggacagag ttcactctca ccatcagcag cctgcagtct    240
gaagattttg cagtttatta ctgtcagcag tataacagct atcctctcac gttcggccaa    300
gggaccaagg tggaaatcaa a                                               321

<210> SEQ ID NO 24
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Asp Ile Val Met Thr Gln Thr Pro Leu Ser Leu Pro Val Thr Pro Gly
1               5                   10                  15

Glu Pro Ala Ser Ile Ser Cys Lys Ala Ser Gln Asp Val Gly Thr Ala
                20                  25                  30

Val Ala Trp Tyr Leu Gln Lys Pro Gly Gln Ser Pro Gln Leu Leu Ile
            35                  40                  45

Tyr Trp Ala Ser Thr Arg His Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Ser Tyr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
```

```
                145                 150                 155                 160
Glu Ser Val Thr Glu Gln Asp Ser Lys Asp Ser Thr Tyr Ser Leu Ser
                    165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
        210
```

<210> SEQ ID NO 25
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25

```
gatattgtga tgacccagac tccactctcc ctgcccgtca cccctggaga gccggcctcc      60
atctcctgca aggccagtca ggatgtgggt actgctgtag cctggtacct gcagaagcca     120
gggcagtctc cacagctcct gatctattgg gcatccaccc ggcacactgg gatcccagcc     180
aggttcagtg gcagtgggtc tgggacagag ttcactctca ccatcagcag cctgcagtct     240
gaagattttg cagtttatta ctgtcagcag tataacagct atcctctcac gttcggccaa     300
gggaccaagg tggaaatcaa acgtacggtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac aggggagagt gt                        642
```

<210> SEQ ID NO 26
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Gly Thr Ala
            20                  25                  30

Val Ala Trp Tyr Leu Gln Lys Pro Gly Gln Ser Pro Gln Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gln Gly Thr Lys Val Glu Ile Lys
            100                 105
```

<210> SEQ ID NO 27
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27

```
gacatccaga tgacccagtc tccatcctcc ctgtctgcat ctgtaggaga cagagtcacc      60
atcacttgca aggccagtca ggatgtgggt actgctgtag cctggtacct gcagaagcca     120
gggcagtctc cacagctcct gatctattgg gcatccaccc ggcacactgg ggtcccatca     180
aggttcagcg gcagtggatc tgggacagat ttcactctca ccatcagcag cctgcagcct     240
gaagattttg caacttatta ctgtcagcag tataacagct atcctctcac gttcggccaa     300
gggaccaagg tggaaatcaa a                                                321
```

<210> SEQ ID NO 28
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Gly Thr Ala
            20                  25                  30

Val Ala Trp Tyr Leu Gln Lys Pro Gly Gln Ser Pro Gln Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 29
<211> LENGTH: 642

<210> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29

```
gacatccaga tgacccagtc tccatcctcc ctgtctgcat ctgtaggaga cagagtcacc    60
atcacttgca aggccagtca ggatgtgggt actgctgtag cctggtacct gcagaagcca   120
gggcagtctc cacagctcct gatctattgg gcatccaccc ggcacactgg ggtcccatca   180
aggttcagcg gcagtggatc tgggacagat ttcactctca ccatcagcag cctgcagcct   240
gaagattttg caacttatta ctgtcagcag tataacagct atcctctcac gttcggccaa   300
gggaccaagg tggaaatcaa acgtacggtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag caccctgacg   540
ctgagcaaag cagactacga gaaacacaaa gtctacgcct gcgaagtcac ccatcagggc   600
ctgagctcgc ccgtcacaaa gagcttcaac aggggagagt gt                      642
```

<210> SEQ ID NO 30
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

```
Glu Val Gln Leu Val Gln Ser Gly Ala Glu Val Lys Lys Pro Gly Ala
1               5                   10                  15
Thr Val Lys Ile Ser Cys Lys Val Ser Gly Tyr Thr Phe Thr Ser Tyr
            20                  25                  30
Trp Met Tyr Trp Val Arg Gln Ala Thr Gly Gln Gly Leu Glu Trp Met
        35                  40                  45
Gly Arg Ile Asp Pro Asn Ser Gly Ser Thr Lys Tyr Asn Glu Lys Phe
    50                  55                  60
Lys Asn Arg Val Thr Ile Thr Ala Asp Lys Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Asp Tyr Arg Lys Gly Leu Tyr Ala Met Asp Tyr Trp Gly Gln
            100                 105                 110
Gly Thr Thr Val Thr Val Ser Ser
        115                 120
```

<210> SEQ ID NO 31
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31

```
gaggtccagc tggtacagtc tggggctgag gtgaagaagc ctggggctac agtgaaaatc    60
tcctgcaagg tttctggcta caccttcacc agttactgga tgtactgggt gcgacaggcc   120
```

```
actggacaag ggcttgagtg gatgggtagg attgatccta atagtgggag tactaagtac    180
aatgagaagt tcaagaacag agtcacgatt accgcggaca atccacgag cacagcctac     240 atggagctga gcagcctgag atctgaggac acggccgtgt attactgtgc aagggactat    300 agaaagggc tctatgctat ggactactgg ggccagggca ccaccgtgac cgtgtcctcc    360
```

<210> SEQ ID NO 32
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

```
Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Ser Tyr
            20                  25                  30

Trp Met Tyr Trp Val Arg Gln Ala Thr Gly Gln Gly Leu Glu Trp Met
        35                  40                  45

Gly Arg Ile Asp Pro Asn Ser Gly Ser Thr Lys Tyr Asn Glu Lys Phe
    50                  55                  60

Lys Asn Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Arg Lys Gly Leu Tyr Ala Met Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320
```

```
Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 33
<211> LENGTH: 1341
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33
```

| | | | | | |
|---|---|---|---|---|---|
| gaggtccagc | tggtacagtc | tggggctgag | gtgaagaagc | tggggctac | agtgaaaatc | 60 |
| tcctgcaagg | tttctggcta | caccttcacc | agttactgga | tgtactgggt | gcgacaggcc | 120 |
| actggacaag | gcttgagtg | gatgggtagg | attgatccta | atagtgggag | tactaagtac | 180 |
| aatgagaagt | tcaagaacag | agtcacgatt | accgcggaca | aatccacgag | cacagcctac | 240 |
| atggagctga | gcagcctgag | atctgaggac | acggccgtgt | attactgtgc | aagggactat | 300 |
| agaaagggc | tctatgctat | ggactactgg | ggccagggca | ccaccgtgac | cgtgtcctcc | 360 |
| gcttccacca | agggcccatc | cgtcttcccc | ctggcgccct | gctccaggag | cacctccgag | 420 |
| agcacagccg | ccctgggctg | cctggtcaag | gactacttcc | ccgaaccggt | gacggtgtcg | 480 |
| tggaactcag | gcgccctgac | cagcggcgtg | cacaccttcc | cggctgtcct | acagtcctca | 540 |
| ggactctact | ccctcagcag | cgtggtgacc | gtgccctcca | gcagcttggg | cacgaagacc | 600 |
| tacacctgca | acgtagatca | caagcccagc | aacaccaagg | tggacaagag | agttgagtcc | 660 |
| aaatatggtc | ccccatgccc | accgtgccca | gcacctgagt | tcctgggggg | accatcagtc | 720 |
| ttcctgttcc | ccccaaaacc | caaggacact | ctcatgatct | cccggacccc | tgaggtcacg | 780 |
| tgcgtggtgg | tggacgtgag | ccaggaagac | cccgaggtcc | agttcaactg | gtacgtggat | 840 |
| ggcgtggagg | tgcataatgc | caagacaaag | ccgcgggagg | agcagttcaa | cagcacgtac | 900 |
| cgtgtggtca | gcgtcctcac | cgtcctgcac | caggactggc | tgaacggcaa | ggagtacaag | 960 |
| tgcaaggtgt | ccaacaaagg | cctcccgtcc | tccatcgaga | aaaccatctc | caaagccaaa | 1020 |
| gggcagcccc | gagagccaca | ggtgtacacc | ctgcccccat | cccaggagga | gatgaccaag | 1080 |
| aaccaggtca | gcctgacctg | cctggtcaaa | ggcttctacc | ccagcgacat | cgccgtggag | 1140 |
| tgggagagca | atgggcagcc | ggagaacaac | tacaagacca | cgcctcccgt | gctggactcc | 1200 |
| gacggctcct | tcttcctcta | cagcaggcta | accgtggaca | agagcaggtg | gcaggagggg | 1260 |
| aatgtcttct | catgctccgt | gatgcatgag | gctctgcaca | accactacac | acagaagagc | 1320 |

-continued

```
ctctccctgt ctctgggtaa a                                              1341
```

<210> SEQ ID NO 34
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Glu Ile Val Leu Thr Gln Ser Pro Asp Phe Gln Ser Val Thr Pro Lys
1               5                   10                  15

Glu Lys Val Thr Ile Thr Cys Lys Ala Ser Gln Asp Val Gly Thr Ala
            20                  25                  30

Val Ala Trp Tyr Leu Gln Lys Pro Gly Gln Ser Pro Gln Leu Leu Ile
        35                  40                  45

Tyr Trp Ala Ser Thr Arg His Thr Gly Val Pro Asp Arg Phe Ser Gly
    50                  55                  60

Ser Gly Ser Gly Thr Asp Phe Thr Leu Lys Ile Ser Arg Val Glu Ala
65                  70                  75                  80

Glu Asp Val Gly Val Tyr Tyr Cys Gln Gln Tyr Asn Ser Tyr Pro Leu
                85                  90                  95

Thr Phe Gly Gln Gly Thr Lys Val Glu Ile Lys
            100                 105

<210> SEQ ID NO 35
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35

```
gaaattgtgc tgactcagtc tccagacttt cagtctgtga ctccaaagga gaaagtcacc    60
atcacctgca aggccagtca ggatgtgggt actgctgtag cctggtacct gcagaagcca   120
gggcagtctc cacagctcct gatctattgg gcatccaccc ggcacactgg ggtcccagac   180
aggttcagtg gcagtgggtc aggcactgat ttcacactga aaatcagcag ggtggaggct   240
gaggatgttg gagtttatta ctgtcagcag tataacagct atcctctcac gttcggccaa   300
gggaccaagg tggaaatcaa a                                             321
```

<210> SEQ ID NO 36
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Glu Ile Val Leu Thr Gln Ser Pro Asp Phe Gln Ser Val Thr Pro Lys
1               5                   10                  15

Glu Lys Val Thr Ile Thr Cys Lys Ala Ser Gln Asp Val Gly Thr Ala
            20                  25                  30

Val Ala Trp Tyr Leu Gln Lys Pro Gly Gln Ser Pro Gln Leu Leu Ile
        35                  40                  45

Tyr Trp Ala Ser Thr Arg His Thr Gly Val Pro Asp Arg Phe Ser Gly

```
                    50                  55                  60
Ser Gly Ser Gly Thr Asp Phe Thr Leu Lys Ile Ser Arg Val Glu Ala
 65                  70                  75                  80

Glu Asp Val Gly Val Tyr Tyr Cys Gln Gln Tyr Asn Ser Tyr Pro Leu
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 37
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37

```
gaaattgtgc tgactcagtc tccagacttt cagtctgtga ctccaaagga gaaagtcacc    60
atcacctgca aggccagtca ggatgtgggt actgctgtag cctggtacct gcagaagcca   120
gggcagtctc cacagctcct gatctattgg catccacccc ggcacactgg ggtcccagac   180
aggttcagtg gcagtgggtc aggcactgat ttcacactga aaatcagcag ggtggaggct   240
gaggatgttg gagtttatta ctgtcagcag tataacagct atcctctcac gttcggccaa   300
gggaccaagg tggaaatcaa acgtacggtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag caccctgacg   540
ctgagcaaag cagactacga gaaacacaaa gtctacgcct gcgaagtcac ccatcagggc   600
ctgagctcgc ccgtcacaaa gagcttcaac aggggagagt gt                      642
```

<210> SEQ ID NO 38
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

```
Glu Val Gln Leu Val Gln Ser Gly Ala Glu Val Lys Lys Pro Gly Glu
 1               5                  10                  15
```

```
Ser Leu Arg Ile Ser Cys Lys Gly Ser Gly Tyr Thr Phe Thr Ser Tyr
            20                  25                  30

Trp Met Tyr Trp Val Arg Gln Ala Pro Gly Gln Gly Leu Glu Trp Met
        35                  40                  45

Gly Arg Ile Asp Pro Asn Ser Gly Ser Thr Lys Tyr Asn Glu Lys Phe
    50                  55                  60

Lys Asn Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asp Tyr Arg Lys Gly Leu Tyr Ala Met Asp Tyr Trp Gly Gln
            100                 105                 110

Gly Thr Thr Val Thr Val Ser Ser
        115                 120

<210> SEQ ID NO 39
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39
gaagtgcagc tggtgcagtc tggagcagag gtgaaaaagc cggggagtc tctgaggatc        60 tcctgtaagg gttctggcta caccttcacc agttactgga tgtactgggt gcgacaggcc      120
cctggacaag gcttgagtg gatgggtagg attgatccta atagtgggag tactaagtac       180
aatgagaagt tcaagaacag agtcaccata tcagtagaca cgtccaagaa ccagttctcc      240
ctgaagctga gctctgtgac cgccgcggac acggctgtgt attactgtgc aaggactat       300 agaaagggc tctatgctat ggactactgg ggccagggca ccaccgtgac cgtgtcctcc      360

<210> SEQ ID NO 40
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Ser Tyr
            20                  25                  30

Trp Met Tyr Trp Val Arg Gln Ala Pro Gly Gln Gly Leu Glu Trp Met
        35                  40                  45

Gly Arg Ile Asp Pro Asn Ser Gly Ser Thr Lys Tyr Asn Glu Lys Phe
    50                  55                  60

Lys Asn Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asp Tyr Arg Lys Gly Leu Tyr Ala Met Asp Tyr Trp Gly Gln
            100                 105                 110

Gly Thr Thr Val Thr Val Ser Ser Ala Ser Thr Lys Gly Pro Ser Val
        115                 120                 125
```

Phe Pro Leu Ala Pro Cys Ser Arg Ser Thr Ser Glu Ser Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 41
<211> LENGTH: 1341
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
gaagtgcagc tggtgcagtc tggagcagag gtgaaaaagc ccggggagtc tctgaggatc        60
tcctgtaagg gttctggcta caccttcacc agttactgga tgtactgggt gcgacaggcc       120
cctggacaag gcttgagtg gatgggtagg attgatccta atagtgggag tactaagtac       180
aatgagaagt tcaagaacag agtcaccata tcagtagaca cgtccaagaa ccagttctcc       240

| | | | | |
|---|---|---|---|---|
| ctgaagctga | gctctgtgac | cgccgcggac | acggctgtgt | attactgtgc aagggactat | 300 |
| agaaaggggc | tctatgctat | ggactactgg | ggccagggca | ccaccgtgac cgtgtcctcc | 360 |
| gcttccacca | agggcccatc | cgtcttcccc | ctggcgccct | gctccaggag cacctccgag | 420 |
| agcacagccg | ccctgggctg | cctggtcaag | gactacttcc | ccgaaccggt gacggtgtcg | 480 |
| tggaactcag | gcgccctgac | cagcggcgtg | cacaccttcc | cggctgtcct acagtcctca | 540 |
| ggactctact | ccctcagcag | cgtggtgacc | gtgccctcca | gcagcttggg cacgaagacc | 600 |
| tacacctgca | acgtagatca | caagcccagc | aacaccaagg | tggacaagag agttgagtcc | 660 |
| aaatatggtc | ccccatgccc | accgtgccca | gcacctgagt | tcctgggggg accatcagtc | 720 |
| ttcctgttcc | ccccaaaacc | caaggacact | ctcatgatct | cccggacccc tgaggtcacg | 780 |
| tgcgtggtgg | tggacgtgag | ccaggaagac | cccgaggtcc | agttcaactg gtacgtggat | 840 |
| ggcgtggagg | tgcataatgc | caagacaaag | ccgcgggagg | agcagttcaa cagcacgtac | 900 |
| cgtgtggtca | gcgtcctcac | cgtcctgcac | caggactggc | tgaacggcaa ggagtacaag | 960 |
| tgcaaggtgt | ccaacaaagg | cctcccgtcc | tccatcgaga | aaaccatctc caaagccaaa | 1020 |
| gggcagcccc | gagagccaca | ggtgtacacc | ctgcccccat | cccaggagga tgaccaag | 1080 |
| aaccaggtca | gcctgacctg | cctggtcaaa | ggcttctacc | ccagcgacat cgccgtggag | 1140 |
| tgggagagca | atgggcagcc | ggagaacaac | tacaagacca | cgcctcccgt gctggactcc | 1200 |
| gacggctcct | tcttcctcta | cagcaggcta | accgtggaca | agagcaggtg gcaggagggg | 1260 |
| aatgtcttct | catgctccgt | gatgcatgag | gctctgcaca | accactacac acagaagagc | 1320 |
| ctctcccctgt | ctctgggtaa | a | | | 1341 |

<210> SEQ ID NO 42
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Glu Ile Val Leu Thr Gln Ser Pro Asp Phe Gln Ser Val Thr Pro Lys
1               5                   10                  15

Glu Lys Val Thr Ile Thr Cys Lys Ala Ser Gln Asp Val Gly Thr Ala
            20                  25                  30

Val Ala Trp Tyr Leu Gln Lys Pro Gly Gln Ser Pro Gln Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asn Ser Tyr Pro Leu
                85                  90                  95

Thr Phe Gly Gln Gly Thr Lys Val Glu Ile Lys
            100                 105

<210> SEQ ID NO 43
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

```
<400> SEQUENCE: 43
gaaattgtgc tgactcagtc tccagacttt cagtctgtga ctccaaagga gaaagtcacc      60
atcacctgca aggccagtca ggatgtgggt actgctgtag cctggtacct gcagaagcca     120
gggcagtctc cacagctcct gatctattgg gcatccaccc ggcacactgg ggtcccatca     180
aggttcagtg gaagtggatc tgggacagat tttactttca ccatcagcag cctgcagcct     240
gaagatattg caacatatta ctgtcagcag tataacagct atcctctcac gttcggccaa     300
gggaccaagg tggaaatcaa a                                                321

<210> SEQ ID NO 44
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Glu Ile Val Leu Thr Gln Ser Pro Asp Phe Gln Ser Val Thr Pro Lys
1               5                   10                  15

Glu Lys Val Thr Ile Thr Cys Lys Ala Ser Gln Asp Val Gly Thr Ala
            20                  25                  30

Val Ala Trp Tyr Leu Gln Lys Pro Gly Gln Ser Pro Gln Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asn Ser Tyr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 45
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45
gaaattgtgc tgactcagtc tccagacttt cagtctgtga ctccaaagga gaaagtcacc      60
```

```
atcacctgca aggccagtca ggatgtgggt actgctgtag cctggtacct gcagaagcca    120
gggcagtctc cacagctcct gatctattgg gcatccaccc ggcacactgg ggtcccatca    180
aggttcagtg gaagtggatc tgggacagat tttactttca ccatcagcag cctgcagcct    240
gaagatattg caacatatta ctgtcagcag tataacagct atcctctcac gttcggccaa    300
gggaccaagg tggaaatcaa acgtacggtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gt                      642
```

<210> SEQ ID NO 46
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Ser Tyr
            20                  25                  30

Trp Met Tyr Trp Ile Arg Gln Ser Pro Ser Arg Gly Leu Glu Trp Leu
        35                  40                  45

Gly Arg Ile Asp Pro Asn Ser Gly Ser Thr Lys Tyr Asn Glu Lys Phe
    50                  55                  60

Lys Asn Arg Leu Thr Ile Ser Lys Asp Thr Ser Lys Asn Gln Val Val
65                  70                  75                  80

Leu Thr Met Thr Asn Met Asp Pro Val Asp Thr Ala Thr Tyr Tyr Cys
                85                  90                  95

Ala Arg Asp Tyr Arg Lys Gly Leu Tyr Ala Met Asp Tyr Trp Gly Gln
            100                 105                 110

Gly Thr Thr Val Thr Val Ser Ser
        115                 120

<210> SEQ ID NO 47
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47

```
gaggtccagc tggtacagtc tggggctgag gtgaagaagc ctggggctac agtgaaaatc     60
tcctgcaagg tttctggcta caccttcacc agttactgga tgtactggat caggcagtcc    120
ccatcgagag gccttgagtg gctgggtagg attgatccta atagtgggag tactaagtac    180
aatgagaagt tcaagaacag actcaccatc tccaaggaca cctccaaaaa ccaggtggtc    240
cttacaatga ccaacatgga ccctgtggac acagccacgt attactgtgc aagggactat    300
agaaaggggc tctatgctat ggactactgg ggccagggca ccaccgtgac cgtgtcctcc    360
```

```
<210> SEQ ID NO 48
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48
```

| | | | | | | | | | | | | | | | |
|---|---|---|---|---|---|---|---|---|---|---|---|---|---|---|---|
| Glu | Val | Gln | Leu | Val | Gln | Ser | Gly | Ala | Glu | Val | Lys | Lys | Pro | Gly | Ala |
| 1 | | | | 5 | | | | | 10 | | | | | 15 | |
| Thr | Val | Lys | Ile | Ser | Cys | Lys | Val | Ser | Gly | Tyr | Thr | Phe | Thr | Ser | Tyr |
| | | | 20 | | | | | 25 | | | | | 30 | | |
| Trp | Met | Tyr | Trp | Ile | Arg | Gln | Ser | Pro | Ser | Arg | Gly | Leu | Glu | Trp | Leu |
| | | 35 | | | | | 40 | | | | | 45 | | | |
| Gly | Arg | Ile | Asp | Pro | Asn | Ser | Gly | Ser | Thr | Lys | Tyr | Asn | Glu | Lys | Phe |
| 50 | | | | | 55 | | | | | 60 | | | | | |
| Lys | Asn | Arg | Leu | Thr | Ile | Ser | Lys | Asp | Thr | Ser | Lys | Asn | Gln | Val | Val |
| 65 | | | | 70 | | | | | 75 | | | | | 80 | |
| Leu | Thr | Met | Thr | Asn | Met | Asp | Pro | Val | Asp | Thr | Ala | Thr | Tyr | Tyr | Cys |
| | | | | 85 | | | | | 90 | | | | | 95 | |
| Ala | Arg | Asp | Tyr | Arg | Lys | Gly | Leu | Tyr | Ala | Met | Asp | Tyr | Trp | Gly | Gln |
| | | | 100 | | | | | 105 | | | | | 110 | | |
| Gly | Thr | Thr | Val | Thr | Val | Ser | Ser | Ala | Ser | Thr | Lys | Gly | Pro | Ser | Val |
| | | 115 | | | | | 120 | | | | | 125 | | | |
| Phe | Pro | Leu | Ala | Pro | Cys | Ser | Arg | Ser | Thr | Ser | Glu | Ser | Thr | Ala | Ala |
| 130 | | | | | 135 | | | | | 140 | | | | | |
| Leu | Gly | Cys | Leu | Val | Lys | Asp | Tyr | Phe | Pro | Glu | Pro | Val | Thr | Val | Ser |
| 145 | | | | 150 | | | | | 155 | | | | | 160 | |
| Trp | Asn | Ser | Gly | Ala | Leu | Thr | Ser | Gly | Val | His | Thr | Phe | Pro | Ala | Val |
| | | | | 165 | | | | | 170 | | | | | 175 | |
| Leu | Gln | Ser | Ser | Gly | Leu | Tyr | Ser | Leu | Ser | Ser | Val | Val | Thr | Val | Pro |
| | | | 180 | | | | | 185 | | | | | 190 | | |
| Ser | Ser | Ser | Leu | Gly | Thr | Lys | Thr | Tyr | Thr | Cys | Asn | Val | Asp | His | Lys |
| | | 195 | | | | | 200 | | | | | 205 | | | |
| Pro | Ser | Asn | Thr | Lys | Val | Asp | Lys | Arg | Val | Glu | Ser | Lys | Tyr | Gly | Pro |
| 210 | | | | | 215 | | | | | 220 | | | | | |
| Pro | Cys | Pro | Pro | Cys | Pro | Ala | Pro | Glu | Phe | Leu | Gly | Gly | Pro | Ser | Val |
| 225 | | | | 230 | | | | | 235 | | | | | 240 | |
| Phe | Leu | Phe | Pro | Pro | Lys | Pro | Lys | Asp | Thr | Leu | Met | Ile | Ser | Arg | Thr |
| | | | | 245 | | | | | 250 | | | | | 255 | |
| Pro | Glu | Val | Thr | Cys | Val | Val | Val | Asp | Val | Ser | Gln | Glu | Asp | Pro | Glu |
| | | | 260 | | | | | 265 | | | | | 270 | | |
| Val | Gln | Phe | Asn | Trp | Tyr | Val | Asp | Gly | Val | Glu | Val | His | Asn | Ala | Lys |
| | | 275 | | | | | 280 | | | | | 285 | | | |
| Thr | Lys | Pro | Arg | Glu | Glu | Gln | Phe | Asn | Ser | Thr | Tyr | Arg | Val | Val | Ser |
| | 290 | | | | | 295 | | | | | 300 | | | | |
| Val | Leu | Thr | Val | Leu | His | Gln | Asp | Trp | Leu | Asn | Gly | Lys | Glu | Tyr | Lys |
| 305 | | | | | 310 | | | | | 315 | | | | | 320 |
| Cys | Lys | Val | Ser | Asn | Lys | Gly | Leu | Pro | Ser | Ser | Ile | Glu | Lys | Thr | Ile |
| | | | | 325 | | | | | 330 | | | | | 335 | |
| Ser | Lys | Ala | Lys | Gly | Gln | Pro | Arg | Glu | Pro | Gln | Val | Tyr | Thr | Leu | Pro |
| | | | 340 | | | | | 345 | | | | | 350 | | |
| Pro | Ser | Gln | Glu | Glu | Met | Thr | Lys | Asn | Gln | Val | Ser | Leu | Thr | Cys | Leu |
| | | 355 | | | | | 360 | | | | | 365 | | | |

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
                435                 440                 445

```
<210> SEQ ID NO 49
<211> LENGTH: 1341
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49
gaggtccagc tggtacagtc tggggctgag gtgaagaagc tggggctac agtgaaaatc      60 tcctgcaagg tttctggcta caccttcacc agttactgga tgtactggat caggcagtcc    120
ccatcgagag gccttgagtg gctgggtagg attgatccta atagtgggag tactaagtac    180
aatgagaagt tcaagaacag actcaccatc tccaaggaca cctccaaaaa ccaggtggtc    240
cttacaatga ccaacatgga ccctgtggac acagccacgt attactgtgc aagggactat    300 agaaagggc tctatgctat ggactactgg ggccagggca ccaccgtgac cgtgtcctcc     360
gcttccacca agggcccatc cgtcttcccc ctggcgccct gctccaggag cacctccgag    420
agcacagccg ccctgggctg cctggtcaag gactacttcc ccgaaccggt gacggtgtcg    480
tggaactcag gcgccctgac cagcggcgtg cacaccttcc cggctgtcct acagtcctca    540
ggactctact ccctcagcag cgtggtgacc gtgccctcca gcagcttggg cacgaagacc    600
tacacctgca acgtagatca caagcccagc aacaccaagg tggacaagag agttgagtcc    660
aaatatggtc ccccatgccc accgtgccca gcacctgagt tcctgggggg accatcagtc    720
ttcctgttcc ccccaaaacc caaggacact ctcatgatct cccggacccc tgaggtcacg    780
tgcgtggtgg tggacgtgag ccaggaagac cccgaggtcc agttcaactg gtacgtggat    840
ggcgtggagg tgcataatgc caagacaaag ccgcgggagg agcagttcaa cagcacgtac    900
cgtgtggtca gcgtcctcac cgtcctgcac caggactggc tgaacggcaa ggagtacaag    960
tgcaaggtgt ccaacaaagg cctcccgtcc tccatcgaga aaaccatctc caaagccaaa   1020
gggcagcccc gagagccaca ggtgtacacc ctgcccccat cccaggagga gatgaccaag   1080
aaccaggtca gcctgacctg cctggtcaaa ggcttctacc ccagcgacat cgccgtggag   1140
tgggagagca atgggcagcc ggagaacaac tacaagacca cgcctcccgt gctggactcc   1200
gacggctcct tcttcctcta cagcaggcta accgtggaca gagcaggtg gcaggagggg   1260 aatgtcttct catgctccgt gatgcatgag gctctgcaca accactacac acagaagagc   1320 ctctcccctgt ctctgggtaa a                                            1341

<210> SEQ ID NO 50
<211> LENGTH: 120
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 50

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Ser Tyr
            20                  25                  30

Trp Met Tyr Trp Ile Arg Gln Pro Pro Gly Lys Gly Leu Glu Trp Ile
        35                  40                  45

Gly Arg Ile Asp Pro Asn Ser Gly Ser Thr Lys Tyr Asn Glu Lys Phe
    50                  55                  60

Lys Asn Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Arg Lys Gly Leu Tyr Ala Met Asp Tyr Trp Gly Gln
            100                 105                 110

Gly Thr Thr Val Thr Val Ser Ser
        115                 120

<210> SEQ ID NO 51
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51
gaagtgcagc tggtgcagtc tggagcagag gtgaaaaagc ccggggagtc tctgaggatc     60
tcctgtaagg gttctggcta caccttcacc agttactgga tgtactggat ccgccagccc    120
ccagggaagg gctggagtg gattggtagg attgatccta atagtgggag tactaagtac     180
aatgagaagt tcaagaacag agtcacgatt accgcggaca atccacgag cacagcctac     240 atggagctga gcagcctgag atctgaggac acggccgtgt attactgtgc aagggactat    300 agaaagggc tctatgctat ggactactgg ggccagggca ccaccgtgac cgtgtcctcc    360

<210> SEQ ID NO 52
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Ser Tyr
            20                  25                  30

Trp Met Tyr Trp Ile Arg Gln Pro Pro Gly Lys Gly Leu Glu Trp Ile
        35                  40                  45

Gly Arg Ile Asp Pro Asn Ser Gly Ser Thr Lys Tyr Asn Glu Lys Phe
    50                  55                  60

Lys Asn Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys 85                  90                  95
Ala Arg Asp Tyr Arg Lys Gly Leu Tyr Ala Met Asp Tyr Trp Gly Gln
                100                 105                 110

Gly Thr Thr Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 53
<211> LENGTH: 1341
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53

```
gaagtgcagc tggtgcagtc tggagcagag gtgaaaaagc ccggggagtc tctgaggatc      60
tcctgtaagg gttctggcta caccttcacc agttactgga tgtactggat ccgccagccc     120
ccagggaagg ggctggagtg gattggtagg attgatccta atagtgggag tactaagtac     180
aatgagaagt tcaagaacag agtcacgatt accgcggaca atccacgag cacagcctac      240
atggagctga gcagcctgag atctgaggac acggccgtgt attactgtgc aagggactat     300
agaaaggggc tctatgctat ggactactgg ggccagggca ccaccgtgac cgtgtcctcc     360
gcttccacca agggcccatc cgtcttcccc ctggcgccct gctccaggag cacctccgag     420
agcacagccg ccctgggctg cctggtcaag gactacttcc ccgaaccggt gacggtgtcg     480
tggaactcag gcgccctgac cagcggcgtg cacaccttcc cggctgtcct acagtcctca     540
ggactctact ccctcagcag cgtggtgacc gtgccctcca gcagcttggg cacgaagacc     600
tacacctgca acgtagatca caagcccagc aacaccaagg tggacaagag agttgagtcc     660
aaatatggtc ccccatgccc accgtgccca gcacctgagt tcctgggggg accatcagtc     720
ttcctgttcc cccaaaaacc caaggacact ctcatgatct cccggacccc tgaggtcacg     780
tgcgtggtgg tggacgtgag ccaggaagac cccgaggtcc agttcaactg gtacgtggat     840
ggcgtggagg tgcataatgc caagacaaag ccgcgggagg agcagttcaa cagcacgtac     900
cgtgtggtca gcgtcctcac cgtcctgcac caggactggc tgaacggcaa ggagtacaag     960
tgcaaggtgt ccaacaaagg cctcccgtcc tccatcgaga aaaccatctc caaagccaaa    1020
gggcagcccc gagagccaca ggtgtacacc ctgcccccat cccaggagga gatgaccaag    1080
aaccaggtca gcctgacctg cctggtcaaa ggcttctacc ccagcgacat cgccgtggag    1140
tgggagagca atgggcagcc ggagaacaac tacaagacca cgcctcccgt gctggactcc    1200
gacggctcct tcttcctcta cagcaggcta accgtggaca agagcaggtg gcaggagggg    1260
aatgtcttct catgctccgt gatgcatgag gctctgcaca accactacac acagaagagc    1320
ctctcccctgt ctctgggtaa a                                             1341
```

<210> SEQ ID NO 54  
<211> LENGTH: 120  
<212> TYPE: PRT  
<213> ORGANISM: Artificial Sequence  
<220> FEATURE:  
<223> OTHER INFORMATION: Description of Artificial Sequence: Synthetic polypeptide

<400> SEQUENCE: 54

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Tyr Trp Ile Arg Gln Ser Pro Ser Arg Gly Leu Glu Trp Leu
        35                  40                  45

Gly Arg Ile Asp Pro Asn Ser Gly Ser Thr Lys Tyr Asn Glu Lys Phe
    50                  55                  60

Lys Asn Arg Phe Thr Ile Ser Arg Asp Asp Ser Lys Asn Thr Ala Tyr
65                  70                  75                  80

Leu Gln Met Asn Ser Leu Lys Thr Glu Asp Thr Ala Val Tyr Tyr Cys
                85                  90                  95

Ala Arg Asp Tyr Arg Lys Gly Leu Tyr Ala Met Asp Tyr Trp Gly Gln
            100                 105                 110

Gly Thr Thr Val Thr Val Ser Ser
        115                 120
```

115                 120

<210> SEQ ID NO 55
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55
caggttcagc tggtgcagtc tggagctgag gtgaagaagc ctggggcctc agtgaaggtc      60
tcctgcaagg cttctggcta caccttcacc agttactgga tgtactggat caggcagtcc     120
ccatcgagag gccttgagtg gctgggtagg attgatccta atagtgggag tactaagtac     180
aatgagaagt tcaagaacag attcaccatc tccagagatg attcaaagaa cacggcgtat     240
ctgcaaatga acagcctgaa aaccgaggac acggccgtgt attactgtgc aagggactat     300
agaaaggggc tctatgctat ggactactgg ggccagggca ccaccgtgac cgtgtcctcc     360

<210> SEQ ID NO 56
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Tyr Trp Ile Arg Gln Ser Pro Ser Arg Gly Leu Glu Trp Leu
        35                  40                  45

Gly Arg Ile Asp Pro Asn Ser Gly Ser Thr Lys Tyr Asn Glu Lys Phe
    50                  55                  60

Lys Asn Arg Phe Thr Ile Ser Arg Asp Asp Ser Lys Asn Thr Ala Tyr
65                  70                  75                  80

Leu Gln Met Asn Ser Leu Lys Thr Glu Asp Thr Ala Val Tyr Tyr Cys
                85                  90                  95

Ala Arg Asp Tyr Arg Lys Gly Leu Tyr Ala Met Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val

```
            225                 230                 235                 240
Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 57
<211> LENGTH: 1341
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57
caggttcagc tggtgcagtc tggagctgag gtgaagaagc ctggggcctc agtgaaggtc    60
tcctgcaagg cttctggcta caccttcacc agttactgga tgtactggat caggcagtcc   120
ccatcgagag gccttgagtg gctgggtagg attgatccta atagtgggag tactaagtac   180
aatgagaagt tcaagaacag attcaccatc tccagagatg attcaaagaa cacggcgtat   240
ctgcaaatga acagcctgaa aaccgaggac acggccgtgt attactgtgc aagggactat   300 agaaagggc tctatgctat ggactactgg ggccagggca ccaccgtgac cgtgtcctcc   360
gcttccacca agggcccatc cgtcttcccc ctggcgccct gctccaggag cacctccgag   420
agcacagccg ccctgggctg cctggtcaag gactacttcc ccgaaccggt gacggtgtcg   480
tggaactcag gcgccctgac cagcggcgtg cacaccttcc cggctgtcct acagtcctca   540
ggactctact ccctcagcag cgtggtgacc gtgccctcca gcagcttggg cacgaagacc   600
tacacctgca acgtagatca caagcccagc aacaccaagg tggacaagag agttgagtcc   660
aaatatggtc cccatgccc accgtgccca gcacctgagt tcctgggggg accatcagtc   720
ttcctgttcc ccccaaaacc caaggacact ctcatgatct cccggacccc tgaggtcacg   780
tgcgtggtgg tggacgtgag ccaggaagac cccgaggtcc agttcaactg gtacgtggat   840
```

```
ggcgtggagg tgcataatgc aagacaaag ccgcgggagg agcagttcaa cagcacgtac    900
cgtgtggtca gcgtcctcac cgtcctgcac caggactggc tgaacggcaa ggagtacaag    960
tgcaaggtgt ccaacaaagg cctcccgtcc tccatcgaga aaccatctc caaagccaaa   1020 gggcagcccc gagagccaca ggtgtacacc ctgcccccat cccaggagga gatgaccaag   1080
aaccaggtca gcctgacctg cctggtcaaa ggcttctacc ccagcgacat cgccgtggag   1140
tgggagagca atgggcagcc ggagaacaac tacaagacca cgcctcccgt gctggactcc   1200
gacggctcct tcttcctcta cagcaggcta accgtggaca agagcaggtg gcaggagggg   1260
aatgtcttct catgctccgt gatgcatgag gctctgcaca accactacac acagaagagc   1320
ctctccctgt ctctgggtaa a                                             1341
```

<210> SEQ ID NO 58
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

```
Glu Ile Val Leu Thr Gln Ser Pro Ala Thr Leu Ser Leu Ser Pro Gly
1               5                   10                  15

Glu Arg Ala Thr Leu Ser Cys Lys Ala Ser Gln Asp Val Gly Thr Ala
            20                  25                  30

Val Ala Trp Tyr Leu Gln Lys Pro Gly Gln Ser Pro Gln Leu Leu Ile
        35                  40                  45

Tyr Trp Ala Ser Thr Arg His Thr Gly Ile Pro Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Gln Gln Tyr Asn Ser Tyr Pro Leu
                85                  90                  95

Thr Phe Gly Gln Gly Thr Lys Val Glu Ile Lys
            100                 105
```

<210> SEQ ID NO 59
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59

```
gaaattgtgt tgacacagtc tccagccacc ctgtctttgt ctccagggga aagagccacc     60
ctctcctgca aggccagtca ggatgtgggt actgctgtag cctggtacct gcagaagcca    120
gggcagtctc cacagctcct gatctattgg gcatccaccc ggcacactgg gatcccacct    180
cgattcagtg gcagcgggta tggaacagat tttaccctca caattaataa catagaatct    240
gaggatgctg catattactt ctgtcagcag tataacagct atcctctcac gttcggccaa    300
gggaccaagg tggaaatcaa a                                              321
```

<210> SEQ ID NO 60
<211> LENGTH: 214
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 60

Glu Ile Val Leu Thr Gln Ser Pro Ala Thr Leu Ser Leu Ser Pro Gly
1               5                   10                  15

Glu Arg Ala Thr Leu Ser Cys Lys Ala Ser Gln Asp Val Gly Thr Ala
            20                  25                  30

Val Ala Trp Tyr Leu Gln Lys Pro Gly Gln Ser Pro Gln Leu Leu Ile
        35                  40                  45

Tyr Trp Ala Ser Thr Arg His Thr Gly Ile Pro Pro Arg Phe Ser Gly
50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Gln Gln Tyr Asn Ser Tyr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 61
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61
gaaattgtgt tgacacagtc tccagccacc ctgtctttgt ctccagggga aagagccacc        60
ctctcctgca aggccagtca ggatgtgggt actgctgtag cctggtacct gcagaagcca       120
gggcagtctc cacagctcct gatctattgg gcatccaccc ggcacactgg gatcccacct       180
cgattcagtg gcagcgggta tggaacagat tttacccctca caattaataa catagaatct       240
gaggatgctg catattactt ctgtcagcag tataacagct atcctctcac gttcggccaa       300
gggaccaagg tggaaatcaa acgtacggtg gctgcaccat ctgtcttcat cttcccgcca       360
tctgatgagc agttgaaatc tggaactgcc tctgttgtgt gcctgctgaa taacttctat       420
cccagagagg ccaaagtaca gtggaaggtg gataacgccc tccaatcggg taactcccag       480
gagagtgtca cagagcagga cagcaaggac agcacctaca gcctcagcag caccctgacg       540
ctgagcaaag cagactacga gaaacacaaa gtctacgcct gcgaagtcac ccatcagggc       600
```
ctgagctcgc ccgtcacaaa gagcttcaac aggggagagt gt                        642

<210> SEQ ID NO 62
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Ser Tyr
            20                  25                  30

Trp Met Tyr Trp Val Arg Gln Ala Arg Gly Gln Arg Leu Glu Trp Ile
        35                  40                  45

Gly Arg Ile Asp Pro Asn Ser Gly Ser Thr Lys Tyr Asn Glu Lys Phe
    50                  55                  60

Lys Asn Arg Leu Thr Ile Ser Lys Asp Thr Ser Lys Asn Gln Val Val
65                  70                  75                  80

Leu Thr Met Thr Asn Met Asp Pro Val Asp Thr Ala Thr Tyr Tyr Cys
                85                  90                  95

Ala Arg Asp Tyr Arg Lys Gly Leu Tyr Ala Met Asp Tyr Trp Gly Gln
            100                 105                 110

Gly Thr Thr Val Thr Val Ser Ser
        115                 120

<210> SEQ ID NO 63
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63
gaagtgcagc tggtgcagtc tggagcagag gtgaaaaagc ccggggagtc tctgaggatc      60
tcctgtaagg gttctggcta caccttcacc agttactgga tgtactgggt gcgacaggct     120
cgtggacaac gccttgagtg gataggtagg attgatccta atagtgggag tactaagtac     180
aatgagaagt tcaagaacag actcaccatc tccaaggaca cctccaaaaa ccaggtggtc     240
cttacaatga ccaacatgga ccctgtggac acagccacgt attactgtgc aagggactat     300 agaaagggc tctatgctat ggactactgg ggccagggca ccaccgtgac cgtgtcctcc     360

<210> SEQ ID NO 64
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Ser Tyr
            20                  25                  30

Trp Met Tyr Trp Val Arg Gln Ala Arg Gly Gln Arg Leu Glu Trp Ile
        35                  40                  45

```
Gly Arg Ile Asp Pro Asn Ser Gly Ser Thr Lys Tyr Asn Glu Lys Phe
 50                  55                  60

Lys Asn Arg Leu Thr Ile Ser Lys Asp Thr Ser Lys Asn Gln Val Val
 65                  70                  75                  80

Leu Thr Met Thr Asn Met Asp Pro Val Asp Thr Ala Thr Tyr Tyr Cys
                 85                  90                  95

Ala Arg Asp Tyr Arg Lys Gly Leu Tyr Ala Met Asp Tyr Trp Gly Gln
                100                 105                 110

Gly Thr Thr Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Lys Thr Tyr Thr Cys Asn Val Asp His Lys
                195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
                260                 265                 270

Val Gln Phe Asn Trp Tyr Val Asp Gly Val Glu Val His Asn Ala Lys
                275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Gln Glu Glu Met Thr Lys Asn Gln Val Ser Leu Thr Cys Leu
                355                 360                 365

Val Lys Gly Phe Tyr Pro Ser Asp Ile Ala Val Glu Trp Glu Ser Asn
                370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Leu Gly Lys
                435                 440                 445

<210> SEQ ID NO 65
<211> LENGTH: 1341
```

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65

```
gaagtgcagc tggtgcagtc tggagcagag gtgaaaaagc ccggggagtc tctgaggatc    60
tcctgtaagg gttctggcta caccttcacc agttactgga tgtactgggt gcgacaggct   120
cgtggacaac gccttgagtg gataggtagg attgatccta atagtgggag tactaagtac   180
aatgagaagt tcaagaacag actcaccatc tccaaggaca cctccaaaaa ccaggtggtc   240
cttacaatga ccaacatgga ccctgtggac acagccacgt attactgtgc aagggactat   300
agaaaggggc tctatgctat ggactactgg ggccagggca ccaccgtgac cgtgtcctcc   360
gcttccacca agggcccatc cgtcttcccc ctggcgccct gctccaggag cacctccgag   420
agcacagccg ccctgggctg cctggtcaag gactacttcc ccgaaccggt gacggtgtcg   480
tggaactcag gcgccctgac cagcggcgtg cacaccttcc cggctgtcct acagtcctca   540
ggactctact ccctcagcag cgtggtgacc gtgccctcca gcagcttggg cacgaagacc   600
tacacctgca acgtagatca caagcccagc aacaccaagg tggacaagag agttgagtcc   660
aaatatggtc ccccatgccc accgtgccca gcacctgagt tcctgggggg accatcagtc   720
ttcctgttcc ccccaaaacc caaggacact ctcatgatct cccggacccc tgaggtcacg   780
tgcgtggtgg tggacgtgag ccaggaagac cccgaggtcc agttcaactg gtacgtggat   840
ggcgtggagg tgcataatgc caagacaaag ccgcgggagg agcagttcaa cagcacgtac   900
cgtgtggtca gcgtcctcac cgtcctgcac caggactggc tgaacggcaa ggagtacaag   960
tgcaaggtgt ccaacaaagg cctcccgtcc tccatcgaga aaaccatctc caaagccaaa  1020
gggcagcccc gagagccaca ggtgtacacc ctgcccccat cccaggagga tgaccaag    1080
aaccaggtca gcctgacctg cctggtcaaa ggcttctacc ccagcgacat cgccgtggag  1140
tgggagagca atgggcagcc ggagaacaac tacaagacca cgcctcccgt gctggactcc  1200
gacggctcct tcttcctcta cagcaggcta accgtggaca agagcaggtg gcaggagggg  1260
aatgtcttct catgctccgt gatgcatgag gctctgcaca accactacac acagaagagc  1320
ctctcccctgt ctctgggtaa a                                            1341
```

<210> SEQ ID NO 66
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

```
Asp Val Val Met Thr Gln Ser Pro Leu Ser Leu Pro Val Thr Leu Gly
1               5                   10                  15

Gln Pro Ala Ser Ile Ser Cys Lys Ala Ser Gln Asp Val Gly Thr Ala
            20                  25                  30

Val Ala Trp Tyr Gln Gln Lys Pro Gly Gln Ala Pro Arg Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80
```

Asp Asp Phe Ala Thr Tyr Tyr Cys Gln Gln Tyr Asn Ser Tyr Pro Leu
                85                  90                  95

Thr Phe Gly Gln Gly Thr Lys Val Glu Ile Lys
            100                 105

<210> SEQ ID NO 67
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 67
gatgttgtga tgactcagtc tccactctcc ctgcccgtca cccttggaca gccggcctcc      60
atctcctgca aggccagtca ggatgtgggt actgctgtag cctggtacca gcagaaacct    120
ggccaggctc ccaggctcct catctattgg catccacccc ggcacactgg ggtcccatca    180
aggttcagcg gcagtggatc tgggacagaa ttcactctca ccatcagcag cctgcagcct    240
gatgattttg caacttatta ctgtcagcag tataacagct atcctctcac gttcggccaa    300
gggaccaagg tggaaatcaa a                                              321

<210> SEQ ID NO 68
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Asp Val Val Met Thr Gln Ser Pro Leu Ser Leu Pro Val Thr Leu Gly
1               5                   10                  15

Gln Pro Ala Ser Ile Ser Cys Lys Ala Ser Gln Asp Val Gly Thr Ala
            20                  25                  30

Val Ala Trp Tyr Gln Gln Lys Pro Gly Gln Ala Pro Arg Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 69
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 69
gatgttgtga tgactcagtc tccactctcc ctgcccgtca cccttggaca gccggcctcc      60
atctcctgca aggccagtca ggatgtgggt actgctgtag cctggtacca gcagaaacct     120
ggccaggctc ccaggctcct catctattgg catccacccc ggcacactgg ggtcccatca     180
aggttcagcg gcagtggatc tgggacagaa ttcactctca ccatcagcag cctgcagcct     240
gatgattttg caacttatta ctgtcagcag tataacagct atcctctcac gttcggccaa     300
gggaccaagg tggaaatcaa acgtacggtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac aggggagagt gt                         642

<210> SEQ ID NO 70
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Tyr Thr Phe Thr Ser Tyr
            20                  25                  30

Trp Met Tyr Trp Val Arg Gln Ala Pro Gly Lys Gly Leu Glu Trp Val
        35                  40                  45

Ser Arg Ile Asp Pro Asn Ser Gly Ser Thr Lys Tyr Asn Glu Lys Phe
    50                  55                  60

Lys Asn Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Arg Lys Gly Leu Tyr Ala Met Asp Tyr Trp Gly Gln
            100                 105                 110

Gly Thr Thr Val Thr Val Ser Ser
        115                 120

<210> SEQ ID NO 71
<211> LENGTH: 360
<212> TYPE: DNA
<213> ORGANISM: Artificial Sequence
<220> FEATURE:
<223> OTHER INFORMATION: Description of Artificial Sequence: Synthetic -continued polynucleotide

<400> SEQUENCE: 71

```
cagatcacct tgaaggagtc tggtcctacg ctggtgaaac ccacacagac cctcacgctg    60
acctgcacct tctctggcta caccttcacc agttactgga tgtactgggt ccgccaggct   120
ccagggaagg ggctggagtg ggtcagtagg attgatccta atagtgggag tactaagtac   180
aatgagaagt tcaagaacag agtcacgatt accgcggaca atccacgag cacagcctac    240
atggagctga gcagcctgag atctgaggac acggccgtgt attactgtgc aagggactat    300
agaaaggggc tctatgctat ggactactgg ggccagggca ccaccgtgac cgtgtcctcc    360
```

<210> SEQ ID NO 72
<211> LENGTH: 447
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 72

```
Gln Ile Thr Leu Lys Glu Ser Gly Pro Thr Leu Val Lys Pro Thr Gln
 1               5                  10                  15

Thr Leu Thr Leu Thr Cys Thr Phe Ser Gly Tyr Thr Phe Thr Ser Tyr
             20                  25                  30

Trp Met Tyr Trp Val Arg Gln Ala Pro Gly Lys Gly Leu Glu Trp Val
         35                  40                  45

Ser Arg Ile Asp Pro Asn Ser Gly Ser Thr Lys Tyr Asn Glu Lys Phe
 50                  55                  60

Lys Asn Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Tyr Arg Lys Gly Leu Tyr Ala Met Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
```

|  | 275 |  |  |  | 280 |  |  |  | 285 |  |  |
|---|---|---|---|---|---|---|---|---|---|---|---|

Thr Lys Pro Arg Glu Glu Gln Phe Asn Ser Thr Tyr Arg Val Val Ser
                290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Gln Glu Glu Met Thr Lys Asn Gln Val Ser Leu Thr Cys Leu
                355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Leu Gly Lys
                435                 440                 445

```
<210> SEQ ID NO 73
<211> LENGTH: 1341
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 73
cagatcacct tgaaggagtc tggtcctacg ctggtgaaac ccacacagac cctcacgctg      60
acctgcacct tctctggcta caccttcacc agttactgga tgtactgggt ccgccaggct     120
ccagggaagg gctggagtg gtcagtagg attgatccta atagtgggag tactaagtac      180
aatgagaagt tcaagaacag agtcacgatt accgcgaca aatccacgag cacagcctac     240
atggagctga gcagcctgag atctgaggac acggccgtgt attactgtgc aagggactat     300
agaaaggggc tctatgctat ggactactgg ggccagggca ccaccgtgac cgtgtcctcc     360
gcttccacca agggcccatc cgtcttcccc ctggcgccct gctccaggag cacctccgag     420
agcacagccg ccctgggctg cctggtcaag gactacttcc ccgaaccggt gacggtgtcg     480
tggaactcag gcgccctgac cagcggcgtg cacaccttcc cggctgtcct acagtcctca     540
ggactctact ccctcagcag cgtggtgacc gtgccctcca gcagcttggg cacgaagacc     600
tacacctgca acgtagatca caagcccagc aacaccaagg tggacaagag agttgagtcc     660
aaatatggtc cccatgccc accgtgccca gcacctgagt tcctgggggg accatcagtc     720
ttcctgttcc ccccaaaacc caaggacact ctcatgatct cccggacccc tgaggtcacg     780
tgcgtggtgg tggacgtgag ccaggaagac cccgaggtcc agttcaactg gtacgtggat     840
ggcgtggagg tgcataatgc caagacaaag ccgcgggagg agcagttcaa cagcacgtac     900
cgtgtggtca gcgtcctcac cgtcctgcac caggactggc tgaacggcaa ggagtacaag     960
tgcaaggtgt ccaacaaagg cctcccgtcc tccatcgaga aaaccatctc caaagccaaa    1020
gggcagcccc gagagccaca ggtgtacacc ctgcccccat cccaggagga gatgaccaag    1080
```

```
aaccaggtca gcctgacctg cctggtcaaa ggcttctacc ccagcgacat cgccgtggag    1140
tgggagagca atgggcagcc ggagaacaac tacaagacca cgcctcccgt gctggactcc    1200
gacggctcct tcttcctcta cagcaggcta accgtggaca gagcaggtg gcaggagggg     1260 aatgtcttct catgctccgt gatgcatgag gctctgcaca accactacac acagaagagc    1320
ctctccctgt ctctgggtaa a                                              1341

<210> SEQ ID NO 74
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Gly Thr Ala
            20                  25                  30

Val Ala Trp Tyr Gln Gln Lys Pro Gly Gln Ala Pro Arg Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asn Ser Tyr Pro Leu
                85                  90                  95

Thr Phe Gly Gln Gly Thr Lys Val Glu Ile Lys
            100                 105

<210> SEQ ID NO 75
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 75
gacatccaga tgacccagtc tccatcctcc ctgtctgcat ctgtaggaga cagagtcacc     60
atcacttgca aggccagtca ggatgtgggt actgctgtag cctggtacca gcagaaacct    120
ggccaggctc ccaggctcct catctattgg gcatccaccc ggcacactgg ggtcccatca    180
aggttcagtg gaagtggatc tgggacagat tttactttca ccatcagcag cctgcagcct    240
gaagatattg caacatatta ctgtcagcag tataacagct atcctctcac gttcggccaa    300
gggaccaagg tggaaatcaa a                                              321

<210> SEQ ID NO 76
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Asp Ile Gln Met Thr Gln Ser Pro Ser Ser Leu Ser Ala Ser Val Gly
1               5                   10                  15
```

Asp Arg Val Thr Ile Thr Cys Lys Ala Ser Gln Asp Val Gly Thr Ala
            20                  25                  30

Val Ala Trp Tyr Gln Gln Lys Pro Gly Gln Ala Pro Arg Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asn Ser Tyr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 77
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 77
gacatccaga tgacccagtc tccatcctcc ctgtctgcat ctgtaggaga cagagtcacc    60
atcacttgca aggccagtca ggatgtgggt actgctgtag cctggtacca gcagaaacct   120
ggccaggctc ccaggctcct catctattgg gcatccaccc ggcacactgg ggtcccatca   180
aggttcagtg gaagtggatc tgggacagat tttactttca ccatcagcag cctgcagcct   240
gaagatattg caacatatta ctgtcagcag tataacagct atcctctcac gttcggccaa   300
gggaccaagg tggaaatcaa acgtacggtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag caccctgacg   540
ctgagcaaag cagactacga gaaacacaaa gtctacgcct gcgaagtcac ccatcagggc   600
ctgagctcgc ccgtcacaaa gagcttcaac aggggagagt gt                      642

<210> SEQ ID NO 78
<211> LENGTH: 120
<212> TYPE: PRT
<213> ORGANISM: Artificial Sequence
<220> FEATURE:
<223> OTHER INFORMATION: Description of Artificial Sequence: Synthetic -continued polypeptide

<400> SEQUENCE: 78

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Ser Tyr
            20                  25                  30

Trp Met Tyr Trp Val Arg Gln Ala Arg Gly Gln Arg Leu Glu Trp Ile
        35                  40                  45

Gly Arg Ile Asp Pro Asn Ser Gly Ser Thr Lys Tyr Asn Glu Lys Phe
    50                  55                  60

Lys Asn Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Arg Lys Gly Leu Tyr Ala Met Asp Tyr Trp Gly Gln
            100                 105                 110

Gly Thr Thr Val Thr Val Ser Ser
        115                 120

<210> SEQ ID NO 79
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 79
gaggtccagc tggtacagtc tggggctgag gtgaagaagc ctggggctac agtgaaaatc      60
tcctgcaagg tttctggcta caccttcacc agttactgga tgtactgggt gcgacaggct     120
cgtggacaac gccttgagtg gataggtagg attgatccta atagtgggag tactaagtac     180
aatgagaagt tcaagaacag attcaccatc tccagagaca attccaagaa cacgctgtat     240
cttcaaatga acagcctgag agccgaggac acggccgtgt attactgtgc aagggactat     300
agaaaggggc tctatgctat ggactactgg ggccaggca ccaccgtgac cgtgtcctcc      360

<210> SEQ ID NO 80
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Ser Tyr
            20                  25                  30

Trp Met Tyr Trp Val Arg Gln Ala Arg Gly Gln Arg Leu Glu Trp Ile
        35                  40                  45

Gly Arg Ile Asp Pro Asn Ser Gly Ser Thr Lys Tyr Asn Glu Lys Phe
    50                  55                  60

Lys Asn Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

```
Ala Arg Asp Tyr Arg Lys Gly Leu Tyr Ala Met Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
        435                 440                 445

<210> SEQ ID NO 81
<211> LENGTH: 1341
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 81
gaggtccagc tggtacagtc tggggctgag gtgaagaagc ctggggctac agtgaaaatc    60
```

```
tcctgcaagg tttctggcta caccttcacc agttactgga tgtactgggt gcgacaggct    120
cgtggacaac gccttgagtg gataggtagg attgatccta atagtgggag tactaagtac    180
aatgagaagt tcaagaacag attcaccatc tccagagaca attccaagaa cacgctgtat    240
cttcaaatga acagcctgag agccgaggac acggccgtgt attactgtgc aagggactat    300
agaaaggggc tctatgctat ggactactgg ggccagggca ccaccgtgac cgtgtcctcc    360
gcttccacca agggcccatc cgtcttcccc ctggcgccct gctccaggag cacctccgag    420
agcacagccg ccctgggctg cctggtcaag gactacttcc ccgaaccggt gacggtgtcg    480
tggaactcag gcgccctgac cagcggcgtg cacaccttcc cggctgtcct acagtcctca    540
ggactctact ccctcagcag cgtggtgacc gtgccctcca gcagcttggg cacgaagacc    600
tacacctgca acgtagatca caagcccagc aacaccaagg tggacaagag agttgagtcc    660
aaatatggtc ccccatgccc accgtgccca gcacctgagt tcctgggggg accatcagtc    720
ttcctgttcc cccaaaaacc caaggacact ctcatgatct cccggacccc tgaggtcacg    780
tgcgtggtgg tggacgtgag ccaggaagac cccgaggtcc agttcaactg gtacgtggat    840
ggcgtggagg tgcataatgc caagacaaag ccgcgggagg agcagttcaa cagcacgtac    900
cgtgtggtca gcgtcctcac cgtcctgcac caggactggc tgaacggcaa ggagtacaag    960
tgcaaggtgt ccaacaaagg cctcccgtcc tccatcgaga aaaccatctc caaagccaaa    1020
gggcagcccc gagagccaca ggtgtacacc ctgcccccat cccaggagga gatgaccaag    1080
aaccaggtca gcctgacctg cctggtcaaa ggcttctacc ccagcgacat cgccgtggag    1140
tgggagagca atgggcagcc ggagaacaac tacaagacca cgcctcccgt gctggactcc    1200
gacggctcct tcttcctcta cagcaggcta accgtggaca agagcaggtg gcaggagggg    1260
aatgtcttct catgctccgt gatgcatgag gctctgcaca accactacac acagaagagc    1320
ctctccctgt ctctgggtaa a                                             1341
```

<210> SEQ ID NO 82
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 82

Ala Ile Gln Leu Thr Gln Ser Pro Ser Ser Leu Ser Ala Ser Val Gly
1               5                   10                  15

Asp Arg Val Thr Ile Thr Cys Lys Ala Ser Gln Asp Val Gly Thr Ala
            20                  25                  30

Val Ala Trp Tyr Leu Gln Lys Pro Gly Gln Ser Pro Gln Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Gln Tyr Asn Ser Tyr Pro Leu
                85                  90                  95

Thr Phe Gly Gln Gly Thr Lys Val Glu Ile Lys
            100                 105

<210> SEQ ID NO 83

<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 83

```
gccatccagt tgacccagtc tccatcctcc ctgtctgcat ctgtaggaga cagagtcacc      60
atcacttgca aggccagtca ggatgtgggt actgctgtag cctggtacct gcagaagcca     120
gggcagtctc cacagctcct gatctattgg gcatccaccc ggcacactgg ggtcccctcg     180
aggttcagtg gcagtggatc tgggacagat ttcacctttta ccatcagtag cctggaagct     240
gaagatgctg caacatatta ctgtcagcag tataacagct atcctctcac gttcggccaa     300
gggaccaagg tggaaatcaa a                                                321
```

<210> SEQ ID NO 84
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 84

```
Ala Ile Gln Leu Thr Gln Ser Pro Ser Ser Leu Ser Ala Ser Val Gly
1               5                   10                  15
Asp Arg Val Thr Ile Thr Cys Lys Ala Ser Gln Asp Val Gly Thr Ala
            20                  25                  30
Val Ala Trp Tyr Leu Gln Lys Pro Gly Gln Ser Pro Gln Leu Leu Ile
        35                  40                  45
Tyr Trp Ala Ser Thr Arg His Thr Gly Val Pro Ser Arg Phe Ser Gly
    50                  55                  60
Ser Gly Ser Gly Thr Asp Phe Thr Phe Thr Ile Ser Ser Leu Glu Ala
65                  70                  75                  80
Glu Asp Ala Ala Thr Tyr Tyr Cys Gln Gln Tyr Asn Ser Tyr Pro Leu
                85                  90                  95
Thr Phe Gly Gln Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210
```

<210> SEQ ID NO 85
<211> LENGTH: 642
<212> TYPE: DNA
<213> ORGANISM: Artificial Sequence

```
<220> FEATURE:
<223> OTHER INFORMATION: Description of Artificial Sequence: Synthetic
      polynucleotide

<400> SEQUENCE: 85
gccatccagt tgacccagtc tccatcctcc ctgtctgcat ctgtaggaga cagagtcacc      60
atcacttgca aggccagtca ggatgtgggt actgctgtag cctggtacct gcagaagcca     120
gggcagtctc cacagctcct gatctattgg gcatccaccc ggcacactgg ggtcccctcg     180
aggttcagtg gcagtggatc tgggacagat ttcaccttta ccatcagtag cctggaagct     240
gaagatgctg caacatatta ctgtcagcag tataacagct atcctctcac gttcggccaa     300
gggaccaagg tggaaatcaa acgtacggtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac aggggagagt gt                        642

<210> SEQ ID NO 86
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Glu Ile Val Leu Thr Gln Ser Pro Asp Phe Gln Ser Val Thr Pro Lys
1               5                   10                  15

Glu Lys Val Thr Ile Thr Cys Lys Ala Ser Gln Asp Val Gly Thr Ala
            20                  25                  30

Val Ala Trp Tyr Gln Gln Lys Pro Gly Gln Ala Pro Arg Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Pro Leu
                85                  90                  95

Thr Phe Gly Gln Gly Thr Lys Val Glu Ile Lys
            100                 105

<210> SEQ ID NO 87
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 87
gaaattgtgc tgactcagtc tccagacttt cagtctgtga ctccaaagga gaaagtcacc      60
atcacctgca aggccagtca ggatgtgggt actgctgtag cctggtacca gcagaaacct     120
ggccaggctc ccaggctcct catctattgg gcatccaccc ggcacactgg ggtcccatca     180
aggttcagcg gcagtggatc tgggacagaa ttcactctca ccatcagcag cctgcagcct     240
```

```
gatgattttg caacttatta ctgtcagcag tataacagct atcctctcac gttcggccaa    300
gggaccaagg tggaaatcaa a                                              321
```

<210> SEQ ID NO 88
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

```
Glu Ile Val Leu Thr Gln Ser Pro Asp Phe Gln Ser Val Thr Pro Lys
1               5                   10                  15

Glu Lys Val Thr Ile Thr Cys Lys Ala Ser Gln Asp Val Gly Thr Ala
            20                  25                  30

Val Ala Trp Tyr Gln Gln Lys Pro Gly Gln Ala Pro Arg Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 89
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 89

```
gaaattgtgc tgactcagtc tccagacttt cagtctgtga ctccaaagga gaaagtcacc    60
atcacctgca aggccagtca ggatgtgggt actgctgtag cctggtacca gcagaaacct   120
ggccaggctc ccaggctcct catctattgg gcatccaccc ggcacactgg ggtcccatca   180
aggttcagcg gcagtggatc tgggacagaa ttcactctca ccatcagcag cctgcagcct   240
gatgattttg caacttatta ctgtcagcag tataacagct atcctctcac gttcggccaa   300
gggaccaagg tggaaatcaa acgtacggtg gctgcaccat ctgtcttcat cttcccgcca   360
```

```
tctgatgagc agttgaaatc tggaactgcc tctgttgtgt gcctgctgaa taacttctat    420
cccagagagg ccaaagtaca gtggaaggtg ataacgccc tccaatcggg taactcccag     480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gt                      642
```

<210> SEQ ID NO 90
<211> LENGTH: 360
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 90

```
gaagtgcagc tggtgcagtc aggcgccgaa gtgaagaagc ccggcgagtc actgagaatt    60
agctgtaaag gttcaggcta caccttcact agctactgga tgtactgggt ccgacaggcc    120
ccagggcaag gcctggagtg gatgggtaga atcgacccta atagcggctc tactaagtat   180
aacgagaagt ttaagaatag agtgactatt agcgtggaca cctctaagaa tcagtttagc    240
ctgaagctgt ctagcgtgac cgccgctgac accgccgtct actactgcgc tagagactat    300
agaaagggcc tgtacgctat ggactactgg ggtcaaggca ctaccgtgac cgtgtcttca    360
```

<210> SEQ ID NO 91
<211> LENGTH: 446
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 91

```
Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Ser Tyr
            20                  25                  30

Trp Met Tyr Trp Val Arg Gln Ala Pro Gly Gln Gly Leu Glu Trp Met
        35                  40                  45

Gly Arg Ile Asp Pro Asn Ser Gly Ser Thr Lys Tyr Asn Glu Lys Phe
    50                  55                  60

Lys Asn Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asp Tyr Arg Lys Gly Leu Tyr Ala Met Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
```

```
            180                 185                 190
Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
        210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
        435                 440                 445

<210> SEQ ID NO 92
<211> LENGTH: 1338
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 92
gaagtgcagc tggtgcagtc aggcgccgaa gtgaagaagc cggcgagtc actgagaatt        60 agctgtaaag gttcaggcta caccttcact agctactgga tgtactgggt ccgacaggcc      120
ccagggcaag gcctggagtg gatgggtaga atcgacccta tagcggctc tactaagtat       180 aacgagaagt ttaagaatag agtgactatt agcgtggaca cctctaagaa tcagtttagc      240
ctgaagctgt ctagcgtgac cgccgctgac accgccgtct actactgcgc tagagactat      300
agaaagggcc tgtacgctat ggactactgg ggtcaaggca ctaccgtgac cgtgtcttca      360
gctagcacta agggcccgtc cgtgttcccc ctggcacctt gtagccggag cactagcgaa      420
tccaccgctg ccctcggctg cctggtcaag gattacttcc cggagcccgt gaccgtgtcc      480
tggaacagcg gagccctgac ctccggagtg cacaccttcc ccgctgtgct gcagagctcc      540
```

```
gggctgtact cgctgtcgtc ggtggtcacg gtgccttcat ctagcctggg taccaagacc      600
tacacttgca acgtggacca caagccttcc aacactaagg tggacaagcg cgtcgaatcg      660
aagtacggcc caccgtgccc gccttgtccc gcgccggagt tcctcggcgg tccctcggtc      720
tttctgttcc caccgaagcc caaggacact ttgatgattt cccgcacccc tgaagtgaca      780
tgcgtggtcg tggacgtgtc acaggaagat ccggaggtgc agttcaattg gtacgtggat      840
ggcgtcgagg tgcacaacgc caaaaccaag ccgagggagg agcagttcaa ctccacttac      900
cgcgtcgtgt ccgtgctgac ggtgctgcat caggactggc tgaacgggaa ggagtacaag      960
tgcaaagtgt ccaacaaggg acttcctagc tcaatcgaaa agaccatctc gaaagccaag     1020
ggacagcccc gggaacccca gtgtatacc ctgccaccga gccaggaaga aatgactaag      1080
aaccaagtct cattgacttg ccttgtgaag ggcttctacc catcggatat cgccgtggaa     1140
tgggagtcca acggccagcc ggaaaacaac tacaagacca ccctccggt gctggactca      1200 gacggatcct tcttcctcta ctcgcggctg accgtggata agagcagatg gcaggaggga     1260
aatgtgttca gctgttctgt gatgcatgaa gccctgcaca ccactacac tcagaagtcc      1320 ctgtccctct ccctggga                                                   1338

<210> SEQ ID NO 93
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 93
gagatcgtcc tgactcagtc acccgacttt cagtcagtga cccctaaaga gaaagtcact       60
atcacctgta aagcctctca ggacgtgggc accgccgtgg cctggtatct gcagaagcct      120
ggtcaatcac ctcagctgct gatctactgg gcctctacta gacacaccgg cgtgccctct      180
aggtttagcg gtagcggtag tggcaccgac ttcaccttca ctatctcttc actgcagccc      240
gaggatatcg ctacctacta ctgtcagcag tataatagct accccctgac cttcggtcaa      300
ggcactaagg tcgagattaa g                                                321

<210> SEQ ID NO 94
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 94
gagatcgtcc tgactcagtc acccgacttt cagtcagtga cccctaaaga gaaagtcact       60
atcacctgta aagcctctca ggacgtgggc accgccgtgg cctggtatct gcagaagcct      120
ggtcaatcac ctcagctgct gatctactgg gcctctacta gacacaccgg cgtgccctct      180
aggtttagcg gtagcggtag tggcaccgac ttcaccttca ctatctcttc actgcagccc      240
gaggatatcg ctacctacta ctgtcagcag tataatagct accccctgac cttcggtcaa      300
ggcactaagg tcgagattaa gcgtacggtg gccgctccca gcgtgttcat cttccccccc      360
agcgacgagc agctgaagag cggcaccgcc agcgtggtgt gcctgctgaa caacttctac      420 cccgggagg ccaaggtgca gtggaaggtg acaacgccc tgcagagcgg caacagccag       480
gagagcgtca ccgagcagga cagcaaggac tccacctaca gcctgagcag caccctgacc      540
```

```
ctgagcaagg ccgactacga gaagcataag gtgtacgcct gcgaggtgac ccaccagggc    600
ctgtccagcc ccgtgaccaa gagcttcaac aggggcgagt gc                       642
```

<210> SEQ ID NO 95
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 95

```
gaagtgcagc tggtgcagtc aggcgccgaa gtgaagaaac ccggcgctac cgtgaagatt    60
agctgtaaag tctcaggcta caccttcact agctactgga tgtactgggt ccgacaggct   120
accggtcaag gcctggagtg gatgggtaga atcgacccta tagcggctc tactaagtat    180 aacgagaagt ttaagaatag agtgactatc accgccgata agtctactag caccgcctat   240
atggaactgt ctagcctgag atcagaggac accgccgtct actactgcgc tagagactat   300
agaaagggcc tgtacgctat ggactactgg ggtcaaggca ctaccgtgac cgtgtcttca   360
```

<210> SEQ ID NO 96
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

```
Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Ser Tyr
            20                  25                  30

Trp Met Tyr Trp Val Arg Gln Ala Thr Gly Gln Gly Leu Glu Trp Met
        35                  40                  45

Gly Arg Ile Asp Pro Asn Ser Gly Ser Thr Lys Tyr Asn Glu Lys Phe
    50                  55                  60

Lys Asn Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Arg Lys Gly Leu Tyr Ala Met Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
```

Pro Cys Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser Gln Glu Asp Pro Glu
                260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
        435                 440                 445

<210> SEQ ID NO 97
<211> LENGTH: 1338
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 97
gaagtgcagc tggtgcagtc aggcgccgaa gtgaagaaac ccggcgctac cgtgaagatt      60
agctgtaaag tctcaggcta caccttcact agctactgga tgtactgggt ccgacaggct     120
accggtcaag gcctggagtg gatgggtaga atcgacccta atagcggctc tactaagtat     180
aacgagaagt ttaagaatag agtgactatc accgccgata gtctactagt caccgcctat     240
atggaactgt ctagcctgag atcagaggac accgccgtct actactgcgc tagagactat     300
agaaagggcc tgtacgctat ggactactgg ggtcaaggca ctaccgtgac cgtgtcttca     360
gctagcacta agggcccgtc cgtgttcccc ctggcacctt gtagccggag cactagcgaa     420
tccaccgctg ccctcggctg cctggtcaag gattacttcc cggagcccgt gaccgtgtcc     480
tggaacagcg gagccctgac ctccggagtg cacaccttcc ccgctgtgct gcagagctcc     540
gggctgtact cgctgtcgtc ggtggtcacg gtgccttcat ctagcctggg taccaagacc     600
tacacttgca acgtggacca caagccttcc aacactaagg tggacaagcg cgtcgaatcg     660
aagtacggcc caccgtgccc gccttgtccc gcgccggagt tcctcggcgg tcccctcggtc    720

```
tttctgttcc caccgaagcc caaggacact tgatgattt cccgcacccc tgaagtgaca    780
tgcgtggtcg tggacgtgtc acaggaagat ccggaggtgc agttcaattg gtacgtggat    840
ggcgtcgagg tgcacaacgc caaaaccaag ccgagggagg agcagttcaa ctccacttac    900
cgcgtcgtgt ccgtgctgac ggtgctgcat caggactggc tgaacgggaa ggagtacaag    960
tgcaaagtgt ccaacaaggg acttcctagc tcaatcgaaa agaccatctc gaaagccaag   1020
ggacagcccc gggaaccccca agtgtatacc ctgccaccga gccaggaaga atgactaag   1080 aaccaagtct cattgacttg ccttgtgaag ggcttctacc catcggatat cgccgtggaa   1140
tgggagtcca acggccagcc ggaaaacaac tacaagacca cccctccggt gctggactca   1200
gacggatcct tcttcctcta ctcgcggctg accgtggata agagcagatg gcaggaggga   1260
aatgtgttca gctgttctgt gatgcatgaa gccctgcaca accactacac tcagaagtcc   1320
ctgtccctct ccctggga                                                 1338

<210> SEQ ID NO 98
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 98
gacgtcgtga tgactcagtc accctgagc ctgcccgtga ccctggggca gcccgcctct      60
attagctgta aagcctctca ggacgtgggc accgccgtgg cctggtatca gcagaagcca   120
gggcaagccc ctagactgct gatctactgg gcctctacta gacacaccgg cgtgccctct   180
aggtttagcg gtagcggtag tggcaccgag ttcaccctga ctatctcttc actgcagccc   240
gacgacttcg ctacctacta ctgtcagcag tataatagct acccccctgac cttcggtcaa   300 ggcactaagg tcgagattaa g                                             321

<210> SEQ ID NO 99
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 99
gacgtcgtga tgactcagtc accctgagc ctgcccgtga ccctggggca gcccgcctct      60
attagctgta aagcctctca ggacgtgggc accgccgtgg cctggtatca gcagaagcca   120
gggcaagccc ctagactgct gatctactgg gcctctacta gacacaccgg cgtgccctct   180
aggtttagcg gtagcggtag tggcaccgag ttcaccctga ctatctcttc actgcagccc   240
gacgacttcg ctacctacta ctgtcagcag tataatagct acccccctgac cttcggtcaa   300 ggcactaagg tcgagattaa gcgtacggtg gccgctccca gcgtgttcat cttccccccc   360
agcgacgagc agctgaagag cggcaccgcc agcgtggtgt gcctgctgaa caacttctac   420
ccccgggagg ccaaggtgca gtggaaggtg acaacgccc tgcagagcgg caacagccag   480
gagagcgtca ccgagcagga cagcaaggac tccacctaca gcctgagcag cacctgacc   540 ctgagcaagg ccgactacga gaagcataag gtgtacgcct gcgaggtgac ccaccagggc   600
ctgtccagcc ccgtgaccaa gagcttcaac aggggcgagt gc                      642
```

```
<210> SEQ ID NO 100
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 100
gaagtgcagc tggtgcagtc aggcgccgaa gtgaagaaac ccggcgctac cgtgaagatt     60
agctgtaaag tctcaggcta caccttcact agctactgga tgtactgggt ccgacaggct    120
agagggcaaa gactggagtg gatcggtaga atcgacccta atagcggctc tactaagtat    180
aacgagaagt ttaagaatag gttcactatt agtagggata actctaagaa caccctgtac    240
ctgcagatga atagcctgag agccgaggac accgccgtct actactgcgc tagagactat    300
agaaagggcc tgtacgctat ggactactgg ggtcaaggca ctaccgtgac cgtgtcttca    360

<210> SEQ ID NO 101
<211> LENGTH: 1338
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 101
gaagtgcagc tggtgcagtc aggcgccgaa gtgaagaaac ccggcgctac cgtgaagatt     60
agctgtaaag tctcaggcta caccttcact agctactgga tgtactgggt ccgacaggct    120
agagggcaaa gactggagtg gatcggtaga atcgacccta atagcggctc tactaagtat    180
aacgagaagt ttaagaatag gttcactatt agtagggata actctaagaa caccctgtac    240
ctgcagatga atagcctgag agccgaggac accgccgtct actactgcgc tagagactat    300
agaaagggcc tgtacgctat ggactactgg ggtcaaggca ctaccgtgac cgtgtcttca    360
gctagcacta agggcccgtc cgtgttcccc ctggcacctt gtagccggag cactagcgaa    420
tccaccgctg ccctcggctg cctggtcaag gattacttcc cggagcccgt gaccgtgtcc    480
tggaacagcg gagccctgac ctccggagtg cacaccttcc ccgctgtgct gcagagctcc    540
gggctgtact cgctgtcgtc ggtggtcacg gtgccttcat ctagcctggg taccaagacc    600
tacacttgca acgtggacca caagccttcc aacactaagg tggacaagcg cgtcgaatcg    660
aagtacggcc accgtgcccg ccttgtccc gcgccggagt tcctcggcgg tccctcggtc    720
tttctgttcc caccgaagcc caaggacact ttgatgattt cccgcacccc tgaagtgaca    780
tgcgtggtcg tggacgtgtc acaggaagat ccggaggtgc agttcaattg gtacgtggat    840
ggcgtcgagg tgcacaacgc caaaaccaag ccgagggagg agcagttcaa ctccacttac    900
cgcgtcgtgt ccgtgctgac ggtgctgcat caggactggc tgaacgggaa ggagtacaag    960
tgcaaagtgt ccaacaaggg acttcctagc tcaatcgaaa agaccatctc gaaagccaag   1020
ggacagcccc gggaaccca agtgtatacc ctgccaccga gccaggaaga aatgactaag   1080
aaccaagtct cattgacttg ccttgtgaag ggcttctacc catcggatat cgccgtggaa   1140
tgggagtcca acgccagcc ggaaaacaac tacaagacca cccctccggt gctggactca   1200
gacggatcct tcttcctcta ctcgcggctg accgtggata gagcagatg gcaggaggga   1260 aatgtgttca gctgttctgt gatgcatgaa gccctgcaca accactacac tcagaagtcc   1320
ctgtccctct ccctggga                                                1338
```

<210> SEQ ID NO 102
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 102
gctattcagc tgactcagtc acctagtagc ctgagcgcta gtgtgggcga tagagtgact    60
atcacctgta aagcctctca ggacgtgggc accgccgtgg cctggtatct gcagaagcct   120
ggtcaatcac ctcagctgct gatctactgg gcctctacta gacacaccgg cgtgccctct   180
aggtttagcg gtagcggtag tggcaccgac ttcaccttca ctatctcttc actggaagcc   240
gaggacgccg ctacctacta ctgtcagcag tataatagct accccctgac cttcggtcaa   300
ggcactaagg tcgagattaa g                                             321

<210> SEQ ID NO 103
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 103
gctattcagc tgactcagtc acctagtagc ctgagcgcta gtgtgggcga tagagtgact    60
atcacctgta aagcctctca ggacgtgggc accgccgtgg cctggtatct gcagaagcct   120
ggtcaatcac ctcagctgct gatctactgg gcctctacta gacacaccgg cgtgccctct   180
aggtttagcg gtagcggtag tggcaccgac ttcaccttca ctatctcttc actggaagcc   240
gaggacgccg ctacctacta ctgtcagcag tataatagct accccctgac cttcggtcaa   300
ggcactaagg tcgagattaa gcgtacggtg gccgctccca gcgtgttcat cttcccccc    360 agcgacgagc agctgaagag cggcaccgcc agcgtggtgt gcctgctgaa caacttctac   420
ccccgggagg ccaaggtgca gtggaaggtg acaacgcccc tgcagagcgg caacagccag   480
gagagcgtca ccgagcagga cagcaaggac tccacctaca gcctgagcag caccctgacc   540
ctgagcaagg ccgactacga aagcataag gtgtacgcct gcgaggtgac ccaccagggc   600
ctgtccagcc ccgtgaccaa gagcttcaac aggggcgagt gc                      642

<210> SEQ ID NO 104
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
agttactgga tgtac                                                     15

<210> SEQ ID NO 105
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
aggattgatc ctaatagtgg gagtactaag tacaatgaga agttcaagaa c    51

<210> SEQ ID NO 106
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
gactatagaa aggggctcta tgctatggac tac    33

<210> SEQ ID NO 107
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
ggctacacct tcaccagtta c    21

<210> SEQ ID NO 108
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
gatcctaata gtgggagt    18

<210> SEQ ID NO 109
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
cagcagtata acagctatcc tctcacg    27

<210> SEQ ID NO 110
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
agtcaggatg tgggtactgc t    21

<210> SEQ ID NO 111
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111

```
tgggcatcc                                                              9
```

<210> SEQ ID NO 112
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112

```
tataacagct atcctctc                                                   18
```

<210> SEQ ID NO 113
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113

```
agctactgga tgtac                                                      15
```

<210> SEQ ID NO 114
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114

```
agaatcgacc ctaatagcgg ctctactaag tataacgaga agtttaagaa t              51
```

<210> SEQ ID NO 115
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115

```
gactatagaa agggcctgta cgctatggac tac                                  33
```

<210> SEQ ID NO 116
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116

```
ggctacacct tcactagcta c                                               21
```

<210> SEQ ID NO 117
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117

```
gaccctaata gcggctct                                                   18
```

<210> SEQ ID NO 118
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
aaagcctctc aggacgtggg caccgccgtg gcc                               33

<210> SEQ ID NO 119
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
tgggcctcta ctagacacac c                                           21

<210> SEQ ID NO 120
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
cagcagtata atagctaccc cctgacc                                     27

<210> SEQ ID NO 121
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
tctcaggacg tgggcaccgc c                                           21

<210> SEQ ID NO 122
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122 tgggcctct                                                          9

<210> SEQ ID NO 123
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
tataatagct accccctg                                               18

<210> SEQ ID NO 124
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Gln Val Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 125
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
caggttcagc tggtgcagtc tggagctgag gtgaagaagc ctggggcctc agtgaaggtc    60
tcctgcaagg cttct                                                    75

<210> SEQ ID NO 126
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Glu Val Gln Leu Val Gln Ser Gly Ala Glu Val Lys Lys Pro Gly Glu
1               5                   10                  15

Ser Leu Arg Ile Ser Cys Lys Gly Ser
            20                  25

<210> SEQ ID NO 127
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
gaagtgcagc tggtgcagtc tggagcagag gtgaaaaagc ccggggagtc tctgaggatc    60
tcctgtaagg gttct                                                    75

<210> SEQ ID NO 128
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Glu Val Gln Leu Val Gln Ser Gly Ala Glu Val Lys Lys Pro Gly Ala
1               5                   10                  15

Thr Val Lys Ile Ser Cys Lys Val Ser

<210> SEQ ID NO 129
<211> LENGTH: 75
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 129
gaggtccagc tggtacagtc tggggctgag gtgaagaagc ctggggctac agtgaaaatc    60
tcctgcaagg tttct    75

<210> SEQ ID NO 130
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 130

Gln Ile Thr Leu Lys Glu Ser Gly Pro Thr Leu Val Lys Pro Thr Gln
1               5                   10                  15

Thr Leu Thr Leu Thr Cys Thr Phe Ser
            20                  25

<210> SEQ ID NO 131
<211> LENGTH: 75
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 131
cagatcacct tgaaggagtc tggtcctacg ctggtgaaac ccacacagac cctcacgctg    60
acctgcacct tctct    75

<210> SEQ ID NO 132
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 132

Trp Val Arg Gln Ala Thr Gly Gln Gly Leu Glu Trp Met Gly
1               5                   10

<210> SEQ ID NO 133
<211> LENGTH: 42
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 133
tgggtgcgac aggccactgg acaagggctt gagtggatgg gt    42

<210> SEQ ID NO 134
<211> LENGTH: 14

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Trp Val Arg Gln Ala Pro Gly Gln Gly Leu Glu Trp Met Gly
1               5                   10

<210> SEQ ID NO 135
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
tgggtgcgac aggcccctgg acaagggctt gagtggatgg gt                          42

<210> SEQ ID NO 136
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Trp Ile Arg Gln Pro Pro Gly Lys Gly Leu Glu Trp Ile Gly
1               5                   10

<210> SEQ ID NO 137
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
tggatccgcc agcccccagg gaagggctg gagtggattg gt                           42

<210> SEQ ID NO 138
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Trp Ile Arg Gln Ser Pro Ser Arg Gly Leu Glu Trp Leu Gly
1               5                   10

<210> SEQ ID NO 139
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
tggatcaggc agtccccatc gagaggcctt gagtggctgg gt                          42
```

<210> SEQ ID NO 140
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Trp Val Arg Gln Ala Arg Gly Gln Arg Leu Glu Trp Ile Gly
1               5                   10

<210> SEQ ID NO 141
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
tgggtgcgac aggctcgtgg acaacgcctt gagtggatag gt                          42

<210> SEQ ID NO 142
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Trp Val Arg Gln Ala Pro Gly Lys Gly Leu Glu Trp Val Ser
1               5                   10

<210> SEQ ID NO 143
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
tgggtccgcc aggctccagg gaagggctg gagtgggtca gt                           42

<210> SEQ ID NO 144
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Arg Phe Thr Ile Ser Arg Asp Asp Ser Lys Asn Thr Ala Tyr Leu Gln
1               5                   10                  15

Met Asn Ser Leu Lys Thr Glu Asp Thr Ala Val Tyr Tyr Cys Ala Arg
            20                  25                  30

<210> SEQ ID NO 145
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 145
agattcacca tctccagaga tgattcaaag aacacggcgt atctgcaaat gaacagcctg    60
aaaaccgagg acacggccgt gtattactgt gcaagg                              96

<210> SEQ ID NO 146
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Arg Val Thr Ile Thr Ala Asp Lys Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 147
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
agagtcacga ttaccgcgga caaatccacg agcacagcct acatggagct gagcagcctg    60
agatctgagg acacggccgt gtattactgt gcaagg                              96

<210> SEQ ID NO 148
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 149
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
agagtcacca tatcagtaga cacgtccaag aaccagttct ccctgaagct gagctctgtg    60
accgccgcgg acacggctgt gtattactgt gcaagg                              96

<210> SEQ ID NO 150
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 150

Arg Leu Thr Ile Ser Lys Asp Thr Ser Lys Asn Gln Val Val Leu Thr
1               5                   10                  15
Met Thr Asn Met Asp Pro Val Asp Thr Ala Thr Tyr Tyr Cys Ala Arg
            20                  25                  30

<210> SEQ ID NO 151
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
agactcacca tctccaagga cacctccaaa aaccaggtgg tccttacaat gaccaacatg    60
gaccctgtgg acacagccac gtattactgt gcaagg                              96

<210> SEQ ID NO 152
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Arg Phe Thr Ile Ser Arg Asp Asn Ser Lys Asn Thr Leu Tyr Leu Gln
1               5                   10                  15
Met Asn Ser Leu Arg Ala Glu Asp Thr Ala Val Tyr Tyr Cys Ala Arg
            20                  25                  30

<210> SEQ ID NO 153
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
agattcacca tctccagaga caattccaag aacacgctgt atcttcaaat gaacagcctg    60
agagccgagg acacggccgt gtattactgt gcaagg                              96

<210> SEQ ID NO 154
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Trp Gly Gln Gly Thr Thr Val Thr Val Ser Ser
1               5                   10

<210> SEQ ID NO 155
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
tggggccagg gcaccaccgt gaccgtgtcc tcc                                    33

<210> SEQ ID NO 156
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Glu Ile Val Leu Thr Gln Ser Pro Asp Phe Gln Ser Val Thr Pro Lys
1               5                   10                  15

Glu Lys Val Thr Ile Thr Cys
            20

<210> SEQ ID NO 157
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
gaaattgtgc tgactcagtc tccagacttt cagtctgtga ctccaaagga gaaagtcacc     60
atcacctgc                                                              69

<210> SEQ ID NO 158
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Asp Val Val Met Thr Gln Ser Pro Leu Ser Leu Pro Val Thr Leu Gly
1               5                   10                  15

Gln Pro Ala Ser Ile Ser Cys
            20

<210> SEQ ID NO 159
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
gatgttgtga tgactcagtc tccactctcc ctgcccgtca cccttggaca gccggcctcc     60
atctcctgc                                                              69

<210> SEQ ID NO 160
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Asp Ile Val Met Thr Gln Thr Pro Leu Ser Leu Pro Val Thr Pro Gly

Glu Pro Ala Ser Ile Ser Cys
            20

<210> SEQ ID NO 161
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
gatattgtga tgacccagac tccactctcc ctgcccgtca cccctggaga gccggcctcc    60
atctcctgc                                                           69

<210> SEQ ID NO 162
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 163
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
gacatccaga tgacccagtc tccatcctcc ctgtctgcat ctgtaggaga cagagtcacc    60
atcacttgc                                                           69

<210> SEQ ID NO 164
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Glu Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 165
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165

```
gaaattgtgt tgacacagtc tccagccacc ctgtctttgt ctccagggga aagagccacc    60
ctctcctgc                                                            69
```

<210> SEQ ID NO 166
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Ala Ile Gln Leu Thr Gln Ser Pro Ser Ser Leu Ser Ala Ser Val Gly
1               5                   10                  15

Asp Arg Val Thr Ile Thr Cys
            20

<210> SEQ ID NO 167
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167

```
gccatccagt tgacccagtc tccatcctcc ctgtctgcat ctgtaggaga cagagtcacc    60
atcacttgc                                                            69
```

<210> SEQ ID NO 168
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Trp Tyr Gln Gln Lys Pro Gly Gln Ala Pro Arg Leu Leu Ile Tyr
1               5                   10                  15

<210> SEQ ID NO 169
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169

```
tggtaccagc agaaacctgg ccaggctccc aggctcctca tctat                    45
```

<210> SEQ ID NO 170
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Trp Tyr Leu Gln Lys Pro Gly Gln Ser Pro Gln Leu Leu Ile Tyr
1               5                   10                  15

<210> SEQ ID NO 171
<211> LENGTH: 45
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 171
tggtacctgc agaagccagg gcagtctcca cagctcctga tctat    45

<210> SEQ ID NO 172
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 172

Gly Val Pro Ser Arg Phe Ser Gly Ser Gly Ser Gly Thr Glu Phe Thr
1               5                   10                  15

Leu Thr Ile Ser Ser Leu Gln Pro Asp Asp Phe Ala Thr Tyr Tyr Cys
            20                  25                  30

<210> SEQ ID NO 173
<211> LENGTH: 96
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 173
ggggtcccat caaggttcag cggcagtgga tctgggacag aattcactct caccatcagc    60
agcctgcagc ctgatgattt tgcaacttat tactgt    96

<210> SEQ ID NO 174
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 174

Gly Val Pro Ser Arg Phe Ser Gly Ser Gly Ser Gly Thr Asp Phe Thr
1               5                   10                  15

Phe Thr Ile Ser Ser Leu Gln Pro Glu Asp Ile Ala Thr Tyr Tyr Cys
            20                  25                  30

<210> SEQ ID NO 175
<211> LENGTH: 96
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 175
ggggtcccat caaggttcag tggaagtgga tctgggacag attttacttt caccatcagc    60
agcctgcagc ctgaagatat tgcaacatat tactgt    96

<210> SEQ ID NO 176
<211> LENGTH: 32

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 176

Gly Ile Pro Ala Arg Phe Ser Gly Ser Gly Ser Gly Thr Glu Phe Thr
1               5                   10                  15

Leu Thr Ile Ser Ser Leu Gln Ser Glu Asp Phe Ala Val Tyr Tyr Cys
            20                  25                  30

<210> SEQ ID NO 177
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
gggatcccag ccaggttcag tggcagtggg tctgggacag agttcactct caccatcagc      60
agcctgcagt ctgaagattt tgcagtttat tactgt                                96

<210> SEQ ID NO 178
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 179
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
ggggtcccat caaggttcag cggcagtgga tctgggacag atttcactct caccatcagc      60
agcctgcagc ctgaagattt tgcaacttat tactgt                                96

<210> SEQ ID NO 180
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 180

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30
```

```
<210> SEQ ID NO 181
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
ggggtcccag acaggttcag tggcagtggg tcaggcactg atttcacact gaaaatcagc      60
agggtggagg ctgaggatgt tggagtttat tactgt                                96

<210> SEQ ID NO 182
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 182

Gly Ile Pro Pro Arg Phe Ser Gly Ser Gly Tyr Gly Thr Asp Phe Thr
1               5                   10                  15

Leu Thr Ile Asn Asn Ile Glu Ser Glu Asp Ala Ala Tyr Tyr Phe Cys
            20                  25                  30

<210> SEQ ID NO 183
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
gggatcccac ctcgattcag tggcagcggg tatggaacag attttaccct cacaattaat      60
aacatagaat ctgaggatgc tgcatattac ttctgt                                96

<210> SEQ ID NO 184
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 184

Gly Val Pro Ser Arg Phe Ser Gly Ser Gly Ser Gly Thr Asp Phe Thr
1               5                   10                  15

Phe Thr Ile Ser Ser Leu Glu Ala Glu Asp Ala Ala Thr Tyr Tyr Cys
            20                  25                  30

<210> SEQ ID NO 185
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
ggggtcccct cgaggttcag tggcagtgga tctgggacag atttcacctt taccatcagt      60
agcctggaag ctgaagatgc tgcaacatat tactgt                                96
```

-continued

<210> SEQ ID NO 186
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Phe Gly Gln Gly Thr Lys Val Glu Ile Lys
1               5                   10

<210> SEQ ID NO 187
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
ttcggccaag ggaccaaggt ggaaatcaaa                                    30

<210> SEQ ID NO 188
<211> LENGTH: 327
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 188

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

```
Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
        260                 265                 270

Thr Thr Pro Pro Val Leu Asp Ser Asp Gly Ser Phe Phe Leu Tyr Ser
    275                 280                 285

Arg Leu Thr Val Asp Lys Ser Arg Trp Gln Gln Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 189
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 189

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 190
<211> LENGTH: 326
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 190

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80
```

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 191
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 191

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 192
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 192

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys

```
            130                 135                 140
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 193
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 193

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Ala Val Ser His Glu Asp Pro Glu Val Lys Phe Asn Trp
145                 150                 155                 160
```

```
Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Ala Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 194
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 194

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190
```

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 195
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Gly Tyr Thr Phe Thr Ser Tyr Trp Met Tyr
1               5                   10

<210> SEQ ID NO 196
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 196
gaagtgcagc tggtgcagtc tggcgccgaa gtgaagaaac ccggcgctac cgtgaagatc      60
tcctgcaagg tgtccggcta caccttcacc agctactgga tgtactgggt gcgacaggct     120
accggccagg gcctggaatg gatgggcaga atcgacccca ctccggctc accaagtac      180 aacgagaagt tcaagaaccg cgtgaccatc accgccgaca gtccacctc accgcctac      240 atggaactgt cctccctgcg gagcgaggac accgccgtgt actactgcgc cagagactac     300
cggaagggcc tgtacgccat ggactattgg ggccagggca ccaccgtgac cgtgtcctct     360

<210> SEQ ID NO 197
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 197

Glu Val Gln Leu Val Gln Ser Gly Ala Glu Val Lys Lys Pro Gly Ala
1               5                   10                  15

-continued

```
Thr Val Lys Ile Ser Cys Lys Val Ser Gly Tyr Thr Phe Ser Tyr
             20                  25                  30

Trp Met Tyr Trp Val Arg Gln Ala Thr Gly Gln Gly Leu Glu Trp Met
         35                  40                  45

Gly Arg Ile Asp Pro Asn Ser Gly Ser Thr Lys Tyr Asn Glu Lys Phe
     50                  55                  60

Lys Asn Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Tyr Arg Lys Gly Leu Tyr Ala Met Asp Tyr Trp Gly Gln
             100                 105                 110

Gly Thr Thr Val Thr Val Ser Ser Ala Ser Thr Lys Gly Pro Ser Val
         115                 120                 125

Phe Pro Leu Ala Pro Cys Ser Arg Ser Thr Ser Glu Ser Thr Ala Ala
     130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                 165                 170                 175

Leu Gln Ser Ser Gly Leu Tyr Ser Leu Ser Ser Val Val Thr Val Pro
             180                 185                 190

Ser Ser Ser Leu Gly Thr Lys Thr Tyr Thr Cys Asn Val Asp His Lys
         195                 200                 205

Pro Ser Asn Thr Lys Val Asp Lys Arg Val Glu Ser Lys Tyr Gly Pro
     210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                 245                 250                 255

Pro Glu Val Thr Cys Val Val Val Asp Val Ser Gln Glu Asp Pro Glu
             260                 265                 270

Val Gln Phe Asn Trp Tyr Val Asp Gly Val Glu Val His Asn Ala Lys
         275                 280                 285

Thr Lys Pro Arg Glu Glu Gln Phe Asn Ser Thr Tyr Arg Val Val Ser
     290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                 325                 330                 335

Ser Lys Ala Lys Gly Gln Pro Arg Glu Pro Gln Val Tyr Thr Leu Pro
             340                 345                 350

Pro Ser Gln Glu Glu Met Thr Lys Asn Gln Val Ser Leu Thr Cys Leu
         355                 360                 365

Val Lys Gly Phe Tyr Pro Ser Asp Ile Ala Val Glu Trp Glu Ser Asn
     370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                 405                 410                 415

Trp Gln Glu Gly Asn Val Phe Ser Cys Ser Val Met His Glu Ala Leu
             420                 425                 430

His Asn His Tyr Thr Gln Lys Ser Leu Ser Leu Ser Leu Gly
```

<210> SEQ ID NO 198
<211> LENGTH: 1348
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 198

```
gaagtgcagc tggtgcagtc tggcgccgaa gtgaagaaac ccggcgctac cgtgaagatc      60
tcctgcaagg tgtccggcta caccttcacc agctactgga tgtactgggt gcgacaggct     120
accggccagg gcctggaatg gatgggcaga atcgacccca actccggctc caccaagtac     180
aacgagaagt tcaagaaccg cgtgaccatc accgccgaca gtccactcc caccgcctac     240
atggaactgt cctccctgcg gagcgaggac accgccgtgt actactgcgc cagagactac     300
cggaagggcc tgtacgccat ggactattgg ggcagggca ccaccgtgac cgtgtcctct     360
gcttccacca agggcccaag cgtgttcccc ctggccccct gctccagaag caccagcgag     420
agcacagccg ccctgggctg cctggtgaag gactacttcc ccgagcccgt gaccgtgtcc     480
tggaacagcg gagccctgac cagcggcgtg cacaccttcc ccgccgtgct gcagagcagc     540
ggcctgtaca gcctgagcag cgtggtgacc gtgcccagca gcagcctggg caccaagacc     600
tacacctgta acgtggacca caagcccagc aacaccaagg tggacaagag ggtggagagc     660
aagtacggcc caccctgccc ccctgccca gccccgagt tcctgggcgg acccagcgtg     720
ttcctgttcc cccccaagcc caaggacacc ctgatgatca gcagaacccc cgaggtgacc     780
tgtgtggtgg tggacgtgtc ccaggaggac cccgaggtcc agttcaactg gtacgtggac     840
ggcgtggagg tgcacaacgc caagaccaag cccagagagg agcagtttaa cagcacctac     900
cgggtggtgt ccgtgctgac cgtgctgcac caggactggc tgaacggcaa agagtacaag     960
tgtaaggtct ccaacaaggg cctgccaagc agcatcgaaa agaccatcag caaggccaag    1020
ggccagccta gagagcccca ggtctacacc ctgccaccca gccaagagga tgatgaccaag    1080
aaccaggtgt ccctgacctg tctggtgaag ggcttctacc caagcgacat cgccgtggag    1140
tgggagagca acggccagcc cgagaacaac tacaagacca cccccccagt gctggacagc    1200
gacggcagct tcttcctgta cagcaggctg accgtggaca agtccagatg gcaggagggc    1260
aacgtcttta gctgctccgt gatgcacgag gccctgcaca accactacac ccagaagagc    1320
ctgagcctgt ccctgggctg atgaattc                                       1348
```

<210> SEQ ID NO 199
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 199

```
gagatcgtgc tgacccagtc ccccgacttc cagtccgtga ccccaaaga aaaagtgacc      60
atcacatgca aggcctccca ggacgtgggc accgccgtgg cttggtatct gcagaagcct     120
ggccagtccc ctcagctgct gatctactgg gcctctacca gacacaccgg cgtgcccgac     180
agattctccg gctctggctc tggcaccgac ttcaccctga gatctcccg ggtggaagcc     240
gaggatgtgg gcgtgtacta ctgccagcag tacaactcct acccctgac cttcggccag     300
```

```
ggcaccaagg tggaaatcaa g                                             321
```

<210> SEQ ID NO 200
<211> LENGTH: 652
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 200

```
gagatcgtgc tgacccagtc ccccgacttc cagtccgtga cccccaaaga aaaagtgacc    60
atcacatgca aggcctccca ggacgtgggc accgccgtgg cttggtatct gcagaagcct   120
ggccagtccc ctcagctgct gatctactgg gcctctacca gacacaccgg cgtgcccgac   180
agattctccg gctctggctc tggcaccgac ttcaccctga gatctcccg ggtggaagcc    240 gaggatgtgg gcgtgtacta ctgccagcag tacaactcct accccctgac cttcggccag   300
ggcaccaagg tggaaatcaa gcgtacggtg gccgctccca gcgtgttcat cttccccca    360 agcgacgagc agctgaagag cggcaccgcc agcgtggtgt gtctgctgaa caacttctac   420
cccagggagg ccaaggtgca gtggaaggtg acaacgccc tgcagagcgg caacagccag   480
gagagcgtca ccgagcagga cagcaaggac tccacctaca gcctgagcag caccctgacc   540
ctgagcaagg ccgactacga aagcacaag gtgtacgcct gtgaggtgac ccaccagggc   600
ctgtccagcc ccgtgaccaa gagcttcaac aggggcgagt gctgatgaat tc           652
```

<210> SEQ ID NO 201
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 201

```
gaagtgcagc tggtgcagtc tggcgccgaa gtgaagaagc ctggcgagtc cctgcggatc    60
tcctgcaagg gctccggcta caccttcacc agctactgga tgtactggat ccggcagccc   120
cctggcaagg gcctggaatg gatcggcaga atcgacccca ctccggctc caccaagtac    180 aacgagaagt tcaagaaccg cgtgaccatc accgccgaca gtccacctc caccgcctac    240 atggaactgt cctccctgag atccgaggac accgccgtgt actactgcgc cagagactac    300
cggaagggcc tgtacgccat ggactattgg ggccagggca ccaccgtgac cgtgtcctct    360
```

<210> SEQ ID NO 202
<211> LENGTH: 1348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 202

```
gaagtgcagc tggtgcagtc tggcgccgaa gtgaagaagc ctggcgagtc cctgcggatc    60
tcctgcaagg gctccggcta caccttcacc agctactgga tgtactggat ccggcagccc   120
cctggcaagg gcctggaatg gatcggcaga atcgacccca ctccggctc caccaagtac    180 aacgagaagt tcaagaaccg cgtgaccatc accgccgaca gtccacctc caccgcctac    240 atggaactgt cctccctgag atccgaggac accgccgtgt actactgcgc cagagactac    300
```

```
cggaagggcc tgtacgccat ggactattgg ggccagggca ccaccgtgac cgtgtcctct      360
gcttctacca agggcccaag cgtgttcccc ctggcccct gctccagaag caccagcgag       420
agcacagccg ccctgggctg cctggtgaag gactacttcc ccgagcccgt gaccgtgtcc      480
tggaacagcg gagccctgac cagcggcgtg cacaccttcc ccgccgtgct gcagagcagc      540
ggcctgtaca gcctgagcag cgtggtgacc gtgcccagca gcagcctggg caccaagacc      600
tacacctgta acgtggacca caagcccagc aacaccaagg tggacaagag ggtggagagc      660
aagtacggcc cccctgccc ccctgcccca gccccgagt tcctgggcgg acccagcgtg        720
ttcctgttcc cccccaagcc caaggacacc ctgatgatca gcagaacccc cgaggtgacc      780
tgtgtggtgg tggacgtgtc ccaggaggac cccgaggtcc agttcaactg gtacgtggac      840
ggcgtggagg tgcacaacgc caagaccaag cccagagagg agcagtttaa cagcacctac      900
cgggtggtgt ccgtgctgac cgtgctgcac caggactggc tgaacggcaa agagtacaag      960
tgtaaggtct ccaacaaggg cctgccaagc agcatcgaaa agaccatcag caaggccaag     1020
ggccagccta gagagcccca ggtctacacc ctgccaccca gccaagagga gatgaccaag     1080
aaccaggtgt ccctgacctg tctggtgaag ggcttctacc caagcgacat cgccgtggag     1140
tgggagagca acggccagcc cgagaacaac tacaagacca cccccccagt gctggacagc     1200
gacggcagct tcttcctgta cagcaggctg accgtggaca gtccagatg gcaggagggc      1260 aacgtcttta gctgctccgt gatgcacgag gccctgcaca accactacac ccagaagagc     1320
ctgagcctgt ccctgggctg atgaattc                                        1348
```

```
<210> SEQ ID NO 203
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 203
gagatcgtgc tgacccagtc ccccgacttc cagtccgtga ccccaaaga aaaagtgacc        60 atcacatgca aggcctccca ggacgtgggc accgccgtgg cttggtatct gcagaagcct      120
ggccagtccc ctcagctgct gatctactgg gcctctacca gacacaccgg cgtgccctcc      180
agattctccg gctctggctc tggcaccgac tttaccttca ccatctccag cctgcagccc      240
gaggatatcg ccacctacta ctgccagcag tacaactcct accccctgac cttcggccag      300
ggcaccaagg tggaaatcaa g                                                321
```

```
<210> SEQ ID NO 204
<211> LENGTH: 652
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 204
gagatcgtgc tgacccagtc ccccgacttc cagtccgtga ccccaaaga aaaagtgacc        60 atcacatgca aggcctccca ggacgtgggc accgccgtgg cttggtatct gcagaagcct      120
ggccagtccc ctcagctgct gatctactgg gcctctacca gacacaccgg cgtgccctcc      180
agattctccg gctctggctc tggcaccgac tttaccttca ccatctccag cctgcagccc      240
```

```
gaggatatcg ccacctacta ctgccagcag tacaactcct accccctgac cttcggccag    300
ggcaccaagg tggaaatcaa gcgtacggtg gccgctccca gcgtgttcat cttccccca    360 agcgacgagc agctgaagag cggcaccgcc agcgtggtgt gtctgctgaa caacttctac    420
cccagggagg ccaaggtgca gtggaaggtg gacaacgccc tgcagagcgg caacagccag    480
gagagcgtca ccgagcagga cagcaaggac tccacctaca gcctgagcag caccctgacc    540
ctgagcaagg ccgactacga aagcacaag gtgtacgcct gtgaggtgac ccaccagggc    600
ctgtccagcc ccgtgaccaa gagcttcaac aggggcgagt gctgatgaat tc           652
```

<210> SEQ ID NO 205
<211> LENGTH: 51
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 205

```
agaatcgacc ccaactccgg ctccaccaag tacaacgaga agttcaagaa c              51
```

<210> SEQ ID NO 206
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 206

```
gactaccgga agggcctgta cgccatggac tat                                  33
```

<210> SEQ ID NO 207
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 207

```
ggctacacct tcaccagcta c                                               21
```

<210> SEQ ID NO 208
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 208

```
gaccccaact ccggctcc                                                   18
```

<210> SEQ ID NO 209
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 209

```
aaggcctccc aggacgtggg caccgccgtg gct                                  33
```

<210> SEQ ID NO 210
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 210
tgggcctcta ccagacacac c                                           21

<210> SEQ ID NO 211
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 211
cagcagtaca actcctaccc cctgacc                                     27

<210> SEQ ID NO 212
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 212
tcccaggacg tgggcaccgc c                                           21

<210> SEQ ID NO 213
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 213 tgggcctct                                                          9

<210> SEQ ID NO 214
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 214
tacaactcct accccctg                                               18

<210> SEQ ID NO 215
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 215
gaagtgcagc tggtgcagtc aggcgccgaa gtgaagaagc ccggcgagtc actgagaatt   60
agctgtaaag gttca                                                  75

<210> SEQ ID NO 216
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 216
gaagtgcagc tggtgcagtc tggcgccgaa gtgaagaagc ctggcgagtc cctgcggatc      60
tcctgcaagg gctcc                                                      75

<210> SEQ ID NO 217
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 217
gaagtgcagc tggtgcagtc tggcgccgaa gtgaagaaac ccggcgctac cgtgaagatc      60
tcctgcaagg tgtcc                                                      75

<210> SEQ ID NO 218
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 218
gaagtgcagc tggtgcagtc aggcgccgaa gtgaagaaac ccggcgctac cgtgaagatt      60
agctgtaaag tctca                                                      75

<210> SEQ ID NO 219
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 219
tgggtgcgac aggctaccgg ccagggcctg gaatggatgg gc                         42

<210> SEQ ID NO 220
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 220
tgggtccgac aggctaccgg tcaaggcctg gagtggatgg gt                         42

<210> SEQ ID NO 221
<211> LENGTH: 42
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 221
tgggtccgac aggccccagg gcaaggcctg gagtggatgg gt                42

<210> SEQ ID NO 222
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 222
tggatccggc agcccctgg caagggcctg gaatggatcg gc                42

<210> SEQ ID NO 223
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 223
tgggtccgac aggctagagg gcaaagactg gagtggatcg gt                42

<210> SEQ ID NO 224
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 224
cgcgtgacca tcaccgccga caagtccacc tccaccgcct acatggaact gtcctccctg     60
cggagcgagg acaccgccgt gtactactgc gccaga                              96

<210> SEQ ID NO 225
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 225
cgcgtgacca tcaccgccga caagtccacc tccaccgcct acatggaact gtcctccctg     60
agatccgagg acaccgccgt gtactactgc gccaga                              96

<210> SEQ ID NO 226
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 226
agagtgacta tcaccgccga taagtctact agcaccgcct atatggaact gtctagcctg     60
agatcagagg acaccgccgt ctactactgc gctaga                              96

<210> SEQ ID NO 227

```
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 227
agagtgacta ttagcgtgga cacctctaag aatcagttta gcctgaagct gtctagcgtg    60
accgccgctg acaccgccgt ctactactgc gctaga                              96

<210> SEQ ID NO 228
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 228
aggttcacta ttagtaggga taactctaag aacaccctgt acctgcagat gaatagcctg    60
agagccgagg acaccgccgt ctactactgc gctaga                              96

<210> SEQ ID NO 229
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229
tggggccagg gcaccaccgt gaccgtgtcc tct                                 33

<210> SEQ ID NO 230
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 230
tggggtcaag gcactaccgt gaccgtgtct tca                                 33

<210> SEQ ID NO 231
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 231
gagatcgtgc tgacccagtc ccccgacttc cagtccgtga cccccaaaga aaaagtgacc    60
atcacatgc                                                            69

<210> SEQ ID NO 232
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 232
```

```
gagatcgtcc tgactcagtc acccgacttt cagtcagtga cccctaaaga gaaagtcact      60
atcacctgt                                                              69
```

<210> SEQ ID NO 233
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 233

```
gacgtcgtga tgactcagtc acccctgagc ctgcccgtga ccctggggca gcccgcctct      60
attagctgt                                                              69
```

<210> SEQ ID NO 234
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 234

```
gctattcagc tgactcagtc acctagtagc ctgagcgcta gtgtgggcga tagagtgact      60
atcacctgt                                                              69
```

<210> SEQ ID NO 235
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 235

```
tggtatcagc agaagccagg gcaagcccct agactgctga tctac                      45
```

<210> SEQ ID NO 236
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 236

```
tggtatctgc agaagcctgg ccagtcccct cagctgctga tctac                      45
```

<210> SEQ ID NO 237
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 237

```
tggtatctgc agaagcctgg tcaatcacct cagctgctga tctac                      45
```

<210> SEQ ID NO 238
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 238
ggcgtgccct ctaggtttag cggtagcggt agtggcaccg agttcaccct gactatctct    60
tcactgcagc ccgacgactt cgctacctac tactgt                              96

<210> SEQ ID NO 239
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 239
ggcgtgccct ctaggtttag cggtagcggt agtggcaccg acttcacctt cactatctct    60
tcactgcagc ccgaggatat cgctacctac tactgt                              96

<210> SEQ ID NO 240
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 240
ggcgtgccct ccagattctc cggctctggc tctggcaccg actttacctt caccatctcc    60
agcctgcagc ccgaggatat cgccacctac tactgc                              96

<210> SEQ ID NO 241
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 241
ggcgtgcccg acagattctc cggctctggc tctggcaccg acttcaccct gaagatctcc    60
cgggtggaag ccgaggatgt gggcgtgtac tactgc                              96

<210> SEQ ID NO 242
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 242
ggcgtgccct ctaggtttag cggtagcggt agtggcaccg acttcacctt cactatctct    60
tcactggaag ccgaggacgc cgctacctac tactgt                              96

<210> SEQ ID NO 243
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 243
ttcggccagg gcaccaaggt ggaaatcaag                                              30

<210> SEQ ID NO 244
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 244
ttcggtcaag gcactaaggt cgagattaag                                              30

<210> SEQ ID NO 245
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 245
aaggccagtc aggatgtggg tactgctgta gcc                                          33

<210> SEQ ID NO 246
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 246
tgggcatcca cccggcacac t                                                       21

<210> SEQ ID NO 247
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 247

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Ser Tyr
            20                  25                  30

Trp Met Tyr Trp Val Arg Gln Ala Arg Gly Gln Arg Leu Glu Trp Ile
        35                  40                  45

Gly Arg Ile Asp Pro Asn Ser Gly Ser Thr Lys Tyr Asn Glu Lys Phe
    50                  55                  60

Lys Asn Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Arg Lys Gly Leu Tyr Ala Met Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 248
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 248

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Arg Gly Leu Glu Trp Ile
        35                  40                  45

```
Gly Arg Ile Asp Pro Asn Ser Gly Gly Thr Lys Tyr Asn Glu Lys Phe
        50                  55                  60

Lys Ser Lys Ala Thr Leu Thr Val Asp Lys Pro Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg

<210> SEQ ID NO 249
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 249

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Thr Ala
                20                  25                  30

Val Ala Trp Tyr Gln Gln Lys Pro Gly Gln Ser Pro Lys Leu Leu Ile
            35                  40                  45

Tyr Trp Ala Ser Thr Arg His Thr Gly Val Pro Asp Arg Phe Thr Gly
        50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Ser Tyr Pro Leu
                85                  90                  95

Thr Phe Gly Ala Gly Ser Lys Leu Glu Leu Lys
            100                 105

<210> SEQ ID NO 250
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 250

Glu Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Ser Tyr
                20                  25                  30

Trp Met Tyr Trp Val Lys Gln Gly Pro Gly Arg Gly Leu Glu Trp Ile
            35                  40                  45

Gly Arg Ile Asp Pro Asn Ser Gly Ser Thr Lys Tyr Asn Glu Lys Phe
        50                  55                  60

Lys Asn Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Asp Tyr Arg Lys Gly Leu Tyr Ala Met Asp Tyr Trp Gly Gln
            100                 105                 110

Gly

<210> SEQ ID NO 251
```

<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 251

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Tyr Trp Val Arg Gln Ala Thr Gly Gln Gly Leu Glu Trp Met
        35                  40                  45

Gly Arg Ile Asp Pro Asn Ser Gly Ser Thr Lys Tyr Asn Glu Lys Phe
    50                  55                  60

Lys Asn Arg Phe Thr Ile Ser Arg Asp Asp Ser Lys Asn Thr Ala Tyr
65                  70                  75                  80

Leu Gln Met Asn Ser Leu Lys Thr Glu Asp Thr Ala Val Tyr Tyr Cys
                85                  90                  95

Ala Arg Asp Tyr Arg Lys Gly Leu Tyr Ala Met Asp Tyr Trp Gly Gln
            100                 105                 110

Gly

<210> SEQ ID NO 252
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 252

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Ser Tyr
            20                  25                  30

Trp Met Tyr Trp Ile Arg Gln Pro Pro Gly Lys Gly Leu Glu Trp Ile
        35                  40                  45

Gly Arg Ile Asp Pro Asn Ser Gly Ser Thr Lys Tyr Asn Glu Lys Phe
    50                  55                  60

Lys Asn Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Arg Lys Gly Leu Tyr Ala Met Asp Tyr Trp Gly Gln
            100                 105                 110

Gly

<210> SEQ ID NO 253
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 253

Glu Val Gln Leu Val Gln Ser Gly Ala Glu Val Lys Lys Pro Gly Ala
1               5                   10                  15

```
Thr Val Lys Ile Ser Cys Lys Val Ser Gly Tyr Thr Phe Thr Ser Tyr
            20                  25                  30

Trp Met Tyr Trp Val Arg Gln Ala Thr Gly Gln Gly Leu Glu Trp Met
        35                  40                  45

Gly Arg Ile Asp Pro Asn Ser Gly Ser Thr Lys Tyr Asn Glu Lys Phe
50                  55                  60

Lys Asn Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Arg Lys Gly Leu Tyr Ala Met Asp Tyr Trp Gly Gln
            100                 105                 110

Gly

<210> SEQ ID NO 254
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 254

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Ser Tyr
            20                  25                  30

Trp Met Tyr Trp Val Arg Gln Ala Pro Gly Gln Gly Leu Glu Trp Met
        35                  40                  45

Gly Arg Ile Asp Pro Asn Ser Gly Ser Thr Lys Tyr Asn Glu Lys Phe
50                  55                  60

Lys Asn Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asp Tyr Arg Lys Gly Leu Tyr Ala Met Asp Tyr Trp Gly Gln
            100                 105                 110

Gly

<210> SEQ ID NO 255
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 255

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Tyr Trp Ile Arg Gln Pro Ser Arg Gly Leu Glu Trp Leu
        35                  40                  45

Gly Arg Ile Asp Pro Asn Ser Gly Ser Thr Lys Tyr Asn Glu Lys Phe
50                  55                  60

Lys Asn Arg Phe Thr Ile Ser Arg Asp Asp Ser Lys Asn Thr Ala Tyr
```

```
                65                  70                  75                  80
Leu Gln Met Asn Ser Leu Lys Thr Glu Asp Thr Ala Val Tyr Tyr Cys
                85                  90                  95

Ala Arg Asp Tyr Arg Lys Gly Leu Tyr Ala Met Asp Tyr Trp Gly Gln
            100                 105                 110

Gly

<210> SEQ ID NO 256
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 256

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Ser Tyr
            20                  25                  30

Trp Met Tyr Trp Val Arg Gln Ala Arg Gly Gln Arg Leu Glu Trp Ile
        35                  40                  45

Gly Arg Ile Asp Pro Asn Ser Gly Ser Thr Lys Tyr Asn Glu Lys Phe
    50                  55                  60

Lys Asn Arg Leu Thr Ile Ser Lys Asp Thr Ser Lys Asn Gln Val Val
65                  70                  75                  80

Leu Thr Met Thr Asn Met Asp Pro Val Asp Thr Ala Thr Tyr Tyr Cys
                85                  90                  95

Ala Arg Asp Tyr Arg Lys Gly Leu Tyr Ala Met Asp Tyr Trp Gly Gln
            100                 105                 110

Gly

<210> SEQ ID NO 257
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 257

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Ser Tyr
            20                  25                  30

Trp Met Tyr Trp Ile Arg Gln Ser Pro Ser Arg Gly Leu Glu Trp Leu
        35                  40                  45

Gly Arg Ile Asp Pro Asn Ser Gly Ser Thr Lys Tyr Asn Glu Lys Phe
    50                  55                  60

Lys Asn Arg Leu Thr Ile Ser Lys Asp Thr Ser Lys Asn Gln Val Val
65                  70                  75                  80

Leu Thr Met Thr Asn Met Asp Pro Val Asp Thr Ala Thr Tyr Tyr Cys
                85                  90                  95

Ala Arg Asp Tyr Arg Lys Gly Leu Tyr Ala Met Asp Tyr Trp Gly Gln
            100                 105                 110

Gly
```

```
<210> SEQ ID NO 258
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 258
```

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Tyr Thr Phe Thr Ser Tyr
            20                  25                  30

Trp Met Tyr Trp Val Arg Gln Ala Pro Gly Lys Gly Leu Glu Trp Val
        35                  40                  45

Ser Arg Ile Asp Pro Asn Ser Gly Ser Thr Lys Tyr Asn Glu Lys Phe
50                  55                  60

Lys Asn Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Arg Lys Gly Leu Tyr Ala Met Asp Tyr Trp Gly Gln
            100                 105                 110

Gly

```
<210> SEQ ID NO 259
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 259
```

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Ser Tyr
            20                  25                  30

Trp Met Tyr Trp Val Arg Gln Ala Arg Gly Gln Arg Leu Glu Trp Ile
        35                  40                  45

Gly Arg Ile Asp Pro Asn Ser Gly Ser Thr Lys Tyr Asn Glu Lys Phe
50                  55                  60

Lys Asn Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Arg Lys Gly Leu Tyr Ala Met Asp Tyr Trp Gly Gln
            100                 105                 110

Gly

```
<210> SEQ ID NO 260
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 260
```

Glu Val Gln Leu Val Gln Ser Gly Ala Glu Val Lys Lys Pro Gly Glu

-continued

```
1               5                   10                  15
Ser Leu Arg Ile Ser Cys Lys Gly Ser Gly Tyr Thr Phe Thr Ser Tyr
                20                  25                  30

Trp Met Tyr Trp Ile Arg Gln Pro Pro Gly Lys Gly Leu Glu Trp Ile
            35                  40                  45

Gly Arg Ile Asp Pro Asn Ser Gly Ser Thr Lys Tyr Asn Glu Lys Phe
        50                  55                  60

Lys Asn Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Arg Lys Gly Leu Tyr Ala Met Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430
```

His Asn His Tyr Thr Gln Lys Ser Leu Ser Leu Ser Leu Gly
        435                 440                 445

<210> SEQ ID NO 261

<400> SEQUENCE: 261

000

<210> SEQ ID NO 262

<400> SEQUENCE: 262

000

<210> SEQ ID NO 263

<400> SEQUENCE: 263

000

<210> SEQ ID NO 264

<400> SEQUENCE: 264

000

<210> SEQ ID NO 265

<400> SEQUENCE: 265

000

<210> SEQ ID NO 266

<400> SEQUENCE: 266

000

<210> SEQ ID NO 267

<400> SEQUENCE: 267

000

<210> SEQ ID NO 268

<400> SEQUENCE: 268

000

<210> SEQ ID NO 269

<400> SEQUENCE: 269

000

<210> SEQ ID NO 270

<400> SEQUENCE: 270

000

<210> SEQ ID NO 271

<400> SEQUENCE: 271

000

<210> SEQ ID NO 272

<400> SEQUENCE: 272

000

<210> SEQ ID NO 273

<400> SEQUENCE: 273

000

<210> SEQ ID NO 274

<400> SEQUENCE: 274

000

<210> SEQ ID NO 275

<400> SEQUENCE: 275

000

<210> SEQ ID NO 276

<400> SEQUENCE: 276

000

<210> SEQ ID NO 277

<400> SEQUENCE: 277

000

<210> SEQ ID NO 278

<400> SEQUENCE: 278

000

<210> SEQ ID NO 279

<400> SEQUENCE: 279

000

<210> SEQ ID NO 280

<400> SEQUENCE: 280

000

<210> SEQ ID NO 281

<400> SEQUENCE: 281

000

<210> SEQ ID NO 282

<400> SEQUENCE: 282

000

<210> SEQ ID NO 283

<400> SEQUENCE: 283

000

<210> SEQ ID NO 284

<400> SEQUENCE: 284

000

<210> SEQ ID NO 285

<400> SEQUENCE: 285

000

<210> SEQ ID NO 286

<400> SEQUENCE: 286

000

<210> SEQ ID NO 287

<400> SEQUENCE: 287

000

<210> SEQ ID NO 288

<400> SEQUENCE: 288

000

<210> SEQ ID NO 289
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 289

Ala Ala Ser
1

<210> SEQ ID NO 290

<400> SEQUENCE: 290

000

<210> SEQ ID NO 291

<400> SEQUENCE: 291

000

<210> SEQ ID NO 292

<400> SEQUENCE: 292

000

```
<210> SEQ ID NO 293
<400> SEQUENCE: 293
000

<210> SEQ ID NO 294
<400> SEQUENCE: 294
000

<210> SEQ ID NO 295
<400> SEQUENCE: 295
000

<210> SEQ ID NO 296
<400> SEQUENCE: 296
000

<210> SEQ ID NO 297
<400> SEQUENCE: 297
000

<210> SEQ ID NO 298
<400> SEQUENCE: 298
000

<210> SEQ ID NO 299
<400> SEQUENCE: 299
000

<210> SEQ ID NO 300
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 300

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Asn
            20                  25                  30

Val Ile Ser Trp Val Arg Gln Ala Pro Gly Gln Gly Leu Glu Trp Met
        35                  40                  45

Gly Gly Val Ile Pro Ile Val Asp Ile Ala Asn Tyr Ala Gln Arg Phe
    50                  55                  60

Lys Gly Arg Val Thr Ile Thr Ala Asp Glu Ser Thr Ser Thr Thr Tyr
65                  70                  75                  80

Met Glu Leu Ser Ser Leu Arg Ser Glu Asp Thr Ala Val Tyr Tyr Cys
                85                  90                  95

Ala Ser Thr Leu Gly Leu Val Leu Asp Ala Met Asp Tyr Trp Gly Gln
            100                 105                 110
```

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
210                 215                 220

Pro Cys Pro Ser Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 301
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 301

Glu Thr Val Leu Thr Gln Ser Pro Gly Thr Leu Ser Leu Ser Pro Gly
1               5                   10                  15

Glu Arg Ala Thr Leu Ser Cys Arg Ala Ser Gln Ser Leu Gly Ser Ser

```
                20                  25                  30
Tyr Leu Ala Trp Tyr Gln Gln Lys Pro Gly Gln Ala Pro Arg Leu Leu
            35                  40                  45

Ile Tyr Gly Ala Ser Ser Arg Ala Pro Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ala Asp Ser Pro
                85                  90                  95

Ile Thr Phe Gly Gln Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 302
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 302

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Leu Trp Glu Val Arg Ala Leu Pro Ser Val Tyr Trp Gly
            100                 105                 110

Gln Gly Thr Leu Val Thr Val Ser Ser
        115                 120

<210> SEQ ID NO 303
<211> LENGTH: 109
<212> TYPE: PRT
<213> ORGANISM: Artificial Sequence
<220> FEATURE:
```

<223> OTHER INFORMATION: Description of Artificial Sequence: Synthetic
       polypeptide

<400> SEQUENCE: 303

Ser Tyr Glu Leu Thr Gln Pro Pro Ser Val Ser Val Ala Pro Gly Gln
1               5                   10                  15

Thr Ala Arg Ile Thr Cys Gly Ala Asn Asp Ile Gly Ser Lys Ser Val
            20                  25                  30

His Trp Tyr Gln Gln Lys Ala Gly Gln Ala Pro Val Leu Val Val Ser
        35                  40                  45

Glu Asp Ile Ile Arg Pro Ser Gly Ile Pro Glu Arg Ile Ser Gly Ser
50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Arg Asp Ser Asp Gln
                85                  90                  95

Tyr Val Phe Gly Thr Gly Thr Lys Val Thr Val Leu Gly
            100                 105

<210> SEQ ID NO 304
<211> LENGTH: 440
<212> TYPE: PRT
<213> ORGANISM: Artificial Sequence
<220> FEATURE:
<223> OTHER INFORMATION: Description of Artificial Sequence: Synthetic
       polypeptide

<400> SEQUENCE: 304

Gln Val Gln Leu Val Glu Ser Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
210                 215                 220

-continued

```
Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
            245                 250                 255

Val Asp Val Ser Gln Glu Asp Pro Glu Val Gln Phe Asn Trp Tyr Val
        260                 265                 270

Asp Gly Val Glu Val His Asn Ala Lys Thr Lys Pro Arg Glu Glu Gln
    275                 280                 285

Phe Asn Ser Thr Tyr Arg Val Val Ser Val Leu Thr Val Leu His Gln
290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
            325                 330                 335

Arg Glu Pro Gln Val Tyr Thr Leu Pro Pro Ser Gln Glu Glu Met Thr
        340                 345                 350

Lys Asn Gln Val Ser Leu Thr Cys Leu Val Lys Gly Phe Tyr Pro Ser
    355                 360                 365

Asp Ile Ala Val Glu Trp Glu Ser Asn Gly Gln Pro Glu Asn Asn Tyr
370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Gln Gly Asn Val Phe
            405                 410                 415

Ser Cys Ser Val Met His Glu Ala Leu His Asn His Tyr Thr Gln Lys
        420                 425                 430

Ser Leu Ser Leu Ser Leu Gly Lys
    435                 440

<210> SEQ ID NO 305
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 305

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 306
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 306

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Tyr Met Tyr Trp Val Arg Gln Ala Pro Gly Gln Gly Leu Glu Trp Met
            35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
```

```
                    275                 280                 285
Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 307
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 307

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190
```

His Lys Val Tyr Ala Cys Glu Val Thr His Gln Gly Leu Ser Ser Pro
            195                 200                 205

Val Thr Lys Ser Phe Asn Arg Gly Glu Cys
    210                 215

<210> SEQ ID NO 308
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 308

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Met Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg
                85                  90                  95

Ile Lys Leu Gly Thr Val Thr Thr Val Asp Tyr Trp Gly Gln Gly Thr
            100                 105                 110

Leu Val Thr Val Ser Ser
        115

<210> SEQ ID NO 309
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 309

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Arg Val Phe Gly Thr Gly Thr Lys Val Thr Val Leu
            100                 105                 110

<210> SEQ ID NO 310
<211> LENGTH: 253
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 310

Met Ala Pro Arg Arg Ala Arg Gly Cys Arg Thr Leu Gly Leu Pro Ala
1               5                   10                  15

Leu Leu Leu Leu Leu Leu Leu Arg Pro Pro Ala Thr Arg Gly Asp Tyr
            20                  25                  30

Lys Asp Asp Asp Lys Ile Glu Gly Arg Ile Thr Cys Pro Pro Pro
            35                  40                  45

Met Ser Val Glu His Ala Asp Ile Trp Val Lys Ser Tyr Ser Leu Tyr
    50                  55                  60

Ser Arg Glu Arg Tyr Ile Cys Asn Ser Gly Phe Lys Arg Lys Ala Gly
65                  70                  75                  80

Thr Ser Ser Leu Thr Glu Cys Val Leu Asn Lys Ala Thr Asn Val Ala
                85                  90                  95

His Trp Thr Thr Pro Ser Leu Lys Cys Ile Arg Asp Pro Ala Leu Val
            100                 105                 110

His Gln Arg Pro Ala Pro Pro Ser Gly Gly Ser Gly Gly Gly Gly Ser
            115                 120                 125

Gly Gly Gly Ser Gly Gly Gly Ser Leu Gln Asn Trp Val Asn Val
            130                 135                 140

Ile Ser Asp Leu Lys Lys Ile Glu Asp Leu Ile Gln Ser Met His Ile
145                 150                 155                 160

Asp Ala Thr Leu Tyr Thr Glu Ser Asp Val His Pro Ser Cys Lys Val
                165                 170                 175

Thr Ala Met Lys Cys Phe Leu Leu Glu Leu Gln Val Ile Ser Leu Glu
            180                 185                 190

Ser Gly Asp Ala Ser Ile His Asp Thr Val Glu Asn Leu Ile Ile Leu
            195                 200                 205

Ala Asn Asn Ser Leu Ser Ser Asn Gly Asn Val Thr Glu Ser Gly Cys
            210                 215                 220

Lys Glu Cys Glu Glu Leu Glu Glu Lys Asn Ile Lys Glu Phe Leu Gln
225                 230                 235                 240

Ser Phe Val His Ile Val Gln Met Phe Ile Asn Thr Ser
                245                 250

<210> SEQ ID NO 311
<211> LENGTH: 263
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 311

Met Asp Ser Lys Gly Ser Ser Gln Lys Ala Gly Ser Arg Leu Leu Leu
1               5                   10                  15

Leu Leu Val Val Ser Asn Leu Leu Cys Gln Gly Val Val Ser Thr
            20                  25                  30

Thr Arg Asp Tyr Lys Asp Asp Asp Lys Ile Glu Gly Arg Asn Trp
            35                  40                  45

Val Asn Val Ile Ser Asp Leu Lys Lys Ile Glu Asp Leu Ile Gln Ser
    50                  55                  60

Met His Ile Asp Ala Thr Leu Tyr Thr Glu Ser Asp Val His Pro Ser
65                  70                  75                  80

```
Cys Lys Val Thr Ala Met Lys Cys Phe Leu Glu Leu Gln Val Ile
                 85                  90                  95

Ser Leu Glu Ser Gly Asp Ala Ser Ile His Asp Thr Val Glu Asn Leu
            100                 105                 110

Ile Ile Leu Ala Asn Asn Ser Leu Ser Ser Asn Gly Asn Val Thr Glu
            115                 120                 125

Ser Gly Cys Lys Glu Cys Glu Glu Leu Glu Glu Lys Asn Ile Lys Glu
130             135                 140

Phe Leu Gln Ser Phe Val His Ile Val Gln Met Phe Ile Asn Thr Ser
145                 150                 155                 160

Ser Gly Gly Gly Ser Gly Gly Gly Ser Gly Gly Gly Ser
                165                 170                 175

Gly Gly Gly Ser Gly Gly Gly Ser Leu Gln Ile Thr Cys Pro Pro Pro
            180                 185                 190

Met Ser Val Glu His Ala Asp Ile Trp Val Lys Ser Tyr Ser Leu Tyr
            195                 200                 205

Ser Arg Glu Arg Tyr Ile Cys Asn Ser Gly Phe Lys Arg Lys Ala Gly
210                 215                 220

Thr Ser Ser Leu Thr Glu Cys Val Leu Asn Lys Ala Thr Asn Val Ala
225                 230                 235                 240

His Trp Thr Thr Pro Ser Leu Lys Cys Ile Arg Asp Pro Ala Leu Val
                245                 250                 255

His Gln Arg Pro Ala Pro Pro
            260

<210> SEQ ID NO 312
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 312

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Gly Ser Tyr Gly Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Val Asn Phe Gly Met Asp Tyr Trp Gly Gln Gly Thr Leu
            100                 105                 110

Val Thr Val Ser Ser
        115

<210> SEQ ID NO 313
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 313

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Arg Asn Pro Pro
                85                  90                  95

Thr Phe Gly Gln Gly Thr Lys Leu Glu Ile Lys
            100                 105

<210> SEQ ID NO 314
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 314

Gly Phe Thr Phe Ser Ser Tyr Ala
1               5

<210> SEQ ID NO 315
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 315

Ile Gly Ser Tyr Gly Gly Gly Thr
1               5

<210> SEQ ID NO 316
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 316

Ala Arg Tyr Val Asn Phe Gly Met Asp Tyr
1               5                   10

<210> SEQ ID NO 317
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 317

Gln Ser Ile Ser Ser Tyr
1               5

<210> SEQ ID NO 318
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 318

Gln Gln Tyr Gly Arg Asn Pro Pro Thr
1               5

<210> SEQ ID NO 319
<211> LENGTH: 116
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 319

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Val Trp Gly Phe Asp Tyr Trp Gly Gln Gly Thr Leu Val
            100                 105                 110

Thr Val Ser Ser
        115

<210> SEQ ID NO 320
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 320

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Val Tyr Pro Phe
                85                  90                  95

```
Thr Phe Gly Gln Gly Thr Lys Leu Glu Ile Lys
            100                 105
```

<210> SEQ ID NO 321
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 321

```
Ile Ser Gly Ser Gly Gly Ser Thr
1               5
```

<210> SEQ ID NO 322
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 322

```
Ala Arg Arg Val Trp Gly Phe Asp Tyr
1               5
```

<210> SEQ ID NO 323
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 323

```
Gln Gln Tyr Gly Val Tyr Pro Phe Thr
1               5
```

<210> SEQ ID NO 324
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (120)..(120)
<223> OTHER INFORMATION: Any amino acid
<220> FEATURE:
<221> NAME/KEY: MOD_RES
<222> LOCATION: (124)..(125)
<223> OTHER INFORMATION: Any amino acid

<400> SEQUENCE: 324

```
Glu Val Arg Leu Gln Gln Ser Gly Ala Asp Leu Val Lys Pro Gly Ala
1               5                   10                  15

Ser Val Lys Leu Ser Cys Ala Ser Gly Phe Ile Ile Lys Ala Thr Tyr
                20                  25                  30

Met His Trp Val Arg Gln Arg Pro Glu Gln Gly Leu Glu Trp Ile Gly
            35                  40                  45

Arg Ile Asp Pro Ala Asn Gly Glu Lys Tyr Asp Pro Lys Phe Gln Val
        50                  55                  60

Lys Ala Ile Thr Ala Asp Thr Ser Ser Ser Thr Ala Tyr Leu Gln Leu
65                  70                  75                  80
```

```
Asn Ser Leu Thr Ser Asp Asp Thr Ala Val Tyr Tyr Cys Ala Arg Tyr
                85                  90                  95

Ala Trp Tyr Phe Asp Val Trp Gly Ala Gly Thr Thr Val Thr Val Ser
            100                 105                 110

Ser Ala Lys Thr Thr Pro Pro Xaa Val Tyr Pro Xaa Xaa Pro Gly Ser
        115                 120                 125

<210> SEQ ID NO 325
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 325

Asp Ile Gln Met Thr Gln Ser Pro Ala Ser Leu Ser Ala Ser Val Gly
1               5                   10                  15

Asp Thr Val Thr Ile Thr Cys Arg Ala Ser Glu Asn Ile Tyr Ser Phe
            20                  25                  30

Leu Ala Trp Tyr His Gln Lys Gln Gly Arg Ser Pro Gln Leu Leu Val
        35                  40                  45

Tyr His Ala Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Ala
65                  70                  75                  80

Glu Asp Phe Gly Ser Tyr Tyr Cys Gln His Tyr Tyr Gly Ser Pro Leu
                85                  90                  95

Thr Phe Gly Ala Gly Thr Lys Leu Glu Val Lys Arg Ala Asp Ala Ala
            100                 105                 110

Pro Thr Val Ser Ile Phe Pro Pro Ser Ser Glu Glu Leu Ser Leu
        115                 120                 125

<210> SEQ ID NO 326
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 326

Gly Phe Ile Ile Lys Ala Thr Tyr Met His
1               5                   10

<210> SEQ ID NO 327
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 327

Arg Ile Asp Pro Ala Asn Gly Glu Thr Lys Tyr Asp Pro Lys Phe Gln
1               5                   10                  15

Val

<210> SEQ ID NO 328
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 328

Tyr Ala Trp Tyr Phe Asp Val
1               5

<210> SEQ ID NO 329
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 329

Arg Ala Ser Glu Asn Ile Tyr Ser Phe Leu Ala
1               5                   10

<210> SEQ ID NO 330
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 330

His Ala Lys Thr Leu Ala Glu
1               5

<210> SEQ ID NO 331
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 331

Gln His Tyr Tyr Gly Ser Pro Leu Thr
1               5

<210> SEQ ID NO 332
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 332

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Asn Trp Val Arg Gln Ala Pro Gly Lys Gly Leu Glu Trp Val
        35                  40                  45

Ala Ala Ile Asn Gln Asp Gly Ser Glu Lys Tyr Tyr Val Gly Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Val Tyr Tyr Cys
                85                  90                  95
```

```
Val Arg Asp Tyr Tyr Asp Ile Leu Thr Asp Tyr Tyr Ile His Tyr Trp
            100                 105                 110

Tyr Phe Asp Leu Trp Gly Arg Gly Thr Leu Val Thr Val Ser Ser
        115                 120                 125

<210> SEQ ID NO 333
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 333

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Asn Trp Val Arg Gln Ala Pro Gly Lys Gly Leu Glu Trp Val
        35                  40                  45

Ala Ala Ile Asn Gln Asp Gly Ser Glu Lys Tyr Tyr Val Gly Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Val Tyr Tyr Cys
                85                  90                  95

Val Arg Asp Tyr Tyr Asp Ile Leu Thr Asp Tyr Tyr Ile His Tyr Trp
            100                 105                 110

Tyr Phe Asp Leu Trp Gly Arg Gly Thr Leu Val Thr Val Ser Ser
        115                 120                 125

<210> SEQ ID NO 334
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 334

Asn Tyr Trp Met Asn
1               5

<210> SEQ ID NO 335
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 335

Ala Ile Asn Gln Asp Gly Ser Glu Lys Tyr Tyr Val Gly Ser Val Lys
1               5                   10                  15

Gly

<210> SEQ ID NO 336
<211> LENGTH: 18
<212> TYPE: PRT
<213> ORGANISM: Artificial Sequence
<220> FEATURE:
<223> OTHER INFORMATION: Description of Artificial Sequence: Synthetic
```

```
                   peptide

<400> SEQUENCE: 336

Asp Tyr Tyr Asp Ile Leu Thr Asp Tyr Tyr Ile His Tyr Trp Tyr Phe
1               5                   10                  15

Asp Leu

<210> SEQ ID NO 337
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 337

Arg Ala Ser Gln Ser Val Ser Ser Ser Tyr Leu Ala
1               5                   10

<210> SEQ ID NO 338
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 338

Gly Ala Ser Ser Arg Ala Thr
1               5

<210> SEQ ID NO 339
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 339

Glu Val Gln Leu Val Glu Ser Gly Gly Asp Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Ser Leu Tyr Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
```

```
              165                 170                 175
Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 340
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 340

Ala Ile Gln Leu Thr Gln Ser Pro Ser Ser Leu Ser Ala Ser Val Gly
1               5                  10                  15

Asp Arg Val Thr Ile Thr Cys Arg Pro Ser Gln Gly Ile Asn Trp Glu
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Gln Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

-continued

```
Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 341
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 341

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asp Tyr
            20                  25                  30

His Ile His Trp Val Arg Gln Ala Pro Gly Gln Gly Leu Glu Trp Met
        35                  40                  45

Gly Val Ile Asn Pro Met Tyr Gly Thr Thr Asp Tyr Asn Gln Arg Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Tyr Phe Thr Gly Thr Gly Val Tyr Trp Gly Gln Gly
            100                 105                 110

Thr Leu Val Thr Val Ser Ser
        115

<210> SEQ ID NO 342
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 342

Asp Ile Val Met Thr Gln Thr Pro Leu Ser Leu Ser Val Thr Pro Gly
1               5                   10                  15

Gln Pro Ala Ser Ile Ser Cys Arg Ser Ser Arg Ser Leu Val His Ser
            20                  25                  30
```

Arg Gly Asn Thr Tyr Leu His Trp Tyr Leu Gln Lys Pro Gly Gln Ser
            35                  40                  45

Pro Gln Leu Leu Ile Tyr Lys Val Ser Asn Arg Phe Ile Gly Val Pro
 50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Leu Pro Phe Thr Phe Gly Gln Gly Thr Lys Leu Glu Ile Lys
            100                 105                 110

<210> SEQ ID NO 343
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 343

Arg Tyr Gly Ile Ser
1               5

<210> SEQ ID NO 344
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 344

Trp Ile Ser Thr Tyr Ser Gly Asn Thr Asn Tyr Ala Gln Lys Leu Gln
1               5                   10                  15

Gly

<210> SEQ ID NO 345
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 345

Arg Gln Leu Tyr Phe Asp Tyr
1               5

<210> SEQ ID NO 346
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 346

Arg Ala Ser Gln Ser Val Ser Ser Asn Leu Ala
1               5                   10

<210> SEQ ID NO 347
<211> LENGTH: 7
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 347

Asp Ala Ser Thr Arg Ala Thr
1               5

<210> SEQ ID NO 348
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 348

Gln Gln Tyr Asp Asn Trp Pro Leu Thr
1               5

<210> SEQ ID NO 349
<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 349

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Val Tyr Gly Met Asn Trp Val Arg Gln Ala Pro Gly Lys Gly Leu
    50                  55                  60

Glu Trp Val Ala Ile Ile Trp Tyr Asp Gly Asp Asn Gln Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Gly Leu Arg Ala Glu Asp Thr Ala Val
            100                 105                 110

Tyr Tyr Cys Ala Arg Asp Leu Arg Thr Gly Pro Phe Asp Tyr Trp Gly
        115                 120                 125

Gln Gly Thr Leu Val Thr Val Ser Ser
    130                 135

<210> SEQ ID NO 350
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 350

Met Leu Pro Ser Gln Leu Ile Gly Phe Leu Leu Leu Trp Val Pro Ala
1               5                   10                  15

Ser Arg Gly Glu Ile Val Leu Thr Gln Ser Pro Asp Phe Gln Ser Val
            20                  25                  30

Thr Pro Lys Glu Lys Val Thr Ile Thr Cys Arg Ala Ser Gln Ser Ile
        35                  40                  45

Gly Ser Ser Leu His Trp Tyr Gln Gln Lys Pro Asp Gln Ser Pro Lys
            50                  55                  60

Leu Leu Ile Lys Tyr Ala Ser Gln Ser Phe Ser Gly Val Pro Ser Arg
 65                  70                  75                  80

Phe Ser Gly Ser Gly Ser Gly Thr Asp Phe Thr Leu Thr Ile Asn Ser
                 85                  90                  95

Leu Glu Ala Glu Asp Ala Ala Ala Tyr Tyr Cys His Gln Ser Ser Ser
            100                 105                 110

Leu Pro Phe Thr Phe Gly Pro Gly Thr Lys Val Asp Ile Lys
            115                 120                 125

<210> SEQ ID NO 351
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 351

Gly Asp Ser Val Ser Ser Asn Ser Ala Ala Trp Gly
 1               5                  10

<210> SEQ ID NO 352
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 352

Arg Ile Tyr Tyr Arg Ser Lys Trp Tyr Asn Ser Tyr Ala Val Ser Val
 1               5                  10                  15

Lys Ser

<210> SEQ ID NO 353
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 353

Arg Ala Ser Gln Phe Ile Ser Ser Ser Tyr Leu Ser
 1               5                  10

<210> SEQ ID NO 354
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 354

Leu Leu Ile Tyr Gly Ser Ser Ser Arg Ala Thr
 1               5                  10

<210> SEQ ID NO 355
<211> LENGTH: 8
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 355

Gln Gln Leu Tyr Ser Ser Pro Met
1               5

<210> SEQ ID NO 356
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 356

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Gly Trp Ile Arg Gln Ser Pro Gly Arg Gly Leu Glu
        35                  40                  45

Trp Leu Gly Arg Ile Tyr Tyr Arg Ser Lys Trp Tyr Asn Ser Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Tyr Asp Trp Val Pro Lys Ile Gly Val Phe Asp
            100                 105                 110

Ser Trp Gly Gln Gly Thr Leu Val Thr Val Ser Ser
        115                 120

<210> SEQ ID NO 357
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 357

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Phe Ile Ser Ser Ser
            20                  25                  30

Tyr Leu Ser Trp Tyr Gln Gln Lys Pro Gly Gln Ala Pro Arg Leu Leu
        35                  40                  45

Ile Tyr Gly Ser Ser Ser Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Leu Tyr Ser Ser Pro
                85                  90                  95

Met Thr Phe Gly Gln Gly Thr Lys Val Glu Ile Lys Arg Thr
            100                 105                 110

<210> SEQ ID NO 358
<211> LENGTH: 454
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 358

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Gly Trp Ile Arg Gln Ser Pro Gly Arg Gly Leu Glu
        35                  40                  45

Trp Leu Gly Arg Ile Tyr Tyr Arg Ser Lys Trp Tyr Asn Ser Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Tyr Asp Trp Val Pro Lys Ile Gly Val Phe Asp
            100                 105                 110

Ser Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380
```

```
Ala Val Glu Trp Glu Ser Asn Gly Gln Pro Glu Asn Tyr Lys Thr
385                 390                 395                 400

Thr Pro Pro Val Leu Asp Ser Asp Gly Ser Phe Phe Leu Tyr Ser Lys
            405                 410                 415

Leu Thr Val Asp Lys Ser Arg Trp Gln Gln Gly Asn Val Phe Ser Cys
        420                 425                 430

Ser Val Met His Glu Ala Leu His Asn His Tyr Thr Gln Lys Ser Leu
        435                 440                 445

Ser Leu Ser Pro Gly Lys
    450

<210> SEQ ID NO 359
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 359

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Phe Ile Ser Ser Ser
            20                  25                  30

Tyr Leu Ser Trp Tyr Gln Gln Lys Pro Gly Gln Ala Pro Arg Leu Leu
        35                  40                  45

Ile Tyr Gly Ser Ser Ser Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Leu Tyr Ser Ser Pro
                85                  90                  95

Met Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 360
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 360
```

```
Arg Gly Asp Ser
1

<210> SEQ ID NO 361
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 361

Gln Gln Tyr Gly Ser Ser Pro Cys Thr
1               5

<210> SEQ ID NO 362
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 362

Tyr Asp Trp Val Pro Lys Ile Gly Val Phe Asp Ser
1               5                   10
```